(12) United States Patent
Baird et al.

(10) Patent No.: US 7,087,378 B1
(45) Date of Patent: Aug. 8, 2006

(54) DESIGN, SYNTHESIS AND USE OF SPECIFIC POLYAMIDE DNA-BINDING LIGANDS

(75) Inventors: Eldon E. Baird, W. Columbia, SC (US); Peter B. Dervan, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/372,474

(22) Filed: Aug. 11, 1999

Related U.S. Application Data

(63) Continuation of application No. PCT/US98/01714, filed on Jan. 29, 1998, which is a continuation-in-part of application No. PCT/US97/12722, filed on Jul. 21, 1997, which is a continuation-in-part of application No. 08/853,522, filed on May 8, 1997, now Pat. No. 6,635,417, and a continuation-in-part of application No. 08/837,524, filed on Apr. 21, 1997, now Pat. No. 6,143,901, which is a continuation-in-part of application No. PCT/US97/03332, filed on Feb. 20, 1997, and a continuation-in-part of application No. 08/607,078, filed on Feb. 26, 1996, now Pat. No. 6,090,947.

(60) Provisional application No. 60/042,022, filed on Apr. 16, 1997, provisional application No. 60/044,444, filed on Apr. 8, 1997, provisional application No. 60/038,384, filed on Feb. 14, 1997, provisional application No. 60/026,713, filed on Sep. 25, 1996, provisional application No. 60/024,374, filed on Aug. 1, 1996, provisional application No. 60/023,309, filed on Jul. 31, 1996.

(51) Int. Cl.
*C12Q 1/68* (2006.01)
*C07H 21/00* (2006.01)

(52) U.S. Cl. .................................. 435/6; 536/25.3
(58) Field of Classification Search ............... 530/300, 530/333; 702/27; 435/6; 536/25.3; 548/312.4
See application file for complete search history.

(56) References Cited

U.S. PATENT DOCUMENTS 6,472,537 B1 * 10/2002 Baird et al. .................. 435/6
6,506,906 B1 * 1/2003 Dervan ................... 548/312.4

FOREIGN PATENT DOCUMENTS

| WO | WO 96/05196 A | 2/1996 |
|---|---|---|
| WO | WO 97/30975 | 8/1997 |
| WO | WO 98/35702 | 8/1998 |
| WO | WO 98/37066 | 8/1998 |
| WO | WO 98/37087 | 8/1998 |
| WO | WO 98/45284 | 10/1998 |
| WO | WO 98/50582 | 11/1998 |

OTHER PUBLICATIONS

Baird et al. (1996) "Solid Phase Synthesis of Polyamides Containing Imidazole and Pyrrole Amino Acids." JACS 118: 6141-6146.
Parks et al. (1996) "Optimization of the Hairpin Polyamide Design for Recognition of the Minor Groove of DNA." JACS 118: 6147-6152.
Parks et al. (1996) "Recognition of 5'-(A,T)GG(A,T)$_2$-3' Sequences in the Minor Groove of DNA by Hairpin Polyamides." JACS 118: 6153-6159.
Swalley et al. (1996) "Recognition of 5'-(A,T)GGG(A,T)$_2$-3' Sequences in the Minor Groove of DNA by an Eight-Ring Hairpin Polyamide" JACS 118: 8198-8206.
Swalley et al. (1997) "Discrimaination of 5'-GGGG-3', 5'-GCGC-3', and 5'-GGCC-3' Sequences in the Minor Groove of DNA by Eight-Ring Hairpin Polyamides." JACS 119: 6953-6961.
Trauger et al. (1996) "Recognition of DNA by designed ligands at subnanomolar concentrations." Nature 382: 559-561.
Walker et al. (1997) "Estimation of the DNA sequence discriminatory ability of hairpin-linked lexitropsins." PNAS, USA 94:5634-5639.
White et al. (1998) "Recognition of the four Watson-Crick base pairs in the DNA minor groove by synthetic ligands." Nature 391: 468-471.

* cited by examiner

Primary Examiner—Marianne P. Allen
(74) Attorney, Agent, or Firm—Foley & Lardner, LLP

(57) ABSTRACT

The invention encompasses improved selective polyamides for binding to specific nucleotide sequences of double stranded DNA as well as methods for designing and synthesizing polyamide DNA binding ligands that are selective for an identified specific nucleotide sequence. The 3-hydroxy-N-methylpyrrole/N-methylpyrrole carboxamide pair specifically recognizes the T•A base pair, while the N-methylpyrrole/3-hydroxy-N-methylpyrrole pair recognizes A•T nucleotide pairs. Similarly, an N-methylimidizole/N-methylpyrrole carboxamide pair specifically recognizes the G•C nucleotide pair, and the N-methylpyrrole/N-methylimidizole carboxamide pair recognizes the C•G nucleotide pair.

9 Claims, 14 Drawing Sheets

1  ImImPyPy-γ-ImPyPyPy-β-Dp

2  ImImPyPy-γ-ImHpPyPy-β-Dp

3  ImImHpPy-γ-ImPyPyPy-β-Dp

Py/Py with T•A

Py/Py with A•T

Py/Hp with T•A

Py/Hp with A•T

Hp/Py with T•A

Hp/Py with A•T

6-Ring Hairpin Hp-Py-Im-Polyamides $K_d = 0.20$ μM $K_d = 0.28$ μM $K_d = 0.008$ μM $K_d = 0.33$ μM

8-Ring Hairpin Hp-Py-Im-Polyamides $K_d = 0.48$ nM $K_d = 0.83$ nM $K_d = 2.5$ nM

10-Ring Hairpin Hp-Py-Im-Polyamides $K_d = 0.2$ nM $K_d = 5$ nM

DESIGN, SYNTHESIS AND USE OF SPECIFIC POLYAMIDE DNA-BINDING LIGANDS

CROSS REFERENCE TO RELATED APPLICATIONS

This application is a continuation of PCT/US 98/01714, filed Jan. 29, 1998, which in turn is a continuation in part of applications:
PCT/US 97/03332, filed Feb. 20, 1997,
U.S. application Ser. No. 08/853,522, filed May 8, 1997, now issued as U.S. Pat. No. 6,635,417,
PCT/US 97/12722, filed Jul. 21, 1997,
U.S. Provisional App. No. 60/042,022, filed Apr. 16, 1997, now abandoned, and
U.S. Provisional App. No. 60/044,444, filed Apr. 8, 1997, now abandoned.
Application PCT/US 97/03332, filed Feb. 20, 1997, in turn is a continuation in part of U.S. application Ser. No. 08/607,078, filed Feb. 26, 1996, now issued as U.S. Pat. No. 6,090,947.
U.S. application Ser. No. 08/853,522, filed May 8, 1997, now issued as U.S. Pat. No. 6,635,417, in turn is a continuation in part of applications:
U.S. application Ser. No. 08/837,524, filed Apr. 21, 1997, now issued as U.S. Pat. No. 6,143,901, and
U.S. application Ser. No. 08/607,078, filed Feb. 26, 1996, now issued as U.S. Pat. No. 6,090,947.
U.S. application Ser. No. 08/837,524, filed Apr. 21, 1997, now issued as U.S. Pat. No. 6,143,901, in turn is a continuation in part of applications:
U.S. application Ser. No. 08/607,078, filed Feb. 26, 1996, now issued as U.S. Pat. No. 6,090,947,
U.S. Provisional App. No. 60/038,384, filed Feb. 14, 1997, now abandoned,
U.S. Provisional App. No. 60/026,713, filed Sep. 25, 1996, now abandoned,
U.S. Provisional App. No. 60/024,374, filed Aug. 1, 1996, now abandoned; and
U.S. Provisional App. No. 60/023,309, filed Jul. 31, 1996, now abandoned.
The U.S. Government has certain rights in this invention pursuant to Grant Nos. GM 26453, 27681 and 47530 awarded by the National Institute of Health.

BACKGROUND OF THE INVENTION

1. Field of the Invention

This invention relates to polyamides which bind to predetermined sequences in the minor groove of double stranded DNA.

2. Description of the Related Art

The design of synthetic ligands that read the information stored in the DNA double helix has been a long standing goal of chemistry. Cell-permeable small molecules which target predetermined DNA sequences are useful for the regulation of gene-expression. Oligodeoxynucleotides that recognize the major groove of double-helical DNA via triple-helix formation bind to a broad range of sequences with high affinity and specificity. Although oligonucleotides and their analogs have been shown to interfere with gene expression, the triple helix approach is limited to purine tracks and suffers from poor cellular uptake. The development of pairing rules for minor groove binding polyamides derived from N-methylpyrrole (Py) and N-niethylimidazole (Im) amino acids provides another code to control sequence specificity. An Im/Py pair distinguishes G•C from C•G and both of these from A•T or T•A base pairs. Wade, W. S., Mrksich, M. & Dervan, P. B. describes the design of peptides that bind in the minor groove of DNA at 5'-(A,T) G(A,T)C(A,T)-3' sequences by a dimeric side-by-side motif. *J. Am. Chem. Soc.* 114, 8783–8794 (1992); Mrksich, M. et al. describes antiparallel side-by-side motif for sequence specific-recognition in the minor groove of DNA by the designed peptide 1-methylimidazole-2-carboxamidenetropsin. *Proc. Natl. Acad. Sci. USA* 89, 7586–7590 (1992); Trauger, J. W., Baird, E. E. Dervan, P. B. describes the recognition of DNA by designed ligands at subnanomolar concentrations. *Nature* 382, 559–561 (1996). A Py/Py pair specifies A•T from G•C but does not distinguish A•T from T•A. Pelton, J. G. & Wemmer, D. E. describes the structural characterization of a 2-1 distamycin A-d(CG-CAAATTTGGC) (SEQ ID NO: 1) complex by two-dimensional NMR. *Pro. Natl. Acad. Sci. USA* 86, 5723–5727 (1989); White, S., Baird, E. E. Dervan, P. B. Describes the effect of the A•T/T•A degeneracy of pyrrole-imidazole polyamide recognition in the minor groove of DNA. *Biochemistry* 35, 12532–12537 (1996); White, S., Baird, E. E. & Dervan, P. B. describes the pairing rules for recognition in the minor groove of DNA by pyrrole-imidazole polyamides. *Chem. & Biol.* 4, 569–578 (1997); White, S., Baird, E. E. & Dervan, P. B. describes the 5'-3' N-C orientation preference for polyamide binding in the minor groove. New methods of designing selective compounds and the resulting specific polyamide binding ligands that are designed to target an identified sequence of double stranded DNA are needed to overcome the A•T/T•A degeneracy of pyrrole-imidazole polyamide recognition.

SUMMARY OF THE INVENTION

It has been found that a new aromatic amino acid, 3-hydroxy-N-methylpyrrole (Hp) when incorporated into a polyamide and paired opposite Py, provides the means to discriminate A•T from T•A. Unexpectedly, the replacement of a single hydrogen atom on the pyrrole with a hydroxy, group in a Hp/Py pair regulates the affinity and the specificity of a polyamide by an order of magnitude. Utilizing Hp together with Py and Im in polyamides to form four aromatic amino acid pairs (Im/Py, Py/Im, Hp/Py, and Py/Hp) provides a code to distinguish all four Watson-Crick base pairs in the minor groove of DNA.

The present invention provides a method for designing specific polyamides suitable for use as DNA-binding ligands, as well as compositions comprising such polyamides, that are selective for an identified target sequence of double stranded DNA. Preferably, the designed specific polyamides are characterized by a dissociation constant of less than 1 nM, as measured by DNase I footprint titration, and greater than ten-fold selectivity for the identified target sequence over related mismatch sequences, based on the ratio of the corresponding dissociation constants measured by DNase I footprint titrations.

The invention encompasses improved polyamides for binding to the minor groove of double stranded ("duplex") DNA. The polyamides are in the form of a hairpin comprising two groups of at least three consecutive carboxamide residues, the two groups covalently linked by an aliphatic amino acid residue, preferably γ-aminobutyric acid or 2,4 diaminobutyric acid, the consecutive carboxamide residues of the first group pairing in an antiparallel manner with the consecutive carboxamide residues of the second group in the minor groove of double stranded DNA. The improvement relates to the inclusion of a binding pair of Hp/Py carboxamides in the polyamide to bind to a T•A base pair in the minor groove of double stranded DNA or Py/Hp carboxamide binding pair in the polyamide to bind to an A•T base pair in the minor groove of double stranded DNA. The improved polyamides have at least three consecutive carboxamide pairs for binding to at least three DNA base pairs in the minor groove of a duplex DNA sequence that has at least one A•T or T•A DNA base pair, the improvement comprising selecting a Hp/Py carboxamide pair to correspond to a T•A base pair in the minor groove or a Py/Hp carboxamide pair to bind to an A•T DNA base pair in the minor groove. Preferably the binding of the carboxamide pairs to the DNA base pairs modulates the expression of a gene.

In general, the method provides specific polyamides suitable for use as DNA-binding ligands that are selective for identified target sequences of double stranded DNA having a coding strand sequence of the form 5'-$WN_1N_2 \ldots N_mW$-3' where N is a nucleotide chosen from the group A, T, C and G, W is a nucleotide chosen from the group A and T, and with the coresponding paired antiparallel strand 3'-$W'N'_1N'_2 \ldots N'_mW'$-5' where N' is a nucleotide chosen from the group T, A, G and C respectively to form Watson-Crick pase pairs. W is a nucleotide chosen from the group T and A respectively to form Watson-Crick pase pairs, and m is an integer having a value from 3 to 6 inclusive.

The preferred corresponding designed specific polyamides resulting from this invention are of the form

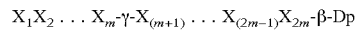

$X_1X_2 \ldots X_m$-γ-$X_{(m+1)} \ldots X_{(2m-1)}X_{2m}$-β-Dp wherein $X_1$, $X_2$, $X_m$, $X_{(m+1)}$, $X_{(2m-1)}$, and $X_{2m}$ are carboxamide residues forming carboxamide binding pairs $X_1/X_{2m}$, $X_2/X_{(2m-1)}$, $X_m/X_{(m+1)}$, γ and is γ-aminobuytic acid or 2,4 diaminobutyric acid and Dp is dimethylaminopropylamide, and where carboxamide binding pair $X_1/X_{2m}$ corresponds to base pair $N_1•N'_1$.

carboxamide binding pair $X_2/X_{(2m-1)}$ corresponds to base pair $N_2•N'_2$, carboxamide binding pair $X_m/X_{(m+1)}$ corresponds to base pair $N_m•N'_m$.

In general, the specific polyamide DNA-binding ligands were designed by using a method that comprises the steps of identifying the target DNA sequence 5'-$WN_1N_2 \ldots N_mW$-3'; representing the identified sequence as 5'-Wab . . . xW-3', wherein a is a first nucleotide to be bound by the $X_1$ carboxamide residue, b is a second nucleotide to be bound by the $X_2$ carboxamide residue, and x is the corresponding nucleotide to be bound by the $X_m$ carboxamide residue; defining a as A, G, C, or T to correspond to the first nucleotide to be bound by a carboxamide residue in the identified six base pair sequence.

Carboxamide residues were selected sequentially as follows: Im was selected as the $X_1$ carboxamide residue and Py as the $X_{2m}$ carboxamide residue if a was G. Py was selected as the $X_1$ carboxamide residue and Im as the $X_{2m}$ carboxamide residue if a was C. Hp was selected as the $X_1$ carboxamide residue and Py as the $X_{2m}$ carboxamide residue if a was T. Py was selected as the $X_1$ carboxamide residue and Hp as the $X_{2m}$ carboxamide residue if a was A.

The remaining carboxamide residues were selected in the same fashion. Im was selected as the $X_2$ carboxamide residue and Py as the $X_{2m-1}$ carboxamide residue if b was G. Py was selected as the $X_2$ carboxamide residue and Im as the $X_{2m-1}$ carboxamide residue if b was C. Hp was selected as the $X_2$ carboxamide residue and Py as the $X_{2-1}$ carboxamide residue if b was T. Py was selected as the $X_2$ carboxamide residue and Hp as the $X_{2-1}$ carboxamide residue if b was A.

The selection of carboxamide residues was continued through m iterations. In the last iteration, Im was selected as the $X_m$ carboxamide residue and Py as the $X_{m+1}$ carboxamide residue if x was G. Py was selected as the $X_m$ carboxamide residue and Im as the $X_{m+1}$ carboxamide residue if x was C. Hp was selected as the $X_m$ carboxamide residue and Py as the $X_{m+1}$ carboxamide residue if x was T. Py was selected as the $X_m$ carboxamide residue and Hp as the $X_{m+1}$ carboxamide residue if x was A.

In one preferred embodiment, the polyamide includes at least four consecutive carboxamide pairs for binding to at least four base pairs in a duplex DNA sequence. In another preferred embodiment, the polyamide includes at least five consecutive carboxamide pairs for binding to at least five base pairs in a duplex DNA sequence. In yet another preferred embodiment, the polyamide includes at least six consecutive carboxamide pairs for binding to at least six base pairs in a duplex DNA sequence. In one preferred embodiment, the improved polyamides have four carboxamide binding pairs that will distinguish A•T, T•A, C•G and G•C base pairs in the minor groove of a duplex DNA sequence. The duplex DNA sequence can be a regulatory sequence, such as a promoter sequence or an enhancer sequence, or a gene sequence, such as a coding sequence or a non-coding sequence. Preferably, the duplex DNA sequence is a promoter sequence.

More specifically, "polyamide" refers to a polymer of polyamide subunits of the formula.

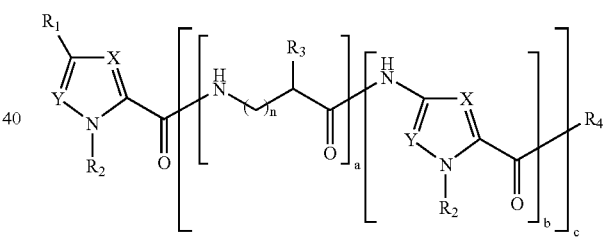

where R is chosen from H, $NH_2$, SH, Cl, Br, F, N-acetyl, or N-formyl.

where $R^2$ is $C_{1-100}$ alkyl (preferably $C_{1-10}$ alkyl such as methyl, ethyl, isopropyl), $C_{1-100}$ alkylamine (preferably $C_{1-10}$ alkylamine such as ethylamine), $C_{1-100}$ alkyldiamine (preferably $C_{1-10}$ alkyldiamine such as N,N-dimethylpropylamine), a $C_{1-100}$ alkylcarboxylate (preferably a $C_{1-10}$ alkylcarboxylate such as —$CH_2COOH$), $C_{1-100}$ alkenyl (preferably $C_{1-10}$ alkenyl such as $CH_2CH=CH_2$), or a $C_{1-100}$ alkynyl (preferably $C_{1-10}$ alkynyl such as—$CH_2C\equiv CH_3$), or a $C_{1-100}L$, where L groups can be independently chosen from but is not limited to arylboronic acids, biotins, polyhistidines comprised from about 2 to 8 amino acids, haptens to which an antibody binds, solid phase supports, oligodeoxynucleotide, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, isosulfan blue, malachite green, psoralen, ethyl red, 4-(psoraen-8-yloxy)-butyrate, tartaric acid, (+)-α-tocopheral. Most preferably $R^2$ is H, $(CH_2)_mCH_3$, $(CH_2)_mNH_2$, $(CH_2)_mSH$, $(CH_2)_mOH$, $(CH_2)_mNR^5_2$, $(CH_2)_m$ OR⁵, $(CH_2)_m SR^5$, where $R^5=(CH_2)_m CH_3$, $(CH_2)_m NH_2$, $(CH_2)_m SH$, $(CH_2)_m OH$ and m is an integer from 0 to 6.

where $R^3$ is chosen from H, $NH_2$, OH, SH, Br, Cl, F, OMe, $CH_2OH$, $CH_2SH$, $CH_2NH_2$.

where $R^4$ is —$NH(CH_2)_{0-100}NR^6R^7$ or $NH(CH_2)_p CO$ $NH(CH^2)_{0-100}NR^6R^7$ or $NHR^6$ or $NH(CH_2)_p CONHR^6$. Where $R^6$ and $R^7$ are independently chosen from H, Cl, NO, N-acetyl, benzyl, $C_{1-100}$ alkyl, $C_{1-100}$ alkylamine, $C_{1-100}$ alkyldiamine, $C_{1-100}$ alkylcarboxylate, $C_{1-100}$ alkenyl, a $C_{1-100}$ alkynyl, or a $C_{1-100}L$, where L groups can be independently chosen from but is not limited to arylboronic acids, biotins, polyhistidines comprised from about 2 to 8 amino acids, haptens to which an antibody binds, solid phase supports, oligodeoxynucleotide, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, an oligodeoxynucleotide, isosulfan blue, malachite green, psoralen, ethyl red, 4-(psoraen-8-yloxy)-butyrate, tartaric acid, (+)-α-tocopheral. Where p is an integer value ranging from 0 to 12. In the preferred form of the present invention $R^6$ and $R^7$ are H, and the resulting amine modified polyamide is coupled to an amine reactive molecule in order to generate a bifunction polyamide conjugate. Where the amine reactive molecule is chosen from but not limited to the following: arylboronic acids, biotins, polyhistidines comprised from about 2 to 8 amino acids, haptens to which an antibody binds, solid phase supports, an oligodeoxynucleotide, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, isosulfan blue, malachite green, psoralen, ethyl red, 4-(psoraen-8-yloxy)-butyrate, tartaric acid, (+)-α-tocopheral.

where X and Y are chosen from the following, N, CH, $COH$, $CCH_3$, $CNH_2$, CCl, CF.

a is an integer chosen from values of 0 or 1 b is an integer chosen integer values ranging from 1 to 5.

c is an integer value ranging from 2 to 10.

Hereinafter, N-methylpyrrolecarboxamide may be referred to as "Py", N-methylimidazolecarboxamide may be referred to as "Im", γ-aminobutyric acid may referred to as "γ", β-alanine may be referred to as "β", glycine may be referred to as "G", dimethylaminopropylamide may be referred to as "Dp", and ethylenediaminetetraacetic acid may be referred to as "EDTA".

The preparation and the use of polyamides for binding in the minor groove of double stranded DNA are extensively described in the art. This invention is an improvement of the existing technology that uses 3-hydroxy-N-methylpyrrole to provide carboxamide binding pairs for DNA binding polyamides.

The invention encompasses polyamides having γ-aminobutyric acid or a substituted γ-aminobutyric acid to form a hairpin with a member of each carboxamide pairing on each side of it. Preferably the substituted γ-aminobutyric acid is a chiral substituted γ-aminobutyric acid such as (R)-2,4-diaminobutyric acid. In addition, the polyamides may contain an aliphatic amino acid residue, preferably a β-alanine residue, in place of a Hp or Py carboxamide. The β-alanine residue is represented in formulas as β. The β-alanine residue becomes a member of a carboxamide binding pair. The invention further includes the substitution as a β/β binding pair for non-Im containing binding pair. Thus, binding pairs in addition to the Im/Py, Py/Im, Hp/Py and Py/Hp are Im/β, β/Im, Py/β, β/Py, Hp/β, β/Hp, and β/β.

The polyamides of the invention can have additional moieties attached covalently to the polyamide. Preferably the additional moieties are attached as substituents at the amino terminus of the polyamide, the carboxy terminus of the polyamide, or at a chiral (R)-2,4-diaminobutyric acid residue. Suitable additional moieties include a detectable labeling group such as a dye, biotin or a hapten. Other suitable additional moieties are DNA reactive moieties that provide for sequence specific cleavage of the duplex DNA.

DETAILED DESCRIPTION OF THE INVENTION

Figure 1:
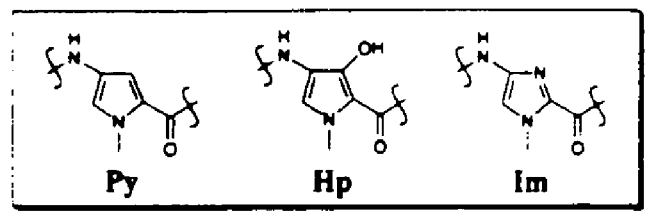
FIG. 1 illustrates the structure of polyamide 1, 2, and 3.
Figure 1:
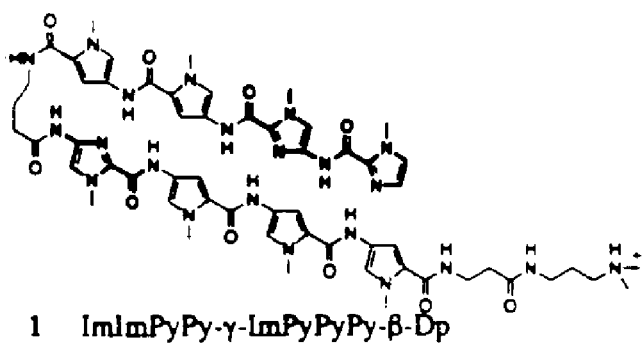
Figure 1:
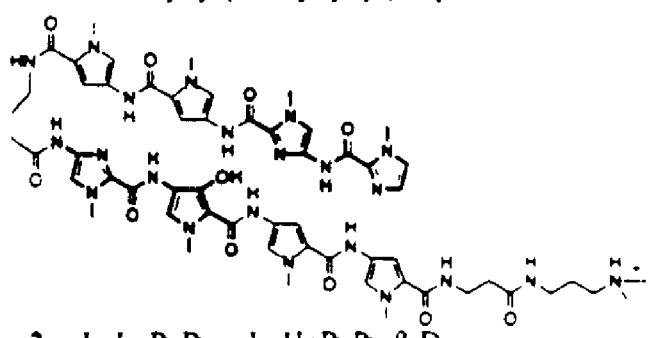
Figure 1:
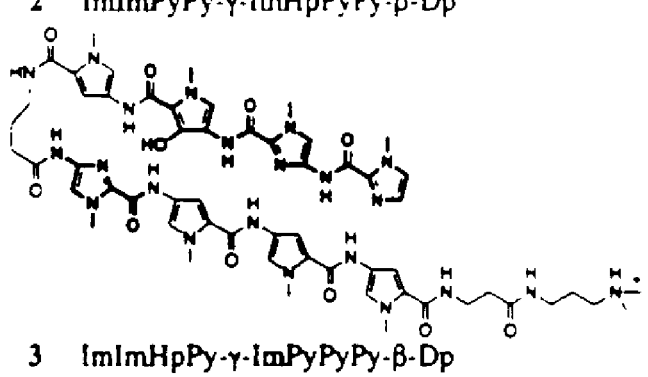

Within this application, unless otherwise stated, definitions of the terms and illustration of the techniques of this application may be found in any of several well-known references such as: Sambrook, J., et al., *Molecular Cloning: A Laboratory Manual*, Cold Spring Harbor Laboratory Press (1989); Goeddel, D., ed., *Gene Expression Technology, Methods in Enzymology*, 185, Academic Press, San Diego, Calif. (1991); "Guide to Protein Purification" in Deutshcer, M. P., ed., *Methods in Enzymology*, Academic Press, San Diego, Calif. (1989); Innis. et al., *PCR Protocols: A Guide to Methods and Applications*, Academic Press, San Diego, Calif. (1990); Freshney, R. I., *Culture of Animal Cells: A Manual of Basic Technique*, 2nd Ed. Alan Liss, Inc. New York, N.Y. (1987); Murray, E. J., ed., *Gene Transfer and Expression Protocols*. pp. 109–128, The Humana Press Inc., Clifton, N.J. and Lewin, B., *Genes VI*, Oxford University Press, New York (1997).

For the purposes of this application, a promoter is a regulatory sequence of DNA that is involved in the binding of RNA polymerase to initiate transcription of a gene. A gene is a segment of DNA involved in producing a peptide, polypeptide or protein, including the coding region, non-coding regions preceding ("leader") and following ("trailer") the coding region, as well as intervening non-coding sequences ("introns") between individual coding segments ("exons"). Coding refers to the representation of amino acids, start and stop signals in a three base "triplet" code. Promoters are often upstream ("5 to") the transcription initiation site of the corresponding gene. Other regulatory sequences of DNA in addition to promoters are known, including sequences involved with the binding of transcription factors, including response elements that are the DNA sequences bound by inducible factors. Enhancers comprise yet another group of regulatory sequences of DNA that can increase the utilization of promoters, and can function in either orientation (5'-3' or 3'-5') and in any location (upstream or downstream) relative to the promoter. Preferably, the regulatory sequence has a positive activity, i.e., binding of an endogeneous ligand (e.g. a transcription factor) to the regulatory sequence increases transcription, thereby resulting in increased expression of the corresponding target gene. In such a case, interference with transcription by binding a polyamide to a regulatory sequence would reduce or abolish expression of a gene.

The promoter may also include or be adjacent to a regulatory sequence known in the art as a silencer. A silencer sequence generally has a negative regulatory effect on expression of the gene. In such a case, expression of a gene may be increased directly by using a polyamide to prevent binding of a factor to a silencer regulatory sequence or indirectly, by using a polyamide to block transcription of a factor to a silencer regulatory sequence.

It is to be understood that the polyamides of this invention bind to double stranded DNA in a sequence specific manner. The function of a segment of DNA of a given sequence, such as 5'-TATAAA-3', depends on its position relative to other functional regions in the DNA sequence. In this case, if the sequence 5'-TATAAA-3' on the coding strand of DNA is positioned about 30 base pairs upstream of the transcription start site, the sequence forms part of the promoter region (Lewin, *Genes VI*, pp. 831–835). On the other hand, if the sequence 5'-TATAAA-3' is downstream of the transcription start site in a coding region and in proper register with the reading frame, the sequence encodes the tyrosyl and lysyl amino acid residues (Lewin, *Genes VI*, pp. 213–215).

While not being held to one hypothesis, it is believed that the binding of the polyamides of this invention modulate gene expression by altering the binding of DNA binding proteins, such as RNA polymerase, transcription factors, TBF, TFIIIB and other proteins. The effect on gene expression of polyamide binding to a segment of double stranded DNA is believed to be related to the function, e.g., promoter, of that segment of DNA.

It is to be understood by one skilled in the art that the improved polyamides of the present invention may bind to any of the above-described DNA sequences or any other sequence having a desired effect upon expression of a gene. In addition, U.S. Pat. No. 5,578,444 describes numerous promoter targeting sequences from which base pair sequences for targeting an improved polyamide of the present invention may be identified.

It is generally understood by those skilled in the art that the basic structure of DNA in a living cell includes both major and a minor groove. For the purposes of describing the present invention, the minor groove is the narrow groove of DNA as illustrated in common molecular biology references such as Lewin, B., *Genes VI*, Oxford University Press, New York (1997).

To affect gene expression in a cell, which may include causing an increase or a decrease in gene expression, a effective quantity of one or more polyamide is contacted with the cell and internalized by the cell. The cell may be contacted in vivo or in vitro. Effective extracellular concentrations of polyamides that can modulate gene expression range from about 10 nanomolar to about 1 micromolar. Gottesfeld, J. M., et al., *Nature* 387 202–205 (1997). To determine effective amounts and concentrations of polyamides in vitro, a suitable number of cells is plated on tissue culture plates and various quantities of one or more polyamide are added to separate wells. Gene expression following exposure to a polyamide can be monitored in the cells or medium by detecting the amount of the protein gene product present as determined by various techniques utilizing specific antibodies, including ELISA and western blot. Alternatively, gene expression following exposure to a polyamide can be monitored by detecting the amount of messenger RNA present as determined by various techniques, including northern blot and RT-PCR.

Similarly, to determine effective amounts and concentrations of polyamides for in vivo administration, a sample of body tissue or fluid, such as plasma, blood, urine, cerebrospinal fluid, saliva, or biopsy of skin, muscle, liver, brain or other appropriate tissue source is analyzed. Gene expression following exposure to a polyamide can be monitored by detecting the amount of the protein gene product present as determined by various techniques utilizing specific antibodies, including ELISA and western blot. Alternatively, gene expression following exposure to a polyamide can be monitored by the detecting the amount of messenger RNA present as determined by various techniques, including northern blot and RT-PCR.

The polyamides of this invention may be formulated into diagnostic and therapeutic compositions for in viva or in vitro use. Representative methods of formulation may be found in *Remington. The Science and Practice of Pharmacy*, 19th ed., Mack Publishing Co., Easton, Pa. (1995).

For in vivo use, the polyamides may be incorporated into a physiologically acceptable pharmaceutical composition that is administered to a patient in need of treatment or an animal for medical or research purposes. The polyamide composition comprises pharmaceutically acceptable carriers, excipients, adjuvants, stabilizers, and vehicles. The composition may be in solid, liquid, gel, or aerosol form. The polyamide composition of the present invention may be administered in various dosage forms orally, parentally, by inhalation spray, rectally, or topically. The term parenteral as used herein includes, subcutaneous, intravenous, intramuscular, intrasternal, infusion techniques or intraperitoneally.

The selection of the precise concentration, composition, and delivery regimen is influenced by, inter alia, the specific pharmacological properties of the particular selected compound, the intended use, the nature and severity of the condition being treated or diagnosed, the age, weight, gender, physical condition and mental acuity of the intended recipient as well as the route of administration. Such considerations are within the purview of the skilled artisan.

Thus, the dosage regimen may vary widely, but can be determined routinely using standard methods.

Polyamides of the present invention are also useful for detecting the presence of double stranded DNA of a specific sequence for diagnostic or preparative purposes. The sample containing the double stranded DNA can be contacted by polyamide linked to a solid substrate, thereby isolating DNA comprising a desired sequence. Alternatively, polyamides linked to a suitable detectable marker, such as biotin, a hapten, a radioisotope or a dye molecule, can be contacted by a sample containing double stranded DNA.

The design of bifunctional sequence specific DNA binding molecules requires the integration of two separate entities: recognition and functional activity. Polyamides that specifically bind with subnanomolar affinity to the minor groove of a predetermined sequence of double stranded DNA are linked to a functional molecule, providing the corresponding bifunctional conjugates useful in molecular biology, genomic sequencing, and human medicine. Polyamides of this invention can be conjugated to a variety of functional molecules, which can be independently chosen from but is not limited to arylboronic acids, biotins, polyhistidines comprised from about 2 to 8 amino acids, haptens to which an antibody binds, solid phase supports, oligodeoxynucleotides, N-ethylnitrosourea, fluorescein, bromoacetamide, iodoacetamide, DL-α-lipoic acid, acridine, capthothesin, pyrene, mitomycin, texas red, anthracene, anthrinilic acid, avidin, DAPI, isosulfan blue, malachite green, psoralen, ethyl red, 4-(psoraen-8-yloxy)-butyrate, tartaric acid, (+)-α-tocopheral, psoralen, EDTA, methidium, acridine, Ni(II)•Gly-Gly-His, TO, Dansyl, pyrene, N-bromoacetamide, and gold particles. Such bifunctional polyamides are useful for DNA affinity capture, covalent DNA modification, oxidative DNA cleavage, and DNA photocleavage. Such bifunctional polyamides are useful for DNA detection by providing a polyamide linked to a detectable label. Detailed instructions for synthesis of such bifunctional polyamides can be found in copending U.S. provisional application 60/043,444, the teachings of which are incorporated by reference.

DNA complexed to a labeled polyamide can then be determined using the appropriate detection system as is well known to one skilled in the art. For example, DNA associated with a polyamide linked to biotin can be detected by a streptavidin/alkaline phosphatase system.

The present invention also describes a diagnostic system, preferably in kit form, for assaying for the presence of the double stranded DNA sequence bound by the polyamide of this invention in a body sample, such brain tissue, cell suspensions or tissue sections, or body fluid samples such as CSF, blood, plasma or serum, where it is desirable to detect the presence, and preferably the amount, of the double stranded DNA sequence bound by the polyamide in the sample according to the diagnostic methods described herein.

The diagnostic system includes, in an amount sufficient to perform at least one assay, a specific polyamide as a separately packaged reagent. Instructions for use of the packaged reagent(s) are also typically included. As used herein, the term "package" refers to a solid matrix or material such as glass, plastic (e.g., polyethylene, polypropylene or polycarbonate), paper, foil and the like capable of holding within fixed limits a polyamide of the present invention. Thus, for example, a package can be a glass vial used to contain milligram quantities of a contemplated polyamide or it can be a microliter plate well to which microgram quantities of a contemplated polyamide have been operatively affixed, i.e., linked so as to be capable of being bound by the target DNA sequence. "Instructions for use" typically include a tangible expression describing the reagent concentration or at least one assay method parameter such as the relative amounts of reagent and sample to be admixed, maintenance time periods for reagent or sample admixtures, temperature, buffer conditions and the like. A diagnostic system of the present invention preferably also includes a detectable label and a detecting or indicating means capable of signaling the binding of the contemplated polyamide of the present invention to the target DNA sequence. As noted above, numerous detectable labels, such as biotin, and detecting or indicating means, such as enzyme-linked (direct or indirect) streptavidin, are well known in the art.

As used herein, "subnanomolar affinity" means binding that is characterized by a dissociation constant, $K_d$, of less than 1 nM, as measured by DNase I footprint titration. Preferably, polyamides of the present invention are characterized by subnanomolar binding affinity for the identified target DNA sequence. As used herein, the "selectivity" of the binding of a polyamide to a DNA sequence is the ratio of the dissociation constant, $K_d$, as measured by DNase I footprint titration of binding the polyamide to a mismatch DNA sequence divided by the corresponding dissociation constant of the binding of the polyamide to the identified target DNA sequence. Preferably, polyamides of the present invention are characterized by a selectivity of 5 or greater, more preferably a selectivity of greater that 10.

The exemplary polyamide that illustrates the compositions and methods of the present invention is polyamide 3 of FIG. 1, ImImHpPy-γ-ImPyPyPy-β-Dp. This polyamide was designed according to the method of the present invention to target the identified sequence 5'-WGGTCW-3'. See Table 5, below, Sequence No. 36 and the corresponding sequence of carboxamide binding pairs. Polyamide 3 binds an identified target sequence 5'-TGGTCA-3' with a dissociation constant, as measured by DNase I footprint titration, of 0.48 nM, i.e. with subnanomolar affinity as defined herein (see Table 1, below). The polyamide binds to the mismatch sequence 5'-TGGACA-3' with a dissociation contant of 37 nM, yielding a selectivity, as defined herein, of 77 (Table 1).

FIG. 1 shows representative structures of polyamides. ImImPyPy-γ-ImPyPyPy-β-Dp (1), ImImPyPy-γ-ImHpPyPy-β-Dp (2), and ImImHpPy-β-ImPyPyPy-β-Dp (3). (Hp=3-hydroxy-N-methylpyrrole, Im=N-methylimidazole, Py=N-methylpyrrole, β=β-alanine, γ=γ-aminobutyric acid, Dp=Dimethylaminopropylamide). Polyamides were synthesized by solid phase methods using Boc-protected 3-methoxypyrrole, imidazole, and pyrrole aromatic amino acids, cleaved from the support by aminolysis, deprotected with sodium thiophenoxide, and purified by reversed phase HPLC. Baird, E. E. & Dervan, P. B. describes the solid phase synthesis of polyamides containing imidazole and pyrrole amino acids. *J. Am. Chem. Soc.* 118, 6141–6146 (1996); also see PCT US 97/003332. The identity and purity of the polyamides were verified by $^1$H NMR, analytical HPLC, and matrix-assisted laser-desorption ionization time-of-flight mass spectrometry (MALDI-TOF MS-monoisotopic): 1 1223.6 (1223.6 calculated), 2 1239.6 (1239.6 calculated); 3 1239.6 (1239.6 calculated).

Figure 2:
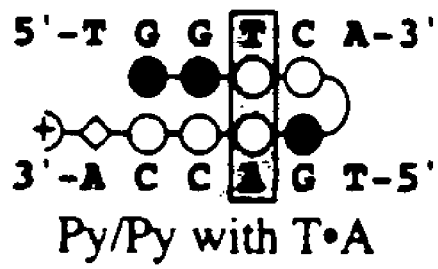
FIG. 2 illustrates the pairing of polyamides to DNA base pairs.
Figure 2:
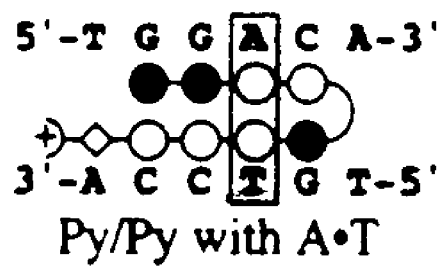
Figure 2:
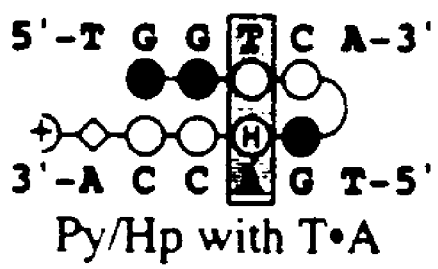
Figure 2:
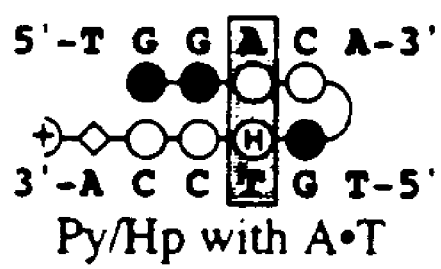
Figure 2:
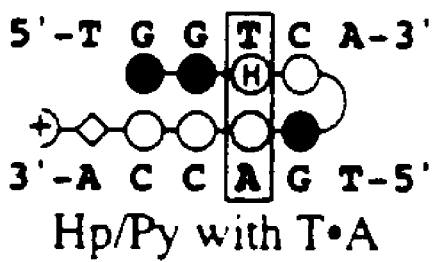
Figure 2:
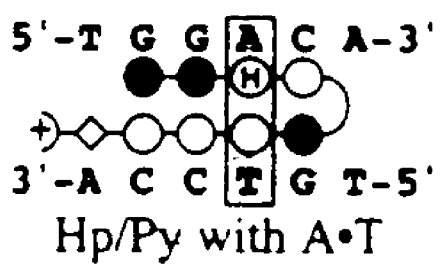

FIG. 2 illustrates binding models for polyamides 1–3 in complex with 5'-TGGTCA-3' and 5'-TGGACA-3' (A•T and T•A in fourth position highlighted). Filled and unfilled circles represent imidazole and pyrrole rings respectively; circles containing an H represent 3-hydroxypyrrole, the curved line connecting the polyamide subunits represents γ-aminobutyric acid, the diamond represents β-alanine, and the + represents the positively charged dimethylaminopropylamide tail group.

Figure 3:
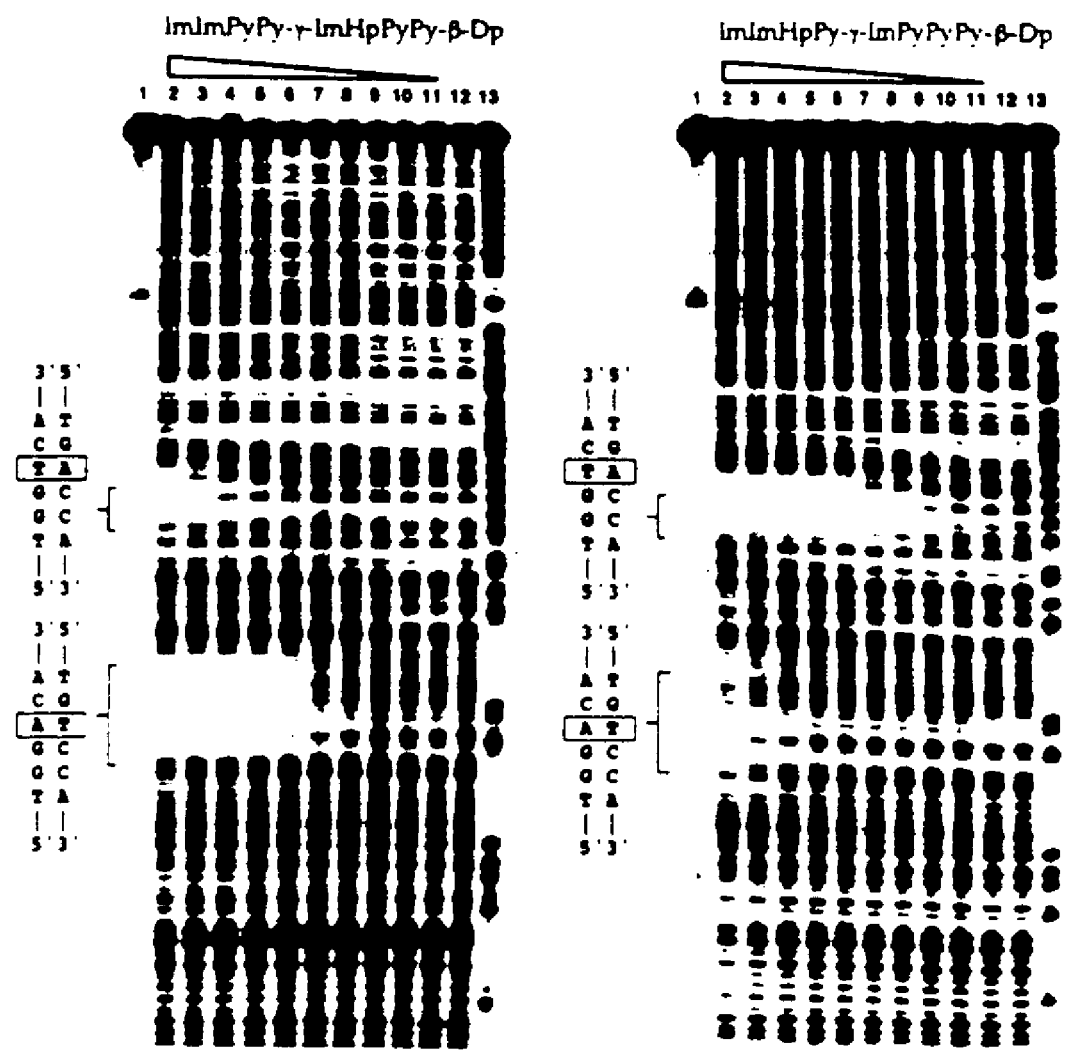
FIG. 3 illustrates the DNase footprint titration of compounds 2 and 3.

FIG. 3 shows quantitative DNase I footprint titration experiments with polyamides 2 and 3 on the 3'$^{32}$P labeled 250-bp pJK6 EcoRI/PvuII restriction fragment. Lane 1, intact DNA; lanes 2–11 DNase I digestion products in the presence of 100, 50, 20, 10, 5, 2, 1, 0.5, 0.2, 0.1 nM polyamide, respectively; lane 12, DNase I digestion products in the absence of polyamide; lane 13, adenine-specific chemical sequencing. Iverson, B. L. & Dervan, P. B. describes an adenine-specific DNA chemical sequencing reaction. *Methods Enzymol.* 15, 7823–7830 (1987). All reactions were done in a total volume of 400 μL. A polyamide stock solution or H$_2$O was added to an assay buffer containing radiolabeled restriction fragment, with the final solution conditions of 10 mM Tris-HCl, 10 mM KCl, 10 mM MgCl$_2$, 5 mM CaCl$_2$, pH 7.0. Solutions were allowed to equilibrate for 4–12 h at 22° C. before initiation of footprinting reactions. Footprinting reactions, separation of cleavage products, and data analysis were carried out as described. White, S., Baird, E. E. & Dervan, P. B. Effects of the A•T/T•A degeneracy of pyrrole-imidazole polyamide recognition in the minor groove of DNA. *Biochemistry* 35, 12532–12537(1996).

Figure 4:
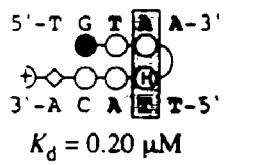
FIG. 4 illustrates a list of the structures of representative Hp containing polyamides.
Figure 4:
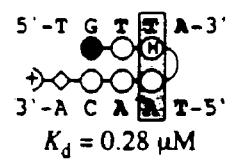
Figure 4:
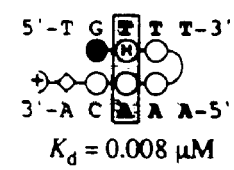
Figure 4:
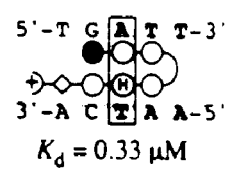
Figure 4:
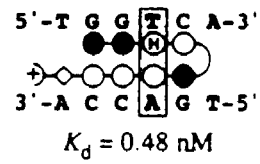
Figure 4:
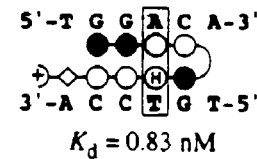
Figure 4:
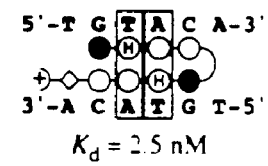
Figure 4:
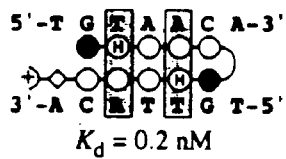
Figure 4:
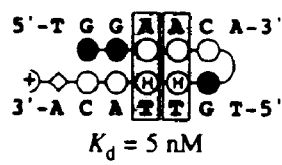

FIG. 4 shows the structure and equilibrium dissociation constant for numerous compounds of the present invention. Polyamides are shown in complex with their respective match site. Filled and unfilled circles represent imidazole (Im) and pyrrole (Py) rings, respectively; circles containing an H represent 3-hydroxypyrrole (Hp), the curved line connecting the polyamide subunits represents γ-aminobutyric acid (γ), the diamond represents β-alanine (β), and the + represents the positively charged dimethylaminopropylamide tail group (Dp). The equilibrium dissociation constants are the average values obtained from three DNase I footprint titration experiments. The standard deviation for each set is less than 15% of the reported number. Assays were carried out in the presence of 10 mM Tris•HCl, 10 mM KCl, 10 mM MgCl$_2$, and 5 mM CaCl$_2$ at pH 7.0 and 22° C.

Four-ring polyamide subunits, covalently coupled to form eight-ring hairpin structures, bind specifically to 6-bp target sequences at subnanomolar concentrations. Trauger, J. W., Baird, E. E. & Dervan, P. B. describe the recognition of DNA by designed ligands at subnanomolar concentrations. *Nature* 382, 559–561 (1996); Swalley, S. E., Baird, E. E. & Dervan, P. B. describe the discrimination of 5'-GGGG-3',5'-GCGC-3', and 5'-GGCC'3' sequences in the minor groove of DNA by eight-ring hairpin polyamides. *J Am. Chem. Soc.* 119, 6953–6961(1997). The DNA-binding affinities of three eight-ring hairpin polyamides shown in FIG. 1 as compound 1, 2, and 3 containing pairings of Im/Py, Py/Im opposite G•C, C•G and either Py/Py, Hp/Py, or Py/Hp at a common single point opposite T•A and A•T has been determined. Equilibrium dissociation constants (K$_d$) for ImImPyPy-γ-ImPyPyPy-β-Dp 1, ImImPyPy-γ-ImHpPyPy-β-Dp 2, ImImHpPy-γ-ImPyPyPy-β-Dp 3 of FIG. 1 are shown in Table 1. Brenowitz, M., Senear, D. F., Shea, M. A. & Ackers, G. K. describe a quantitative DNase footprint titration method for studying protein-DNA interactions. *Methods Enzymol.* 130, 132–181 (1986); The K$_d$ values were determined by quantitative DNase I footprint titration experiments: on a 3'$^{32}$P-labeled 250-b DNA fragment containing the target sites, 5'-TGGACA-3' and 5'-TGGTCA-3' which differ by a single A•T base pair in the fourth position. The DNase footprint gels are shown in FIG. 3.

TABLE 1

Equilibrium dissociation constants*

| | Polyamide† | 5'-TGGTCA-3' | 5'-TGGACA-3' | K$_{rel}$‡ |
|---|---|---|---|---|
| 1 | Py/Py | K$_d$ = 0.077 nM | K$_d$ = 0.15 nM | 2.0 |
| 2 | Py/Hp | K$_d$ = 15 nM | K$_d$ = 0.83 nM | 0.06 |
| 3 | Hp/Py | K$_d$ = 0.48 nM | K$_d$ = 37 nM | 77 |

*The reported dissociation constants are the average values obtained from three Dnase I footprint titration experiments. The standard deviation for each data set is less than 15% of the reported number. Assays were carried out in the presence of 10 mM Tris.HCl, 10 mM KCl, 10 mM MgCl$_2$, and 5 mM CaCl$_2$ at pH 7.0 and 22° C.
†Ring pairing opposite T.A and A.T in the fourth position.
‡Calculated as K$_d$(5'-TGGACA-3')/K$_d$(5'-TGGTCA-3').

Based on the pairing rules for polyamide-DNA complexes both of these sequences are a match for control polyamide 1 which places a Py/Py pairing opposite A•T and T•A at both sites. It was determined that polyamide 1 (Py/Py) binds to 5'-TGG<u>T</u>CA-3' and 5'-TGG<u>A</u>CA-3' within a factor of 2 ($K_d$=0.077 or 0.15 nM respectively). In contrast, polyamide 2 (Py/Hp) binds to 5'-TGG<u>T</u>CA-3' and 5'-TGG<u>A</u>CA-3' with dissociation constants which differ by a factor of 18 ($K_d$=15 nM and 0.83 nM respectively). By reversing the pairing in polyamide 3 (Hp/Py) the dissociation constants differ again in the opposite direction by a factor of 77 ($K_D$=0.48 nM and 37 nM respectively). Control experiments performed on separate DNA fragments; reveal that neither a 5'-TGG <u>G</u>CA-3' or a 5'-TGG<u>C</u>CA-3' site is bound by polyamide 2 or 3 at concentrations ≦100 nM, indicating that the Hp/Py and Py/Hp ring pairings do not bind opposite G•C or C•G.

The specificity of polyamides 2 and 3 for sites which differ by a single A•T/T•A base pair results from small chemical changes. Replacing the Py/Py pair in 1 with a Py/Hp pairing as in 2, a single substitution of C3—OH for C3—H, destabilizes interaction with 5'-TGG<u>T</u>CA-3' by 191-fold, a free energy difference of 3.1 kcal $mol_{-1}$. Interaction of 2 with 5'-TGG<u>A</u>CA-3' is destabilized only 6-fold relative to 1, a free energy difference of 1.1 kcal $mol_{-1}$. Similarly, replacing the Py/Py pair in 1 with Hp/Py as in 3 destabilizes interaction with 5'-TGG<u>A</u>CA-3' by 252-fold, a free energy difference of 3.2 kcal $mol^{-1}$. Interaction of 3 with 5'TGG <u>T</u>CA-3' is destabilized only 6-fold relative to 1, a free energy difference of 1.0 kcal $mol^{-1}$.

The polyamides of this invention provide for coded targeting of predetermined DNA sequences with affinity and specificity comparable to sequence-specific DNA binding proteins. Hp, Im, and Py polyamides complete the minor groove recognition code using three aromatic amino acids which combine to form four ring pairings (Im/Py, Py/Im, Hp/Py, and Py/Hp) which complement the four Watson-Crick base pairs, as shown in TABLE 2. There are a possible 240 four base pair sequences which contain at least 1 A•T or T•A base pair and therefore can advantageously use an Hp/Py, or Py/Hp carboxamide binding. Polyamides binding to any of these sequences can be designed in accordance with the code of TABLE 2.

TABLE 2

Pairing code for minor groove recognition*

| Pair | G*C | C*G | T*A | A*T |
|------|-----|-----|-----|-----|
| Im/Py | + | – | – | – |
| Py/Im | – | + | – | – |
| Hp/Py | – | – | + | – |
| Py/Hp | – | – | – | + |

*favored (+), disfavored (–)

For certain G•C rich sequences the affinity of polyamide•DNA complexes may be enhanced by substitution of an Im/β pair for Im/Py at G•C and β/Im for Py/Im at C•G. At A•T and T•A base pairs, either a Py/β, β/Py, Hp/β, β/Hp, and β/β may be used. The alternate aliphatic/aromatic amino acid pairing code is described in Table 3.

TABLE 3

Aliphatic/Aromatic substitution for ring pairings*

| Pair | Substitution |
|------|--------------|
| Im/Py | Im/β |
| Py/Im | β/Im |
| Hp/Py | Py/β, β/Py, Hp/β, β/β |
| Py/Hp | Py/β, β/Py, β/Hp, β/β |

U.S. Pat. No. 5,578,444 describes numerous promoter region targeting sequences from which base pair sequences for targeting a polyamide can be identified.

PCT U.S. 97/003332 describes methods for synthesis of polyamides which are suitable for preparing polyamides of this invention. The use of β-alanine in place of a pyrrole amino acid in the synthetic methods provides aromatic/aliphatic pairing (Im/β, β/Im, Hp/β, β/Hp, Py/β, and β/Py) and aliphatic/aliphatic pairing (β/β) substitution. The use of γ-aminobutyric acid, or a substituted γ-aminobutyric acid such as (R)-2,4 diaminobutyric acid, provides for preferred hairpin turns. The following examples illustrate the synthesis of polyamides of the present invention.

Figure 5:
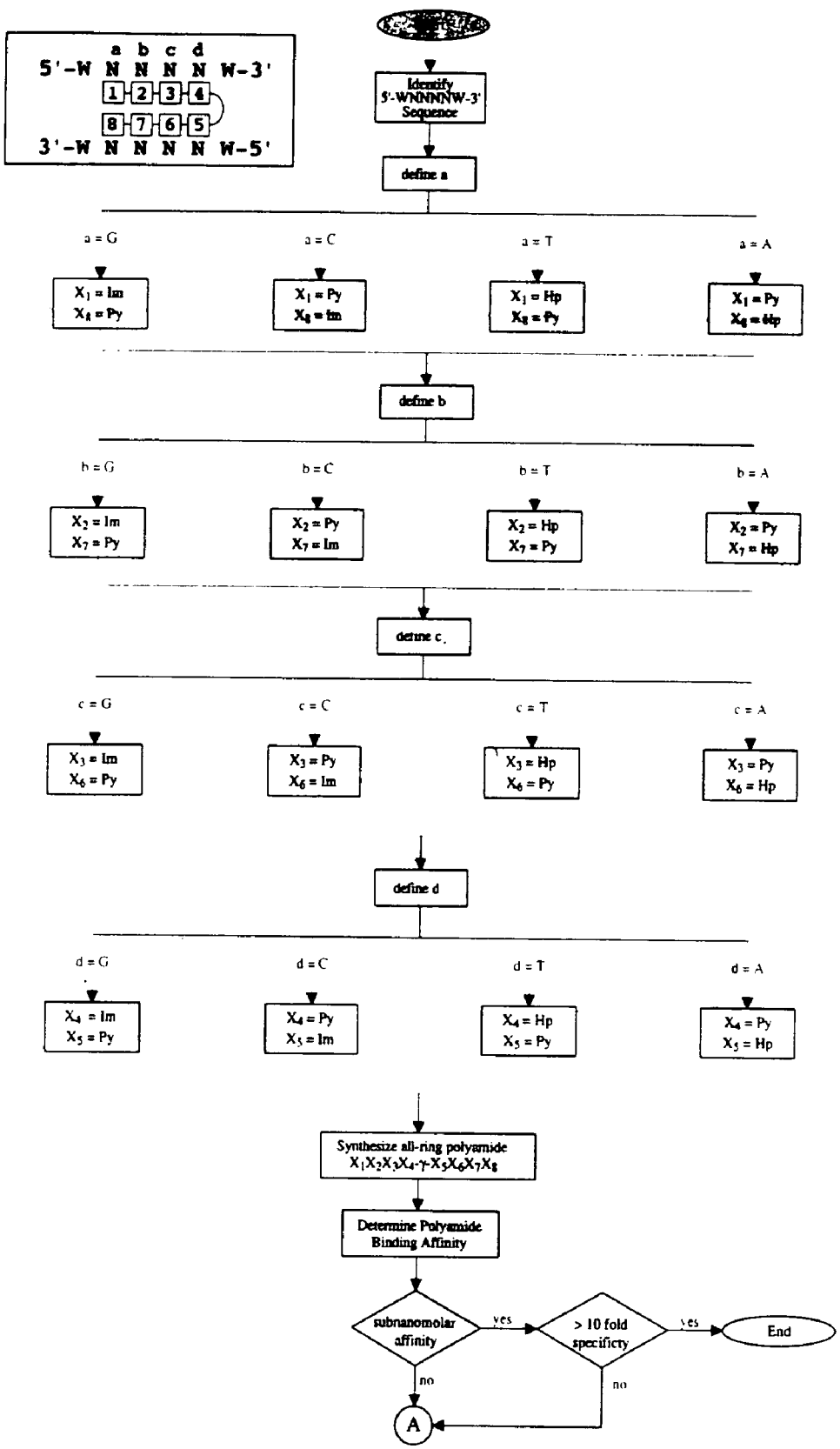
FIG. 5 schematically illustrates a method for the design of eight carboxamide residue hairpin polyamide compounds suitable for recognition of 6-bp 5'-WNNNNW-3' sequences in the minor groove of double stranded DNA.

The process of designing a preferred polyamide molecule $X_1X_2X_3X_4$-γ-$X_5X_6X_7X_8$ comprising eight aromatic amino acid residues of this invention is shown schematically in FIG. 5. The polyamide design process provides a method for designing an eight carboxamide residue molecule comprising four carboxamide binding pairs for detection and binding of a target six base pair 5'-WNNNNW-3' sequence in the minor groove of double stranded DNA. The design process identifies an appropriate polyamide ligand for recognition of a predetermined 6-bp, 5'-WNNNNW-3' sequence with sub-nanomolar affinity and >10-fold specificity versus mismatch sites. Trauger, J. W., Baird, E. E. Dervan, P. B. describes the recognition of DNA by designed ligands at subnanomolar concentrations. *Nature* 382, 559–561 (1996).

In order to prepare a polyamide molecule specific for an identified six base pair sequence of double stranded DNA, a user starts the 8-ring polyamide design process that implements the minor groove recognition pairing code summarized in Table 2 above. In the design process a 5'-WNNNNW-3' sequence was identified. In a preferred embodiment, the identified sequence was located within a gene promoter. U.S. Pat. No. 5,578,444 describes numerous promoter region targeting sequences from which target six base pair sequences for targeting a polyamide can be identified. The identified sequence was then defined as 5'-Wab-cdW-3' in a stepwise process wherein a, b, c, and d, were sequentially and independently defined as A, G, C, or T. The structure of the polyamide molecule was then correspondingly defined by sequentially choosing antiparallel carboxamide binding pairs according to the minor groove pairing code summarized in Table 2 above. Thus, if a was G, then $X_1$ was defined as Im, and $X_8$ was defined as Py. If a was C, then $X_1$ was defined as Py, and $X_8$ was defined as Im. If a was T, then $X_1$ was defined as Hp, and $X_8$ was defined as Py. If a was A, then $X_1$ was defined as Py, and $X_8$ was defined as Hp.

Similarly, b was defined as A, G, C, or T and corresponding carboxamide binding pairs were defined. According to the same rules, if b was G, then $X_2$ was defined as Im, and $X_7$ was defined as Py. If b was C, then $X_2$ was defined as Py, and $X_7$ was defined as Im. Likewise, if b was T, then $X_2$ was defined as Hp, and $X_7$ was defined as Py. If b was A, then $X_2$ was defined as Py, and $X_7$ was defined as Hp.

The next step was to define c as A, G, C, or T and then define corresponding carboxamide binding pairs. Following the same rules, if c was G, then $X_3$ was defined as Im, and $X_6$ was defined as Py. If c was C, then $X_3$ was defined as Py, and $X_6$ was defined as Im. Similarly, if c was T, then $X_3$ was defined as Hp, and $X_6$ was defined as Py. If c was A, then $X_3$ was defined as Py, and $X_6$ was defined as Hp. Lastly, d was defined as A, G, C, or T and the last corresponding carboxamide binding pair was defined. According to above rules, if d was G, then $X_4$ was defined as Im, and $X_5$ was defined as Py. If d was C, then $X_4$ was defined as Py, and $X_5$ was defined as Im. If d was T, then $X_4$ was defined as Hp, and $X_5$ was defined as Py. If d was A, then $X_4$ was defined as Py, and $X_5$ was defined as Hp.

With all eight carboxamide residues that participate in binding pairs now defined, the designed polyamide $X_1X_2X_3X_4$-$\gamma$-$X_5X_6X_7X_8$ suitable for binding to the identified sequence was synthesized using known techniques. Baird, E. E. & Dervan, P. B. describes the solid phase synthesis of polyamides containing imidazole and pyrrole amino acids. *J. Am. Chem. Soc.* 118, 6141–6146 (1996); also see PCT US 97/003332.

The binding affinity of the synthesized polyamide to the identified sequence was determined using a quantitative DNase footprint titration method for studying protein-DNA interactions described by Brenowitz, M., Senear, D. F., Shea, M. A. & Ackers, G. K., *Methods Enzymol.* 130, 132–181 (1986). If the affinity of the synthesized polyamide at the target site was not subnanomolar affinity then adding a β-alanine (process A) was considered in order to optimize the exact positions of the binding pairs of aromatic amino acids. If the affinity of the said polyamide at said target site was subnanomolar affinity then the sequence specificity of the polyamide versus mismatch sequences was determined. If the specificity versus mismatch sites was not >10-fold specificity then adding a β-alanine (process A schematically shown in FIG. 6) was considered, in order to optimize the positions of the aromatic amino acids in relationship to the base pairs in the minor groove. Specificity of the polyamide molecule for the target identified sequence versus mismatch sequence sites of greater than 10-fold was considered a successful result of design process.

The 256 polyamide molecules comprising four carboxamide binding pairs that were designed using this method are useful for binding to the 256 target 5'-NNNN-3' core sequences, and are listed in Tables 4–11. A corresponding polyamide molecule was designed for each DNA sequence (1–240) and (G1–G16) using the process outlined above and shown schematically in FIG. 5.

If the synthesized polyamide molecule did not bind to the target identified sequence with subnanomolar affinity or if the synthesized polyamide molecule did not exhibit a specificity for the target identified sequence versus mismatch sequence sites of greater than 10-fold, the option of substituting an aliphatic amino acid residues for one of the carboxamide residues was considered. The preferred aliphatic amino acid residue is β-alanine. At least one aliphatic amino acid residue such as a β-alanine residue provided some flexibility to the central portion of the polyamide molecule, acting as a "spring" to permit optimization of the hydrogen bonding between the carboxamide binding pairs and the nucleotide bases of the double stranded DNA.

In general, it was not found to be advantageous to replace either member of the terminal carboxamide binding pair, $X_1$/$X_8$, with β-alanine. Similarly, β-alanine was not substituted for members of the binding pair, $X_4$/$X_5$, adjacent to the γ hairpin residue. β-alanine residues were not substituted for N-methylimidazole residues. The use of β-alanine in place of a pyrrole or 3-hydroxypyrrole amino acid residue provides aromatic/aliphatic pairing (Im/β, β/Im, Hp/β, β/Hp, Py/β, and β/Py) and aliphatic/aliphatic pairing (β/β) substitution.

Figure 6:
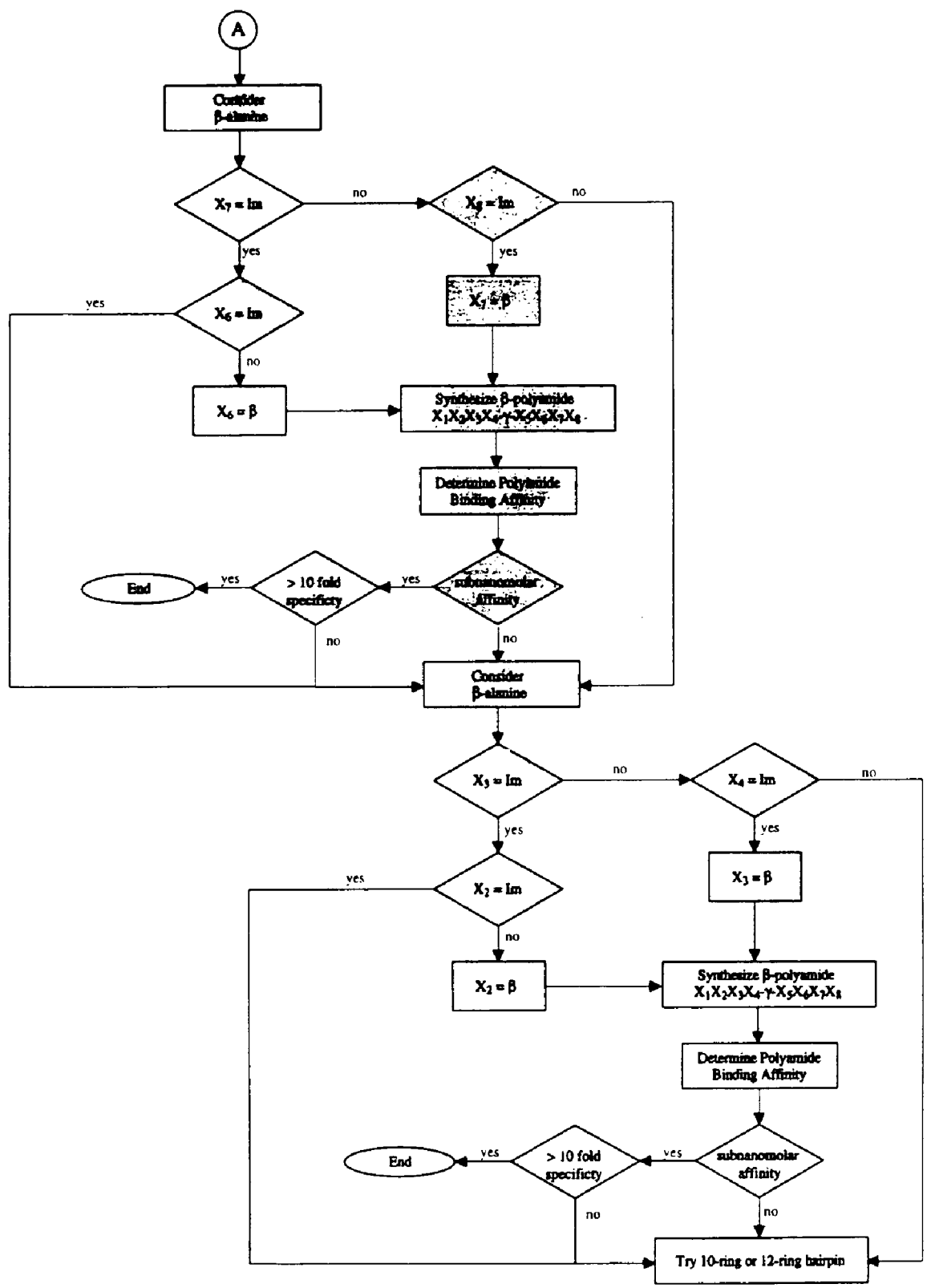
FIG. 6 schematically illustrates a method for determining the position of an aromatic amino acid residue that should be replaced with a β-alanine residue in order to enhance the DNA binding properties of certain eight carboxamide residue hairpin polyamide compounds.

The method for selecting which pyrrole amino acid to substitute with β-alanine is schematically illustrated in FIG. 6. Selective placement of an aliphatic β-alanine (β) residue paired with either a pyrrole (Py), 3-hydroxypyrrole (Hp), or imidazole (Im) aromatic amino acid or another β-alanine residue is found to compensate for sequence composition effects to improve recognition and binding of the minor groove of DNA by pyrrole-imidazole polyamides of the present invention. If an all-ring polyamide has been found to have an affinity which is not subnanomolar, or a specificity versus mismatch sequences which is less than 10-fold it may be caused by DNA sequence-composition effects which can be reduced by replacement of an aromatic amino acid with an aliphatic β-alanine residue. In a polyamide molecule that comprises four binding pairs it is only beneficial to place β-alanine in positions $X_2$, $X_3$, $X_6$, and $X_7$. No more than two β-alanine residues may be placed within a single hairpin structure. No more than a single β-residue may be placed within each individual polyamide subunit, e.g., if $X_2$ is replaced with β-alanine, then $X_3$ cannot be replaced.

These rules and others were implemented in the method schematically illustrated in FIG. 6. This process is suitable for the refinement of the design polyamide comprising four binding pairs that has been designed by the method illustrated in FIG. 5, but which lacks subnanomolar affinity or greater than 10-fold specificity at the identified target DNA sequence. As in the basic design method, the designed polyamides are synthesized and the affinity and specificity of binding to the target DNA were determined.

For a given polyamide molecule $X_1X_2X_3X_4$-$\gamma$-$X_5X_6X_7X_8$ there are five possible outcomes for the process of substituting a β-alanine residue for an aromatic amino acid residue. First, there may be no position at which it is possible to add a β-alanine residue; in such case, a better binding affinity or selectivity can be sought in the design and synthesis of a polyamide with five or six carboxamide binding pairs, described below. Second, the process may result in a derivative which contains a single β-alanine substitution (such derivatives are numbered according to the parent numbering scheme such that a single β-derivative of compound 5 would be called 5β), which is sufficient to produce subnanomolar binding affinity and >10-fold specificity, and at which point the process is deemed complete.

Third, the process of FIG. 5 may result in a polyamide which contains a single β-alanine substitution which is not sufficient to produce subnanomolar binding affinity and >10-fold specificity, but where there are no additional positions in which it is possible to substitute a β-alanine residue, and in such a case a polyamide with five or six carboxamide binding pairs, should be designed and synthesized, as described below. Fourth, the process of FIG. 5 may result in a polyamide that contains a single β-alanine substitution that is not sufficient to produce subnanomolar binding affinity and >10-fold specificity, but where there is an additional position for β-alanine substitution that does produce a polyamide with the criterion level of affinity and selectivity and therefore the design process is deemed complete. Polyamides that were designed by the process that produces polyamide molecules that contain two β-alanine residues are labeled β2 in Tables 12–19.

A fifth possibility is that substitution at a second position by the method illustrated in FIG. 6 with a second β-alanine residue is not sufficient to produce a polyamide having the subnanomolar binding affinity and >10-fold specificity, and a polyamide with five or six carboxamide binding pairs, should be designed and synthesized, as described below. Tables 12–19 list polyamides corresponding to sequences 1–240 and G1–G16 which contain either one or two β-alanine residues.

TABLE 4

8-ring Hairpin Polyamides for recognition of 6-bp 5'-WGWNNW-3'

| | DNA sequence | aromatic amino acid sequence |
|---|---|---|
| 1) | 5'-W G T T T W-3' | ImHpHpHp-γ-PyPyPyPy |
| 2) | 5'-W G T T A W-3' | ImHpHpPy-γ-HpPyPyPy |
| 3) | 5'-W G T T G W-3' | ImHpHpIm-γ-PyPyPyPy |
| 4) | 5'-W G T T C W-3' | ImHpHpPy-γ-ImPyPyPy |
| 5) | 5'-W G T A T W-3' | ImHpPyHp-γ-PyHpPyPy |
| 6) | 5'-W G T A A W-3' | ImHpPyPy-γ-HpHpPyPy |
| 7) | 5'-W G T A G W-3' | ImHpPyIm-γ-PyHpPyPy |
| 8) | 5'-W G T A C W-3' | ImHpPyPy-γ-ImHpPyPy |
| 9) | 5'-W G T G T W-3' | ImHpImHp-γ-PyPyPyPy |
| 10) | 5'-W G T G A W-3' | ImHpImPy-γ-HpPyPyPy |
| 11) | 5'-W G T G G W-3' | ImHpImIm-γ-PyPyPyPy |
| 12) | 5'-W G T G C W-3' | ImHpImPy-γ-ImPyPyPy |
| 13) | 5'-W G T C T W-3' | ImHpPyHp-γ-PyImPyPy |
| 14) | 5'-W G T C A W-3' | ImHpPyPy-γ-HpImPyPy |
| 15) | 5'-W G T C G W-3' | ImHpPyIm-γ-PyImPyPy |
| 16) | 5'-W G T C C W-3' | ImHpPyPy-γ-ImImPyPy |
| 17) | 5'-W G A T T W-3' | ImPyHpHp-γ-PyPyHpPy |
| 18) | 5'-W G A T A W-3' | ImPyHpPy-γ-HpPyHpPy |
| 19) | 5'-W G A T G W-3' | ImPyHpIm-γ-PyPyHpPy |
| 20) | 5'-W G A T C W-3' | ImPyHpPy-γ-ImPyHpPy |
| 21) | 5'-W G A A T W-3' | ImPyPyHp-γ-PyHpHpPy |
| 22) | 5'-W G A A A W-3' | ImPyPyPy-γ-HpHpHpPy |
| 23) | 5'-W G A A G W-3' | ImPyPyIm-γ-PyHpHpPy |
| 24) | 5'-W G A A C W-3' | ImPyPyPy-γ-ImHpHpPy |
| 25) | 5'-W G A G T W-3' | ImPyImHp-γ-PyPyHpPy |
| 26) | 5'-W G A G A W-3' | ImPyImPy-γ-HpPyHpPy |
| 27) | 5'-W G A G G W-3' | ImPyImIm-γ-PyPyHpPy |
| 28) | 5'-W G A G C W-3' | ImPyImPy-γ-ImPyHpPy |
| 29) | 5'-W G A C T W-3' | ImPyPyHp-γ-PyImHpPy |
| 30) | 5'-W G A C A W-3' | ImPyPyPy-γ-HpImHpPy |
| 31) | 5'-W G A C G W-3' | ImPyPyIm-γ-PyImHpPy |
| 32) | 5'-W G A C C W-3' | ImPyPyPy-γ-ImImHpPy |

TABLE 5

8-ring Hairpin Polyamides for recognition of 6-bp 5'-WGSNNW-3'

| | DNA sequence | aromatic amino acid sequence |
|---|---|---|
| 33) | 5'-W G G T T W-3' | ImImHpHp-γ-PyPyPyPy |
| 34) | 5'-W G G T A W-3' | ImImHpPy-γ-HpPyPyPy |
| 35) | 5'-W G G T G W-3' | ImImHpIm-γ-PyPyPyPy |
| 36) | 5'-W G G T C W-3' | ImImHpPy-γ-ImPyPyPy |
| 37) | 5'-W G G A T W-3' | ImImPyHp-γ-PyHpPyPy |
| 38) | 5'-W G G A A W-3' | ImImPyPy-γ-HpHpPyPy |
| 39) | 5'-W G G A G W-3' | ImImPyIm-γ-PyHpPyPy |
| 40) | 5'-W G G A C W-3' | ImImPyPy-γ-ImHpPyPy |
| 41) | 5'-W G G G T W-3' | ImImImHp-γ-PyPyPyPy |
| 42) | 5'-W G G G A W-3' | ImImImPy-γ-HpPyPyPy |
| 43) | 5'-W G G C T W-3' | ImImPyHp-γ-PyImPyPy |
| 44) | 5'-W G G C A W-3' | ImImPyPy-γ-HpImPyPy |
| 45) | 5'-W G C T T W-3' | ImPyHpHp-γ-PyPyImPy |
| 46) | 5'-W G C T A W-3' | ImPyHpPy-γ-HpPyImPy |
| 47) | 5'-W G C T G W-3' | ImPyHpIm-γ-PyPyImPy |
| 48) | 5'-W G C T C W-3' | ImPyHpPy-γ-ImPyImPy |
| 49) | 5'-W G C A T W-3' | ImPyPyHp-γ-PyHpImPy |
| 50) | 5'-W G C A A W-3' | ImPyPyPy-γ-HpHpImPy |
| 51) | 5'-W G C A G W-3' | ImPyPyIm-γ-PyHpImPy |
| 52) | 5'-W G C A C W-3' | ImPyPyPy-γ-ImHpImPy |
| 53) | 5'-W G C G T W-3' | ImPyImHp-γ-PyPyImPy |
| 54) | 5'-W G C G A W-3' | ImPyImPy-γ-HpPyImPy |
| 55) | 5'-W G C C T W-3' | ImPyPyHp-γ-PyImImPy |
| 56) | 5'-W G C C A W-3' | ImPyPyPy-γ-HpImImPy |
| G1) | 5'-W G G G G W-3' | ImImImIm-γ-PyPyPyPy |

TABLE 5-continued 8-ring Hairpin Polyamides for recognition of 6-bp 5'-WGSNNW-3'

| | DNA sequence | aromatic amino acid sequence |
|---|---|---|
| G2) | 5'-W G G G C W-3' | ImImImPy-γ-ImPyPyPy |
| G3) | 5'-W G G C G W-3' | ImImPyIm-γ-PyImPyPy |
| G4) | 5'-W G G C C W-3' | ImImPyPy-γ-ImImPyPy |
| G5) | 5'-W G C G G W-3' | ImPyImIm-γ-PyPyImPy |
| G6) | 5'-W G C G C W-3' | ImPyImPy-γ-ImPyImPy |
| G7) | 5'-W G C C G W-3' | ImPyPyIm-γ-PyImImPy |
| G8) | 5'-W G C C C W-3' | ImPyPyPy-γ-ImImImPy |

TABLE 6

8-ring Hairpin Polyamides for recognition of 6-bp 5'-WTWNNW-3'

| | DNA sequence | aromatic amino acid sequence |
|---|---|---|
| 57) | 5'-W T T T T W-3' | HpHpHpHp-γ-PyPyPyPy |
| 58) | 5'-W T T T A W-3' | HpHpHpPy-γ-HpPyPyPy |
| 59) | 5'-W T T T G W-3' | HpHpHpIm-γ-PyPyPyPy |
| 60) | 5'-W T T T C W-3' | HpHpHpPy-γ-ImPyPyPy |
| 61) | 5'-W T T A T W-3' | HpHpPyHp-γ-PyHpPyPy |
| 62) | 5'-W T T A A W-3' | HpHpPyPy-γ-HpHpPyPy |
| 63) | 5'-W T T A G W-3' | HpHpPyIm-γ-PyHpPyPy |
| 64) | 5'-W T T A C W-3' | HpHpPyPy-γ-ImHpPyPy |
| 65) | 5'-W T T G T W-3' | HpHpImHp-γ-PyPyPyPy |
| 66) | 5'-W T T G A W-3' | HpHpImPy-γ-HpPyPyPy |
| 67) | 5'-W T T G G W-3' | HpHpImIm-γ-PyPyPyPy |
| 68) | 5'-W T T G C W-3' | HpHpImPy-γ-ImPyPyPy |
| 69) | 5'-W T T C T W-3' | HpHpPyHp-γ-PyImPyPy |
| 70) | 5'-W T T C A W-3' | HpHpPyPy-γ-HpImPyPy |
| 71) | 5'-W T T C G W-3' | HpHpPyIm-γ-PyImPyPy |
| 72) | 5'-W T T C C W-3' | HpHpPyPy-γ-ImImPyPy |
| 73) | 5'-W T A T T W-3' | HpPyHpHp-γ-PyPyHpPy |
| 74) | 5'-W T A T A W-3' | HpPyHpPy-γ-HpPyHpPy |
| 75) | 5'-W T A T G W-3' | HpPyHpIm-γ-PyPyHpPy |
| 76) | 5'-W T A T C W-3' | HpPyHpPy-γ-ImPyHpPy |
| 77) | 5'-W T A A T W-3' | HpPyPyHp-γ-PyHpHpPy |
| 78) | 5'-W T A A A W-3' | HpPyPyPy-γ-HpHpHpPy |
| 79) | 5'-W T A A G W-3' | HpPyPyIm-γ-PyHpHpPy |
| 80) | 5'-W T A A C W-3' | HpPyPyPy-γ-ImHpHpPy |
| 81) | 5'-W T A G T W-3' | HpPyImHp-γ-PyPyHpPy |
| 82) | 5'-W T A G A W-3' | HpPyImPy-γ-HpPyHpPy |
| 83) | 5'-W T A G G W-3' | HpPyImIm-γ-PyPyHpPy |
| 84) | 5'-W T A G C W-3' | HpPyImPy-γ-ImPyHpPy |
| 85) | 5'-W T A C T W-3' | HpPyPyHp-γ-PyImHpPy |
| 86) | 5'-W T A C A W-3' | HpPyPyPy-γ-HpImHpPy |
| 87) | 5'-W T A C G W-3' | HpPyPyIm-γ-PyImHpPy |
| 88) | 5'-W T A C C W-3' | HpPyPyPy-γ-ImImHpPy |

TABLE 7

8-ring Hairpin Polyamides for recognition of 6-bp 5'-WTSNNW-3'

| | DNA sequence | aromatic amino acid sequence |
|---|---|---|
| 89) | 5'-W T G T T W-3' | HpImHpHp-γ-PyPyPyPy |
| 90) | 5'-W T G T A W-3' | HpImHpPy-γ-HpPyPyPy |
| 91) | 5'-W T G T G W-3' | HpImHpIm-γ-PyPyPyPy |
| 92) | 5'-W T G T C W-3' | HpImHpPy-γ-ImPyPyPy |
| 93) | 5'-W T G A T W-3' | HpImPyHp-γ-PyHpPyPy |
| 94) | 5'-W T G A A W-3' | HpImPyPy-γ-HpHpPyPy |
| 95) | 5'-W T G A G W-3' | HpImPyIm-γ-PyHpPyPy |
| 96) | 5'-W T G A C W-3' | HpImPyPy-γ-ImHpPyPy |
| 97) | 5'-W T G G T W-3' | HpImImHp-γ-PyPyPyPy |
| 98) | 5'-W T G G A W-3' | HpImImPy-γ-HpPyPyPy |
| 99) | 5'-W T G C T W-3' | HpImPyHp-γ-PyImPyPy |
| 100) | 5'-W T G C A W-3' | HpImPyPy-γ-HpImPyPy |
| 101) | 5'-W T G G G W-3' | HpImImIm-γ-PyPyPyPy |
| 102) | 5'-W T G G C W-3' | HpImImPy-γ-ImPyPyPy |
| 103) | 5'-W T G C G W-3' | HpImPyIm-γ-PyImPyPy |
| 104) | 5'-W T G C C W-3' | HpImPyPy-γ-ImImPyPy |
| 105) | 5'-W T C T T W-3' | HpPyHpHp-γ-PyPyImPy |

TABLE 7-continued 8-ring Hairpin Polyamides for recognition of 6-bp 5'-WTSNNW-3'

| | DNA sequence | aromatic amino acid sequence |
|---|---|---|
| 106) | 5'-W T C T A W-3' | HpPyHpPy-γ-HpPyImPy |
| 107) | 5'-W T C T G W-3' | HpPyHpIm-γ-PyPyImPy |
| 108) | 5'-W T C T C W-3' | HpPyHpPy-γ-ImPyImPy |
| 109) | 5'-W T C A T W-3' | HpPyPyHp-γ-PyHpImPy |
| 110) | 5'-W T C A A W-3' | HpPyPyPy-γ-HpPyImPy |
| 111) | 5'-W T C A G W-3' | HpPyPyIm-γ-PyPyImPy |
| 112) | 5'-W T C A C W-3' | HpPyPyPy-γ-ImHpImPy |
| 113) | 5'-W T C G T W-3' | HpPyImHp-γ-PyPyImPy |
| 114) | 5'-W T C C A W-3' | HpPyImPy-γ-HpPyImPy |
| 115) | 5'-W T C C T W-3' | HpPyPyHp-γ-PyImImPy |
| 116) | 5'-W T C C A W-3' | HpPyPyPy-γ-HpImImPy |
| 117) | 5'-W T C G G W-3' | HpPyImIm-γ-PyPyImPy |
| 118) | 5'-W T C G C W-3' | HpPyImPy-γ-ImPyImPy |
| 119) | 5'-W T C C G W-3' | HpPyPyIm-γ-PyImImPy |
| 120) | 5'-W T C C C W-3' | HpPyPyPy-γ-ImImImPy |

TABLE 8

8-ring Hairpin Polyamides for recognition of 6-bp 5'-WAWNNW-3'

| | DNA sequence | aromatic amino acid sequence |
|---|---|---|
| 121) | 5'-W A T T T W-3' | PyHpHpHp-γ-PyPyPyHp |
| 122) | 5'-W A T T A W-3' | PyHpHpPy-γ-HpPyPyHp |
| 123) | 5'-W A T T G W-3' | PyHpHpIm-γ-PyPyPyHp |
| 124) | 5'-W A T T C W-3' | PyHpHpPy-γ-ImPyPyHp |
| 125) | 5'-W A T A T W-3' | PyHpPyHp-γ-PyHpPyHp |
| 126) | 5'-W A T A A W-3' | PyHpPyPy-γ-HpHpPyHp |
| 127) | 5'-W A T A G W-3' | PyHpPyIm-γ-PyHpPyHp |
| 128) | 5'-W A T A C W-3' | PyHpPyPy-γ-ImHpPyHp |
| 129) | 5'-W A T G T W-3' | PyHpImHp-γ-PyPyPyHp |
| 130) | 5'-W A T G A W-3' | PyHpImPy-γ-HpPyPyHp |
| 131) | 5'-W A T G G W-3' | PyHpImIm-γ-PyPyPyHp |
| 132) | 5'-W A T G C W-3' | PyHpImPy-γ-ImPyPyHp |
| 133) | 5'-W A T C T W-3' | PyHpPyHp-γ-PyImPyHp |
| 134) | 5'-W A T C A W-3' | PyHpPyPy-γ-HpImPyHp |
| 135) | 5'-W A T C G W-3' | PyHpPyIm-γ-PyImPyHp |
| 136) | 5'-W A T C C W-3' | PyHpPyPy-γ-ImImPyHp |
| 137) | 5'-W A A T T W-3' | PyPyHpHp-γ-PyPyHpHp |
| 138) | 5'-W A A T A W-3' | PyPyHpPy-γ-HpPyHpHp |
| 139) | 5'-W A A T G W-3' | PyPyHpIm-γ-PyPyHpHp |
| 140) | 5'-W A A T C W-3' | PyPyHpPy-γ-ImPyHpHp |
| 141) | 5'-W A A A T W-3' | PyPyPyHp-γ-PyHpHpHp |
| 142) | 5'-W A A A A W-3' | PyPyPyPy-γ-HpHpHpHp |
| 143) | 5'-W A A A G W-3' | PyPyPyIm-γ-PyHpHpHp |
| 144) | 5'-W A A A C W-3' | PyPyPyPy-γ-ImHpHpHp |
| 145) | 5'-W A A G T W-3' | PyPyImHp-γ-PyPyHpHp |
| 146) | 5'-W A A G A W-3' | PyPyImPy-γ-HpPyHpHp |
| 147) | 5'-W A A G G W-3' | PyPyImIm-γ-PyPyHpHp |
| 148) | 5'-W A A G C W-3' | PyPyImPy-γ-ImPyHpHp |
| 149) | 5'-W A A C T W-3' | PyPyPyHp-γ-PyImHpHp |
| 150) | 5'-W A A C A W-3' | PyPyPyPy-γ-HpImHpHp |
| 151) | 5'-W A A C G W-3' | PyPyPyIm-γ-PyImHpHp |
| 152) | 5'-W A A C C W-3' | PyPyPyPy-γ-ImImHpHp |

TABLE 9

8-ring Hairpin Polyamides for recognition of 6-bp 5'-WASNNW-3'

| | DNA sequence | aromatic amino acid sequence |
|---|---|---|
| 153) | 5'-W A G T T W-3' | PyImHpHp-γ-PyPyPyHp |
| 154) | 5'-W A G T A W-3' | PyImHpPy-γ-HpPyPyHp |
| 155) | 5'-W A G T G W-3' | PyImHpIm-γ-PyPyPyHp |
| 156) | 5'-W A G T C W-3' | PyImHpPy-γ-ImPyPyHp |
| 157) | 5'-W A G A T W-3' | PyImPyHp-γ-PyHpPyHp |
| 158) | 5'-W A G A A W-3' | PyImPyPy-γ-HpHpPyHp |
| 159) | 5'-W A G A G W-3' | PyImPyIm-γ-PyHpPyHp |
| 160) | 5'-W A G A C W-3' | PyImPyPy-γ-ImHpPyHp |
| 161) | 5'-W A G G T W-3' | PyImImHp-γ-PyPyPyHp |

TABLE 9-continued 8-ring Hairpin Polyamides for recognition of 6-bp 5'-WASNNW-3'

| | DNA sequence | aromatic amino acid sequence |
|---|---|---|
| 162) | 5'-W A G G A W-3' | PyImImPy-γ-HpPyPyHp |
| 163) | 5'-W A G C T W-3' | PyImPyHp-γ-PyImPyHp |
| 164) | 5'-W A G C A W-3' | PyImPyPy-γ-HpImPyHp |
| 165) | 5'-W A G G G W-3' | PyImImIm-γ-PyPyPyHp |
| 166) | 5'-W A G G C W-3' | PyImImPy-γ-ImPyPyHp |
| 167) | 5'-W A G C G W-3' | PyImPyIm-γ-PyImPyHp |
| 168) | 5'-W A G C C W-3' | PyImPyPy-γ-ImImPyHp |
| 169) | 5'-W A C T T W-3' | PyPyHpHp-γ-PyPyImHp |
| 170) | 5'-W A C T A W-3' | PyPyHpPy-γ-HpPyImHp |
| 171) | 5'-W A C T G W-3' | PyPyHpIm-γ-PyPyImHp |
| 172) | 5'-W A C T C W-3' | PyPyHpPy-γ-ImPyImHp |
| 173) | 5'-W A C A T W-3' | PyPyPyHp-γ-PyHpImHp |
| 174) | 5'-W A C A A W-3' | PyPyPyPy-γ-HpHpImHp |
| 175) | 5'-W A C A G W-3' | PyPyPyIm-γ-PyHpImHp |
| 176) | 5'-W A C A C W-3' | PyPyPyPy-γ-ImHpImHp |
| 177) | 5'-W A C G T W-3' | PyPyImHp-γ-PyPyImHp |
| 178) | 5'-w A C G A W-3' | PyPyImPy-γ-HpPyImHp |
| 179) | 5'-W A C C T W-3' | PyPyPyHp-γ-PyImImHp |
| 180) | 5'-W A C C A W-3' | PyPyPyPy-γ-HpImImHp |
| 181) | 5'-W A C G G W-3' | PyPyImIm-γ-PyPyImHp |
| 182) | 5'-W A C G C W-3' | PyPyImPy-γ-ImPyImHp |
| 183) | 5'-W A C C G W-3' | PyPyPyIm-γ-PyImImHp |
| 184) | 5'-W A C C C W-3' | PyPyPyPy-γ-ImImImHp |

TABLE 10

8-ring Hairpin Polyamides for recognition of 6-bp 5'-WCWNNW-3'

| | DNA sequence | aromatic amino acid sequence |
|---|---|---|
| 185) | 5'-W C T T T W-3' | PyHpHpHp-γ-PyPyPyIm |
| 186) | 5'-W C T T A W-3' | PyHpHpPy-γ-HpPyPyIm |
| 187) | 5'-W C T T G W-3' | PyHpHpIm-γ-PyPyPyIm |
| 188) | 5'-W C T T C W-3' | PyHpHpPy-γ-ImPyPyIm |
| 189) | 5'-W C T A T W-3' | PyHpPyHp-γ-PyHpPyIm |
| 190) | 5'-W C T A A W-3' | PyHpPyPy-γ-HpHpPyIm |
| 191) | 5'-W C T A G W-3' | PyHpPyIm-γ-PyHpPyIm |
| 192) | 5'-W C T A C W-3' | PyHpPyPy-γ-ImHpPyIm |
| 193) | 5'-W C T G T W-3' | PyHpImHp-γ-PyPyPyIm |
| 194) | 5'-W C T G A W-3' | PyHpImPy-γ-HpPyPyIm |
| 195) | 5'-W C T G G W-3' | PyHpImIm-γ-PyPyPyIm |
| 196) | 5'-W C T G C W-3' | PyHpImPy-γ-ImPyPyIm |
| 197) | 5'-W C T C T W-3' | PyHpPyHp-γ-PyImPyIm |
| 198) | 5'-W C T C A W-3' | PyHpPyPy-γ-HpImPyIm |
| 199) | 5'-W C T C G W-3' | PyHpPyIm-γ-PyImPyIm |
| 200) | 5'-W C T C C W-3' | PyHpPyPy-γ-ImImPyIm |
| 201) | 5'-W C A T T W-3' | PyPyHpHp-γ-PyPyHpIm |
| 202) | 5'-W C A T A W-3' | PyPyHpPy-γ-HpPyHpIm |
| 203) | 5'-W C A T G W-3' | PyPyHpIm-γ-PyPyHpIm |
| 204) | 5'-W C A T C W-3' | PyPyHpPy-γ-ImPyHpIm |
| 205) | 5'-W C A A T W-3' | PyPyPyHp-γ-PyHpHpIm |
| 206) | 5'-W C A A A W-3' | PyPyPyPy-γ-HpHpHpIm |
| 207) | 5'-W C A A G W-3' | PyPyPyIm-γ-PyHpHpIm |
| 208) | 5'-W C A A C W-3' | PyPyPyPy-γ-ImHpHpIm |
| 209) | 5'-W C A G T W-3' | PyPyImHp-γ-PyPyHpIm |
| 210) | 5'-W C A G A W-3' | PyPyImPy-γ-HpPyHpIm |
| 211) | 5'-W C A G G W-3' | PyPyImIm-γ-PyPyHpIm |
| 212) | 5'-W C A G C W-3' | PyPyImPy-γ-ImPyHpIm |
| 213) | 5'-W C A C T W-3' | PyPyPyHp-γ-PyImHpIm |
| 214) | 5'-W C A C A W-3' | PyPyPyPy-γ-HpImHpIm |
| 215) | 5'-W C A C G W-3' | PyPyPyIm-γ-PyImHpIm |
| 216) | 5'-W C A C C W-3' | PyPyPyPy-γ-ImImHpIm |

TABLE 11

8-ring Hairpin Polyamides for recognition of 6-bp 5'-WCSNNW-3'

| | DNA sequence | aromatic amino acid sequence |
|---|---|---|
| 217) | 5'-W C G T T W-3' | PyImHpHp-γ-PyPyPyIm |
| 218) | 5'-W C G T A W-3' | PyImHpPy-γ-HpPyPyIm |
| 219) | 5'-W C G T G W-3' | PyImHpIm-γ-PyPyPyIm |
| 220) | 5'-W C G T C W-3' | PyImHpPy-γ-ImPyPyIm |
| 221) | 5'-W C G A T W-3' | PyImPyHp-γ-PyHpPyIm |
| 222) | 5'-W C G A A W-3' | PyImPyPy-γ-HpHpPyIm |
| 223) | 5'-W C G A G W-3' | PyImPyIm-γ-PyHpPyIm |
| 224) | 5'-W C G A C W-3' | PyImPyPy-γ-ImHpPyIm |
| 225) | 5'-W C G G T W-3' | PyImImHp-γ-PyPyPyIm |
| 226) | 5'-W C G G A W-3' | PyImImPy-γ-HpPyPyIm |
| 227) | 5'-W C G C T W-3' | PyImPyHp-γ-PyImPyIm |
| 228) | 5'-W C G C A W-3' | PyImPyPy-γ-HpImPyIm |
| 229) | 5'-W C C T T W-3' | PyPyHpHp-γ-PyPyImIm |
| 230) | 5'-W C C T A W-3' | PyPyHpPy-γ-HpPyImIm |
| 231) | 5'-W C C T G W-3' | PyPyHpIm-γ-PyPyImIm |
| 232) | 5'-W C C T C W-3' | PyPyHpPy-γ-ImPyImIm |
| 233) | 5'-W C C A T W-3' | PyPyPyHp-γ-PyHpImIm |
| 234) | 5'-W C C A A W-3' | PyPyPyPy-γ-HpHpImIm |
| 235) | 5'-W C C A G W-3' | PyPyPyIm-γ-PyHpImIm |
| 236) | 5'-W C C A C W-3' | PyPyPyPy-γ-ImHpImIm |
| 237) | 5'-W C C G T W-3' | PyPyImHp-γ-PyPyImIm |
| 238) | 5'-W C C G A W-3' | PyPyImPy-γ-HpPyImIm |
| 239) | 5'-W C C C T W-3' | PyPyPyHp-γ-PyImImIm |
| 240) | 5'-W C C C A W-3' | PyPyPyPy-γ-HpImImIm |
| G9) | 5'-W C G G G W-3' | PyImImIm-γ-PyPyPyIm |
| G10) | 5'-W C G G C W-3' | PyImImPy-γ-ImPyPyIm |
| G11) | 5'-W C G C G W-3' | PyImPyIm-γ-PyImPyIm |
| G12) | 5'-W C G C C W-3' | PyImPyPy-γ-ImImPyIm |
| G13) | 5'-W C C G G W-3' | PyPyImIm-γ-PyPyImIm |
| G14) | 5'-W C C G C W-3' | PyPyImPy-γ-ImPyImIm |
| G15) | 5'-W C C C G W-3' | PyPyPyIm-γ-PyImImIm |
| G16) | 5'-W C C C C W-3' | PyPyPyPy-γ-ImImImIm |

TABLE 12

8-ring Hairpin Polyamides for recognition of 6-bp 5'-WGWNNW-3' with β-substitutions included.

| | DNA sequence | aromatic amino acid sequence |
|---|---|---|
| 3β) | 5'-W G T T G W-3' | ImHp-β-Im-γ-PyPyPyPy |
| 7β) | 5'-W G T A G W-3' | ImHp-β-Im-γ-PyHpPyPy |
| 9β) | 5'-W G T G T W-3' | Im-β-ImHp-γ-PyPyPyPy |
| 10β) | 5'-W G T G A W-3' | Im-β-ImPy-γ-HpPyPyPy |
| 11β) | 5'-W G T G G W-3' | Im-β-ImIm-γ-PyPyPyPy |
| 12β) | 5'-W G T G C W-3' | Im-β-ImPy-γ-ImPyPyPy |
| 15β) | 5'-W G T C G W-3' | ImHp-β-Im-γ-PyImPyPy |
| 19β) | 5'-W G A T G W-3' | ImPy-β-Im-γ-PyPyHpPy |
| 23β) | 5'-W G A A G W-3' | ImPy-β-Im-γ-PyHpHpPy |
| 25β) | 5'-W G A G T W-3' | Im-β-ImHp-γ-PyPyHpPy |
| 26β) | 5'-W G A G A W-3' | Im-β-ImPy-γ-HpPyHpPy |
| 27β) | 5'-W G A G G W-3' | Im-β-ImIm-γ-PyPyHpPy |
| 28β) | 5'-W G A G C W-3' | Im-β-ImPy-γ-ImPyHpPy |
| 31β) | 5'-W G A C G W-3' | ImPy-β-Im-γ-PyImHpPy |

TABLE 13

8-ring Hairpin Polyamides for recognition of 6-bp 5'-WGSNNW-3' with β-substitutions included.

| | DNA sequence | aromatic amino acid sequence |
|---|---|---|
| 35β) | 5'-W G G T G W-3' | ImIm-β-Im-γ-PyPyPyPy |
| 39β) | 5'-W G G A G W-3' | ImIm-β-Im-γ-PyHpPyPy |
| 45β) | 5'-W G C T T W-3' | ImPyHpHp-γ-Py-β-ImPy |
| 46β) | 5'-W G C T A W-3' | ImPyHpPy-γ-Hp-β-ImPy |
| 47β) | 5'-W G C T G W-3' | ImPyHpIm-γ-Py-β-ImPy |
| 47β2) | 5'-W G C T G W-3' | ImPy-β-Im-γ-Py-β-ImPy |
| 48β) | 5'-W G C T C W-3' | ImPyHpPy-γ-Im-β-ImPy |
| 49β) | 5'-W G C A T W-3' | ImPyPyHp-γ-Py-β-ImPy |
| 50β) | 5'-W G C A A W-3' | ImPyPyPy-γ-Hp-β-ImPy |
| 51β) | 5'-W G C A G W-3' | ImPyPyIm-γ-Py-β-ImPy |
| 51β2) | 5'-W G C A G W-3' | ImPy-β-Im-γ-Py-β-ImPy |
| 52β) | 5'-W G C A C W-3' | ImPyPyPy-γ-Im-β-ImPy |
| 53β) | 5'-W G C G T W-3' | ImPyImHp-γ-Py-β-ImPy |
| 53β2) | 5'-W G C G T W-3' | Im-β-ImHp-γ-Py-β-ImPy |
| 54β) | 5'-W G C G A W-3' | ImPyImPy-γ-Hp-β-ImPy |
| 54β2) | 5'-W G C G A W-3' | Im-β-ImPy-γ-Hp-β-ImPy |
| G3β) | 5'-W G G C G W-3' | ImIm-β-Im-γ-PyImPyPy |
| G5β) | 5'-W G C G G W-3' | ImPyImIm-γ-Py-β-ImPy |
| G5β2) | 5'-W G C G G W-3' | Im-β-ImIm-γ-Py-β-ImPy |
| G6β) | 5'-W G C G C W-3' | ImPyImPy-γ-Im-β-ImPy |
| G6β2) | 5'-W G C G C W-3' | Im-β-ImPy-γ-Im-β-ImPy |
| G7β) | 5'-W G C C G W-3' | ImPy-β-Im-γ-PyImImPy |

TABLE 14

8-ring Hairpin Polyamides for recognition of 6-bp 5'-WTWNNW-3' with β-substitutions included.

| | DNA sequence | aromatic amino acid sequence |
|---|---|---|
| 59β) | 5'-W T T T G W-3' | HpHp-β-Im-γ-PyPyPyPy |
| 63β) | 5'-W T T A G W-3' | HpHp-β-Im-γ-PyHpPyPy |
| 65β) | 5'-W T T G T W-3' | Hp-β-ImHp-γ-PyPyPyPy |
| 66β) | 5'-W T T G A W-3' | Hp-β-ImPy-γ-HpPyPyPy |
| 67β) | 5'-W T T G G W-3' | Hp-β-ImIm-γ-PyPyPyPy |
| 68β) | 5'-W T T G C W-3' | Hp-β-ImPy-γ-ImPyPyPy |
| 71β) | 5'-W T T C G W-3' | HpHp-β-Im-γ-PyImPyPy |
| 75β) | 5'-W T A T G W-3' | HpPy-β-Im-γ-PyPyHpPy |
| 79β) | 5'-W T A A G W-3' | HpPy-β-Im-γ-PyHpHpPy |
| 81β) | 5'-W T A G T W-3' | Hp-β-ImHp-γ-PyPyHpPy |
| 82β) | 5'-W T A G A W-3' | Hp-β-ImPy-γ-HpPyHpPy |
| 83β) | 5'-W T A G G W-3' | Hp-β-ImIm-γ-PyPyHpPy |
| 84β) | 5'-W T A G C W-3' | Hp-β-ImPy-γ-ImPyHpPy |
| 87β) | 5'-W T A C G W-3' | HpPy-β-Im-γ-PyImHpPy |

TABLE 15

8-ring Hairpin Polyamides for recognition of 6-bp 5'-WTSNNW-3' with β-substitutions included.

| | DNA sequence | aromatic amino acid sequence |
|---|---|---|
| 91β) | 5'-W T G T G W-3' | HpIm-β-Im-γ-PyPyPyPy |
| 95β) | 5'-W T G A G W-3' | HpIm-β-Im-γ-PyHpPyPy |
| 103β) | 5'-W T G C G W-3' | HpIm-β-Im-γ-PyImPyPy |
| 105β) | 5'-W T C T T W-3' | HpPyHpHp-γ-Py-β-ImPy |
| 106β) | 5'-W T C T A W-3' | HpPyHpPy-γ-Hp-β-ImPy |
| 107β) | 5'-W T C T G W-3' | HpPyHpIm-γ-Py-β-ImPy |
| 107β2) | 5'-W T C T G W-3' | HpPy-β-Im-γ-Py-β-ImPy |
| 108β) | 5'-W T C T C W-3' | HpPyHpPy-γ-Im-β-ImPy |
| 109β) | 5'-W T C A T W-3' | HpPyPyHp-γ-Py-β-ImPy |
| 110β) | 5'-W T C A A W-3' | HpPyPyPy-γ-Hp-β-ImPy |
| 111β) | 5'-W T C A G W-3' | HpPyPyIm-γ-Py-β-ImPy |
| 111β2) | 5'-W T C A G W-3' | HpPy-β-Im-γ-Py-β-ImPy |
| 112β) | 5'-W T C A C W-3' | HpPyPyPy-γ-Im-β-ImPy |
| 113β) | 5'-W T C G T W-3' | HpPyImHp-γ-Py-β-ImPy |
| 113β2) | 5'-W T C G T W-3' | Hp-β-ImHp-γ-Py-β-ImPy |
| 114β) | 5'-W T C G A W-3' | HpPyImPy-γ-Hp-β-ImPy |
| 114β2) | 5'-W T C G A W-3' | Hp-β-ImPy-γ-Hp-β-ImPy |
| 117β) | 5'-W T C G G W-3' | HpPyImIm-γ-Py-β-ImPy |
| 117β2) | 5'-W T C G G W-3' | Hp-β-ImIm-γ-Py-β-ImPy |
| 118β) | 5'-W T C G C W-3' | HpPyImPy-γ-Im-β-ImPy |
| 118β2) | 5'-W T C G C W-3' | Hp-β-ImPy-γ-Im-β-ImPy |
| 119β) | 5'-W T C C G W-3' | HpPy-β-Im-γ-PyImImPy |

TABLE 16

8-ring Hairpin Polyamides for recognition of
6-bp 5'-WAWNNW-3' with β-substitutions included.

| | DNA sequence | aromatic amino acid sequence |
|---|---|---|
| 123β) | 5'-W A T T G W-3' | PyHp-β-Im-γ-PyPyPyHp |
| 127β) | 5'-W A T A G W-3' | PyHp-β-Im-γ-PyHpPyHp |
| 129β) | 5'-W A T G T W-3' | Py-β-ImHp-γ-PyPyPyHp |
| 130β) | 5'-W A T G A W-3' | Py-β-ImPy-γ-HpPyPyHp |
| 131β) | 5'-W A T G G W-3' | Py-β-ImIm-γ-PyPyPyHp |
| 132β) | 5'-W A T G C W-3' | Py-β-ImPy-γ-ImPyPyHp |
| 135β) | 5'-W A T C G W-3' | PyHp-β-Im-γ-PyImPyHp |
| 139β) | 5'-W A A T G W-3' | PyPy-β-Im-γ-PyPyHpHp |
| 143β) | 5'-W A A A G W-3' | PyPy-β-Im-γ-PyHpHpHp |
| 145β) | 5'-W A A G T W-3' | Py-β-ImHp-γ-PyPyHpHp |
| 146β) | 5'-W A A G A W-3' | Py-β-ImPy-γ-HpPyHpHp |
| 147β) | 5'-W A A G G W-3' | Py-β-ImIm-γ-PyPyHpHp |
| 148β) | 5'-W A A G C W-3' | Py-β-ImPy-γ-ImPyHpHp |
| 151β) | 5'-W A A C G W-3' | PyPy-β-Im-γ-PyImHpHp |

TABLE 17

8-ring Hairpin Polyamides for recognition of
6-bp 5'-WASNNW-3' with β-substitutions included.

| | DNA sequence | aromatic amino acid sequence |
|---|---|---|
| 155β) | 5'-W A G T G W-3' | PyIm-β-Im-γ-PyPyPyHp |
| 159β) | 5'-W A G A G W-3' | PyIm-β-Im-γ-PyHpPyHp |
| 167β) | 5'-W A G C G W-3' | PyIm-β-Im-γ-PyImPyHp |
| 169β) | 5'-W A C T T W-3' | PyPyHpHp-γ-Py-β-ImHp |
| 170β) | 5'-W A C T A W-3' | PyPyHpPy-γ-Hp-β-ImHp |
| 171β) | 5'-W A C T G W-3' | PyPyHpIm-γ-Py-β-ImHp |
| 171β2) | 5'-W A C T G W-3' | PyPy-β-Im-γ-Py-β-ImHp |
| 172β) | 5'-W A C T C W-3' | PyPyHpPy-γ-Im-β-ImHp |
| 173β) | 5'-W A C A T W-3' | PyPyPyHp-γ-Py-β-ImHp |
| 174β) | 5'-W A C A A W-3' | PyPyPyPy-γ-Hp-β-ImHp |
| 175β) | 5'-W A C A G W-3' | PyPyPyIm-γ-Py-β-ImHp |
| 175β2) | 5'-W A C A G W-3' | PyPy-β-Im-γ-Py-β-ImHp |
| 176β) | 5'-W A C A C W-3' | PyPyPyPy-γ-Im-β-ImHp |
| 177β) | 5'-W A C G T W-3' | PyPyImHp-γ-Py-β-ImHp |
| 177β2) | 5'-W A C G T W-3' | Py-β-ImHp-γ-Py-β-ImHp |
| 178β) | 5'-W A C G A W-3' | PyPyImPy-γ-Hp-β-ImHp |
| 178β2) | 5'-W A C G A W-3' | Py-β-ImPy-γ-Hp-β-ImHp |
| 181β) | 5'-W A C G G W-3' | PyPyImIm-γ-Py-β-ImHp |
| 181β2) | 5'-W A C G G W-3' | Py-β-ImIm-γ-Py-β-ImHp |
| 182β) | 5'-W A C G C W-3' | PyPyImPy-γ-Im-β-ImHp |
| 182β2) | 5'-W A C G C W-3' | Py-β-ImPy-γ-Im-β-ImHp |
| 183β2) | 5'-W A C C G W-3' | PyPy-β-Im-γ-PyImImHp |

TABLE 18

8-ring Hairpin Polyamides for recognition of
6-bp 5'-WCWNNW-3' with β-substitutions included.

| | DNA sequence | aromatic amino acid sequence |
|---|---|---|
| 185β) | 5'-W C T T T W-3' | PyHpHpHp-γ-PyPy-β-Im |
| 186β) | 5'-W C T T A W-3' | PyHpHpPy-γ-HpPy-β-Im |
| 187β) | 5'-W C T T G W-3' | PyHpHpIm-γ-PyPy-β-Im |
| 187β2) | 5'-W C T T G W-3' | PyHp-β-Im-γ-PyPy-β-Im |
| 188β) | 5'-W C T T C W-3' | PyHpHpPy-γ-ImPy-β-Im |
| 189β) | 5'-W C T A T W-3' | PyHpPyHp-γ-PyHp-β-Im |
| 190β) | 5'-W C T A A W-3' | PyHpPyPy-γ-HpHp-β-Im |
| 191β) | 5'-W C T A G W-3' | PyHpPyIm-γ-PyHp-β-Im |
| 191β2) | 5'-W C T A G W-3' | PyHp-β-Im-γ-PyHp-β-Im |
| 192β) | 5'-W C T A C W-3' | PyHpPyPy-γ-ImHp-β-Im |
| 193β) | 5'-W C T G T W-3' | PyHpImHp-γ-PyPy-β-Im |
| 193β2) | 5'-W C T G T W-3' | Py-β-ImHp-γ-PyPy-β-Im |
| 194β) | 5'-W C T G A W-3' | PyHpImPy-γ-HpPy-β-Im |
| 194β2) | 5'-W C T G A W-3' | Py-β-ImPy-γ-HpPy-β-Im |
| 195β) | 5'-W C T G G W-3' | PyHpImIm-γ-PyPy-β-Im |
| 195β2) | 5'-W C T G G W-3' | Py-β-ImIm-γ-PyPy-β-Im |
| 196β) | 5'-W C T G C W-3' | PyHpImPy-γ-ImPy-β-Im |
| 196β2) | 5'-W C T G C W-3' | Py-β-ImPy-γ-ImPy-β-Im |
| 197β) | 5'-W C T C T W-3' | PyHpPyHp-γ-PyIm-β-Im |
| 198β) | 5'-W C T C A W-3' | PyHpPyPy-γ-HpIm-β-Im |
| 199β) | 5'-W C T C G W-3' | PyHpPyIm-γ-PyIm-β-Im |
| 199β2) | 5'-W C T C G W-3' | PyHp-β-Im-γ-PyIm-β-Im |
| 200β) | 5'-W C T C C W-3' | PyHpPyPy-γ-ImIm-β-Im |
| 201β) | 5'-W C A T T W-3' | PyPyHpHp-γ-PyPy-β-Im |
| 202β) | 5'-W C A T A W-3' | PyPyHpPy-γ-HpPy-β-Im |
| 203β) | 5'-W C A T G W-3' | PyPyHpIm-γ-PyPy-β-Im |
| 203β2) | 5'-W C A T G W-3' | PyPy-β-Im-γ-PyPy-β-Im |
| 204β) | 5'-W C A T C W-3' | PyPyHpPy-γ-ImPy-β-Im |
| 205β) | 5'-W C A A T W-3' | PyPyPyHp-γ-PyHp-β-Im |
| 206β) | 5'-W C A A A W-3' | PyPyPyPy-γ-HpHp-β-Im |
| 207β) | 5'-W C A A G W-3' | PyPyPyIm-γ-PyHp-β-Im |
| 207β2) | 5'-W C A A G W-3' | PyPy-β-Im-γ-PyHp-P-Im |
| 208β) | 5'-W C A A C W-3' | PyPyPyPy-γ-ImHp-β-Im |
| 209β) | 5'-W C A G T W-3' | PyPyImHp-γ-PyPy-β-Im |
| 209β) | 5'-W C A G T W-3' | Py-β-ImHp-γ-PyPy-β-Im |
| 210β) | 5'-W C A G A W-3' | PyPyImPy-γ-HpPy-β-Im |
| 210β2) | 5'-W C A G A W-3' | Py-β-ImPy-γ-HpPy-β-Im |
| 211β) | 5'-W C A G G W-3' | PyPyImIm-γ-PyPy-β-Im |
| 211β2) | 5'-W C A G G W-3' | Py-β-ImIm-γ-PyPy-β-Im |
| 212β) | 5'-W C A G C W-3' | PyPyImPy-γ-ImPy-β-Im |
| 212β2) | 5'-W C A G C W-3' | Py-β-ImPy-γ-ImPy-β-Im |
| 213β) | 5'-W C A C T W-3' | PyPyPyHp-γ-PyIm-β-Im |
| 214β) | 5'-W C A C A W-3' | PyPyPyPy-γ-HpIm-β-Im |
| 215β) | 5'-W C A C G W-3' | PyPyPyIm-γ-PyIm-β-Im |
| 215β2) | 5'-W C A C G W-3' | PyPy-β-Im-γ-PyIm-β-Im |
| 216β) | 5'-W C A C C W-3' | PyPyPyPy-γ-ImIm-β-Im |

TABLE 19

8-ring Hairpin Polyamides for recognition of
6-bp 5'-WCSNNW-3' with β-substitutions included.

| | DNA sequence | aromatic amino acid sequence |
|---|---|---|
| 217β) | 5'-W C G T T W-3' | PyImHpHp-γ-PyPy-β-Im |
| 218β) | 5'-W C G T A W-3' | PyImHpPy-γ-HpPy-β-Im |
| 219β) | 5'-W C G T G W-3' | PyImHpIm-γ-PyPy-β-Im |
| 219β2) | 5'-W C G T G W-3' | PyIm-β-Im-γ-PyPy-β-Im |
| 220β) | 5'-W C G T C W-3' | PyImHpPy-γ-ImPy-β-Im |
| 221β) | 5'-W C G A T W-3' | PyImPyHp-γ-PyHp-β-Im |
| 222β) | 5'-W C G A A W-3' | PyImPyPy-γ-HpPy-β-Im |
| 223β) | 5'-W C G A G W-3' | PyImPyIm-γ-PyHp-β-Im |
| 223β2) | 5'-W C G A G W-3' | PyIm-β-Im-γ-PyHp-β-Im |
| 224β) | 5'-W C G A C W-3' | PyImPyPy-γ-ImHp-β-Im |
| 225β) | 5'-W C G G T W-3' | PyImImHp-γ-PyPy-β-Im |
| 226β) | 5'-W C G G A W-3' | PyImImPy-γ-HpPy-β-Im |
| 227β) | 5'-W C G G T W-3' | PyImImHp-γ-PyIm-β-Im |
| 228β) | 5'-W C G C A W-3' | PyImPyPy-γ-HpIm-β-Im |
| 229β) | 5'-W C C T T W-3' | PyPyHpHp-γ-Py-β-ImIm |
| 230β) | 5'-W C C T A W-3' | PyPyHpPy-γ-Hp-β-ImIm |
| 231β) | 5'-W C C T G W-3' | PyPyHpIm-γ-Py-β-ImIm |
| 231β2) | 5'-W C C T G W-3' | PyPy-β-Im-γ-Py-β-ImIm |
| 232β) | 5'-W C C T C W-3' | PyPyHpPy-γ-Im-β-ImIm |
| 233β) | 5'-W C C A T W-3' | PyPyPyHp-γ-Py-β-ImIm |
| 234β) | 5'-W C C A A W-3' | PyPyPyPy-γ-Hp-β-ImIm |
| 235β) | 5'-W C C A G W-3' | PyPyPyIm-γ-Py-β-ImIm |
| 235β2) | 5'-W C C A G W-3' | PyPy-β-Im-γ-Py-β-ImIm |
| 236β) | 5'-W C C A C W-3' | PyPyPyPy-γ-Im-β-ImIm |
| 237β) | 5'-W C C G T W-3' | PyPyImHp-γ-Py-β-ImIm |
| 237β2) | 5'-W C C G T W-3' | Py-β-ImHp-γ-Py-β-ImIm |
| 238β) | 5'-W C C G A W-3' | PyPyImPy-γ-Hp-β-ImIm |
| 238β2) | 5'-W C C G A W-3' | Py-β-ImPy-γ-Hp-β-ImIm |
| G9β) | 5'-W C G G G W-3' | PyImImIm-γ-PyPy-β-Im |
| G10β) | 5'-W C G G C W-3' | PyImImPy-γ-ImPy-β-Im |
| G11β) | 5'-W C G C G W-3' | PyImPyIm-γ-PyIm-β-Im |
| G11β2) | 5'-W C G C G W-3' | PyIm-β-Im-γ-PyIm-β-Im |
| G12β) | 5'-W C G C C W-3' | PyImPyPy-γ-ImIm-β-Im |
| G13β) | 5'-W C C G G-3' | PyPyImIm-γ-Py-β-ImIm |

TABLE 19-continued 8-ring Hairpin Polyamides for recognition of
6-bp 5'-WCSNNW-3' with β-substitutions included.

| DNA sequence | aromatic amino acid sequence |
| --- | --- |
| G13β2) 5'-W C C G G-W-3' | Py-β-ImIm-γ-Py-β-ImIm |
| G14β) 5'-W C C G-C-W-3' | PyPyImPy-γ-Im-β-ImIm |
| G14β2) 5'-W C C G-C-W-3' | Py-β-ImPy-γ-Im-β-ImIm |
| G15β) 5'-W C C C-G-W-3' | PyPy-β-Im-γ-PyImImIm |

If the process described above of designing a preferred polyamide molecule $X_1X_2X_3X_4$-γ-$X_5X_6X_7X_8$ comprising eight aromatic aminoacid residues does not produce a selective polyamide that binds to the target identified DNA sequence with subnanomolar affinity and with a selectivity over mismatch sequences of greater than a factor of ten, a polyamide molecule $X_1X_2X_3X_4X_5$-γ-$X_6X_7X_8X_9X_{10}$ having five carboxamide binding pairs can be designed that is selective for a seven base pair identified target 5'-W-3' sequence. The design and synthesis of the five binding pair polyamide is similar to that of the four binding pair polyamide $X_1X_2X_3X_4$-γ-$X_5X_6X_7X_8$ described above.

Figure 7A:
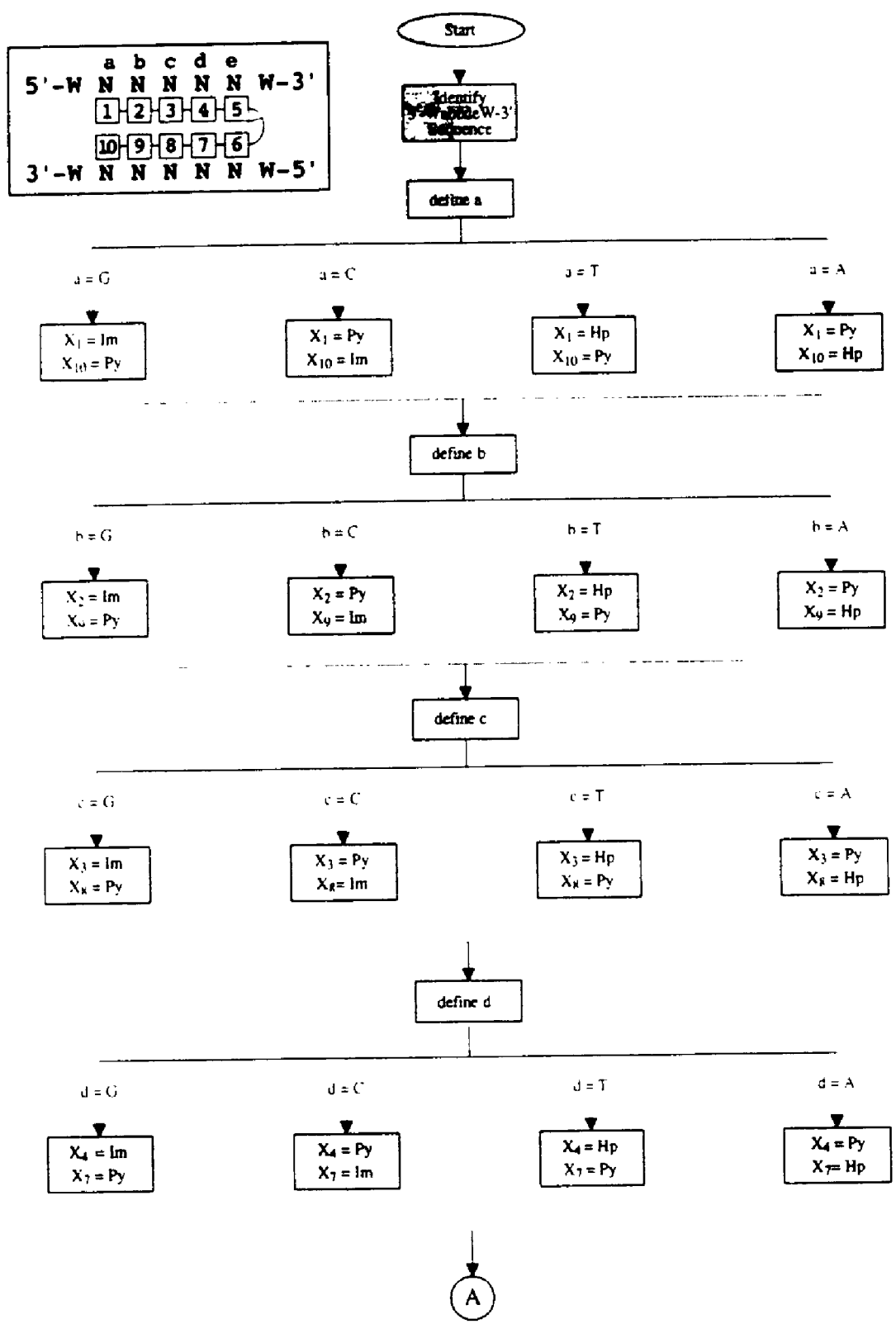
FIGS. 7A–7B schematically illustrate a method for the design of ten carboxamide residue hairpin polyamide compounds suitable for recognition of 7-bp 5'-WNNNNNW-3' sequences in the minor groove of double stranded DNA.
Figure 7B:
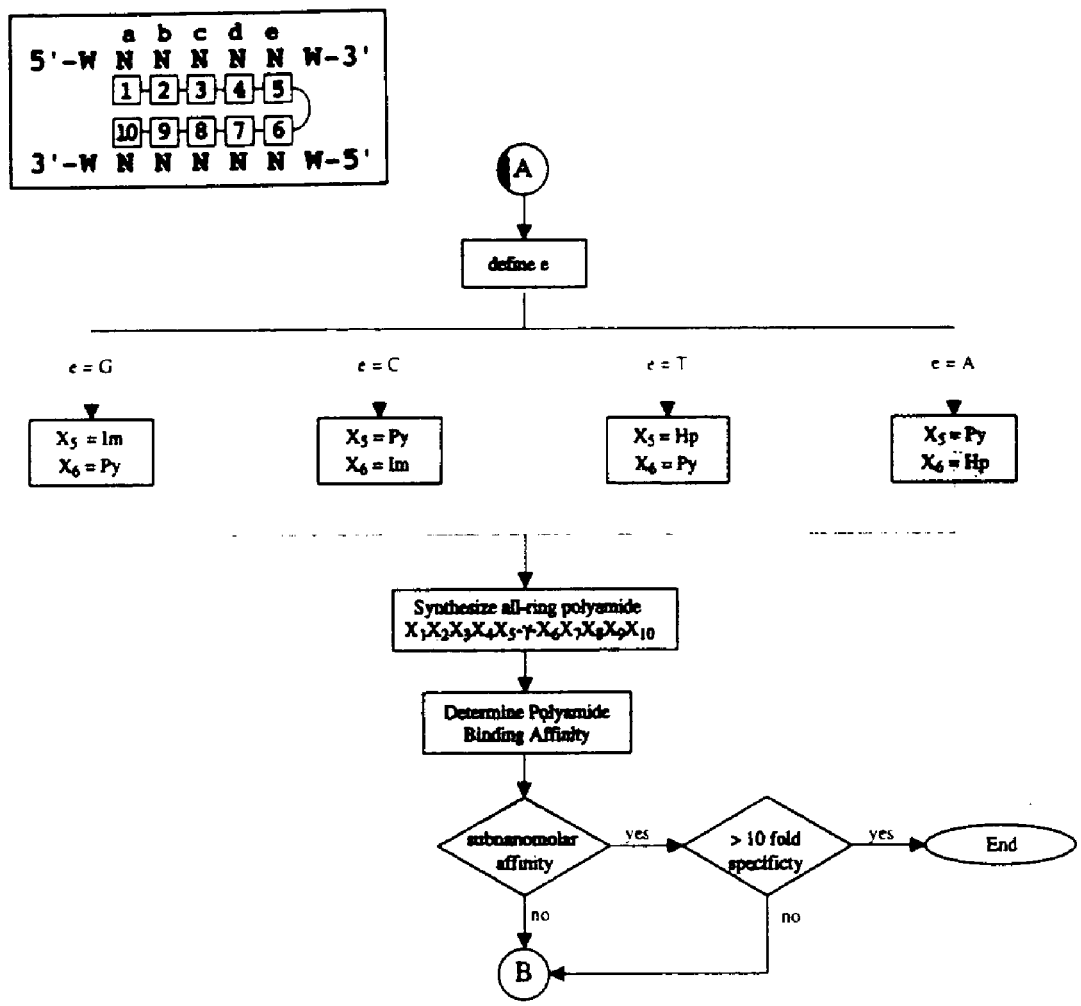

The polyamide design process, shown schematically in FIG. 7 provides a method for designing a ten carboxamide residue molecule comprising five carboxamide binding pairs for selective detection and binding of a target seven base pair 5'-WNNNNNW-3' sequence in the minor groove of double stranded DNA. The design process identifies an appropriate polyamide ligand for recognition of a predetermined seven base pair, 5'-WNNNNNW-3' sequence with subnanomolar affinity and >10-fold specificity versus mismatch sites. Trauger, J. W., Baird, E. E. Dervan, P. B. describes the recognition of DNA by designed ligands at subnanomolar concentrations. *Nature* 382, 559–561 (1996).

In order to prepare a polyamide molecule specific for an identified seven base pair sequence of double stranded DNA, a user starts the 10-ring hairpin design process that implements the minor groove recognition pairing code summarized in Table 2 above. In the design process a 5'-WNNNW-3' sequence was identified. In a preferred embodiment, the identified sequence was located within a gene promoter. The identified sequence was then defined as 5'-WabcdeW-3' in a stepwise process wherein a, b, c, d, and e, were sequentially and independently defined as A, G, C, or T. The structure of the polyamide molecule was then correspondingly defined by sequentially chosing antiparallel carboxamide binding pairs according to the minor groove pairing code summarized in Table 2 above. Thus, if a was G, then $X_1$ was defined as Im, and $X_{10}$ was defined as Py. If a was C, then $X_1$ was defined as Py, and $X_{10}$ was defined as Im. If a was T, then $X_{10}$ was defined as Hp, and $X_{10}$ was defined as Py. If a was A, then $X_1$ was defined as Py, and $X_{10}$ was defined as Hp.

Similarly, b was defined as A, G, C, or T and corresponding carboxamide binding pairs were defined. According to the same rules, if b was G, then $X_2$ was defined as Im, and $X_9$ was defined as Py. If b was C, then $X_2$ was defined as Py, and $X_9$ was defined as Im. Likewise, if b was T, then $X_2$ was defined as Hp, and $X_9$ was defined as Py. If b was A, then $X_2$ was defined as Py, and $X_9$ was defined as Hp.

The next step was to define c as A, G, C, or T and then define corresponding carboxamide binding pairs. Following the same rules, if c was G, then $X_3$ was defined as Im, and $X_8$ was defined as Py. If c was C, then $X_3$ was defined as Py, and $X_8$ was defined as Im. Similarly, if c was T, then $X_3$ was defined as Hp, and $X_8$ was defined as Py. If c was A, then $X_3$ was defined as Py, and $X_8$ was defined as Hp. Similarly, d was defined as A, G, C, or T and the corresponding carboxamide binding pair was defined. According to the above rules, if d was G, then $X_4$ was defined as Im, and $X_7$ was defined as Py. If d was C, then $X_4$ was defined as Py, and $X_7$ was defined as Im. If d was T, then $X_4$ was defined as Hp, and $X_7$ was defined as Py. If d was A, then $X_4$ was defined as Py, and $X_7$ was defined as Hp. Finally, e was defined as A, G, C, or T and the corresponding carboxamide binding pair was defined. According to the above rules, if e was G, then $X_5$ was defined as Im, and $X_6$ was defined as Py. If e was C, then $X_5$ was defined as Py, and $X_6$ was defined as Im. If e was T, then $X_5$ was defined as Hp, and $X_6$ was defined as Py. If e was A, then $X_5$ was defined as Py, and $X_6$ was defined as Hp.

With all ten carboxamide residues that participate in the binding pairs now defined, the designed polyamide $X_1X_2X_3X_4X_5$-γ-$X_6X_7X_8X_9X_{10}$ suitable for binding to the identified sequence was synthesized using known techniques. Baird, E. E. & Dervan, P. B. describes the solid phase synthesis of polyamides containing imidazole and pyrrole amino acids. *J. Am. Chem. Soc.* 118, 6141–6146 (1996); also see PCT US 97/003332.

The binding affinity of the synthesized polyamide to the identified sequence was determined using a quantitative DNase footprint titration method for studying protein-DNA interactions described by Brenowitz, M., Senear, D. F., Shea, M. A. & Ackers, G. K., *Methods Enzymol.* 130, 132–181 (1986). If the affinity of the synthesized polyamide at the target site was not subnanomolar affinity then substituting at least one β-alanine residue for a pyrrole or 3-hydroxypyrrole residue was considered in order to optimize the exact positions of the binding pairs of aromatic amino acids. If the affinity of the polyamide at the target site was subnanomolar affinity then the sequence specificity of the polyamide versus mismatch sequences was determined. If the specificity versus mismatch sites was not >10-fold specificity then adding a β-alanine (shown schematically in FIG. 8) was considered, in order to optimize the positions of the aromatic amino acids in relationship to the base pairs in the minor groove. Specificity of the polyamide molecule for the target identified sequence versus mismatch sequence sites of greater than 10-fold was considered a successful result of design process.

The 1024 polyamide molecules comprising five carboxamide binding pairs that were designed using this method are useful for binding to the 1024 target 5'-NNNNN-3' core sequences, and are listed in Tables 20–51. A corresponding polyamide molecule was designed for each DNA sequence (241–1232) and (G17–G48) using the process outlined above and shown schematically in FIG. 7.

If the synthesized polyamide molecule did not bind to the target identified sequence with subnanomolar affinity or if the synthesized polyamide molecule did not exhibit a specificity for the target identified sequence versus mismatch sequence sites of greater than 10-fold, the option of substituting an aliphatic amino acid residue for one of the carboxamide residues was considered. The preferred aliphatic amino acid residue is β-alanine. At least one aliphatic amino acid residue such as a β-alanine residue provided some flexibility to the central portion of the polyamide molecule, acting as a "spring" to permit optimization of the hydrogen bonding between the carboxamide binding pairs and the nucleotide bases of the double stranded DNA.

In general, it was not found to be advantageous to replace either member of the terminal carboxamide binding pair, $X_1/X_{10}$, with β-alanine. Similarly, β-alanine was not substituted for members of the binding pair, $X_5/X_6$, adjacent to the γ hairpin residue. β-alanine residues were not substituted for N-methylimidazole residues. The use of β-alanine in place of a pyrrole or 3-hydroxypyrrole amino acid residue provides aromatic/aliphatic pairing (Im/β, β/Im, Hp/β, β/Hp, Py/β, and β/Py) and aliphatic/aliphatic pairing (β/β) substitution.

Figure 8:
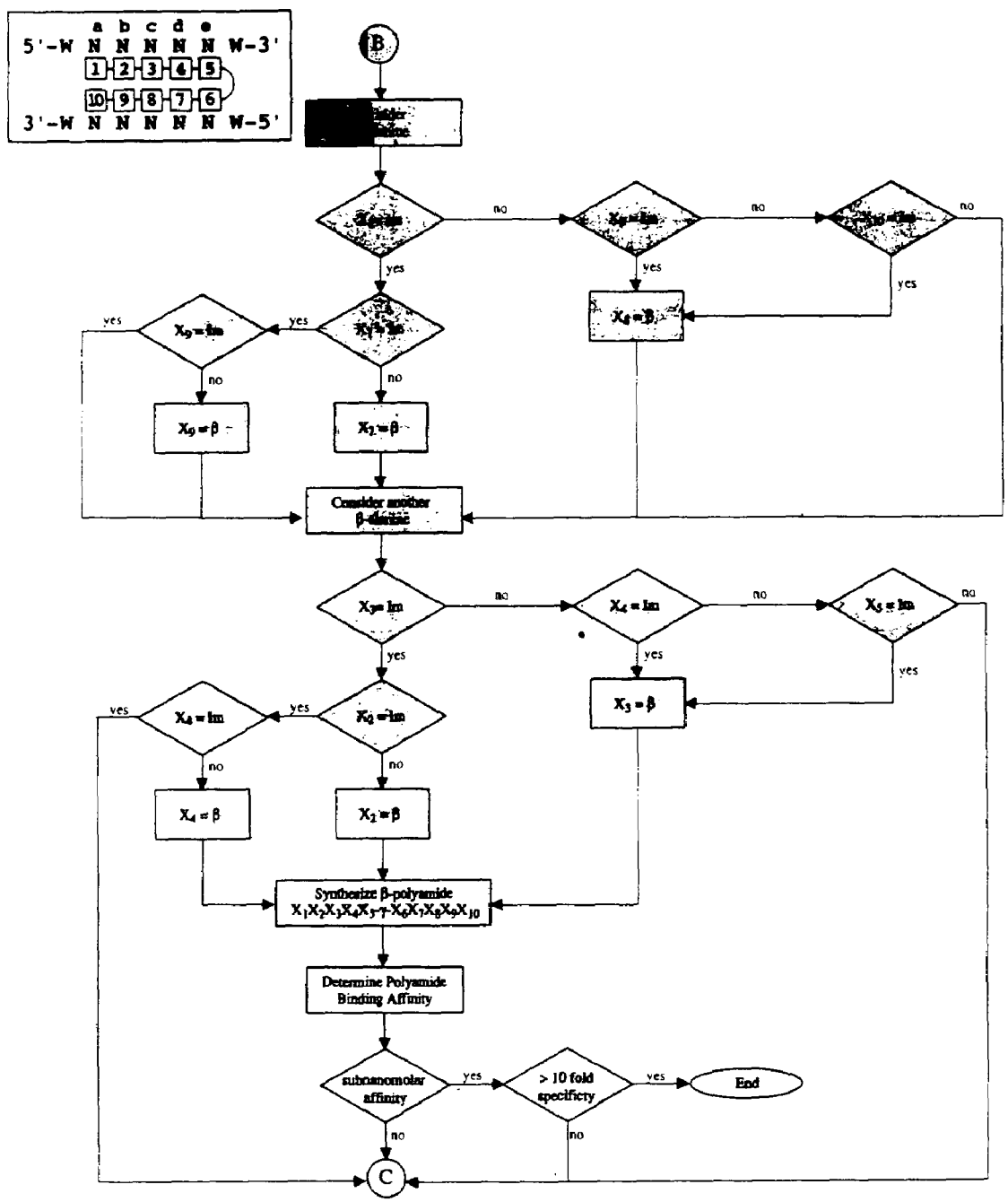
FIG. 8 schematically illustrates a method for determining the position of an aromatic amino acid residue that should be replaced with a β-alanine residue in order to enhance the DNA binding properties of certain ten carboxamide residue hairpin polyamide compounds.

The method for selecting which pyrrole amino acid to substitute with β-alanine is schematically illustrated in FIG. 8. Selective placement of an aliphatic β-alanine (β) residue paired with either a pyrrole (Py), 3-hydroxypyrrole (Hp), or imidazole (Im) aromatic amino acid or another β-alanine residue is found to compensate for sequence composition effects to improve recognition and binding of the minor groove of DNA by pyrrole-imidazole polyamides of the present invention. If an all-ring polyamide has been found to have an affinity which is not subnanomolar, or a specificity versus mismatch sequences which is less than 10-fold it may be caused by DNA sequence-composition effects which can be reduced by replacement of an aromatic amino acid with an aliphatic β-alanine residue. In a polyamide molecule that comprises five binding pairs it is only beneficial to place β-alanine in positions $X_2$, $X_3$, $X_4$, $X_7$, $X_8$, and $X_9$. No more than two β-alanine residues may be placed within a single hairpin structure. No more than a single β-residue may be placed within each individual polyamide subunit, e.g., if $X_2$ is replaced with β-alanine, $X_3$ or $X_4$ cannot be replaced as well.

These rules and others were implemented in the method schematically illustrated in FIG. 8. This process is suitable for the refinement of the design polyamide comprising five binding pairs that has been designed by the method illustrated in FIG. 7, but which lacks subnanomolar affinity or greater than 10-fold specificity at the identified target DNA sequence. As in the basic design method, the designed polyamides are synthesized and the affinity and specificity of binding to the target DNA were determined.

As discussed above, for a given 10-ring polyamide molecule there are six possible outcomes for the process of substituting a β-alanine residue for an aromatic amino acid residue. First, there may be no position at which it is possible to add a β-alanine residue; in such case, a better binding affinity or selectivity can be sought in the design and synthesis of a polyamide with four or six carboxamide binding pairs, described below. Second, the process may result in a derivative which contains a single β-alanine substitution (such derivatives are numbered according to the parent numbering scheme such that a single β-derivative of compound 5 would be called 5β), which is sufficient to produce subnanomolar binding affinity and >10-fold specificity, and at which point the process is deemed complete.

Figure 9:
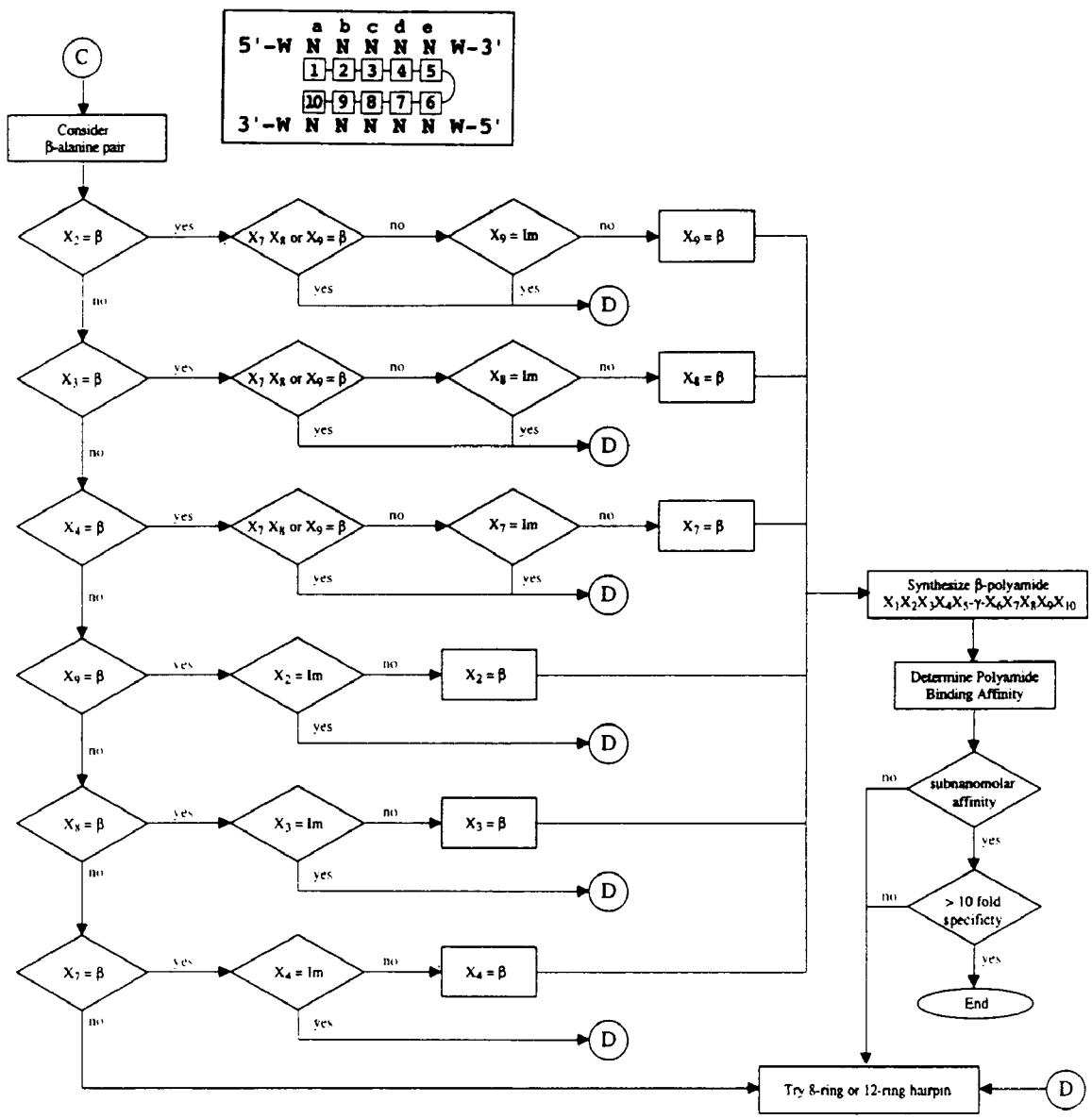
FIG. 9 schematically illustrates a method for determining the position of an additional aromatic amino acid residue that should be replaced with a β-alanine residue in order to enhance the DNA binding properties of certain ten carboxamide residue hairpin polyamide compounds.

Third, the process of FIG. 8 may result in a polyamide which contains a single β-alanine substitution which is not sufficient to produce subnanomolar binding affinity and >10-fold specificity, but where there are no additional positions in which it is possible to substitute a β-alanine residue, and in such a case a paired β-alanine residue should be added as described in FIG. 9 and text below. Fourth, the process of FIG. 7 may result in a polyamide that contains a single β-alanine substitution that is not sufficient to produce subnanomolar binding affinity and >10-fold specificity, but where there is an additional position for β-alanine substitution that does produce a polyamide with the criterion level of affinity and selectivity. Tables 52–83 list polyamide compounds 241β–1232β and G17β–G48β, corresponding to DNA sequences 241–1232 and G17–G48, that contain one or two β-alanine residues.

A fifth possibility is that substitution at a second position by the method illustrated in FIG. 9 with a paired β-alanine residue is not sufficient to produce a polyamide having the subnanomolar binding affinity and >10-fold specificity, and a polyamide with four or six carboxamide binding pairs, should be designed and synthesized, as described below. Finally, the design process may result in a polyamide that has a paired β-alanine substitution that is sufficient to produce subnanomolar binding affinity and >10-fold specificity, and therefore the design process is deemed complete. Tables 52–83 list polyamide compounds 241β–1232β and G17β–G48β, corresponding to DNA sequences 241–1232 and G17–G48, that contain one or two β-alanine residues. In addition, Tables 52–83 list polyamides corresponding to sequences (241–1232) and (G17–G48) labeled (241βp–1232βp) and (G17βp–G48βp) that contain paired β/β residues added by the process described in FIG. 9.

TABLE 20

10-ring Hairpin Polyamides for recognition of
7-bp 5'-WGGWNNW-3'

| | DNA sequence | aromatic amino acid sequence |
|---|---|---|
| 241) | 5'-W G G T T T W-3' | ImImHpHpHp-γ-PyPyPyPyPy |
| 242) | 5'-W G G T T A W-3' | ImImHpHpPy-γ-HpPyPyPyPy |
| 243) | 5'-W G G T T G W-3' | ImImHpHpIm-γ-PyPyPyPyPy |
| 244) | 5'-W G G T T C W-3' | ImImHpHpPy-γ-ImPyPyPyPy |
| 245) | 5'-W G G T A T W-3' | ImImHpPyHp-γ-PyHpPyPyPy |
| 246) | 5'-W G G T A A W-3' | ImImHpPyPy-γ-HpPyPyPyPy |
| 247) | 5'-W G G T A G W-3' | ImImHpPyIm-γ-PyHpPyPyPy |
| 248) | 5'-W G G T A C W-3' | ImImHpPyPy-γ-ImPyPyPyPy |
| 249) | 5'-W G G T G T W-3' | ImImHpImHp-γ-PyPyPyPyPy |
| 250) | 5'-W G G T G A W-3' | ImImHpImPy-γ-HpPyPyPyPy |
| 251) | 5'-W G G T G G W-3' | ImImHpImIm-γ-PyPyPyPyPy |
| 252) | 5'-W G G T G C W-3' | ImImHpImPy-γ-ImPyPyPyPy |
| 253) | 5'-W G G T C T W-3' | ImImHpPyHp-γ-PyImPyPyPy |
| 254) | 5'-W G G T C A W-3' | ImImHpPyPy-γ-HpImPyPyPy |
| 255) | 5'-W G G T C G W-3' | ImImHpPyIm-γ-PyImPyPyPy |
| 256) | 5'-W G G T C C W-3' | ImImHpPyPy-γ-ImImPyPyPy |
| 257) | 5'-W G G A T T W-3' | ImImPyHpBp-γ-PyPyHpPyPy |
| 258) | 5'-W G G A T A W-3' | ImImPyHpPy-γ-HpPyHpPyPy |
| 259) | 5'-W G G A T G W-3' | ImImPyHpIm-γ-PyPyHpPyPy |
| 260) | 5'-W G G A T C W-3' | ImImPyHpPy-γ-ImPyHpPyPy |
| 261) | 5'-W G G A A T W-3' | ImImPyPyHp-γ-PyHpHpPyPy |
| 262) | 5'-W G G A A A W-3' | ImImPyPyPy-γ-HpHpHpPyPy |
| 263) | 5'-W G G A A G W-3' | ImImPyPyIm-γ-PyHpHpPyPy |
| 264) | 5'-W G G A A C W-3' | ImImPyPyPy-γ-ImHpHpPyPy |
| 265) | 5'-W G G A G T W-3' | ImImPyImHp-γ-PyPyHpPyPy |
| 266) | 5'-W G G A G A W-3' | ImImPyImPy-γ-HpPyHpPyPy |
| 267) | 5'-W G G A G G W-3' | ImImPyImIm-γ-PyFyHpPyPy |
| 268) | 5'-W G G A G C W-3' | ImImPyImPy-γ-ImPyHpPyPy |
| 269) | 5'-W G G A C T W-3' | ImImPyPyHp-γ-PyImHpPyPy |
| 270) | 5'-W G G A C A W-3' | ImImPyPyPy-γ-HpImHpPyPy |
| 271) | 5'-W G G A C G W-3' | ImImPyPyIm-γ-PyImHpPyPy |
| 272) | 5'-W G G A C C W-3' | ImImPyPyPy-γ-ImImHpPyPy |

TABLE 21

10-ring Hairpin Polyamides for recognition of
7-bp 5'-WGGSNNW-3'

| | DNA sequence | aromatic amino acid sequence |
|---|---|---|
| 273) | 5'-W G G G T T W-3' | ImImImHpHp-γ-PyPyPyPyPy |
| 274) | 5'-W G G G T A W-3' | ImImImHpPy-γ-HpPyPyPyPy |
| 275) | 5'-W G G G T G W-3' | ImImImnpIm-γ-PyPyPyPyPy |
| 276) | 5'-W G G G T C W-3' | ImImImnpPy-γ-ImPyPyPyPy |
| 277) | 5'-W G G G A T W-3' | ImImImPyHp-γ-PyHpPyPyPy |
| 278) | 5'-W G G G A A W-3' | ImImImPyPy-γ-WpHpPyPyPy |
| 279) | 5'-W G G G A G W-3' | ImImImPyIm-γ-PyHpPyPyPy |
| 280) | 5'-W G G G A C W-3' | ImImImPyPy-γ-ImHpPyPyPy |
| 281) | 5'-W G G G G T W-3' | ImImImImHp-γ-PyPyPyPyPy |
| 282) | 5'-W G G G G A W-3' | ImImImImPy-γ-HpPyPyPyPy |

TABLE 21-continued 10-ring Hairpin Polyamides for recognition of 7-bp 5'-WGGSNNW-3'

| | DNA sequence | aromatic amino acid sequence |
|---|---|---|
| 283) | 5'-W G G G C T W-3' | ImImImPyHp-γ-PyImPyPyPy |
| 284) | 5'-W G G G C A W-3' | ImImImPyPy-γ-HpImPyPyPy |
| 285) | 5'-W G G C T T W-3' | ImImPyHpHp-γ-PyPyImPyPy |
| 286) | 5'-W G G C T A W-3' | ImImPyHpPy-γ-HpPyImPyPy |
| 287) | 5'-W G G C T G W-3' | ImImPyHpIm-γ-PyPyImPyPy |
| 288) | 5'-W G G C T C W-3' | ImImPyHpPy-γ-ImPyImPyPy |
| 289) | 5'-W G G C A T W-3' | ImImPyPyHp-γ-PyHpImPyPy |
| 290) | 5'-W G G C A A W-3' | ImImPyPyPy-γ-HpHpImPyPy |
| 291) | 5'-W G G C A G W-3' | ImImPyPyIm-γ-PyHpImPyPy |
| 292) | 5'-W G G C A C W-3' | ImImPyPyPy-γ-ImHpImPyPy |
| 293) | 5'-W G G C G T W-3' | ImImPyImHp-γ-PyPyImPyPy |
| 294) | 5'-W G G C G A W-3' | ImImPyImPy-γ-HpPyImPyPy |
| 295) | 5'-W G G C C T W-3' | ImImPyPyHp-γ-PyImImPyPy |
| 296) | 5'-W G G C C A W-3' | ImImPyPyPy-γ-HpImImPyPy |
| G17) | 5'-W G G G G G W-3' | ImImImImIm-γ-PyPyPyPyPy |
| G18) | 5'-W G G G G C W-3' | ImImImPy-γ-ImPyPyPyPy |
| G19) | 5'-W G G G C G W-3' | ImImImPyIm-γ-PyImPyPyPy |
| G20) | 5'-W G G G C C W-3' | ImImImPyPy-γ-ImImPyPyPy |
| G21) | 5'-W G G C G G W-3' | ImImPyImIm-γ-PyPyImPyPy |
| G22) | 5'-W G G C G C W-3' | ImImPyImPy-γ-ImPyImPyPy |
| G23) | 5'-W G G C C G W-3' | ImImPyPyIm-γ-PyImImPyPy |
| G24) | 5'-W G G C C C W-3' | ImImPyPyPy-γ-ImImImPyPy |

TABLE 22

10-ring Hairpin Polyamides for recognition of 7-bp 5'-WGTWNNW-3'

| | DNA sequence | aromatic amino acid sequence |
|---|---|---|
| 297) | 5'-W G T T T T W-3' | ImHpHpHpHp-γ-PyPyPyPyPy |
| 298) | 5'-W G T T T A W-3' | ImHpHpHpPy-γ-HpPyPyPyPy |
| 299) | 5'-W G T T T G W-3' | ImHpHpHpIm-γ-PyPyPyPyPy |
| 300) | 5'-W G T T T C W-3' | ImHpHpHpPy-γ-ImPyPyPyPy |
| 301) | 5'-W G T T A T W-3' | ImHpHpPyHp-γ-PyHpPyPyPy |
| 302) | 5'-W G T T A A W-3' | ImHpHpPyPy-γ-HpHpPyPyPy |
| 303) | 5'-W G T T A G W-3' | ImHpHpPyIm-γ-PyHpPyPyPy |
| 304) | 5'-W G T T A C W-3' | ImHpHpPyPy-γ-ImHpPyPyPy |
| 305) | 5'-W G T T G T W-3' | ImHpHpImHp-γ-PyPyPyPyPy |
| 306) | 5'-W G T T G A W-3' | ImHpHpImPy-γ-HpPyPyPyPy |
| 307) | 5'-W G T T G G W-3' | ImHpHpImIm-γ-PyPyPyPyPy |
| 308) | 5'-W G T T G C W-3' | ImHpHpImPy-γ-ImPyPyPyPy |
| 309) | 5'-W G T T C T W-3' | ImHpHpPyHp-γ-PyImPyPyPy |
| 310) | 5'-W G T T C A W-3' | ImHpHpPyPy-γ-HpImPyPyPy |
| 311) | 5'-W G T T C G W-3' | ImHpHpPyIm-γ-PyImPyPyPy |
| 312) | 5'-W G T T C C W-3' | ImHpHpPyPy-γ-ImImPyPyPy |
| 313) | 5'-W G T A T T W-3' | ImHpPyHpHp-γ-PyPyHpPyPy |
| 314) | 5'-W G T A T A W-3' | ImHpPyHpPy-γ-HpPyHpPyPy |
| 315) | 5'-W G T A T G W-3' | ImHpPyHpIm-γ-PyPyHpPyPy |
| 316) | 5'-W G T A T C W-3' | ImHpPyHpPy-γ-ImPyHpPyPy |
| 317) | 5'-W G T A A T W-3' | ImHpPyPyHp-γ-PyHpHpPyPy |
| 318) | 5'-W G T A A A W-3' | ImHpPyPyPy-γ-HpHpHpPyPy |
| 319) | 5'-W G T A A G W-3' | ImHpPyPyIm-γ-PyHpHpPyPy |
| 320) | 5'-W G T A A C W-3' | ImHpPyPyPy-γ-ImHpHpPyPy |
| 321) | 5'-W G T A G T W-3' | ImHpPyImHp-γ-PyPyHpPyPy |
| 322) | 5'-W G T A G A W-3' | ImHpPyImPy-γ-HpPyHpPyPy |
| 323) | 5'-W G T A G G W-3' | ImHpPyImIm-γ-PyPyHpPyPy |
| 324) | 5'-W G T A G C W-3' | ImHpPyImPy-γ-ImPyHpPyPy |
| 325) | 5'-W G T A C T W-3' | ImHpPyPyHp-γ-PyImHpPyPy |
| 326) | 5'-W G T A C A W-3' | ImHpPyPyPy-γ-HpImHpPyPy |
| 327) | 5'-W G T A C G W-3' | ImHpPyPyIm-γ-PyImHpPyPy |
| 328) | 5'-W G T A C C W-3' | ImHpPyPyPy-γ-ImImHpPyPy |

TABLE 23

10-ring Hairpin Polyamides for recognition of 7-bp 5'-WGTSNNW-3'

| | DNA sequence | aromatic amino acid sequence |
|---|---|---|
| 329) | 5'-W G T G T T W-3' | ImHpImHpHp-γ-PyPyPyPyPy |
| 330) | 5'-W G T G T A W-3' | ImHpImHpPy-γ-HpPyPyPyPy |
| 331) | 5'-W G T G T G W-3' | ImHpImHpIm-γ-PyPyPyPyPy |
| 332) | 5'-W G T G T C W-3' | ImHpImHpPy-γ-ImPyPyPyPy |
| 333) | 5'-W G T G A T W-3' | ImHpImPyHp-γ-PyHpPyPyPy |
| 334) | 5'-W G T G A A W-3' | ImHpImPyPy-γ-HpHpPyPyPy |
| 335) | 5'-W G T G A G W-3' | ImHpImPyIm-γ-PyHpPyPyPy |
| 336) | 5'-W G T G A C W-3' | ImHpImPyPy-γ-ImHpPyPyPy |
| 337) | 5'-W G T G G T W-3' | ImHpImImHp-γ-PyPyPyPyPy |
| 338) | 5'-W G T G G A W-3' | ImHpImImPy-γ-HpPyPyPyPy |
| 339) | 5'-W G T G C T W-3' | ImHpImPyHp-γ-PyImPyPyPy |
| 340) | 5'-W G T G C A W-3' | ImHpImPyPy-γ-HpImPyPyPy |
| 341) | 5'-W G T G G G W-3' | ImHpImImIm-γ-PyPyPyPyPy |
| 342) | 5'-W G T G G C W-3' | ImHpImImPy-γ-ImPyPyPyPy |
| 343) | 5'-W G T G C G W-3' | ImHpImPyIm-γ-PyImPyPyPy |
| 344) | 5'-W G T G C C W-3' | ImHpImPyPy-γ-ImImPyPyPy |
| 345) | 5'-W G T C T T W-3' | ImHpPyHpHp-γ-PyPyImPyPy |
| 346) | 5'-W G T C T A W-3' | ImHpPyHpPy-γ-HpPyImPyPy |
| 347) | 5'-W G T C T G W-3' | ImHpPyHpIm-γ-PyPyImPyPy |
| 348) | 5'-W G T C T C W-3' | ImHpPyHpPy-γ-ImPyImPyPy |
| 349) | 5'-W G T C A T W-3' | ImHpPyPyHp-γ-PyHpImPyPy |
| 350) | 5'-W G T C A A W-3' | ImHpPyPyPy-γ-HpHpImPyPy |
| 351) | 5'-W G T C A G W-3' | ImHpPyPyIm-γ-PyHpImPyPy |
| 352) | 5'-W G T C A C W-3' | ImHpPyPyPy-γ-ImHpImPyPy |
| 353) | 5'-W G T C G T W-3' | ImHpPyImHp-γ-PyPyImPyPy |
| 354) | 5'-W G T C G A W-3' | ImHpPyImPy-γ-HpPyImPyFy |
| 355) | 5'-W G T C C T W-3' | ImHpPyPyHp-γ-PyImImPyPy |
| 356) | 5'-W G T C C A W-3' | ImHpPyPyPy-γ-HpImImPyPy |
| 357) | 5'-W G T C G G W-3' | ImHpPyImIm-γ-PyPyImPyPy |
| 358) | 5'-W G T C G C W-3' | ImHpPyImPy-γ-ImPyImPyPy |
| 359) | 5'-W G T C C G W-3' | ImHpPyPyIm-γ-PyImImPyPy |
| 360) | 5'-W G T C C C W-3' | ImHpPyPyPy-γ-ImImImPyPy |

TABLE 24

10-ring Hairpin Polyamides for recognition of 7-bp 5'-WGAWNNW-3'

| | DNA sequence | aromatic amino acid sequence |
|---|---|---|
| 361) | 5'-W G A T T T W-3' | ImPyHpHpHp-γ-PyPyPyPyHpPy |
| 362) | 5'-W G A T T A W-3' | ImPyHpHpPy-γ-HpPyPyPyHpPy |
| 363) | 5'-W G A T T G W-3' | ImPyHpHpIm-γ-PyPyPyPyHpPy |
| 364) | 5'-W G A T T C W-3' | ImPyHpHpPy-γ-ImPyPyPyHpPy |
| 365) | 5'-W G A T A T W-3' | ImPyHpPyHp-γ-PyHpPyPyHpPy |
| 366) | 5'-W G A T A A W-3' | ImPyHpPyPy-γ-HpHpPyPyHpPy |
| 367) | 5'-W G A T A G W-3' | ImPyHpPyIm-γ-PyHpPyPyHpPy |
| 368) | 5'-W G A T A C W-3' | ImPyHpPyPy-γ-ImHpPyPyHpPy |
| 369) | 5'-W G A T G T W-3' | ImPyHpImHp-γ-PyPyPyPyHpPy |
| 370) | 5'-W G A T G A W-3' | ImPyHpImPy-γ-HpPyPyPyHpPy |
| 371) | 5'-W G A T G G W-3' | ImPyHpImIm-γ-PyPyPyPyHpPy |
| 372) | 5'-W G A T G C W-3' | ImPyHpImPy-γ-ImPyPyPyHpPy |
| 373) | 5'-W G A T C T W-3' | ImPyHpPyHp-γ-PyImPyPyHpPy |
| 374) | 5'-W G A T C A W-3' | ImPyHpPyPy-γ-HpImPyPyHpPy |
| 375) | 5'-W G A T C G W-3' | ImPyHpPyIm-γ-PyImPyPyHpPy |
| 376) | 5'-W G A T C C W-3' | ImPyHpPyPy-γ-ImImPyPyHpPy |
| 377) | 5'-W G A A T T W-3' | ImPyPyHpHp-γ-PyPyHpPyHpPy |
| 378) | 5'-W G A A T A W-3' | ImPyPyHpPy-γ-HpPyHpPyHpPy |
| 379) | 5'-W G A A T G W-3' | ImPyPyHpIm-γ-PyPyHpPyHpPy |
| 380) | 5'-W G A A T C W-3' | ImPyPyHpPy-γ-ImPyHpPyHpPy |
| 381) | 5'-W G A A A T W-3' | ImPyPyPyHp-γ-PyHpHpPyHpPy |
| 382) | 5'-W G A A A A W-3' | ImPyPyPyPy-γ-HpHpHpPyHpPy |
| 383) | 5'-W G A A A G W-3' | ImPyPyPyIm-γ-PyHpHpPyHpPy |
| 384) | 5'-W G A A A C W-3' | ImPyPyPyPy-γ-ImHpHpPyHpPy |
| 385) | 5'-W G A A G T W-3' | ImPyPyImHp-γ-PyPyHpPyHpPy |
| 386) | 5'-W G A A G A W-3' | ImPyPyImPy-γ-HpPyHpPyHpPy |
| 387) | 5'-W G A A G G W-3' | ImPyPyImIm-γ-PyPyHpPyHpPy |
| 388) | 5'-W G A A G C W-3' | ImPyPyImPy-γ-ImPyHpPyHpPy |
| 389) | 5'-W G A A C T W-3' | ImPyPyPyHp-γ-PyImHpPyHpPy |

TABLE 24-continued 10-ring Hairpin Polyamides for recognition of 7-bp 5'-WGAWNNW-3'

| | DNA sequence | aromatic amino acid sequence |
|---|---|---|
| 390) | 5'-W G A A C A W-3' | ImPyPyPyPy-γ-HpImHpHpPy |
| 391) | 5'-W G A A C G W-3' | ImPyPyPyIm-γ-PyImHpHpPy |
| 392) | 5'-W G A A C C W-3' | ImPyPyPyPy-γ-ImImHpHpPy |

TABLE 25

10-ring Hairpin Polyamides for recognition of 7-bp 5'-WGASNNW-3'

| | DNA sequence | aromatic amino acid sequence |
|---|---|---|
| 393) | 5'-W G A G T T W-3' | ImPyImHpHp-γ-PyPyPyHpPy |
| 394) | 5'-W G A G T A W-3' | ImPyImHpPy-γ-HpPyPyHpPy |
| 395) | 5'-W G A G T G W-3' | ImPyImHpIm-γ-PyPyPyHpPy |
| 396) | 5'-W G A G T C W-3' | ImPyImHpPy-γ-ImPyPyHpPy |
| 397) | 5'-W G A G A T W-3' | ImPyImPyHp-γ-PyPyPyHpPy |
| 398) | 5'-W G A G A A W-3' | ImPyImPyPy-γ-HpHpPyHpPy |
| 399) | 5'-W G A G A G W-3' | ImPyImPyIm-γ-PyHpPyHpPy |
| 400) | 5'-W G A G A C W-3' | ImPyImPyPy-γ-ImHpPyHpPy |
| 401) | 5'-W G A G G T W-3' | ImPyImImHp-γ-PyPyPyHpPy |
| 402) | 5'-W G A G G A W-3' | ImPyImImPy-γ-HpPyPyHpPy |
| 403) | 5'-W G A G C T W-3' | ImPyImPyHp-γ-PyImPyHpPy |
| 404) | 5'-W G A G C A W-3' | ImPyImPyPy-γ-HpImPyHpPy |
| 405) | 5'-W G A G G G W-3' | ImPyImImIm-γ-PyPyPyHpPy |
| 406) | 5'-W G A G G C W-3' | ImPyImPyPy-γ-ImPyPyHpPy |
| 407) | 5'-W G A G C G W-3' | ImPyImPyIm-γ-PyImPyHpPy |
| 408) | 5'-W G A G C C W-3' | ImPyImPyPy-γ-ImImHpHpPy |
| 409) | 5'-W G A C T T W-3' | ImPyPyImHp-γ-PyHpHpPy |
| 410) | 5'-W G A C T A W-3' | ImPyPyHpPy-γ-HpPyImHpPy |
| 411) | 5'-W G A C T G W-3' | ImPyPyHpIm-γ-PyPyImHpPy |
| 412) | 5'-W G A C T C W-3' | ImPyPyHpPy-γ-ImPyImHpPy |
| 413) | 5'-W G A C A T W-3' | ImPyPyPyHp-γ-PyHpImHpPy |
| 414) | 5'-W G A C A A W-3' | ImPyPyPyPy-γ-HpHpImHpPy |
| 415) | 5'-W G A C A G W-3' | ImPyPyPyIm-γ-PyHpImHpPy |
| 416) | 5'-W G A C A C W-3' | ImPyPyPyPy-γ-ImHpImHpPy |
| 417) | 5'-W G A C G T W-3' | ImPyPyImHp-γ-PyPyImHpPy |
| 418) | 5'-W G A C G A W-3' | ImPyPyImPy-γ-HpPyImHpPy |
| 419) | 5'-W G A C C T W-3' | ImPyPyPyHp-γ-PyImImHpPy |
| 420) | 5'-W G A C C A W-3' | ImPyPyPyPy-γ-HpImImHpPy |
| 421) | 5'-W G A C G G W-3' | ImPyPyImIm-γ-PyPyImHpPy |
| 422) | 5'-W G A C G C W-3' | ImPyPyPyPy-γ-ImPyImHpPy |
| 423) | 5'-W G A C C G W-3' | ImPyPyPyIm-γ-PyImImHpPy |
| 424) | 5'-W G A C C C W-3' | ImPyPyPyPy-γ-ImImImHpPy |

TABLE 26

10-ring Hairpin Polyamides for recognition of 7-bp 5'-WGCWNNW-3'

| | DNA sequence | aromatic amino acid sequence |
|---|---|---|
| 425) | 5'-W G C T T T W-3' | ImImHpHpHp-γ-PyPyPyPyPy |
| 426) | 5'-W G C T T A W-3' | ImPyHpHpPy-γ-HpPyPyImPy |
| 427) | 5'-W G C T T G W-3' | ImPyHpHpIm-γ-PyPyPyImPy |
| 428) | 5'-W G C T T C W-3' | ImPyHpHpPy-γ-ImPyPyImPy |
| 429) | 5'-W G C T A T W-3' | ImPyRpPyHp-γ-PyHpPyImPy |
| 430) | 5'-W G C T A A W-3' | ImPyHpPyPy-γ-HpHpPyImPy |
| 431) | 5'-W G C T A G W-3' | ImPyHpPyIm-γ-PyHpPyImPy |
| 432) | 5'-W G C T A C W-3' | ImPyHpPyPy-γ-ImHpPyImPy |
| 433) | 5'-W G C T G T W-3' | ImPyHpImHp-γ-PyPyPyImPy |
| 434) | 5'-W G C T G A W-3' | ImPyHpImPy-γ-HpPyPyImPy |
| 435) | 5'-W G C T G G W-3' | ImPyHpImIm-γ-PyPyPyImPy |
| 436) | 5'-W G C T G C W-3' | ImPyHpImPy-γ-ImPyPyImPy |
| 437) | 5'-W G C T C T W-3' | ImPyHpPyHp-γ-PyImPyImPy |
| 438) | 5'-W G C T C A W-3' | ImPyHpPyPy-γ-HpImPyImPy |
| 439) | 5'-W G C T C G W-3' | ImPyHpPyIm-γ-PyImPyImPy |
| 440) | 5'-W G C T C C W-3' | ImPyHpPyPy-γ-ImImPyImPy |
| 441) | 5'-W G C A T T W-3' | ImPyPyHpHp-γ-PyPyHpImPy |
| 442) | 5'-W G C A T A W-3' | ImPyPyHpPy-γ-HpPyHpImPy |

TABLE 26-continued 10-ring Hairpin Polyamides for recognition of 7-bp 5'-WGCWNNW-3'

| | DNA sequence | aromatic amino acid sequence |
|---|---|---|
| 443) | 5'-W G C A T G W-3' | ImPyPyHpIm-γ-PyPyHpImPy |
| 444) | 5'-W G C A T C W-3' | ImPyPyHpPy-γ-ImPyHpImPy |
| 445) | 5'-W G C A A T W-3' | ImPyPyPyHp-γ-PyHpHpImPy |
| 446) | 5'-W G C A A A W-3' | ImPyPyPyPy-γ-HpHpHpImPy |
| 447) | 5'-W G C A A G W-3' | ImPyPyPyIm-γ-PyHpHpImPy |
| 448) | 5'-W G C A A C W-3' | ImPyPyPyPy-γ-ImHpHpImPy |
| 449) | 5'-W G C A G T W-3' | ImPyPyImHp-γ-PyPyHpImPy |
| 450) | 5'-W G C A G A W-3' | ImPyPyImPy-γ-HpPyHpImPy |
| 451) | 5'-W G C A G G W-3' | ImPyPyImIm-γ-PyPyHpImPy |
| 452) | 5'-W G C A G C W-3' | ImPyPyImPy-γ-ImPyHpImPy |
| 453) | 5'-W G C A C T W-3' | ImPyPyPyHp-γ-PyImHpImPy |
| 454) | 5'-W G C A C A W-3' | ImPyPyPyPy-γ-HpImHpImPy |
| 455) | 5'-W G C A C G W-3' | ImPyPyPyIm-γ-PyImHpImPy |
| 456) | 5'-W G C A C C W-3' | ImPyPyPyPy-γ-ImImHpImPy |

TABLE 27

10-ring Hairpin Polyamides for recognition of 7-bp 5'-WGCSNNW-3'

| | DNA sequence | aromatic amino acid sequence |
|---|---|---|
| 457) | 5'-W G C G T T W-3' | ImPyImHpHp-γ-PyPyPyImPy |
| 458) | 5'-W G C G T A W-3' | ImPyImHpPy-γ-HpPyPyImPy |
| 459) | 5'-W G C G T G W-3' | ImPyImHpIm-γ-PyPyPyImPy |
| 460) | 5'-W G C G T C W-3' | ImPyImHpPy-γ-ImPyPyImPy |
| 461) | 5'-W G C G A T W-3' | ImPyImPyHp-γ-PyHpPyImPy |
| 462) | 5'-W G C G A A W-3' | ImPyImPyPy-γ-HpHpPyImPy |
| 463) | 5'-W G C G A G W-3' | ImPyImPyIm-γ-PyHpPyImPy |
| 464) | 5'-W G C G A C W-3' | ImPyImPyPy-γ-ImHpPyImPy |
| 465) | 5'-W G C G G T W-3' | ImPyImImHp-γ-PyPyPyImPy |
| 466) | 5'-W G C G G A W-3' | ImPyImImPy-γ-HpPyPyImPy |
| 467) | 5'-W G C G C T W-3' | ImPyImPyHp-γ-PyImPyImPy |
| 468) | 5'-W G C G C A W-3' | ImPyImPyPy-γ-HpImPyImPy |
| 469) | 5'-W G C C T T W-3' | ImPyPyHpHp-γ-PyPyImImPy |
| 470) | 5'-W G C C T A W-3' | ImPyPyHpPy-γ-HpPyImImPy |
| 471) | 5'-W G C C T G W-3' | ImPyPyHpIm-γ-PyPyImImPy |
| 472) | 5'-W G C C T C W-3' | ImPyPyHpPy-γ-ImPyImImPy |
| 473) | 5'-W G C C A T W-3' | ImPyPyPyHp-γ-PyHpImImPy |
| 474) | 5'-W G C C A A W-3' | ImPyPyPyPy-γ-HpHpImImPy |
| 475) | 5'-W G C C A G W-3' | ImPyPyPyIm-γ-PyHpImImPy |
| 476) | 5'-W G C C A C W-3' | ImPyPyPyPy-γ-ImHpImImPy |
| 477) | 5'-W G C C G T W-3' | ImPyPyImHp-γ-PyPyImImPy |
| 478) | 5'-W G C C G A W-3' | ImPyPyImPy-γ-HpPyImImPy |
| 479) | 5'-W G C C C T W-3' | ImPyPyPyHp-γ-PyImImImPy |
| 480) | 5'-W G C C C A W-3' | ImPyPyPyPy-γ-HpImImImPy |
| G25) | 5'-W G C G G G W-3' | ImPyImImIm-γ-PyPyPyImPy |
| G26) | 5'-W G C G G C W-3' | ImPyImImPy-γ-ImPyPyImPy |
| G27) | 5'-W G C G C G W-3' | ImPyImPyIm-γ-PyImPyImPy |
| G28) | 5'-W G C G C C W-3' | ImPyImPyPy-γ-ImImPyImPy |
| G29) | 5'-W G C C G G W-3' | ImPyPyImIm-γ-PyPyImImPy |
| G30) | 5'-W G C C G C W-3' | ImPyPyImPy-γ-ImPyImImPy |
| G31) | 5'-W G C C C G W-3' | ImPyPyPyIm-γ-PyImImImPy |
| G32) | 5'-W G C C C C W-3' | ImPyPyPyPy-γ-ImImImImPy |

TABLE 28

10-ring Hairpin Polyamides for recognition of 7-bp 5'-WCGWNNW-3'

| | DNA sequence | aromatic amino acid sequence |
|---|---|---|
| 481) | 5'-W C G T T T W-3' | PyImHpHpHp-γ-PyPyPyPyIm |
| 482) | 5'-W C G T T A W-3' | PyImHpHpPy-γ-HpPyPyPyIm |
| 483) | 5'-W C G T T G W-3' | PyImHpHpIm-γ-PyPyPyPyIm |
| 484) | 5'-W C G T T C W-3' | PyImHpHpPy-γ-ImPyPyPyIm |
| 485) | 5'-W C G T A T W-3' | PyImHpPyHp-γ-PyHpPyPyIm |
| 486) | 5'-W C G T A A W-3' | PyImHpPyPy-γ-HpHpPyPyIm |
| 487) | 5'-W C G T A G W-3' | PyThHpPyIm-γ-PyHpPyPyIm |

TABLE 28-continued

10-ring Hairpin Polyamides for recognition of 7-bp 5'-WCGWNNW-3'

| | DNA sequence | aromatic amino acid sequence |
|---|---|---|
| 488) | 5'-W C G T A C W-3' | PyImHpPyPy-γ-ImHpPyPyIm |
| 489) | 5'-W C G T G T W-3' | PyImHpImHp-γ-PyPyPyPyIm |
| 490) | 5'-W C G T G A W-3' | PyImHpImPy-γ-HpPyPyPyIm |
| 491) | 5'-W C G T G G W-3' | PyImHpImIm-γ-PyPyPyPyIm |
| 492) | 5'-W C G T G C W-3' | PyImHpImPy-γ-ImPyPyPyIm |
| 493) | 5'-W C G T C T W-3' | PyImHpPyHp-γ-PyImPyPyIm |
| 494) | 5'-W C G T C A W-3' | PyImHpPyPy-γ-HpImPyPyIm |
| 495) | 5'-W C G T C G W-3' | PyImMpPyIm-γ-PyImPyPyIm |
| 496) | 5'-W C G T C C W-3' | PyImHpPyPy-γ-ImImPyPyIm |
| 497) | 5'-W C G A T T W-3' | PyImPyHpHp-γ-PyPyHpPyIm |
| 498) | 5'-W C G A T A W-3' | PyImPyHpPy-γ-HpPyHpPyIm |
| 499) | 5'-W C G A T G W-3' | PyImPyHpIm-γ-PyPyHpPyIm |
| 500) | 5'-W C G A T C W-3' | PyImPyHpPy-γ-ImPyHpPyIm |
| 501) | 5'-W C G A A T W-3' | PyImPyPyHp-γ-PyHpHpPyIm |
| 502) | 5'-W C G A A A W-3' | PyImPyPyPy-γ-HpHpHpPyIm |
| 503) | 5'-W C G A A G W-3' | PyImPyPyIm-γ-PyHpHpPyIm |
| 504) | 5'-W C G A A C W-3' | PyImPyPyPy-γ-ImHpHpPyIm |
| 505) | 5'-W C G A G T W-3' | PyImPyImHp-γ-PyPyHpPyIm |
| 506) | 5'-W C G A G A W-3' | PyImPyImPy-γ-HpPyHpPyIm |
| 507) | 5'-W C G A G G W-3' | PyImPyImIm-γ-PyPyHpPyIm |
| 508) | 5'-W C G A G C W-3' | PyImPyImPy-γ-ImPyHpPyIm |
| 509) | 5'-W C G A C T W-3' | PyImPyPyHp-γ-PyImHpPyIm |
| 510) | 5'-W C G A C A W-3' | PyImPyPyPy-γ-HpImHpPyIm |
| 511) | 5'-W C G A C G W-3' | PyImPyPyIm-γ-PyImHpPyIm |
| 512) | 5'-W C G A C C W-3' | PyImPyPyPy-γ-ImImHpPyIm |

TABLE 29

10-ring Hairpin Polyamides for recognition of 7-bp 5'-WCGSNNW-3'

| | DNA sequence | aromatic amino acid sequence |
|---|---|---|
| 513) | 5'-W C G G T T W-3' | PyImImHpHp-γ-PyPyPyPyIm |
| 514) | 5'-W C G G T A W-3' | PyImImHpPy-γ-HpPyPyPyIm |
| 515) | 5'-W C G G T G W-3' | PyImImHpIm-γ-PyPyPyPyIm |
| 516) | 5'-W C G G T C W-3' | PyImImHpPy-γ-ImPyPyPyIm |
| 517) | 5'-W C G G A T W-3' | PyImImPyHp-γ-PyHpPyPyIm |
| 518) | 5'-W C G G A A W-3' | PyImImPyPy-γ-HpHpPyPyIm |
| 519) | 5'-W C G G A G W-3' | PyImImPyIm-γ-PyHpPyPyIm |
| 520) | 5'-W C G G A C W-3' | PyImImPyPy-γ-ImHpPyPyIm |
| 521) | 5'-W C G G G T W-3' | PyImImImHp-γ-PyPyPyPyIm |
| 522) | 5'-W C G G G A W-3' | PyImImImPy-γ-HpPyPyPyIm |
| 523) | 5'-W C G G C T W-3' | PyImImPyHp-γ-PyImPyPyIm |
| 524) | 5'-W C G G C A W-3' | PyImImPyPy-γ-HpImPyPyIm |
| 525) | 5'-W C G C T T W-3' | PyImPyHpHp-γ-PyPyImPyIm |
| 526) | 5'-W C G C T A W-3' | PyImPyHpPy-γ-HpPyImPyIm |
| 527) | 5'-W C G C T G W-3' | PyImPyHpIm-γ-PyPyImPyIm |
| 528) | 5'-W C G C T C W-3' | PyImPyHpPy-γ-ImPyImPyIm |
| 529) | 5'-W C G C A T W-3' | PyImPyPyHp-γ-PyHpImPyIm |
| 530) | 5'-W C G C A A W-3' | PyImPyPyPy-γ-HpHpImPyIm |
| 531) | 5'-W C G C A G W-3' | PyImPyPyIm-γ-PyHpImPyIm |
| 532) | 5'-W C G C A C W-3' | PyImPyPyPy-γ-ImHpImPyIm |
| 533) | 5'-W C G C G T W-3' | PyImPyImHp-γ-PyPyImPyIm |
| 534) | 5'-W C G C G A W-3' | PyImPyImPy-γ-HpPyImPyIm |
| 535) | 5'-W C G C C T W-3' | PyImPyPyHp-γ-PyImImPyIm |
| 536) | 5'-W C G C C A W-3' | PyImPyPyPy-γ-HpImImPyIm |
| G33) | 5'-W C G G G G W-3' | PyImImImIm-γ-PyPyPyPyIm |
| G34) | 5'-W C G G G C W-3' | PyImImImPy-γ-ImPyPyPyIm |
| G35) | 5'-W C G G C G W-3' | PyImImPyIm-γ-PyImPyPyIm |
| G36) | 5'-W C G G C C W-3' | PyImImPyPy-γ-ImImPyPyIm |
| G37) | 5'-W C G C G G W-3' | PyImPyImIm-γ-PyPyImPyIm |
| G38) | 5'-W C C C G C W-3' | PyImPyImPy-γ-ImPyImPyIm |
| G39) | 5'-W C G C C G W-3' | PyImPyPyIm-γ-PyImImPyIm |
| G40) | 5'-W C G C C C W-3' | PyImPyPyPy-γ-ImImImPyIm |

TABLE 30

10-ring Hairpin Polyamides for recognition of 7-bp 5'-WCTWNNW-3'

| | DNA sequence | aromatic amino acid sequence |
|---|---|---|
| 537) | 5'-W C T T T T W-3' | PyHpHpHpHp-γ-PyPyPyPyIm |
| 538) | 5'-W C T T T A W-3' | PyHpHpHpPy-γ-HpPyPyPyIm |
| 539) | 5'-W C T T T G W-3' | PyHpHpHpIm-γ-PyPyPyPyIm |
| 540) | 5'-W C T T T C W-3' | PyHpHpHpPy-γ-ImPyPyPyIm |
| 541) | 5'-W C T T A T W-3' | PyHpHpPyHp-γ-PyHpPyPyIm |
| 542) | 5'-W C T T A A W-3' | PyHpHpPyPy-γ-HpHpPyPyIm |
| 543) | 5'-W C T T A G W-3' | PyHpHpPyIm-γ-PyHpPyPyIm |
| 544) | 5'-W C T T A C W-3' | PyHpHpPyPy-γ-ImHpPyPyIm |
| 545) | 5'-W C T T G T W-3' | PyHpHpImHp-γ-PyPyPyPyIm |
| 546) | 5'-W C T T G A W-3' | PyHpHpImPy-γ-HpPyPyPyIm |
| 547) | 5'-W C T T G G W-3' | PyHpHpImIm-γ-PyPyPyPyIm |
| 548) | 5'-W C T T G C W-3' | PyHpHpImPy-γ-ImPyPyPyIm |
| 549) | 5'-W C T T C T W-3' | PyHpHpPyHp-γ-PyImPyPyIm |
| 550) | 5'-W C T T C A W-3' | PyHpHpPyPy-γ-HpImPyPyIm |
| 551) | 5'-W C T T C G W-3' | PyHpHpPyIm-γ-PyImPyPyIm |
| 552) | 5'-W C T T C C W-3' | PyHpHpPyPy-γ-ImImPyPyIm |
| 553) | 5'-W C T A T T W-3' | PyHpPyHpHp-γ-PyPyHpPyIm |
| 554) | 5'-W C T A T A W-3' | PyRPPyHpPy-γ-HpPyHpPyIm |
| 555) | 5'-W C T A T G W-3' | PyHpPyHpIm-γ-PyPyHpPyIm |
| 556) | 5'-W C T A T C W-3' | PyHpPyHpPy-γ-ImPyHpPyIm |
| 557) | 5'-W C T A A T W-3' | PyHpPyPyHp-γ-PyHpHpPyIm |
| 558) | 5'-W C T A A A W-3' | PyHPPyPyPy-γ-HpHpHpPyIm |
| 559) | 5'-W C T A A G W-3' | PyHpPyPyIm-γ-PyHpHpPyIm |
| 560) | 5'-W C T A A C W-3' | PyHpPyPyPy-γ-ImHpHpPyIm |
| 561) | 5'-W C T A G T W-3' | PyHpPyImHp-γ-PyPyHpPyIm |
| 562) | 5'-W C T A G A W-3' | PyHpPyImPy-γ-HpPyHpPyIm |
| 563) | 5'-W C T A G G W-3' | PyHpPyImIm-γ-PyPyHpPyIm |
| 564) | 5'-W C T A G C W-3' | PyHpPyImPy-γ-ImPyHpPyIm |
| 565) | 5'-W C T A C T W-3' | PyHpPyPyHp-γ-PyImnpPyIm |
| 566) | 5'-W C T A C A W-3' | PyHpPyPyPy-γ-HpImHpPyIm |
| 567) | 5'-W C T A C G W-3' | PyHpPyPyIm-γ-PyImHpPyIm |
| 568) | 5'-W C T A C C W-3' | PyHpPyPyPy-γ-ImImHpPyIm |

TABLE 31

10-ring Hairpin Polyamides for recognition of 7-bp 5'-WCTSNNW-3'

| | DNA sequence | aromatic amino acid sequence |
|---|---|---|
| 569) | 5'-W C T G T T W-3' | PyHpImHpHp-γ-PyPyPyPyIm |
| 570) | 5'-W C T G T A W-3' | PyHpImHpPy-γ-HpPyPyPyIm |
| 571) | 5'-W C T G T G W-3' | PyHpImHpIm-γ-PyPyPyPyIm |
| 572) | 5'-W C T G T C W-3' | PyHpImHpPy-γ-ImPyPyPyIm |
| 573) | 5'-W C T G A T W-3' | PyHpImPyHp-γ-PyHpPyPyIm |
| 574) | 5'-W C T G A A W-3' | PyHpImPyPy-γ-HpHpPyPyIm |
| 575) | 5'-W C T G A G W-3' | PyHpImPyIm-γ-PyHpPyPyIm |
| 576) | 5'-W C T G A C W-3' | PyHpImPyPy-γ-ImHpPyPyIm |
| 577) | 5'-W C T G G T W-3' | PyHpImImHp-γ-PyPyPyPyIm |
| 578) | 5'-W C T G G A W-3' | PyHpImImPy-γ-HpPyPyPyIm |
| 579) | 5'-W C T G C T W-3' | PyHpImPyHp-γ-PyImPyPyIm |
| 580) | 5'-W C T G C A W-3' | PyHpImPyPy-γ-HpImPyPyIm |
| 581) | 5'-W C T G G G W-3' | PyHpImImIm-γ-PyPyPyPyIm |
| 582) | 5'-W C T G G C W-3' | PyHpImImPy-γ-ImPyPyPyIm |
| 583) | 5'-W C T G C G W-3' | PyHpImPyIm-γ-PyImPyPyIm |
| 584) | 5'-W C T G C C W-3' | PyHpImPyPy-γ-ImImPyPyIm |
| 585) | 5'-W C T C T T W-3' | PyHpPyHpHp-γ-PyPyImPyIm |
| 586) | 5'-W C T C T A W-3' | PyHpPyHpPy-γ-HpPyImPyIm |
| 587) | 5'-W C T C T G W-3' | PyHpPyHpIm-γ-PyPyImPyIm |
| 588) | 5'-W C T C T C W-3' | PyHpPyHpPy-γ-ImPyImPyIm |
| 589) | 5'-W C T C A T W-3' | PyHpPyPyHp-γ-PyHpImPyIm |
| 590) | 5'-W C T C A A W-3' | PyHpPyPyPy-γ-HpHpImPyIm |
| 591) | 5'-W C T C A G W-3' | PyHpPyPyIm-γ-PyHpImPyIm |
| 592) | 5'-W C T C A C W-3' | PyHpPyPyPy-γ-ImHpImPyIm |
| 593) | 5'-W C T C G T W-3' | PyHpPyImHp-γ-PyPyImPyIm |
| 594) | 5'-W C T C G A W-3' | PyHpPyImPy-γ-HpPyImPyIm |
| 595) | 5'-W C T C C T W-3' | PyHpPyPyHp-γ-PyImImPyIm |
| 596) | 5'-W C T C C A W-3' | PyHpPyPyPy-γ-HpImImPyIm |
| 597) | 5'-W C T C G G W-3' | PyHpPyImIm-γ-PyPyImPyIm |
| 598) | 5'-W C T C G C W-3' | PyHpPyImPy-γ-ImPyImPyIm |
| 599) | 5'-W C T C C G W-3' | PyHpPyPyIm-γ-PyImImPyIm |
| 600) | 5'-W C T C C C W-3' | PyHpPyPyPy-γ-ImImImPyIm |

TABLE 32

10-ring Hairpin Polyamides for recognition of 7-bp 5'-WCAWNNW-3'

| | DNA sequence | aromatic amino acid sequence |
|---|---|---|
| 601) | 5'-W C A T T T W-3' | PyPyHpHpHp-γ-PyPyPyHpIm |
| 602) | 5'-W C A T T A W-3' | PyPyHpHpPy-γ-HpPyPyHpIm |
| 603) | 5'-W C A T T G W-3' | PyPyHpHpIm-γ-PyPyPyHpIm |
| 604) | 5'-W C A T T C W-3' | PyPyHpHpPy-γ-ImPyPyHpIm |
| 605) | 5'-W C A T A T W-3' | PyPyHpPyHp-γ-PyHpPyHpIm |
| 606) | 5'-W C A T A A W-3' | PyPyHpPyPy-γ-HpHpPyHpIm |
| 607) | 5'-W C A T A G W-3' | PyPyHpPyIm-γ-PyHpPyHpIm |
| 608) | 5'-W C A T A C W-3' | PyPyHpPyPy-γ-ImHpPyHpIm |
| 609) | 5'-W C A T G T W-3' | PyPyHpImHp-γ-PyPyPyHpIm |
| 610) | 5'-W C A T G A W-3' | PyPyHpImPy-γ-HpPyPyHpIm |
| 611) | 5'-W C A T G G W-3' | PyPyHpImIm-γ-PyPyPyHpIm |
| 612) | 5'-W C A T G C W-3' | PyPyHpImPy-γ-ImPyPyHpIm |
| 613) | 5'-W C A T C T W-3' | PyPyHpPyHp-γ-PyImPyHpIm |
| 614) | 5'-W C A T C A W-3' | PyPyHpPyPy-γ-HpImPyHpIm |
| 615) | 5'-W C A T C G W-3' | PyPyHpPyIm-γ-PyImPyHpIm |
| 616) | 5'-W C A T C C W-3' | PyPyHpPyPy-γ-ImImPyHpIm |
| 617) | 5'-W C A A T T W-3' | PyPyPyHpHp-γ-PyPyHpHpIm |
| 618) | 5'-W C A A T A W-3' | PyPyPyHpPy-γ-HpPyHpHpIm |
| 619) | 5'-W C A A T G W-3' | PyPyPyHpIm-γ-PyPyHpHpIm |
| 620) | 5'-W C A A T C W-3' | PyPyPyHpPy-γ-ImPyHpHpIm |
| 621) | 5'-W C A A A T W-3' | PyPyPyPyHp-γ-PyHpHpHpIm |
| 622) | 5'-W C A A A A W-3' | PyPyPyPyPy-γ-HpHpHpHpIm |
| 623) | 5'-W C A A A G W-3' | PyPyPyPyIm-γ-PyHpHpHpIm |
| 624) | 5'-W C A A A C W-3' | PyPyPyPyPy-γ-ImHpHpHpIm |
| 625) | 5'-W C A A G T W-3' | PyPyPyImHp-γ-PyPyHpHpIm |
| 626) | 5'-W C A A G A W-3' | PyPyPyImPy-γ-HpPyHpHpIm |
| 627) | 5'-W C A A G G W-3' | PyPyPyImIm-γ-PyPyHpHpIm |
| 628) | 5'-W C A A G C W-3' | PyPyPyImPy-γ-ImPyHpHpIm |
| 629) | 5'-W C A A C T W-3' | PyPyPyPyHp-γ-PyImHpHpIm |
| 630) | 5'-W C A A C A W-3' | PyPyPyPyPy-γ-HpImHpHpIm |
| 631) | 5'-W C A A C G W-3' | PyPyPyPyIm-γ-PyImHpHpIm |
| 632) | 5'-W C A A C C W-3' | PyPyPyPyPy-γ-ImImHpHpIm |

TABLE 33

10-ring Hairpin Polyamides for recognition of 7-bp 5'-WCASNNW-3'

| | DNA sequence | aromatic amino acid sequence |
|---|---|---|
| 633) | 5'-W C A G T T W-3' | PyPyImHpHp-γ-PyPyPyHpIm |
| 634) | 5'-W C A G T A W-3' | PyPyImHpPy-γ-HpPyPyHpIm |
| 635) | 5'-W C A G T G W-3' | PyPyImHpIm-γ-PyPyPyHpIm |
| 636) | 5'-W C A G T C W-3' | PyPyImHpPy-γ-ImPyPyHpIm |
| 637) | 5'-W C A G A T W-3' | PyPyImPyHp-γ-PyHpPyHpIm |
| 638) | 5'-W C A G A A W-3' | PyPyImPyPy-γ-HpHpPyHpIm |
| 639) | 5'-W C A G A G W-3' | PyPyImPyIm-γ-PyHpPyHpIm |
| 640) | 5'-W C A G A C W-3' | PyPyImPyPy-γ-ImHpPyHpIm |
| 641) | 5'-W C A G G T W-3' | PyPyImImHp-γ-PyPyPyHpIm |
| 642) | 5'-W C A G G A W-3' | PyPyImImPy-γ-HpPyPyHpIm |
| 643) | 5'-W C A G C T W-3' | PyPyImPyHp-γ-PyImPyHpIm |
| 644) | 5'-W C A G C A W-3' | PyPyImPyPy-γ-HpImPyHpIm |
| 645) | 5'-W C A G G G W-3' | PyPyImImIm-γ-PyPyPyHpIm |
| 646) | 5'-W C A G G C W-3' | PyPyImImPy-γ-ImPyPyHpIm |
| 647) | 5'-W C A G C G W-3' | PyPyImPyIm-γ-PyImPyHpIm |
| 648) | 5'-W C A G C C W-3' | PyPyImPyPy-γ-ImImPyHpIm |
| 649) | 5'-W C A C T T W-3' | PyPyPyHpHp-γ-PyPyImHpIm |
| 650) | 5'-W C A C T A W-3' | PyPyPyHpPy-γ-HpPyImHpIm |
| 651) | 5'-W C A C T G W-3' | PyPyPyHpIm-γ-PyPyImHpIm |
| 652) | 5'-W C A C T C W-3' | PyPyPyHpPy-γ-ImPyImHpIm |
| 653) | 5'-W C A C A T W-3' | PyPyPyPyHp-γ-PyHpImHpIm |
| 654) | 5'-W C A C A A W-3' | PyPyPyPyPy-γ-HpHpImHpIm |
| 655) | 5'-W C A C A G W-3' | PyPyPyPyIm-γ-PyHpImHpIm |
| 656) | 5'-W C A C A C W-3' | PyPyPyPyPy-γ-ImHpImHpIm |
| 657) | 5'-W C A C G T W-3' | PyPyPyImHp-γ-PyPyImHpIm |
| 658) | 5'-W C A C G A W-3' | PyPyPyImPy-γ-HpPyImHpIm |
| 659) | 5'-W C A C C T W-3' | PyPyPyPyHp-γ-PyImImHpIm |
| 660) | 5'-W C A C C A W-3' | PyPyPyPyPy-γ-HpImImHpIm |
| 661) | 5'-W C A C G G W-3' | PyPyPyImIm-γ-PyPyImHpIm |

TABLE 33-continued

10-ring Hairpin Polyamides for recognition of 7-bp 5'-WCASNNW-3'

| | DNA sequence | aromatic amino acid sequence |
|---|---|---|
| 662) | 5'-W C A C G C W-3' | PyPyPyImPy-γ-ImPyImHpIm |
| 663) | 5'-W C A C C G W-3' | PyPyPyPyIm-γ-PyImImHpIm |
| 664) | 5'-W C A C C C W-3' | PyPyPyPyPy-γ-ImImImHpIm |

TABLE 34

10-ring Hairpin Polyamides for recognition of 7-bp 5'-WCCWNNW-3'

| | DNA sequence | aromatic amino acid sequence |
|---|---|---|
| 665) | 5'-W C C T T T W-3' | PyPyHpHpHp-γ-PyPyPyImIm |
| 666) | 5'-W C C T T A W-3' | PyPyHpHpPy-γ-HpPyPyImIm |
| 667) | 5'-W C C T T G W-3' | PyPyHpHpIm-γ-PyPyPyImIm |
| 668) | 5'-W C C T T C W-3' | PyPyHpHpPy-γ-ImPyPyImIm |
| 669) | 5'-W C C T A T W-3' | PyPyHpPyHp-γ-PyHpPyImIm |
| 670) | 5'-W C C T A A W-3' | PyPyHpPyPy-γ-HpHpPyImIm |
| 671) | 5'-W C C T A G W-3' | PyPyHpPyIm-γ-PyHpPyImIm |
| 672) | 5'-W C C T A C W-3' | PyPyHpPyPy-γ-ImHpPyImIm |
| 673) | 5'-W C C T G T W-3' | PyPyHpImHp-γ-PyPyPyImIm |
| 674) | 5'-W C C T G A W-3' | PyPyHpImPy-γ-HpPyPyImIm |
| 675) | 5'-W C C T G G W-3' | PyPyHpImIm-γ-PyPyPyImIm |
| 676) | 5'-W C C T G C W-3' | PyPyHpImPy-γ-ImPyPyImIm |
| 677) | 5'-W C C T C T W-3' | PyPyHpPyHp-γ-PyImPyImIm |
| 678) | 5'-W C C T C A W-3' | PyPyHpPyPy-γ-HpImPyImIm |
| 679) | 5'-W C C T C G W-3' | PyPyHpPyIm-γ-PyImPyImIm |
| 680) | 5'-W C C T C C W-3' | PyPyHpPyPy-γ-ImImPyImIm |
| 681) | 5'-W C C A T T W-3' | PyPyPyHpHp-γ-PyPyHpImIm |
| 682) | 5'-W C C A T A W-3' | PyPyPyHpPy-γ-HpPyHpImIm |
| 683) | 5'-W C C A T G W-3' | PyPyPyHpIm-γ-PyPyHpImIm |
| 684) | 5'-W C C A T C W-3' | PyPyPyHpPy-γ-ImPyHpImIm |
| 685) | 5'-W C C A A T W-3' | PyPyPyPyHp-γ-PyHpHpImIm |
| 686) | 5'-W C C A A A W-3' | PyPyPyPyPy-γ-HpHpHpImIm |
| 687) | 5'-W C C A A G W-3' | PyPyPyPyIm-γ-PyHpHpImIm |
| 688) | 5'-W C C A A C W-3' | PyPyPyPyPy-γ-ImHpHpImIm |
| 689) | 5'-W C C A G T W-3' | PyPyPyImHp-γ-PyPyHpImIm |
| 690) | 5'-W C C A G A W-3' | PyPyPyImPy-γ-HpPyHpImIm |
| 691) | 5'-W C C A G G W-3' | PyPyPyImIm-γ-PyPyHpImIm |
| 692) | 5'-W C C A G C W-3' | PyPyPyImPy-γ-ImPyHpImIm |
| 693) | 5'-W C C A C T W-3' | PyPyPyPyHp-γ-PyImHpImIm |
| 694) | 5'-W C C A C A W-3' | PyPyPyPyPy-γ-HpImHpImIm |
| 695) | 5'-W C C A C G W-3' | PyPyPyPyIm-γ-PyImHpImIm |
| 696) | 5'-W C C A C C W-3' | PyPyPyPyPy-γ-ImImHpImIm |

TABLE 35

10-ring Hairpin Polyamides for recognition of 7-bp 5'-WCCSNNW-3'

| | DNA sequence | aromatic amino acid sequence |
|---|---|---|
| 697) | 5'-W C C G T T W-3' | PyPyImHpHp-γ-PyPyPyImIm |
| 698) | 5'-W C C G T A W-3' | PyPyImHpPy-γ-HpPyPyImIm |
| 699) | 5'-W C C G T G W-3' | PyPyImHpIm-γ-PyPyPyImIm |
| 700) | 5'-W C C G T C W-3' | PyPyImHpPy-γ-ImPyPyImIm |
| 701) | 5'-W C C G A T W-3' | PyPyImPyHp-γ-PyHpPyImIm |
| 702) | 5'-W C C G A A W-3' | PyPyImPyPy-γ-HpHpPyImIm |
| 703) | 5'-W C C G A G W-3' | PyPyImPyIm-γ-PyHpPyImIm |
| 704) | 5'-W C C G A C W-3' | PyPyImPyPy-γ-ImHpPyImIm |
| 705) | 5'-W C C G G T W-3' | PyPyImImHp-γ-PyPyPyImIm |
| 706) | 5'-W C C G G A W-3' | PyPyImImPy-γ-HpPyPyImIm |
| 707) | 5'-W C C G C T W-3' | PyPyImPyHp-γ-PyImPyImIm |
| 708) | 5'-W C C G C A W-3' | PyPyImPyPy-γ-HpImPyImIm |
| 709) | 5'-W C C T T T W-3' | PyPyHpHpHp-γ-PyPyIm PyImIm |
| 710) | 5'-W C C T A W-3' | PyPyHpHpPy-γ-HpPyPyImIm |
| 711) | 5'-W C C T G W-3' | PyPyHpHpIm-γ-PyPyPyImIm |
| 712) | 5'-W C C C T C W-3' | PyPyHpHpPy-γ-ImPyImImIm |
| 713) | 5'-W C C C A T W-3' | PyPyPyHp-γ-PyHpImImIm |
| 714) | 5'-W C C C A A W-3' | PyPyPyPy-γ-HpHpImImIm |

TABLE 35-continued 10-ring Hairpin Polyamides for recognition of
7-bp 5'-WCCSNNW-3'

| | DNA sequence | aromatic amino acid sequence |
|---|---|---|
| 715) | 5'-W C C C A G W-3' | PyPyPyPyIm-γ-PyHpImImIm |
| 716) | 5'-W C C C A C W-3' | PyPyPyPyPy-γ-ImHpImImIm |
| 717) | 5'-W C C C G T W-3' | PyPyPyImHp-γ-PyPyImImIm |
| 718) | 5'-W C C C G A W-3' | PyPyPyImPy-γ-HpPyImImIm |
| 719) | 5'-W C C C C T W-3' | PyPyPyPyHp-γ-PyImImImIm |
| 720) | 5'-W C C C C A W-3' | PyPyPyPyPy-γ-HpImImImIm |
| G41) | 5'-W C C G G G W-3' | PyPyImImIm-γ-PyPyPyImIm |
| G42) | 5'-W C C G G C W-3' | PyPyImImPy-γ-ImPyPyImIm |
| G43) | 5'-W C C G C G W-3' | PyPyImPyIm-γ-PyImPyImIm |
| G44) | 5'-W C C G C C W-3' | PyPyImPyPy-γ-ImImPyImIm |
| G45) | 5'-W C C C G G W-3' | PyPyImImIm-γ-PyPyImImIm |
| G46) | 5'-W C C C G C W-3' | PyPyImImPy-γ-ImPyImImIm |
| G47) | 5'-W C C C C G W-3' | PyPyPyPyIm-γ-PyImImImIm |
| G48) | 5'-W C C C C C W-3' | PyPyPyPyPy-γ-ImImImImIm |

TABLE 36

10-ring Hairpin Polyamides for recognition of
7-bp 5'-WAGWNNW-3'

| | DNA sequence | aromatic amino acid sequence |
|---|---|---|
| 721) | 5'-W A G T T T W-3' | PyImHpHpHp-γ-PyPyPyPyHp |
| 722) | 5'-W A G T T A W-3' | PyImHpHpPy-γ-HpPyPyPyHp |
| 723) | 5'-W A G T T G W-3' | PyImHpHpIm-γ-PyPyPyPyHp |
| 724) | 5'-W A G T T C W-3' | PyImHpHpPy-γ-ImPyPyPyHp |
| 725) | 5'-W A G T A T W-3' | PyImHpPyHp-γ-PyHpPyPyHp |
| 726) | 5'-W A G T A A W-3' | PyImHpPyPy-γ-HpHpPyPyHp |
| 727) | 5'-W A G T A G W-3' | PyImHpPyIm-γ-PyHpPyPyHp |
| 728) | 5'-W A G T A C W-3' | PyImHpPyPy-γ-ImHpPyPyHp |
| 729) | 5'-W A G T G T W-3' | PyImHpImHp-γ-PyPyPyPyHp |
| 730) | 5'-W A G T G A W-3' | PyImHpImPy-γ-HpPyPyPyHp |
| 731) | 5'-W A G T G G W-3' | PyImHpImIm-γ-PyPyPyPyHp |
| 732) | 5'-W A G T G C W-3' | PyImHpImPy-γ-ImPyPyPyHp |
| 733) | 5'-W A G T C T W-3' | PyImHpPyHp-γ-PyImPyPyHp |
| 734) | 5'-W A G T C A W-3' | PyImHpPyPy-γ-HpImPyPyHp |
| 735) | 5'-W A G T C G W-3' | PyImHpPyIm-γ-PyImPyPyHp |
| 736) | 5'-W A G T C C W-3' | PyImHpPyPy-γ-ImImPyPyHp |
| 737) | 5'-W A G A T T W-3' | PyImPyHpHp-γ-PyPyHpPyHp |
| 738) | 5'-W A G A T A W-3' | PyImPyHpPy-γ-HpPyHpPyHp |
| 739) | 5'-W A G A T G W-3' | PyImPyHpIm-γ-PyPyHpPyHp |
| 740) | 5'-W A G A T C W-3' | PyImPyHpPy-γ-ImPyHpPyHp |
| 741) | 5'-W A G A A T W-3' | PyImPyPyHp-γ-PyHpHpPyHp |
| 742) | 5'-W A G A A A W-3' | PyImPyPyPy-γ-HpHpHpPyHp |
| 743) | 5'-W A G A A G W-3' | PyImPyPyIm-γ-PyHpHpPyHp |
| 744) | 5'-W A G A A C W-3' | PyImPyPyPy-γ-ImHpHpPyHp |
| 745) | 5'-W A G A G T W-3' | PyImPyImHp-γ-PyPyHpPyHp |
| 746) | 5'-W A G A G A W-3' | PyImPyImPy-γ-HpPyHpPyHp |
| 747) | 5'-W A G A G G W-3' | PyImPyImIm-γ-PyPyHpPyHp |
| 748) | 5'-W A G A G C W-3' | PyImPyImPy-γ-ImPyHpPyHp |
| 749) | 5'-W A G A C T W-3' | PyImPyPyHp-γ-PyImHpPyHp |
| 750) | 5'-W A G A C A W-3' | PyImPyPyPy-γ-HpImHpPyHp |
| 751) | 5'-W A G A C G W-3' | PyImPyPyIm-γ-PyImHpPyHp |
| 752) | 5'-W A G A C C W-3' | PyImPyPyPy-γ-ImImHpPyHp |

TABLE 37

10-ring Hairpin Polyamides for recognition of
7-bp 5'-WAGSNNW-3'

| | DNA sequence | aromatic amino acid sequence |
|---|---|---|
| 753) | 5'-W A G G T T W-3' | PyImImHpHp-γ-PyPyPyPyHp |
| 754) | 5'-W A G G T A W-3' | PyImImHpPy-γ-HpPyPyPyHp |
| 755) | 5'-W A G G T G W-3' | PyImImHpIm-γ-PyPyPyPyHp |
| 756) | 5'-W A G G T C W-3' | PyImImHpPy-γ-ImPyPyPyHp |
| 757) | 5'-W A G G A T W-3' | PyImImPyHp-γ-PyHpPyPyHp |
| 758) | 5'-W A C C A A W-3' | PyImImPyPy-γ-HpHpPyPyHp |
| 759) | 5'-W A G G A G W-3' | PyImImPyIm-γ-PyHpPyPyHp |

TABLE 37-continued 10-ring Hairpin Polyamides for recognition of
7-bp 5'-WAGSNNW-3'

| | DNA sequence | aromatic amino acid sequence |
|---|---|---|
| 760) | 5'-W A C G A C W-3' | PyImImPyPy-γ-ImHpPyPyHp |
| 761) | 5'-W A G G G T W-3' | PyImImImHp-γ-PyPyPyPyHp |
| 762) | 5'-W A C G C A W-3' | PyImImImPy-γ-HpPyPyPyHp |
| 763) | 5'-W A C G C T W-3' | PyImImPyHp-γ-PyImPyPyHp |
| 764) | 5'-W A G G C A W-3' | PyImImPyPy-γ-HpImPyPyHp |
| 765) | 5'-W A C C T T W-3' | PyImPyHpHp-γ-PyPyImPyHp |
| 766) | 5'-W A C C T A W-3' | PyImPyHpPy-γ-HpPyImPyHp |
| 767) | 5'-W A G C T G W-3' | PyImPyHpIm-γ-PyPyImPyHp |
| 768) | 5'-W A G C T C W-3' | PyImPyHpPy-γ-ImPyImPyHp |
| 769) | 5'-W A G C A T W-3' | PyImPyPyHp-γ-PyHpImPyHp |
| 770) | 5'-W A G C A A W-3' | PyImPyPyPy-γ-HpHpImPyHp |
| 771) | 5'-W A G C A G W-3' | PyImPyPyIm-γ-PyHpImPyHp |
| 772) | 5'-W A G C A C W-3' | PyImPyPyPy-γ-ImHpImPyHp |
| 773) | 5'-W A G C G T W-3' | PyImPyImHp-γ-PyPyImPyHp |
| 774) | 5'-W A C C C A W-3' | PyImPyImPy-γ-HpPyImPyHp |
| 775) | 5'-W A G C C T W-3' | PyImPyPyHp-γ-PyImImPyHp |
| 776) | 5'-W A C C C A W-3' | PyImPyPyPy-γ-HpImImPyHp |
| 777) | 5'-W A G C G G W-3' | PyImImImIm-γ-PyPyPyPyHp |
| 778) | 5'-W A G G G C W-3' | PyImImImPy-γ-ImPyPyPyHp |
| 779) | 5'-W A C G C C W-3' | PyImImPyIm-γ-PyImPyPyHp |
| 780) | 5'-W A G G C C W-3' | PyImImPyPy-γ-ImImPyPyHp |
| 781) | 5'-W A C C C C W-3' | PyImPyImIm-γ-PyPyImPyHp |
| 782) | 5'-W A G C C C W-3' | PyImPyImPy-γ-ImPyImPyHp |
| 783) | 5'-W A C C C G W-3' | PyImPyPyIm-γ-PyImImPyHp |
| 784) | 5'-W A G C C C W-3' | PyImPyPyPy-γ-ImImImPyHp |

TABLE 38

10-ring Hairpin Polyamides for recognition of
7-bp 5'-WATWNNW-3'

| | DNA sequence | aromatic amino acid sequence |
|---|---|---|
| 785) | 5'-W A T T T T W-3' | PyHpHpHpHp-γ-PyPyPyPyHp |
| 786) | 5'-W A T T T A W-3' | PyHpHpHpPy-γ-HpPyPyPyHp |
| 787) | 5'-W A T T T G W-3' | PyHpHpHpIm-γ-PyPyPyPyHp |
| 788) | 5'-W A T T T C W-3' | PyHpHpHpPy-γ-ImPyPyPyHp |
| 789) | 5'-W A T T A T W-3' | PyHpHpPyHp-γ-PyHpPyPyHp |
| 790) | 5'-W A T T A A W-3' | PyHpHpPyPy-γ-HpHpPyPyHp |
| 791) | 5'-W A T T A G W-3' | PyHpHpPyIm-γ-PyHpPyPyHp |
| 792) | 5'-W A T T A C W-3' | PyHpHpPyPy-γ-ImHpPyPyHp |
| 793) | 5'-W A T T G T W-3' | PyHpHpImHp-γ-PyPyPyPyHp |
| 794) | 5'-W A T T G A W-3' | PyHpHpImPy-γ-HpPyPyPyHp |
| 795) | 5'-W A T T G G W-3' | PyHpHpImIm-γ-PyPyPyPyHp |
| 796) | 5'-W A T T G C W-3' | PyHpHpImPy-γ-ImPyPyPyHp |
| 797) | 5'-W A T T C T W-3' | PyHpHpPyHp-γ-PyImPyPyHp |
| 798) | 5'-W A T T C A W-3' | PyHpHpPyPy-γ-HpImPyPyHp |
| 799) | 5'-W A T T C G W-3' | PyHpHpPyIm-γ-PyImPyPyHp |
| 800) | 5'-W A T T C C W-3' | PyHpHpPyPy-γ-ImImPyPyHp |
| 801) | 5'-W A T A T T W-3' | PyHpPyHpHp-γ-PyPyHpPyHp |
| 802) | 5'-W A T A T A W-3' | PyHpPyHpPy-γ-HpPyHpPyHp |
| 803) | 5'-W A T A T G W-3' | PyHpPyHpIm-γ-PyPyHpPyHp |
| 804) | 5'-W A T A T C W-3' | PyHpPyHpPy-γ-ImPyHpPyHp |
| 805) | 5'-W A T A A T W-3' | PyHpPyPyHp-γ-PyHpHpPyHp |
| 806) | 5'-W A T A A A W-3' | PyHpPyPyPy-γ-HpHpHpPyHp |
| 807) | 5'-W A T A A G W-3' | PyHpPyPyIm-γ-PyHpHpPyHp |
| 808) | 5'-W A T A A C W-3' | PyHpPyPyPy-γ-ImHpHpPyHp |
| 809) | 5'-W A T A G T W-3' | PyHpPyImHp-γ-PyPyHpPyHp |
| 810) | 5'-W A T A G A W-3' | PyHpPyImPy-γ-HpPyHpPyHp |
| 811) | 5'-W A T A G G W-3' | PyHpPyImIm-γ-PyPyHpPyHp |
| 812) | 5'-W A T A G C W-3' | PyHpPyImPy-γ-ImPyHpPyHp |
| 813) | 5'-W A T A C T W-3' | PyHpPyPyHp-γ-PyImHpPyHp |
| 814) | 5'-W A T A C A W-3' | PyHpPyPyPy-γ-HpImHpPyHp |
| 815) | 5'-W A T A C G W-3' | PyHpPyPyIm-γ-PyImHpPyHp |
| 816) | 5'-W A T A C C W-3' | PyHpPyPyPy-γ-ImImHpPyHp |

TABLE 39

10-ring Hairpin Polyamides for recognition of 7-bp 5'-WATSNNW-3'

| | DNA sequence | aromatic amino acid sequence |
|---|---|---|
| 817) | 5'-W A T G T T W-3' | PyHpImHpHp-γ-PyPyPyPyHp |
| 818) | 5'-W A T G T A W-3' | PyHpImHpPy-γ-HpPyPyPyHp |
| 819) | 5'-W A T G T G W-3' | PyHpImHpIm-γ-PyPyPyPyHp |
| 820) | 5'-W A T G T C W-3' | PyHpImHpPy-γ-ImPyPyPyHp |
| 821) | 5'-W A T G A T W-3' | PyHpImPyHp-γ-PyHpPyPyHp |
| 822) | 5'-W A T G A A W-3' | PyHpImPyPy-γ-HpHpPyPyHp |
| 823) | 5'-W A T G A G W-3' | PyHpImPyIm-γ-PyHpPyPyHp |
| 824) | 5'-W A T G A C W-3' | PyHpImPyPy-γ-ImHpPyPyHp |
| 825) | 5'-W A T G G T W-3' | PyHpImImHp-γ-PyPyPyPyHp |
| 826) | 5'-W A T G G A W-3' | PyHpImImPy-γ-HpPyPyPyHp |
| 827) | 5'-W A T G C T W-3' | PyHpImPyHp-γ-PyImPyPyHp |
| 828) | 5'-W A T G C A W-3' | PyHpImPyPy-γ-HpImPyPyHp |
| 829) | 5'-W A T G G G W-3' | PyHpImImIm-γ-PyPyPyPyHp |
| 830) | 5'-W A T G G C W-3' | PyHpImImPy-γ-ImPyPyPyHp |
| 831) | 5'-W A T G C G W-3' | PyHpImPyIm-γ-PyImPyPyHp |
| 832) | 5'-W A T G C C W-3' | PyHpImPyPy-γ-ImImPyPyHp |
| 833) | 5'-W A T C T T W-3' | PyHpPyHpHp-γ-PyPyImPyHp |
| 834) | 5'-W A T C T A W-3' | PyHpPyHpPy-γ-HpPyImPyHp |
| 835) | 5'-W A T C T G W-3' | PyHpPyHpIm-γ-PyPyImPyHp |
| 836) | 5'-W A T C T C W-3' | PyHpPyHpPy-γ-ImPyImPyHp |
| 837) | 5'-W A T C A T W-3' | PyHpPyPyHp-γ-PyHpImPyHp |
| 838) | 5'-W A T C A A W-3' | PyHpPyPyPy-γ-HpHpImPyHp |
| 839) | 5'-W A T C A G W-3' | PyHpPyPyIm-γ-PyHpImPyHp |
| 840) | 5'-W A T C A C W-3' | PyHpPyPyPy-γ-ImHpImPyHp |
| 841) | 5'-W A T C G T W-3' | PyHpPyImHp-γ-PyPyImPyHp |
| 842) | 5'-W A T C G A W-3' | PyHpPyImPy-γ-HpPyImPyHp |
| 843) | 5'-W A T C C T W-3' | PyHpPyPyHp-γ-PyImImPyHp |
| 844) | 5'-W A T C C A W-3' | PyHpPyPyPy-γ-HpImImPyHp |
| 845) | 5'-W A T C G G W-3' | PyHpPyImIm-γ-PyPyImPyHp |
| 846) | 5'-W A T C G C W-3' | PyHpPyImPy-γ-ImPyImPyHp |
| 847) | 5'-W A T C C G W-3' | PyHpPyPyIm-γ-PyImImPyHp |
| 848) | 5'-W A T C C C W-3' | PyHpPyPyPy-γ-ImImImPyHp |

TABLE 40

10-ring Hairpin Polyamides for recognition of 7-bp 5'-WAAWNNW-3'

| | DNA sequence | aromatic amino acid sequence |
|---|---|---|
| 849) | 5'-W A A T T T W-3' | PyPyHpHpHp-γ-PyPyPyHpHp |
| 850) | 5'-W A A T T A W-3' | PyPyHpHpPy-γ-HpPyPyHpHp |
| 851) | 5'-W A A T T G W-3' | PyPyHpHpIm-γ-PyPyPyHpHp |
| 852) | 5'-W A A T T C W-3' | PyPyHpHpPy-γ-ImPyPyHpHp |
| 853) | 5'-W A A T A T W-3' | PyPyHpPyHp-γ-PyHpPyHpHp |
| 854) | 5'-W A A T A A W-3' | PyPyHpPyPy-γ-HpHpPyHpHp |
| 855) | 5'-W A A T A G W-3' | PyPyHpPyIm-γ-PyHpPyHpHp |
| 856) | 5'-W A A T A C W-3' | PyPyHpPyPy-γ-ImHpPyHpHp |
| 857) | 5'-W A A T G T W-3' | PyPyHpImHp-γ-PyPyPyHpHp |
| 858) | 5'-W A A T G A W-3' | PyPyHpImPy-γ-HpPyPyHpHp |
| 859) | 5'-W A A T G G W-3' | PyPyHpImIm-γ-PyPyPyHpHp |
| 860) | 5'-W A A T G C W-3' | PyPyHpImPy-γ-ImPyPyHpHp |
| 861) | 5'-W A A T C T W-3' | PyPyHpPyHp-γ-PyImPyHpHp |
| 862) | 5'-W A A T C A W-3' | PyPyHpPyPy-γ-HpImPyHpHp |
| 863) | 5'-W A A T C G W-3' | PyPyHpPyIm-γ-PyImPyHpHp |
| 864) | 5'-W A A T C C W-3' | PyPyHpPyPy-γ-ImImPyHpHp |
| 865) | 5'-W A A A T T W-3' | PyPyPyHpHp-γ-PyPyHpHpHp |
| 866) | 5'-W A A A T A W-3' | PyPyPyHpPy-γ-HpPyHpHpHp |
| 867) | 5'-W A A A T G W-3' | PyPyPyHpIm-γ-PyPyHpHpHp |
| 868) | 5'-W A A A T C W-3' | PyPyPyHpPy-γ-ImPyHpHpHp |
| 869) | 5'-W A A A A T W-3' | PyPyPyPyHp-γ-PyHpHpHpHp |
| 870) | 5'-W A A A A A W-3' | PyPyPyPyPy-γ-HpHpHpHpHp |
| 871) | 5'-W A A A A G W-3' | PyPyPyPyIm-γ-PyHpHpHpHp |
| 872) | 5'-W A A A A C W-3' | PyPyPyPyPy-γ-ImHpHpHpHp |
| 873) | 5'-W A A A G T W-3' | PyPyPyImHp-γ-PyPyHpHpHp |
| 874) | 5'-W A A A G A W-3' | PyPyPyImPy-γ-HpPyHpHpHp |
| 875) | 5'-W A A A G G W-3' | PyPyPyImIm-γ-PyPyHpHpHp |
| 876) | 5'-W A A A G C W-3' | PyPyPyImPy-γ-ImPyHpHpHp |
| 877) | 5'-W A A A C T W-3' | PyPyPyPyHp-γ-PyImHpHpHp |

TABLE 40-continued 10-ring Hairpin Polyamides for recognition of 7-bp 5'-WAAWNNW-3'

| | DNA sequence | aromatic amino acid sequence |
|---|---|---|
| 878) | 5'-W A A A C A W-3' | PyPyPyPyPy-γ-HpImHpHpHp |
| 879) | 5'-W A A A C G W-3' | PyPyPyPyIm-γ-PyImHpHpHp |
| 880) | 5'-W A A A C C W-3' | PyPyPyPyPy-γ-ImImHpHpHp |

TABLE 41

10-ring Hairpin Polyamides for recognition of 7-bp 5'-WAASNNW-3'

| | DNA sequence | aromatic amino acid sequence |
|---|---|---|
| 881) | 5'-W A A G T T W-3' | PyPyImHpHp-γ-PyPyPyHpHp |
| 882) | 5'-W A A G T A W-3' | PyPyImHpPy-γ-HpPyPyHpHp |
| 883) | 5'-W A A G T G W-3' | PyPyImHpIm-γ-PyPyPyHpHp |
| 884) | 5'-W A A G T C W-3' | PyPyImHpPy-γ-ImPyPyHpHp |
| 885) | 5'-W A A G A T W-3' | PyPyImPyHp-γ-PyHpPyHpHp |
| 886) | 5'-W A A G A A W-3' | PyPyImPyPy-γ-HpHpPyHpHp |
| 887) | 5'-W A A G A G W-3' | PyPyImPyIm-γ-PyHpPyHpHp |
| 888) | 5'-W A A G A C W-3' | PyPyImPyPy-γ-ImHpPyHpHp |
| 889) | 5'-W A A G G T W-3' | PyPyImImHp-γ-PyPyPyHpHp |
| 890) | 5'-W A A G G A W-3' | PyPyImImPy-γ-HpPyPyHpHp |
| 891) | 5'-W A A G C T W-3' | PyPyImPyHp-γ-PyImPyHpHp |
| 892) | 5'-W A A G C A W-3' | PyPyImPyPy-γ-HpImPyHpHp |
| 893) | 5'-W A A G G G W-3' | PyPyImImIm-γ-PyPyPyHpHp |
| 894) | 5'-W A A G G C W-3' | PyPyImImPy-γ-ImPyPyHpHp |
| 895) | 5'-W A A G C G W-3' | PyPyImPyIm-γ-PyImPyHpHp |
| 896) | 5'-W A A G C C W-3' | PyPyImPyPy-γ-ImImPyHpHp |
| 897) | 5'-W A A C T T W-3' | PyPyPyHpHp-γ-PyPyImHpHp |
| 898) | 5'-W A A C T A W-3' | PyPyPyHpPy-γ-HpPyImHpHp |
| 899) | 5'-W A A C T G W-3' | PyPyPyHpIm-γ-PyPyImHpHp |
| 900) | 5'-W A A C T C W-3' | PyPyPyHpPy-γ-ImPyImHpHp |
| 901) | 5'-W A A C A T W-3' | PyPyPyPyHp-γ-PyHpImHpHp |
| 902) | 5'-W A A C A A W-3' | PyPyPyPyPy-γ-HpHpImHpHp |
| 903) | 5'-W A A C A G W-3' | PyPyPyPyIm-γ-PyHpImHpHp |
| 904) | 5'-W A A C A C W-3' | PyPyPyPyPy-γ-ImHpImHpHp |
| 905) | 5'-W A A C G T W-3' | PyPyPyImHp-γ-PyPyImHpHp |
| 906) | 5'-W A A C G A W-3' | PyPyPyImPy-γ-HpPyImHpHp |
| 907) | 5'-W A A C C T W-3' | PyPyPyPyHp-γ-PyImImHpHp |
| 908) | 5'-W A A C C A W-3' | PyPyPyPyPy-γ-HpImImHpHp |
| 909) | 5'-W A A C G G W-3' | PyPyPyImIm-γ-PyPyImHpHp |
| 910) | 5'-W A A C G C W-3' | PyPyPyImPy-γ-ImPyImHpHp |
| 911) | 5'-W A A C C G W-3' | PyPyPyPyIm-γ-PyImImHpHp |
| 912) | 5'-W A A C C C W-3' | PyPyPyPyPy-γ-ImImImHpHp |

TABLE 42

10-ring Hairpin Polyamides for recognition of 7-bp 5'-WACWNNW-3'

| | DNA sequence | aromatic amino acid sequence |
|---|---|---|
| 913) | 5'-W A C T T T W-3' | PyPyHpHpHp-γ-PyPyPyImHp |
| 914) | 5'-W A C T T A W-3' | PyPyHpHpPy-γ-HpPyPyImHp |
| 915) | 5'-W A C T T G W-3' | PyPyHpHpIm-γ-PyPyPyImHp |
| 916) | 5'-W A C T T C W-3' | PyPyHpHpPy-γ-ImPyPyImHp |
| 917) | 5'-W A C T A T W-3' | PyPyHpPyHp-γ-PyHpPyImHp |
| 918) | 5'-W A C T A A W-3' | PyPyHpPyPy-γ-HpHpPyImHp |
| 919) | 5'-W A C T A G W-3' | PyPyHpPyIm-γ-PyHpPyImHp |
| 920) | 5'-W A C T A C W-3' | PyPyHpPyPy-γ-ImHpPyImHp |
| 921) | 5'-W A C T G T W-3' | PyPyHpImHp-γ-PyPyPyImHp |
| 922) | 5'-W A C T G A W-3' | PyPyHpImPy-γ-HpPyPyImHp |
| 923) | 5'-W A C T G G W-3' | PyPyHpImIm-γ-PyPyPyImHp |
| 924) | 5'-W A C T G C W-3' | PyPyHpImPy-γ-ImPyPyImHp |
| 925) | 5'-W A C T C T W-3' | PyPyHpPyHp-γ-PyImPyImHp |
| 926) | 5'-W A C T C A W-3' | PyPyHpPyPy-γ-HpImPyImHp |
| 927) | 5'-W A C T C G W-3' | PyPyHpPyIm-γ-PyImPyImHp |
| 928) | 5'-W A C T C C W-3' | PyPyHpPyPy-γ-ImImPyImHp |
| 929) | 5'-W A C A T T W-3' | PyPyPyHpHp-γ-PyPyHpImHp |
| 930) | 5'-W A C A T A W-3' | PyPyPyHpPy-γ-HpPyHpImHp |

TABLE 42-continued 10-ring Hairpin Polyamides for recognition of 7-bp 5'-WACWNNW-3'

| | DNA sequence | aromatic amino acid sequence |
|---|---|---|
| 931) | 5'-W A C A T G W-3' | PyPyPyHpIm-γ-PyPyHpImHp |
| 932) | 5'-W A C A T C W-3' | PyPyPyHpPy-γ-ImPyHpImHp |
| 933) | 5'-W A C A A T W-3' | PyPyPyPyHp-γ-PyHpHpImHp |
| 934) | 5'-W A C A A A W-3' | PyPyPyPyPy-γ-HpHpHpImHp |
| 935) | 5'-W A C A A G W-3' | PyPyPyPyIm-γ-PyHpHpImHp |
| 936) | 5'-W A C A A C W-3' | PyPyPyPyPy-γ-ImHpHpImHp |
| 937) | 5'-W A C A G T W-3' | PyPyPyImHp-γ-PyPyHpImHp |
| 938) | 5'-W A C A G A W-3' | PyPyPyImPy-γ-HpPyHpImHp |
| 939) | 5'-W A C A G G W-3' | PyPyPyImIm-γ-PyPyHpImHp |
| 940) | 5'-W A C A G C W-3' | PyPyPyImPy-γ-ImPyHpHpHp |
| 941) | 5'-W A C A C T W-3' | PyPyPyPyHp-γ-PyImHpImHp |
| 942) | 5'-W A C A C A W-3' | PyPyPyPyPy-γ-HpImHpImHp |
| 943) | 5'-W A C A C G W-3' | PyPyPyPyIm-γ-PyImHpImHp |
| 944) | 5'-W A C A C C W-3' | PyPyPyPyPy-γ-ImImHpImHp |

TABLE 43

10-ring Hairpin Polyamides for recognition of 7-bp 5'-WACSNNW-3'

| | DNA sequence | aromatic amino acid sequence |
|---|---|---|
| 945) | 5'-W A C G T T W-3' | PyPyImHpHp-γ-PyPyPyImHp |
| 946) | 5'-W A C G T A W-3' | PyPyImHpPy-γ-HpPyPyImHp |
| 947) | 5'-W A C G T G W-3' | PyPyImHpIm-γ-PyPyPyImHp |
| 948) | 5'-W A C G T C W-3' | PyPyImHpPy-γ-ImPyPyImHp |
| 949) | 5'-W A C G A T W-3' | PyPyImPyBp-γ-PyHpPyImHp |
| 950) | 5'-W A C G A A W-3' | PyPyImPyPy-γ-HpHpPyImHp |
| 951) | 5'-W A C G A G W-3' | PyPyImPyIm-γ-PyHpPyImHp |
| 952) | 5'-W A C G A C W-3' | PyPyImPyPy-γ-ImHpPyImHp |
| 953) | 5'-W A C G G T W-3' | PyPyImImHp-γ-PyPyPyImHp |
| 954) | 5'-W A C G G A W-3' | PyPyImImPy-γ-HpPyPyImHp |
| 955) | 5'-W A C G C T W-3' | PyPyImPyHp-γ-PyImPyImHp |
| 956) | 5'-W A C G C A W-3' | PyPyImPyPy-γ-HpImPyImHp |
| 957) | 5'-W A C C T T W-3' | PyPyPyHpHp-γ-PyPyImHpHp |
| 958) | 5'-W A C C T A W-3' | PyPyPyHpPy-γ-HpPyImHpHp |
| 959) | 5'-W A C C T G W-3' | PyPyPyHpIm-γ-PyPyImHpHp |
| 960) | 5'-W A C C T C W-3' | PyPyPyHpPy-γ-ImPyImHpHp |
| 961) | 5'-W A C C A T W-3' | PyPyPyPyHp-γ-PyHpImHpHp |
| 962) | 5'-W A C C A A W-3' | PyPyPyPyPy-γ-HpHpImHpHp |
| 963) | 5'-W A C C A G W-3' | PyPyPyPyIm-γ-PyHpImHpHp |
| 964) | 5'-W A C C A C W-3' | PyPyPyPyPy-γ-ImHpImHpHp |
| 965) | 5'-W A C C G T W-3' | PyPyPyImHp-γ-PyPyImHpHp |
| 966) | 5'-W A C C G A W-3' | PyPyPyImPy-γ-HpPyImHpHp |
| 967) | 5'-W A C C C T W-3' | PyPyPyPyHp-γ-PyImImHpHp |
| 968) | 5'-W A C C C A W-3' | PyPyPyPyPy-γ-HpImImHpHp |
| 969) | 5'-W A C G G G W-3' | PyPyImImIm-γ-PyPyPyImHp |
| 970) | 5'-W A C G G C W-3' | PyPyImImPy-γ-ImPyPyImHp |
| 971) | 5'-W A C G C G W-3' | PyPyImPyIm-γ-PyImPyImHp |
| 972) | 5'-W A C G C C W-3' | PyPyImPyPy-γ-ImImPyImHp |
| 973) | 5'-W A C C G G W-3' | PyPyPyImIm-γ-PyPyImHpHp |
| 974) | 5'-W A C C G C W-3' | PyPyPyImPy-γ-ImPyImHpHp |
| 975) | 5'-W A C C C G W-3' | PyPyPyPyIm-γ-PyImImHpHp |
| 976) | 5'-W A C C C C W-3' | PyPyPyPyPy-γ-ImImImImHp |

TABLE 44

10-ring Hairpin Polyamides for recognition of 7-bp 5'-WTGWNNW-3'

| | DNA sequence | aromatic amino acid sequence |
|---|---|---|
| 977) | 5'-W T G T T T W-3' | HpImHpHpHp-γ-PyPyPyPyPy |
| 978) | 5'-W T G T T A W-3' | HpImHpHpPy-γ-HpPyPyPyPy |
| 979) | 5'-W T G T T G W-3' | HpImHpHpIm-γ-PyPyPyPyPy |
| 980) | 5'-W T G T T C W-3' | HpImHpHpPy-γ-ImPyPyPyPy |
| 981) | 5'-W T G T A T W-3' | HpImHpPyHp-γ-PyHpPyPyPy |
| 982) | 5'-W T G T A A W-3' | HpImHpPyPy-γ-HpHpPyPyPy |
| 983) | 5'-W T G T A G W-3' | HpImHpPyIm-γ-PyHpPyPyPy |

TABLE 44-continued 10-ring Hairpin Polyamides for recognition of 7-bp 5'-WTGWNNW-3'

| | DNA sequence | aromatic amino acid sequence |
|---|---|---|
| 984) | 5'-W T G T A C W-3' | HpImHpPyPy-γ-ImHpPyPyPy |
| 985) | 5'-W T G T G T W-3' | HpImHpImHp-γ-PyPyPyPyPy |
| 986) | 5'-W T G T G A W-3' | HpImHpImPy-γ-HpPyPyPyPy |
| 987) | 5'-W T G T G G W-3' | HpImHpImIm-γ-PyPyPyPyPy |
| 988) | 5'-W T G T G C W-3' | HpImHpImPy-γ-ImPyPyPyPy |
| 989) | 5'-W T G T C T W-3' | HpImHpPyHp-γ-PyImPyPyPy |
| 990) | 5'-W T G T C A W-3' | HpImHpPyPy-γ-HpImPyPyPy |
| 991) | 5'-W T G T C G W-3' | HpImHpPyIm-γ-PyImPyPyPy |
| 992) | 5'-W T G T C C W-3' | HpImHpPyPy-γ-ImImPyPyPy |
| 993) | 5'-W T G A T T W-3' | HpImPyHpHp-γ-PyPyHpPyPy |
| 994) | 5'-W T G A T A W-3' | HpImPyHpPy-γ-HpPyHpPyPy |
| 995) | 5'-W T G A T G W-3' | HpImPyHpIm-γ-PyPyHpPyPy |
| 996) | 5'-W T G A T C W-3' | HpImPyHpPy-γ-ImPyHpPyPy |
| 997) | 5'-W T G A A T W-3' | HpImPyPyHp-γ-PyHpHpPyPy |
| 998) | 5'-W T G A A A W-3' | HpImPyPyPy-γ-HpHpHpPyPy |
| 999) | 5'-W T G A A G W-3' | HpImPyPyIm-γ-PyHpHpPyPy |
| 1000) | 5'-W T G A A C W-3' | HpImPyPyPy-γ-ImHpHpPyPy |
| 1001) | 5'-W T G A G T W-3' | HpImPyImHp-γ-PyPyHpPyPy |
| 1002) | 5'-W T G A G A W-3' | HpImPyImPy-γ-HpPyHpPyPy |
| 1003) | 5'-W T G A G G W-3' | HpImPyImIm-γ-PyPyHpPyPy |
| 1004) | 5'-W T G A G C W-3' | HpImPyImPy-γ-ImPyHpPyPy |
| 1005) | 5'-W T G A C T W-3' | HpImPyPyHp-γ-PyImHpPyPy |
| 1006) | 5'-W T G A C A W-3' | HpImPyPyPy-γ-HpImHpPyPy |
| 1007) | 5'-W T G A C G W-3' | HpImPyPyIm-γ-PyImHpPyPy |
| 1008) | 5'-W T G A C C W-3' | HpImPyPyPy-γ-ImImHpPyPy |

TABLE 45

10-ring Hairpin Polyamides for recognition of 7-bp 5'-WTGSNNW-3'

| | DNA sequence | aromatic amino acid sequence |
|---|---|---|
| 1009) | 5'-W T G G T T W-3' | HpImImHpHp-γ-PyPyPyPyPy |
| 1010) | 5'-W T G G T A W-3' | HpImImHpPy-γ-HpPyPyPyPy |
| 1011) | 5'-W T G G T G W-3' | HpImImHpIm-γ-PyPyPyPyPy |
| 1012) | 5'-W T G G T C W-3' | HpImImHpPy-γ-ImPyPyPyPy |
| 1013) | 5'-W T G G A T W-3' | HpImImPyHp-γ-PyHpPyPyPy |
| 1014) | 5'-W T G G A A W-3' | HpImImPyPy-γ-HpHpPyPyPy |
| 1015) | 5'-W T G G A G W-3' | HpImImPyIm-γ-PyHpPyPyPy |
| 1016) | 5'-W T G G A C W-3' | HpImImPyPy-γ-ImHpPyPyPy |
| 1017) | 5'-W T G G G T W-3' | HpImImImHp-γ-PyPyPyPyPy |
| 1018) | 5'-W T G G G A W-3' | HpImImImPy-γ-HpPyPyPyPy |
| 1019) | 5'-W T G G C T W-3' | HpImImPyHp-γ-PyImPyPyPy |
| 1020) | 5'-W T G G C A W-3' | HpImImPyPy-γ-HpImPyPyPy |
| 1021) | 5'-W T G C T T W-3' | HpImPyHpHp-γ-PyPyImPyPy |
| 1022) | 5'-W T G C T A W-3' | HpImPyHpPy-γ-HpPyImPyPy |
| 1023) | 5'-W T G C T G W-3' | HpImPyHpIm-γ-PyPyImPyPy |
| 1024) | 5'-W T G C T C W-3' | HpImPyHpPy-γ-ImPyImPyPy |
| 1025) | 5'-W T G C A T W-3' | HpImPyPyHp-γ-PyHpImPyPy |
| 1026) | 5'-W T G C A A W-3' | HpImPyPyPy-γ-HpHpImPyPy |
| 1027) | 5'-W T G C A G W-3' | HpImPyPyIm-γ-PyHpImPyPy |
| 1028) | 5'-W T G C A C W-3' | HpImPyPyPy-γ-ImHpImPyPy |
| 1029) | 5'-W T G C G T W-3' | HpImPyImHp-γ-PyPyImPyPy |
| 1030) | 5'-W T G C G A W-3' | HpImPyImPy-γ-HpPyImPyPy |
| 1031) | 5'-W T G C C T W-3' | HpImPyPyHp-γ-PyImImPyPy |
| 1032) | 5'-W T G C C A W-3' | HpImPyPyPy-γ-HpImImPyPy |
| 1033) | 5'-W T G G G G W-3' | HpImImImIm-γ-PyPyPyPyPy |
| 1034) | 5'-W T G G G C W-3' | HpImImImPy-γ-ImPyPyPyPy |
| 1035) | 5'-W T G G C G W-3' | HpImImPyIm-γ-PyImPyPyPy |
| 1036) | 5'-W T G G C C W-3' | HpImImPyPy-γ-ImImPyPyPy |
| 1037) | 5'-W T G C G G W-3' | HpImPyImIm-γ-PyPyImPyPy |
| 1038) | 5'-W T G C G C W-3' | HpImPyImPy-γ-ImPyImPyPy |
| 1039) | 5'-W T G C C G W-3' | HpImPyPyIm-γ-PyImImPyPy |
| 1040) | 5'-W T G C C C W-3' | HpImPyPyPy-γ-ImImImPyPy |

TABLE 46

10-ring Hairpin Polyamides for recognition of
7-bp 5'-WTTWNNW-3'

| | DNA sequence | aromatic amino acid sequence |
|---|---|---|
| 1041) | 5'-W T T T T T W-3' | HpHpHpHpHp-γ-PyPyPyPyPy |
| 1042) | 5'-W T T T T A W-3' | HpHpHpHpPy-γ-HpPyPyPyPy |
| 1043) | 5'-W T T T T G W-3' | HpHpHpHpIm-γ-PyPyPyPyPy |
| 1044) | 5'-W T T T T C W-3' | HpHpHpHpPy-γ-ImPyPyPyPy |
| 1045) | 5'-W T T T A T W-3' | HpHpHpPyHp-γ-PyHpPyPyPy |
| 1046) | 5'-W T T T A A W-3' | HpHpHpPyPy-γ-HpHpPyPyPy |
| 1047) | 5'-W T T T A G W-3' | HpHpHpPyIm-γ-PyHpPyPyPy |
| 1048) | 5'-W T T T A C W-3' | HpHpHpPyPy-γ-ImHpPyPyPy |
| 1049) | 5'-W T T T G T W-3' | HpHpHpImHp-γ-PyPyPyPyPy |
| 1050) | 5'-W T T T G A W-3' | HpHpHpImPy-γ-HpPyPyPyPy |
| 1051) | 5'-W T T T G G W-3' | HpHpHpImIm-γ-PyPyPyPyPy |
| 1052) | 5'-W T T T G C W-3' | HpHpHpImPy-γ-ImPyPyPyPy |
| 1053) | 5'-W T T T C T W-3' | HpHpHpPyHp-γ-PyImPyPyPy |
| 1054) | 5'-W T T T C A W-3' | HpHpHpPyPy-γ-HpImPyPyPy |
| 1055) | 5'-W T T T C G W-3' | HpHpHpPyIm-γ-PyImPyPyPy |
| 1056) | 5'-W T T T C C W-3' | HpHpHpPyPy-γ-ImImPyPyPy |
| 1057) | 5'-W T T A T T W-3' | HpHpPyHpHp-γ-PyPyHpPyPy |
| 1058) | 5'-W T T A T A W-3' | HpHpPyHpPy-γ-HpPyHpPyPy |
| 1059) | 5'-W T T A T G W-3' | HpHpPyHpIm-γ-PyPyHpPyPy |
| 1060) | 5'-W T T A T C W-3' | HpHpPyHpPy-γ-ImPyHpPyPy |
| 1061) | 5'-W T T A A T W-3' | HpHpPyPyHp-γ-PyHpHpPyPy |
| 1062) | 5'-W T T A A A W-3' | HpHpPyPyPy-γ-HpHpHpPyPy |
| 1063) | 5'-W T T A A G W-3' | HpHpPyPyIm-γ-PyHpHpPyPy |
| 1064) | 5'-W T T A A C W-3' | HpHpPyPyPy-γ-ImHpHpPyPy |
| 1065) | 5'-W T T A G T W-3' | HpHpPyImHp-γ-PyPyHpPyPy |
| 1066) | 5'-W T T A G A W-3' | HpHpPyImPy-γ-HpPyHpPyPy |
| 1067) | 5'-W T T A G G W-3' | HpHpPyImIm-γ-PyPyHpPyPy |
| 1068) | 5'-W T T A G C W-3' | HpHpPyImPy-γ-ImPyHpPyPy |
| 1069) | 5'-W T T A C T W-3' | HpHpPyPyHp-γ-PyImHpPyPy |
| 1070) | 5'-W T T A C A W-3' | HpHPPyPyPy-γ-HpImHpPyPy |
| 1071) | 5'-W T T A C G W-3' | HpHpPyPyIm-γ-PyImHpPyPy |
| 1072) | 5'-W T T A C C W-3' | HpHpPyPyPy-γ-ImImHpPyPy |

TABLE 47

10-ring Hairpin Polyamides for recognition of
7-bp 5'-WTTSNNW-3'

| | DNA sequence | aromatic amino acid sequence |
|---|---|---|
| 1073) | 5'-W T T G T T W-3' | HpHpImHpHp-γ-PyPyPyPyPy |
| 1074) | 5'-W T T G T A W-3' | HpHpImHpPy-γ-HpPyPyPyPy |
| 1075) | 5'-W T T G T G W-3' | HpHpImHpIm-γ-PyPyPyPyPy |
| 1076) | 5'-W T T G T C W-3' | HpHpImHpPy-γ-ImPyPyPyPy |
| 1077) | 5'-W T T G A T W-3' | HpHpImPyHp-γ-PyHpPyPyPy |
| 1078) | 5'-W T T G A A W-3' | HpHpImPyPy-γ-HpHpPyPyPy |
| 1079) | 5'-W T T G A G W-3' | HpHpImPyIm-γ-PyHpPyPyPy |
| 1080) | 5'-W T T G A C W-3' | HpHpImPyPy-γ-ImHpPyPyPy |
| 1081) | 5'-W T T G G T W-3' | HpHpImImHp-γ-PyPyPyPyPy |
| 1082) | 5'-W T T G G A W-3' | HpHpImImPy-γ-HpPyPyPyPy |
| 1083) | 5'-W T T G C T W-3' | HpHPImPyHp-γ-PyImPyPyPy |
| 1084) | 5'-W T T G C A W-3' | HpHpImPyPy-γ-HpImPyPyPy |
| 1085) | 5'-W T T G G G W-3' | HpHpImImIm-γ-PyPyPyPyPy |
| 1086) | 5'-W T T G G C W-3' | HpHpImImPy-γ-ImPyPyPyPy |
| 1087) | 5'-W T T G C G W-3' | HpHpImPyIm-γ-PyImPyPyPy |
| 1088) | 5'-W T T G C C W-3' | HpHpImPyPy-γ-ImImPyPyPy |
| 1089) | 5'-W T T C T T W-3' | HpHpPyHpHp-γ-PyPyImPyPy |
| 1090) | 5'-W T T C T A W-3' | HpHpPyHpPy-γ-HpPyImPyPy |
| 1091) | 5'-W T T C T G W-3' | HpHpPyHpIm-γ-PyPyImPyPy |
| 1092) | 5'-W T T C T C W-3' | HpHpPyHpPy-γ-ImPyImPyPy |
| 1093) | 5'-W T T C A T W-3' | HpHpPyPyHp-γ-PyHpImPyPy |
| 1094) | 5'-W T T C A A W-3' | HpHpPyPyPy-γ-HpHpImPyPy |
| 1095) | 5'-W T T C A G W-3' | HpHpPyPyIm-γ-PyHpImPyPy |
| 1096) | 5'-W T T C A C W-3' | HpHpPyPyPy-γ-ImHpImPyPy |
| 1097) | 5'-W T T C G T W-3' | HpHpPyImHp-γ-PyPyImPyPy |
| 1098) | 5'-W T T C G A W-3' | HpHpPyImPy-γ-HpPyImPyPy |
| 1099) | 5'-W T T C C T W-3' | HpHpPyPyHp-γ-PyImImPyPy |
| 1100) | 5'-W T T C C A W-3' | HpHpPyPyPy-γ-HpImImPyPy |
| 1101) | 5'-W T T C G G W-3' | HpHpPyImIm-γ-PyPyImPyPy |

TABLE 47-continued 10-ring Hairpin Polyamides for recognition of
7-bp 5'-WTTSNNW-3'

| | DNA sequence | aromatic amino acid sequence |
|---|---|---|
| 1102) | 5'-W T T C G C W-3' | HpHpPyImPy-γ-ImPyImPyPy |
| 1103) | 5'-W T T C C G W-3' | HpHpPyPyIm-γ-PyImImPyPy |
| 1104) | 5'-W T T C C C W-3' | HpHpPyPyPy-γ-ImImImPyPy |

TABLE 48

10-ring Hairpin Polyamides for recognition of
7-bp 5'-WTAWNNW-3'

| | DNA sequence | aromatic amino acid sequence |
|---|---|---|
| 1105) | 5'-W T A T T T W-3' | HpPyHpHpHp-γ-PyPyPyHpPy |
| 1106) | 5'-W T A T T A W-3' | HpPyHpHpPy-γ-HpPyPyHpPy |
| 1107) | 5'-W T A T T G W-3' | HpPyHpHpIm-γ-PyPyPyHpPy |
| 1108) | 5'-W T A T T C W-3' | HpPyHpHpPy-γ-ImPyPyHpPy |
| 1109) | 5'-W T A T A T W-3' | HpPyHpPyHp-γ-PyHpPyHpPy |
| 1110) | 5'-W T A T A A W-3' | HpPyHpPyPy-γ-HpHpPyHpPy |
| 1111) | 5'-W T A T A G W-3' | HpPyHpPyIm-γ-PyHpPyHpPy |
| 1112) | 5'-W T A T A C W-3' | HpPyHpPyPy-γ-ImHpPyHpPy |
| 1113) | 5'-W T A T G T W-3' | HpPyNpImHp-γ-PyPyPyHpPy |
| 1114) | 5'-W T A T G A W-3' | HpPyHpImPy-γ-HpPyPyHpPy |
| 1115) | 5'-W T A T G G W-3' | HpPyHpImIm-γ-PyPyPyHpPy |
| 1116) | 5'-W T A T G C W-3' | HpPyHpImPy-γ-ImPyPyHpPy |
| 1117) | 5'-W T A T C T W-3' | HpPyHpPyHp-γ-PyImPyHpPy |
| 1118) | 5'-W T A T C A W-3' | HpPyHpPyPy-γ-HpImPyHpPy |
| 1119) | 5'-W T A T C G W-3' | HpPyHpPyIm-γ-PyImPyHpPy |
| 1120) | 5'-W T A T C C W-3' | HpPyHpPyPy-γ-ImImPyHpPy |
| 1121) | 5'-W T A A T T W-3' | HpPyPyHpHp-γ-PyPyHpHpPy |
| 1122) | 5'-W T A A T A W-3' | HpPyPyHpPy-γ-HpPyHpHpPy |
| 1123) | 5'-W T A A T G W-3' | HpPyPyHpIm-γ-PyPyHpHpPy |
| 1124) | 5'-W T A A T C W-3' | HpPyPyHpPy-γ-ImPyHpHpPy |
| 1125) | 5'-W T A A A T W-3' | HpPyPyPyHp-γ-PyHpHpHpPy |
| 1126) | 5'-W T A A A A W-3' | HpPyPyPyPy-γ-HpHpHpHpPy |
| 1127) | 5'-W T A A A G W-3' | HpPyPyPyIm-γ-PyHpHpHpPy |
| 1128) | 5'-W T A A A C W-3' | HpPyPyPyPy-γ-ImHpHpHpPy |
| 1129) | 5'-W T A A G T W-3' | HpPyPyImHp-γ-PyPyHpHpPy |
| 1130) | 5'-W T A A G A W-3' | HpPyPyImPy-γ-HpPyHpHpPy |
| 1131) | 5'-W T A A G G W-3' | HpPyPyImIm-γ-PyPyHpHpPy |
| 1132) | 5'-W T A A G C W-3' | HpPyPyImPy-γ-ImPyHpHpPy |
| 1133) | 5'-W T A A C T W-3' | HpPyPyPyHp-γ-PyImHpHpPy |
| 1134) | 5'-W T A A C A W-3' | HpPyPyPyPy-γ-HpImHpHpPy |
| 1135) | 5'-W T A A C G W-3' | HpPyPyPyIm-γ-PyImHpHpPy |
| 1136) | 5'-W T A A C C W-3' | HpPyPyPyPy-γ-ImImIpHpPy |

TABLE 49

10-ring Hairpin Polyamides for recognition of
7-bp 5'-WTASNNW-3'

| | DNA sequence | aromatic amino acid sequence |
|---|---|---|
| 1137) | 5'-W T A G T T W-3' | HpPyImHpHp-γ-PyPyPyHpPy |
| 1138) | 5'-W T A G T A W-3' | HpPyImHpPy-γ-HpPyPyHpPy |
| 1139) | 5'-W T A G T G W-3' | HpPyImHpIm-γ-PyPyPyHpPy |
| 1140) | 5'-W T A G T C W-3' | HpPyImHpPy-γ-ImPyPyHpPy |
| 1141) | 5'-W T A G A T W-3' | HpPyImPyHp-γ-PyHpPyHpPy |
| 1142) | 5'-W T A G A A W-3' | HpPyImPyPy-γ-HpHpPyHpPy |
| 1143) | 5'-W T A G A G W-3' | HpPyImPyIm-γ-PyHpPyHpPy |
| 1144) | 5'-W T A G A C W-3' | HpPyImPyPy-γ-ImHpPyHpPy |
| 1145) | 5'-W T A G G T W-3' | HpPyImImHp-γ-PyPyPyHpPy |
| 1146) | 5'-W T A G G A W-3' | HpPyImImPy-γ-HpPyPyHpPy |
| 1147) | 5'-W T A G C T W-3' | HpPyImPyHp-γ-PyImPyHpPy |
| 1148) | 5'-W T A G C A W-3' | HpPyImPyPy-γ-HpImPyHpPy |
| 1149) | 5'-W T A G G G W-3' | HpPyImImIm-γ-PyPyPyHpPy |
| 1150) | 5'-W T A G G C W-3' | HpPyImImPy-γ-ImPyPyHpPy |
| 1151) | 5'-W T A G C G W-3' | HpPyImPyIm-γ-PyImPyHpPy |
| 1152) | 5'-W T A G C C W-3' | HpPyImPyPy-γ-ImImPyHpPy |
| 1153) | 5'-W T A C T T W-3' | HpPyPyHpHp-γ-PyPyImPyHpPy |
| 1154) | 5'-W T A C T A W-3' | HpPyPyHpPy-γ-HpPyImHpPy |

TABLE 49-continued 10-ring Hairpin Polyamides for recognition of 7-bp 5'-WTASNNW-3'

| | DNA sequence | aromatic amino acid sequence |
|---|---|---|
| 1155) | 5'-W T A C T G W-3' | HpPyPyHpIm-γ-PyPyImHpPy |
| 1156) | 5'-W T A C T C W-3' | HpPyPyHpPy-γ-ImPyImHpPy |
| 1157) | 5'-W T A C A T W-3' | HpPyPyPyHp-γ-PyHpImHpPy |
| 1158) | 5'-W T A C A A W-3' | HpPyPyPyPy-γ-HpHpImHpPy |
| 1159) | 5'-W T A C A G W-3' | HpPyPyPyIm-γ-PyHpImHpPy |
| 1160) | 5'-W T A C A C W-3' | HpPyPyPyPy-γ-ImHpImHpPy |
| 1161) | 5'-W T A C G T W-3' | HpPyPyImHp-γ-PyHpImHpPy |
| 1162) | 5'-W T A C G A W-3' | HpPyPyImPy-γ-HpPyImHpPy |
| 1163) | 5'-W T A C C T W-3' | HpPyPyPyHp-γ-PyImImHpPy |
| 1164) | 5'-W T A C C A W-3' | HpPyPyPyPy-γ-HpImImHpPy |
| 1165) | 5'-W T A C G G W-3' | HpPyPyImIm-γ-PyPyImHpPy |
| 1166) | 5'-W T A C G C W-3' | HpPyPyImPy-γ-ImPyImHpPy |
| 1167) | 5'-W T A C C G W-3' | HpPyPyPyIm-γ-PyImImHpPy |
| 1168) | 5'-W T A C C C W-3' | HpPyPyPyPy-γ-ImImImHpPy |

TABLE 50

10-ring Hairpin Polyamides for recognition of 7-bp 5'-WTCWNNW-3'

| | DNA sequence | aromatic amino acid sequence |
|---|---|---|
| 1169) | 5'-W T C T T T W-3' | HpPyHpHpHp-γ-PyPyPyImPy |
| 1170) | 5'-W T C T T A W-3' | HpPyHpHpPy-γ-HpPyPyImPy |
| 1171) | 5'-W T C T T G W-3' | HpPyHpHpIm-γ-PyPyPyImPy |
| 1172) | 5'-W T C T T C W-3' | HpPyHpHpPy-γ-ImPyPyImPy |
| 1173) | 5'-W T C T A T W-3' | HpPyHpPyHp-γ-PyHpPyImPy |
| 1174) | 5'-W T C T A A W-3' | HpPyHpPyPy-γ-HpHpPyImPy |
| 1175) | 5'-W T C T A G W-3' | HpPyHpPyIm-γ-PyHpPyImPy |
| 1176) | 5'-W T C T A C W-3' | HpPyHpPyPy-γ-ImHpPyImPy |
| 1177) | 5'-W T C T G T W-3' | HpPyHpImHp-γ-PyPyPyImPy |
| 1178) | 5'-W T C T G A W-3' | HpPyHpImPy-γ-HpPyPyImPy |
| 1179) | 5'-W T C T G G W-3' | HpPyHpImIm-γ-PyPyPyImPy |
| 1180) | 5'-W T C T G C W-3' | HpPyHpImPy-γ-ImPyPyImPy |
| 1181) | 5'-W T C T C T W-3' | HpPyHpPyHp-γ-PyImPyImPy |
| 1182) | 5'-W T C T C A W-3' | HpPyHpPyPy-γ-HpImPyImPy |
| 1183) | 5'-W T C T C G W-3' | HpPyHpPyIm-γ-PyImPyImPy |
| 1184) | 5'-W T C T C C W-3' | HpPyHpPyPy-γ-ImImPyImPy |
| 1185) | 5'-W T C A T T W-3' | HpPyPyHpHp-γ-PyPyHpImPy |
| 1186) | 5'-W T C A T A W-3' | HpPyPyHpPy-γ-HpPyHpImPy |
| 1187) | 5'-W T C A T G W-3' | HpPyPyHpIm-γ-PyPyHpImPy |
| 1188) | 5'-W T C A T C W-3' | HpPyPyHpPy-γ-ImPyHpImPy |
| 1189) | 5'-W T C A A T W-3' | HpPyPyPyHp-γ-PyHpHpImPy |
| 1190) | 5'-W T C A A A W-3' | HpPyPyPyPy-γ-HpHpUpImPy |
| 1191) | 5'-W T C A A G W-3' | HpPyPyPyIm-γ-PyHpHpImPy |
| 1192) | 5'-W T C A A C W-3' | HpPyPyPyPy-γ-ImHpHpImPy |
| 1193) | 5'-W T C A G T W-3' | HpPyPyImHp-γ-PyPyHpImPy |
| 1194) | 5'-W T C A G A W-3' | HpPyPyImPy-γ-HpPyHpImPy |
| 1195) | 5'-W T C A G G W-3' | HpPyPyImIm-γ-PyPyHpImPy |
| 1196) | 5'-W T C A G C W-3' | HpPyPyImPy-γ-ImPyHpImPy |
| 1197) | 5'-W T C A C T W-3' | HpPyPyPyHp-γ-PyImHpImPy |
| 1198) | 5'-W T C A C A W-3' | HpPyPyPyPy-γ-HpImHpImPy |
| 1199) | 5'-W T C A C G W-3' | HpPyPyPyIm-γ-PyImHpImPy |
| 1200) | 5'-W T C A C C W-3' | HpPyPyPyPy-γ-ImImHpImPy |

TABLE 51

10-ring Hairpin Polyamides for recognition of 7-bp 5'-WTCSNNW-3'

| | DNA sequence | aromatic amino acid sequence |
|---|---|---|
| 1201) | 5'-W T C G T T W-3' | HpPyImHpHp-γ-PyPyPyImPy |
| 1202) | 5'-W T C G T A W-3' | HpPyImHpPy-γ-HpPyPyImPy |
| 1203) | 5'-W T C G T G W-3' | HpPyImHpIm-γ-PyPyPyImPy |
| 1204) | 5'-W T C G T C W-3' | HpPyImHpPy-γ-ImPyPyImPy |
| 1205) | 5'-W T C G A T W-3' | HpPyImPyHp-γ-PyHpPyImPy |
| 1206) | 5'-W T C G A A W-3' | HpPyImPyPy-γ-HpHpPyImPy |
| 1207) | 5'-W T C G A G W-3' | HpPyImPyIm-γ-PyHpPyImPy |

TABLE 51-continued 10-ring Hairpin Polyamides for recognition of 7-bp 5'-WTCSNNW-3'

| | DNA sequence | aromatic amino acid sequence |
|---|---|---|
| 1208) | 5'-W T C G A C W-3' | HpPyImPyPy-γ-ImHpPyImPy |
| 1209) | 5'-W T C G G T W-3' | HpPyImImHp-γ-PyPyPyImPy |
| 1210) | 5'-W T C G G A W-3' | HpPyImImPy-γ-HpPyPyImPy |
| 1211) | 5'-W T C G C T W-3' | HpPyImPyHp-γ-PyImPyImPy |
| 1212) | 5'-W T C G C A W-3' | HpPyImPyPy-γ-HpImPyImPy |
| 1213) | 5'-W T C C T T W-3' | HpPyPyHpHp-γ-PyPyImImPy |
| 1214) | 5'-W T C C T A W-3' | HpPyPyHpPy-γ-HpPyImImPy |
| 1215) | 5'-W T C C T G W-3' | HpPyPyHpIm-γ-PyPyImImPy |
| 1216) | 5'-W T C C T C W-3' | HpPyPyHpPy-γ-ImPyImImPy |
| 1217) | 5'-W T C C A T W-3' | HpPyPyPyHp-γ-PyHpImImPy |
| 1218) | 5'-W T C C A A W-3' | HpPyPyPyPy-γ-HpHpImImPy |
| 1219) | 5'-W T C C A G W-3' | HpPyPyPyIm-γ-PyHpImImPy |
| 1220) | 5'-W T C C A C W-3' | HpPyPyPyPy-γ-ImHpImImPy |
| 1221) | 5'-W T C C G T W-3' | HpPyPyImHp-γ-PyPyImImPy |
| 1222) | 5'-W T C C G A W-3' | HpPyPyImPy-γ-HpPyImImPy |
| 1223) | 5'-W T C C C T W-3' | HpPyPyPyHp-γ-PyImImImPy |
| 1224) | 5'-W T C C C A W-3' | HpPyPyPyPy-γ-HpImImImPy |
| 1225) | 5'-W T C G G G W-3' | HpPyImImIm-γ-PyPyPyImPy |
| 1226) | 5'-W T C G G C W-3' | HpPyImImPy-γ-ImPyPyImPy |
| 1227) | 5'-W T C G C G W-3' | HpPyImPyIm-γ-PyImPyImPy |
| 1228) | 5'-W T C G C C W-3' | HpPyImPyPy-γ-ImImPyImPy |
| 1229) | 5'-W T C C G G W-3' | HpPyPyImIm-γ-PyPyImImPy |
| 1230) | 5'-W T C C G C W-3' | HpPyPyImPy-γ-ImPyImImPy |
| 1231) | 5'-W T C C C G W-3' | HpPyPyPyIm-γ-PyImImImPy |
| 1232) | 5'-W T C C C C W-3' | HpPyPyPyPy-γ-ImImImImPy |

TABLE 52

10-ring Hairpin Polyamides for recognition of 7-bp 5'-WGGWNNW-3' With β substitutions.

| | DNA sequence | aromatic amino acid sequence |
|---|---|---|
| 243β) | 5'-W G G T T G W-3' | ImIm-β-HpIm-γ-PyPyPyPyPy |
| 243βp) | 5'-W G G T T G W-3' | ImIm-β-HpIm-γ-PyPy-β-PyPy |
| 247β) | 5'-W G G T A G W-3' | ImIm-β-PyIm-γ-PyHpPyPyPy |
| 247βp) | 5'-W G G T A G W-3' | ImIm-β-PyIm-γ-PyHp-β-PyPy |
| 249β) | 5'-W G G T G T W-3' | ImIm-β-ImHp-γ-PyPyPyPyPy |
| 249βp) | 5'-W G G T G T W-3' | ImIm-β-ImHp-γ-PyPy-β-PyPy |
| 250β) | 5'-W G G T G A W-3' | ImIm-β-ImPy-γ-HpPyPyPyPy |
| 250βp) | 5'-W G G T G A W-3' | ImIm-β-ImPy-γ-HpPy-β-PyPy |
| 251β) | 5'-W G G T G G W-3' | ImIm-β-ImIm-γ-PyPyPyPyPy |
| 251βp) | 5'-W G G T G G W-3' | ImIm-β-ImIm-γ-PyPy-β-PyPy |
| 252β) | 5'-W G G T G C W-3' | ImIm-β-ImPy-γ-ImPyPyPyPy |
| 252βp) | 5'-W G G T G C W-3' | ImIm-β-ImPy-γ-ImPy-β-PyPy |
| 255β) | 5'-W G G T C G W-3' | ImIm-β-PyIm-γ-PyImPyPyPy |
| 255βp) | 5'-W G G T C G W-3' | ImIm-β-PyIm-γ-PyIm-β-PyPy |
| 259β) | 5'-W G G A T G W-3' | ImIm-β-HpIm-γ-PyPyHpPyPy |
| 259βp) | 5'-W G G A T G W-3' | ImIm-β-HpIm-γ-PyPy-β-PyPy |
| 263β) | 5'-W G G A A G W-3' | ImIm-β-PyIm-γ-PyHpHpPyPy |
| 263βp) | 5'-W G G A A G W-3' | ImIm-β-PyIm-γ-PyHp-β-PyPy |
| 265β) | 5'-W G G A G T W-3' | ImIm-β-ImHp-γ-PyPyHpPyPy |
| 265βp) | 5'-W G G A G T W-3' | ImIm-β-ImHp-γ-PyPy-β-PyPy |
| 266β) | 5'-W G G A G A W-3' | ImIm-β-ImPy-γ-HpPyHpPyPy |
| 266βp) | 5'-W G G A G A W-3' | ImIm-β-ImPy-γ-HpPy-β-PyPy |
| 267β) | 5'-W G G A G G W-3' | ImIm-β-ImIm-γ-PyPyHpPyPy |
| 267βp) | 5'-W G G A G G W-3' | ImIm-β-ImIm-γ-PyPy-β-PyPy |
| 268β) | 5'-W G G A G C W-3' | ImIm-β-ImPy-γ-ImPyHpPyPy |
| 268βp) | 5'-W G G A G C W-3' | ImIm-β-ImPy-γ-ImPy-β-PyPy |
| 271β) | 5'-W G G A C G W-3' | ImIm-β-PyIm-γ-PyImHpPyPy |
| 271βp) | 5'-W G G A C G W-3' | ImIm-β-PyIm-γ-PyIm-β-PyPy |

TABLE 53

10-ring Hairpin Polyamides for recognition of
7-bp 5'-WGGSNNW-3' With β substitutions.

| | DNA sequence | aromatic amino acid sequence |
|---|---|---|
| 273β) | 5'-W G G G T T W-3' | ImImIm-β-Hp-γ-PyPyPyPy |
| 273βp) | 5'-W G G G T T W-3' | ImImIm-β-Hp-γ-Py-β-PyPy |
| 274β) | 5'-W G G G T A W-3' | ImImIm-β-Py-γ-HpPyPyPy |
| 274βp) | 5'-W G G G T A W-3' | ImImIm-β-Py-γ-Hp-β-PyPy |
| 275β) | 5'-W G G G T G W-3' | ImImIm-β-Im-γ-PyPyPyPy |
| 275βp) | 5'-W G G G T G W-3' | ImImIm-β-Im-γ-Py-β-PyPy |
| 276β) | 5'-W G G G T C W-3' | ImImIm-β-Py-γ-ImPyPyPy |
| 276βp) | 5'-W G G G T C W-3' | ImImIm-β-Py-γ-Im-β-PyPy |
| 277β) | 5'-W G G G A T W-3' | ImImIm-β-Hp-γ-PyHpPyPy |
| 277βp) | 5'-W G G G A T W-3' | ImImIm-β-Hp-γ-Py-β-PyPy |
| 278β) | 5'-W G G G A A W-3' | ImImIm-β-Py-γ-HpHpPyPy |
| 278βp) | 5'-W G G G A A W-3' | ImImIm-β-Py-γ-Hp-β-PyPy |
| 279β) | 5'-W G G G A G W-3' | ImImIm-β-Im-γ-PyHpPyPy |
| 279(βp) | 5'-W G G G A G W-3' | ImImIm-β-Im-γ-Py-β-PyPy |
| 280β) | 5'-W G G G A C W-3' | ImImIm-β-Py-γ-ImHpPyPy |
| 280βp) | 5'-W G G G A C W-3' | ImImIm-β-Py-γ-Im-β-PyPy |
| 283β) | 5'-W G G G C T W-3' | ImImIm-β-Hp-γ-PyImPyPy |
| 284β) | 5'-W G G G C A W-3' | ImImIm-β-Py-γ-HpImPyPy |
| 285β) | 5'-W G G C T T W-3' | ImImPyHpPy-γ-Py-β-ImPyPy |
| 285βp) | 5'-W G G C T T W-3' | ImImPy-β-Hp-γ-Py-β-ImPyPy |
| 286β) | 5'-W G G C T A W-3' | ImImPyHpPy-γ-Hp-β-ImPyPy |
| 286βp) | 5'-W G G C T A W-3' | ImImPy-β-Py-γ-Hp-β-ImPyPy |
| 287β) | 5'-W G G C T G W-3' | ImIm-β-HpIm-γ-Py-β-ImPyPy |
| 288β) | 5'-W G G C T C W-3' | ImImPyHpPy-γ-Im-β-ImPyPy |
| 288βp) | 5'-W G G C T C W-3' | ImImPy-β-Py-γ-Im-β-ImPyPy |
| 289β) | 5'-W G G C A T W-3' | ImImPyHp-γ-Py-β-ImPyPy |
| 289βp) | 5'-W G G C A T W-3' | ImImPy-β-Hp-γ-Py-β-ImPyPy |
| 290β) | 5'-W G G C A A W-3' | ImImPyPyPy-γ-Hp-β-ImPyPy |
| 290βp) | 5'-W G G C A A W-3' | ImImPy-β-Py-γ-Hp-β-ImPyPy |
| 291β) | 5'-W G G C A G W-3' | ImIm-β-PyIm-γ-Py-β-ImPyPy |
| 292β) | 5'-W G G C A C W-3' | ImImPyPyPy-γ-Im-β-ImPyPy |
| 292βp) | 5'-W G G C A C W-3' | ImImPy-β-Py-γ-Im-β-ImPyPy |
| 293β) | 5'-W G G C G T W-3' | ImIm-β-ImHp-γ-Py-β-ImPyPy |
| 294β) | 5'-W G G C G A W-3' | ImIm-β-ImPy-γ-Hp-β-ImPyPy |
| 295β) | 5'-W G G C C T W-3' | ImImPyHp-γ-PyImIm-β-Py |
| 296β) | 5'-W G G C C A W-3' | ImImPyPy-γ-HpImIm-β-Py |
| G19β) | 5'-W G G G C G W-3' | ImImIm-β-Im-γ-PyImPyPy |
| G20β) | 5'-W G G G C C W-3' | ImImIm-β-Py-γ-ImImPyPy |
| G21β) | 5'-W G G C G G W-3' | ImIm-β-ImIm-γ-Py-β-ImPyPy |
| G22β) | 5'-W G G C G C W-3' | ImIm-β-ImPy-γ-Im-β-ImPyPy |
| G23β) | 5'-W G G C C G W-3' | ImIm-β-PyIm-γ-PyImIm-β-Py |
| G24β) | 5'-W G G C C C W-3' | ImImPyPyPy-γ-ImImIm-β-Py |

TABLE 54

10-ring Hairpin Polyamides for recognition of
7-bp 5'-WGTWNNW-3' With β substitutions.

| | DNA sequence | aromatic amino acid sequence |
|---|---|---|
| 299β) | 5'-W G T T T G W-3' | ImHp-β-HpIm-γ-PyPyPyPyPy |
| 299βp) | 5'-W G T T T G W-3' | ImHp-β-HpIm-γ-PyPy-β-PyPy |
| 303β) | 5'-W G T T A G W-3' | ImHp-β-PyIm-γ-PyHpPyPy |
| 303βp) | 5'-W G T T A G W-3' | ImHp-β-PyIm-γ-PyHp-β-PyPy |
| 305β) | 5'-W G T T G T W-3' | ImHp-β-ImHp-γ-PyPyPyPy |
| 305βp) | 5'-W G T T G T W-3' | ImHp-β-ImHp-γ-PyPy-β-PyPy |
| 306β) | 5'-W G T T G A W-3' | ImHp-β-ImPy-γ-HpPyPyPy |
| 306βp) | 5'-W G T T G A W-3' | ImHp-β-ImPy-γ-HpPy-β-PyPy |
| 307β) | 5'-W G T T G G W-3' | ImHp-β-ImIm-γ-PyPyPyPy |
| 307βp) | 5'-W G T T G G W-3' | ImHp-β-ImIm-γ-PyPy-β-PyPy |
| 308β) | 5'-W G T T G C W-3' | ImHp-β-ImPy-γ-ImPyPyPy |
| 308βp) | 5'-W G T T G C W-3' | ImHp-β-ImPy-γ-ImPy-β-PyPy |
| 311β) | 5'-W G T T C G W-3' | ImHp-β-PyIm-γ-PyImPyPy |
| 311βp) | 5'-W G T T C G W-3' | ImHp-β-PyIm-γ-PyIm-β-PyPy |
| 315β) | 5'-W G T A T G W-3' | ImHp-β-HpIm-γ-PyPyHpPyPy |
| 315βp) | 5'-W G T A T G W-3' | ImHp-β-HpIm-γ-PyPy-β-PyPy |
| 319β) | 5'-W G T A A G W-3' | ImHp-β-PyIm-γ-PyHpHpPyPy |
| 319βp) | 5'-W G T A A G W-3' | ImHp-β-PyIm-γ-PyHp-β-PyPy |
| 321β) | 5'-W G T A G T W-3' | ImHp-β-ImHp-γ-PyPyHpPyPy |
| 321βp) | 5'-W G T A G T W-3' | ImHp-β-ImHp-γ-PyPy-β-PyPy |
| 322β) | 5'-W G T A G A W-3' | ImHp-β-ImPy-γ-HpPyHpPyPy |
| 322βp) | 5'-W G T A G A W-3' | ImHp-β-ImPy-γ-HpPy-β-PyPy |
| 323β) | 5'-W G T A G G W-3' | ImHp-β-ImIm-γ-PyPyHpPyPy |
| 323βp) | 5'-W G T A G G W-3' | ImHp-β-ImIm-γ-PyPy-β-PyPy |
| 324β) | 5'-W G T A G C W-3' | ImHp-β-ImPy-γ-ImPyHpPyPy |
| 324βp) | 5'-W G T A G C W-3' | ImHp-β-ImPy-γ-ImPy-β-PyPy |
| 327β) | 5'-W G T A C G W-3' | ImHp-β-PyIm-γ-PyImHpPyPy |
| 327βp) | 5'-W G T A C G W-3' | ImHp-β-PyIm-γ-PyIm-β-PyPy |

TABLE 55

10-ring Hairpin Polyamides for recognition of
7-bp 5'-WGTSNNW-3' With β substitutions.

| | DNA sequence | aromatic amino acid sequence |
|---|---|---|
| 329β) | 5'-W G T G T T W-3' | Im-β-ImHpHp-γ-PyPyPyPyPy |
| 329βp) | 5'-W G T G T T W-3' | Im-β-ImHpHp-γ-PyPyPy-β-Py |
| 330β) | 5'-W G T G T A W-3' | Im-β-ImHpPy-γ-HpPyPyPy |
| 330βp) | 5'-W G T G T A W-3' | Im-β-ImHpPy-γ-HpPyPy-β-Py |
| 331β) | 5'-W G T G T G W-3' | Im-β-ImHpIm-γ-PyPyPyPy |
| 331βp) | 5'-W G T G T G W-3' | Im-β-ImHpIm-γ-PyPyPy-β-Py |
| 332β) | 5'-W G T G T C W-3' | Im-β-ImHpPy-γ-ImPyPyPy |
| 332βp) | 5'-W G T G T C W-3' | Im-β-ImHpPy-γ-ImPyPy-β-Py |
| 333β) | 5'-W G T G A T W-3' | Im-β-ImHpHp-γ-PyHpPyPy |
| 333βp) | 5'-W G T G A T W-3' | Im-β-ImHpHp-γ-PyHpPy-β-Py |
| 334β) | 5'-W G T G A A W-3' | Im-β-ImPyPy-γ-HpHpPyPy |
| 334βp) | 5'-W G T G A A W-3' | Im-β-ImPyPy-γ-HpHpPy-β-Py |
| 335β) | 5'-W G T G A G W-3' | Im-β-ImPyIm-γ-PyHpPyPy |
| 335βp) | 5'-W G T G A G W-3' | Im-β-ImPyIm-γ-PyHpPy-β-Py |
| 336β) | 5'-W G T G A C W-3' | Im-β-ImPyPy-γ-ImHpPyPy |
| 336βp) | 5'-W G T G A C W-3' | Im-β-ImPyPy-γ-ImHpPy-β-Py |
| 337β) | 5'-W G T G G T W-3' | Im-β-ImImHp-γ-PyPyPyPy |
| 337βp) | 5'-W G T G G T W-3' | Im-β-ImImHp-γ-PyPyPy-β-Py |
| 338β) | 5'-W G T G G A W-3' | Im-β-ImImPy-γ-HpPyPyPy |
| 338βp) | 5'-W G T G G A W-3' | Im-β-ImImPy-γ-HpPyPy-β-Py |
| 339β) | 5'-W G T G C T W-3' | Im-β-ImPyHp-γ-PyImPyPy |
| 339βp) | 5'-W G T G C T W-3' | Im-β-ImPyHp-γ-PyImPy-β-Py |
| 340β) | 5'-W G T G C A W-3' | Im-β-ImPyPy-γ-HpImPyPy |
| 340βp) | 5'-W G T G C A W-3' | Im-β-ImPyPy-γ-HpImPy-β-Py |
| 341β) | 5'-W G T G G G W-3' | Im-β-ImImIm-γ-PyPyPyPy |
| 341βp) | 5'-W G T G G G W-3' | Im-β-ImImIm-γ-PyPyPy-β-Py |
| 342β) | 5'-W G T G G C W-3' | Im-β-ImImPy-γ-ImPyPyPy |
| 342βp) | 5'-W G T G G C W-3' | Im-β-ImImPy-γ-ImPyPy-β-Py |
| 343β) | 5'-W G T G C G W-3' | Im-β-ImPyIm-γ-PyImPyPy |
| 343βp) | 5'-W G T G C G W-3' | Im-β-ImPyIm-γ-PyImPy-β-Py |
| 344β) | 5'-W G T G C C W-3' | Im-β-ImPyPy-γ-ImImPyPy |
| 344βp) | 5'-W G T G C C W-3' | Im-β-ImPyPy-γ-ImImPy-β-Py |
| 345β) | 5'-W G T C T T W-3' | ImHpPyHpHp-γ-Py-β-ImPyPy |
| 345βp) | 5'-W G T C T T W-3' | ImHpPy-β-Hp-γ-Py-β-ImPyPy |
| 346β) | 5'-W G T C T A W-3' | ImHpPyHpPy-γ-Hp-β-ImPyPy |
| 346βp) | 5'-W G T C T A W-3' | ImHpPy-β-Py-γ-Hp-β-ImPyPy |
| 347β) | 5'-W G T C T G W-3' | ImHp-β-HpIm-γ-Py-β-ImPyPy |
| 348β) | 5'-W G T C T C W-3' | ImHpPyHpPy-γ-Im-β-ImPyPy |
| 348βp) | 5'-W G T C T C W-3' | ImHpPy-β-Py-γ-Im-β-ImPyPy |
| 349β) | 5'-W G T C A T W-3' | ImHpPyPyHp-γ-Py-β-ImPyPy |
| 349βp) | 5'-W G T C A T W-3' | ImHpPyPy-β-Hp-γ-Py-β-ImPyPy |
| 350β) | 5'-W G T C A A W-3' | ImHpPyPyPy-γ-Hp-β-ImPyPy |
| 350βp) | 5'-W G T C A A W-3' | ImHpPy-β-Py-γ-Hp-β-ImPyPy |
| 351β) | 5'-W G T C A G W-3' | ImHp-β-PyIm-γ-Py-β-ImPyPy |
| 352β) | 5'-W G T C A C W-3' | ImHpPyPyPy-γ-Im-β-ImPyPy |
| 352βp) | 5'-W G T C A C W-3' | ImHpPy-β-Py-γ-Im-β-ImPyPy |
| 353β) | 5'-W G T C G T W-3' | ImHp-β-ImHp-γ-Py-β-ImPyPy |
| 354β) | 5'-W G T C G A W-3' | ImHp-β-ImPy-γ-Hp-β-ImPyPy |
| 355β) | 5'-W G T C C T W-3' | ImHpPyPyHp-γ-PyImIm-β-Py |
| 356β) | 5'-W G T C C A W-3' | ImHpPyPyPy-γ-HpImIm-β-Py |
| 356βp) | 5'-W G T C C A W-3' | Im-β-PyPyPy-γ-HpImIm-β-Py |
| 357β) | 5'-W G T C G G W-3' | ImHp-β-ImIm-γ-Py-β-ImPyPy |
| 358β) | 5'-W G T C G C W-3' | ImHp-β-ImPy-γ-Im-β-ImPyPy |

TABLE 55-continued 10-ring Hairpin Polyamides for recognition of
7-bp 5'-WGTSNNW-3' With β substitutions.

| | DNA sequence | aromatic amino acid sequence |
|---|---|---|
| 359β) | 5'-W G T C C G W-3' | ImHp-β-PyIm-γ-PyImIm-β-Py |
| 360β) | 5'-W G T C C C W-3' | ImHpPyPyPy-γ-ImImIm-β-Py |
| 360βp) | 5'-W G T C C C W-3' | Im-β-PyPyPy-γ-ImImIm-β-Py |

TABLE 56

10-ring Hairpin Polyamides for recognition of
7-bp 5'-WGAWNNW-3' With β substitutions.

| | DNA sequence | aromatic amino acid sequence |
|---|---|---|
| 363β) | 5'-W G A T T G W-3' | ImPy-β-HpIm-γ-PyPyPyHpPy |
| 363βp) | 5'-W G A T T G W-3' | ImPy-β-HpIm-γ-PyPy-β-HpPy |
| 367β) | 5'-W G A T A G W-3' | ImPy-β-PyIm-γ-PyHpPyHpPy |
| 367βp) | 5'-W G A T A G W-3' | ImPy-β-PyIm-γ-PyHpHpPyPy |
| 369β) | 5'-W G A T G T W-3' | ImPy-β-ImHp-γ-PyPyPyHpPy |
| 369βp) | 5'-W G A T G T W-3' | ImPy-β-ImHp-γ-PyPy-β-HpPy |
| 370β) | 5'-W G A T G A W-3' | ImPy-β-ImPy-γ-HpPyPyHpPy |
| 370βp) | 5'-W G A T G A W-3' | ImPy-β-ImPy-γ-HpPyHbHpPy |
| 371β) | 5'-W G A T G G W-3' | ImPy-β-ImIm-γ-PyPyPyHpPy |
| 371βp) | 5'-W G A T G G W-3' | ImPy-β-ImIm-γ-PyPy-β-HpPy |
| 372β) | 5'-W G A T G C W-3' | ImPy-β-ImPy-γ-ImPyPyHpPy |
| 372βp) | 5'-W G A T G C W-3' | ImPy-β-ImPy-γ-ImPy-β-HpPy |
| 375β) | 5'-W G A T C G W-3' | ImPy-β-PyIm-γ-PyImPyHpPy |
| 375βp) | 5'-W G A T C G W-3' | ImPy-β-PyIm-γ-PyIm-β-HpPy |
| 379β) | 5'-W G A A T G W-3' | ImPy-β-HpIm-γ-PyPyHpHpPy |
| 379βp) | 5'-W G A A T G W-3' | ImPy-β-HpIm-γ-PyPy-β-HpPy |
| 383β) | 5'-W G A A A G W-3' | ImPy-β-PyIm-γ-PyHpHpHpPy |
| 383βp) | 5'-W G A A A G W-3' | ImPy-β-PyIm-γ-PyHp-β-HpPy |
| 385β) | 5'-W G A A G T W-3' | ImPy-β-ImHp-γ-PyPyHpHpPy |
| 385βp) | 5'-W G A A G T W-3' | ImPy-β-ImHp-γ-PyPy-β-HpPy |
| 386β) | 5'-W G A A G A W-3' | ImPy-β-ImPy-γ-HpPyPyHpPy |
| 386βp) | 5'-W G A A G A W-3' | ImPy-β-ImPy-γ-HpPy-β-HpPy |
| 387β) | 5'-W G A A G G W-3' | ImPy-β-ImIm-γ-PyPyHpHpPy |
| 387βp) | 5'-W G A A G G W-3' | ImPy-β-ImIm-γ-PyPy-β-HpPy |
| 388β) | 5'-W G A A G C W-3' | ImPy-β-ImPy-γ-ImPyHpHpPy |
| 388βp) | 5'-W G A A G C W-3' | ImPy-β-ImPy-γ-ImPy-β-HpPy |
| 391β) | 5'-W G A A C G W-3' | ImPy-β-PyIm-γ-PyImHpHpPy |
| 391βp) | 5'-W G A A C G W-3' | ImPy-β-PyIm-γ-PyIm-β-HpPy |

TABLE 57

10-ring Hairpin Polyamides for recognition of
7-bp 5-'WGASNNW-3' With β substitutions.

| | DNA sequence | aromatic amino acid sequence |
|---|---|---|
| 393β) | 5'-W G A G T T W-3' | Im-β-ImHpPy-γ-PyPyPyHpPy |
| 394βp) | 5'-W G A G T A W-3' | Im-β-ImHpPy-γ-HpPyPy-β-Py |
| 395β) | 5'-W G A G T G W-3' | Im-β-ImHpIm-γ-PyPyPyHpPy |
| 395βp) | 5'-W G A G T G W-3' | Im-β-ImHpIm-γ-PyPyPy-β-Py |
| 396β) | 5'-W G A G T C W-3' | Im-β-ImHpPy-γ-ImPyPyHpPy |
| 396βp) | 5'-W G A G T C W-3' | Im-β-ImHpPy-γ-ImPyPy-β-Py |
| 397β3) | 5'-W G A G A T W-3' | Im-β-ImPyHp-γ-PyHpPyHpPy |
| 397βp) | 5'-W G A G A T W-3' | Im-β-ImPyHp-γ-HpPyPy-β-Py |
| 398β) | 5'-W G A G A A W-3' | Im-β-ImPyPy-γ-HpPyPyHpPy |
| 398βp) | 5'-W G A G A A W-3' | Im-β-ImPyPy-γ-HpPyPy-β-Py |
| 399β) | 5'-W G A G A G W-3' | Im-β-ImPyIm-γ-PyHpPyHpPy |
| 399βp) | 5'-W G A G A G W-3' | Im-β-ImPyIm-γ-HpPyPy-β-Py |
| 400β) | 5'-W G A G A C W-3' | Im-β-ImPyPy-γ-ImHpPyHpPy |
| 400βp) | 5'-W G A G A C W-3' | Im-β-ImPyPy-γ-ImHpPy-β-Py |
| 401β) | 5'-W G A G G T W-3' | Im-β-ImImHp-γ-PyPyPyHpPy |
| 401βp) | 5'-W G A G G T W-3' | Im-β-ImImHp-γ-PyPyPy-β-Py |
| 402β) | 5'-W G A G G A W-3' | Im-β-ImImPy-γ-HpPyPyHpPy |
| 402βp) | 5'-W G A G G A W-3' | Im-β-ImImPy-γ-HpPyPy-β-Py |
| 403β) | 5'-W G A G C T W-3' | Im-β-ImPyHp-γ-PyImPyHpPy |
| 403βp) | 5'-W G A G C T W-3' | Im-β-ImPyHp-γ-PyImPy-β-Py |
| 404β) | 5'-W G A G C A W-3' | Im-β-ImPyPy-γ-HpImPyHpPy |
| 404βp) | 5'-W G A G C A W-3' | Im-β-ImPyPy-γ-HpImPy-β-Py |

TABLE 57-continued 10-ring Hairpin Polyamides for recognition of
7-bp 5-'WGASNNW-3' With β substitutions.

| | DNA sequence | aromatic amino acid sequence |
|---|---|---|
| 405β) | 5'-W G A G G G W-3' | Im-β-ImImIm-γ-PyPyPyHpPy |
| 405βp) | 5'-W G A G G G W-3' | Im-β-ImImIm-γ-PyPyPy-β-Py |
| 406β) | 5'-W G A G G C W-3' | Im-β-ImImPy-γ-ImPyPyHpPy |
| 406βp) | 5'-W G A G G C W-3' | Im-β-ImImPy-γ-ImPyPy-β-Py |
| 407β) | 5'-W G A G C G W-3' | Im-β-ImPyIm-γ-PyImPyHpPy |
| 407βp) | 5'-W G A G C G W-3' | Im-β-ImPyIm-γ-PyImPy-β-Py |
| 408β) | 5'-W G A G C C W-3' | Im-β-ImPyPy-γ-ImImPyHpPy |
| 408βp) | 5'-W G A G C C W-3' | Im-β-ImPyPy-γ-ImImPy-β-Py |
| 409β) | 5'-W G A C T T W-3' | ImPyPyHpHp-γ-Py-β-ImHpPy |
| 409βp) | 5'-W G A C T T W-3' | ImPyPy-β-Hp-γ-Py-β-ImHpPy |
| 410β) | 5'-W G A C T A W-3' | ImPyPyHpPy-γ-Hp-β-ImHpPy |
| 410βp) | 5'-W G A C T A W-3' | ImPyPy-β-Py-γ-Hp-β-ImHpPy |
| 411β) | 5'-W G A C T G W-3' | ImPy-β-HpIm-γ-Py-β-ImHpPy |
| 412β) | 5'-W G A C T C W-3' | ImPyPyHpPy-γ-Im-β-ImHpPy |
| 412βp) | 5'-W G A C T C W-3' | ImPyPy-β-Py-γ-Im-β-ImHpPy |
| 413β) | 5'-W G A C A T W-3' | ImPyPyHpPy-γ-Py-β-ImHpPy |
| 413βp) | 5'-W G A C A T W-3' | ImPyPy-β-Hp-γ-Py-β-ImHpPy |
| 414β) | 5'-W G A C A A W-3' | ImPyPyPyPy-γ-Hp-β-ImHpPy |
| 414βp) | 5'-W G A C A A W-3' | ImPyPy-β-Py-γ-Hp-β-ImHpPy |
| 415β) | 5'-W G A C A G W-3' | ImPy-β-PyIm-γ-Py-β-ImHpPy |
| 416β) | 5'-W G A C A C W-3' | ImPyPyPyPy-γ-Im-β-ImHpPy |
| 416βp) | 5'-W G A C A C W-3' | ImPyPy-β-Py-γ-Im-β-ImHpPy |
| 417β) | 5'-W G A C G T W-3' | ImPy-β-ImHp-γ-Py-β-ImHpPy |
| 418β) | 5'-W G A C G A W-3' | ImPy-β-ImPy-γ-Hp-β-ImHpPy |
| 419β) | 5'-W G A C C T W-3' | Im-β-PyPyHp-γ-PyImIm-β-Py |
| 419βp) | 5'-W G A C C T W-3' | ImPyPyHp-γ-PyImIm-β-Py |
| 420β) | 5'-W G A C C A W-3' | Im-β-PyPyPy-γ-HpImIm-β-Py |
| 420βp) | 5'-W G A C C A W-3' | ImPyPyPy-γ-HpImIm-β-Py |
| 421β) | 5'-W G A C G C W-3' | ImPy-β-ImIm-γ-Py-β-ImHpPy |
| 422β) | 5'-W G A C G C W-3' | ImPy-β-ImPy-γ-Im-β-ImHpPy |
| 423β) | 5'-W G A C C G W-3' | ImPy-β-PyIm-γ-PyImIm-β-Py |
| 424β) | 5'-W G A C C C W-3' | ImPyPyPyPy-γ-ImImIm-β-Py |
| 424βp) | 5'-W G A C C C W-3' | Im-β-PyPyPy-γ-ImImIm-β-Py |

TABLE 58

10-ring Hairpin Polyamides for recognition of
7-bp 5'-WGCWNNW-3' With β substitutions.

| | DNA sequence | aromatic amino acid sequence |
|---|---|---|
| 425β) | 5'-W G C T T T W-3' | ImPyHpHpHp-γ-PyPy-β-ImPy |
| 425βp) | 5'-W G C T T T W-3' | ImPy-β-HpHp-γ-PyPy-β-ImPy |
| 426β) | 5'-W G C T T A W-3' | ImPyHpHpPy-γ-HpPy-β-ImPy |
| 426βp) | 5'-W G C T T A W-3' | ImPy-β-HpPy-γ-HpPy-β-ImPy |
| 427β) | 5'-W G C T T G W-3' | ImPy-β-HpIm-γ-PyPy-β-ImPy |
| 428β) | 5'-W G C T T C W-3' | ImPyHpHpPy-γ-ImPy-β-ImPy |
| 428βp) | 5'-W G C T T C W-3' | ImPy-β-HpPy-γ-ImPy-β-ImPy |
| 429β) | 5'-W G C T A T W-3' | ImPyHpPyHp-γ-PyHp-β-ImPy |
| 429βp) | 5'-W G C T A T W-3' | ImPy-β-PyHp-γ-PyHp-β-ImPy |
| 430β) | 5'-W G C T A A W-3' | ImPyHpPyPy-γ-HpHp-β-ImPy |
| 430βp) | 5'-W G C T A A W-3' | ImPy-β-PyPy-γ-HpHp-β-ImPy |
| 431β) | 5'-W G C T A G W-3' | ImPy-β-PyIm-γ-PyHp-β-ImPy |
| 432β) | 5'-W G C T A C W-3' | ImPyHpPyPy-γ-ImHp-β-ImPy |
| 432βp) | 5'-W G C T A C W-3' | ImPy-β-PyPy-γ-ImHp-β-ImPy |
| 433β) | 5'-W G C T G T W-3' | ImPy-β-ImHp-γ-PyPy-β-ImPy |
| 434β) | 5'-W G C T G A W-3' | ImPy-β-ImPy-γ-HpPy-β-ImPy |
| 435β) | 5'-W G C T G G W-3' | ImPy-β-ImIm-γ-PyPy-β-ImPy |
| 436β) | 5'-W G C T G C W-3' | ImPy-β-ImPy-γ-ImPy-β-ImPy |
| 437β) | 5'-W G C T C T W-3' | ImPyHpPyHp-γ-PyIm-β-ImPy |
| 437βp) | 5'-W G C T C T W-3' | ImPy-β-PyHp-γ-PyIm-β-ImPy |
| 438β) | 5'-W G C T C A W-3' | ImPyHpPyPy-γ-HpIm-β-ImPy |
| 438βp) | 5'-W G C T C A W-3' | ImPy-β-PyPy-γ-HpIm-β-ImPy |
| 439β) | 5'-W G C T C G W-3' | ImPy-β-PyIm-γ-PyIm-β-ImPy |
| 440β) | 5'-W G C T C C W-3' | ImPyHpPyPy-γ-ImIm-β-ImPy |
| 440βp) | 5'-W G C T C C W-3' | ImPy-β-PyPy-γ-ImIm-β-ImPy |
| 441β) | 5'-W G C A T T W-3' | ImPyHpHpHp-γ-PyPy-β-ImPy |
| 441βp) | 5'-W G C A T T W-3' | ImPy-β-HpHp-γ-PyPy-β-ImPy |
| 442β) | 5'-W G C A T A W-3' | ImPyHpHpPy-γ-HpPy-β-ImPy |
| 442βp) | 5'-W G C A T A W-3' | ImPy-β-HpPy-γ-HpPy-β-ImPy |
| 443β) | 5'-W G C A T G W-3' | ImPy-β-HpIm-γ-PyPy-β-ImPy |

TABLE 58-continued 10-ring Hairpin Polyamides for recognition of 7-bp 5'-WGCWNNW-3' With β substitutions.

| | DNA sequence | aromatic amino acid sequence |
|---|---|---|
| 444β) | 5'-W G C A T C W-3' | ImPyPyHpPy-γ-ImPy-β-ImPy |
| 444βp) | 5'-W G C A T C W-3' | ImPy-β-HpPy-γ-ImPy-β-ImPy |
| 445β) | 5'-W G C A A T W-3' | ImPyPyPyHp-γ-PyHp-β-ImPy |
| 445βp) | 5'-W G C A A T W-3' | ImPy-β-PyHp-γ-PyHp-β-ImPy |
| 446β) | 5'-W G C A A A W-3' | ImPyPyPyPy-γ-HpHp-β-ImPy |
| 446βp) | 5'-W G C A A A W-3' | ImPy-β-PyPy-γ-HpHp-β-ImPy |
| 447β) | 5'-W G C A A G W-3' | ImPy-β-PyIm-γ-PyHp-β-ImPy |
| 448β) | 5'-W G C A A C W-3' | ImPyPyPyPy-γ-ImHp-β-ImPy |
| 448βp) | 5'-W G C A A C W-3' | ImPy-β-PyPy-γ-ImHp-β-ImPy |
| 449β) | 5'-W G C A G T W-3' | ImPy-β-ImHp-γ-PyPy-β-ImPy |
| 450β) | 5'-W G C A G A W-3' | ImPy-β-ImPy-γ-HpPy-β-ImPy |
| 451β) | 5'-W G C A G G W-3' | ImPy-β-ImIm-γ-PyPy-β-ImPy |
| 452β) | 5'-W G C A G C W-3' | ImPy-β-ImPy-γ-ImPy-β-ImPy |
| 453β) | 5'-W G C A C T W-3' | ImPyPyPyHp-γ-PyIm-β-ImPy |
| 453βp) | 5'-W G C A C T W-3' | ImPy-β-PyHp-γ-PyIm-β-ImPy |
| 454β) | 5'-W G C A C A W-3' | ImPyPyPyPy-γ-HpIm-β-ImPy |
| 454βp) | 5'-W G C A C A W-3' | ImPy-β-PyPy-γ-HpIm-β-ImPy |
| 455β) | 5'-W G C A C G W-3' | ImPy-β-PyIm-γ-PyIm-β-ImPy |
| 456β) | 5'-W G C A C C W-3' | ImPyPyPyPy-γ-ImIm-β-ImPy |
| 456βp) | 5'-W G C A C C W-3' | ImPy-β-PyPy-γ-ImIm-β-ImPy |

TABLE 59

10-ring Hairpin Polyamides for recognition of 7-bp 5'-WGCSNNW-3' With β substitutions.

| | DNA sequence | aromatic amino acid sequence |
|---|---|---|
| 457β) | 5'-W G C G T T W-3' | Im-β-ImHpHp-γ-PyPy-β-ImPy |
| 458β) | 5'-W G C G T A W-3' | Im-β-ImHpPy-γ-HpPy-β-ImPy |
| 459β) | 5'-W G C G T G W-3' | Im-β-ImHpIm-γ-PyPy-β-ImPy |
| 460β) | 5'-W G C G T C W-3' | Im-β-ImHpPy-γ-ImPy-β-ImPy |
| 461β) | 5'-W G C G A T W-3' | Im-β-ImPyHp-γ-PyHp-β-ImPy |
| 462β) | 5'-W G C G A A W-3' | Im-β-ImPyPy-γ-HpHp-β-ImPy |
| 463β) | 5'-W G C G A G W-3' | Im-β-ImPyIm-γ-PyHp-β-ImPy |
| 464β) | 5'-W G C G A C W-3' | Im-β-ImPyPy-γ-ImHp-β-ImPy |
| 465β) | 5'-W G C G G T W-3' | Im-β-ImImHp-γ-PyPy-β-ImPy |
| 466β) | 5'-W G C G G A W-3' | Im-β-ImImPy-γ-HpPy-β-ImPy |
| 467β) | 5'-W G C G C T W-3' | Im-β-ImPyHp-γ-PyIm-β-ImPy |
| 468β) | 5'-W G C G C A W-3' | Im-β-ImPyPy-γ-HpIm-β-ImPy |
| 469β) | 5'-W G C C T T W-3' | ImPyPyHpHp-γ-Py-β-ImImPy |
| 469βp) | 5'-W G C C T T W-3' | ImPyPy-β-Hp-γ-Py-β-ImImPy |
| 470β) | 5'-W G C C T A W-3' | ImPyPyHpPy-γ-Hp-β-ImImPy |
| 470βp) | 5'-W G C C T A W-3' | ImPyPy-β-Py-γ-Hp-β-ImImPy |
| 471β) | 5'-W G C C T G W-3' | ImPy-β-HpIm-γ-Py-β-ImImPy |
| 472β) | 5'-W G C C T C W-3' | ImPyPyHpPy-γ-Im-β-ImImPy |
| 472βp) | 5'-W G C C T C W-3' | ImPyPy-β-Py-γ-Im-β-ImImPy |
| 473β) | 5'-W G C C A T W-3' | ImPyPyPyHp-γ-Py-β-ImImPy |
| 473βp) | 5'-W G C C A T W-3' | ImPyPy-β-Hp-γ-Py-β-ImImPy |
| 474β) | 5'-W G C C A A W-3' | ImPyPyPyPy-γ-Hp-β-ImImPy |
| 474βp) | 5'-W G C C A A W-3' | ImPyPy-β-Py-γ-Hp-β-ImImPy |
| 475β) | 5'-W G C C A G W-3' | ImPy-β-PyIm-γ-Py-β-ImImPy |
| 476β) | 5'-W G C C A C W-3' | ImPyPyPyPy-γ-Im-β-ImImPy |
| 476βp) | 5'-W G C C A C W-3' | ImPyPy-β-Py-γ-Im-β-ImImPy |
| 477β) | 5'-W G C C G T W-3' | ImPy-β-ImHp-γ-Py-β-ImImPy |
| 478β) | 5'-W G C C G A W-3' | ImPy-β-ImPy-γ-Hp-β-ImImPy |
| G25β) | 5'-W G C G G G W-3' | Im-β-ImImIm-γ-PyPy-β-ImPy |
| G26β) | 5'-W G C G G C W-3' | Im-β-ImImPy-γ-ImPy-β-ImPy |
| G27β) | 5'-W G C G C G W-3' | Im-β-ImPyIm-γ-PyIm-β-ImPy |
| G28β) | 5'-W G C G C C W-3' | Im-β-ImPyPy-γ-ImIm-β-ImPy |
| G29β) | 5'-W G C G G W-3' | ImPy-β-ImIm-γ-Py-β-ImImPy |
| G30β) | 5'-W G C C G C W-3' | ImPy-β-ImPy-γ-Im-β-ImImPy |
| G31β) | 5'-W G C C C G W-3' | ImPy-β-PyIm-γ-PyImImImPy |

TABLE 60

10-ring Hairpin Polyamides for recognition of 7-bp 5'-WCGWNNW-3' With β substitutions.

| | DNA sequence | aromatic amino acid sequence |
|---|---|---|
| 481β) | 5'-W C G T T T W-3' | PyImHpHpHp-γ-PyPy-β-PyIm |
| 481βp) | 5'-W C G T T T W-3' | PyIm-β-HpHp-γ-PyPy-β-PyIm |
| 482β) | 5'-W C G T T A W-3' | PyImHpHpPy-γ-HpPy-β-PyIm |
| 482βp) | 5'-W C G T T A W-3' | PyIm-β-HpPy-γ-HpPy-β-PyIm |
| 483β) | 5'-W C G T T G W-3' | PyIm-β-HpIm-γ-PyPy-β-PyIm |
| 484β) | 5'-W C G T T C W-3' | PyImHpHpPy-γ-ImPy-β-PyIm |
| 484βp) | 5'-W C G T T C W-3' | PyIm-β-HpPy-γ-ImPy-β-PyIm |
| 485β) | 5'-W C G T A T W-3' | PyImHpPyHp-γ-PyHp-β-PyIm |
| 485βp) | 5'-W C G T A T W-3' | PyIm-β-PyHp-γ-PyHp-β-PyIm |
| 486β) | 5'-W C G T A A W-3' | PyImHpPyPy-γ-HpHp-β-PyIm |
| 486βp) | 5'-W C G T A A W-3' | PyIm-β-PyPy-γ-HpHp-β-PyIm |
| 487β) | 5'-W C G T A G W-3' | PyIm-β-PyIm-γ-PyHp-β-PyIm |
| 488β) | 5'-W C G T A C W-3' | PyImHpPyPy-γ-ImHp-β-PyIm |
| 488βp) | 5'-W C G T A C W-3' | PyIm-β-PyPy-γ-ImHp-β-PyIm |
| 489β) | 5'-W C G T G T W-3' | PyIm-β-ImHp-γ-PyPy-β-PyIm |
| 490β) | 5'-W C G T G A W-3' | PyIm-β-ImPy-γ-HpPy-β-PyIm |
| 491β) | 5'-W C G T G G W-3' | PyIm-β-ImIm-γ-PyPy-β-PyIm |
| 492β) | 5'-W C G T G C W-3' | PyIm-β-ImPy-γ-ImPy-β-PyIm |
| 493β) | 5'-W C G T C T W-3' | PyImHpHpPy-γ-PyIm-β-PyIm |
| 493βp) | 5'-W C G T C T W-3' | PyIm-β-HpPy-γ-PyIm-β-PyIm |
| 494β) | 5'-W C G T C A W-3' | PyImHpPyPy-γ-HpIm-β-PyIm |
| 494βp) | 5'-W C G T C A W-3' | PyIm-β-PyPy-γ-HpIm-β-PyIm |
| 495β) | 5'-W C G T C G W-3' | PyIm-β-PyIm-γ-PyIm-β-PyIm |
| 496β) | 5'-W C G T C C W-3' | PyImHpPyPy-γ-ImIm-β-PyIm |
| 496βp) | 5'-W C G T C C W-3' | PyIm-β-PyPy-γ-ImIm-β-PyIm |
| 497β) | 5'-W C G A T T W-3' | PyImPyHpHp-γ-PyPy-β-PyIm |
| 497βp) | 5'-W C G A T T W-3' | PyIm-β-HpHp-γ-PyPy-β-PyIm |
| 498β) | 5'-W C G A T A W-3' | PyImPyHpPy-γ-HpPy-β-PyIm |
| 498βp) | 5'-W C G A T A W-3' | PyIm-β-HpPy-γ-HpPy-β-PyIm |
| 499β) | 5'-W C G A T G W-3' | PyIm-β-HpIm-γ-PyPy-β-PyIm |
| 500β) | 5'-W C G A T C W-3' | PyImPyHpPy-γ-ImPy-β-PyIm |
| 500βp) | 5'-W C G A T C W-3' | PyIm-β-HpPy-γ-ImPy-β-PyIm |
| 501β) | 5'-W C G A A T W-3' | PyImPyPyHp-γ-PyHp-β-PyIm |
| 501βp) | 5'-W C G A A T W-3' | PyIm-β-PyHp-γ-PyHp-β-PyIm |
| 502β) | 5'-W C G A A A W-3' | PyImPyPyPy-γ-HpHp-β-PyIm |
| 502βp) | 5'-W C G A A A W-3' | PyIm-β-PyPy-γ-HpHp-β-PyIm |
| 503β) | 5'-W C G A A G W-3' | PyIm-β-PyIm-γ-PyHp-β-PyIm |
| 504β) | 5'-W C G A A C W-3' | PyImPyPyPy-γ-ImHp-β-PyIm |
| 504βp) | 5'-W C G A A C W-3' | PyIm-β-PyPy-γ-ImHp-β-PyIm |
| 505β) | 5'-W C G A G T W-3' | PyIm-β-ImHp-γ-PyPy-β-PyIm |
| 506β) | 5'-W C G A G A W-3' | PyIm-β-ImPy-γ-HpPy-β-PyIm |
| 507β) | 5'-W C G A G G W-3' | PyIm-β-ImIm-γ-PyPy-β-PyIm |
| 508β) | 5'-W C G A G C W-3' | PyIm-β-ImPy-γ-ImPy-β-PyIm |
| 509β) | 5'-W C G A C T W-3' | PyImPyPyHp-γ-PyIm-β-PyIm |
| 509βp) | 5'-W C G A C T W-3' | PyIm-β-PyHp-γ-PyIm-β-PyIm |
| 510β) | 5'-W C G A C A W-3' | PyImPyPyPy-γ-HpIm-β-PyIm |
| 510βp) | 5'-W C G A C A W-3' | PyIm-β-PyPy-γ-HpIm-β-PyIm |
| 511β) | 5'-W C G A C G W-3' | PyIm-β-PyIm-γ-PyIm-β-PyIm |
| 512β) | 5'-W C G A C C W-3' | PyImPyPyPy-γ-ImIm-β-PyIm |
| 512βp) | 5'-W C G A C C W-3' | PyIm-β-PyPy-γ-ImIm-β-PyIm |

TABLE 61

10-ring Hairpin Polyamides for recognition of 7-bp 5'-WCGSNNW-3' with β substitutions.

| | DNA sequence | aromatic amino acid sequence |
|---|---|---|
| 513β) | 5'-W C G G T T W-3' | PyImIm-β-Hp-γ-PyPy-β-PyIm |
| 514β) | 5'-W C G G T A W-3' | PyImIm-β-Py-γ-HpPy-β-PyIm |
| 515β) | 5'-W C G G T G W-3' | PyImIm-β-Im-γ-PyPy-β-PyIm |
| 516β) | 5'-W C G G T C W-3' | PyImIm-β-Py-γ-ImPy-β-PyIm |
| 517β) | 5'-W C G G A T W-3' | PyImIm-β-Hp-γ-PyHp-β-PyIm |
| 518β) | 5'-W C G G A A W-3' | PyImIm-β-Py-γ-HpHp-β-PyIm |
| 519β) | 5'-W C G G A G W-3' | PyImIm-β-Im-γ-PyHp-β-PyIm |
| 520β) | 5'-W C G G A C W-3' | PyImIm-β-Py-γ-ImHp-β-PyIm |
| 521β) | 5'-W C G G G T W-3' | PyImImImHp-γ-PyPy-β-PyIm |
| 522β) | 5'-W C G G G A W-3' | PyImImImPy-γ-HpPy-β-PyIm |
| 523β) | 5'-W C G G C T W-3' | PyImIm-β-Hp-γ-PyIm-β-PyIm |
| 524β) | 5'-W C G G C A W-3' | PyImIm-β-Py-γ-HpIm-β-PyIm |
| 525β) | 5'-W C G C T T W-3' | PyImPyHpHp-γ-Py-β-ImPyIm |

TABLE 61-continued 10-ring Hairpin Polyamides for recognition of 7-bp 5'-WCGSNNW-3' with β substitutions.

| | DNA sequence | aromatic amino acid sequence |
|---|---|---|
| 525βp) | 5'-W C G C T T W-3' | PyImPy-β-Hp-γ-Py-β-ImPyIm |
| 526β) | 5'-W C G C T A W-3' | PyImPy-β-Py-γ-Hp-β-ImPyIm |
| 526βp) | 5'-W C G C T A W-3' | PyImPy-β-Py-γ-Hp-β-ImPyIm |
| 527β) | 5'-W C G C T G W-3' | PyIm-β-HpIm-γ-Py-β-ImPyIm |
| 528β) | 5'-W C G C T C W-3' | PyImPyHpPy-γ-Im-β-ImPyIm |
| 528βp) | 5'-W C G C T C W-3' | PyImPy-β-Py-γ-Im-β-ImPyIm |
| 529β) | 5'-W C G C A T W-3' | PyImPyPyHp-γ-Py-β-ImPyIm |
| 529βp) | 5'-W C G C A T W-3' | PyImPy-β-Hp-γ-Py-β-ImPyIm |
| 530β) | 5'-W C G C A A W-3' | PyImPyPyPy-γ-Hp-β-ImPyIm |
| 530βp) | 5'-W C G C A A W-3' | PyImPy-β-Py-γ-Hp-β-ImPyIm |
| 531β) | 5'-W C G C A G W-3' | PyIm-β-PyIm-γ-Py-β-ImPyIm |
| 532β) | 5'-W C G C A C W-3' | PyImPyPyPy-γ-Im-β-ImPyIm |
| 532βp) | 5'-W C G C A C W-3' | PyImPy-β-Py-γ-Im-β-ImPyIm |
| 533β) | 5'-W C G C G T W-3' | PyIm-β-ImHp-γ-Py-β-ImPyIm |
| 534β) | 5'-W C G C G A W-3' | PyIm-β-ImPy-γ-Hp-β-ImPyIm |
| 535β) | 5'-W C G C C T W-3' | PyImPyPyHp-γ-PyIm-β-Im |
| 536β) | 5'-W C G C C A W-3' | PyImPyPyPy-γ-HpImIm-β-Im |
| G33β) | 5'-W C G G G G W-3' | PyImImImIm-γ-PyPy-β-PyIm |
| G34β) | 5'-W C G G G C W-3' | PyImImImPy-γ-ImPy-β-PyIm |
| G35β) | 5'-W C G G C G W-3' | PyImIm-β-Im-γ-PyIm-β-PyIm |
| G36β) | 5'-W C G G C C W-3' | PyImIm-β-Py-γ-ImIm-β-PyIm |
| G37β) | 5'-W C G C G G W-3' | PyIm-β-ImIm-γ-Py-β-ImPyIm |
| G38β) | 5'-W C G C G C W-3' | PyIm-β-ImPy-γ-Im-β-ImPyIm |
| G39β) | 5'-W C G C C G W-3' | PyIm-β-PyIm-γ-PyImIm-β-Im |
| G40β) | 5'-W C G C C C W-3' | PyImPyPyPy-γ-ImImIm-β-Im |

TABLE 62

10-ring Hairpin Polyamides for recognition of 7-bp 5'-WCTWNNW-3' with β substitutions.

| | DNA sequence | aromatic amino acid sequence |
|---|---|---|
| 537β) | 5'-WCTTTTW-3' | PyHpHpHpHp-γ-PyPy-β-PyIm |
| 537βp) | 5'-WCTTTTW-3' | PyHp-β-HpHp-γ-PyPy-β-PyIm |
| 538β) | 5'-WCTTTAW-3' | PyHpHpHpPy-γ-HpPy-β-PyIm |
| 538βp) | 5'-WCTTTAW-3' | PyHp-β-HpPy-γ-HpPy-β-PyIm |
| 539β) | 5'-WCTTTGW-3' | PyHp-β-HpIm-γ-PyPy-β-PyIm |
| 540β) | 5'-WCTTTCW-3' | PyHpHpHpPy-γ-ImPy-β-PyIm |
| 540βp) | 5'-WCTTTCW-3' | PyHp-β-HpPy-γ-ImPy-P-PyIm |
| 541β) | 5'-WCTTATW-3' | PyHpHpPyHp-γ-PyHp-β-PyIm |
| 541βp) | 5'-WCTTATW-3' | PyHp-β-PyHp-γ-PyHp-β-PyIm |
| 542β) | 5'-WCTTAAW-3' | PyHpHpPyPy-γ-HpPy-β-PyIm |
| 542βp) | 5'-WCTTAAW-3' | PyHp-β-PyPy-γ-HpPy-β-PyIm |
| 543β) | 5'-WCTTAGW-3' | PyHp-β-PyIm-γ-HpPy-β-PyIm |
| 544β) | 5'-WCTTACW-3' | PyHpHpPyPy-γ-ImPy-β-PyIm |
| 544βp) | 5'-WCTTACW-3' | PyHp-β-PyPy-γ-ImPy-β-PyIm |
| 545β) | 5'-WCTTGTW-3' | PyHp-β-ImHp-γ-PyPy-β-PyIm |
| 546β) | 5'-WCTTGAW-3' | PyHp-β-ImPy-γ-HpPy-β-PyIm |
| 547β) | 5'-WCTTGGW-3' | PyHp-β-ImIm-γ-PyPy-β-PyIm |
| 548β) | 5'-WCTTGCW-3' | PyHp-β-ImPy-γ-ImPy-β-PyIm |
| 549β) | 5'-WCTTCTW-3' | PyHpHpPyHp-γ-PyIm-β-PyIm |
| 549βp) | 5'-WCTTCTW-3' | PyHp-β-PyHp-γ-PyIm-β-PyIm |
| 550β) | 5'-WCTTCAW-3' | PyHpHpPyPy-γ-HpIm-β-PyIm |
| 550βp) | 5'-WCTTCAW-3' | PyHp-β-PyPy-γ-HpIm-β-PyIm |
| 551β) | 5'-WCTTCGW-3' | PyHp-β-PyIm-γ-PyIm-β-PyIm |
| 552β) | 5'-WCTTCCW-3' | PyHpHpPyPy-γ-ImIm-β-PyIm |
| 552βp) | 5'-WCTTCCW-3' | PyHp-β-PyPy-γ-ImIm-β-PyIm |
| 553β) | 5'-WCTATTW-3' | PyHpPyHpHp-γ-PyPy-β-PyIm |
| 553βp) | 5'-WCTATTW-3' | PyHp-β-HpHp-γ-PyPy-β-PyIm |
| 554β) | 5-WCTATAW-3' | PyHpPyHpPy-γ-HpPy-β-PyIm |
| 554βp) | 5'-WCTATAW-3' | PyHp-β-HpPy-γ-HpPy-β-PyIm |
| 555β) | 5'-WCTATGW-3' | PyHp-β-HpIm-γ-PyPy-β-PyIm |
| 556β) | 5'-WCTATCW-3' | PyHpPyHpPy-γ-ImPy-β-PyIm |
| 556βp) | 5'-WCTATCW-3' | PyHp-β-HpPy-γ-ImPy-β-PyIm |
| 557β) | 5'-WCTAATW-3' | PyHpPyPyHp-γ-PyHp-β-PyIm |
| 557βp) | 5'-WCTAATW-3' | PyHp-β-PyHp-γ-PyHp-β-PyIm |
| 558β) | 5'-WCTAAAW-3' | PyHpPyPyPy-γ-HpPy-β-PyIm |
| 558βp) | 5'-WCTAAAW-3' | PyHp-β-PyPy-γ-HpPy-β-PyIm |
| 559β) | 5'-WCTAAGW-3' | PyHp-β-PyIm-γ-HpPy-β-PyIm |

TABLE 62-continued 10-ring Hairpin Polyamides for recognition of 7-bp 5'-WCTWNNW-3' with β substitutions.

| | DNA sequence | aromatic amino acid sequence |
|---|---|---|
| 560β) | 5'-WCTAACW-3' | PyHpPyPyPy-γ-ImHp-β-PyIm |
| 560βp) | 5'-WCTAACW-3' | PyHp-β-PyPy-γ-ImHp-β-PyIm |
| 561β) | 5'-WCTAGTW-3' | PyHp-β-ImHp-γ-PyPy-β-PyIm |
| 562β) | 5'-WCTAGAW-3' | PyHp-β-ImPy-γ-HpPy-β-PyIm |
| 563β) | 5'-WCTAGGW-3' | PyHp-β-ImIm-γ-PyPy-β-PyIm |
| 564β) | 5'-WCTAGCW-3' | PyHp-β-ImPy-γ-ImPy-β-PyIm |
| 565β) | 5'-WCTACTW-3' | PyHpPyPyHp-γ-PyIm-β-PyIm |
| 565βp) | 5'-WCTACTW-3' | PyHp-β-PyHp-γ-PyIm-β-PyIm |
| 566β) | 5'-WCTACAW-3' | PyHpPyPyPy-γ-HpIm-β-PyIm |
| 566βp) | 5'-WCTACAW-3' | PyHp-β-PyPy-γ-HpIm-β-PyIm |
| 567β) | 5'-WCTACGW-3' | PyHp-β-PyIm-γ-PyIm-β-PyIm |
| 568β) | 5'-WCTACCW-3' | PyHpPyPyPy-γ-ImIm-β-PyIm |
| 568βp) | 5'-WCTACCW-3' | PyHp-β-PyPy-γ-ImIm-β-PyIm |

TABLE 63

10-ring Hairpin Polyamides for recognition of 7-bp 5'-WCTSNNW-3' with β substitutions.

| | DNA sequence | aromatic amino acid sequence |
|---|---|---|
| 569β) | 5'-WCTGTTW-3' | Py-β-ImHpHp-γ-PyPy-β-PyIm |
| 570β) | 5'-WCTGTAW-3' | Py-β-ImHpPy-γ-HpPy-β-PyIm |
| 571β) | 5'-WCTGTGW-3' | Py-β-ImHpIm-γ-PyPy-β-PyIm |
| 572β) | 5'-WCTGTCW-3' | Py-β-ImHpPy-γ-ImPy-β-PyIm |
| 573β) | 5'-WCTGATW-3' | Py-β-ImPyHp-γ-PyHp-β-PyIm |
| 574β) | 5'-WCTGAAW-3' | Py-β-ImPyPy-γ-HpPy-β-PyIm |
| 575β) | 5'-WCTGAGW-3' | Py-β-ImPyIm-γ-PyHp-β-PyIm |
| 576β) | 5'-WCTGACW-3' | Py-β-ImPyPy-γ-ImHp-β-PyIm |
| 577β) | 5'-WCTGGTW-3' | Py-β-ImImHp-γ-PyPy-β-PyIm |
| 578β) | 5'-WCTGGAW-3' | Py-β-ImImPy-γ-HpPy-β-PyIm |
| 579β) | 5'-WCTGCTW-3' | Py-β-ImPyHp-γ-PyIm-β-PyIm |
| 580β) | 5'-WCTGCAW-3' | Py-β-ImPyPy-γ-HpIm-β-PyIm |
| 581β) | 5'-WCTGGGW-3' | Py-β-ImImIm-γ-PyPy-β-PyIm |
| 582β) | 5'-WCTGGCW-3' | Py-β-ImImPy-γ-ImPy-β-PyIm |
| 583β) | 5'-WCTGCGW-3' | Py-β-ImPyIm-γ-PyIm-β-PyIm |
| 584β) | 5'-WCTGCCW-3' | Py-β-ImPyPy-γ-ImIm-β-PyIm |
| 585β) | 5'-WCTCTTW-3' | PyHpPyHpHp-γ-Py-β-ImPyIm |
| 585βp) | 5'-WCTCTTW-3' | PyHp-β-Hp-γ-Py-β-ImPyIm |
| 586β) | 5'-WCTCTAW-3' | PyHpPyHpPy-γ-Hp-β-ImPyIm |
| 586βp) | 7-WCTCTAW-3' | PyHpPy-β-Py-γ-Hp-β-ImPyIm |
| 587β) | 5'-WCTCTGW-3' | PyHp-β-HpIm-γ-Py-β-ImPyIm |
| 588β) | 5'-WCTCTCW-3' | PyHpPyHpPy-γ-Im-β-ImPyIm |
| 588βp) | 5'-WCTCTCW-3' | PyHpPy-β-Py-γ-Im-β-ImPyIm |
| 589β) | 5'-WCTCATW-3' | PyHpPyPyHp-γ-Py-β-ImPyIm |
| 589βp) | 5'-WCTCATW-3' | PyHpPy-β-Hp-γ-Py-β-ImPyIm |
| 590β) | 5'-WCTCAAW-3' | PyHpPyPyPy-γ-Hp-β-ImPyIm |
| 590βp) | 5'-WCTCAAW-3' | PyHpPy-β-Py-γ-Hp-β-ImPyIm |
| 591β) | 5'-WCTCAGW-3' | PyHp-β-PyIm-γ-Py-β-ImPyIm |
| 592β) | 5'-WCTCACW-3' | PyHpPyPyPy-γ-Im-β-ImPyIm |
| 592βp) | 5'-WCTCACW-3' | PyHpPy-β-Py-γ-Im-β-ImPyIm |
| 593β) | 5'-WCTCGTW-3' | PyHp-β-ImHp-γ-Py-β-ImPyIm |
| 594β) | 5'-WCTCGAW-3' | PyHp-β-ImPy-γ-Hp-β-ImPyIm |
| 595β) | 5'-WCTCCTW-3' | PyHpPyPyHp-γ-PyImIm-β-Im |
| 595βp) | 5'-WCTCCTW-3' | Py-β-PyPyHp-γ-PyImIm-β-Im |
| 596β) | 5'-WCTCCAW-3' | PyHpPyPyPy-γ-HpImIm-β-Im |
| 596βp) | 5'-WCTCCAW-3' | Py-β-PyPyPy-γ-HpImIm-β-Im |
| 597β) | 5'-WCTCGGW-3' | PyHp-β-ImIm-γ-Py-β-ImPyIm |
| 598β) | 5'-WCTCGCW-3' | PyHp-β-ImPy-γ-Im-β-ImPyIm |
| 599β) | 5'-WCTCCGW-3' | PyHp-β-PyIm-γ-PyImIm-β-Im |
| 600β) | 5'-WCTCCCW-3' | PyHpPyPyPy-γ-ImImIm-β-Im |
| 600βp) | 5'-WCTCCCW-3' | Py-β-PyPyPy-γ-ImImIm-β-Im |

TABLE 64

10-ring Hairpin Polyamides for recognition of 7-bp 5'-WCAWNNW-3' with β substitutions.

| | DNA sequence | aromatic amino acid sequence |
|---|---|---|
| 601β) | 5'-W C A T T T W-3' | PyPyHpHpHp-γ-PyPy-β-HpIm |
| 601βp) | 5'-W C A T T T W-3' | PyPy-β-HpHp-γ-PyPy-β-HpIm |
| 602β) | 5'-W C A T T A W-3' | PyPyHpHpPy-γ-HpPy-β-HpIm |
| 602βp) | 5'-W C A T T A W-3' | PyPy-β-HpPy-γ-HpPy-β-HpIm |
| 603β) | 5'-W C A T T G W-3' | PyPy-β-HpIm-γ-PyPy-β-HpIm |
| 604β) | 5'-W C A T T C W-3' | PyPyHpHpPy-γ-ImPy-β-HpIm |
| 604βp) | 5'-W C A T T C W-3' | PyPy-β-HpPy-γ-ImPy-β-HpIm |
| 605β) | 5'-W C A T A T W-3' | PyPyHpPyHp-γ-PyHp-β-HpIm |
| 605βp) | 5'-W C A T A T W-3' | PyPy-β-PyHp-γ-PyHp-β-HpIm |
| 606β) | 5'-W C A T A A W-3' | PyPyHpPyPy-γ-HpHp-β-HpIm |
| 606βp) | 5'-W C A T A A W-3' | PyPy-β-PyPy-γ-HpHp-β-HpIm |
| 607β) | 5'-W C A T A G W-3' | PyPy-β-PyIm-γ-PyHp-β-HpIm |
| 608β) | 5'-W C A T A C W-3' | PyPyHpPyPy-γ-ImHp-β-HpIm |
| 608βp) | 5'-W C A T A C W-3' | PyPy-β-PyPy-γ-ImHp-β-HpIm |
| 609β) | 5'-W C A T G T W-3' | PyPy-β-ImHp-γ-PyPy-β-HpIm |
| 610β) | 5'-W C A T G A W-3' | PyPy-β-ImPy-γ-HpPy-β-HpIm |
| 611β) | 5'-W C A T G G W-3' | PyPy-β-ImIm-γ-PyPy-β-HpIm |
| 612β) | 5'-W C A T G C W-3' | PyPy-β-ImPy-γ-ImPy-β-HpIm |
| 613β) | 5'-W C A T C T W-3' | PyPyHpPyHp-γ-PyIm-β-HpIm |
| 613βp) | 5'-W C A T C T W-3' | PyPy-β-PyHp-γ-PyIm-β-HpIm |
| 614β) | 5'-W C A T C A W-3' | PyPyHpPyPy-γ-HpIm-β-HpIm |
| 614βp) | 5'-W C A T C A W-3' | PyPy-β-PyPy-γ-HpIm-β-HpIm |
| 615β) | 5'-W C A T C G W-3' | PyPy-β-PyIm-γ-PyIm-β-HpIm |
| 616β) | 5'-W C A T C C W-3' | PyPyHpPyPy-γ-ImIm-β-HpIm |
| 616βp) | 5'-W C A T C C W-3' | PyPy-β-PyPy-γ-ImIm-β-HpIm |
| 617β) | 5'-W C A A T T W-3' | PyPyPyHpHp-γ-PyPy-β-HpIm |
| 617βp) | 5'-W C A A T T W-3' | PyPy-β-HpHp-γ-PyPy-β-HpIm |
| 618β) | 5'-W C A A T A W-3' | PyPyPyHpPy-γ-HpPy-β-HpIm |
| 618βp) | 5'-W C A A T A W-3' | PyPy-β-HpPy-γ-HpPy-β-HpIm |
| 619β) | 5'-W C A A T G W-3' | PyPy-β-HpIm-γ-PyPy-β-HpIm |
| 620β) | 5'-W C A A T C W-3' | PyPyPyHpPy-γ-ImPy-β-HpIm |
| 620βp) | 5'-W C A A T C W-3' | PyPy-β-HpPy-γ-ImPy-β-HpIm |
| 621β) | 5'-W C A A A T W-3' | PyPyPyPyHp-γ-PyHp-β-HpIm |
| 621βp) | 5'-W C A A A T W-3' | PyPy-β-PyHp-γ-PyHp-β-HpIm |
| 622β) | 5'-W C A A A A W-3' | PyPyPyPyPy-γ-HpHp-β-HpIm |
| 622βp) | 5'-W C A A A A W-3' | PyPy-β-PyPy-γ-HpHp-β-HpIm |
| 623β) | 5'-W C A A A G W-3' | PyPy-β-PyIm-γ-PyHp-β-HpIm |
| 624β) | 5'-W C A A A C W-3' | PyPyPyPyPy-γ-ImHp-β-HpIm |
| 624βp) | 5'-W C A A A C W-3' | PyPy-β-PyPy-γ-ImHp-β-HpIm |
| 625β) | 5'-W C A A G T W-3' | PyPy-β-ImHp-γ-PyPy-β-HpIm |
| 626β) | 5'-W C A A G A W-3' | PyPy-β-ImPy-γ-PyPy-β-HpIm |
| 627β) | 5'-W C A A G G W-3' | PyPy-β-ImIm-γ-PyPy-β-HpIm |
| 628β) | 5'-W C A A G C W-3' | PyPy-β-ImPy-γ-ImPy-β-HpIm |
| 629β) | 5'-W C A A C T W-3' | PyPyPyPyHp-γ-PyIm-β-HpIm |
| 629βp) | 5'-W C A A C T W-3' | PyPy-β-PyHp-γ-PyIm-β-HpIm |
| 630β) | 5'-W C A A C A W-3' | PyPyPyPyPy-γ-HpIm-β-HpIm |
| 630βp) | 5'-W C A A C A W-3' | PyPy-β-PyPy-γ-HpIm-β-HpIm |
| 631β) | 5'-W C A A C G W-3' | PyPy-β-PyIm-γ-PyIm-β-HpIm |
| 632β) | 5'-W C A A C C W-3' | PyPyPyPyPy-γ-ImIm-β-HpIm |
| 632βp) | 5'-W C A A C C W-3' | PyPy-β-PyPy-γ-ImIm-β-HpIm |

TABLE 65

10-ring Hairpin Polyamides for recognition of 7-bp 5'-WCASNNW-3' with β substitutions.

| | DNA sequence | aromatic amino acid sequence |
|---|---|---|
| 633β) | 5'-W C A G T T W-3' | Py-β-ImHpHp-γ-PyPy-β-HpIm |
| 634β) | 5'-W C A G T A W-3' | Py-β-ImHpPy-γ-HpPy-β-HpIm |
| 635β) | 5'-W C A G T G W-3' | Py-β-ImHpIm-γ-PyPy-β-HpIm |
| 636β) | 5'-W C A G T C W-3' | Py-β-ImHpPy-γ-ImPy-β-HpIm |
| 637β) | 5'-W C A G A T W-3' | Py-β-ImPyHp-γ-PyHp-β-HpIm |
| 638β) | 5'-W C A G A A W-3' | Py-β-ImPyPy-γ-HpPy-β-HpIm |
| 639β) | 5'-W C A G A G W-3' | Py-β-ImPyIm-γ-PyHp-β-HpIm |
| 640β) | 5'-W C A G A C W-3' | Py-β-ImPyPy-γ-ImPy-β-HpIm |
| 641β) | 5'-W C A G G T W-3' | Py-β-ImImHp-γ-PyPy-β-HpIm |
| 642β) | 5'-W C A G G A W-3' | Py-β-ImImPy-γ-HpPy-β-HpIm |
| 643β) | 5'-W C A G C T W-3' | Py-β-ImPyHp-γ-PyIm-β-HpIm |
| 644β) | 5'-W C A G C A W-3' | Py-β-ImPyPy-γ-HpIm-β-HpIm |
| 645β) | 5'-W C A G G G W-3' | Py-β-ImImIm-γ-PyPy-β-HpIm |
| 646β) | 5'-W C A G G C W-3' | Py-β-ImImPy-γ-ImPy-β-HpIm |
| 647β) | 5'-W C A G C G W-3' | Py-β-ImPyIm-γ-PyIm-β-HpIm |
| 648β) | 5'-W C A G C C W-3' | Py-β-ImPyPy-γ-ImIm-β-HpIm |
| 649β) | 5'-W C A C T T W-3' | PyPyPyHpHp-γ-Py-β-ImHpIm |
| 649βp) | 5'-W C A C T T W-3' | PyPyPy-β-Hp-γ-Py-β-ImHpIm |
| 650β) | 5'-W C A C T A W-3' | PyPyPyHpPy-γ-Hp-β-ImHpIm |
| 650βp) | 5'-W C A C T A W-3' | PyPyPy-β-Py-γ-Hp-β-ImHpIm |
| 651β) | 5'-W C A C T G W-3' | PyPy-β-HpIm-γ-Py-β-ImHpIm |
| 652β) | 5'-W C A C T C W-3' | PyPyPyHpPy-γ-Im-β-ImHpIm |
| 652βp) | 5'-W C A C T C W-3' | PyPyPy-β-Py-γ-Im-β-ImHpIm |
| 653β) | 5'-W C A C A T W-3' | PyPyPyPyHp-γ-Py-β-ImHpIm |
| 653βp) | 5'-W C A C A T W-3' | PyPyPy-β-Hp-γ-Py-β-ImHpIm |
| 654β) | 5'-W C A C A A W-3' | PyPyPyPyPy-γ-Hp-β-ImHpIm |
| 654βp) | 5'-W C A C A A W-3' | PyPyPy-β-Py-γ-Hp-β-ImHpIm |
| 655β) | 5'-W C A C A G W-3' | PyPy-β-PyIm-γ-Py-β-ImHpIm |
| 656β) | 5'-W C A C A C W-3' | PyPyPyPyPy-γ-Im-β-ImHpIm |
| 656β) | 5'-W C A C A C W-3' | PyPyPy-β-Py-γ-Im-β-ImHpIm |
| 657β) | 5'-W C A C G T W-3' | PyPy-β-ImHp-γ-Py-β-ImHpIm |
| 658βp) | 5'-W C A C G A W-3' | PyPy-β-ImPy-γ-Hp-β-ImHpIm |
| 659β) | 5'-W C A C C T W-3' | PyPyPyHp-γ-PyImIm-β-Im |
| 659βp) | 5'-W C A C C T W-3' | Py-β-PyPyHp-γ-PyImIm-β-Im |
| 660β) | 5'-W C A C C A W-3' | PyPyPyPy-γ-HpImIm-β-Im |
| 660βp) | 5'-W C A C C A W-3' | Py-β-PyPyPy-γ-HpImIm-β-Im |
| 661β) | 5'-W C A C G G W-3' | PyPy-β-ImIm-γ-Py-β-ImHpIm |
| 662β) | 5'-W C A C G C W-3' | PyPy-β-ImPy-γ-Im-β-ImHpIm |
| 663β) | 5'-W C A C C G W-3' | PyPy-β-PyIm-γ-PyImIm-β-Im |
| 664β) | 5'-W C A C C C W-3' | PyPyPyPy-γ-ImImIm-β-Im |
| 664βp) | 5'-W C A C C C W-3' | Py-β-PyPyPy-γ-ImImIm-β-Im |

TABLE 66

10-ring Hairpin Polyamides for recognition of 7-bp 5'-WCCWNNW-3' with β substitutions.

| | DNA sequence | aromatic amino acid sequence |
|---|---|---|
| 665β) | 5'-W C C T T T W-3' | PyPyHpHpHp-γ-PyPy-β-ImIm |
| 665βp) | 5'-W C C T T T W-3' | PyPy-β-HpHp-γ-PyPy-β-ImIm |
| 666β) | 5'-W C C T T A W-3' | PyPyHpHpPy-γ-HpPy-β-ImIm |
| 666βp) | 5'-W C C T T A W-3' | PyPy-β-HpPy-γ-HpPy-β-ImIm |
| 667β) | 5'-W C C T T G W-3' | PyPy-β-HpIm-γ-PyPy-β-ImIm |
| 668β) | 5'-W C C T T C W-3' | PyPyHpHpPy-γ-ImPy-β-ImIm |
| 668βp) | 5'-W C C T T C W-3' | PyPy-β-HpPy-γ-ImPy-β-ImIm |
| 669β) | 5'-W C C T A T W-3' | PyPyHpPyHp-γ-PyHp-β-ImIm |
| 669βp) | 5'-W C C T A T W-3' | PyPy-β-PyHp-γ-PyHp-β-ImIm |
| 670β) | 5'-W C C T A A W-3' | PyPyHpPyPy-γ-HpHp-β-ImIm |
| 670βp) | 5'-W C C T A A W-3' | PyPy-β-PyPy-γ-HpHp-β-ImIm |
| 671β) | 5'-W C C T A G W-3' | PyPy-β-PyIm-γ-PyHp-β-ImIm |
| 672β) | 5'-W C C T A C W-3' | PyPyHpPyPy-γ-ImHp-β-ImIm |
| 672βp) | 5'-W C C T A C W-3' | PyPy-β-PyPy-γ-ImHp-β-ImIm |
| 673β) | 5'-W C C T G T W-3' | PyPy-β-ImHp-γ-PyPy-β-ImIm |
| 674β) | 5'-W C C T G A W-3' | PyPy-β-ImPy-γ-HpPy-β-ImIm |
| 675β) | 5'-W C C T G G W-3' | PyPy-β-ImIm-γ-PyPy-β-ImIm |
| 676β) | 5'-W C C T G C W-3' | PyPy-β-ImPy-γ-ImPy-β-ImIm |
| 677β) | 5'-W C C T C T W-3' | PyPyHpPyHp-γ-PyIm-β-ImIm |
| 677βp) | 5'-W C C T C T W-3' | PyPy-β-PyHp-γ-PyIm-β-ImIm |
| 678β) | 5'-W C C T C A W-3' | PyPyHpPyPy-γ-HpIm-β-ImIm |
| 678βp) | 5'-W C C T C A W-3' | PyPy-β-PyPy-γ-HpIm-β-ImIm |
| 679β) | 5'-W C C T C G W-3' | PyPy-β-PyIm-γ-PyIm-β-ImIm |
| 680β) | 5'-W C C T C C W-3' | PyPyHpPyPy-γ-ImIm-β-ImIm |
| 680βp) | 5'-W C C T C C W-3' | PyPy-β-PyPy-γ-ImIm-β-ImIm |
| 681β) | 5'-W C C A T T W-3' | PyPyPyHpHp-γ-PyPy-β-ImIm |
| 681βp) | 5'-W C C A T T W-3' | PyPy-β-HpHp-γ-PyPy-β-ImIm |
| 682β) | 5'-W C C A T A W-3' | PyPyPyHpPy-γ-HpPy-β-ImIm |
| 682βp) | 5'-W C C A T A W-3' | PyPy-β-HpPy-γ-HpPy-β-ImIm |
| 683β) | 5'-W C C A T G W-3' | PyPy-β-HpIm-γ-PyPy-β-ImIm |
| 684β) | 5'-W C C A T C W-3' | PyPyPyHpPy-γ-ImPy-β-ImIm |
| 684βp) | 5'-W C C A T C W-3' | PyPy-β-HpPy-γ-ImPy-β-ImIm |
| 685β) | 5'-W C C A A T W-3' | PyPyPyPyHp-γ-PyHp-β-ImIm |
| 686βp) | 5'-W C C A A T W-3' | PyPy-β-PyHp-γ-PyHp-β-ImIm |
| 686β) | 5'-W C C A A A W-3' | PyPyPyPyPy-γ-HpHp-β-ImIm |

TABLE 66-continued 10-ring Hairpin Polyamides for recognition of 7-bp 5'-WCCWNNW-3' with β substitutions.

| | DNA sequence | aromatic amino acid sequence |
|---|---|---|
| 686βp) | 5'-W C C A A A W-3' | PyPy-β-PyPy-γ-HpHp-β-ImIm |
| 687β) | 5'-W C C A A G W-3' | PyPy-β-PyIm-γ-PyHp-β-ImIm |
| 688β) | 5'-W C C A A C W-3' | PyPyPyPyPy-γ-ImHp-β-ImIm |
| 688βp) | 5'-W C C A A C W-3' | PyPy-β-PyPy-γ-ImHp-β-ImIm |
| 689β) | 5'-W C C A G T W-3' | PyPy-β-ImHp-γ-PyPy-β-ImIm |
| 690β) | 5'-W C C A G A W-3' | PyPy-β-ImPy-γ-HpPy-β-ImIm |
| 691β) | 5'-W C C A G G W-3' | PyPy-β-ImIm-γ-PyPy-β-ImIm |
| 692β) | 5'-W C C A G C W-3' | PyPy-β-ImPy-γ-ImPy-β-ImIm |
| 693β) | 5'-W C C A C T W-3' | PyPyPyPyHp-γ-PyIm-β-ImIm |
| 693βp) | 5'-W C C A C T W-3' | PyPy-β-PyHp-γ-PyIm-β-ImIm |
| 694β) | 5'-W C C A C A W-3' | PyPyPyPyPy-γ-HpIm-β-ImIm |
| 694βp) | 5'-W C C A C A W-3' | PyPy-β-PyPy-γ-HpIm-β-ImIm |
| 695β) | 5'-W C C A C G W-3' | PyPy-β-PyIm-γ-PyIm-β-ImIm |
| 696β) | 5'-W C C A C C W-3' | PyPyPyPyPy-γ-ImIm-β-ImIm |
| 696βp) | 5'-W C C A C C W-3' | PyPy-β-PyPy-γ-ImIm-β-ImIm |

TABLE 67

10-ring Hairpin Polyamides for recognition of 7-bp 5'-WCCSNNW-3' with β substitutions.

| | DNA sequence | aromatic amino acid sequence |
|---|---|---|
| 697β) | 5'-W C C G T T W-3' | Py-β-ImHpHp-γ-PyPy-β-ImIm |
| 698β) | 5'-W C C G T A W-3' | Py-β-ImHpPy-γ-HpPy-β-ImIm |
| 699β) | 5'-W C C G T G W-3' | Py-β-ImHpIm-γ-PyPy-β-ImIm |
| 700β) | 5'-W C C G T C W-3' | Py-β-ImHpPy-γ-ImPy-β-ImIm |
| 701β) | 5'-W C C G A T W-3' | Py-β-ImPyHp-γ-PyHp-β-ImIm |
| 702β) | 5'-W C C G A A W-3' | Py-β-ImPyPy-γ-HpPy-β-ImIm |
| 703β) | 5'-W C C G A G W-3' | Py-β-ImPyIm-γ-PyHp-β-ImIm |
| 704β) | 5'-W C C G A C W-3' | Py-β-ImPyPy-γ-ImHp-β-ImIm |
| 705β) | 5'-W C C G G T W-3' | Py-β-ImImHp-γ-PyPy-β-ImIm |
| 706β) | 5'-W C C G G A W-3' | Py-β-ImImPy-γ-HpPy-β-ImIm |
| 707β) | 5'-W C C G C T W-3' | Py-β-ImPyHp-γ-PyIm-β-ImIm |
| 708β) | 5'-W C C G C A W-3' | Py-β-ImPyPy-γ-HpIm-β-ImIm |
| 709β) | 5'-W C C C T T W-3' | PyPyPyHpHp-γ-Py-β-ImIm |
| 709βp) | 5'-W C C C T T W-3' | PyPyPy-β-Hp-γ-Py-β-ImIm |
| 710β) | 5'-W C C C T A W-3' | PyPyPyHpPy-γ-Hp-β-ImIm |
| 710βp) | 5'-W C C C T A W-3' | PyPyPy-β-Py-γ-Hp-β-ImIm |
| 711β) | 5'-W C C C T G W-3' | PyPy-β-HpIm-γ-Py-β-ImIm |
| 712β) | 5'-W C C C T C W-3' | PyPyPyHpPy-γ-Im-β-ImIm |
| 712βp) | 5'-W C C C T C W-3' | PyPyPy-β-Py-γ-Im-β-ImIm |
| 713 β) | 5'-W C C C A T W-3' | PyPyPyPyHp-γ-Py-β-ImIm |
| 713βp) | 5'-W C C C A T W-3' | PyPy-β-Hp-γ-Py-β-ImIm |
| 714β) | 5'-W C C C A A W-3' | PyPyPyPyPy-γ-Hp-β-ImIm |
| 714βp) | 5'-W C C C A A W-3' | PyPy-β-Py-γ-Hp-β-ImIm |
| 715β) | 5'-W C C C A G W-3' | PyPy-β-PyIm-γ-Py-β-ImIm |
| 716β) | 5'-W C C C A C W-3' | PyPyPyPyPy-γ-Im-β-ImIm |
| 716βp) | 5'-W C C C A C W-3' | PyPyPy-β-Py-γ-Im-β-ImIm |
| 717β) | 5'-W C C C G T W-3' | PyPy-β-ImHp-γ-Py-β-ImIm |
| 718β) | 5'-W C C C G A W-3' | PyPy-β-ImPy-γ-Hp-β-ImIm |
| G41β) | 5'-W C C G G G W-3' | Py-β-ImImIm-γ-PyPy-β-ImIm |
| G42β) | 5'-W C C G G C W-3' | Py-β-ImImPy-γ-ImPy-β-ImIm |
| G43β) | 5'-W C C G C G W-3' | Py-β-ImPyIm-γ-PyIm-β-ImIm |
| G44β) | 5'-W C C G C C W-3' | Py-β-ImPyPy-γ-ImIm-β-ImIm |
| G45β) | 5'-W C C C G G W-3' | PyPy-β-ImIm-γ-Py-β-ImIm |
| G46β) | 5'-W C C C G C W-3' | PyPy-β-ImPy-γ-Im-β-ImIm |
| G47β) | 5'-W C C C C G W-3' | PyPy-β-PyIm-γ-PyImImIm |

TABLE 68

10-ring Hairpin Polyamides for recognition of 7-bp 5'-WAGWNNW-3' with β substitutions.

| | DNA sequence | aromatic amino acid sequence |
|---|---|---|
| 723β) | 5'-W A G T T G W-3' | PyIm-β-HpIm-γ-PyPyPyPyHp |
| 723βp) | 5'-W A G T T G W-3' | PyIm-β-HpIm-γ-PyPy-β-PyHp |
| 727β) | 5'-W A G T A G W-3' | PyIm-β-PyIm-γ-PyHpPyPyHp |
| 727βp) | 5'-W A G T A G W-3' | PyIm-β-PyIm-γ-PyHp-β-PyHp |
| 729β) | 5'-W A G T G T W-3' | PyIm-β-ImHp-γ-PyPyPyPyHp |
| 729βp) | 5'-W A G T G T W-3' | PyIm-β-ImHp-γ-PyPy-β-PyHp |
| 730β) | 5'-W A G T G A W-3' | PyIm-β-ImPy-γ-HpPyPyPyHp |
| 730βp) | 5'-W A G T G A W-3' | PyIm-β-ImPy-γ-HpPy-β-PyHp |
| 731β) | 5'-W A G T G G W-3' | PyIm-β-ImIm-γ-PyPyPyPyHp |
| 731βp) | 5'-W A G T G G W-3' | PyIm-β-ImIm-γ-PyPy-β-PyHp |
| 732β) | 5'-W A G T G C W-3' | PyIm-β-ImPy-γ-ImPyPyPyHp |
| 732βp) | 5'-W A G T G C W-3' | PyIm-β-ImPy-γ-ImPy-β-PyHp |
| 735β) | 5'-W A G T C G W-3' | PyIm-β-PyIm-γ-PyImPyPyHp |
| 735βp) | 5'-W A G T C G W-3' | PyIm-β-PyIm-γ-PyIm-β-PyHp |
| 739β) | 5'-W A G A T G W-3' | PyIm-β-HpIm-γ-PyPyHpPyHp |
| 739βp) | 5'-W A G A T G W-3' | PyIm-β-HpIm-γ-PyPy-β-PyHp |
| 743β) | 5'-W A G A A G W-3' | PyIm-β-PyIm-γ-PyHpPpPyHp |
| 743βp) | 5'-W A G A A G W-3' | PyIm-β-PyIm-γ-PyHp-β-PyHp |
| 745β) | 5'-W A G A G T W-3' | PyIm-β-ImHp-γ-PyPyHpPyHp |
| 745βp) | 5'-W A G A G T W-3' | PyIm-β-ImHp-γ-PyPy-β-PyHp |
| 746β) | 5'-W A G A G A W-3' | PyIm-β-ImPy-γ-HpPyHpPyHp |
| 746βp) | 5'-W A G A G A W-3' | PyIm-β-ImPy-γ-HpPy-β-PyHp |
| 747β) | 5'-W A G A G G W-3' | PyIm-β-ImIm-γ-PyPyHpPyHp |
| 747βp) | 5'-W A G A G G W-3' | PyIm-β-ImIm-γ-PyPy-β-PyHp |
| 748β) | 5'-W A G A G C W-3' | PyIm-β-ImPy-γ-ImPyHpPyHp |
| 748βp) | 5'-W A G A G C W-3' | PyIm-β-ImPy-γ-ImPy-β-PyHp |
| 751β) | 5'-W A G A C G W-3' | PyIm-β-PyIm-γ-PyImHpPyHp |
| 751βp) | 5'-W A G A C G W-3' | PyIm-β-PyIm-γ-PyIm-β-PyHp |

TABLE 69

10-ring Hairpin Polyamides for recognition of 7-bp 5'-WAGSNNW-3' with β substitutions.

| | DNA sequence | aromatic amino acid sequence |
|---|---|---|
| 753β) | 5'-W A G G T T W-3' | PyImIm-β-Hp-γ-PyPyPyPyHp |
| 753βp) | 5'-W A G G T T W-3' | PyImIm-β-Hp-γ-Py-β-PyPyHp |
| 754β) | 5'-W A G G T A W-3' | PyImIm-β-Py-γ-HpPyPyPyHp |
| 754βp) | 5'-W A G G T A W-3' | PyImIm-β-Py-γ-Hp-β-PyPyHp |
| 755β) | 5'-W A G G T G W-3' | PyImIm-β-Im-γ-PyPyPyPyHp |
| 755βp) | 5'-W A G G T G W-3' | PyImIm-β-Im-γ-Py-β-PyPyHp |
| 756β) | 5'-W A G G T C W-3' | PyImIm-β-Py-γ-ImPyPyPyHp |
| 756βp) | 5'-W A G G T C W-3' | PyImIm-β-Py-γ-Im-β-PyPyHp |
| 757β) | 5'-W A G G A T W-3' | PyImIm-β-Hp-γ-PyPyHpPyHp |
| 757βp) | 5'-W A G G A T W-3' | PyImIm-β-Hp-γ-Py-β-PyPyHp |
| 758β) | 5'-W A G G A A W-3' | PyImIm-β-Py-γ-HpHpPyPyHp |
| 758βp) | 5'-W A G G A A W-3' | PyImIm-β-Py-γ-Hp-β-PyPyHp |
| 759β) | 5'-W A G G A G W-3' | PyImIm-β-Im-γ-PyHpPyPyHp |
| 759βp) | 5'-W A G G A G W-3' | PyImIm-β-Im-γ-Py-β-PyPyHp |
| 760β) | 5'-W A G G A C W-3' | PyImIm-β-Py-γ-ImHpPyPyHp |
| 760βp) | 5'-W A G G A C W-3' | PyImIm-β-Py-γ-Im-β-PyPyHp |
| 763β) | 5'-W A G G C T W-3' | PyImIm-β-Hp-γ-PyImPyPyHp |
| 764β) | 5'-W A G G C A W-3' | PyImIm-β-Py-γ-HpImPyPyHp |
| 765β) | 5'-W A G C T T W-3' | PyImPyHpHp-γ-Py-β-ImPyHp |
| 765βp) | 5'-W A G C T T W-3' | PyImPy-β-Hp-γ-Py-β-ImPyHp |
| 766β) | 5'-W A G C T A W-3' | PyImPyHpPy-γ-Hp-β-ImPyHp |
| 766βp) | 5'-W A G C T A W-3' | PyImPy-β-Py-γ-Hp-β-ImPyHp |
| 767β) | 5'-W A G C T G W-3' | PyIm-β-HpIm-γ-Py-β-ImPyHp |
| 768β) | 5'-W A G C T C W-3' | PyImHpPy-γ-Im-β-ImPyHp |
| 768βp) | 5'-W A G C T C W-3' | PyImPy-β-Py-γ-Im-β-ImPyHp |
| 769β) | 5'-W A G C A T W-3' | PyImPyHp-γ-Py-β-ImPyHp |
| 769βp) | 5'-W A G C A T W-3' | PyImPy-β-Hp-γ-Py-β-ImPyHp |
| 770β) | 5'-W A G C A A W-3' | PyImPyPy-γ-Hp-β-ImPyHp |
| 770βp) | 5'-W A G C A A W-3' | PyImPy-β-Py-γ-Hp-β-ImPyHp |
| 771β) | 5'-W A G C A G W-3' | PyIm-β-PyIm-γ-Py-β-ImPyHp |
| 772β) | 5'-W A G C A C W-3' | PyImPyPyPy-γ-Im-β-ImPyHp |
| 772βp) | 5'-W A G C A C W-3' | PyImPy-β-Py-γ-Im-β-ImPyHp |
| 773β) | 5'-W A G C G T W-3' | PyIm-β-ImHp-γ-Py-β-ImPyHp |
| 774β) | 5'-W A G C G A W-3' | PyIm-β-ImPy-γ-Hp-β-ImPyHp |
| 775β) | 5'-W A G C C T W-3' | PyImPyPyHp-γ-PyImIm-β-Hp |
| 776β) | 5'-W A G C C A W-3' | PyImPyPyPy-γ-HpImIm-β-Hp |
| 779β) | 5'-W A G G C G W-3' | PyImIm-β-Im-γ-PyImPyPyHp |

TABLE 69-continued 10-ring Hairpin Polyamides for recognition of
7-bp 5'-WAGSNNW-3' with β substitutions.

| | DNA sequence | aromatic amino acid sequence |
|---|---|---|
| 780β) | 5'-W A G G C C W-3' | PyImIm-β-Py-γ-ImImPyPyHp |
| 781β) | 5'-W A G C G G W-3' | PyIm-β-ImIm-γ-Py-β-ImPyHp |
| 782β) | 5'-W A G C G C W-3' | PyIm-β-ImPy-γ-Im-β-ImPyHp |
| 783β) | 5'-W A G C C G W-3' | PyIm-β-PyIm-γ-PyImIm-β-Hp |
| 784β) | 5'-W A G C C C W-3' | PyImPyPy-γ-ImImIm-β-Hp |

TABLE 70

10-ring Hairpin Polyamides for recognition of
7-bp 5'-WATWNNW-3' with β substitutions.

| | DNA sequence | aromatic amino acid sequence |
|---|---|---|
| 787β) | 5'-W A T T T G W-3' | PyHp-β-HpIm-γ-PyPyPyPyHp |
| 787βp) | 5'-W A T T T G W-3' | PyHp-β-HpIm-γ-PyPy-β-PyHp |
| 791β) | 5'-W A T T A G W-3' | PyHp-β-PyIm-γ-PyHpPyPyHp |
| 791βp) | 5'-W A T T A G W-3' | PyHp-β-PyIm-γ-PyHp-β-PyHp |
| 793β) | 5'-W A T T G T W-3' | PyHp-β-ImHp-γ-PyPyPyPyHp |
| 793βp) | 5'-W A T T G T W-3' | PyHp-β-ImHp-γ-PyPy-β-PyHp |
| 794β) | 5'-W A T T G A W-3' | PyHp-β-ImPy-γ-HpPyPyPyHp |
| 794βp) | 5'-W A T T G A W-3' | PyHp-β-ImPy-γ-HpPy-β-PyHp |
| 795β) | 5'-W A T T G G W-3' | PyHp-β-ImIm-γ-PyPyPyPyHp |
| 795βp) | 5'-W A T T G G W-3' | PyHp-β-ImPy-γ-ImPyPyHp |
| 796β) | 5'-W A T T G C W-3' | PyHp-β-ImPy-γ-ImPy-β-PyHp |
| 799β) | 5'-W A T T C G W-3' | PyHp-β-PyIm-γ-PyImPyPyHp |
| 799βp) | 5'-W A T T C G W-3' | PyHp-β-PyIm-γ-PyIm-β-PyHp |
| 803β) | 5'-W A T A T G W-3' | PyHp-β-HpIm-γ-PyPyHpPyHp |
| 803βp) | 5'-W A T A T G W-3' | PyHp-β-HpIm-γ-PyPy-β-PyHp |
| 807β) | 5'-W A T A A G W-3' | PyHp-β-PyIm-γ-PyHpHpPyHp |
| 807βp) | 5'-W A T A A G W-3' | PyHp-β-PyIm-γ-PyHp-β-PyHp |
| 809β) | 5'-W A T A G T W-3' | PyHp-β-ImHp-γ-PyPyHpPyHp |
| 809βp) | 5'-W A T A G T W-3' | PyHp-β-ImHp-γ-PyPy-β-PyHp |
| 810β) | 5'-W A T A G A W-3' | PyHp-β-ImPy-γ-HpPyHpPyHp |
| 810βp) | 5'-W A T A G A W-3' | PyHp-β-ImPy-γ-HpPy-β-PyHp |
| 811β) | 5'-W A T A G G W-3' | PyHp-β-ImIm-γ-PyPyHpPyHp |
| 811βp) | 5'-W A T A G G W-3' | PyHp-β-ImIm-γ-PyPy-β-PyHp |
| 812β) | 5'-W A T A G C W-3' | PyHp-β-ImPy-γ-ImPyHpPyHp |
| 812βp) | 5'-W A T A G C W-3' | PyHp-β-ImPy-γ-ImPy-β-PyHp |
| 815β) | 5'-W A T A C G W-3' | PyHp-β-PyIm-γ-PyImHpPyHp |
| 815βp) | 5'-W A T A C G W-3' | PyHp-β-PyIm-γ-PyIm-β-PyHp |

TABLE 71

10-ring Hairpin Polyamides for recognition of
7-bp 5'-WATSNNW-3' with β substitutions.

| | DNA sequence | aromatic amino acid sequence |
|---|---|---|
| 817β) | 5'-W A T G T T W-3' | Py-β-ImHpHp-γ-PyPyPyPyHp |
| 817βp) | 5'-W A T G T T W-3' | Py-β-ImHpHp-γ-PyPyPy-β-Hp |
| 818β) | 5'-W A T G T A W-3' | Py-β-ImHpPy-γ-HpPyPyPyHp |
| 818βp) | 5'-W A T G T A W-3' | Py-β-ImHpPy-γ-HpPyPy-β-Hp |
| 819β) | 5'-W A T G T G W-3' | Py-β-ImHpIm-γ-PyPyPyPyHp |
| 819βp) | 5'-W A T G T G W-3' | Py-β-ImHpIm-γ-PyPyPy-β-Hp |
| 820β) | 5'-W A T G T C W-3' | Py-β-ImHpPy-γ-ImPyPyPyHp |
| 820βp) | 5'-W A T G T C W-3' | Py-β-ImHpPy-γ-ImPyPy-β-Hp |
| 821β) | 5'-W A T G A T W-3' | Py-β-ImPyHp-γ-PyHpPyPyHp |
| 821βp) | 5'-W A T G A T W-3' | Py-β-ImPyHp-γ-PyHpPy-β-Hp |
| 822β) | 5'-W A T G A A W-3' | Py-β-ImPyPy-γ-HpHpPyPyHp |
| 822βp) | 5'-W A T G A A W-3' | Py-β-ImPyPy-γ-HpHpPy-β-Hp |
| 823β) | 5'-W A T G A G W-3' | Py-β-ImPyIm-γ-PyHpPyPyHp |
| 823βp) | 5'-W A T G A G W-3' | Py-β-ImPyIm-γ-PyHpPy-β-Hp |
| 824β) | 5'-W A T G A C W-3' | Py-β-ImPyPy-γ-ImHpPyPyHp |
| 824βp) | 5'-W A T G A C W-3' | Py-β-ImPyPy-γ-ImHpPy-β-Hp |
| 825β) | 5'-W A T G G T W-3' | Py-β-ImImHp-γ-PyPyPyPyHp |
| 825βp) | 5'-W A T G G T W-3' | Py-β-ImImHp-γ-PyPyPy-β-Hp |
| 826β) | 5'-W A T G G A W-3' | Py-β-ImImPy-γ-HpPyPyPyHp |
| 826βp) | 5'-W A T G G A W-3' | Py-β-ImImPy-γ-HpPyPy-β-Hp |
| 827β) | 5'-W A T G C T W-3' | Py-β-ImPyHp-γ-PyImPyPyHp |

TABLE 71-continued 10-ring Hairpin Polyamides for recognition of
7-bp 5'-WATSNNW-3' with β substitutions.

| | DNA sequence | aromatic amino acid sequence |
|---|---|---|
| 827βp) | 5'-W A T G C T W-3' | Py-β-ImPyHp-γ-PyImPy-β-Hp |
| 828β) | 5'-W A T G C A W-3' | Py-β-ImPyPy-γ-HpImPyPyHp |
| 828βp) | 5'-W A T G C A W-3' | Py-β-ImPyPy-γ-HpImPy-β-Hp |
| 829β) | 5'-W A T G G G W-3' | Py-β-ImImIm-γ-PyPyPyPyHp |
| 829βp) | 5'-W A T C C G W-3' | Py-β-ImImIm-γ-PyPyPy-β-Hp |
| 830β) | 5'-W A T G G C W-3' | Py-β-ImImPy-γ-ImPyPyPyHp |
| 830βp) | 5'-W A T G G C W-3' | Py-β-ImImPy-γ-ImPy-β-Hp |
| 831β) | 5'-W A T G C G W-3' | Py-β-ImPyIm-γ-PyImPyPyHp |
| 831βp) | 5'-W A T G C G W-3' | Py-β-ImPyIm-γ-PyImPy-β-Hp |
| 832β) | 5'-W A T G C C W-3' | Py-β-ImPyPy-γ-ImImPyPyHp |
| 832βp) | 5'-W A T G C C W-3' | Py-β-ImPyPy-γ-ImImPy-β-Hp |
| 833β) | 5'-W A T C T T W-3' | PyHpPyHpHp-γ-Py-β-ImPyHp |
| 833βp) | 5'-W A T C T T W-3' | PyHpPy-β-Hp-γ-Py-β-ImPyHp |
| 834β) | 5'-W A T C T A W-3' | PyHpPyHpPy-γ-Hp-β-ImPyHp |
| 834βp) | 5'-W A T C T A W-3' | PyHpPy-β-Py-γ-Hp-β-ImPyHp |
| 835β) | 5'-W A T C T G W-3' | PyHp-β-HpIm-γ-Py-β-ImPyHp |
| 836β) | 5'-W A T C T C W-3' | PyHpPyHpPy-γ-Im-β-ImPyHp |
| 836βp) | 5'-W A T C T C W-3' | PyHpPy-β-Py-γ-Im-β-ImPyHp |
| 837β) | 5'-W A T C A T W-3' | PyHpPyPyHp-γ-Py-β-ImPyHp |
| 837βp) | 5'-W A T C A T W-3' | PyHpPy-β-Hp-γ-Py-β-ImPyHp |
| 838β) | 5'-W A T C A A W-3' | PyHpPyPyPy-γ-Hp-β-ImPyHp |
| 838βp) | 5'-W A T C A A W-3' | PyHpPy-β-Py-γ-Hp-β-ImPyHp |
| 839β) | 5'-W A T C A G W-3' | PyHp-β-PyIm-γ-Py-β-ImPyHp |
| 840β) | 5'-W A T C A C W-3' | PyHpPyPyPy-γ-Im-β-ImPyHp |
| 840βp) | 5'-W A T C A C W-3' | PyHpPy-β-Py-γ-Im-β-ImPyHp |
| 841β) | 5'-W A T C G T W-3' | PyHp-β-ImHp-γ-Py-β-ImPyHp |
| 842β) | 5'-W A T C G A W-3' | PyHp-β-ImPy-γ-Hp-β-ImPyHp |
| 843β) | 5'-W A T C C T W-3' | PyHpPyHp-γ-PyImIm-β-Hp |
| 843βp) | 5'-W A T C C T W-3' | Py-β-PyPyHp-γ-PyImIm-β-Hp |
| 844β) | 5'-W A T C C A W-3' | PyHpPyPyPy-γ-HpImIm-β-Hp |
| 844βp) | 5'-W A T C C A W-3' | Py-β-PyPyPy-γ-HpImIm-β-Hp |
| 845β) | 5'-W A T C G G W-3' | PyHp-β-ImIm-γ-Py-β-ImPyHp |
| 846β) | 5'-W A T C G C W-3' | PyHp-β-ImPy-γ-Im-β-ImPyHp |
| 847β) | 5'-W A T C C G W-3' | PyHp-β-PyIm-γ-PyImIm-β-Hp |
| 848β) | 5'-W A T C C C W-3' | PyHpPyPyPy-γ-ImImIm-β-Hp |
| 848βp) | 5'-W A T C C C W-3' | Py-β-PyPyPy-γ-ImImIm-β-Hp |

TABLE 72

10-ring Hairpin Polyamides for recognition of
7-bp 5'-WAAWNNW-3' with β substitutions.

| | DNA sequence | aromatic amino acid sequence |
|---|---|---|
| 851β) | 5'-W A A T T G W-3' | PyPy-β-HpIm-γ-PyPyPyHpHp |
| 851βp) | 5'-W A A T T G W-3' | PyPy-β-HpIm-γ-PyPy-β-HpHp |
| 855β) | 5'-W A A T A G W-3' | PyPy-β-PyIm-γ-PyHpPyHpHp |
| 855βp) | 5'-W A A T A G W-3' | PyPy-β-PyIm-γ-PyHp-β-HpHp |
| 857β) | 5'-W A A T G T W-3' | PyPy-β-ImHp-γ-PyPyPyHpHp |
| 857βp) | 5'-W A A T G T W-3' | PyPy-β-ImHp-γ-PyPy-β-HpHp |
| 858β) | 5'-W A A T G A W-3' | PyPy-β-ImPy-γ-HpPyPyHpHp |
| 858βp) | 5'-W A A T G A W-3' | PyPy-β-ImPy-γ-HpPy-β-HpHp |
| 859β) | 5'-W A A T G G W-3' | PyPy-β-ImIm-γ-PyPyPyHpHp |
| 859βp) | 5'-W A A T G G W-3' | PyPy-β-ImIm-γ-PyPy-β-HpHp |
| 860β) | 5'-W A A T G C W-3' | PyPy-β-ImPy-γ-ImPyPyHpHp |
| 860βp) | 5'-W A A T G C W-3' | PyPy-β-ImPy-γ-ImPy-β-HpHp |
| 863β) | 5'-W A A T C G W-3' | PyPy-β-PyIm-γ-PyImPyHpHp |
| 863βp) | 5'-W A A T C G W-3' | PyPy-β-PyIm-γ-PyIm-β-HpHp |
| 867β) | 5'-W A A A T G W-3' | PyPy-β-HpIm-γ-PyPyHpHpHp |
| 867βp) | 5'-W A A A T G W-3' | PyPy-β-HpIm-γ-PyPy-β-HpHp |
| 871β) | 5'-W A A A A G W-3' | PyPy-β-PyIm-γ-PyHpHpHpHp |
| 871βp) | 5'-W A A A A G W-3' | PyPy-β-PyIm-γ-PyHp-β-HpHp |
| 873β) | 5'-W A A A G T W-3' | PyPy-β-ImHp-γ-PyPyHpHpHp |
| 873βp) | 5'-W A A A G T W-3' | PyPy-β-ImHp-γ-PyPy-β-HpHp |
| 874β) | 5'-W A A A G A W-3' | PyPy-β-ImPy-γ-HpPyHpHpHp |
| 874βp) | 5'-W A A A G A W-3' | PyPy-β-ImPy-γ-HpPy-β-HpHp |
| 875β) | 5'-W A A A G G W-3' | PyPy-β-ImIm-γ-PyPyHpHpHp |
| 875βp) | 5'-W A A A G G W-3' | PyPy-β-ImIm-γ-PyPy-β-HpHp |
| 876β) | 5'-W A A A G C W-3' | PyPy-β-ImPy-γ-ImPyHpHpHp |

TABLE 72-continued 10-ring Hairpin Polyamides for recognition of
7-bp 5'-WAAWNNW-3' with β substitutions.

| | DNA sequence | aromatic amino acid sequence |
|---|---|---|
| 876βp) | 5'-W A A A G C W-3' | PyPy-β-ImPy-γ-ImPy-β-HpHp |
| 879β) | 5'-W A A A C G W-3' | PyPy-β-PyIm-γ-PyImHpHpHp |
| 879βp) | 5'-W A A A C G W-3' | PyPy-β-PyIm-γ-PyIm-β-HpHp |

TABLE 73

10-ring Hairpin Polyamides for recognition of
7-bp 5'-WAASNNW-3' with β substitutions.

| | DNA sequence | aromatic amino acid sequence |
|---|---|---|
| 881β) | 5'-W A A G T T W-3' | Py-β-ImHpHp-γ-PyPyPyHpHp |
| 881βp) | 5'-W A A G T T W-3' | Py-β-ImHpHp-γ-PyPyPy-β-Hp |
| 882β) | 5'-W A A G T A W-3' | Py-β-ImHpPy-γ-HpPyPyHpHp |
| 882βp) | 5'-W A A G T A W-3' | Py-β-ImHpPy-γ-HpPyPy-β-Hp |
| 883β) | 5'-W A A G T G W-3' | Py-β-ImHpIm-γ-PyPyPyHpHp |
| 883βp) | 5'-W A A G T G W-3' | Py-β-ImHpIm-γ-PyPyPy-β-Hp |
| 884β) | 5'-W A A G T C W-3' | Py-β-ImHpPy-γ-ImPyPyHpHp |
| 884βp) | 5'-W A A G T C W-3' | Py-β-ImHpPy-γ-ImPyPy-β-Hp |
| 885β) | 5'-W A A G A T W-3' | Py-β-ImPyHp-γ-PyHpPyHpHp |
| 885βp) | 5'-W A A G A T W-3' | Py-β-ImPyHp-γ-PyHpPy-β-Hp |
| 886β) | 5'-W A A G A A W-3' | Py-β-ImPyPy-γ-HpHpPyHpHp |
| 886βp) | 5'-W A A G A A W-3' | Py-β-ImPyPy-γ-HpHpPy-β-Hp |
| 887β) | 5'-W A A G A G W-3' | Py-β-ImPyIm-γ-PyHpPyHpHp |
| 887βp) | 5'-W A A G A G W-3' | Py-β-ImPyIm-γ-PyHpPy-β-Hp |
| 888β) | 5'-W A A G A C W-3' | Py-β-ImPyPy-γ-ImHpPyHpHp |
| 888βp) | 5'-W A A G A C W-3' | Py-β-ImPyPy-γ-ImHpPy-β-Hp |
| 889β) | 5'-W A A G G T W-3' | Py-β-ImImHp-γ-PyPyPyHpHp |
| 889βp) | 5'-W A A G G T W-3' | Py-β-ImImHp-γ-PyPyPy-β-Hp |
| 890β) | 5'-W A A G G A W-3' | Py-β-ImImPy-γ-HpPyPyHpHp |
| 890βp) | 5'-W A A G G A W-3' | Py-β-ImImPy-γ-HpPyPy-β-Hp |
| 891β) | 5'-W A A G C T W-3' | Py-β-ImPyHp-γ-PyImPyHpHp |
| 891βp) | 5'-W A A G C T W-3' | Py-β-ImPyHp-γ-PyImPy-β-Hp |
| 892β) | 5'-W A A G C A W-3' | Py-β-ImPyPy-γ-HpImPyHpHp |
| 892βp) | 5'-W A A G C A W-3' | Py-β-ImPyPy-γ-HpImPy-β-Hp |
| 893β) | 5'-W A A G G G W-3' | Py-β-ImImIm-γ-PyPyPyHpHp |
| 893βp) | 5'-W A A G G G W-3' | Py-β-ImImIm-γ-PyPyPy-β-Hp |
| 894β) | 5'-W A A G G C W-3' | Py-β-ImImPy-γ-ImPyPyHpHp |
| 894βp) | 5'-W A A G G C W-3' | Py-β-ImImPy-γ-ImPyPy-β-Hp |
| 895β) | 5'-W A A G C G W-3' | Py-β-ImPyIm-γ-PyImPyHpHp |
| 895βp) | 5'-W A A G C G W-3' | Py-β-ImPyIm-γ-PyImPy-β-Hp |
| 896β) | 5'-W A A G C C W-3' | Py-β-ImPyPy-γ-ImImPyHpHp |
| 896βp) | 5'-W A A G C C W-3' | Py-β-ImPyPy-γ-ImImPy-β-Hp |
| 897β) | 5'-W A A C T T W-3' | PyPyPyHpHp-γ-Py-β-ImHpHp |
| 897βp) | 5'-W A A C T T W-3' | PyPyPy-β-Hp-γ-Py-β-ImHpHp |
| 898β) | 5'-W A A C T A W-3' | PyPyHpPy-γ-Hp-β-ImHpHp |
| 898βp) | 5'-W A A C T A W-3' | PyPyPy-β-Py-γ-Hp-β-ImHpHp |
| 899β) | 5'-W A A C T G W-3' | PyPy-β-HpIm-γ-Py-β-ImHpHp |
| 900β) | 5'-W A A C T C W-3' | PyPyHpPy-γ-Im-β-ImHpHp |
| 900βp) | 5'-W A A C T C W-3' | PyPyPy-β-Py-γ-Im-β-ImHpHp |
| 901β) | 5'-W A A C A T W-3' | PyPyPyPyHp-γ-Py-β-ImHpHp |
| 901βp) | 5'-W A A C A T W-3' | PyPyPy-β-Hp-γ-Py-β-ImHpHp |
| 902β) | 5'-W A A C A A W-3' | PyPyPyPy-γ-Hp-β-ImHpHp |
| 902βp) | 5'-W A A C A A W-3' | PyPyPy-β-Py-γ-Hp-β-ImHpHp |
| 903β) | 5'-W A A C A G W-3' | PyPy-β-PyIm-γ-Py-β-ImHpHp |
| 904β) | 5'-W A A C A C W-3' | PyPyPyPy-γ-Im-β-ImHpHp |
| 904βp) | 5'-W A A C A C W-3' | PyPyPy-β-Py-γ-Im-β-ImHpHp |
| 905β) | 5'-W A A C G T W-3' | PyPy-β-ImHp-γ-Py-β-ImHpHp |
| 906β) | 5'-W A A C G A W-3' | PyPy-β-ImPy-γ-Hp-β-ImHpHp |
| 907β) | 5'-W A A C C T W-3' | PyPyPyHp-γ-PyIm-β-ImHp |
| 907βp) | 5'-W A A C C T W-3' | Py-β-PyPyHp-γ-PyImIm-β-Hp |
| 908β) | 5'-W A A C C A W-3' | PyPyPyPy-γ-HpImIm-β-Hp |
| 908βp) | 5'-W A A C C A W-3' | Py-β-PyPyPy-γ-HpImIm-β-Hp |
| 909β) | 5'-W A A C G G W-3' | PyPy-β-ImIm-γ-Py-β-ImHpHp |
| 910β) | 5'-W A A C G C W-3' | PyPy-β-ImPy-γ-Im-β-ImHpHp |
| 911β) | 5'-W A A C C G W-3' | PyPy-β-PyIm-γ-PyIm-β-ImHp |
| 912β) | 5'-W A A C C C W-3' | PyPyPyPy-γ-ImImIm-β-Hp |
| 912βp) | 5'-W A A C C C W-3' | Py-β-PyPyPy-γ-ImImIm-β-Hp |

TABLE 74

10-ring Hairpin Polyamides for recognition of
7-bp 5'-WACWNNW-3' with β substitutions.

| | DNA sequence | aromatic amino acid sequence |
|---|---|---|
| 913β) | 5'-W A C T T T W-3' | PyPyHpHpHp-γ-PyPy-β-ImHp |
| 913βp) | 5'-W A C T T T W-3' | PyPy-βHpHp-γ-PyPy-β-ImHp |
| 914β) | 5'-W A C T T A W-3' | PyPyHpHpPy-γ-HpPy-β-ImHp |
| 914βp) | 5'-W A C T T A W-3' | PyPy-β-HpPy-γ-HpPy-β-ImHp |
| 915β) | 5'-W A C T T G W-3' | PyPy-β-HpIm-γ-PyPy-β-ImHp |
| 916β) | 5'-W A C T T C W-3' | PyPyHpHpPy-γ-ImPy-β-ImHp |
| 916βp) | 5'-W A C T T C W-3' | PyPy-β-HpPy-γ-ImPy-β-ImHp |
| 917β) | 5'-W A C T A T W-3' | PyPyHpPyHp-γ-PyHp-β-ImHp |
| 917βp) | 5'-W A C T A T W-3' | PyPyHpPyHp-γ-PyHp-β-ImHp |
| 918β) | 5'-W A C T A A W-3' | PyPyHpPyPy-γ-HpPy-β-ImHp |
| 918βp) | 5'-W A C T A A W-3' | PyPy-β-PyPy-γ-HpHp-β-ImHp |
| 919β) | 5'-W A C T A G W-3' | PyPy-β-PyIm-γ-PyHp-β-ImHp |
| 920β) | 5'-W A C T A C W-3' | PyPyHpPyPy-γ-ImHp-β-ImHp |
| 920βp) | 5'-W A C T A C W-3' | PyPy-β-PyPy-γ-ImHp-β-ImHp |
| 921β) | 5'-W A C T G T W-3' | PyPy-β-ImPy-γ-PyPy-β-ImHp |
| 922β) | 5'-W A C T G A W-3' | PyPy-β-ImPy-γ-HpPy-β-ImHp |
| 923β) | 5'-W A C T G G W-3' | PyPy-β-ImIm-γ-PyPy-β-ImHp |
| 924β) | 5'-W A C T G C W-3' | PyPy-β-ImPy-γ-ImPy-β-ImHp |
| 925β) | 5'-W A C T C T W-3' | PyPyHpHpPy-γ-PyIm-β-ImHp |
| 925βp) | 5'-W A C T C T W-3' | PyPy-β-HpPy-γ-PyIm-β-ImHp |
| 926β) | 5'-W A C T C A W-3' | PyPyHpPyHp-γ-HpIm-β-ImHp |
| 926βp) | 5'-W A C T C A W-3' | PyPy-β-PyPy-γ-HpIm-β-ImHp |
| 927β) | 5'-W A C T C G W-3' | PyPy-β-PyIm-γ-PyIm-β-ImHp |
| 928β) | 5'-W A C T C C W-3' | PyPyHpPyPy-γ-ImIm-β-ImHp |
| 928βp) | 5'-W A C T C C W-3' | PyPy-β-PyPy-γ-ImIm-β-ImHp |
| 929β) | 5'-W A C A T T W-3' | PyPyHpHpHp-γ-PyPy-β-ImHp |
| 929βp) | 5'-W A C A T T W-3' | PyPy-β-HpHp-γ-PyPy-β-ImHp |
| 930β) | 5'-W A C A T A W-3' | PyPyHpHpPy-γ-HpPy-β-ImHp |
| 930βp) | 5'-W A C A T A W-3' | PyPy-β-HpPy-γ-HpPy-β-ImHp |
| 931β) | 5'-W A C A T G W-3' | PyPy-β-HpIm-γ-PyPy-β-ImHp |
| 932β) | 5'-W A C A T C W-3' | PyPyHpHpPy-γ-ImPy-β-ImHp |
| 932βp) | 5'-W A C A T C W-3' | PyPy-β-HpPy-γ-ImPy-β-ImHp |
| 933β) | 5'-W A C A A T W-3' | PyPyPyPyHp-γ-PyHp-β-ImHp |
| 933βp) | 5'-W A C A A T W-3' | PyPy-β-PyHp-γ-PyHp-β-ImHp |
| 934β) | 5'-W A C A A A W-3' | PyPyPyPyPy-γ-HpHp-β-ImHp |
| 934βp) | 5'-W A C A A A W-3' | PyPy-β-PyPy-γ-HpHp-β-ImHp |
| 935β) | 5'-W A C A A G W-3' | PyPy-β-PyIm-γ-PyHp-β-ImHp |
| 936β) | 5'-W A C A A C W-3' | PyPyPyPyPy-γ-ImHp-β-ImHp |
| 936βp) | 5'-W A C A A C W-3' | PyPy-β-PyPy-γ-ImHp-β-ImHp |
| 937β) | 5'-W A C A G T W-3' | PyPy-β-ImHp-γ-PyPy-β-ImHp |
| 938β) | 5'-W A C A G A W-3' | PyPy-β-ImPy-γ-HpPy-β-ImHp |
| 939β) | 5'-W A C A G G W-3' | PyPy-β-ImIm-γ-PyPy-β-ImHp |
| 940β) | 5'-W A C A G C W-3' | PyPy-β-ImPy-γ-ImPy-β-ImHp |
| 941β) | 5'-W A C A C T W-3' | PyPyPyPyHp-γ-PyIm-β-ImHp |
| 941βp) | 5'-W A C A C T W-3' | PyPy-β-PyHp-γ-PyIm-β-ImHp |
| 942β) | 5'-W A C A C A W-3' | PyPyPyPyPy-γ-HpIm-β-ImHp |
| 942βp) | 5'-W A C A C A W-3' | PyPy-β-PyPy-γ-HpIm-β-ImHp |
| 943β) | 5'-W A C A C G W-3' | PyPy-β-PyIm-γ-PyIm-β-ImHp |
| 944β) | 5'-W A C A C C W-3' | PyPyPyPy-γ-ImIm-β-ImHp |
| 944βp) | 5'-W A C A C C W-3' | PyPy-β-PyPy-γ-ImIm-β-ImHp |

TABLE 75

10-ring Hairpin Polyamides for recognition of
7-bp 5'-WACSNNW-3' with β substitutions.

| | DNA sequence | aromatic amino acid sequence |
|---|---|---|
| 945β) | 5'-W A C G T T W-3' | Py-β-ImHpHp-γ-PyPy-β-ImHp |
| 946β) | 5'-W A C G T A W-3' | Py-β-ImpHpPy-γ-HpPy-β-ImHp |
| 947β) | 5'-W A C G T G W-3' | Py-β-ImHpIm-γ-PyPy-β-ImHp |
| 948β) | 5'-W A C G T C W-3' | Py-β-ImHpPy-γ-ImPy-β-ImHp |
| 949β) | 5'-W A C G A T W-3' | Py-β-ImPyHp-γ-PyHp-β-ImHp |
| 950β) | 5'-W A C G A A W-3' | Py-β-ImPyPy-γ-HpHp-β-ImHp |
| 951β) | 5'-W A C G A G W-3' | Py-β-ImPyIm-γ-PyHp-β-ImHp |
| 952β) | 5'-W A C G A C W-3' | Py-β-ImPyPy-γ-ImHp-β-ImHp |
| 953β) | 5'-W A C G G T W-3' | Py-β-ImImHp-γ-PyPy-β-ImHp |
| 954β) | 5'-W A C G G A W-3' | Py-β-ImImPy-γ-HpPy-β-ImHp |
| 955β) | 5'-W A C G C T W-3' | Py-β-ImPyHp-γ-PyIm-β-ImHp |
| 956β) | 5'-W A C G C A W-3' | Py-β-ImPyPy-γ-HpIm-β-ImHp |
| 957β) | 5'-W A C C T T W-3' | PyPyPyHpHp-γ-Py-β-ImImHp |

TABLE 75-continued 10-ring Hairpin Polyamides for recognition of
7-bp 5'-WACSNNW-3' with β substitutions.

| | DNA sequence | aromatic amino acid sequence |
|---|---|---|
| 957βp) | 5'-W A C C T T W-3' | PyPyPy-β-Hp-γ-Py-β-ImImHp |
| 958β) | 5'-W A C C T A W-3' | PyPyPyHpPy-γ-Hp-β-ImImHp |
| 958βp) | 5'-W A C C T A W-3' | PyPyPy-β-Py-γ-Hp-β-ImImHp |
| 959β) | 5'-W A C C T G W-3' | PyPy-β-HpIm-γ-Py-β-ImImHp |
| 960β) | 5'-W A C C T C W-3' | PyPyPyHpPy-γ-Im-β-ImImHp |
| 960βp) | 5'-W A C C T C W-3' | PyPyPy-β-Py-γ-Im-β-ImImHp |
| 961β) | 5'-W A C C A T W-3' | PyPyPyPyHp-γ-Py-β-ImImHp |
| 961βp) | 5'-W A C C A T W-3' | PyPyPy-β-Hp-γ-Py-β-ImImHp |
| 962β) | 5'-W A C C A A W-3' | PyPyPyPyPy-γ-Hp-β-ImImHp |
| 962βp) | 5'-W A C C A A W-3' | PyPyPy-β-Py-γ-Hp-β-ImImHp |
| 963β) | 5'-W A C C A G W-3' | PyPy-β-PyIm-γ-Py-β-ImImHp |
| 964β) | 5'-W A C C A C W-3' | PyPyPyPyPy-γ-Im-β-ImImHp |
| 964βp) | 5'-W A C C A C W-3' | PyPyPy-β-Py-γ-Im-β-ImImHp |
| 965β) | 5'-W A C C G T W-3' | PyPy-β-ImHp-γ-Py-β-ImImHp |
| 966β) | 5'-W A C C G A W-3' | PyPy-β-ImPy-γ-Hp-β-ImImHp |
| 969β) | 5'-W A C G G G W-3' | Py-β-ImImIm-γ-PyPy-β-ImHp |
| 970β) | 5'-W A C G G C W-3' | Py-β-ImImPy-γ-ImPy-β-ImHp |
| 971β) | 5'-W A C G C G W-3' | Py-β-ImPyIm-γ-PyIm-β-ImHp |
| 972β) | 5'-W A C G C C W-3' | Py-β-ImPyPy-γ-ImIm-β-ImHp |
| 973β) | 5'-W A C C G G W-3' | PyPy-β-ImIm-γ-Py-β-ImImHp |
| 974β) | 5'-W A C C G C W-3' | PyPy-β-ImPy-γ-Im-β-ImImHp |
| 975β) | 5'-W A C C C G W-3' | PyPy-β-PyIm-γ-PyImImImHp |

TABLE 76

10-ring Hairpin Polyamides for recognition of
7-bp 5'-WTGWNNW-3' with β substitutions.

| | DNA sequence | aromatic amino acid sequence |
|---|---|---|
| 979β) | 5'-W T G T T G W-3' | HpIm-β-HpIm-γ-PyPyPyPyPy |
| 979βp) | 5'-W T G T T G W-3' | HpIm-β-HpIm-γ-PyPy-β-PyPy |
| 983β) | 5'-W T G T A G W-3' | HpIm-β-PyIm-γ-PyHpPyPyPy |
| 983βp) | 5'-W T G T A G W-3' | HpIm-β-PyIm-γ-PyHp-β-PyPy |
| 985β) | 5'-W T G T G T W-3' | HpIm-β-ImHp-γ-PyPyPyPyPy |
| 985βp) | 5'-W T G T G T W-3' | HpIm-β-ImHp-γ-PyPy-β-PyPy |
| 986β) | 5'-W T G T G A W-3' | HpIm-β-ImPy-γ-HpPyPyPyPy |
| 986βp) | 5'-W T G T G A W-3' | HpIm-β-ImPy-γ-HpPy-β-PyPy |
| 987β) | 5'-W T G T G G W-3' | HpIm-β-ImIm-γ-PyPyPyPyPy |
| 987βp) | 5'-W T G T G G W-3' | HpIm-β-ImIm-γ-PyPy-β-PyPy |
| 988β) | 5'-W T G T G C W-3' | HpIm-β-ImPy-γ-ImPyPyPyPy |
| 988βp) | 5'-W T G T G C W-3' | HpIm-β-ImPy-γ-ImPy-β-PyPy |
| 991β) | 5'-W T G T C G W-3' | HpIm-β-PyIm-γ-PyImPyPyPy |
| 991βp) | 5'-W T G T C G W-3' | HpIm-β-PyIm-γ-PyIm-β-PyPy |
| 995β) | 5'-W T G A T G W-3' | HpIm-β-HpIm-γ-PyPyHpPyPy |
| 995βp) | 5'-W T G A T G W-3' | HpIm-β-HpIm-γ-PyPy-β-PyPy |
| 999β) | 5'-W T G A A G W-3' | HpIm-β-PyIm-γ-PyHpHpPyPy |
| 999βp) | 5'-W T G A A G W-3' | HpIm-β-PyIm-γ-PyHp-β-PyPy |
| 1001β) | 5'-W T G A G T W-3' | HpIm-β-ImHp-γ-PyPyHpPyPy |
| 1001βp) | 5'-W T G A G T W-3' | HpIm-β-ImHp-γ-PyPy-β-PyPy |
| 1002β) | 5'-W T G A G A W-3' | HpIm-β-ImPy-γ-HpPyHpPyPy |
| 1002βp) | 5'-W T G A G A W-3' | HpIm-β-ImPy-γ-HpPy-β-PyPy |
| 1003β) | 5'-W T G A G G W-3' | HpIm-β-ImIm-γ-PyPyHpPyPy |
| 1003βp) | 5'-W T G A G G W-3' | HpIm-β-ImIm-γ-PyPy-β-PyPy |
| 1004β) | 5'-W T G A G C W-3' | HpIm-β-ImPy-γ-ImPyHpPyPy |
| 1004βp) | 5'-W T G A G C W-3' | HpIm-β-ImPy-γ-ImPy-β-PyPy |
| 1007β) | 5'-W T G A C G W-3' | HpIm-β-PyIm-γ-PyImHpPyPy |
| 1007βp) | 5'-W T G A C G W-3' | HpIm-β-PyIm-γ-PyIm-β-PyPy |

TABLE 77

10-ring Hairpin Polyamides for recognition of
7-bp 5'-WTGSNNW-3' with β substitutions.

| | DNA sequence | aromatic amino acid sequence |
|---|---|---|
| 1009β) | 5'-W T G G T T W-3' | HpImIm-β-Hp-γ-PyPyPyPyPy |
| 1009βp) | 5'-W T G G T T W-3' | HpImIm-β-Hp-γ-PyPy-β-PyPy |
| 1010β) | 5'-W T G G T A W-3' | HpImIm-β-Py-γ-HpPyPyPyPy |

TABLE 77-continued 10-ring Hairpin Polyamides for recognition of
7-bp 5'-WTGSNNW-3' with β substitutions.

| | DNA sequence | aromatic amino acid sequence |
|---|---|---|
| 1010βp) | 5'-W T G G T A W-3' | HpImIm-β-Py-γ-Hp-β-PyPyPyPy |
| 1011β) | 5'-W T G G T G W-3' | HpImIm-β-Im-γ-PyPyPyPyPy |
| 1011βp) | 5'-W T G G T G W-3' | HpImIm-β-Im-γ-Py-β-PyPyPy |
| 1012β) | 5'-W T G G T C W-3' | HpImIm-β-Py-γ-ImPyPyPyPy |
| 1012βp) | 5'-W T G G T C W-3' | HpImIm-β-Py-γ-Im-β-PyPyPy |
| 1013β) | 5'-W T G G A T W-3' | HpImIm-β-Hp-γ-PyHpPyPyPy |
| 1013βp) | 5'-W T G G A T W-3' | HpImIm-β-Hp-γ-Py-β-PyPyPy |
| 1014β) | 5'-W T G G A A W-3' | HpImIm-β-Py-γ-HpHpPyPyPy |
| 1014βp) | 5'-W T G G A A W-3' | HpImIm-β-Py-γ-Hp-β-PyPyPy |
| 1015β) | 5'-W T G G A G W-3' | HpImIm-β-Im-γ-PyHpPyPyPy |
| 1015βp) | 5'-W T G G A G W-3' | HpImIm-β-Im-γ-Py-β-PyPyPy |
| 1016β) | 5'-W T G G A C W-3' | HpImIm-β-Py-γ-ImHpPyPyPy |
| 1016βp) | 5'-W T G G A C W-3' | HpImIm-β-Py-γ-Im-β-PyPyPy |
| 1019β) | 5'-W T G G C T W-3' | HpImIm-β-Hp-γ-PyImPyPyPy |
| 1020β) | 5'-W T G G C A W-3' | HpImIm-β-Py-γ-HpImPyPyPy |
| 1021β) | 5'-W T G C T T W-3' | HpImPyHpPy-γ-Py-β-ImPyPy |
| 1021βp) | 5'-W T G C T T W-3' | HpImPy-β-Hp-γ-Py-β-ImPyPy |
| 1022β) | 5'-W T G C T A W-3' | HpImPyHpPy-γ-Hp-β-ImPyPy |
| 1022βp) | 5'-W T G C T A W-3' | HpImPy-β-Py-γ-Hp-β-ImPyPy |
| 1023β) | 5'-W T G C T G W-3' | HpIm-β-HpIm-γ-Py-β-ImPyPy |
| 1024β) | 5'-W T G C T C W-3' | HpImHpPy-γ-Im-β-ImPyPy |
| 1024βp) | 5'-W T G C T C W-3' | HpImPy-β-Py-γ-Im-β-ImPyPy |
| 1025β) | 5'-W T G C A T W-3' | HpImPyPyHp-γ-Py-β-ImPyPy |
| 1025βp) | 5'-W T G C A T W-3' | HpImPy-β-Hp-γ-Py-β-ImPyPy |
| 1026β) | 5'-W T G C A A W-3' | HpImPyPyPy-γ-Hp-β-ImPyPy |
| 1026βp) | 5'-W T G C A A W-3' | HpImPy-β-Py-γ-Hp-β-ImPyPy |
| 1027β) | 5'-W T G C A G W-3' | HpIm-β-PyIm-γ-Py-β-ImPyPy |
| 1028β) | 5'-W T G C A C W-3' | HpImPyPy-γ-Im-β-ImPyp |
| 1028βp) | 5'-W T G C A C W-3' | HpImPy-β-Py-γ-Im-β-ImPyPy |
| 1029β) | 5'-W T G C G T W-3' | HpIm-β-ImHp-γ-Py-β-ImPyPy |
| 1030β) | 5'-W T G C G A W-3' | HpIm-β-ImPy-γ-Hp-β-ImPyPy |
| 1031β) | 5'-W T G C C T W-3' | HpImPyHp-γ-PyImIm-β-Py |
| 1031βp) | 5'-W T G C C T W-3' | HpImPy-β-Hp-γ-PyImIm-β-Py |
| 1032β) | 5'-W T G C C A W-3' | HpImPyPy-γ-HpImIm-β-Py |
| 1032βp) | 5'-W T G C C A W-3' | HpImPy-β-Py-γ-HpImIm-β-Py |
| 1035β) | 5'-W T G G C G W-3' | HpImIm-β-Im-γ-PyImPyPyPy |
| 1036β) | 5'-W T G G C C W-3' | HpImIm-β-Py-γ-ImImPyPyPy |
| 1037β) | 5'-W T G C G G W-3' | HpIm-β-ImIm-γ-Py-β-ImPyPy |
| 1038β) | 5'-W T G C G C W-3' | HpIm-β-ImPy-γ-Im-β-ImPyPy |
| 1039β) | 5'-W T G C C G W-3' | HpIm-β-PyIm-γ-PyImIm-β-Py |
| 1040β) | 5'-W T G C C C W-3' | HpImPyPyPy-γ-ImImIm-β-Py |

TABLE 78

10-ring Hairpin Polyamides for recognition of
7-bp 5'-WTTWNNW-3' with β substitutions.

| | DNA sequence | aromatic amino acid sequence |
|---|---|---|
| 1043β) | 5'-W T T T T G W-3' | HpHp-β-HpIm-γ-PyPyPyPyPy |
| 1043βp) | 5'-W T T T T G W-3' | HpHp-β-HpIm-γ-PyPy-β-PyPy |
| 1047β) | 5'-W T T T A G W-3' | HpHp-β-PyIm-γ-PyHpPyPyPy |
| 1047βp) | 5'-W T T T A G W-3' | HpHp-β-PyIm-γ-PyHp-β-PyPy |
| 1049β) | 5'-W T T T G T W-3' | HpHp-β-ImHp-γ-PyPyPyPyPy |
| 1049βp) | 5'-W T T T G T W-3' | HpHp-β-ImHp-γ-PyPy-β-PyPy |
| 1050β) | 5'-W T T T G A W-3' | HpHp-β-ImPy-γ-HpPyPyPyPy |
| 1050βp) | 5'-W T T T G A W-3' | HpHp-β-ImPy-γ-HpPy-β-PyPy |
| 1051β) | 5'-W T T T G G W-3' | HpHp-β-ImIm-γ-PyPyPyPyPy |
| 1051βp) | 5'-W T T T G G W-3' | HpHp-β-ImIm-γ-PyPy-β-PyPy |
| 1052β) | 5'-W T T T G C W-3' | HpHp-β-ImPy-γ-ImPyPyPyPy |
| 1052βp) | 5'-W T T T G C W-3' | HpHp-β-ImPy-γ-ImPy-β-PyPy |
| 1055β) | 5'-W T T T C G W-3' | HpHp-β-PyIm-γ-PyImPyPyPy |
| 1055βp) | 5'-W T T T C G W-3' | HpHp-β-PyIm-γ-PyIm-β-PyPy |
| 1059β) | 5'-W T T A T G W-3' | HpHp-β-HpIm-γ-PyPyHpPyPy |
| 1059βp) | 5'-W T T A T G W-3' | HpHp-β-HpIm-γ-PyPy-β-PyPy |
| 1063β) | 5'-W T T A A G W-3' | HpHp-β-PyIm-γ-PyHpHpPyPy |
| 1063βp) | 5'-W T T A A G W-3' | HpHp-β-PyIm-γ-PyHp-β-PyPy |
| 1065β) | 5'-W T T A G T W-3' | HpHp-β-ImHp-γ-PyPyHpPyPy |
| 1065βp) | 5'-W T T A G T W-3' | HpHp-β-ImHp-γ-PyPy-β-PyPy |
| 1066β) | 5'-W T T A G A W-3' | HpHp-β-ImPy-γ-HpPyHpPyPy |
| 1066βp) | 5'-W T T A G A W-3' | HpHp-β-ImPy-γ-HpPy-β-PyPy |

TABLE 78-continued 10-ring Hairpin Polyamides for recognition of
7-bp 5'-WTTWNNW-3' with β substitutions.

| | DNA sequence | aromatic amino acid sequence |
|---|---|---|
| 1067β) | 5'-W T T A G G W-3' | HpHp-β-ImIm-γ-PyPyHpPyPy |
| 1067βp) | 5'-W T T A G G W-3' | HpHp-β-ImIm-γ-PyPy-β-PyPy |
| 1068β) | 5'-W T T A G C W-3' | HpHp-β-ImPy-γ-ImPyHpPyPy |
| 1068βp) | 5'-W T T A G C W-3' | HpHp-β-ImPy-γ-ImPy-β-PyPy |
| 1071β) | 5'-W T T A C G W-3' | HpHp-β-PyIm-γ-PyImHpPyPy |
| 1071βp) | 5'-W T T A C G W-3' | HpHp-β-PyIm-γ-PyIm-β-PyPy |

TABLE 79

10-ring Hairpin Polyamides for recognition of
7-bp 5'-WTTSNNW-3' with β substitutions

| | DNA sequence | aromatic amino acid sequence |
|---|---|---|
| 1073β) | 5'-W T T G T T W-3' | Hp-β-ImHpHp-γ-PyPyPyPyPy |
| 1073βp) | 5'-W T T G T T W-3' | Hp-β-ImHpHp-γ-PyPyPy-β-Py |
| 1074β) | 5'-W T T G T A W-3' | Hp-β-ImHpPy-γ-HpPyPyPyPy |
| 1074βp) | 5'-W T T G T A W-3' | Hp-β-ImHpPy-γ-HpPyPy-β-Py |
| 1075β) | 5'-W T T G T G W-3' | Hp-β-ImHpIm-γ-PyPyPyPyPy |
| 1075βp) | 5'-W T T G T G W-3' | Hp-β-ImHpIm-γ-PyPyPy-β-Py |
| 1076β) | 5'-W T T G T C W-3' | Hp-β-ImHpPy-γ-ImPyPyPyPy |
| 1076βp) | 5'-W T T G T C W-3' | Hp-β-ImHpPy-γ-ImPyPy-β-Py |
| 1077β) | 5'-W T T G A T W-3' | Hp-β-ImPyHp-γ-PyHpPyPyPy |
| 1077βp) | 5'-W T T G A T W-3' | Hp-β-ImPyHp-γ-PyHpPy-β-Py |
| 1078β) | 5'-W T T G A A W-3' | Hp-β-ImPyPy-γ-HpHpPyPyPy |
| 1078βp) | 5'-W T T G A A W-3' | Hp-β-ImPyPy-γ-HpHpPy-β-Py |
| 1079β) | 5'-W T T G A G W-3' | Hp-β-ImPyIm-γ-PyHpPyPyPy |
| 1079βp) | 5'-W T T G A G W-3' | Hp-β-ImPyIm-γ-PyHpPy-β-Py |
| 1080β) | 5'-W T T G A C W-3' | Hp-β-ImPyPy-γ-ImHpPyPyPy |
| 1080βp) | 5'-W T T G A C W-3' | Hp-β-ImPyPy-γ-ImHpPy-β-Py |
| 1081β) | 5'-W T T G G T W-3' | Hp-β-ImImHp-γ-PyPyPyPyPy |
| 1081βp) | 5'-W T T G G T W-3' | Hp-β-ImImHp-γ-PyPyPy-β-Py |
| 1082β) | 5'-W T T G G A W-3' | Hp-β-ImImPy-γ-HpPyPyPyPy |
| 1082βp) | 5'-W T T G G A W-3' | Hp-β-ImImPy-γ-HpPyPy-β-Py |
| 1083β) | 5'-W T T G C T W-3' | Hp-β-ImPyHp-γ-PyImPyPyPy |
| 1083βp) | 5'-W T T G C T W-3' | Hp-β-ImPyHp-γ-PyImPy-β-Py |
| 1084β) | 5'-W T T G C A W-3' | Hp-β-ImPyPy-γ-HpImPyPyPy |
| 1084βp) | 5'-W T T G C A W-3' | Hp-β-ImPyPy-γ-HpImPy-β-Py |
| 1085β) | 5'-W T T G G G W-3' | Hp-β-ImImIm-γ-PyPyPyPyPy |
| 1085βp) | 5'-W T T G G G W-3' | Hp-β-ImImIm-γ-PyPyPy-β-Py |
| 1086β) | 5'-W T T G G C W-3' | Hp-β-ImImPy-γ-ImPyPyPyPy |
| 1086βp) | 5'-W T T G G C W-3' | Hp-β-ImImPy-γ-ImPyPy-β-Py |
| 1087β) | 5'-W T T G C G W-3' | Hp-β-ImPyIm-γ-PyImPyPyPy |
| 1087βp) | 5'-W T T G C G W-3' | Hp-β-ImPyIm-γ-PyImPy-β-Py |
| 1088β) | 5'-W T T G C C W-3' | Hp-β-ImPyPy-γ-ImImPyPyPy |
| 1088βp) | 5'-W T T G C C W-3' | Hp-β-ImPyPy-γ-ImImPy-β-Py |
| 1089β) | 5'-W T T C T T W-3' | HpHpPyHpHp-γ-Py-β-ImPyPy |
| 1089βp) | 5'-W T T C T T W-3' | HpHpPy-β-Hp-γ-Py-β-ImPyPy |
| 1090β) | 5'-W T T C T A W-3' | HpHpPyHpPy-γ-Hp-β-ImPyPy |
| 1090βp) | 5'-W T T C T A W-3' | HpHpPy-β-Py-γ-Hp-β-ImPyPy |
| 1091β) | 5'-W T T C T G W-3' | HpHp-β-HpIm-γ-Py-β-ImPyPy |
| 1092β) | 5'-W T T C T C W-3' | HpHpPyHpPy-γ-Im-β-ImPyPy |
| 1092βp) | 5'-W T T C T C W-3' | HpHpPy-β-Py-γ-Im-β-ImPyPy |
| 1093β) | 5'-W T T C A T W-3' | HpHpPyPyHp-γ-Py-β-ImPyPy |
| 1093βp) | 5'-W T T C A T W-3' | HpHpPy-β-Hp-γ-Py-β-ImPyPy |
| 1094β) | 5'-W T T C A A W-3' | HpHpPyPyPy-γ-Hp-β-ImPyPy |
| 1094βp) | 5'-W T T C A A W-3' | HpHpPy-β-Py-γ-Hp-β-ImPyPy |
| 1095β) | 5'-W T T C A G W-3' | HpHp-β-PyIm-γ-Py-β-ImPyPy |
| 1096β) | 5'-W T T C A C W-3' | HpHpPyPyPy-γ-Im-β-ImPyPy |
| 1096βp) | 5'-W T T C A C W-3' | HpHpPy-β-Py-γ-Im-β-ImPyPy |
| 1097β) | 5'-W T T C G T W-3' | HpHp-β-ImHp-γ-Py-β-ImPyPy |
| 1098β) | 5'-W T T C G A W-3' | Hp-β-ImPy-γ-Hp-β-ImPyPy |
| 1099β) | 5'-W T T C C T W-3' | HpHpPyPyHp-γ-PyImIm-β-Py |
| 1099βp) | 5'-W T T C C T W-3' | Hp-β-PyPyHp-γ-PyImIm-β-Py |
| 1100β) | 5'-W T T C C A W-3' | HpHpPyPyPy-γ-HpImIm-β-Py |
| 1100βp) | 5'-W T T C C A W-3' | Hp-β-PyPyPy-γ-HpImIm-β-Py |
| 1101β) | 5'-W T T C G G W-3' | Hp-β-ImIm-γ-Py-β-ImPyPy |
| 1102β) | 5'-W T T C G C W-3' | HpHp-β-ImPy-γ-Im-β-ImPyPy |
| 1103β) | 5'-W T T C C G W-3' | HpHp-β-PyIm-γ-PyImIm-β-Py |

TABLE 80

10-ring Hairpin Polyamides for recognition of
7-bp 5'-WTAWNNW-3' with β substitutions

| | DNA sequence | aromatic amino acid sequence |
|---|---|---|
| 1107β) | 5'-W T A T T G W-3' | HpPy-β-HpIm-γ-PyPyPyHpPy |
| 1107βp) | 5'-W T A T T G W-3' | HpPy-β-HpIm-γ-PyPy-β-HpPy |
| 1111β) | 5'-W T A T A G W-3' | HpPy-β-PyIm-γ-PyHpPyHpPy |
| 1111βp) | 5'-W T A T A G W-3' | HpPy-β-PyIm-γ-PyHp-β-HpPy |
| 1113β) | 5'-W T A T G T W-3' | HpPy-β-ImHp-γ-PyPyPyHpPy |
| 1113βp) | 5'-W T A T G T W-3' | HpPy-β-ImHp-γ-PyPy-β-HpPy |
| 1114β) | 5'-W T A T G A W-3' | HpPy-β-ImPy-γ-HpPyPyHpPy |
| 1114βp) | 5'-W T A T G A W-3' | HpPy-β-ImPy-γ-HpPy-β-HpPy |
| 1115β) | 5'-W T A T G G W-3' | HpPy-β-ImIm-γ-PyPyPyHpPy |
| 1115βp) | 5'-W T A T G G W-3' | HpPy-β-ImIm-γ-PyPy-β-HpPy |
| 1116β) | 5'-W T A T G C W-3' | HpPy-β-ImPy-γ-ImPyPyHpPy |
| 1116βp) | 5'-W T A T G C W-3' | HpPy-β-ImPy-γ-ImPy-β-HpPy |
| 1119β) | 5'-W T A T C G W-3' | HpPy-β-PyIm-γ-PyImPyHpPy |
| 1119βp) | 5'-W T A T C G W-3' | HpPy-β-PyIm-γ-PyIm-β-HpPy |
| 1123β) | 5'-W T A A T G W-3' | HpPy-β-HpIm-γ-PyHpPyHpPy |
| 1123βp) | 5'-W T A A T G W-3' | HpPy-β-HpIm-γ-PyPy-β-HpPy |
| 1127β) | 5'-W T A A A G W-3' | HpPy-β-PyIm-γ-PyHpHpPyPy |
| 1127βp) | 5'-W T A A A G W-3' | HpPy-β-PyIm-γ-PyHp-β-HpPy |
| 1129β) | 5'-W T A A G T W-3' | HpPy-β-ImHp-γ-PyPyHpHpPy |
| 1129βp) | 5'-W T A A G T W-3' | HpPy-β-ImHp-γ-PyPy-β-HpPy |
| 1130β) | 5'-W T A A G A W-3' | HpPy-β-ImPy-γ-HpPyHpHpPy |
| 1130βp) | 5'-W T A A G A W-3' | HpPy-β-ImPy-γ-HpPy-β-HpPy |
| 1131β) | 5'-W T A A G G W-3' | HpPy-β-ImIm-γ-PyPyHpHpPy |
| 1131βp) | 5'-W T A A G G W-3' | HpPy-β-ImIm-γ-PyPy-β-HpPy |
| 1132β) | 5'-W T A A G C W-3' | HpPy-β-ImPy-γ-ImPyHpHpPy |
| 1132βp) | 5'-W T A A G C W-3' | HpPy-β-ImPy-γ-ImPy-β-HpPy |
| 1135β) | 5'-W T A A C G W-3' | HpPy-β-PyIm-γ-PyImHpHpPy |
| 1135βp) | 5'-W T A A C G W-3' | HpPy-β-PyIm-γ-PyIm-β-HpPy |

TABLE 81

10-ring Hairpin Polyamides for recognition of
7-bp 5'-WTASNNW-3' with β substitutions

| | DNA sequence | aromatic amino acid sequence |
|---|---|---|
| 1137β) | 5'-W T A G T T W-3' | Hp-β-ImHpHp-γ-PyPyPyHpPy |
| 1137βp) | 5'-W T A G T T W-3' | Hp-β-ImHpHp-γ-PyPyPy-β-Py |
| 1138β) | 5'-W T A G T A W-3' | Hp-β-ImHpPy-γ-HpPyPyHpPy |
| 1138βp) | 5'-W T A G T A W-3' | Hp-β-ImHpPy-γ-HpPyPy-β-Py |
| 1139β) | 5'-W T A G T G W-3' | Hp-β-ImHpIm-γ-PyPyPyHpPy |
| 1139βp) | 5'-W T A G T G W-3' | Hp-β-ImHpIm-γ-PyPyPy-β-Py |
| 1140β) | 5'-W T A G T C W-3' | Hp-β-ImHpPy-γ-ImPyPyHpPy |
| 1140βp) | 5'-W T A G T C W-3' | Hp-β-ImHpPy-γ-ImPyPy-β-Py |
| 1141β) | 5'-W T A G A T W-3' | Hp-β-ImPyHp-γ-PyHpPyHpPy |
| 1141βp) | 5'-W T A G A T W-3' | Hp-β-ImPyHp-γ-PyHpPy-β-Py |
| 1142β) | 5'-W T A G A A W-3' | Hp-β-ImPyPy-γ-HpPyPyHpPy |
| 1142βp) | 5'-W T A G A A W-3' | Hp-β-ImPyPy-γ-HpHpPy-β-Py |
| 1143β) | 5'-W T A G A 0 W-3' | Hp-β-ImPyIm-γ-PyHpPyHpPy |
| 1143βp) | 5'-W T A G A G W-3' | Hp-β-ImPyIm-γ-PyHpPy-β-Py |
| 1144β) | 5'-W T A G A C W-3' | Hp-β-ImPyPy-γ-ImHpPyHpPy |
| 1144βp) | 5'-W T A G A C W-3' | Hp-β-ImPyPy-γ-ImHpPy-β-Py |
| 1145β) | 5'-W T A G G T W-3' | Hp-β-ImImHp-γ-PyPyPyHpPy |
| 1145βp) | 5'-W T A G G T W-3' | Hp-β-ImImHp-γ-PyPyPy-β-Py |
| 1146β) | 5'-W T A G G A W-3' | Hp-β-ImImPy-γ-HpPyPyHpPy |
| 1146βp) | 5'-W T A G G A W-3' | Hp-β-ImImPy-γ-HpPyPy-β-Py |
| 1147β) | 5'-W T A G C T W-3' | Hp-β-ImPyHp-γ-PyImPyHpPy |
| 1147βp) | 5'-W T A G C T W-3' | Hp-β-ImPyHp-γ-PyImPy-β-Py |
| 1148β) | 5'-W T A G C A W-3' | Hp-β-ImPyPy-γ-HpImPyHpPy |
| 1148βp) | 5'-W T A G C A W-3' | Hp-β-ImPyPy-γ-HpImPy-β-Py |
| 1149β) | 5'-W T A G G G W-3' | Hp-β-ImImIm-γ-PyPyPyHpPy |
| 1149βp) | 5'-W T A G G G W-3' | Hp-β-ImImIm-γ-PyPyPy-β-Py |
| 1150β) | 5'-W T A G G C W-3' | Hp-β-ImImPy-γ-ImPyPyHpPy |
| 1150βp) | 5'-W T A G G C W-3' | Hp-β-ImImPy-γ-ImPyPy-β-Py |
| 1151β) | 5'-W T A G C G W-3' | Hp-β-ImPyIm-γ-PyImPyHpPy |
| 1151βp) | 5'-W T A G C G W-3' | Hp-β-ImPyIm-γ-PyImPy-β-Py |
| 1152β) | 5'-W T A G C C W-3' | Hp-β-ImPyPy-γ-ImImPyHpPy |
| 1152βp) | 5'-W T A G C C W-3' | Hp-β-ImPyPy-γ-ImImPy-β-Py |
| 1153β) | 5'-W T A C T T W-3' | HpPyPyHpHp-γ-Py-β-ImHpPy |
| 1153βp) | 5'-W T A C T T W-3' | HpPyPy-β-Hp-γ-Py-β-ImHpPy |
| 1154β) | 5'-W T A C T A W-3' | HpPyPyHpPy-γ-Hp-β-ImHpPy |

TABLE 81-continued 10-ring Hairpin Polyamides for recognition of
7-bp 5'-WTASNNW-3' with β substitutions

| | DNA sequence | aromatic amino acid sequence |
|---|---|---|
| 1154βp) | 5'-W T A C T A W-3' | HpPyPy-β-Py-γ-Hp-β-ImHpPy |
| 1155β) | 5'-W T A C T G W-3' | HpPy-β-HpIm-γ-Py-β-ImHpPy |
| 1156β) | 5'-W T A C T C W-3' | HpPyPyHpPy-γ-Im-β-ImHpPy |
| 1156βp) | 5'-W T A C T C W-3' | HpPyPy-β-Py-γ-Im-β-ImHpPy |
| 1157β) | 5'-W T A C A T W-3' | HpPyPyPyHp-γ-Py-β-ImHpPy |
| 1157βp) | 5'-W T A C A T W-3' | HpPyPy-β-Hp-γ-Py-β-ImHpPy |
| 1158β) | 5'-W T A C A A W-3' | HpPyPyPyPy-γ-Hp-β-ImHpPy |
| 1158βp) | 5'-W T A C A A W-3' | HpPyPy-β-Py-γ-Hp-β-ImHpPy |
| 1159β) | 5'-W T A C A G W-3' | HpPy-β-PyIm-γ-Py-β-ImHpPy |
| 1160β) | 5'-W T A C A C W-3' | HpPyPyPyPy-γ-Im-β-ImHpPy |
| 1160βp) | 5'-W T A C A C W-3' | HpPyPy-β-Py-γ-Im-β-ImHpPy |
| 1161β) | 5'-W T A C G T W-3' | HpPy-β-ImHp-γ-Py-β-ImHpPy |
| 1162β) | 5'-W T A C G A W-3' | HpPy-β-ImPy-γ-Hp-β-ImHpPy |
| 1163β) | 5'-W T A C C T W-3' | HpPyPyPyHp-γ-PyImIm-β-Py |
| 1163βp) | 5'-W T A C C T W-3' | Hp-β-PyPyHp-γ-PyImIm-β-Py |
| 1164β) | 5'-W T A C C A W-3' | HpPyPyPyPy-γ-HpImIm-β-Py |
| 1164βp) | 5'-W T A C C A W-3' | Hp-β-PyPyPy-γ-HpImIm-β-Py |
| 1165β) | 5'-W T A C G G W-3' | HpPy-β-ImIm-γ-Py-β-ImHpPy |
| 1166β) | 5'-W T A C G C W-3' | HpPy-β-ImPy-γ-Im-β-ImHpPy |
| 1167β) | 5'-W T A C C G W-3' | HpPy-β-PyIm-γ-PyImIm-β-Py |

TABLE 82

10-ring Hairpin Polyamides for recognition of
7-bp 5'-WTCWNNW-3' with β substitutions

| | DNA sequence | aromatic amino acid sequence |
|---|---|---|
| 1170β) | 5'-W T C T T A W-3' | HpPyHpHpPy-γ-HpPy-β-ImPy |
| 1170βp) | 5'-W T C T T A W-3' | HpPy-β-HpPy-γ-HpPy-β-ImPy |
| 1171β) | 5'-W T C T T G W-3' | HpPy-β-HpIm-γ-PyPy-β-ImPy |
| 1172β) | 5'-W T C T T G W-3' | HpPyHpHpPy-γ-ImPy-β-ImPy |
| 1172βp) | 5'-W T C T T C W-3' | HpPy-β-HpPy-γ-ImPy-β-ImPy |
| 1173β) | 5'-W T C T A T W-3' | HpPyHpPyHp-γ-PyHp-β-ImPy |
| 1173βp) | 5'-W T C T A T W-3' | HpPy-β-PyHp-γ-PyHp-β-ImPy |
| 1174β) | 5'-W T C T A A W-3' | HpPyHpPyPy-γ-HpHp-β-ImPy |
| 1174βp) | 5'-W T C T A A W-3' | HpPy-β-PyPy-γ-HpHp-β-ImPy |
| 1175β) | 5'-W T C T A G W-3' | HpPy-β-PyIm-γ-PyHp-β-ImPy |
| 1176β) | 5'-W T C T A C W-3' | HpPyHpPyPy-γ-ImHp-β-ImPy |
| 1176βp) | 5'-W T C T A C W-3' | HpPy-β-PyPy-γ-ImHp-β-ImPy |
| 1177β) | 5'-W T C T G T W-3' | HpPy-β-ImHp-γ-PyPy-β-ImPy |
| 1178β) | 5'-W T C T G A W-3' | HpPy-β-ImPy-γ-PyPy-β-ImPy |
| 1179β) | 5'-W T C T G G W-3' | HpPy-β-ImIm-γ-PyPy-β-ImPy |
| 1180β) | 5'-W T C T G C W-3' | HpPy-β-ImPy-γ-ImPy-β-ImPy |
| 1181β) | 5'-W T C T C T W-3' | HpPyHpPyHp-γ-PyIm-β-ImPy |
| 1181βp) | 5'-W T C T C T W-3' | HpPy-β-PyHp-γ-PyIm-β-ImPy |
| 1182β) | 5'-W T C T C A W-3' | HpPyHpPyPy-γ-HpIm-β-ImPy |
| 1182βp) | 5'-W T C T C A W-3' | HpPy-β-PyPy-γ-HpIm-β-ImPy |
| 1183β) | 5'-W T C T C G W-3' | HpPy-β-PyIm-γ-PyIm-β-ImPy |
| 1184β) | 5'-W T C T C C W-3' | HpPyHpPyPy-γ-ImIm-β-ImPy |
| 1184βp) | 5'-W T C T C C W-3' | HpPy-β-PyPy-γ-ImIm-β-ImPy |
| 1185β) | 5'-W T C A T T W-3' | HpPyPyHpHp-γ-PyPy-β-ImPy |
| 1185βp) | 5'-W T C A T T W-3' | HpPy-β-HpHp-γ-PyPy-β-ImPy |
| 1186β) | 5'-W T C A T A W-3' | HpPyPyHpPy-γ-HpPy-β-ImPy |
| 1186βp) | 5'-W T C A T A W-3' | HpPy-β-HpPy-γ-HpPy-β-ImPy |
| 1187β) | 5'-W T C A T G W-3' | HpPy-β-HpIm-γ-PyPy-βImPy |
| 1188β) | 5'-W T C A T C W-3' | HpPyPyHpPy-γ-ImPy-β-ImPy |
| 1188βp) | 5'-W T C A T C W-3' | HpPy-β-HpPy-γ-ImPy-β-ImPy |
| 1189β) | 5'-W T C A A T W-3' | HpPyPyPyHp-γ-PyHp-β-ImPy |
| 1189βp) | 5'-W T C A A T W-3' | HpPy-β-PyHp-γ-PyHp-β-ImPy |
| 1190β) | 5'-W T C A A A W-3' | HpPyPyPyPy-γ-HpHp-β-ImPy |
| 1190βp) | 5'-W T C A A A W-3' | HpPy-β-PyPy-γ-HpHp-β-ImPY |
| 1191β) | 5'-W T C A A G W-3' | HpPy-β-PyIm-γ-PyHp-β-ImPy |
| 1192β) | 5'-W T C A A C W-3' | HpPyPyPyPy-γ-ImHp-β-ImPy |
| 1192βp) | 5'-W T C A A C W-3' | HpPy-β-PyPy-γ-ImHp-β-ImPy |
| 1193β) | 5'-W T C A G T W-3' | HpPy-β-ImHp-γ-PyPy-β-ImPy |
| 1194β) | 5'-W T C A G A W-3' | HpPy-β-ImPy-γ-HpPy-β-ImPy |
| 1195β) | 5'-W T C A G G W-3' | HpPy-β-ImIm-γ-PyPy-β-ImPy |
| 1196β) | 5'-W T C A G C W-3' | HpPy-β-ImPy-γ-ImPy-β-ImPy |
| 1197β) | 5'-W T C A C T W-3' | HpPyPyPyHp-γ-PyIm-β-ImPy |
| 1197βp) | 5'-W T C A C T W-3' | HpPy-β-PyHp-γ-PyIm-β-ImPy |

TABLE 82-continued 10-ring Hairpin Polyamides for recognition of
7-bp 5'-WTCWNNW-3' with β substitutions

| | DNA sequence | aromatic amino acid sequence |
|---|---|---|
| 1198β) | 5'-W T C A C A W-3' | HpPyPyPyPy-γ-HpIm-β-ImPy |
| 1198βp) | 5'-W T C A C A W-3' | HpPy-β-PyPy-γ-HpIm-β-ImPy |
| 1199β) | 5'-W T C A C G W-3' | HpPy-β-PyIm-γ-PyIm-β-ImPy |
| 1200β) | 5'-W T C A C C W-3' | HpPyPyPyPy-γ-ImIm-β-ImPy |
| 1200βp) | 5'-W T C A C C W-3' | HpPy-β-PyPy-γ-ImIm-β-ImPy |

TABLE 83

10-ring Hairpin Polyamides for recognition of
7-bp 5'-WTCSNNW-3' with β substitutions

| | DNA sequence | aromatic amino acid sequence |
|---|---|---|
| 1201β) | 5'-W T C G T T W-3' | Hp-β-ImHpHp-γ-PyPy-β-ImPy |
| 1202β) | 5'-W T C G T A W-3' | Hp-β-ImHpPy-γ-HpPy-β-ImPy |
| 1203β) | 5'-W T C G T G W-3' | Hp-β-ImHpIm-γ-PyPy-β-ImPy |
| 1204β) | 5'-W T C G T C W-3' | Hp-β-ImHpPy-γ-ImPy-β-ImPy |
| 1205β) | 5'-W T C G A T W-3' | Hp-β-ImPyHp-γ-PyHp-β-ImPy |
| 1206β) | 5'-W T C G A A W-3' | Hp-β-ImPyPy-γ-HpHp-β-ImPy |
| 1207β) | 5'-W T C G A G W-3' | Hp-β-ImPyIm-γ-PyHp-β-ImPy |
| 1208β) | 5'-W T C G A C W-3' | Hp-β-ImPyPy-γ-ImHp-β-ImPy |
| 1209β) | 5'-W T C G G T W-3' | Hp-β-ImImHp-γ-PyPy-β-ImPy |
| 1210β) | 5'-W T C G G A W-3' | Hp-β-ImImPy-γ-HpPy-β-ImPy |
| 1211β) | 5'-W T C G C T W-3' | Hp-β-ImPyHp-γ-PyIm-β-ImPy |
| 1212β) | 5'-W T C G C A W-3' | Hp-β-ImPyPy-γ-HpIm-β-ImPy |
| 1213β) | 5'-W T C C T T W-3' | HpPyPyHpHp-γ-Py-β-ImImPy |
| 1213βp) | 5'-W T C C T T W-3' | HpPyPy-β-Hp-γ-Py-β-ImImPy |
| 1214β) | 5'-W T C C T A W-3' | HpPyPyHpPy-γ-Hp-β-ImImPy |
| 1214βp) | 5'-W T C C T A W-3' | HpPyPy-β-Py-γ-Hp-β-ImImPy |
| 1215β) | 5'-W T C C T G W-3' | HpPy-β-HpIm-γ-Py-β-ImImPy |
| 1216β) | 5'-W T C C T C W-3' | HpPyPyHpPy-γ-Im-β-ImImPy |
| 1216βp) | 5'-W T C C T C W-3' | HpPyPy-β-Py-γ-Im-β-ImImPy |
| 1217β) | 5'-W T C C A T W-3' | HpPyPyPyHp-γ-Py-β-ImImPy |
| 1217βp) | 5'-W T C C A T W-3' | HpPyPy-β-Hp-γ-Py-β-ImImPy |
| 1218β) | 5'-W T C C A A W-3' | HpPyPyPyPy-γ-Hp-β-ImImPy |
| 1218βp) | 5'-W T C C A A W-3' | HpPyP-β-Py-γ-Hp-β-ImImPy |
| 1219β) | 5'-W T C C A G W-3' | HpPy-β-PyIm-γ-Py-β-ImImPy |
| 1220β) | 5'-W T C C A C W-3' | HpPyPyPyPy-γ-Im-β-ImImPy |
| 1220βp) | 5'-W T C C A C W-3' | HpPyPy-β-Py-γ-Im-β-ImImPy |
| 1221β) | 5'-W T C C G T W-3' | HpPy-β-ImHp-γ-Py-β-ImImPy |
| 1222β) | 5'-W T C C G A W-3' | HpPy-β-ImPy-γ-Hp-β-ImImPy |
| 1225β) | 5'-W T C G G G W-3' | Hp-β-ImImIm-γ-PyPy-β-ImPy |
| 1226β) | 5'-W T C G G C W-3' | Hp-β-ImImPy-γ-ImPy-β-ImPy |
| 1227β) | 5'-W T C G C G W-3' | Hp-β-ImPyIm-γ-PyIm-β-ImPy |
| 1228β) | 5'-W T C G C C W-3' | Hp-β-ImPyPy-γ-ImIm-β-ImPy |
| 1229β) | 5'-W T C C G G W-3' | HpPy-β-ImIm-γ-Py-β-ImImPy |
| 1230β) | 5'-W T C C G C W-3' | HpPy-β-ImPy-γ-Im-β-ImImPy |
| 1231β) | 5'-W T C C C G W-3' | HpPy-β-PyIm-γ-PyImImPy |

If the process described above of designing a preferred polyamide molecule comprising four or five carboxamide binding pairs does not produce a selective polyamide that binds to the target identified DNA sequence with subnanomolar affinity and with a selectivity over mismatch sequences of greater than a factor of ten, a polyamide molecule $X_1X_2X_3X_4X_5X_6$-γ-$X_7X_8X_9X_{10}X_{11}X_{12}$ having six carboxamide binding pairs can be designed that is selective for an eight base pair identified target 5'-WNNNNNNW-3' sequence. The design and synthesis of six binding pair polyamides is essentially the same as that of the four and five binding pair polyamides described above.

Figure 10A:
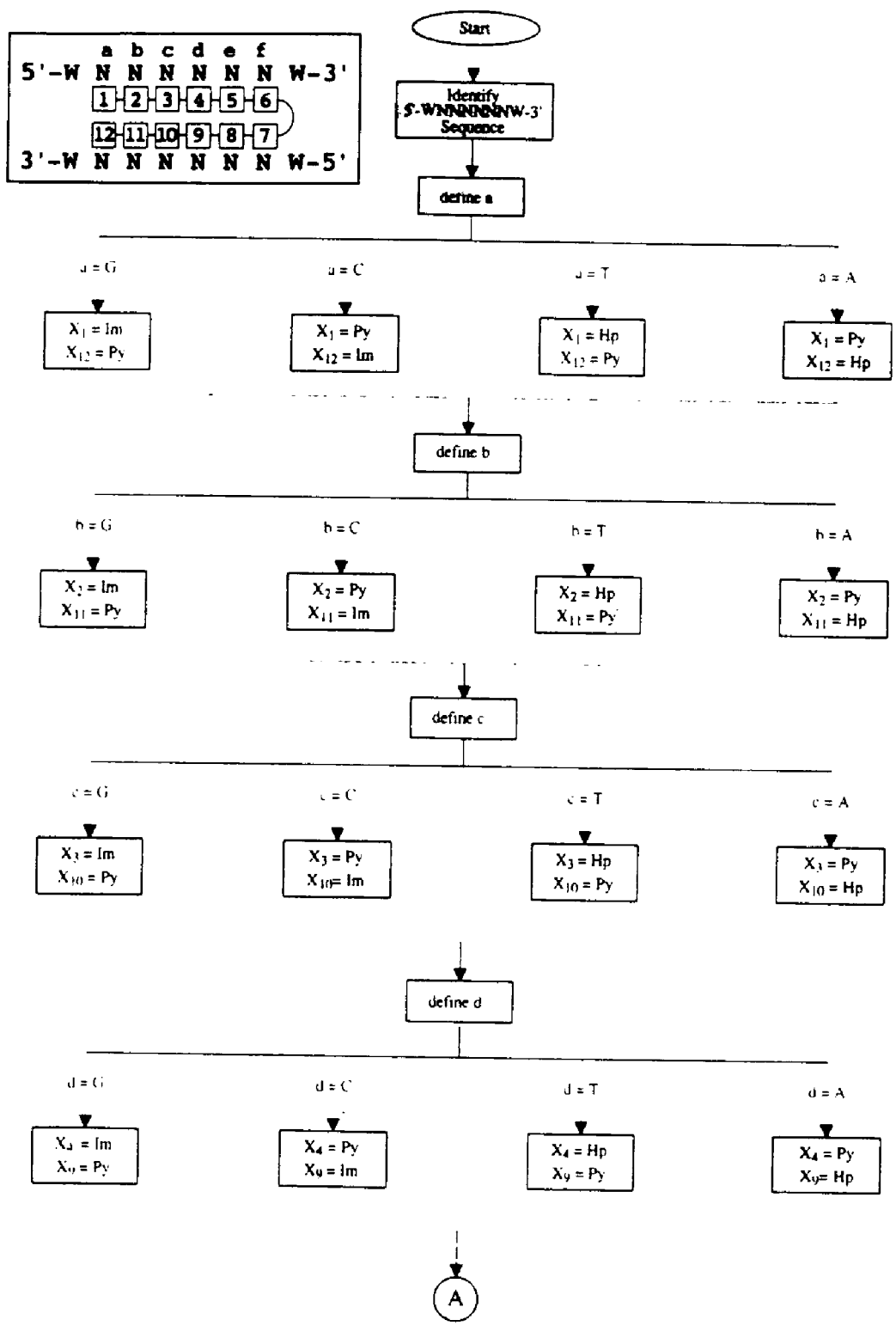
FIGS. 10A–10B schematically illustrate a method for the design of twelve carboxamide residue hairpin polyamide compounds suitable for recognition of 8-bp 5'-WNNNNNNW-3' sequences in the minor groove of double stranded DNA.
Figure 10B:
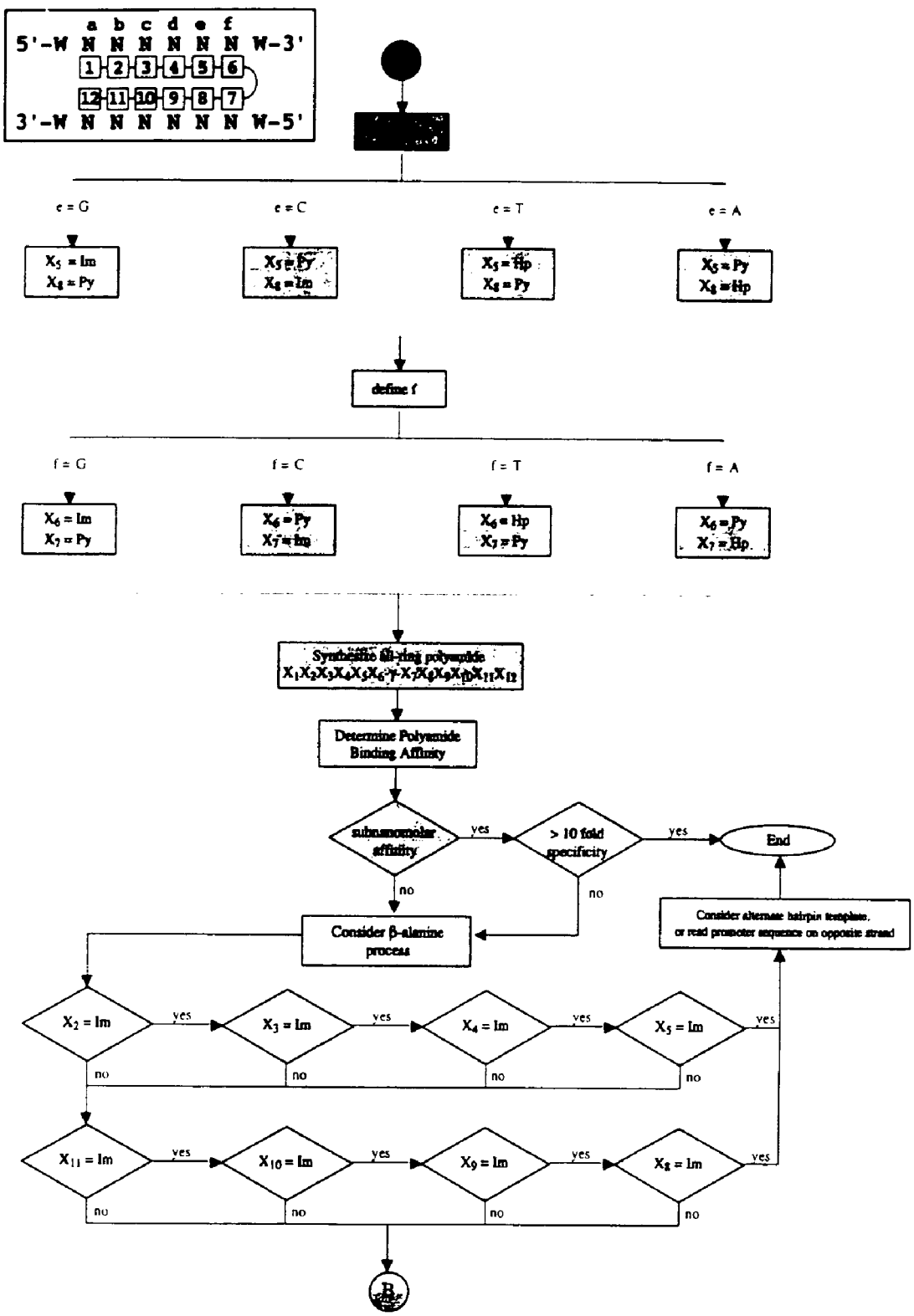

The polyamide design process for six carboxamide binding pair polyamides is shown schematically in FIG. 10A and the upper half of 10B. The method for choosing the residues that can be replaced by a β-alanine residue is shown schematically in the lower half of FIG. 10 B and in FIG. 11. The 1024 possible 12-ring hairpins which target the 1024 5'-GNNN-3' core sequences are listed in Tables 84–115. Each DNA sequence entry can be correlated to its corresponding polyamide recognition sequence using the process outlined in this figure. The 1024 possible 12-ring hairpins which target the 1024 5'-CNNNNN-3' core sequences are listed in Tables 116–147. Each DNA sequence entry can be correlated to its corresponding polyamide recognition sequence using the process outlined in this figure.

Figure 11A:
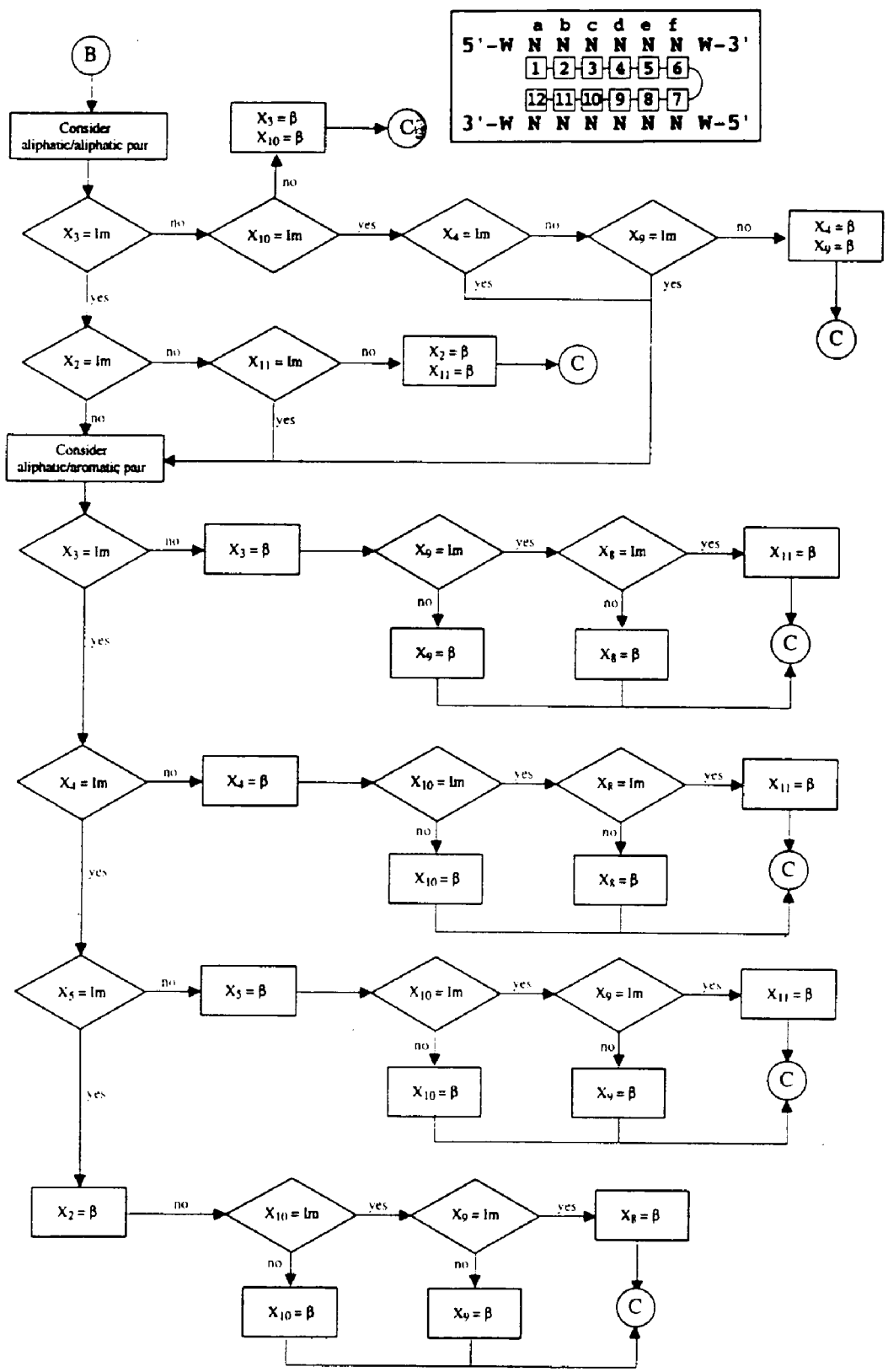
FIGS. 11A–11B schematically illustrate a method for determining the position of an aromatic amino acid residue that should be replaced with a β-alanine residue in order to enhance the DNA binding properties of certain twelve carboxamide residue hairpin polyamide compounds.
Figure 11B:
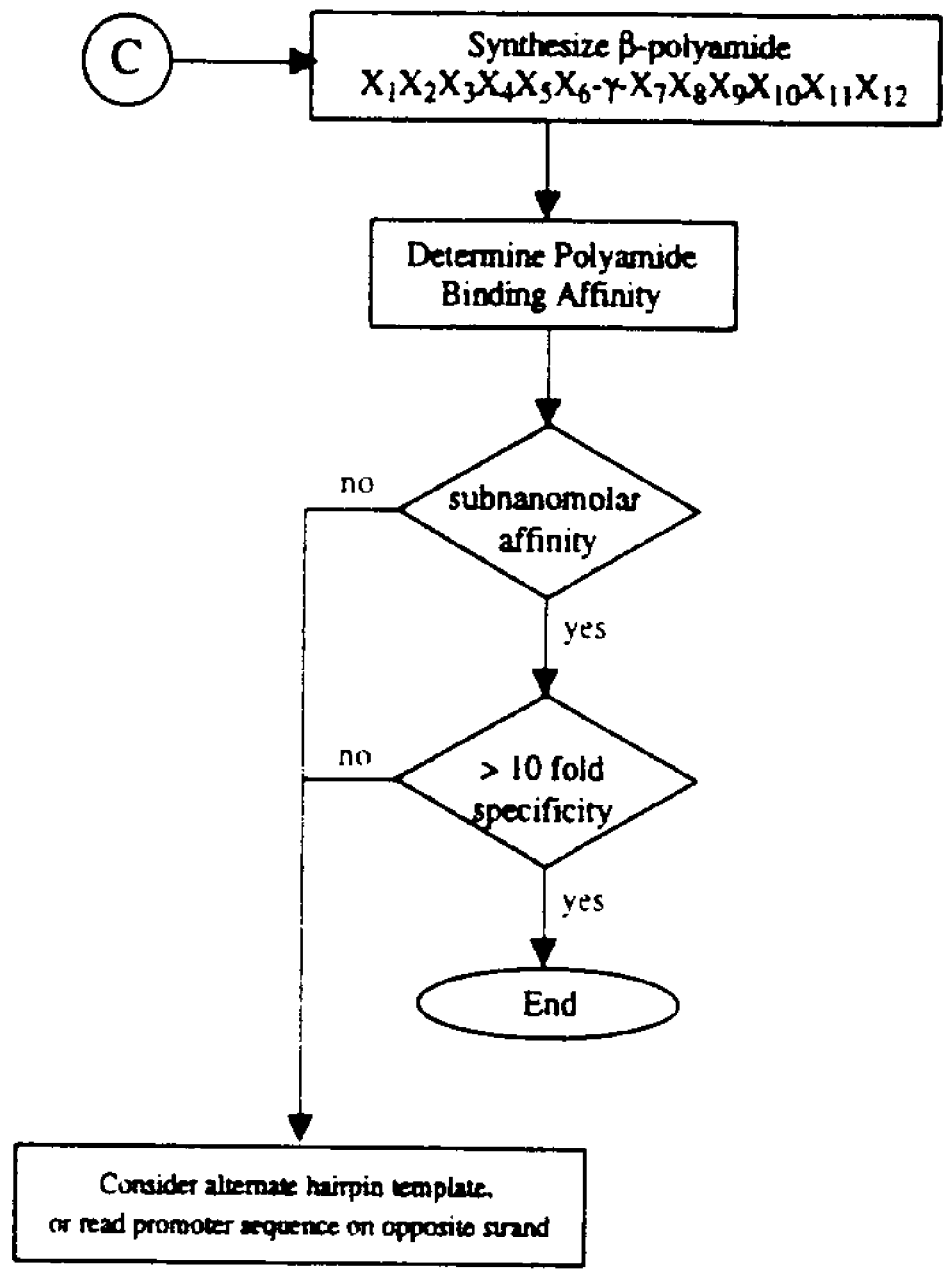

FIG. 11 shows a process for replacement of aromatic amino acid residues with aliphatic β-alanine 'spring' residues in order to enhance the DNA binding properties of 12-ring hairpin polyamides. Selective placement of an aliphatic β-alanine (β) residue paired side-by-side with either a pyrrole (Py) or imidazole (Im) aromatic amino acid or another β-alanine residue is found to compensate for sequence composition effects for recognition of the minor groove of DNA by hairpin pyrrole-imidazole polyamides. If an all-ring polyamide has been found to have an affinity which is not subnanomolar, or a specificity versus mismatch sequences which is less than 10-fold it may be caused by DNA sequence-composition effects which can be tuned out by replacement of an aromatic amino acid with an aliphatic β-alanine spring. Rules have been determined to help determine the exact placement of the β-spring residues. For example, within the 12-ring template, it is only beneficial to place β-alanine within positions $X_2$, $X_3$, $X_4$, $X_5$. $X_8$, $X_9$, and $X_{10}X_{11}$. No more than two β-alanine residues may be placed within a single hairpin structure. No more than a single β-residue may be placed within each individual polyamide subunit. Tables 148–1079 list derivatives of sequences (1233–2224) labeled (1223β–2224β) which contain two β-alanine residues assigned according to the process outlined in FIGS. 11A & B.

TABLE 84

12-ring Hairpin Polyamides for recognition of 8-bp 5'-WGGGWNNW-3'

| | DNA sequence | aromatic amino acid sequence |
|---|---|---|
| 1233) | 5'-W G G G T T T W-3' | ImImImHpHpHp-γ-PyPyPyPyPyPy |
| 1234) | 5'-W G G G T T A W-3' | ImImImHpHpPy-γ-HpPyPyPyPyPy |
| 1235) | 5'-W G G G T T G W-3' | ImImImHpHpIm-γ-PyPyPyPyPyPy |
| 1236) | 5'-W G G G T T C W-3' | ImImImHpHpPy-γ-ImPyPyPyPyPy |
| 1237) | 5'-W G G G T A T W-3' | ImImImHpPyHp-γ-PyHpPyPyPyPy |
| 1238) | 5'-W G G G T A A W-3' | ImImImHpPyPy-γ-HpHpPyPyPyPy |
| 1239) | 5'-W G G G T A G W-3' | ImImImHpPyIm-γ-PyHpPyPyPyPy |
| 1240) | 5'-W G G G T A C W-3' | ImImImHpPyPy-γ-ImHpPyPyPyPy |
| 1241) | 5'-W G G G T G T W-3' | ImImImHpImHp-γ-PyPyPyPyPyPy |
| 1242) | 5'-W G G G T G A W-3' | ImImImHpImPy-γ-HpImPyPyPyPy |
| 1243) | 5'-W G G G T G G W-3' | ImImImHpImIm-γ-PyPyPyPyPyPy |
| 1244) | 5'-W G G G T G C W-3' | ImImImHpImPy-γ-ImPyPyPyPyPy |
| 1245) | 5'-W G G G T C T W-3' | ImImImHpPyHp-γ-PyImPyPyPyPy |
| 1246) | 5'-W G G G T C A W-3' | ImImImHpPyPy-γ-HpImPyPyPyPy |
| 1247) | 5'-W G G G T C G W-3' | ImImImHpPyIm-γ-PyImPyPyPyPy |
| 1248) | 5'-W G G G T C C W-3' | ImImImHpPyPy-γ-ImImPyPyPyPy |
| 1249) | 5'-W G G G A T T W-3' | ImImImPyHpHp-γ-PyPyHpPyPyPy |
| 1250) | 5'-W G G G A T A W-3' | ImImImPyHpPy-γ-HpPyHpPyPyPy |
| 1251) | 5'-W G G G A T G W-3' | ImImImPyHpIm-γ-PyPyHpPyPyPy |
| 1252) | 5'-W G G G A T C W-3' | ImImImPyHpPy-γ-ImPyHpPyPyPy |
| 1253) | 5'-W G G G A A T W-3' | ImImImPyPyHp-γ-PyHpHpPyPyPy |
| 1254) | 5'-W G G G A A A W-3' | ImImImPyPyPy-γ-HpHpHpPyPyPy |
| 1255) | 5'-W G G G A A G W-3' | ImImImPyPyIm-γ-PyHpHpPyPyPy |
| 1256) | 5'-W G G G A A C W-3' | ImImImPyPyPy-γ-ImHpHpPyPyPy |
| 1257) | 5'-W G G G A G T W-3' | ImImImPyImHp-γ-PyHpHpPyPyPy |
| 1258) | 5'-W G G G A G A W-3' | ImImImPyImPy-γ-HpHpHpPyPyPy |
| 1259) | 5'-W G G G A G G W-3' | ImImImPyImIm-γ-PyHpHpPyPyPy |
| 1260) | 5'-W G G G A G C W-3' | ImImImPyImPy-γ-ImHpHpPyPyPy |
| 1261) | 5'-W G G G A C T W-3' | ImImImPyPyHp-γ-PyImHpPyPyPy |
| 1262) | 5'-W G G G A C A W-3' | ImImImPyPyPy-γ-HpImHpPyPyPy |
| 1263) | 5'-W G G G A C G W-3' | ImImImPyPyIm-γ-PyImHpPyPyPy |

TABLE 84-continued 12-ring Hairpin Polyamides for recognition of 8-bp 5'-WGGGWNNW-3'

| | DNA sequence | aromatic amino acid sequence |
|---|---|---|
| 1264) | 5'-W G G G A C C W-3' | ImImImPyPyPy-γ-ImImHpPyPyPy |

TABLE 85

12-ring Hairpin Polyamides for recognition of 8-bp 5'-WGGGSNNW-3'

| | DNA sequence | aromatic amino acid sequence |
|---|---|---|
| 1265) | 5'-W G G G G T T W-3' | ImImImImHpHp-γ-PyPyPyPyPyPy |
| 1266) | 5'-W G G G G T A W-3' | ImImImImHpPy-γ-HpPyPyPyPyPy |
| 1267) | 5'-W G G G G T G W-3' | ImImImImHpIm-γ-PyPyPyPyPyPy |
| 1268) | 5'-W G G G G T C W-3' | ImImImImHpPy-γ-ImPyPyPyPyPy |
| 1269) | 5'-W G G G G A T W-3' | ImImImImPyHp-γ-PyHpPyPyPyPy |
| 1270) | 5'-W G G G G A A W-3' | ImImImImPyPy-γ-HpHpPyPyPyPy |
| 1271) | 5'-W G G G G A G W-3' | ImImImImPyIm-γ-PyHpPyPyPyPy |
| 1272) | 5'-W G G G G A C W-3' | ImImImImPyIm-γ-PyHpPyPyPyPy |
| 1273) | 5'-W G G G G G T W-3' | ImImImImImHp-γ-PyPyPyPyPyPy |
| 1274) | 5'-W G G G G G A W-3' | ImImImImImPy-γ-HpPyPyPyPyPy |
| 1275) | 5'-W G G G G C T W-3' | ImImImImHpHp-γ-PyImPyPyPyPy |
| 1276) | 5'-W G G G G C A W-3' | ImImImImHpPy-γ-HpImPyPyPyPy |
| 1277) | 5'-W G G C T T T W-3' | ImImImPyHpHp-γ-PyPyImPyPyPy |
| 1278) | 5'-W G G C T T A W-3' | ImImImPyHpPy-γ-HpPyImPyPyPy |
| 1279) | 5'-W G G C T T G W-3' | ImImImPyHpIm-γ-PyPyImPyPyPy |
| 1280) | 5'-W G G C T T C W-3' | ImImImPyHpPy-γ-ImPyImPyPyPy |
| 1281) | 5'-W G G C A T T W-3' | ImImImPyPyHp-γ-PyHpImPyPyPy |
| 1282) | 5'-W G G C A A W-3' | ImImImPyPyPy-γ-HpHpImPyPyPy |
| 1283) | 5'-W G G C A G W-3' | ImImImPyIm-γ-PyHpImPyPyPy |
| 1284) | 5'-W G G C A C W-3' | ImImImPyPyPy-γ-ImHpImPyPyPy |
| 1285) | 5'-W G G C G T W-3' | ImImImPyImHp-γ-PyPyImPyPyPy |
| 1286) | 5'-W G G C G A W-3' | ImImImPyImPy-γ-HpPyImPyPyPy |
| 1287) | 5'-W G G C C T W-3' | ImImImPyPyHp-γ-PyImImPyPyPy |
| 1288) | 5'-W G G C C A W-3' | ImImImPyPyPy-γ-HpImImPyPyPy |
| G49) | 5'-W G G G G G W-3' | ImImImImImIm-γ-PyPyPyPyPyPy |
| G50) | 5'-W G G G G G C W-3' | ImImImImImPy-γ-ImPyPyPyPyPy |
| G51) | 5'-W G G G G C G W-3' | ImImImImPyIm-γ-PyImPyPyPyPy |
| G52) | 5'-W G G G G C C W-3' | ImImImImPyPy-γ-PyImPyPyPyPy |
| G53) | 5'-W G G G C G G W-3' | ImImImPyImIm-γ-PyImPyPyPy |
| G54) | 5'-W G G G C G C W-3' | ImImImPyImPy-γ-ImImPyPyPy |
| G55) | 5'-W G G G C C G W-3' | ImImImPyPyIm-γ-PyImImPyPyPy |
| G56) | 5'-W G G G C C C W-3' | ImImImPyPyPy-γ-ImImImPyPyPy |

TABLE 86

12-ring Hairpin Polyamides for recognition of 8-bp 5'-WGGTWNNW3'

| | DNA sequence | aromatic amino acid sequence |
|---|---|---|
| 1289) | 5'-W G G T T T T W-3' | ImImHpHpHpHp-γ-PyPyPyPyPyPy |
| 1290) | 5'-W G G T T T A W-3' | ImImHpHpHpPy-γ-HpPyPyPyPyPy |
| 1291) | 5'-W G G T T T G W-3' | ImImHpHpHpIm-γ-PyPyPyPyPyPy |
| 1292) | 5'-W G G T T T C W-3' | ImImHpHpHpPy-γ-ImPyPyPyPyPy |
| 1293) | 5'-W G G T T A T W-3' | ImImHpHpPyHp-γ-PyHpPyPyPyPy |
| 1294) | 5'-W G G T T A A W-3' | ImImHpHpPyPy-γ-HpHpPyPyPyPy |
| 1295) | 5'-W G G T T A G W-3' | ImImHpHpPyIm-γ-PyHpPyPyPyPy |
| 1296) | 5'-W G G T T A C W-3' | ImImHpHpPyPy-γ-ImPyPyPyPyPy |
| 1297) | 5'-W G G T T G T W-3' | ImImHpHpImHp-γ-PyPyPyPyPyPy |
| 1298) | 5'-W G G T T G A W-3' | ImImHpHpImPy-γ-HpPyPyPyPyPy |
| 1299) | 5'-W G G T T G G W-3' | ImImHpHpImIm-γ-PyPyPyPyPyPy |
| 1300) | 5'-W G G T T G C W-3' | ImImHpHpImPy-γ-ImPyPyPyPyPy |
| 1301) | 5'-W G G T T C T W-3' | ImImHpHpPyHp-γ-PyImPyPyPyPy |
| 1302) | 5'-W G G T T C A W-3' | ImImHpHpPyPy-γ-HpImPyPyPyPy |
| 1303) | 5'-W G G T T C G W-3' | ImImHpHpPyIm-γ-PyImPyPyPyPy |
| 1304) | 5'-W G G T T C C W-3' | ImImHpHpPyPy-γ-ImImPyPyPyPy |
| 1305) | 5'-W G G T A T T W-3' | ImImHpPyHpHp-γ-PyPyHpPyPyPy |
| 1306) | 5'-W G G T A T A W-3' | ImImHpPyHpPy-γ-HpPyHpPyPyPy |
| 1307) | 5'-W G G T A T G W-3' | ImImHpPyHpIm-γ-PyPyHpPyPyPy |
| 1308) | 5'-W G G T A T C W-3' | ImImHpPyHpPy-γ-ImPyHpPyPyPy |

TABLE 86-continued

12-ring Hairpin Polyamides for recognition of 8-bp 5'-WGGTWNNW3'

| | DNA sequence | aromatic amino acid sequence |
|---|---|---|
| 1309) | 5'-W G G T A A T W-3' | ImImHpPyPyHp-γ-PyHpHpPyPyPy |
| 1310) | 5'-W G G T A A A W-3' | ImImHpPyPyPy-γ-HpHpHpPyPyPy |
| 1311) | 5'-W G G T A A G W-3' | ImImHpPyPyIm-γ-PyHpHpPyPyPy |
| 1312) | 5'-W G G T A A C W-3' | ImImHpPyPyPy-γ-ImHpHpPyPyPy |
| 1313) | 5'-W G G T A G T W-3' | ImImHpPyImHp-γ-PyHpHpPyPyPy |
| 1314) | 5'-W G G T A G A W-3' | ImImHpPyImPy-γ-HpPyHpPyPyPy |
| 1315) | 5'-W G G T A G G W-3' | ImImHpPyImIm-γ-PyPyHpPyPyPy |
| 1316) | 5'-W G G T A G C W-3' | ImImHpPyImPy-γ-ImPyHpPyPyPy |
| 1317) | 5'-W G G T A C T W-3' | ImImHpPyPyHp-γ-PyImPyPyPyPy |
| 1318) | 5'-W G G T A C A W-3' | ImImHpPyPyPy-γ-HpImPyPyPyPy |
| 1319) | 5'-W G G T A C G W-3' | ImImHpPyPyIm-γ-PyImPyPyPyPy |
| 1320) | 5'-W G G T A C C W-3' | ImImHpPyPyPy-γ-ImImHpPyPyPy |

TABLE 87

12-ring Hairpin Polyamides for recognition of 8-bp 5'-WGGTSNNW-3'

| | DNA sequence | aromatic amino acid sequence |
|---|---|---|
| 1321) | 5'-W G G T G T T W-3' | ImImHpImHpHp-γ-PyPyPyPyPyPy |
| 1322) | 5'-W G G T G T A W-3' | ImImHpImHpPy-γ-HpPyPyPyPyPy |
| 1323) | 5'-W G G T G T G W-3' | ImImHpImHpIm-γ-PyPyPyPyPyPy |
| 1324) | 5'-W G G T G T C W-3' | ImImHpImHpPy-γ-ImPyPyPyPyPy |
| 1325) | 5'-W G G T G A T W-3' | ImImHpImPyHp-γ-PyHpPyPyPyPy |
| 1326) | 5'-W G G T G A A W-3' | ImImHpImPyPy-γ-HpHpPyPyPyPy |
| 1327) | 5'-W G G T G A G W-3' | ImImHpImPyIm-γ-PyHpPyPyPyPy |
| 1328) | 5'-W G G T G A C W-3' | ImImHpImPyPy-γ-ImHpPyPyPyPy |
| 1329) | 5'-W G G T G G T W-3' | ImImHpImImHp-γ-PyPyPyPyPyPy |
| 1330) | 5'-W G G T G G A W-3' | ImImHpImImPy-γ-HpPyPyPyPyPy |
| 1331) | 5'-W G G T G C T W-3' | ImImHpImPyHp-γ-PyImPyPyPyPy |
| 1332) | 5'-W G G T G C A W-3' | ImImHpImPyPy-γ-HpImPyPyPyPy |
| 1333) | 5'-W G G T G G G W-3' | ImImHpImImIm-γ-PyPyPyPyPyPy |
| 1334) | 5'-W G G T G G C W-3' | ImImHpImImPy-γ-ImPyPyPyPyPy |
| 1335) | 5'-W G G T G C G W-3' | ImImHpImPyIm-γ-PyImPyPyPyPy |
| 1336) | 5'-W G G T G C C W-3' | ImImHpImPyPy-γ-ImImPyPyPyPy |
| 1337) | 5'-W G G T C T T W-3' | ImImHpPyHpHp-γ-PyPyImPyPyPy |
| 1338) | 5'-W G G T C T A W-3' | ImImHpPyHpPy-γ-HpPyImPyPyPy |
| 1339) | 5'-W G G T C T G W-3' | ImImHpPyHpIm-γ-PyPyImPyPyPy |
| 1340) | 5'-W G G T C T C W-3' | ImImHpPyHpPy-γ-ImPyImPyPyPy |
| 1341) | 5'-W G G T C A T W-3' | ImImHpPyPyHp-γ-PyHpImPyPyPy |
| 1342) | 5'-W G G T C A A W-3' | ImImHpPyPyPy-γ-HpHpImPyPyPy |
| 1343) | 5'-W G G T C A G W-3' | ImImHpPyPyIm-γ-PyHpImPyPyPy |
| 1344) | 5'-W G G T C A C W-3' | ImImHpPyPyPy-γ-ImHpImPyPyPy |
| 1345) | 5'-W G G T C G T W-3' | ImImHpPyImHp-γ-PyPyImPyPyPy |
| 1346) | 5'-W G G T C G A W-3' | ImImHpPyImPy-γ-HpPyImPyPyPy |
| 1347) | 5'-W G G T C C T W-3' | ImImHpPyPyHp-γ-PyImImPyPyPy |
| 1348) | 5'-W G G T C C A W-3' | ImImHpPyPyPy-γ-HpImImPyPyPy |
| 1349) | 5'-W G G T C G G W-3' | ImImHpPyImIm-γ-PyPyImPyPyPy |
| 1350) | 5'-W G G T C G C W-3' | ImImHpPyImPy-γ-ImPyImPyPyPy |
| 1351) | 5'-W G G T C C G W-3' | ImImHpPyPyIm-γ-PyImImPyPyPy |
| 1352) | 5'-W G G T C C C W-3' | ImImHpPyPyPy-γ-ImImImPyPyPy |

TABLE 88

12-ring Hairpin Polyamides for recognition of 8-bp 5'-WGGAWNNW-3'

| | DNA sequence | aromatic amino acid sequence |
|---|---|---|
| 1353) | 5'-W G G A T T T W-3' | ImImPyHpHpHp-γ-PyPyPyHpPyPy |
| 1354) | 5'-W G G A T T A W-3' | ImImPyHpHpPy-γ-HpPyPyHpPyPy |
| 1355) | 5'-W G G A T T G W-3' | ImImPyHpHpIm-γ-PyPyPyHpPyPy |
| 1356) | 5'-W G G A T T C W-3' | ImImPyHpHpPy-γ-ImPyPyHpPyPy |
| 1357) | 5'-W G G A T A T W-3' | ImImPyHpPyHp-γ-PyHpPyHpPyPy |
| 1358) | 5'-W G G A T A A W-3' | ImImPyHpPyPy-γ-HpHpPyHpPyPy |
| 1359) | 5'-W G G A T A G W-3' | ImImPyHpPyIm-γ-PyHpPyHpPyPy |
| 1360) | 5'-W G G A T A C W-3' | ImImPyHpPyPy-γ-ImHpPyHpPyPy |
| 1361) | 5'-W G G A T G T W-3' | ImImPyHpImHp-γ-PyPyPyHpPyPy |

TABLE 88-continued

12-ring Hairpin Polyamides for recognition of 8-bp 5'-WGGAWNNW-3'

| | DNA sequence | aromatic amino acid sequence |
|---|---|---|
| 1362) | 5'-W G G A T G A W-3' | ImImPyHpImPy-γ-HpPyPyHpPyPy |
| 1363) | 5'-W G G A T G G W-3' | ImImPyHpImIm-γ-PyPyPyHpPyPy |
| 1364) | 5'-W G G A T G C W-3' | ImImPyHpImPy-γ-ImPyPyHpPyPy |
| 1365) | 5'-W G G A T C T W-3' | ImImPyHpPyHp-γ-PyImPyHpPyPy |
| 1366) | 5'-W G G A T C A W-3' | ImImPyHpPyPy-γ-HpImPyHpPyPy |
| 1367) | 5'-W G G A T C G W-3' | ImImPyHpPyIm-γ-PyImPyHpPyPy |
| 1368) | 5'-W G G A T C C W-3' | ImImPyHpPyPy-γ-ImImPyHpPyPy |
| 1369) | 5'-W G G A A T T W-3' | ImImPyPyHpHp-γ-PyPyHpHpPyPy |
| 1370) | 5'-W G G A A T A W-3' | ImImPyPyHpPy-γ-HpPyHpHpPyPy |
| 1371) | 5'-W G G A A T G W-3' | ImImPyPyHpIm-γ-PyPyHpHpPyPy |
| 1372) | 5'-W G G A A T C W-3' | ImImPyPyHpPy-γ-ImPyHpHpPyPy |
| 1373) | 5'-W G G A A A T W-3' | ImImPyPyPyHp-γ-PyHpHpHpPyPy |
| 1374) | 5'-W G G A A A A W-3' | ImImPyPyPyPy-γ-HpHpHpHpPyPy |
| 1375) | 5'-W G G A A A G W-3' | ImImPyPyPyIm-γ-PyHpHpHpPyPy |
| 1376) | 5'-W G G A A A C W-3' | ImImPyPyPyPy-γ-ImHpHpHpPyPy |
| 1377) | 5'-W G G A A G T W-3' | ImImPyPyImHp-γ-PyPyHpHpPyPy |
| 1378) | 5'-W G G A A G A W-3' | ImImPyPyImPy-γ-HpPyHpHpPyPy |
| 1379) | 5'-W G G A A G G W-3' | ImImPyPyImIm-γ-PyPyHpHpPyPy |
| 1380) | 5'-W G G A A G C W-3' | ImImPyPyImPy-γ-ImPyHpHpPyPy |
| 1381) | 5'-W G G A A C T W-3' | ImImPyPyPyHp-γ-PyImHpHpPyPy |
| 1382) | 5'-W G G A A C A W-3' | ImImPyPyPyPy-γ-HpImHpHpPyPy |
| 1383) | 5'-W G G A A C G W-3' | ImImPyPyPyIm-γ-PyImHpHpPyPy |
| 1384) | 5'-W G G A A C C W-3' | ImImPyPyPyPy-γ-ImImHpHpPyPy |

TABLE 89

12-ring Hairpin Polyamides for recognition of 8-bp 5'-WGGASNNW-3'

| | DNA sequence | aromatic amino acid sequence |
|---|---|---|
| 1385) | 5'-W G G A G T T W-3' | ImImPyImHpHp-γ-PyPyPyHpPyPy |
| 1386) | 5'-W G G A G T A W-3' | ImImPyImHpPy-γ-HpPyPyHpPyPy |
| 1387) | 5'-W G G A G T G W-3' | ImImPyImHpIm-γ-PyPyPyHpPyPy |
| 1388) | 5'-W G G A G T C W-3' | ImImPyImHpPy-γ-ImPyPyHpPyPy |
| 1389) | 5'-W G G A G A T W-3' | ImImPyImPyHp-γ-PyHpPyHpPyPy |
| 1390) | 5'-W G G A G A A W-3' | ImImPyImPyPy-γ-HpHpPyHpPyPy |
| 1391) | 5'-W G G A G A G W-3' | ImImPyImPyIm-γ-PyHpPyHpPyPy |
| 1392) | 5'-W G G A G A C W-3' | ImImPyImPyPy-γ-ImHpPyHpPyPy |
| 1393) | 5'-W G G A G G T W-3' | ImImPyImImHp-γ-PyPyPyHpPyPy |
| 1394) | 5'-W G G A G G A W-3' | ImImPyImImPy-γ-HpPyPyHpPyPy |
| 1395) | 5'-W G G A G C T W-3' | ImImPyImPyHp-γ-PyImPyHpPyPy |
| 1396) | 5'-W G G A G C A W-3' | ImImPyImPyPy-γ-HpImPyHpPyPy |
| 1397) | 5'-W G G A G G G W-3' | ImImPyImImIm-γ-PyPyPyHpPyPy |
| 1398) | 5'-W G G A G G C W-3' | ImImPyImImPy-γ-ImPyPyHpPyPy |
| 1399) | 5'-W G G A G C G W-3' | ImImPyImPyIm-γ-PyImPyHpPyPy |
| 1400) | 5'-W G G A G C C W-3' | ImImPyImPyPy-γ-ImImPyHpPyPy |
| 1401) | 5'-W G G A C T T W-3' | ImImPyPyHpHp-γ-PyPyImHpPyPy |
| 1402) | 5'-W G G A C T A W-3' | ImImPyPyHpPy-γ-HpPyImHpPyPy |
| 1403) | 5'-W G G A C T G W-3' | ImImPyPyHpIm-γ-PyPyImHpPyPy |
| 1404) | 5'-W G G A C T C W-3' | ImImPyPyHpPy-γ-ImPyImHpPyPy |
| 1405) | 5'-W G G A C A T W-3' | ImImPyPyPyHp-γ-PyHpImHpPyPy |
| 1406) | 5'-W G G A C A A W-3' | ImImPyPyPyPy-γ-HpHpImHpPyPy |
| 1407) | 5'-W G G A C A G W-3' | ImImPyPyPyIm-γ-PyHpImHpPyPy |
| 1408) | 5'-W G G A C A C W-3' | ImImPyPyPyPy-γ-ImHpImHpPyPy |
| 1409) | 5'-W G G A C G T W-3' | ImImPyPyImHp-γ-PyPyImHpPyPy |
| 1410) | 5'-W G G A C G A W-3' | ImImPyPyImPy-γ-HpPyImHpPyPy |
| 1411) | 5'-W G G A C C T W-3' | ImImPyPyPyHp-γ-PyImImHpPyPy |
| 1412) | 5'-W G G A C C A W-3' | ImImPyPyPyPy-γ-HpImImHpPyPy |
| 1413) | 5'-W G G A C G G W-3' | ImImPyPyImIm-γ-PyPyImHpPyPy |
| 1414) | 5'-W G G A C G C W-3' | ImImPyPyImPy-γ-ImPyImHpPyPy |
| 1415) | 5'-W G G A C C G W-3' | ImImPyPyPyIm-γ-PyImImHpPyPy |
| 1416) | 5'-W G G A C C C W-3' | ImImPyPyPyPy-γ-ImImImHpPyPy |

TABLE 90

12-ring Hairpin Polyamides for recognition of 8-bp 5'-WGGCWNNW-3'

| | DNA sequence | aromatic amino acid sequence |
|---|---|---|
| 1417) | 5'-W G G C T T T W-3' | ImImPyHpHpHp-γ-PyPyPyImPyPy |
| 1418) | 5'-W G G C T T A W-3' | ImImPyHpHpPy-γ-HpPyPyImPyPy |
| 1419) | 5'-W G G C T T G W-3' | ImImPyHpHpIm-γ-PyPyPyImPyPy |
| 1420) | 5'-W G G C T T C W-3' | ImImPyHpHpPy-γ-ImPyPyImPyPy |
| 1421) | 5'-W G G C T A T W-3' | ImImPyHpPyHp-γ-PyHpPyImPyPy |
| 1422) | 5'-W G G C T A A W-3' | ImImPyHpPyPy-γ-HpHpPyImPyPy |
| 1423) | 5'-W G G C T A G W-3' | ImImPyHpPyIm-γ-PyHpPyImPyPy |
| 1424) | 5'-W G G C T A C W-3' | ImImPyHpPyPy-γ-ImHpPyImPyPy |
| 1425) | 5'-W G G C T G T W-3' | ImImPyHpImHp-γ-PyPyPyImPyPy |
| 1426) | 5'-W G G C T G A W-3' | ImImPyHpImPy-γ-HpPyPyImPyPy |
| 1427) | 5'-W G G C T G G W-3' | ImImPyHpImIm-γ-PyPyPyImPyPy |
| 1428) | 5'-W G G C T G C W-3' | ImImPyHpImPy-γ-ImPyPyImPyPy |
| 1429) | 5'-W G G C T C T W-3' | ImImPyHpPyHp-γ-PyImPyImPyPy |
| 1430) | 5'-W G G C T C A W-3' | ImImPyHpPyPy-γ-HpImPyImPyPy |
| 1431) | 5'-W G G C T C G W-3' | ImImPyHpPyIm-γ-PyImPyImPyPy |
| 1432) | 5'-W G G C T C C W-3' | ImImPyHpPyPy-γ-ImImPyImPyPy |
| 1433) | 5'-W G G C A T T W-3' | ImImPyPyHpHp-γ-PyPyHpImPyPy |
| 1434) | 5'-W G G C A T A W-3' | ImImPyPyHpPy-γ-HpPyHpImPyPy |
| 1435) | 5'-W G G C A T G W-3' | ImImPyPyHpIm-γ-PyPyHpImPyPy |
| 1436) | 5'-W G G C A T C W-3' | ImImPyPyHpPy-γ-ImPyHpImPyPy |
| 1437) | 5'-W G G C A A T W-3' | ImImPyPyPyHp-γ-PyHpHpImPyPy |
| 1438) | 5'-W G G C A A A W-3' | ImImPyPyPyPy-γ-HpHpHpImPyPy |
| 1439) | 5'-W G G C A A G W-3' | ImImPyPyPyIm-γ-PyHpHpImPyPy |
| 1440) | 5'-W G G C A A C W-3' | ImImPyPyPyPy-γ-ImHpHpImPyPy |
| 1441) | 5'-W G G C A G T W-3' | ImImPyPyImHp-γ-PyPyHpImPyPy |
| 1442) | 5'-W G G C A G A W-3' | ImImPyPyImPy-γ-HpPyHpImPyPy |
| 1443) | 5'-W G G C A G G W-3' | ImImPyPyImIm-γ-PyPyHpImPyPy |
| 1444) | 5'-W G G C A G C W-3' | ImImPyPyImPy-γ-ImPyHpImPyPy |
| 1445) | 5'-W G G C A C T W-3' | ImImPyPyPyHp-γ-PyImHpImPyPy |
| 1446) | 5'-W G G C A C A W-3' | ImImPyPyPyPy-γ-HpImHpImPyPy |
| 1447) | 5'-W G G C A C G W-3' | ImImPyPyPyIm-γ-PyImHpImPyPy |
| 1448) | 5'-W G G C A C C W-3' | ImImPyPyPyPy-γ-ImImHpImPyPy |

TABLE 91

12-ring Hairpin Polyamides for recognition of 8-bp 5'-WGGCSNNW-3'

| | DNA sequence | aromatic amino acid sequence |
|---|---|---|
| 1449) | 5'-W G G C G T T W-3' | ImImPyImHpHp-γ-PyPyPyImPyPy |
| 1450) | 5'-W G G C G T A W-3' | ImImPyImHpPy-γ-HpPyPyImPyPy |
| 1451) | 5'-W G G C G T G W-3' | ImImPyImHpIm-γ-PyPyPyImPyPy |
| 1452) | 5'-W G G C G T C W-3' | ImImPyImHpPy-γ-ImPyPyImPyPy |
| 1453) | 5'-W G G C G A T W-3' | ImImPyImPyHp-γ-PyHpPyImPyPy |
| 1454) | 5'-W G G C G A A W-3' | ImImPyImPyPy-γ-HpHpPyImPyPy |
| 1455) | 5'-W G G C G A G W-3' | ImImPyImPyIm-γ-PyHpPyImPyPy |
| 1456) | 5'-W G G C G A C W-3' | ImImPyImPyPy-γ-ImHpPyImPyPy |
| 1457) | 5'-W G G C G G T W-3' | ImImPyImImHp-γ-PyPyPyImPyPy |
| 1458) | 5'-W G G C G G A W-3' | ImImPyImImPy-γ-HpPyPyImPyPy |
| 1459) | 5'-W G G C G C T W-3' | ImImPyImPyHp-γ-PyImPyImPyPy |
| 1460) | 5'-W G G C G C A W-3' | ImImPyImPyPy-γ-HpImPyImPyPy |
| 1461) | 5'-W G G C C T T W-3' | ImImPyPyHpHp-γ-PyPyImImPyPy |
| 1462) | 5'-W G G C C T A W-3' | ImImPyPyHpPy-γ-HpPyImImPyPy |
| 1463) | 5'-W G G C C T G W-3' | ImImPyPyHpIm-γ-PyPyImImPyPy |
| 1464) | 5'-W G G C C T C W-3' | ImImPyPyHpPy-γ-ImPyImImPyPy |
| 1465) | 5'-W G G C C A T W-3' | ImImPyPyPyHp-γ-PyHpImImPyPy |
| 1466) | 5'-W G G C C A A W-3' | ImImPyPyPyPy-γ-HpHpImImPyPy |
| 1467) | 5'-W G G C C A G W-3' | ImImPyPyPyIm-γ-PyHpImImPyPy |
| 1468) | 5'-W G G C C A C W-3' | ImImPyPyPyPy-γ-ImHpImImPyPy |
| 1469) | 5'-W G G C C G T W-3' | ImImPyPyImHp-γ-PyPyImImPyPy |
| 1470) | 5'-W G G C C G A W-3' | ImImPyPyImPy-γ-HpPyImImPyPy |
| 1471) | 5'-W G G C C C T W-3' | ImImPyPyPyHp-γ-PyImImImPyPy |
| 1472) | 5'-W G G C C C A W-3' | ImImPyPyPyPy-γ-HpImImImPyPy |
| G57) | 5'-W G G C G G G W-3' | ImImPyImImIm-γ-PyPyPyImPyPy |
| G58) | 5'-W G G C G G C W-3' | ImImPyImImPy-γ-ImPyPyImPyPy |
| G59) | 5'-W G G C G C G W-3' | ImImPyImPyIm-γ-PyImPyImPyPy |
| G60) | 5'-W G G C G C C W-3' | ImImPyImPyPy-γ-ImImPyImPyPy |
| G61) | 5'-W G G C C G G W-3' | ImImPyPyImIm-γ-PyPyImImPyPy |
| G62) | 5'-W G G C C G C W-3' | ImImPyPyImPy-γ-ImPyImImPyPy |
| G63) | 5'-W G G C C C G W-3' | ImImPyPyPyIm-γ-PyImImImPyPy |
| G64) | 5'-W G G C C C C W-3' | ImImPyPyPyPy-γ-ImImImImPyPy |

TABLE 92

12-ring Hairpin Polyamides for recognition of 8-bp 5'-WGCGWNNW-3'

| | DNA sequence | aromatic amino acid sequence |
|---|---|---|
| 1473) | 5'-W G C G T T T W-3' | ImPyImImHpHpHp-γ-PyPyPyPyImPy |
| 1474) | 5'-W G C G T T A W-3' | ImPyImImHpHpPy-γ-HpPyPyPyImPy |
| 1475) | 5'-W G C G T T G W-3' | ImPyImImHpHpIm-γ-PyPyPyPyImPy |
| 1476) | 5'-W G C G T T C W-3' | ImPyImImHpHpPy-γ-ImPyPyPyImPy |
| 1477) | 5'-W G C G T A T W-3' | ImPyImImHpPyHp-γ-PyHpPyPyImPy |
| 1478) | 5'-W G C G T A A W-3' | ImPyImImHpPyPy-γ-HpHpPyPyImPy |
| 1479) | 5'-W G C G T A G W-3' | ImPyImImHpPyIm-γ-PyHpPyPyImPy |
| 1480) | 5'-W G C G T A C W-3' | ImPyImImHpPyPy-γ-ImHpPyPyImPy |
| 1481) | 5'-W G C G T G T W-3' | ImPyImImHpImHp-γ-PyPyPyPyImPy |
| 1482) | 5'-W G C G T G A W-3' | ImPyImImHpImPy-γ-HpPyPyPyImPy |
| 1483) | 5'-W G C G T G G W-3' | ImPyImImHpImIm-γ-PyPyPyPyImPy |
| 1484) | 5'-W G C G T G C W-3' | ImPyImImHpImPy-γ-ImPyPyPyImPy |
| 1485) | 5'-W G C G T C T W-3' | ImPyImImHpPyHp-γ-PyImPyPyImPy |
| 1486) | 5'-W G C G T C A W-3' | ImPyImImHpPyPy-γ-HpImPyPyImPy |
| 1487) | 5'-W G C G T C G W-3' | ImPyImImHpPyIm-γ-PyImPyPyImPy |
| 1488) | 5'-W G C G T C C W-3' | ImPyImImHpPyPy-γ-ImImPyPyImPy |
| 1489) | 5'-W G C G A T T W-3' | ImPyImImPyHpHp-γ-PyPyHpPyImPy |
| 1490) | 5'-W G C G A T A W-3' | ImPyImImPyHpPy-γ-HpPyHpPyImPy |
| 1491) | 5'-W G C G A T G W-3' | ImPyImImPyHpIm-γ-PyPyHpPyImPy |
| 1492) | 5'-W G C G A T C W-3' | ImPyImImPyHpPy-γ-ImPyHpPyImPy |
| 1493) | 5'-W G C G A A T W-3' | ImPyImImPyPyHp-γ-PyHpHpPyImPy |
| 1494) | 5'-W G C G A A A W-3' | ImPyImImPyPyPy-γ-HpHpHpPyImPy |
| 1495) | 5'-W G C G A A G W-3' | ImPyImImPyPyIm-γ-PyHpHpPyImPy |
| 1496) | 5'-W G C G A A C W-3' | ImPyImImPyPyPy-γ-ImHpHpPyImPy |
| 1497) | 5'-W G C G A G T W-3' | ImPyImImPyImHp-γ-PyPyHpPyImPy |
| 1498) | 5'-W G C G A G A W-3' | ImPyImImPyImPy-γ-HpPyHpPyImPy |
| 1499) | 5'-W G C G A G G W-3' | ImPyImImPyImIm-γ-PyPyHpPyImPy |
| 1490) | 5'-W G C G A G C W-3' | ImPyImImPyImPy-γ-ImPyHpPyImPy |
| 1501) | 5'-W G C G A C T W-3' | ImPyImImPyPyHp-γ-PyImHpPyImPy |
| 1502) | 5'-W G C G A C A W-3' | ImPyImImPyPyPy-γ-HpImHpPyImPy |
| 1503) | 5'-W G C G A C G W-3' | ImPyImImPyPyIm-γ-PyImHpPyImPy |
| 1504) | 5'-W G C G A C C W-3' | ImPyImImPyPyPy-γ-ImImHpPyImPy |

TABLE 93

12-ring Hairpin Polyamides for recognition of 8-bp 5'-WGCGSNNW-3'

| | DNA sequence | aromatic amino acid sequence |
|---|---|---|
| 1505) | 5'-W G C G G T T W-3' | ImPyImImImHpHp-γ-PyPyPyPyImPy |
| 1506) | 5'-W G C G G T A W-3' | ImPyImImImHpPy-γ-HpPyPyPyImPy |
| 1507) | 5'-W G C G G T G W-3' | ImPyImImImHpIm-γ-PyPyPyPyImPy |
| 1508) | 5'-W G C G G T C W-3' | ImPyImImImHpPy-γ-ImPyPyPyImPy |
| 1509) | 5'-W G C G G A T W-3' | ImPyImImImPyHp-γ-PyHpPyPyImPy |
| 1510) | 5'-W G C G G A A W-3' | ImPyImImImPyPy-γ-HpHpPyPyImPy |
| 1511) | 5'-W G C G G A G W-3' | ImPyImImImPyIm-γ-PyHpPyPyImPy |
| 1512) | 5'-W G C G G A C W-3' | ImPyImImImPyPy-γ-ImHpPyPyImPy |
| 1513) | 5'-W G C G G G T W-3' | ImPyImImImImHp-γ-PyPyPyPyImPy |
| 1514) | 5'-W G C G G G A W-3' | ImPyImImImImPy-γ-HpPyPyPyImPy |
| 1515) | 5'-W G C G G C T W-3' | ImPyImImImPyHp-γ-PyImPyPyImPy |
| 1516) | 5'-W G C G G C A W-3' | ImPyImImImPyPy-γ-HpImPyPyImPy |
| 1517) | 5'-W G C G C T T W-3' | ImPyImPyHpHp-γ-PyPyImPyImPy |
| 1518) | 5'-W G C G C T A W-3' | ImPyImPyHpPy-γ-HpPyImPyImPy |
| 1519) | 5'-W G C G C T G W-3' | ImPyImPyHpIm-γ-PyPyImPyImPy |
| 1520) | 5'-W G C G C T C W-3' | ImPyImPyHpPy-γ-ImPyImPyImPy |
| 1521) | 5'-W G C G C A T W-3' | ImPyImPyPyHp-γ-PyHpImPyImPy |
| 1522) | 5'-W G C G C A A W-3' | ImPyImPyPyPy-γ-HpHpImPyImPy |
| 1523) | 5'-W G C G C A G W-3' | ImPyImPyPyIm-γ-PyHpImPyImPy |
| 1524) | 5'-W G C G C A C W-3' | ImPyImPyPyPy-γ-ImHpImPyImPy |
| 1525) | 5'-W G C G C G T W-3' | ImPyImPyImHp-γ-PyPyImPyImPy |
| 1526) | 5'-W G C G C G A W-3' | ImPyImPyImPy-γ-HpPyImPyImPy |
| 1527) | 5'-W G C G C C T W-3' | ImPyImPyPyHp-γ-PyImImPyImPy |
| 1528) | 5'-W G C G C C A W-3' | ImPyImPyPyPy-γ-HpImImPyImPy |
| G65) | 5'-W G C G G G G W-3' | ImPyImImImImIm-γ-PyPyPyPyImPy |
| G66) | 5'-W G C G G G C W-3' | ImPyImImImImPy-γ-ImPyPyPyImPy |
| G67) | 5'-W G C G G C G W-3' | ImPyImImImPyIm-γ-PyImPyPyImPy |
| G68) | 5'-W G C G G C C W-3' | ImPyImImImPyPy-γ-ImImPyPyImPy |
| G69) | 5'-W G C G C G G W-3' | ImPyImImPyImIm-γ-PyPyImPyImPy |
| G70) | 5'-W G C G C G C W-3' | ImPyImPyImPy-γ-ImPyImPyImPy |
| G71) | 5'-W G C G C C G W-3' | ImPyImPyPyIm-γ-PyImImPyImPy |
| G72) | 5'-W G C G C C C W-3' | ImPyImPyPyPy-γ-ImImImPyImPy |

TABLE 94

12-ring Hairpin Polyamides for recognition of 8-bp 5'-WGCTWNNW-3'

| | DNA sequence | aromatic amino acid sequence |
|---|---|---|
| 1529) | 5'-W G C T T T T W-3' | ImPyHpHpHpHp-γ-PyPyPyPyImPy |
| 1530) | 5'-W G C T T T A W-3' | ImPyHpHpHpPy-γ-HpPyPyPyImPy |
| 1531) | 5'-W G C T T T G W-3' | ImPyHpHpHpIm-γ-PyPyPyPyImPy |
| 1532) | 5'-W G C T T T C W-3' | ImPyHpHpHpPy-γ-ImPyPyPyImPy |
| 1533) | 5'-W G C T T A T W-3' | ImPyHpHpPyHp-γ-PyHpPyPyImPy |
| 1534) | 5'-W G C T T A A W-3' | ImPyHpHpPyPy-γ-HpHpPyPyImPy |
| 1535) | 5'-W G C T T A G W-3' | ImPyHpHpPyIm-γ-PyHpPyPyImPy |
| 1536) | 5'-W G C T T A C W-3' | ImPyHpHpPyPy-γ-ImHpPyPyImPy |
| 1537) | 5'-W G C T T G T W-3' | ImPyHpHpImHp-γ-PyPyPyPyImPy |
| 1538) | 5'-W G C T T G A W-3' | ImPyHpHpImPy-γ-HpPyPyPyImPy |
| 1539) | 5'-W G C T T G G W-3' | ImPyHpHpImIm-γ-PyPyPyPyImPy |
| 1540) | 5'-W G C T T G C W-3' | ImPyHpHpImPy-γ-ImPyPyPyImPy |
| 1541) | 5'-W G C T T C T W-3' | ImPyHpHpPyHp-γ-PyImPyPyImPy |
| 1542) | 5'-W G C T T C A W-3' | ImPyHpHpPyPy-γ-HpImPyPyImPy |
| 1543) | 5'-W G C T T C G W-3' | ImPyHpHpPyIm-γ-PyImPyPyImPy |
| 1544) | 5'-W G C T T C C W-3' | ImPyHpHpPyPy-γ-ImImPyPyImPy |
| 1545) | 5'-W G C T A T T W-3' | ImPyHpPyHpHp-γ-PyPyHpPyImPy |
| 1546) | 5'-W G C T A T A W-3' | ImPyHpPyHpPy-γ-HpPyHpPyImPy |
| 1547) | 5'-W G C T A T G W-3' | ImPyHpPyHpIm-γ-PyPyHpPyImPy |
| 1548) | 5'-W G C T A T C W-3' | ImPyHpPyHpPy-γ-ImPyHpPyImPy |
| 1549) | 5'-W G C T A A T W-3' | ImPyHpPyPyHp-γ-PyHpHpPyImPy |
| 1550) | 5'-W G C T A A A W-3' | ImPyHpPyPyPy-γ-HpHpHpPyImPy |
| 1551) | 5'-W G C T A A G W-3' | ImPyHpPyPyIm-γ-PyHpHpPyImPy |
| 1552) | 5'-W G C T A A C W-3' | ImPyHpPyPyPy-γ-ImHpHpPyImPy |
| 1553) | 5'-W G C T A G T W-3' | ImPyHpPyImHp-γ-PyPyHpPyImPy |
| 1554) | 5'-W G C T A G A W-3' | ImPyHpPyImPy-γ-HpPyHpPyImPy |
| 1555) | 5'-W G C T A G G W-3' | ImPyHpPyImIm-γ-PyPyHpPyImPy |
| 1556) | 5'-W G C T A G C W-3' | ImPyHpPyImPy-γ-ImPyHpPyImPy |
| 1557) | 5'-W G C T A C T W-3' | ImPyHpPyPyHp-γ-PyImHpPyImPy |
| 1558) | 5'-W G C T A C A W-3' | ImPyHpPyPyPy-γ-HpImHpPyImPy |
| 1559) | 5'-W G C T A C G W-3' | ImPyHpPyPyIm-γ-PyImHpPyImPy |
| 1560) | 5'-W G C T A C C W-3' | ImPyHpPyPyPy-γ-ImImHpPyImPy |

TABLE 95

12-ring Hairpin Polyamides for recognition of 8-bp 5'-WGCTSNNW-3'

| | DNA sequence | aromatic amino acid sequence |
|---|---|---|
| 1561) | 5'-W G C T G T T W-3' | ImPyHpImHpHp-γ-PyPyPyPyImPy |
| 1562) | 5'-W G C T G T A W-3' | ImPyHpImHpPy-γ-HpPyPyPyImPy |
| 1563) | 5'-W G C T G T G W-3' | ImPyHpImHpIm-γ-PyPyPyPyImPy |
| 1564) | 5'-W G C T G T C W-3' | ImPyHpImHpPy-γ-ImPyPyPyImPy |
| 1565) | 5'-W G C T G A T W-3' | ImPyHpImPyHp-γ-PyHpPyPyImPy |
| 1566) | 5'-W G C T G A A W-3' | ImPyHpImPyPy-γ-HpHpPyPyImPy |
| 1567) | 5'-W G C T G A G W-3' | ImPyHpImPyIm-γ-PyHpPyPyImPy |
| 1568) | 5'-W G C T G A C W-3' | ImPyHpImPyPy-γ-ImHpPyPyImPy |
| 1569) | 5'-W G C T G G T W-3' | ImPyHpImImHp-γ-PyPyPyPyImPy |
| 1570) | 5'-W G C T G G A W-3' | ImPyHpImImPy-γ-HpPyPyPyImPy |
| 1571) | 5'-W G C T G C T W-3' | ImPyHpImPyHp-γ-PyImPyPyImPy |
| 1572) | 5'-W G C T G C A W-3' | ImPyHpImPyPy-γ-HpImPyPyImPy |
| 1573) | 5'-W G C T G G G W-3' | ImPyHpImImIm-γ-PyPyPyPyImPy |
| 1574) | 5'-W G C T G G C W-3' | ImPyHpImImPy-γ-ImPyPyPyImPy |
| 1575) | 5'-W G C T G C G W-3' | ImPyHpImPyIm-γ-PyImPyPyImPy |
| 1576) | 5'-W G C T G C C W-3' | ImPyHpImPyPy-γ-ImImPyPyImPy |
| 1577) | 5'-W G C T C T T W-3' | ImPyHpPyHpHp-γ-PyPyImPyImPy |
| 1578) | 5'-W G C T C T A W-3' | ImPyHpPyHpPy-γ-HpPyImPyImPy |
| 1579) | 5'-W G C T C T G W-3' | ImPyHpPyHpIm-γ-PyPyImPyImPy |
| 1580) | 5'-W G C T C T C W-3' | ImPyHpPyHpPy-γ-ImPyImPyImPy |
| 1581) | 5'-W G C T C A T W-3' | ImPyHpPyPyHp-γ-PyHpImPyImPy |
| 1582) | 5'-W G C T C A A W-3' | ImPyHpPyPyPy-γ-HpHpImPyImPy |
| 1583) | 5'-W G C T C A G W-3' | ImPyHpPyPyIm-γ-PyHpImPyImPy |
| 1584) | 5'-W G C T C A C W-3' | ImPyHpPyPyPy-γ-ImHpImPyImPy |
| 1585) | 5'-W G C T C G T W-3' | ImPyHpPyImHp-γ-PyPyImPyImPy |
| 1586) | 5'-W G C T C G A W-3' | ImPyHpPyImPy-γ-HpPyImPyImPy |
| 1587) | 5'-W G C T C C T W-3' | ImPyHpPyPyHp-γ-PyImImPyImPy |
| 1588) | 5'-W G C T C C A W-3' | ImPyHpPyPyPy-γ-HpImImPyImPy |
| 1589) | 5'-W G C T C G G W-3' | ImPyHpPyImIm-γ-PyPyImPyImPy |
| 1590) | 5'-W G C T C G C W-3' | ImPyHpPyImPy-γ-ImPyImPyImPy |
| 1591) | 5'-W G C T C C G W-3' | ImPyHpPyPyIm-γ-PyImImPyImPy |
| 1592) | 5'-W G C T C C C W-3' | ImPyHpPyPyPy-γ-ImImImPyImPy |

TABLE 96

12-ring Hairpin Polyamides for recognition of 8-bp 5'-WGCAWNNW-3'

| | DNA sequence | aromatic amino acid sequence |
|---|---|---|
| 1593) | 5'-W G C A T T T W-3' | ImPyPyHpHpHp-γ-PyPyPyHpImPy |
| 1594) | 5'-W G C A T T A W-3' | ImPYPyHpHpPy-γ-HpPyPyHpImPy |
| 1595) | 5'-W G C A T T G W-3' | ImPyPyHpHpIm-γ-PyPyPyHpImPy |
| 1596) | 5'-W G C A T T C W-3' | ImPyPyHpHpPy-γ-ImPyPyHpImPy |
| 1597) | 5'-W G C A T A T W-3' | ImPyPyHpPyHp-γ-PyHpPyHpImPy |
| 1598) | 5'-W G C A T A A W-3' | ImPyPyHpPyPy-γ-HpHpPyHpImPy |
| 1599) | 5'-W G C A T A G W-3' | ImPyPyHpPyIm-γ-PyHpPyHpImPy |
| 1600) | 5'-W G C A T A C W-3' | ImPyPyHpPyPy-γ-ImHpPyHpImPy |
| 1601) | 5'-W G C A T G T W-3' | ImPyPyHpImHp-γ-PyPyPyHpImPy |
| 1602) | 5'-W G C A T G A W-3' | ImPyPyHpImPy-γ-HpPyPyHpImPy |
| 1603) | 5'-W G C A T G G W-3' | ImPyPyHpImIm-γ-PyPyPyHpImPy |
| 1604) | 5'-W G C A T G C W-3' | ImPyPyHpImPy-γ-ImPyPyHpImPy |
| 1605) | 5'-W G C A T C T W-3' | ImPyPyHpPyHp-γ-PyImPyHpImPy |
| 1606) | 5'-W G C A T C A W-3' | ImPyPyHpPyPy-γ-HpImPyHpImPy |
| 1607) | 5'-W G C A T C G W-3' | ImPyPyHpPyIm-γ-PyImPyHpImPy |
| 1608) | 5'-W G C A T C C W-3' | ImPyPyHpPyPy-γ-ImImPyHpImPy |
| 1609) | 5'-W G C A A T T W-3' | ImPyPyPyHpHp-γ-PyPyHpHpImPy |
| 1610) | 5'-W G C A A T A W-3' | ImPyPyPyHpPy-γ-HpPyHpHpImPy |
| 1611) | 5'-W G C A A T G W-3' | ImPyPyPyHpIm-γ-PyPyHpHpImPy |
| 1612) | 5'-W G C A A T C W-3' | ImPyPyPyHpPy-γ-ImPyHpHpImPy |
| 1613) | 5'-W G C A A A T W-3' | ImPyPyPyPyHp-γ-PyHpHpHpImPy |
| 1614) | 5'-W G C A A A A W-3' | ImPyPyPyPyPy-γ-HpHpHpHpImPy |
| 1615) | 5'-W G C A A A G W-3' | ImPyPyPyPyIm-γ-PyHpHpHpImPy |
| 1616) | 5'-W G C A A A C W-3' | ImPyPyPyPyPy-γ-ImHpHpHpImPy |
| 1617) | 5'-W G C A A G T W-3' | ImPyPyPyImHp-γ-PyPyHpHpImPy |
| 1618) | 5'-W G C A A G A W-3' | ImPyPyPyImPy-γ-HpPyHpHpImPy |
| 1619) | 5'-W G C A A G G W-3' | ImPyPyPyImIm-γ-PyPyHpHpImPy |
| 1620) | 5'-W G C A A G C W-3' | ImPyPyPyImPy-γ-ImPyHpHpImPy |
| 1621) | 5'-W G C A A C T W-3' | ImPyPyPyPyHp-γ-PyImHpHpImPy |
| 1622) | 5'-W G C A A C A W-3' | ImPyPyPyPyPy-γ-HpImHpHpImPy |
| 1623) | 5'-W G C A A C G W-3' | ImPyPyPyPyIm-γ-PyImHpHpImPy |
| 1624) | 5'-W G C A A C C W-3' | ImPyPyPyPyPy-γ-ImImHpHpImPy |

TABLE 97

12-ring Hairpin Polyamides for recognition of 8-bp 5'-WGCASNNW-3'

| | DNA sequence | aromatic amino acid sequence |
|---|---|---|
| 1625) | 5'-W G C A G T T W-3' | ImPyPyImHpHp-γ-PyPyPyHpImPy |
| 1626) | 5'-W G C A G T A W-3' | ImPyPyImHpPy-γ-HpPyPyHpImPy |
| 1627) | 5'-W G C A G T G W-3' | ImPyPyImHpIm-γ-PyPyPyHpImPy |
| 1628) | 5'-W G C A G T C W-3' | ImPyPyImHpPy-γ-ImPyPyHpImPy |
| 1629) | 5'-W G C A G A T W-3' | ImPyPyImPyHp-γ-PyHpPyHpImPy |
| 1630) | 5'-W G C A G A A W-3' | ImPyPyImPyPy-γ-HpHpPyHpImPy |
| 1631) | 5'-W G C A G A G W-3' | ImPyPyImPyIm-γ-PyHpPyHpImPy |
| 1632) | 5'-W G C A G A C W-3' | ImPyPyImPyPy-γ-ImHpPyHpImPy |
| 1633) | 5'-W G C A G G T W-3' | ImPyPyImImHp-γ-PyPyPyHpImPy |
| 1634) | 5'-W G C A G G A W-3' | ImPyPyImImPy-γ-HpPyPyHpImPy |
| 1635) | 5'-W G C A G C T W-3' | ImPyPyImPyHp-γ-PyImPyHpImPy |
| 1636) | 5'-W G C A G C A W-3' | ImPyPyImPyPy-γ-HpImPyHpImPy |
| 1637) | 5'-W G C A G G G W-3' | ImPyPyImImIm-γ-PyPyPyHpImPy |
| 1638) | 5'-W G C A G G C W-3' | ImPyPyImImPy-γ-ImPyPyHpImPy |
| 1639) | 5'-W G C A G C G W-3' | ImPyPyImPyIm-γ-PyImPyHpImPy |
| 1640) | 5'-W G C A G C C W-3' | ImPyPyImPyPy-γ-ImImPyHpImPy |
| 1641) | 5'-W G C A C T T W-3' | ImPyPyPyHpHp-γ-PyPyImHpImPy |
| 1642) | 5'-W G C A C T A W-3' | ImPyPyPyHpPy-γ-HpPyImHpImPy |
| 1643) | 5'-W G C A C T G W-3' | ImPyPyPyHpIm-γ-PyPyImHpImPy |
| 1644) | 5'-W G C A C T C W-3' | ImPyPyPyHpPy-γ-ImPyImHpImPy |
| 1645) | 5'-W G C A C A T W-3' | ImPyPyPyPyHp-γ-PyHpImHpImPy |
| 1646) | 5'-W G C A C A A W-3' | ImPyPyPyPyPy-γ-HpHpImHpImPy |
| 1647) | 5'-W G C A C A G W-3' | ImPyPyPyPyIm-γ-PyHpImHpImPy |
| 1648) | 5'-W G C A C A C W-3' | ImPyPyPyPyPy-γ-ImHpImHpImPy |
| 1649) | 5'-W G C A C G T W-3' | ImPyPyPyImHp-γ-PyPyImHpImPy |
| 1650) | 5'-W G C A C G A W-3' | ImPyPyPyImPy-γ-HpPyImHpImPy |
| 1651) | 5'-W G C A C C T W-3' | ImPyPyPyPyHp-γ-PyImImHpImPy |
| 1652) | 5'-W G C A C C A W-3' | ImPyPyPyPyPy-γ-HpImImHpImPy |
| 1653) | 5'-W G C A C G G W-3' | ImPyPyPyImIm-γ-PyPyImHpImPy |
| 1654) | 5'-W G C A C G C W-3' | ImPyPyPyImPy-γ-ImPyImHpImPy |
| 1655) | 5'-W G C A C C G W-3' | ImPyPyPyPyIm-γ-PyImImHpImPy |
| 1656) | 5'-W G C A C C C W-3' | ImPyPyPyPyPy-γ-ImImImHpImPy |

TABLE 98

12-ring Hairpin Polyamides for recognition of 8-bp 5'-WGCCWNNW-3'

| | DNA sequence | aromatic amino acid sequence |
|---|---|---|
| 1657) | 5'-W G C C T T T W-3' | ImPyPyHpHpHp-γ-PyPyPyImImPy |
| 1658) | 5'-W G C C T T A W-3' | ImPyPyHpHpPy-γ-HpPyPyImImPy |
| 1659) | 5'-W G C C T T G W-3' | ImPyPyHpHpIm-γ-PyPyPyImImPy |
| 1660) | 5'-W G C C T T C W-3' | ImPyPyHpHpPy-γ-ImPyPyPyImPy |
| 1661) | 5'-W G C C T A T W-3' | ImPyPyHpPyHp-γ-PyPyPyImImPy |
| 1662) | 5'-W G C C T A A W-3' | ImPyPyHpPyPy-γ-HpPyPyImImPy |
| 1663) | 5'-W G C C T A G W-3' | ImPyPyHpPyIm-γ-PyPyPyImImPy |
| 1664) | 5'-W G C C T A C W-3' | ImPyPyHpPyPy-γ-ImPyPyImImPy |
| 1665) | 5'-W G C C T G T W-3' | ImPyPyHpImHp-γ-PyPyPyImImPy |
| 1666) | 5'-W G C C T G A W-3' | ImPyPyHpImPy-γ-HpPyPyImImPy |
| 1667) | 5'-W G C C T G G W-3' | ImPyPyHpImIm-γ-PyPyPyImImPy |
| 1668) | 5'-W G C C T G C W-3' | ImPyPyHpImPy-γ-ImPyPyImImPy |
| 1669) | 5'-W G C C T C T W-3' | ImPyPyHpPyHp-γ-PyImPyImImPy |
| 1670) | 5'-W G C C T C A W-3' | ImPyPyHpPyPy-γ-HpImPyImImPy |
| 1671) | 5'-W G C C T C G W-3' | ImPyPyHpPyIm-γ-PyImPyImImPy |
| 1672) | 5'-W G C C T C C W-3' | ImPyPyHpPyPy-γ-ImImPyImImPy |
| 1673) | 5'-W G C C A T T W-3' | ImPyPyHpHpHp-γ-PyPyHpImImPy |
| 1674) | 5'-W G C C A T A W-3' | ImPyPyHpHpPy-γ-HpPyHpImImPy |
| 1675) | 5'-W G C C A T G W-3' | ImPyPyHpHpIm-γ-PyPyHpImImPy |
| 1676) | 5'-W G C C A T C W-3' | ImPyPyHpHpPy-γ-ImPyHpImImPy |
| 1677) | 5'-W G C C A A T W-3' | ImPyPyHpPyHp-γ-PyHpHpImImPy |
| 1678) | 5'-W G C C A A A W-3' | ImPyPyHpPyPy-γ-HpHpHpImImPy |
| 1679) | 5'-W G C C A A G W-3' | ImPyPyHpPyIm-γ-PyHpHpImImPy |
| 1680) | 5'-W G C C A A C W-3' | ImPyPyHpPyPy-γ-ImHpHpImImPy |
| 1681) | 5'-W G C C A G T W-3' | ImPyPyHpPyImHp-γ-PyPyHpImImPy |
| 1682) | 5'-W G C C A G A W-3' | ImPyPyHpPyImPy-γ-HpPyHpImImPy |
| 1683) | 5'-W G C C A G G W-3' | ImPyPyHpPyImIm-γ-PyPyHpImImPy |
| 1684) | 5'-W G C C A G C W-3' | ImPyPyHpPyImPy-γ-ImPyHpImImPy |
| 1685) | 5'-W G C C A C T W-3' | ImPyPyHpPyPyHp-γ-PyImHpImImPy |
| 1686) | 5'-W G C C A C A W-3' | ImPyPyHpPyPyPy-γ-HpImHpImImPy |
| 1687) | 5'-W G C C A C G W-3' | ImPyPyHpPyPyIm-γ-PyImHpImImPy |
| 1688) | 5'-W G C C A C C W-3' | ImPyPyHpPyPyPy-γ-ImImHpImImPy |

TABLE 99

12-ring Hairpin Polyamides for recognition of 8-bp 5'-WGCCSNNW-3'

| | DNA sequence | aromatic amino acid sequence |
|---|---|---|
| 1689) | 5'-W G C C G T T W-3' | ImPyPyImHpHp-γ-PyPyPyImImPy |
| 1690) | 5'-W G C C G T A W-3' | ImPyPyImHpPy-γ-HpPyPyImImPy |
| 1691) | 5'-W G C C G T G W-3' | ImPyPyImHpIm-γ-PyPyPyImImPy |
| 1692) | 5'-W G C C G T C W-3' | ImPyPyImHpPy-γ-ImPyPyImImPy |
| 1693) | 5'-W G C C G A T W-3' | ImPyPyImPyHp-γ-PyHpPyImImPy |
| 1694) | 5'-W G C C G A A W-3' | ImPyPyImPyPy-γ-HpHpPyImImPy |
| 1695) | 5'-W G C C G A G W-3' | ImPyPyImPyIm-γ-PyHpPyImImPy |
| 1696) | 5'-W G C C G A C W-3' | ImPyPyImPyPy-γ-ImHpPyImImPy |
| 1697) | 5'-W G C C G G T W-3' | ImPyPyImImHp-γ-PyPyPyImImPy |
| 1698) | 5'-W G C C G G A W-3' | ImPyPyImImPy-γ-HpPyPyImImPy |
| 1699) | 5'-W G C C G C T W-3' | ImPyPyImPyHp-γ-PyImPyImImPy |
| 1700) | 5'-W G C C G C A W-3' | ImPyPyImPyPy-γ-HpImPyImImPy |
| 1701) | 5'-W G C C C T T W-3' | ImPyPyPyHpHp-γ-PyPyImImImPy |
| 1702) | 5'-W G C C C T A W-3' | ImPyPyPyHpPy-γ-HpPyImImImPy |
| 1703) | 5'-W G C C C T G W-3' | ImPyPyPyHpIm-γ-PyPyImImImPy |
| 1704) | 5'-W G C C C T C W-3' | ImPyPyPyHpPy-γ-ImPyImImImPy |
| 1705) | 5'-W G C C C A T W-3' | ImPyPyPyPyHp-γ-PyHpImImImPy |
| 1706) | 5'-W G C C C A A W-3' | ImPyPyPyPyPy-γ-HpHpImImImPy |
| 1707) | 5'-W G C C C A G W-3' | ImPyPyPyPyIm-γ-PyHpImImImPy |
| 1708) | 5'-W G C C C A C W-3' | ImPyPyPyPyPy-γ-ImHpImImImPy |
| 1709) | 5'-W G C C C G T W-3' | ImPyPyPyImHp-γ-PyPyImImImPy |
| 1710) | 5'-W G C C C G A W-3' | ImPyPyPyImPy-γ-HpPyImImImPy |
| 1711) | 5'-W G C C C C T W-3' | ImPyPyPyPyHp-γ-PyImImImImPy |
| 1712) | 5'-W G C C C C A W-3' | ImPyPyPyPyPy-γ-HpImImImImPy |
| G73) | 5'-W G C C G G G W-3' | ImPyPyImImIm-γ-PyPyPyImImPy |
| G74) | 5'-W G C C G G C W-3' | ImPyPyImImPy-γ-ImPyPyImImPy |
| G75) | 5'-W G C C G C G W-3' | ImPyPyImPyIm-γ-PyImPyImImPy |
| G76) | 5'-W G C C G C C W-3' | ImPyPyImPyPy-γ-ImImPyImImPy |
| G77) | 5'-W G C C C G G W-3' | ImPyPyPyImIm-γ-PyPyImImImPy |
| G78) | 5'-W G C C C G C W-3' | ImPyPyPyImPy-γ-ImPyImImImPy |
| G79) | 5'-W G C C C C G W-3' | ImPyPyPyPyIm-γ-PyImImImImPy |
| G80) | 5'-W G C C C C C W-3' | ImPyPyPyPyPy-γ-ImImImImImPy |

TABLE 100

12-ring Hairpin Polyamides for recognition of 8-bp 5'-WGAGWNNW-3'

| | DNA sequence | aromatic amino acid sequence |
|---|---|---|
| 1713) | 5'-W G A G T T T W-3' | ImPyImHpHpHp-γ-PyPyPyPyHpPy |
| 1714) | 5'-W G A G T T A W-3' | ImPyImHpHpPy-γ-HpPyPyPyHpPy |
| 1715) | 5'-W G A G T T G W-3' | ImPyImHpHpIm-γ-PyPyPyPyHpPy |
| 1716) | 5'-W G A G T T C W-3' | ImPyImHpHpPy-γ-ImPyPyPyHpPy |
| 1717) | 5'-W G A G T A T W-3' | ImPyImHpPyHp-γ-PyHpPyPyHpPy |
| 1718) | 5'-W G A G T A A W-3' | ImPyImHpPyPy-γ-HpHpPyPyHpPy |
| 1719) | 5'-W G A G T A G W-3' | ImPyImHpPyIm-γ-PyHpPyPyHpPy |
| 1720) | 5'-W G A G T A C W-3' | ImPyImHpPyPy-γ-ImHpPyPyHpPy |
| 1721) | 5'-W G A G T G T W-3' | ImPyImHpImHp-γ-PyPyPyPyHpPy |
| 1722) | 5'-W G A G T G A W-3' | ImPyImHpImPy-γ-HpPyPyPyHpPy |
| 1723) | 5'-W G A G T G G W-3' | ImPyImHpImIm-γ-PyPyPyPyHpPy |
| 1724) | 5'-W G A G T G C W-3' | ImPyImHpImPy-γ-ImPyPyPyHpPy |
| 1725) | 5'-W G A G T C T W-3' | ImPyImHpPyHp-γ-PyImPyPyHpPy |
| 1726) | 5'-W G A G T C A W-3' | ImPyImHpPyPy-γ-HpImPyPyHpPy |
| 1727) | 5'-W G A G T C G W-3' | ImPyImHpPyIm-γ-PyImPyPyHpPy |
| 1728) | 5'-W G A G T C C W-3' | ImPyImHpPyPy-γ-ImImPyPyHpPy |
| 1729) | 5'-W G A G A T T W-3' | ImPyImPyHpHp-γ-PyPyHpPyHpPy |
| 1730) | 5'-W G A G A T A W-3' | ImPyImPyHpPy-γ-HpPyHpPyHpPy |
| 1731) | 5'-W G A G A T G W-3' | ImPyImPyHpIm-γ-PyPyHpPyHpPy |
| 1732) | 5'-W G A G A T C W-3' | ImPyImPyHpPy-γ-ImPyHpPyHpPy |
| 1733) | 5'-W G A G A A T W-3' | ImPyImPyPyHp-γ-PyHpHpPyHpPy |
| 1734) | 5'-W G A G A A A W-3' | ImPyImPyPyPy-γ-HpHpHpPyHpPy |
| 1735) | 5'-W G A G A A G W-3' | ImPyImPyPyIm-γ-PyHpHpPyHpPy |
| 1736) | 5'-W G A G A A C W-3' | ImPyImPyPyPy-γ-ImHpHpPyHpPy |
| 1737) | 5'-W G A G A G T W-3' | ImPyImPyImHp-γ-PyPyHpPyHpPy |
| 1738) | 5'-W G A G A G A W-3' | ImPyImPyImPy-γ-HpPyHpPyHpPy |
| 1739) | 5'-W G A G A G G W-3' | ImPyImPyImIm-γ-PyPyHpPyHpPy |
| 1740) | 5'-W G A G A G C W-3' | ImPyImPyImPy-γ-ImPyHpPyHpPy |
| 1741) | 5'-W G A G A C T W-3' | ImPyImPyPyHp-γ-PyImHpPyHpPy |
| 1742) | 5'-W G A G A C A W-3' | ImPyImPyPyPy-γ-HpImHpPyHpPy |
| 1743) | 5'-W G A G A C G W-3' | ImPyImPyPyIm-γ-PyImHpPyHpPy |
| 1744) | 5'-W G A G A C C W-3' | ImPyImPyPyPy-γ-ImImHpPyHpPy |

TABLE 101

12-ring Hairpin Polyamides for recognition of 8-bp 5'-WGAGSNNW-3'

| | DNA sequence | aromatic amino acid sequence |
|---|---|---|
| 1745) | 5'-W G A G G T T W-3' | ImPyImImHpHp-γ-PyPyPyPyHpPy |
| 1746) | 5'-W G A G G T A W-3' | ImPyImImHpPy-γ-HpPyPyPyHpPy |
| 1747) | 5'-W G A G G T G W-3' | ImPyImImHpIm-γ-PyPyPyPyHpPy |
| 1748) | 5'-W G A G G T C W-3' | ImPyImImHpPy-γ-ImPyPyPyHpPy |
| 1749) | 5'-W G A G G A T W-3' | ImPyImImPyHp-γ-PyHpPyPyHpPy |
| 1750) | 5'-W G A G G A A W-3' | ImPyImImPyPy-γ-HpHpPyPyHpPy |
| 1751) | 5'-W G A G G A G W-3' | ImPyImImPyIm-γ-PyHpPyPyHpPy |
| 1752) | 5'-W G A G G A C W-3' | ImPyImImPyPy-γ-ImHpPyPyHpPy |
| 1753) | 5'-W G A G G G T W-3' | ImPyImImImHp-γ-PyPyPyPyHpPy |
| 1754) | 5'-W G A G G G A W-3' | ImPyImImImPy-γ-HpPyPyPyHpPy |
| 1755) | 5'-W G A G G C T W-3' | ImPyImImPyHp-γ-PyImPyPyHpPy |
| 1756) | 5'-W G A G G C A W-3' | ImPyImImPyPy-γ-HpImPyPyHpPy |
| 1757) | 5'-W G A G C T T W-3' | ImPyImPyHpHp-γ-PyPyImPyHpPy |
| 1758) | 5'-W G A G C T A W-3' | ImPyImPyHpPy-γ-HpPyImPyHpPy |
| 1759) | 5'-W G A G C T G W-3' | ImPyImPyHpIm-γ-PyPyImPyHpPy |
| 1760) | 5'-W G A G C T C W-3' | ImPyImPyHpPy-γ-ImPyImPyHpPy |
| 1761) | 5'-W G A G C A T W-3' | ImPyImPyPyHp-γ-PyHpImPyHpPy |
| 1762) | 5'-W G A G C A A W-3' | ImPyImPyPyPy-γ-HpHpImPyHpPy |
| 1763) | 5'-W G A G C A G W-3' | ImPyImPyPyIm-γ-PyHpImPyHpPy |
| 1764) | 5'-W G A G C A C W-3' | ImPyImPyPyPy-γ-ImHpImPyHpPy |
| 1765) | 5'-W G A G C G T W-3' | ImPyImPyImHp-γ-PyPyImPyHpPy |
| 1766) | 5'-W G A G C G A W-3' | ImPyImPyImPy-γ-HpPyImPyHpPy |
| 1767) | 5'-W G A G C C T W-3' | ImPyImPyPyHp-γ-PyImImPyHpPy |
| 1768) | 5'-W G A G C C A W-3' | ImPyImPyPyPy-γ-HpImImPyHpPy |
| 1769) | 5'-W G A G G G G W-3' | ImPyImImImIm-γ-PyPyPyPyHpPy |
| 1770) | 5'-W G A G G G C W-3' | ImPyImImImPy-γ-ImPyPyPyHpPy |
| 1771) | 5'-W G A G G C G W-3' | ImPyImImPyIm-γ-PyImPyPyHpPy |
| 1772) | 5'-W C A G G C C W-3' | ImPyImImPyPy-γ-ImImPyPyHpPy |
| 1773) | 5'-W G A G C G G W-3' | ImPyImPyImIm-γ-PyPyImPyHpPy |
| 1774) | 5'-W G A G C G C W-3' | ImPyImPyImPy-γ-ImPyImPyHpPy |
| 1775) | 5'-W G A G C C G W-3' | ImPyImPyPyIm-γ-PyImImPyHpPy |
| 1776) | 5'-W G A G C C C W-3' | ImPyImPyPyPy-γ-ImImImPyHpPy |

TABLE 102

12-ring Hairpin Polyamides for recognition of 8-bp 5'-WGATWNNW-3'

| | DNA sequence | aromatic amino acid sequence |
|---|---|---|
| 1777) | 5'-W G A T T T T W-3' | ImPyHpHpHpHp-γ-PyPyPyPyHpPy |
| 1778) | 5'-W G A T T T A W-3' | ImPyHpHpHpPy-γ-HpPyPyPyHpPy |
| 1779) | 5'-W G A T T T G W-3' | ImPyHpHpHpIm-γ-PyPyPyPyHpPy |
| 1780) | 5'-W G A T T T C W-3' | ImPyHpHpHpPy-γ-ImPyPyPyHpPy |
| 1781) | 5'-W G A T T A T W-3' | ImPyHpHpPyHp-γ-PyHpPyPyHpPy |
| 1782) | 5'-W G A T T A A W-3' | ImPyHpHpPyPy-γ-HpHpPyPyHpPy |
| 1783) | 5'-W G A T T A G W-3' | ImPyHpHpPyIm-γ-PyHpPyPyHpPy |
| 1784) | 5'-W G A T T A C W-3' | ImPyHpHpPyPy-γ-ImHpPyPyHpPy |
| 1785) | 5'-W G A T T G T W-3' | ImPyHpHpImHp-γ-PyPyPyPyHpPy |
| 1786) | 5'-W G A T T G A W-3' | ImPyHpHpImPy-γ-HpPyPyPyHpPy |
| 1787) | 5'-W G A T T G G W-3' | ImPyHpHpImIm-γ-PyPyPyPyHpPy |
| 1788) | 5'-W G A T T G C W-3' | ImPyHpHpImPy-γ-ImPyPyPyHpPy |
| 1789) | 5'-W G A T T C T W-3' | ImPyHpHpPyHp-γ-PyImPyPyHpPy |
| 1790) | 5'-W G A T T C A W-3' | ImPyHpHpPyPy-γ-HpImPyPyHpPy |
| 1791) | 5'-W G A T T C G W-3' | ImPyHpHpPyIm-γ-PyImPyPyHpPy |
| 1792) | 5'-W G A T T C C W-3' | ImPyHpHpPyPy-γ-ImImPyPyHpPy |
| 1793) | 5'-W G A T A T T W-3' | ImPyHpPyHpHp-γ-PyPyHpPyHpPy |
| 1794) | 5'-W G A T A T A W-3' | ImPyHpPyHpPy-γ-HpPyHpPyHpPy |
| 1795) | 5'-W G A T A T G W-3' | ImPyHpPyHpIm-γ-PyPyHpPyHpPy |
| 1796) | 5'-W G A T A T C W-3' | ImPyHpPyHpPy-γ-ImPyHpPyHpPy |
| 1797) | 5'-W G A T A A T W-3' | ImPyHpPyPyHp-γ-PyHpHpPyHpPy |
| 1798) | 5'-W G A T A A A W-3' | ImPyHpPyPyPy-γ-HpHpHpPyHpPy |
| 1799) | 5'-W G A T A A G W-3' | ImPyHpPyPyIm-γ-PyHpHpPyHpPy |
| 1800) | 5'-W G A T A A C W-3' | ImPyHpPyPyPy-γ-ImHpHpPyHpPy |
| 1801) | 5'-W G A T A G T W-3' | ImPyHpPyImHp-γ-PyPyHpPyHpPy |
| 1802) | 5'-W G A T A G A W-3' | ImPyHpPyImPy-γ-HpPyHpPyHpPy |
| 1803) | 5'-W G A T A G G W-3' | ImPyHpPyImIm-γ-PyPyHpPyHpPy |
| 1804) | 5'-W G A T A G C W-3' | ImPyHpPyImPy-γ-ImPyHpPyHpPy |
| 1805) | 5'-W G A T A C T W-3' | ImPyHpPyPyHp-γ-PyImHpPyHpPy |
| 1806) | 5'-W G A T A C A W-3' | ImPyHpPyPyPy-γ-HpImHpPyHpPy |
| 1807) | 5'-W G A T A C G W-3' | ImPyHpPyPyIm-γ-PyImHpPyHpPy |
| 1808) | 5'-W G A T A C C W-3' | ImPyHpPyPyPy-γ-ImImHpPyHpPy |

TABLE 103

12-ring Hairpin Polyamides for recognition of 8-bp 5'-WGATSNNW-3'

| | DNA sequence | aromatic amino acid sequence |
|---|---|---|
| 1809) | 5'-W G A T G T T W-3' | ImPyHpImHpHp-γ-PyPyPyPyHpPy |
| 1810) | 5'-W G A T G T A W-3' | ImPyHpImHpPy-γ-HpPyPyPyHpPy |
| 1811) | 5'-W G A T G T G W-3' | ImPyHpImHpIm-γ-PyPyPyPyHpPy |
| 1812) | 5'-W G A T G T C W-3' | ImPyHpImHpPy-γ-ImPyPyPyHpPy |
| 1813) | 5'-W G A T G A T W-3' | ImPyHpImPyHp-γ-PyHpPyPyHpPy |
| 1814) | 5'-W G A T G A A W-3' | ImPyHpImPyPy-γ-HpHpPyPyHpPy |
| 1815) | 5'-W G A T G A G W-3' | ImPyHpImPyIm-γ-PyHpPyPyHpPy |
| 1816) | 5'-W G A T G A C W-3' | ImPyHpImPyPy-γ-ImHpPyPyHpPy |
| 1817) | 5'-W G A T G G T W-3' | ImPyHpImImHp-γ-PyPyPyPyHpPy |
| 1818) | 5'-W G A T G G A W-3' | ImPyHpImImPy-γ-HpPyPyPyHpPy |
| 1819) | 5'-W G A T G C T W-3' | ImPyHpImPyHp-γ-PyImPyPyHpPy |
| 1820) | 5'-W G A T G C A W-3' | ImPyHpImPyPy-γ-HpImPyPyHpPy |
| 1821) | 5'-W G A T G G G W-3' | ImPyHpImImIm-γ-PyPyPyPyHpPy |
| 1822) | 5'-W G A T G G C W-3' | ImPyHpImImPy-γ-ImPyPyPyHpPy |
| 1823) | 5'-W G A T G C G W-3' | ImPyHpImPyIm-γ-PyImPyPyHpPy |
| 1824) | 5'-W G A T G C C W-3' | ImPyHpImPyPy-γ-ImImPyPyHpPy |
| 1825) | 5'-W G A T C T T W-3' | ImPyHpPyHpHp-γ-PyPyImPyHpPy |
| 1826) | 5'-W G A T C T A W-3' | ImPyHpPyHpPy-γ-HpPyImPyHpPy |
| 1827) | 5'-W G A T C T G W-3' | ImPyHpPyHpIm-γ-PyPyImPyHpPy |
| 1828) | 5'-W G A T C T C W-3' | ImPyHpPyHpPy-γ-ImPyImPyHpPy |
| 1829) | 5'-W G A T C A T W-3' | ImPyHpPyPyHp-γ-PyHpImPyHpPy |
| 1830) | 5'-W G A T C A A W-3' | ImPyHpPyPyPy-γ-HpHpImPyHpPy |
| 1831) | 5'-W G A T C A G W-3' | ImPyHpPyPyIm-γ-PyHpImPyHpPy |
| 1832) | 5'-W G A T C A C W-3' | ImPyHpPyPyPy-γ-ImHpImPyHpPy |
| 1833) | 5'-W G A T C G T W-3' | ImPyHpPyImHp-γ-PyPyImPyHpPy |
| 1834) | 5'-W G A T C G A W-3' | ImPyHpPyImPy-γ-HpPyImPyHpPy |
| 1835) | 5'-W G A T C C T W-3' | ImPyHpPyPyHp-γ-PyImImPyHpPy |
| 1836) | 5'-W G A T C C A W-3' | ImPyHpPyPyPy-γ-HpImImPyHpPy |
| 1837) | 5'-W G A T C G G W-3' | ImPyHpPyImIm-γ-PyPyImPyHpPy |
| 1838) | 5'-W G A T C G C W-3' | ImPyHpPyImPy-γ-ImPyImPyHpPy |
| 1839) | 5'-W G A T C C G W-3' | ImPyHpPyPyIm-γ-PyImImPyHpPy |
| 1840) | 5'-W G A T C C C W-3' | ImPyHpPyPyPy-γ-ImImImPyHpPy |

TABLE 104

12-ring Hairpin Polyamides for recognition of 8-bp 5'-WGAAWNNW-3'

| | DNA sequence | aromatic amino acid sequence |
|---|---|---|
| 1841) | 5'-W G A A T T T W-3' | ImPyPyHpHpHp-γ-PyPyPyHpHpPy |
| 1842) | 5'-W G A A T T A W-3' | ImPyPyHpHpPy-γ-HpPyPyHpHpPy |
| 1843) | 5'-W G A A T T G W-3' | ImPyPyHpHpIm-γ-PyPyPyHpHpPy |
| 1844) | 5'-W G A A T T C W-3' | ImPyPyHpHpPy-γ-ImPyPyHpHpPy |
| 1845) | 5'-W G A A T A T W-3' | ImPyPyHpPyHp-γ-PyHpPyHpHpPy |
| 1846) | 5'-W G A A T A A W-3' | ImPyPyHpPyPy-γ-HpHpPyHpHpPy |
| 1847) | 5'-W G A A T A G W-3' | ImPyPyHpPyIm-γ-PyHpPyHpHpPy |
| 1848) | 5'-W G A A T A C W-3' | ImPyPyHpPyPy-γ-ImHpPyHpHpPy |
| 1849) | 5'-W G A A T G T W-3' | ImPyPyHpImHp-γ-PyPyPyHpHpPy |
| 1850) | 5'-W G A A T G A W-3' | ImPyPyHpImPy-γ-HpPyPyHpHpPy |
| 1851) | 5'-W G A A T G G W-3' | ImPyPyHpImIm-γ-PyPyPyHpHpPy |
| 1852) | 5'-W G A A T G C W-3' | ImPyPyHpImPy-γ-ImPyPyHpHpPy |
| 1853) | 5'-W G A A T C T W-3' | ImPyPyHpPyHp-γ-PyImPyHpHpPy |
| 1854) | 5'-W G A A T C A W-3' | ImPyPyHpPyPy-γ-HpImPyHpHpPy |
| 1855) | 5'-W G A A T C G W-3' | ImPyPyHpPyIm-γ-PyImPyHpHpPy |
| 1856) | 5'-W G A A T C C W-3' | ImPyPyHpPyPy-γ-ImImPyHpHpPy |
| 1857) | 5'-W G A A A T T W-3' | ImPyPyPyHpHp-γ-PyPyHpHpHpPy |
| 1858) | 5'-W G A A A T A W-3' | ImPyPyPyHpPy-γ-HpPyHpHpHpPy |
| 1869) | 5'-W G A A A T G W-3' | ImPyPyPyHpIm-γ-PyPyHpHpHpPy |
| 1860) | 5'-W G A A A T C W-3' | ImPyPyPyHpPy-γ-ImPyHpHpHpPy |
| 1861) | 5'-W G A A A A T W-3' | ImPyPyPyPyHp-γ-PyHpHpHpHpPy |
| 1862) | 5'-W G A A A A A W-3' | ImPyPyPyPyPy-γ-HpHpHpHpHpPy |
| 1863) | 5'-W G A A A A G W-3' | ImPyPyPyPyIm-γ-PyHpHpHpHpPy |
| 1864) | 5'-W G A A A A C W-3' | ImPyPyPyPyPy-γ-ImHpHpHpHpPy |
| 1865) | 5'-W G A A A G T W-3' | ImPyPyPyImHp-γ-PyPyHpHpHpPy |
| 1866) | 5'-W G A A A G A W-3' | ImPyPyPyImPy-γ-HpPyHpHpHpPy |
| 1867) | 5'-W G A A A G G W-3' | ImPyPyPyImIm-γ-PyPyHpHpHpPy |
| 1868) | 5'-W G A A A G C W-3' | ImPyPyPyImPy-γ-ImPyHpHpHpPy |
| 1869) | 5'-W G A A A C T W-3' | ImPyPyPyPyHp-γ-PyImHpHpHpPy |
| 1870) | 5'-W G A A A C A W-3' | ImPyPyPyPyPy-γ-HpImHpHpHpPy |
| 1871) | 5'-W G A A A C G W-3' | ImPyPyPyPyIm-γ-PyImHpHpHpPy |
| 1872) | 5'-W G A A A C C W-3' | ImPyPyPyPyPy-γ-ImImHpHpHpPy |

TABLE 105

12-ring Hairpin Polyamides for recognition of 8-bp 5'-WGAASNNW-3'

| | DNA sequence | aromatic amino acid sequence |
|---|---|---|
| 1873) | 5'-W G A A G T T W-3' | ImPyPyImHpHp-γ-PyPyPyHpHpPy |
| 1874) | 5'-W G A A G T A W-3' | ImPyPyImHpPy-γ-HpPyPyHpHpPy |
| 1875) | 5'-W G A A G T G W-3' | ImPyPyImHpIm-γ-PyPyPyHpHpPy |
| 1876) | 5'-W G A A G T C W-3' | ImPyPyImHpPy-γ-ImPyPyHpHpPy |
| 1877) | 5'-W G A A G A T W-3' | ImPyPyImPyHp-γ-PyHpPyHpHpPy |
| 1878) | 5'-W G A A G A A W-3' | ImPyPyImPyPy-γ-HpHpPyHpHpPy |
| 1879) | 5'-W G A A G A G W-3' | ImPyPyImPyIm-γ-PyHpPyHpHpPy |
| 1880) | 5'-W G A A G A C W-3' | ImPyPyImPyPy-γ-ImHpPyHpHpPy |
| 1881) | 5'-W G A A G G T W-3' | ImPyPyImImHp-γ-PyPyPyHpHpPy |
| 1882) | 5'-W G A A G G A W-3' | ImPyPyImImPy-γ-HpPyPyHpHpPy |
| 1883) | 5'-W G A A G C T W-3' | ImPyPyImPyHp-γ-PyImPyHpHpPy |
| 1884) | 5'-W G A A G C A W-3' | ImPyPyImPyPy-γ-HpImPyHpHpPy |
| 1885) | 5'-W G A A G G G W-3' | ImPyPyImImIm-γ-PyPyPyHpHpPy |
| 1886) | 5'-W G A A G G C W-3' | ImPyPyImImPy-γ-ImPyPyHpHpPy |
| 1887) | 5'-W G A A G C G W-3' | ImPyPyImPyIm-γ-PyImPyHpHpPy |
| 1888) | 5'-W G A A G C C W-3' | ImPyPyImPyPy-γ-ImImPyHpHpPy |
| 1889) | 5'-W G A A C T T W-3' | ImPyPyPyHpHp-γ-PyPyImHpHpPy |
| 1890) | 5'-W G A A C T A W-3' | ImPyPyPyHpPy-γ-HpPyImHpHpPy |
| 1891) | 5'-W G A A C T G W-3' | ImPyPyPyHpIm-γ-PyPyImHpHpPy |
| 1892) | 5'-W G A A C T C W-3' | ImPyPyPyHpPy-γ-ImPyImHpHpPy |
| 1893) | 5'-W G A A C A T W-3' | ImPyPyPyPyHp-γ-PyHpImHpHpPy |
| 1894) | 5'-W G A A C A A W-3' | ImPyPyPyPyPy-γ-HpHpImHpHpPy |
| 1895) | 5'-W G A A C A G W-3' | ImPyPyPyPyIm-γ-PyHpImHpHpPy |
| 1896) | 5'-W G A A C A C W-3' | ImPyPyPyPyPy-γ-ImHpImHpHpPy |
| 1897) | 5'-W G A A C G T W-3' | ImPyPyPyImHp-γ-PyPyImHpHpPy |
| 1898) | 5'-W G A A C G A W-3' | ImPyPyPyImPy-γ-HpPyImHpHpPy |
| 1899) | 5'-W G A A C C T W-3' | ImPyPyPyPyHp-γ-PyImImHpHpPy |
| 1900) | 5'-W G A A C C A W-3' | ImPyPyPyPyPy-γ-HpImImHpHpPy |
| 1901) | 5'-W G A A C G G W-3' | ImPyPyPyImIm-γ-PyPyImHpHpPy |

TABLE 105-continued 12-ring Hairpin Polyamides for recognition of
8-bp 5'-WGAASNNW-3'

| | DNA sequence | aromatic amino acid sequence |
|---|---|---|
| 1902) | 5'-W G A A C G C W-3' | ImPyPyPyImPy-γ-ImPyImHpHpPy |
| 1903) | 5'-W G A A C C G W-3' | ImPyPyPyIm-γ-PyImImHpHpPy |
| 1904) | 5'-W G A A C C C W-3' | ImPyPyPyPy-γ-ImImImHpHpPy |

TABLE 106

12-ring Hairpin Polyamides for recognition of
8-bp 5'-WGACWNNW-3'

| | DNA sequence | aromatic amino acid sequence |
|---|---|---|
| 1905) | 5'-W G A C T T T W-3' | ImPyPyHpHpHp-γ-PyPyPyImHpPy |
| 1906) | 5'-W G A C T T A W-3' | ImPyPyHpHpPy-γ-HpPyPyImHpPy |
| 1907) | 5'-W G A C T T G W-3' | ImPyPyHpHpIm-γ-PyPyPyImHpPy |
| 1908) | 5'-W G A C T T C W-3' | ImPyPyHpHpPy-γ-ImPyPyImHpPy |
| 1909) | 5'-W G A C T A T W-3' | ImPyPyHpPyHp-γ-PyHpPyImHpPy |
| 1910) | 5'-W G A C T A A W-3' | ImPyPyHpPyPy-γ-HpHpPyImHpPy |
| 1911) | 5'-W G A C T A G W-3' | ImPyPyHpPyIm-γ-PyHpPyImHpPy |
| 1912) | 5'-W G A C T A C W-3' | ImPyPyHpPyPy-γ-ImHpPyImHpPy |
| 1913) | 5'-W G A C T G T W-3' | ImPyPyHpImHp-γ-PyPyPyImHpPy |
| 1914) | 5'-W G A C T G A W-3' | ImPyPyHpImPy-γ-HpPyPyImHpPy |
| 1915) | 5'-W G A C T G G W-3' | ImPyPyHpImIm-γ-PyPyPyImHpPy |
| 1916) | 5'-W G A C T G C W-3' | ImPyPyHpImPy-γ-ImPyPyImHpPy |
| 1917) | 5'-W G A C T C T W-3' | ImPyPyHpPyHp-γ-PyImPyImHpPy |
| 1918) | 5'-W G A C T C A W-3' | ImPyPyHpPyPy-γ-HpImPyImHpPy |
| 1919) | 5'-W G A C T C G W-3' | ImPyPyHpPyIm-γ-PyImPyImHpPy |
| 1920) | 5'-W G A C T C C W-3' | ImPyPyHpPyPy-γ-ImImPyImHpPy |
| 1921) | 5'-W G A C A T T W-3' | ImPyPyPyHpHp-γ-PyPyHpImHpPy |
| 1922) | 5'-W G A C A T A W-3' | ImPyPyPyHpPy-γ-HpPyHpImHpPy |
| 1923) | 5'-W G A C A T G W-3' | ImPyPyPyHpIm-γ-PyPyHpImHpPy |
| 1924) | 5'-W G A C A T C W-3' | ImPyPyPyHpPy-γ-ImPyHpImHpPy |
| 1925) | 5'-W G A C A A T W-3' | ImPyPyPyPyHp-γ-PyHpHpImHpPy |
| 1926) | 5'-W G A C A A A W-3' | ImPyPyPyPyPy-γ-HpHpHpImHpPy |
| 1927) | 5'-W G A C A A G W-3' | ImPyPyPyPyIm-γ-PyHpHpImHpPy |
| 1928) | 5'-W G A C A A C W-3' | ImPyPyPyPyPy-γ-ImHpHpImHpPy |
| 1929) | 5'-W G A C A G T W-3' | ImPyPyPyImHp-γ-PyPyHpImHpPy |
| 1930) | 5'-W G A C A G A W-3' | ImPyPyPyImPy-γ-HpPyHpImHpPy |
| 1931) | 5'-W G A C A G G W-3' | ImPyPyPyImIm-γ-PyPyHpImHpPy |
| 1932) | 5'-W G A C A G C W-3' | ImPyPyPyImPy-γ-ImPyHpImHpPy |
| 1933) | 5'-W G A C A C T W-3' | ImPyPyPyPyHp-γ-PyImHpImHpPy |
| 1934) | 5'-W G A C A C A W-3' | ImPyPyPyPyPy-γ-HpImHpImHpPy |
| 1935) | 5'-W G A C A C G W-3' | ImPyPyPyPyIm-γ-PyImHpImHpPy |
| 1936) | 5'-W G A C A C C W-3' | ImPyPyPyPyPy-γ-ImImHpImHpPy |

TABLE 107

12-ring Hairpin Polyamides for recognition of
8-bp 5'-WGACSNNW-3'

| | DNA sequence | aromatic amino acid sequence |
|---|---|---|
| 1937) | 5'-W G A C G T T W-3' | ImPyPyImHpHp-γ-PyPyPyImHpPy |
| 1938) | 5'-W G A C G T A W-3' | ImPyPyImHpPy-γ-HpPyPyImHpPy |
| 1939) | 5'-W G A C G T G W-3' | ImPyPyImHpIm-γ-PyPyPyImHpPy |
| 1940) | 5'-W G A C G T C W-3' | ImPyPyImHpPy-γ-ImPyPyImHpPy |
| 1941) | 5'-W G A C G A T W-3' | ImPyPyImPyHp-γ-PyHpPyImHpPy |
| 1942) | 5'-W G A C G A A W-3' | ImPyPyImPyPy-γ-HpHpPyImHpPy |
| 1943) | 5'-W G A C G A G W-3' | ImPyPyImPyIm-γ-PyHpPyImHpPy |
| 1944) | 5'-W G A C G A C W-3' | ImPyPyImPyPy-γ-ImHpPyImHpPy |
| 1945) | 5'-W G A C G G T W-3' | ImPyPyImImHp-γ-PyPyPyImHpPy |
| 1946) | 5'-W G A C G G A W-3' | ImPyPyImImPy-γ-HpPyPyImHpPy |
| 1947) | 5'-W G A C G C T W-3' | ImPyPyImPyHp-γ-PyImPyImHpPy |
| 1948) | 5'-W G A C G C A W-3' | ImPyPyImPyPy-γ-HpImPyImHpPy |
| 1949) | 5'-W G A C C T T W-3' | ImPyPyPyHpHp-γ-PyPyImImHpPy |
| 1950) | 5'-W G A C C T A W-3' | ImPyPyPyHpPy-γ-HpPyImImHpPy |
| 1951) | 5'-W G A C C T G W-3' | ImPyPyPyHpIm-γ-PyPyImImHpPy |
| 1952) | 5'-W G A C C T C W-3' | ImPyPyPyHpPy-γ-ImPyImImHpPy |
| 1953) | 5'-W G A C C A T W-3' | ImPyPyPyPyHp-γ-PyHpImImHpPy |
| 1954) | 5'-W G A C C A A W-3' | ImPyPyPyPyPy-γ-HpHpImImHpPy |

TABLE 107-continued 12-ring Hairpin Polyamides for recognition of
8-bp 5'-WGACSNNW-3'

| | DNA sequence | aromatic amino acid sequence |
|---|---|---|
| 1955) | 5'-W G A C C A G W-3' | ImPyPyPyPyIm-γ-PyHpImImHpPy |
| 1956) | 5'-W G A C C A C W-3' | ImPyPyPyPyPy-γ-ImHpImImHpPy |
| 1957) | 5'-W G A C C G T W-3' | ImPyPyPyImHp-γ-PyPyImImHpPy |
| 1958) | 5'-W G A C C G A W-3' | ImPyPyPyImPy-γ-HpPyImImHpPy |
| 1959) | 5'-W G A C C G T W-3' | ImPyPyPyPyHp-γ-PyImImImHpPy |
| 1960) | 5'-W G A C C C A W-3' | ImPyPyPyPyPy-γ-HpImImImHpPy |
| 1961) | 5'-W G A C G G G W-3' | ImPyPyImImIm-γ-PyPyPyImHpPy |
| 1962) | 5'-W G A C G G C W-3' | ImPyPyImImPy-γ-ImPyPyImHpPy |
| 1963) | 5'-W G A C G C G W-3' | ImPyPyImPyIm-γ-PyImPyImHpPy |
| 1964) | 5'-W G A C G C C W-3' | ImPyPyImPyPy-γ-ImImPyImHpPy |
| 1965) | 5'-W G A C C G G W-3' | ImPyPyPyImIm-γ-PyPyImImHpPy |
| 1966) | 5'-W G A C C G C W-3' | ImPyPyPyImPy-γ-ImPyImImHpPy |
| 1967) | 5'-W G A C C C G W-3' | ImPyPyPyPyIm-γ-PyImImImHpPy |
| 1968) | 5'-W G A C C C C W-3' | ImPyPyPyPyPy-γ-ImImImImHpPy |

TABLE 108

12-ring Hairpin Polyamides for recognition of
8-bp 5'-WGTGWNNW-3'

| | DNA sequence | aromatic amino acid sequence |
|---|---|---|
| 1969) | 5'-W G T G T T T W-3' | ImHpImHpHpHp-γ-PyPyPyPyPyPy |
| 1970) | 5'-W G T G T T A W-3' | ImHpImHpHpPy-γ-HpPyPyPyPyPy |
| 1971) | 5'-W G T G T T G W-3' | ImHpImHpHpIm-γ-PyPyPyPyPyPy |
| 1972) | 5'-W G T G T T C W-3' | ImHpImHpHpPy-γ-ImPyPyPyPyPy |
| 1973) | 5'-W G T G T A T W-3' | ImHpImHpPyHp-γ-PyHpPyPyPyPy |
| 1974) | 5'-W G T G T A A W-3' | ImHpImHpPyPy-γ-HpHpPyPyPyPy |
| 1975) | 5'-W G T G T A G W-3' | ImHpImHpPyIm-γ-PyHpPyPyPyPy |
| 1976) | 5'-W G T G T A C W-3' | ImHpImHpPyPy-γ-ImHpPyPyPyPy |
| 1977) | 5'-W G T G T G T W-3' | ImHpImHpImHp-γ-PyPyPyPyPyPy |
| 1978) | 5'-W G T G T G A W-3' | ImHpImHpImPy-γ-HpPyPyPyPyPy |
| 1979) | 5'-W G T G T G G W-3' | ImHpImHpImIm-γ-PyPyPyPyPyPy |
| 1980) | 5'-W G T G T G C W-3' | ImHpImHpImPy-γ-ImPyPyPyPyPy |
| 1981) | 5'-W G T G T C T W-3' | ImHpImHpPyHp-γ-PyImPyPyPyPy |
| 1982) | 5'-W G T G T C A W-3' | ImHpImHpPyPy-γ-HpImPyPyPyPy |
| 1983) | 5'-W G T G T C G W-3' | ImHpImHpPyIm-γ-PyImPyPyPyPy |
| 1984) | 5'-W G T G T C C W-3' | ImHpImHpPyPy-γ-ImImPyPyPyPy |
| 1985) | 5'-W G T G A T T W-3' | ImHpImPyHpHp-γ-PyPyHpPyPyPy |
| 1986) | 5'-W G T G A T A W-3' | ImHpImPyHpPy-γ-HpPyHpPyPyPy |
| 1987) | 5'-W G T G A T G W-3' | ImHpImPyHpIm-γ-PyPyHpPyPyPy |
| 1988) | 5'-W G T G A T C W-3' | ImHpImPyHpPy-γ-ImPyHpPyPyPy |
| 1989) | 5'-W G T G A A T W-3' | ImHpImPyPyHp-γ-PyHpHpPyPyPy |
| 1990) | 5'-W G T G A A A W-3' | ImHpImPyPyPy-γ-HpHpHpPyPyPy |
| 1991) | 5'-W G T G A A G W-3' | ImHpImPyPyIm-γ-PyHpHpPyPyPy |
| 1992) | 5'-W G T G A A C W-3' | ImHpImPyPyPy-γ-ImHpHpPyPyPy |
| 1993) | 5'-W G T G A G T W-3' | ImHpImPyImHp-γ-PyPyHpPyPyPy |
| 1994) | 5'-W G T G A G A W-3' | ImHpImPyImPy-γ-HpPyHpPyPyPy |
| 1995) | 5'-W G T G A G G W-3' | ImHpImPyImIm-γ-PyPyHpPyPyPy |
| 1996) | 5'-W G T G A G C W-3' | ImHpImPyImPy-γ-ImPyHpPyPyPy |
| 1997) | 5'-W G T G A C T W-3' | ImHpImPyPyHp-γ-PyImHpPyPyPy |
| 1998) | 5'-W G T G A C A W-3' | ImHpImPyPyPy-γ-HpImHpPyPyPy |
| 1999) | 5'-W G T G A C G W-3' | ImHpImPyPyIm-γ-PyImHpPyPyPy |
| 2000) | 5'-W G T G A C C W-3' | ImHpImPyPyPy-γ-ImImHpPyPyPy |

TABLE 109

12-ring Hairpin Polyamides for recognition of
8-bp 5'-WGTGSNNW-3'

| | DNA sequence | aromatic amino acid sequence |
|---|---|---|
| 2001) | 5'-W G T G G T T W-3' | ImHpImImHpHp-γ-PyPyPyPyPyPy |
| 2002) | 5'-W G T G G T A W-3' | ImHpImImHpPy-γ-HpPyPyPyPyPy |
| 2003) | 5'-W G T G G T G W-3' | ImHpImImHpIm-γ-PyPyPyPyPyPy |
| 2004) | 5'-W G T G G T C W-3' | ImHpImImHpPy-γ-ImPyPyPyPyPy |
| 2005) | 5'-W G T G G A T W-3' | ImHpImImPyHp-γ-PyHpPyPyPyPy |
| 2006) | 5'-W G T G G A A W-3' | ImHpImImPyPy-γ-HpHpPyPyPyPy |
| 2007) | 5'-W G T G G A G W-3' | ImHpImImPyIm-γ-PyHpPyPyPyPy |

TABLE 109-continued 12-ring Hairpin Polyamides for recognition of
8-bp 5'-WGTGSNNW-3'

| | DNA sequence | aromatic amino acid sequence |
|---|---|---|
| 2008) | 5'-W G T G G A C W-3' | ImHpImImPyPy-γ-ImHpPyPyPyPy |
| 2009) | 5'-W G T G G G T W-3' | ImHpImImImHp-γ-PyPyPyPyPyPy |
| 2010) | 5'-W G T G G G A W-3' | ImHpImImImPy-γ-HpPyPyPyPyPy |
| 2011) | 5'-W G T G G G C W-3' | ImHpImImPyHp-γ-PyImPyPyPyPy |
| 2012) | 5'-W G T G G C A W-3' | ImHpImImPyPy-γ-HpImPyPyPyPy |
| 2013) | 5'-W G T G C T T W-3' | ImHpImPyHpHp-γ-PyPyImPyPyPy |
| 2014) | 5'-W G T G C T A W-3' | ImHpImPyHpPy-γ-HpPyImPyPyPy |
| 2015) | 5'-W G T G C T G W-3' | ImHpImPyHpIm-γ-PyPyImPyPyPy |
| 2016) | 5'-W G T G C T C W-3' | ImHpImPyHpPy-γ-ImPyImPyPyPy |
| 2017) | 5'-W G T G C A T W-3' | ImHpImPyPyHp-γ-PyHpImPyPyPy |
| 2018) | 5'-W G T G C A A W-3' | ImHpImPyPyPy-γ-HpHpImPyPyPy |
| 2019) | 5'-W G T G C A G W-3' | ImHpImPyPyIm-γ-PyHpImPyPyPy |
| 2020) | 5'-W G T G C A C W-3' | ImHpImPyPyPy-γ-ImHpImPyPyPy |
| 2021) | 5'-W G T G C G T W-3' | ImHpImPyImHp-γ-PyPyImPyPyPy |
| 2022) | 5'-W G T G C G A W-3' | ImHpImPyImPy-γ-HpPyImPyPyPy |
| 2023) | 5'-W G T G C C T W-3' | ImHpImPyPyHp-γ-PyImImPyPyPy |
| 2024) | 5'-W G T G C C A W-3' | ImHpImPyPyPy-γ-HpImImPyPyPy |
| 2025) | 5'-W G T G G G G W-3' | ImHpImImImIm-γ-PyPyPyPyPyPy |
| 2026) | 5'-W G T G G G C W-3' | ImHpImImImPy-γ-ImPyPyPyPyPy |
| 2027) | 5'-W G T G G C G W-3' | ImHpImImPyIm-γ-PyImPyPyPyPy |
| 2028) | 5'-W G T G G C C W-3' | ImHpImImPyPy-γ-ImImPyPyPyPy |
| 2029) | 5'-W G T G C G G W-3' | ImHpImPyImIm-γ-PyPyImPyPyPy |
| 2030) | 5'-W G T G C G C W-3' | ImHpImPyImPy-γ-ImPyImPyPyPy |
| 2031) | 5'-W G T G C C G W-3' | ImHpImPyPyIm-γ-PyImImPyPyPy |
| 2032) | 5'-W G T G C C C W-3' | ImHpImPyPyPy-γ-ImImImPyPyPy |

TABLE 110

12-ring Hairpin Polyamides for recognition of
8-bp 5'-WGTTWNNW-3'

| | DNA sequence | aromatic amino acid sequence |
|---|---|---|
| 2033) | 5'-W G T T T T T W-3' | ImHpHpHpHpHp-γ-PyPyPyPyPyPy |
| 2034) | 5'-W G T T T T A W-3' | ImHpHpHpHpPy-γ-HpPyPyPyPyPy |
| 2035) | 5'-W G T T T T G W-3' | ImHpHpHpHpIm-γ-PyPyPyPyPyPy |
| 2036) | 5'-W G T T T T C W-3' | ImHpHpHpHpPy-γ-ImPyPyPyPyPy |
| 2037) | 5'-W G T T T A T W-3' | ImHpHpHpPyHp-γ-PyHpPyPyPyPy |
| 2038) | 5'-W G T T T A A W-3' | ImHpHpHpPyPy-γ-HpHpPyPyPyPy |
| 2039) | 5'-W G T T T A G W-3' | ImHpHpHpPyIm-γ-PyHpPyPyPyPy |
| 2040) | 5'-W G T T T A C W-3' | ImHpHpHpPyPy-γ-ImHpPyPyPyPy |
| 2041) | 5'-W G T T T G T W-3' | ImHpHpHpImHp-γ-PyPyPyPyPyPy |
| 2042) | 5'-W G T T T G A W-3' | ImHpHpHpImPy-γ-HpPyPyPyPyPy |
| 2043) | 5'-W G T T T G G W-3' | ImHpHpHpImIm-γ-PyPyPyPyPyPy |
| 2044) | 5'-W G T T T G C W-3' | ImHpHpHpImPy-γ-ImPyPyPyPyPy |
| 2045) | 5'-W G T T T C T W-3' | ImHpHpHpPyHp-γ-PyImPyPyPyPy |
| 2046) | 5'-W G T T T C A W-3' | ImHpHpHpPyPy-γ-HpImPyPyPyPy |
| 2047) | 5'-W G T T T C G W-3' | ImHpHpHpPyIm-γ-PyImPyPyPyPy |
| 2048) | 5'-W G T T T C C W-3' | ImHpHpHpPyPy-γ-ImImPyPyPyPy |
| 2049) | 5'-W G T T A T T W-3' | ImHpHpPyHpHp-γ-PyPyHpPyPyPy |
| 2050) | 5'-W G T T A T A W-3' | ImHpHpPyHpPy-γ-HpPyHpPyPyPy |
| 2051) | 5'-W G T T A T G W-3' | ImHpHpPyHpIm-γ-PyPyHpPyPyPy |
| 2052) | 5'-W G T T A T C W-3' | ImHpHpPyHpPy-γ-ImPyHpPyPyPy |
| 2053) | 5'-W G T T A A T W-3' | ImHpHpPyPyHp-γ-PyHpHpPyPyPy |
| 2054) | 5'-W G T T A A A W-3' | ImHpHpPyPyPy-γ-HpHpHpPyPyPy |
| 2055) | 5'-W G T T A A G W-3' | ImHpHpPyPyIm-γ-PyHpHpPyPyPy |
| 2056) | 5'-W G T T A A C W-3' | ImHpHpPyPyPy-γ-ImHpHpPyPyPy |
| 2057) | 5'-W G T T A G T W-3' | ImHpHpPyImHp-γ-PyPyHpPyPyPy |
| 2058) | 5'-W G T T A G A W-3' | ImHpHpPyImPy-γ-HpPyHpPyPyPy |
| 2059) | 5'-W G T T A G G W-3' | ImHpHpPyImIm-γ-PyPyHpPyPyPy |
| 2060) | 5'-W G T T A G C W-3' | ImHpHpPyImPy-γ-ImPyHpPyPyPy |
| 2061) | 5'-W G T T A C T W-3' | ImHpHpPyPyHp-γ-PyImHpPyPyPy |
| 2062) | 5'-W G T T A C A W-3' | ImHpHpPyPyPy-γ-HpImHpPyPyPy |
| 2063) | 5'-W G T T A C G W-3' | ImHpHpPyPyIm-γ-PyImHpPyPyPy |
| 2064) | 5'-W G T T A C C W-3' | ImHpHpPyPyPy-γ-ImImHpPyPyPy |

TABLE 111

12-ring Hairpin Polyamides for recognition of
8-bp 5'-WGTTSNNW-3'

| | DNA sequence | aromatic amino acid sequence |
|---|---|---|
| 2065) | 5'-W G T T G T T W-3' | ImHpHpImHpHp-γ-PyPyPyPyPyPy |
| 2066) | 5'-W G T T G T A W-3' | ImHpHpImHpPy-γ-HpPyPyPyPyPy |
| 2067) | 5'-W G T T G T G W-3' | ImHpHpImHpIm-γ-PyPyPyPyPyPy |
| 2068) | 5'-W G T T G T C W-3' | ImHpHpImHpPy-γ-ImPyPyPyPyPy |
| 2069) | 5'-W G T T G A T W-3' | ImHpHpImPyHp-γ-PyHpPyPyPyPy |
| 2070) | 5'-W G T T G A A W-3' | ImHpHpImPyPy-γ-HpHpPyPyPyPy |
| 2071) | 5'-W G T T G A G W-3' | ImHpHpImPyIm-γ-PyHpPyPyPyPy |
| 2072) | 5'-W G T T G A C W-3' | ImHpHpImPyPy-γ-ImHpPyPyPyPy |
| 2073) | 5'-W G T T G G T W-3' | ImHpHpImImHp-γ-PyPyPyPyPyPy |
| 2074) | 5'-W G T T G G A W-3' | ImHpHpImImPy-γ-HpPyPyPyPyPy |
| 2075) | 5'-W G T T G C T W-3' | ImHpHpImPyHp-γ-PyImPyPyPyPy |
| 2076) | 5'-W G T T G C A W-3' | ImHpHpImPyPy-γ-HpImPyPyPyPy |
| 2077) | 5'-W G T T G G G W-3' | ImHpHpImImIm-γ-PyPyPyPyPyPy |
| 2078) | 5'-W G T T G G C W-3' | ImHpHpImImPy-γ-ImPyPyPyPyPy |
| 2079) | 5'-W G T T G C G W-3' | ImHpHpImPyIm-γ-PyImPyPyPyPy |
| 2080) | 5'-W G T T G C C W-3' | ImHpHpImPyPy-γ-ImImPyPyPyPy |
| 2081) | 5'-W G T T C T T W-3' | ImHpHpPyHpHp-γ-PyPyImPyPyPy |
| 2082) | 5'-W G T T C T A W-3' | ImHpHpPyHpPy-γ-HpPyImPyPyPy |
| 2083) | 5'-W G T T C T G W-3' | ImHpHpPyHpIm-γ-PyPyImPyPyPy |
| 2084) | 5'-W G T T C T C W-3' | ImHpHpPyHpPy-γ-ImPyImPyPyPy |
| 2085) | 5'-W G T T C A T W-3' | ImHpHpPyPyHp-γ-PyHpImPyPyPy |
| 2086) | 5'-W G T T C A A W-3' | ImHpHpPyPyPy-γ-HpHpImPyPyPy |
| 2087) | 5'-W G T T C A G W-3' | ImHpHpPyPyIm-γ-PyHpImPyPyPy |
| 2088) | 5'-W G T T C A C W-3' | ImHpHpPyPyPy-γ-ImHpImPyPyPy |
| 2089) | 5'-W G T T C G T W-3' | ImHpHpPyImHp-γ-PyPyImPyPyPy |
| 2090) | 5'-W G T T C G A W-3' | ImHpHpPyImPy-γ-HpPyImPyPyPy |
| 2091) | 5'-W G T T C C T W-3' | ImHpHpPyPyHp-γ-PyImImPyPyPy |
| 2092) | 5'-W G T T C C A W-3' | ImHpHpPyPyPy-γ-HpImImPyPyPy |
| 2093) | 5'-W G T T C G G W-3' | ImHpHpPyImIm-γ-PyPyImPyPyPy |
| 2094) | 5'-W G T T C G C W-3' | ImHpHpPyImPy-γ-ImPyImPyPyPy |
| 2095) | 5'-W G T T C C G W-3' | ImHpHpPyPyIm-γ-PyImImPyPyPy |
| 2096) | 5'-W G T T C C C W-3' | ImHpHpPyPyPy-γ-ImImImPyPyPy |

TABLE 112

12-ring Hairpin Polyamides for recognition of
8-bp 5'-WGTAWNNW-3'

| | DNA sequence | aromatic amino acid sequence |
|---|---|---|
| 2097) | 5'-W G T A T T T W-3' | ImHpPyHpHpHp-γ-PyPyPyHpPyPy |
| 2098) | 5'-W G T A T T A W-3' | ImHpPyHpHpPy-γ-HpPyPyHpPyPy |
| 2099) | 5'-W G T A T T G W-3' | ImHpPyHpHpIm-γ-PyPyPyHpPyPy |
| 2100) | 5'-W G T A T T C W-3' | ImHpPyHpHpPy-γ-ImPyPyHpPyPy |
| 2101) | 5'-W G T A T A T W-3' | ImHpPyHpPyHp-γ-PyHpPyHpPyPy |
| 2102) | 5'-W G T A T A A W-3' | ImHpPyHpPyPy-γ-HpHpPyHpPyPy |
| 2103) | 5'-W G T A T A G W-3' | ImHpPyHpPyIm-γ-PyHpPyHpPyPy |
| 2104) | 5'-W G T A T A C W-3' | ImHpPyHpPyPy-γ-ImHpPyHpPyPy |
| 2105) | 5'-W G T A T G T W-3' | ImHpPyHpImHp-γ-PyPyPyHpPyPy |
| 2106) | 5'-W G T A T G A W-3' | ImHpPyHpImPy-γ-HpPyPyHpPyPy |
| 2107) | 5'-W G T A T G G W-3' | ImHpPyHpImIm-γ-PyPyPyHpPyPy |
| 2108) | 5'-W G T A T G C W-3' | ImHpPyHpImPy-γ-ImPyPyHpPyPy |
| 2109) | 5'-W G T A T C T W-3' | ImHpPyHpPyHp-γ-PyImPyHpPyPy |
| 2110) | 5'-W G T A T C A W-3' | ImHpPyHpPyPy-γ-HpImPyHpPyPy |
| 2111) | 5'-W G T A T C G W-3' | ImHpPyHpPyIm-γ-PyImPyHpPyPy |
| 2112) | 5'-W G T A T C C W-3' | ImHpPyHpPyPy-γ-ImImPyHpPyPy |
| 2113) | 5'-W G T A A T T W-3' | ImHpPyPyHpHp-γ-PyPyHpHpPyPy |
| 2114) | 5'-W G T A A T A W-3' | ImHpPyPyHpPy-γ-HpPyHpHpPyPy |
| 2115) | 5'-W G T A A T G W-3' | ImHpPyPyHpIm-γ-PyPyHpHpPyPy |
| 2116) | 5'-W G T A A T C W-3' | ImHpPyPyHpPy-γ-ImPyHpHpPyPy |
| 2117) | 5'-W G T A A A T W-3' | ImHpPyPyPyHp-γ-PyHpHpHpPyPy |
| 2118) | 5'-W G T A A A A W-3' | ImHpPyPyPyPy-γ-HpHpHpHpPyPy |
| 2119) | 5'-W G T A A A G W-3' | ImHpPyPyPyIm-γ-PyHpHpHpPyPy |
| 2120) | 5'-W G T A A A C W-3' | ImHpPyPyPyPy-γ-ImHpHpHpPyPy |
| 2121) | 5'-W G T A A G T W-3' | ImHpPyPyImHp-γ-PyPyHpHpPyPy |
| 2122) | 5'-W G T A A G A W-3' | ImHpPyPyImPy-γ-HpPyHpHpPyPy |
| 2123) | 5'-W G T A A G G W-3' | ImHpPyPyImIm-γ-PyPyHpHpPyPy |
| 2124) | 5'-W G T A A G C W-3' | ImHpPyPyImPy-γ-ImPyHpHpPyPy |
| 2125) | 5'-W G T A A C T W-3' | ImHpPyPyPyHp-γ-PyImHpHpPyPy |

TABLE 112-continued

12-ring Hairpin Polyamides for recognition of 8-bp 5'-WGTAWNNW-3'

| | DNA sequence | aromatic amino acid sequence |
|---|---|---|
| 2126) | 5'-W G T A A C A W-3' | ImHpPyPyPyPy-γ-HpImHpHpPyPy |
| 2127) | 5'-W G T A A C G W-3' | ImHpPyPyPyIm-γ-PyImHpHpPyPy |
| 2128) | 5'-W G T A A C C W-3' | ImHpPyPyPyPy-γ-ImImHpHpPyPy |

TABLE 113

12-ring Hairpin Polyamides for recognition of 8-bp 5'-WGTASNNW-3'

| | DNA sequence | aromatic amino acid sequence |
|---|---|---|
| 2129) | 5'-W G T A G T T W-3' | ImHpPyImHpHp-γ-PyPyPyHpPyPy |
| 2130) | 5'-W G T A G T A W-3' | ImHpPyImHpPy-γ-HpPyPyHpPyPy |
| 2131) | 5'-W G T A G T G W-3' | ImHpPyImHpIm-γ-PyPyPyHpPyPy |
| 2132) | 5'-W G T A G T C W-3' | ImHpPyImHpPy-γ-ImPyPyHpPyPy |
| 2133) | 5'-W G T A G A T W-3' | ImHpPyImPyHp-γ-PyHpPyHpPyPy |
| 2134) | 5'-W G T A G A A W-3' | ImHpPyImPyPy-γ-HpHpPyHpPyPy |
| 2135) | 5'-W G T A G A G W-3' | ImHpPyImPyIm-γ-PyHpPyHpPyPy |
| 2136) | 5'-W G T A G A C W-3' | ImHpPyImPyPy-γ-ImHpPyHpPyPy |
| 2137) | 5'-W G T A G G T W-3' | ImHpPyImImHp-γ-PyPyPyHpPyPy |
| 2138) | 5'-W G T A G G A W-3' | ImHpPyImImPy-γ-HpPyPyHpPyPy |
| 2139) | 5'-W G T A G C T W-3' | ImHpPyImPyHp-γ-PyImHpHpPyPy |
| 2140) | 5'-W G T A G C A W-3' | ImHpPyImPyPy-γ-HpImPyHpPyPy |
| 2141) | 5'-W G T A G G G W-3' | ImHpPyImImIm-γ-PyPyPyHpPyPy |
| 2142) | 5'-W G T A G G C W-3' | ImHpPyImImPy-γ-ImPyPyHpPyPy |
| 2143) | 5'-W G T A G C G W-3' | ImHpPyImPyIm-γ-PyImPyHpPyPy |
| 2144) | 5'-W G T A G C C W-3' | ImHpPyImPyPy-γ-ImImPyHpPyPy |
| 2145) | 5'-W G T A C T T W-3' | ImHpPyPyHpHp-γ-PyPyImHpPyPy |
| 2146) | 5'-W G T A C T A W-3' | ImHpPyPyHpPy-γ-HpPyImHpPyPy |
| 2147) | 5'-W G T A C T G W-3' | ImHpPyPyHpIm-γ-PyPyImHpPyPy |
| 2148) | 5'-W G T A C T C W-3' | ImHpPyPyHpPy-γ-ImPyImHpPyPy |
| 2149) | 5'-W G T A C A T W-3' | ImHpPyPyPyHp-γ-PyHpImHpPyPy |
| 2150) | 5'-W G T A C A A W-3' | ImHpPyPyPyPy-γ-HpHpImHpPyPy |
| 2151) | 5'-W G T A C A G W-3' | ImHpPyPyPyIm-γ-PyHpImHpPyPy |
| 2152) | 5'-W G T A C A C W-3' | ImHpPyPyPyPy-γ-ImHpImHpPyPy |
| 2153) | 5'-W G T A C G T W-3' | ImHpPyPyImHp-γ-PyPyImHpPyPy |
| 2154) | 5'-W G T A C G A W-3' | ImHpPyPyImPy-γ-HpPyImHpPyPy |
| 2155) | 5'-W G T A C C T W-3' | ImHpPyPyPyHp-γ-PyImImHpPyPy |
| 2156) | 5'-W G T A C C A W-3' | ImHpPyPyPyPy-γ-HpImImHpPyPy |
| 2157) | 5'-W G T A C G G W-3' | ImHpPyPyImIm-γ-PyPyImHpPyPy |
| 2158) | 5'-W G T A C G C W-3' | ImHpPyPyImPy-γ-ImPyImHpPyPy |
| 2159) | 5'-W G T A C C G W-3' | ImHpPyPyPyIm-γ-PyImImHpPyPy |
| 2160) | 5'-W G T A C C C W-3' | ImHpPyPyPyPy-γ-ImImImHpPyPy |

TABLE 114

12-ring Hairpin Polyamides for recognition of 8-bp 5'-WGTCWNNW-3'

| | DNA sequence | aromatic amino acid sequence |
|---|---|---|
| 2161) | 5'-W G T C T T T W-3' | ImHpPyHpHpHp-γ-PyPyPyImPyPy |
| 2162) | 5'-W G T C T T A W-3' | ImHpPyHpHpPy-γ-HpPyPyImPyPy |
| 2163) | 5'-W G T C T T G W-3' | ImHpPyHpHpIm-γ-PyPyPyImPyPy |
| 2164) | 5'-W G T C T T C W-3' | ImHpPyHpHpPy-γ-ImPyPyImPyPy |
| 2165) | 5'-W G T C T A T W-3' | ImHpPyHpPyHp-γ-PyHpPyImPyPy |
| 2166) | 5'-W G T C T A A W-3' | ImHpPyHpPyPy-γ-HpHpPyImPyPy |
| 2167) | 5'-W G T C T A G W-3' | ImHpPyHpPyIm-γ-PyHpPyImPyPy |
| 2168) | 5'-W G T C T A C W-3' | ImHpPyHpPyPy-γ-ImHpPyImPyPy |
| 2169) | 5'-W G T C T G T W-3' | ImHpPyHpImHp-γ-PyPyPyImPyPy |
| 2170) | 5'-W G T C T G A W-3' | ImHpPyHpImPy-γ-HpPyPyImPyPy |
| 2171) | 5'-W G T C T G G W-3' | ImHpPyHpImIm-γ-PyPyPyImPyPy |
| 2172) | 5'-W G T C T G C W-3' | ImHpPyHpImPy-γ-ImPyPyImPyPy |
| 2173) | 5'-W G T C T C T W-3' | ImHpPyHpPyHp-γ-PyImPyImPyPy |
| 2174) | 5'-W G T C T C A W-3' | ImHpPyHpPyPy-γ-HpImPyImPyPy |
| 2175) | 5'-W G T C T C G W-3' | ImHpPyHpPyIm-γ-PyImPyImPyPy |
| 2176) | 5'-W G T C T C C W-3' | ImHpPyHpPyPy-γ-ImImPyImPyPy |
| 2177) | 5'-W G T C A T T W-3' | ImHpPyPyHpHp-γ-PyPyHpImPyPy |
| 2178) | 5'-W G T C A T A W-3' | ImHpPyPyHpPy-γ-HpPyHpImPyPy |

TABLE 114-continued

12-ring Hairpin Polyamides for recognition of 8-bp 5'-WGTCWNNW-3'

| | DNA sequence | aromatic amino acid sequence |
|---|---|---|
| 2179) | 5'-W G T C A T G W-3' | ImHpPyPyHpIm-γ-PyPyHpImPyPy |
| 2180) | 5'-W G T C A T C W-3' | ImHpPyPyHpPy-γ-ImPyHpImPyPy |
| 2181) | 5'-W G T C A A T W-3' | ImHpPyPyPyHp-γ-PyHpHpImPyPy |
| 2182) | 5'-W G T C A A A W-3' | ImHpPyPyPyPy-γ-HpHpHpImPyPy |
| 2183) | 5'-W G T C A A G W-3' | ImHpPyPyPyIm-γ-PyHpHpImPyPy |
| 2184) | 5'-W G T C A A C W-3' | ImHpPyPyPyPy-γ-ImHpHpImPyPy |
| 2185) | 5'-W G T C A G T W-3' | ImHpPyPyImHp-γ-PyPyHpImPyPy |
| 2186) | 5'-W G T C A G A W-3' | ImHpPyPyImPy-γ-HpPyHpImPyPy |
| 2187) | 5'-W G T C A G G W-3' | ImHpPyPyImIm-γ-PyPyHpImPyPy |
| 2188) | 5'-W G T C A G C W-3' | ImHpPyPyImPy-γ-ImPyHpImPyPy |
| 2189) | 5'-W G T C A C T W-3' | ImHpPyPyPyHp-γ-PyImHpImPyPy |
| 2190) | 5'-W G T C A C A W-3' | ImHpPyPyPyPy-γ-HpImHpImPyPy |
| 2191) | 5'-W G T C A C G W-3' | ImHpPyPyPyIm-γ-PyImHpImPyPy |
| 2192) | 5'-W G T C A C C W-3' | ImHpPyPyPyPy-γ-ImImHpImPyPy |

TABLE 115

12-ring Hairpin Polyamides for recognition of 8-bp 5'-WGTCSNNW-3'

| | DNA sequence | aromatic amino acid sequence |
|---|---|---|
| 2193) | 5'-W G T C G T T W-3' | ImHpPyImHpHp-γ-PyPyPyImPyPy |
| 2194) | 5'-W G T C G T A W-3' | ImHpPyImHpPy-γ-HpPyPyImPyPy |
| 2195) | 5'-W G T C G T G W-3' | ImHpPyImHpIm-γ-PyPyPyImPyPy |
| 2196) | 5'-W G T C G T C W-3' | ImHpPyImHpPy-γ-ImPyPyImPyPy |
| 2197) | 5'-W G T C G A T W-3' | ImHpPyImPyHp-γ-PyHpPyImPyPy |
| 2198) | 5'-W G T C G A A W-3' | ImHpPyImPyPy-γ-HpHpPyImPyPy |
| 2199) | 5'-W G T C G A G W-3' | ImHpPyImPyIm-γ-PyHpPyImPyPy |
| 2200) | 5'-W G T C G A C W-3' | ImHpPyImPyPy-γ-ImHpPyImPyPy |
| 2201) | 5'-W G T C G G T W-3' | ImHpPyImImHp-γ-PyPyPyImPyPy |
| 2202) | 5'-W G T C G G A W-3' | ImHpPyImImPy-γ-HpPyPyImPyPy |
| 2203) | 5'-W G T C G C T W-3' | ImHpPyImPyHp-γ-PyImPyImPyPy |
| 2204) | 5'-W G T C G C A W-3' | ImHpPyImPyPy-γ-HpImPyImPyPy |
| 2205) | 5'-W G T C C T T W-3' | ImHpPyPyHpHp-γ-PyPyImImPyPy |
| 2206) | 5'-W G T C C T A W-3' | ImHpPyPyHpPy-γ-HpPyImImPyPy |
| 2207) | 5'-W G T C C T G W-3' | ImHpPyHpHpIm-γ-PyPyImImPyPy |
| 2208) | 5'-W G T C C T C W-3' | ImHpPyHpHpPy-γ-ImPyImImPyPy |
| 2209) | 5'-W G T C C A T W-3' | ImHpPyPyPyHp-γ-PyHpImImPyPy |
| 2210) | 5'-W G T C C A A W-3' | ImHpPyPyPyPy-γ-HpHpImImPyPy |
| 2211) | 5'-W G T C C A G W-3' | ImHpPyPyPyIm-γ-PyHpImImPyPy |
| 2212) | 5'-W G T C C A C W-3' | ImHpPyPyPyPy-γ-ImHpImImPyPy |
| 2213) | 5'-W G T C C G T W-3' | ImHpPyPyImHp-γ-PyPyImImPyPy |
| 2214) | 5'-W G T C C G A W-3' | ImHpPyPyImPy-γ-HpPyImImPyPy |
| 2215) | 5'-W G T C C C T W-3' | ImHpPyPyPyHp-γ-PyImImImPyPy |
| 2216) | 5'-W G T C C C A W-3' | ImHpPyPyPyPy-γ-HpImImImPyPy |
| 2217) | 5'-W G T C G G G W-3' | ImHpPyImImIm-γ-PyPyPyImPyPy |
| 2218) | 5'-W G T C G G C W-3' | ImHpPyImImPy-γ-ImPyPyImPyPy |
| 2219) | 5'-W G T C G C G W-3' | ImHpPyImPyIm-γ-PyImPyImPyPy |
| 2220) | 5'-W G T C G C C W-3' | ImHpPyImPyPy-γ-ImImPyImPyPy |
| 2221) | 5'-W G T C C G G W-3' | ImHpPyPyImIm-γ-PyPyImImPyPy |
| 2222) | 5'-W G T C C G C W-3' | ImHpPyPyImPy-γ-ImPyImImPyPy |
| 2223) | 5'-W G T C C C G W-3' | ImRpPyPyPyIm-γ-PyImImImPyPy |
| 2224) | 5'-W G T C C C C W-3' | ImHpPyPyPyPy-γ-ImImImImPyPy |

TABLE 116

12-ring Hairpin Polyamides for recognition of 8-bp 5'WCGGWNNW-3'

| | DNA sequence | aromatic amino acid sequence |
|---|---|---|
| 2225) | 5'W C G G T T T W-3' | PyImImHpHpHp-γ-PyPyPyPyPyIm |
| 2226) | 5'W C G G T T A W-3' | PyImImHpHpPy-γ-HpPyPyPyPyIm |
| 2227) | 5'W C G G T T G W-3' | PyImImHpHpIm-γ-PyPyPyPyPyIm |
| 2228) | 5'W C G G T T C W-3' | PyImImHpHpPy-γ-ImPyPyPyPyIm |
| 2229) | 5'W C G G T A T W-3' | PyImImHpPyHp-γ-PyHpPyPyPyIm |
| 2230) | 5'W C G G T A A W-3' | PyImImHpPyPy-γ-HpHpPyPyPyIm |
| 2231) | 5'W C G G T A G W-3' | PyImImHpPyIm-γ-PyHpPyPyPyIm |

TABLE 116-continued

12-ring Hairpin Polyamides for recognition of 8-bp 5'WCGGWNNW-3'

| | DNA sequence | aromatic amino acid sequence |
|---|---|---|
| 2232) | 5'W C G G T A C W-3' | PyImImHpPyPy-γ-ImHpPyPyPyIm |
| 2233) | 5'W C G G T G T W-3' | PyImImHpImHp-γ-PyPyPyPyPyIm |
| 2234) | 5'W C G G T G A W-3' | PyImImHpImPy-γ-HpPyPyPyPyIm |
| 2235) | 5'W C G G T G G W-3' | PyImImHpImIm-γ-PyPyPyPyPyIm |
| 2236) | 5'W C G G T G C W-3' | PyImImHpImPy-γ-ImPyPyPyPyIm |
| 2237) | 5'W C G G T C T W-3' | PyImImHpPyHp-γ-PyImPyPyPyIm |
| 2238) | 5'W C G G T C A W-3' | PyImImHpPyPy-γ-HpImPyPyPyIm |
| 2239) | 5'W C G G T C G W-3' | PyImImHpPyIm-γ-PyImPyPyPyIm |
| 2240) | 5'W C G G T C C W-3' | PyImImHpPyPy-γ-ImImPyPyPyIm |
| 2241) | 5'W C G G A T T W-3' | PyImImPyHpHp-γ-PyPyHpPyPyIm |
| 2242) | 5'W C G G A T A W-3' | PyImImPyHpPy-γ-HpPyHpPyPyIm |
| 2243) | 5'W C G G A T G W-3' | PyImImPyHpIm-γ-PyPyHpPyPyIm |
| 2244) | 5'W C G G A T C W-3' | PyImImPyHpPy-γ-ImPyHpPyPyIm |
| 2245) | 5'W C G G A A T W-3' | PyImImPyPyHp-γ-PyHpHpPyPyIm |
| 2246) | 5'W C G G A A A W-3' | PyImImPyPyPy-γ-HpHpHpPyPyIm |
| 2247) | 5'W C G G A A G W-3' | PyImImPyPyIm-γ-PyHpHpPyPyIm |
| 2248) | 5'W C G G A A C W-3' | PyImImPyPyPy-γ-ImHpHpPyPyIm |
| 2249) | 5'W C G G A G T W-3' | PyImImPyImHp-γ-PyPyHpPyPyIm |
| 2250) | 5'W C G G A G A W-3' | PyImImPyImPy-γ-HpPyHpPyPyIm |
| 2251) | 5'W C G G A G G W-3' | PyImImPyImIm-γ-PyPyHpPyPyIm |
| 2252) | 5'W C G G A G C W-3' | PyImImPyImPy-γ-ImPyHpPyPyIm |
| 2253) | 5'W C G G A C T W-3' | PyImImPyPyHp-γ-PyImHpPyPyIm |
| 2254) | 5'W C G G A C A W-3' | PyImImPyPyPy-γ-HpImHpPyPyIm |
| 2255) | 5'W C G G A C G W-3' | PyImImPyPyIm-γ-PyImHpPyPyIm |
| 2256) | 5'W C G G A C C W-3' | PyImImPyPyPy-γ-ImImHpPyPyIm |

TABLE 117

12-ring Hairpin Polyamides for recognition of 8-bp 5'WCGGSNNW-3'

| | DNA sequence | aromatic amino acid sequence |
|---|---|---|
| 2257) | 5'W C G G G T T W-3' | PyImImImHpHp-γ-PyPyPyPyPyIm |
| 2258) | 5'W C G G G T A W-3' | PyImImImHpPy-γ-HpPyPyPyPyIm |
| 2259) | 5'W C G G G T G W-3' | PyImImImHpIm-γ-PyPyPyPyPyIm |
| 2260) | 5'W C G G G T C W-3' | PyImImImHpPy-γ-ImPyPyPyPyIm |
| 2261) | 5'W C G G G A T W-3' | PyImImImPyHp-γ-PyHpPyPyPyIm |
| 2262) | 5'W C G G G A A W-3' | PyImImImPyPy-γ-HpHpPyPyPyIm |
| 2263) | 5'W C G G G A G W-3' | PyImImImPyIm-γ-PyHpPyPyPyIm |
| 2264) | 5'W C G G G A C W-3' | PyImImImPyPy-γ-ImHpPyPyPyIm |
| 2265) | 5'W C G G G G T W-3' | PyImImImImHp-γ-PyPyPyPyPyIm |
| 2266) | 5'W C G G G G A W-3' | PyImImImImPy-γ-HpPyPyPyPyIm |
| 2267) | 5'W C G G G C T W-3' | PyImImImPyHp-γ-PyImPyPyPyIm |
| 2268) | 5'W C G G G C A W-3' | PyImImImPyPy-γ-HpImPyPyPyIm |
| 2269) | 5'W C G G C T T W-3' | PyImImPyHpHp-γ-PyPyImPyPyIm |
| 2270) | 5'W C G G C T A W-3' | PyImImPyHpPy-γ-HpPyImPyPyIm |
| 2271) | 5'W C G G C T G W-3' | PyImImPyHpIm-γ-PyPyImPyPyIm |
| 2272) | 5'W C G G C T C W-3' | PyImImPyHpPy-γ-ImPyImPyPyIm |
| 2273) | 5'W C G G C A T W-3' | PyImImPyPyHp-γ-PyHpImPyPyIm |
| 2274) | 5'W C G G C A A W-3' | PyImImPyPyPy-γ-HpHpImPyPyIm |
| 2275) | 5'W C G G C A G W-3' | PyImImPyPyIm-γ-PyHpImPyPyIm |
| 2276) | 5'W C G G C A C W-3' | PyImImPyPyPy-γ-ImHpImPyPyIm |
| 2277) | 5'W C G G C G T W-3' | PyImImPyImHp-γ-PyPyImPyPyIm |
| 2278) | 5'W C G G C G A W-3' | PyImImPyImPy-γ-HpPyImPyPyIm |
| 2279) | 5'W C G G C C T W-3' | PyImImPyPyHp-γ-PyImImPyPyIm |
| 2280) | 5'W C G G C C A W-3' | PyImImPyPyPy-γ-HpImImPyPyIm |
| G83) | 5'W C G G G G G W-3' | PyImImImImIm-γ-PyPyPyPyPyIm |
| G84) | 5'W C G G G G C W-3' | PyImImImImPy-γ-ImPyPyPyPyIm |
| G85) | 5'W C G G G C G W-3' | PyImImImPyIm-γ-PyImPyPyPyIm |
| G86) | 5'W C G G G C C W-3' | PyImImImPyPy-γ-ImImPyPyPyIm |
| G87) | 5'W C G G C G G W-3' | PyImImPyImIm-γ-PyPyImPyPyIm |
| G88) | 5'W C G G C G C W-3' | PyImImPyImPy-γ-ImPyImPyPyIm |
| G89) | 5'W C G G C C G W-3' | PyImImPyPyIm-γ-PyImImPyPyIm |
| G90) | 5'W C G G C C C W-3' | PyImImPyPyPy-γ-ImImImPyPyIm |

TABLE 118

12-ring Hairpin Polyamides for recognition of 8-bp 5'-WCGTWNNW-3'

| | DNA sequence | aromatic amino acid sequence |
|---|---|---|
| 2281) | 5'W C G T T T T W-3' | PyImHpHpHpHp-γ-PyPyPyPyPyIm |
| 2282) | 5'W C G T T T A W-3' | PyImHpHpHpPy-γ-HpPyPyPyPyIm |
| 2283) | 5'W C G T T T G W-3' | PyImHpHpHpIm-γ-PyPyPyPyPyIm |
| 2284) | 5'W C G T T T C W-3' | PyImHpHpHpPy-γ-ImPyPyPyPyIm |
| 2285) | 5'W C G T T A T W-3' | PyImHpHpPyHp-γ-PyHpPyPyPyIm |
| 2286) | 5'W C G T T A A W-3' | PyImHpHpPyPy-γ-HpHpPyPyPyIm |
| 2287) | 5'W C G T T A G W-3' | PyImHpHpPyIm-γ-PyHpPyPyPyIm |
| 2288) | 5'W C G T T A C W-3' | PyImHpHpPyPy-γ-ImHpPyPyPyIm |
| 2289) | 5'W C G T T G T W-3' | PyImHpHpImHp-γ-PyPyPyPyPyIm |
| 2290) | 5'W C G T T G A W-3' | PyImHpHpImPy-γ-HpPyPyPyPyIm |
| 2291) | 5'W C G T T G G W-3' | PyImHpHpImIm-γ-PyPyPyPyPyIm |
| 2292) | 5'W C G T T G C W-3' | PyImHpHpImPy-γ-ImPyPyPyPyIm |
| 2293) | 5'W C G T T C T W-3' | PyImHpHpPyHp-γ-PyImPyPyPyIm |
| 2294) | 5'W C G T T C A W-3' | PyImHpHpPyPy-γ-HpImPyPyPyIm |
| 2295) | 5'W C G T T C G W-3' | PyImHpHpPyIm-γ-PyImPyPyPyIm |
| 2296) | 5'W C G T T C C W-3' | PyImHpHpPyPy-γ-ImImPyPyPyIm |
| 2297) | 5'W C G T A T T W-3' | PyImHpPyHpHp-γ-PyPyHpPyPyIm |
| 2298) | 5'W C G T A T A W-3' | PyImHpPyHpPy-γ-HpPyHpPyPyIm |
| 2299) | 5'W C G T A T G W-3' | PyImHpPyHpIm-γ-PyPyHpPyPyIm |
| 2300) | 5'W C G T A T C W-3' | PyImHpPyHpPy-γ-ImPyHpPyPyIm |
| 2301) | 5'W C G T A A T W-3' | PyImHpPyPyHp-γ-PyHpHpPyPyIm |
| 2302) | 5'W C G T A A A W-3' | PyImHpPyPyPy-γ-HpHpHpPyPyIm |
| 2303) | 5'W C G T A A G W-3' | PyImHpPyPyIm-γ-PyHpHpPyPyIm |
| 2304) | 5'W C G T A A C W-3' | PyImHpPyPyPy-γ-ImHpHpPyPyIm |
| 2305) | 5'W C G T A G T W-3' | PyImHpPyImHp-γ-PyPyHpPyPyIm |
| 2306) | 5'W C G T A G A W-3' | PyImHpPyImPy-γ-HpPyHpPyPyIm |
| 2307) | 5'W C G T A G G W-3' | PyImBpPyImIm-γ-PyPyHpPyPyIm |
| 2308) | 5'W C G T A G C W-3' | PyImHpPyImPy-γ-ImPyHpPyPyIm |
| 2309) | 5'W C G T A C T W-3' | PyImHpPyPyHp-γ-PyImHpPyPyIm |
| 2310) | 5'W C G T A C A W-3' | PyImHpPyPyPy-γ-HpImHpPyPyIm |
| 2311) | 5'W C G T A C G W-3' | PyImHpPyPyIm-γ-PyImHpPyPyIm |
| 2312) | 5'W C G T A C C W-3' | PyImHpPyPyPy-γ-ImImHpPyPyIm |

TABLE 119

12-ring Hairpin Polyamides for recognition of 8-bp 5'-WCGTSNNW-3'

| | DNA sequence | aromatic amino acid sequence |
|---|---|---|
| 2313) | 5'W C G T G T T W-3' | PyImHpImHpHp-γ-PyPyPyPyPyIm |
| 2314) | 5'W C G T G T A W-3' | PyImHpImHpPy-γ-HpPyPyPyPyIm |
| 2315) | 5'W C G T G T G W-3' | PyImHpImHpIm-γ-PyPyPyPyPyIm |
| 2316) | 5'W C G T G T C W-3' | PyImHpImHpPy-γ-ImPyPyPyPyIm |
| 2317) | 5'W C G T G A T W-3' | PyImHpImPyHp-γ-PyHpPyPyPyIm |
| 2318) | 5'W C G T G A A W-3' | PyImHpImPyPy-γ-HpHpPyPyPyIm |
| 2319) | 5'W C G T G A G W-3' | PyImHpImPyIm-γ-PyHpPyPyPyIm |
| 2320) | 5'W C G T G A C W-3' | PyImHpImPyPy-γ-ImHpPyPyPyIm |
| 2321) | 5'W C G T G G T W-3' | PyImHpImImHp-γ-PyPyPyPyPyIm |
| 2322) | 5'W C G T G G A W-3' | PyImHpImImPy-γ-HpPyPyPyPyIm |
| 2323) | 5'W C G T G C T W-3' | PyImHpImPyHp-γ-PyImPyPyPyIm |
| 2324) | 5'W C G T G C A W-3' | PyImHpImPyPy-γ-HpImPyPyPyIm |
| 2325) | 5'W C G T G G G W-3' | PyImHpImImIm-γ-PyPyPyPyPyIm |
| 2326) | 5'W C G T G G C W-3' | PyImHpImImPy-γ-ImPyPyPyPyIm |
| 2327) | 5'W C G T G C G W-3' | PyImHpImPyIm-γ-PyImPyPyPyIm |
| 2328) | 5'W C G T G C C W-3' | PyImHpImPyPy-γ-ImImPyPyPyIm |
| 2329) | 5'W C G T C T T W-3' | PyImHpPyHpHp-γ-PyPyImPyPyIm |
| 2330) | 5'W C G T C T A W-3' | PyImHpPyHpPy-γ-HpPyImPyPyIm |
| 2331) | 5'W C G T C T G W-3' | PyImHpPyHpIm-γ-PyPyImPyPyIm |
| 2332) | 5'W C G T C T C W-3' | PyImHpPyHpPy-γ-ImPyImPyPyIm |
| 2333) | 5'W C G T C A T W-3' | PyImHpPyPyHp-γ-PyHpImPyPyIm |
| 2334) | 5'W C G T C A A W-3' | PyImHpPyPyPy-γ-HpHpImPyPyIm |
| 2335) | 5'W C G T C A G W-3' | PyImHpPyPyIm-γ-PyHpImPyPyIm |
| 2336) | 5'W C G T C A C W-3' | PyImHpPyPyPy-γ-ImHpImPyPyIm |
| 2337) | 5'W C G T C G T W-3' | PyImHpPyImHp-γ-PyPyImPyPyIm |
| 2338) | 5'W C G T C G A W-3' | PyImHpPyImPy-γ-HpPyImPyPyIm |
| 2339) | 5'W C G T C C T W-3' | PyImHpPyPyHp-γ-PyImImPyPyIm |
| 2340) | 5'W C G T C C A W-3' | PyImHpPyPyPy-γ-HpImImPyPyIm |
| 2341) | 5'W C G T C G G W-3' | PyImHpPyImIm-γ-PyPyImPyPyIm |

TABLE 119-continued 12-ring Hairpin Polyamides for recognition of 8-bp 5'-WCGTSNNW-3'

| | DNA sequence | aromatic amino acid sequence |
|---|---|---|
| 2342) | 5'W C G T C G C W-3' | PyImHpPyImPy-γ-ImPyImPyPyIm |
| 2343) | 5'W C G T C C G W-3' | PyImHpPyPyIm-γ-PyImImPyPyIm |
| 2344) | 5'W C G T C C C W-3' | PyImHpPyPyPy-γ-ImImImPyPyIm |

TABLE 120

12-ring Hairpin Polyamides for recognition of 8-bp 5'-WCGAWNNW-3'

| | DNA sequence | aromatic amino acid sequence |
|---|---|---|
| 2345) | 5'W C G A T T T W-3' | PyImPyHpHpHp-γ-PyPyPyHpPyIm |
| 2346) | 5'W C G A T T A W-3' | PyImPyHpHpPy-γ-HpPyPyHpPyIm |
| 2347) | 5'W C G A T T G W-3' | PyImPyHpHpIm-γ-PyPyPyHpPyIm |
| 2348) | 5'W C G A T T C W-3' | PyImPyHpHpPy-γ-ImPyPyHpPyIm |
| 2349) | 5'W C G A T A T W-3' | PyImPyHpPyHp-γ-PyHpPyHpPyIm |
| 2350) | 5'W C G A T A A W-3' | PyImPyHpPyPy-γ-HpHpPyHpPyIm |
| 2351) | 5'W C G A T A G W-3' | PyImPyHpPyIm-γ-PyHpPyHpPyIm |
| 2352) | 5'W C G A T A C W-3' | PyImPyHpPyPy-γ-ImHpPyHpPyIm |
| 2353) | 5'W C G A T G T W-3' | PyImPyHpImHp-γ-PyPyPyHpPyIm |
| 2354) | 5'W C G A T G A W-3' | PyImPyHpImPy-γ-HpPyPyHpPyIm |
| 2355) | 5'W C G A T G G W-3' | PyImPyHpImIm-γ-PyPyPyHpPyIm |
| 2356) | 5'W C G A T G C W-3' | PyImPyHpImPy-γ-ImPyPyHpPyIm |
| 2357) | 5'W C G A T C T W-3' | PyImPyHpPyHp-γ-PyImPyHpPyIm |
| 2358) | 5'W C G A T C A W-3' | PyImPyHpPyPy-γ-HpImPyHpPyIm |
| 2359) | 5'W C G A T C G W-3' | PyImPyHpPyIm-γ-PyImPyHpPyIm |
| 2360) | 5'W C G A T C C W-3' | PyImPyHpPyPy-γ-ImImPyHpPyIm |
| 2361) | 5'W C G A A T T W-3' | PyImPyPyHpHp-γ-PyPyHpHpPyIm |
| 2362) | 5'W C G A A T A W-3' | PyImPyPyHpPy-γ-HpPyHpHpPyIm |
| 2363) | 5'W C G A A T G W-3' | PyImPyPyHpIm-γ-PyPyHpHpPyIm |
| 2364) | 5'W C G A A T C W-3' | PyImPyPyHpPy-γ-ImPyHpHpPyIm |
| 2365) | 5'W C G A A A T W-3' | PyImPyPyPyHp-γ-PyHpHpHpPyIm |
| 2366) | 5'W C G A A A A W-3' | PyImPyPyPyPy-γ-HpHpHpHpPyIm |
| 2367) | 5'W C G A A A G W-3' | PyImPyPyPyIm-γ-PyHpHpHpPyIm |
| 2368) | 5'W C G A A A C W-3' | PyImPyPyPyPy-γ-ImHpHpHpPyIm |
| 2369) | 5'W C G A A G T W-3' | PyImPyPyImHp-γ-PyPyHpHpPyIm |
| 2370) | 5'W C G A A G A W-3' | PyImPyPyImPy-γ-HpPyHpHpPyIm |
| 2371) | 5'W C G A A G G W-3' | PyImPyPyImIm-γ-PyPyHpHpPyIm |
| 2372) | 5'W C G A A G C W-3' | PyImPyPyImPy-γ-ImPyHpHpPyIm |
| 2373) | 5'W C G A A C T W-3' | PyImPyPyPyHp-γ-PyImHpHpPyIm |
| 2374) | 5'W C G A A C A W-3' | PyImPyPyPyPy-γ-HpImHpHpPyIm |
| 2375) | 5'W C G A A C G W-3' | PyImPyPyPyIm-γ-PyImHpHpPyIm |
| 2376) | 5'W C G A A C C W-3' | PyImPyPyPyPy-γ-ImImHpHpPyIm |

TABLE 121

12-ring Hairpin Polyamides for recognition of 8-bp 5'-WCGASNNW-3'

| | DNA sequence | aromatic amino acid sequence |
|---|---|---|
| 2377) | 5'W C G A G T T W-3' | PyImPyIrnHpHp-γ-PyPyPyHpPyIm |
| 2378) | 5'W C G A G T A W-3' | PyImPyImHpPy-γ-HpPyPyHpPyIm |
| 2379) | 5'W C G A G T G W-3' | PyImPyImHpIm-γ-PyPyPyHpPyIm |
| 2380) | 5'W C G A G T C W-3' | PyImPyImHpPy-γ-ImPyPyHpPyIm |
| 2381) | 5'W C G A G A T W-3' | PyImPyImPyHp-γ-PyHpPyHpPyIm |
| 2382) | 5'W C G A G A A W-3' | PyImPyImPyPy-γ-HpPyPyHppyIm |
| 2383) | 5'W C G A G A G W-3' | PyImPyImPyIm-γ-PyHpPyHpPyIm |
| 2384) | 5'W C G A G A C W-3' | PyImPyImPyPy-γ-ImHpPyHpPyIm |
| 2385) | 5'W C G A G G T W-3' | PyImPyImImIp-γ-PyPyPyHpPyIm |
| 2386) | 5'W C G A G G A W-3' | PyImPyImImPy-γ-HpPyPyHpPyIm |
| 2387) | 5'W C G A G G G W-3' | PyImPyImImIm-γ-PyPyPyHpPyIm |
| 2388) | 5'W C G A G C T W-3' | PyImPyImPyPy-γ-HpImPyHpPyIm |
| 2389) | 5'W C G A G G G W-3' | PyImPyImImIm-γ-PyPyPyHpPyIm |
| 2390) | 5'W C G A G G C W-3' | PyImPyImImPy-γ-ImPyPyHpPyIm |
| 2391) | 5'W C G A G C G W-3' | PyImPyImPyIm-γ-PyImPyHpPyIm |
| 2392) | 5'W C G A G C C W-3' | PyImPyImPyPy-γ-ImImPyHpPyIm |
| 2393) | 5'W C G A C T T W-3' | PyImPyPyHpHp-γ-PyPyImHpPyIm |
| 2394) | 5'W C G A C T A W-3' | PyImPyPyHpPy-γ-HpPyImHppyIm |
| 2395) | 5'W C G A C T G W-3' | PyImPyPyHpIm-γ-PyPyImHpPyIm |
| 2396) | 5'W C G A C T C W-3' | PyImPyPyHpPy-γ-ImPyImHpPyIm |

TABLE 121-continued 12-ring Hairpin Polyamides for recognition of 8-bp 5'-WCGASNNW-3'

| | DNA sequence | aromatic amino acid sequence |
|---|---|---|
| 2397) | 5'W C G A C A T W-3' | PyImPyPyPyHp-γ-PyHpImHpPyIm |
| 2398) | 5'W C G A C A A W-3' | PyImPyPyPyPy-γ-HpHpImHpPyIm |
| 2399) | 5'W C G A C A G W-3' | PyImPyPyPyIm-γ-PyHpImHpPyIm |
| 2400) | 5'W C G A C A C W-3' | PyImPyPyPyPy-γ-ImHpImHpPyIm |
| 2401) | 5'W C G A C G T W-3' | PyImPyPyImEp-γ-PyPyImHpPyIm |
| 2402) | 5'W C G A C G A W-3' | PyImPyPyImPy-γ-HpPyImHpPyIm |
| 2403) | 5'W C G A C C T W-3' | PyImPyPyPyHp-γ-PyImImHpPyIm |
| 2404) | 5'W C G A C C A W-3' | PyImPyPyPyPy-γ-PpImImHpPyIm |
| 2405) | 5'W C G A C G G W-3' | PyImPyImIm-γ-PyPyImHpPyIm |
| 2406) | 5'W C G A C G C W-3' | PyImPyPyImPy-γ-ImPyImHpPyIm |
| 2407) | 5'W C G A C C G W-3' | PyImPyPyPyIm-γ-PyImImHpPyIm |
| 2408) | 5'W C G A C C C W-3' | PyImPyPyPyPy-γ-ImImImHpPyIm |

TABLE 122

12-ring Hairpin Polyamides for recognition of 8-bp 5'-WCGCWNNW-3'

| | DNA sequence | aromatic amino acid sequence |
|---|---|---|
| 2409) | 5'W C G C T T T W-3' | PyImPyHpHpHp-γ-PyPyPyImPyIm |
| 2410) | 5'W C G C T T A W-3' | PyImPyHpHpPy-γ-HpPyPyImPyIm |
| 2411) | 5'W C G C T T G W-3' | PyImPyHpHpIm-γ-PyPyPyImPyIm |
| 2412) | 5'W C G C T T C W-3' | PyImPyHpHpPy-γ-ImPyPyImPyIm |
| 2413) | 5'W C G C T A T W-3' | PyImPyHpPyHp-γ-PyHpPyImPyIm |
| 2414) | 5'W C G C T A A W-3' | PyImPyHpPyPy-γ-HpHpPyImPyIm |
| 2415) | 5'W C G C T A G W-3' | PyImPyHpPyIm-γ-PyHpPyImPyIm |
| 2416) | 5'W C G C T A C W-3' | PyImPyHpPyPy-γ-ImHpPyImPyIm |
| 2417) | 5'W C G C T G T W-3' | PyImPyHpImHp-γ-PyPyPyImPyIm |
| 2418) | 5'W C G C T G A W-3' | PyImPyHpImPy-γ-HpPyPyImPyIm |
| 2419) | 5'W C G C T G G W-3' | PyImPyHpImIm-γ-PyPyPyImPyIm |
| 2420) | 5'W C G C T G C W-3' | PyImPyHpImPy-γ-ImPyPyImPyIm |
| 2421) | 5'W C G C T C T W-3' | PyImPyHpPyHp-γ-PyImPyImPyIm |
| 2422) | 5'W C G C T C A W-3' | PyImPyHpPyPy-γ-HpImPyImPyIm |
| 2423) | 5'W C G C T C G W-3' | PyImPyHpPyIm-γ-PyImPyImPyIm |
| 2424) | 5'W C G C T C C W-3' | PyImPyHpPyPy-γ-ImImPyImPyIm |
| 2425) | 5'W C G C A T T W-3' | PyImPyPyHpHp-γ-PyPyHpImPyIm |
| 2426) | 5'W C G C A T A W-3' | PyImPyPyHpPy-γ-HpPyHpImPyIm |
| 2427) | 5'W C G C A T G W-3' | PyImPyPyHpIm-γ-PyPyHpImPyIm |
| 2428) | 5'W C G C A T C W-3' | PyImPyPyHpPy-γ-ImPyHpImPyIm |
| 2429) | 5'W C G C A A T W-3' | PyImPyPyPyHp-γ-PyHpHpImPyIm |
| 2430) | 5'W C G C A A A W-3' | PyImPyPyPyPy-γ-HpHpHpImPyIm |
| 2431) | 5'W C G C A A G W-3' | PyImPyPyPyIm-γ-PyHpHpImPyIm |
| 2432) | 5'W C G C A A C W-3' | PyImPyPyPyPy-γ-ImHpHpImPyIm |
| 2433) | 5'W C G C A G T W-3' | PyImPyPyImHp-γ-PyPyHpImPyIm |
| 2434) | 5'W C G C A G A W-3' | PyImPyPyImPy-γ-HpPyHpImPyIm |
| 2435) | 5'W C G C A G G W-3' | PyImPyPyImIm-γ-PyPyHpImPyIm |
| 2436) | 5'W C C C A G C W-3' | PyImPyPyImPy-γ-ImPyHpImPyIm |
| 2437) | 5'W C G C A C T W-3' | PyImPyPyPyHp-γ-PyImHpImPyIm |
| 2438) | 5'W C G C A C A W-3' | PyImPyPyPyPy-γ-HpImHpImPyIm |
| 2439) | 5'W C C C A C G W-3' | PyImPyPyPyIm-γ-PyImHpImPyIm |
| 2440) | 5'W C G C A C C W-3' | PyImPyPyPyPy-γ-ImImHpImPyIm |

TABLE 123

12-ring Hairpin Polyamides for recognition of 8-bp 5'-WCGCSNNW-3'

| | DNA sequence | aromatic amino acid sequence |
|---|---|---|
| 2441) | 5'W C G C G T T W-3' | PyImPyImHpHp-γ-PyPyPyImPyIm |
| 2442) | 5'W C G C G T A W-3' | PyImPyImHpPy-γ-HpPyPyImPyIm |
| 2443) | 5'W C G C G T G W-3' | PyImPyImHpIm-γ-PyPyPyImPyIm |
| 2444) | 5'W C G C G T C W-3' | PyImPyImHpPy-γ-ImPyPyImPyTm |
| 2445) | 5'W C G C G A T W-3' | PyImPyImPyHp-γ-PyHpPyImPyIm |
| 2446) | 5'W C G C G A A W-3' | PyImPyImPyPy-γ-HpHpPyImPyIm |
| 2447) | 5'W C G C G A G W-3' | PyImPyImPyIm-γ-PyHpPyImPyIm |
| 2448) | 5'W C G C G A C W-3' | PyImPyImPyPy-γ-ImHpPyImPyIm |
| 2449) | 5'W C G C G G T W-3' | PyImPyImImHp-γ-PyPyPyImPyIm |
| 2450) | 5'W C G C G G A W-3' | PyImPyImImPy-γ-HpPyPyImPyIm |
| 2451) | 5'W C G C G C T W-3' | PyImPyImPyHp-γ-PyImPyImPyIm |
| 2452) | 5'W C G C G C A W-3' | PyImPyImPyPy-γ-HpImPyImPyIm |

TABLE 123-continued 12-ring Hairpin Polyamides for recognition of 8-bp 5'-WCGCSNNW-3'

| DNA sequence | aromatic amino acid sequence |
|---|---|
| 2453) 5'W C G C C T T W-3' | PyImPyPyHpHp-γ-PyPyImImPyIm |
| 2454) 5'W C G C C T A W-3' | PyImPyPyHpPy-γ-HpPyImImPyIm |
| 2455) 5'W C G C C T G W-3' | PyImPyPyHpIm-γ-PyPyImImPyIm |
| 2456) 5'W C G C C T C W-3' | PyImPyPyHpPy-γ-ImPyPyImImPyIm |
| 2457) 5'W C G C C A T W-3' | PyImPyPyPyHp-γ-PyHpImImPyIm |
| 2458) 5'W C G C C A A W-3' | PyImPyPyPyPy-γ-HpHpImImPyIm |
| 2459) 5'W C G C C A G W-3' | PyImPyPyPyIm-γ-PyHpImImPyIm |
| 2460) 5'W C G C C A C W-3' | PyImPyPyPyPy-γ-ImHpImImPyIm |
| 2461) 5'W C G C C G T W-3' | PyImPyPyImHp-γ-PyPyImImPyIm |
| 2462) 5'W C G C C G A W-3' | PyImPyPyImPy-γ-HpPyImImPyIm |
| 2463) 5'W C G C C C T W-3' | PyImPyPyPyHp-γ-PyImImImPyIm |
| 2464) 5'W C G C C C A W-3' | PyImPyPyPyPy-γ-HpImImImPyIm |
| G91) 5'W C G C G G G W-3' | PyImPyImImIm-γ-PyPyImImPyIm |
| G92) 5'W C G C G G C W-3' | PyImPyImImPy-γ-ImPyImImPyIm |
| G93) 5'W C G C G C G W-3' | PyImPyImPyIm-γ-PyImPyImPyIm |
| G94) 5'W C G C G C C W-3' | PyImPyImPyPy-γ-ImPyImPyImPyIm |
| G95) 5'W C G C C G G W-3' | PyImPyPyImIm-γ-PyPyImImPyIm |
| G96) 5'W C G C C G C W-3' | PyImPyPyImPy-γ-ImPyImImPyIm |
| G97) 5'W C G C C C G W-3' | PyImPyPyPyIm-γ-PyImImImPyIm |
| G98) 5'W C G C C C C W-3' | PyImPyPyPyPy-γ-ImImImImPyIm |

TABLE 124

12-ring Hairpin Polyamides for recognition of 8-bp 5'-WCCGWNNW-3'

| DNA sequence | aromatic amino acid sequence |
|---|---|
| 2465) 5'W C C G T T T W-3' | PyPyImHpHpHp-γ-PyPyPyPyImIm |
| 2466) 5'W C C G T T A W-3' | PyPyImHpHpPy-γ-HpPyPyPyImIm |
| 2467) 5'W C C G T T G W-3' | PyPyImHpHpIm-γ-PyPyPyPyImIm |
| 2468) 5'W C C G T T C W-3' | PyPyImHpHpPy-γ-ImPyPyPyImIm |
| 2469) 5'W C C G T A T W-3' | PyPyImHpPyHp-γ-PyHpPyPyImIm |
| 2470) 5'W C C G T A A W-3' | PyPyImHpPyPy-γ-HpHpPyPyImIm |
| 2471) 5'W C C G T A G W-3' | PyPyImHpPyIm-γ-PyHpPyPyImIm |
| 2472) 5'W C C G T A C W-3' | PyPyImHpPyPy-γ-ImHpPyPyImIm |
| 2473) 5'W C C G T G T W-3' | PyPyImHpImHp-γ-PyPyPyPyImIm |
| 2474) 5'W C C G T G A W-3' | PyPyImHpImPy-γ-HpPyPyPyImIm |
| 2475) 5'W C C G T G G W-3' | PyPyImHpImIm-γ-PyPyPyPyImIm |
| 2476) 5'W C C G T G C W-3' | PyPyImHpImPy-γ-ImPyPyPyImIm |
| 2477) 5'W C C G T C T W-3' | PyPyImHpPyHp-γ-PyImPyPyImIm |
| 2478) 5'W C C G T C A W-3' | PyPyImHpPyPy-γ-HpImPyPyImIm |
| 2479) 5'W C C G T C G W-3' | PyPyImHpPyIm-γ-PyImPyPyImIm |
| 2480) 5'W C C G T C C W-3' | PyPyImHpPyPy-γ-ImImPyPyImIm |
| 2481) 5'W C C G A T T W-3' | PyPyImPyHpHp-γ-PyPyHpPyImIm |
| 2482) 5'W C C G A T A W-3' | PyPyImPyHpPy-γ-HpPyHpPyImIm |
| 2483) 5'W C C G A T G W-3' | PyPyImPyHpIm-γ-PyPyHpPyImIm |
| 2484) 5'W C C G A T C W-3' | PyPyImPyHpPy-γ-ImPyHpPyImIm |
| 2485) 5'W C C G A A T W-3' | PyPyImPyPyHp-γ-PyHpHpPyImIm |
| 2486) 5'W C C G A A A W-3' | PyPyImPyPyPy-γ-HpHpHpPyImIm |
| 2487) 5'W C C G A A G W-3' | PyPyImPyPyIm-γ-PyHpHpPyImIm |
| 2488) 5'W C C G A A C W-3' | PyPyImPyPyPy-γ-ImHpHpPyImIm |
| 2489) 5'W C C G A G T W-3' | PyPyImPyImHp-γ-PyPyHpPyImIm |
| 2490) 5'W C C G A G A W-3' | PyPyImPyImPy-γ-HpPyHpPyImIm |
| 2491) 5'W C C G A G G W-3' | PyPyImPyImIm-γ-PyPyHpPyImIm |
| 2492) 5'W C C G A G C W-3' | PyPyImPyImPy-γ-ImPyHpPyImIm |
| 2493) 5'W C C G A C T W-3' | PyPyImPyPyPp-γ-PyImHpPyImIm |
| 2494) 5'W C C G A C A W-3' | PyPyImPyPyPy-γ-HpImHpPyImIm |
| 2495) 5'W C C G A C G W-3' | PyPyImPyPyIm-γ-PyImHpPyImIm |
| 2496) 5'W C C G A C C W-3' | PyPyImPyPyPy-γ-ImImHpPyImIm |

TABLE 125

12-ring Hairpin Polyamides for recognition of 8-bp 5'-WCCGSNNW-3'

| DNA sequence | aromatic amino acid sequence |
|---|---|
| 2497) 5'W C C G G T T W-3' | PyPyImImHpHp-γ-PyPyPyPyImIm |
| 2498) 5'W C C G G T A W-3' | PyPyImImHpPy-γ-HpPyPyPyImIm |
| 2499) 5'W C C G G T G W-3' | PyPyImImHpIm-γ-PyPyPyPyImIm |
| 2500) 5'W C C G G T C W-3' | PyPyImImHpPy-γ-ImPyPyPyImIm |

TABLE 125-continued 12-ring Hairpin Polyamides for recognition of 8-bp 5'-WCCGSNNW-3'

| DNA sequence | aromatic amino acid sequence |
|---|---|
| 2501) 5'W C C G G A T W-3' | PyPyImImPyHp-γ-PyHpPyPyImIm |
| 2502) 5'W C C G G A A W-3' | PyPyImImPyPy-γ-HpHpPyPyImIm |
| 2503) 5'W C C G G A G W-3' | PyPyImImPyIm-γ-PyHpPyPyImIm |
| 2504) 5'W C C G G A C W-3' | PyPyImImPyPy-γ-ImHpPyPyImIm |
| 2505) 5'W C C G G G T W-3' | PyPyImImImHp-γ-PyPyPyPyImIm |
| 2506) 5'W C C G G G A W-3' | PyPyImImImPy-γ-HpPyPyPyImIm |
| 2507) 5'W C C G G C T W-3' | PyPyImImPyHp-γ-PyImPyPyImIm |
| 2508) 5'W C C G G C A W-3' | PyPyImImPyPy-γ-HpImPyPyImIm |
| 2509) 5'W C C G C T T W-3' | PyPyImPyHpHp-γ-PyPyImPyImIm |
| 2510) 5'W C C G C T A W-3' | PyPyImPyHpPy-γ-HpPyImPyImIm |
| 2511) 5'W C C G C T G W-3' | PyPyImPyHpIm-γ-PyPyImPyImIm |
| 2512) 5'W C C G C T C W-3' | PyPyImPyHpPy-γ-ImPyImPyImIm |
| 2513) 5'W C C G C A T W-3' | PyPyImPyPyHp-γ-PyHpImPyImIm |
| 2514) 5'W C C G C A A W-3' | PyPyImPyPyPy-γ-HpHpImPyImIm |
| 2515) 5'W C C G C A G W-3' | PyPyImPyPyIm-γ-PyHpImPyImIm |
| 2516) 5'W C C G C A C W-3' | PyPyImPyPyPy-γ-ImHpImPyImIm |
| 2517) 5'W C C G C G T W-3' | PyPyImPyImHp-γ-PyPyImPyImIm |
| 2518) 5'W C C G C G A W-3' | PyPyImPyImPy-γ-HpPyImPyImIm |
| 2519) 5'W C C G C C T W-3' | PyPyImPyPyHp-γ-PyImImPyImIm |
| 2520) 5'W C C G C C A W-3' | PyPyImPyPyPy-γ-HpImImPyImIm |
| G99) 5'W C C G G G G W-3' | PyPyImImImIm-γ-PyPyPyPyImIm |
| G100) 5'W C C G G G C W-3' | PyPyImImImPy-γ-ImPyPyPyImIm |
| G101) 5'W C C G G C G W-3' | PyPyImImPyIm-γ-PyImPyPyImIm |
| G102) 5'W C C G G C C W-3' | PyPyImImPyPy-γ-ImImPyPyImIm |
| G103) 5'W C C G C G G W-3' | PyPyImPyImIm-γ-PyPyImPyImIm |
| G104) 5'W C C G C G C W-3' | PyPyImPyImPy-γ-ImPyImPyImIm |
| G105) 5'W C C G C C G W-3' | PyPyImPyPyIm-γ-PyImImPyImIm |
| G106) 5'W C C G C C C W-3' | PyPyImPyPyPy-γ-ImImImPyImIm |

TABLE 126

12-ring Hairpin Polyamides for recognition of 8-bp 5'-WCCTWNNW-3'

| DNA sequence | aromatic amino acid sequence |
|---|---|
| 2521) 5'W C C T T T T W-3' | PyPyHpHpHpHp-γ-PyPyPyPyImIm |
| 2522) 5'W C C T T T A W-3' | PyPyHpHpHpPy-γ-HpPyPyPyImIm |
| 2523) 5'W C C T T T G W-3' | PyPyHpHpHpIm-γ-PyPyPyPyImIm |
| 2524) 5'W C C T T T C W-3' | PyPyHpHpHpPy-γ-ImPyPyPyImIm |
| 2525) 5'W C C T T A T W-3' | PyPyHpHpPyHp-γ-PyHpPyPyImIm |
| 2526) 5'W C C T T A A W-3' | PyPyHpHpPyPy-γ-HpHpPyPyImIm |
| 2527) 5'W C C T T A G W-3' | PyPyHpHpPyIm-γ-PyHpPyPyImIm |
| 2528) 5'W C C T T A C W-3' | PyPyHpHpPyPy-γ-ImHpPyPyImIm |
| 2529) 5'W C C T T G T W-3' | PyPyHpHpImHp-γ-PyPyPyPyImIm |
| 2530) 5'W C C T T G A W-3' | PyPyHpHpImPy-γ-HpPyPyPyImIm |
| 2531) 5'W C C T T G G W-3' | PyPyHpHpImIm-γ-PyPyPyPyImIm |
| 2532) 5'W C C T T G C W-3' | PyPyHpHpImPy-γ-ImPyPyPyImIm |
| 2533) 5'W C C T T C T W-3' | PyPyHpHpPyHp-γ-PyImPyPyImIm |
| 2534) 5'W C C T T C A W-3' | PyPyHpHpPyPy-γ-HpImPyPyImIm |
| 2535) 5'W C C T T C G W-3' | PyPyHpHpPyIm-γ-PyImPyPyImIm |
| 2536) 5'W C C T T C C W-3' | PyPyHpHpPyPy-γ-ImImPyPyImIm |
| 2537) 5'W C C T A T T W-3' | PyPyHpPyHpHp-γ-PyPyHpPyImIm |
| 2538) 5'W C C T A T A W-3' | PyPyHpPyHpPy-γ-HpPyHpPyImIm |
| 2539) 5'W C C T A T G W-3' | PyPyHpPyHpIm-γ-PyPyHpPyImIm |
| 2540) 5'W C C T A T C W-3' | PyPyHpPyHpPy-γ-ImPyHpPyImIm |
| 2541) 5'W C C T A A T W-3' | PyPyHpPyPyHp-γ-PyHpHpPyImIm |
| 2542) 5'W C C T A A A W-3' | PyPyHpPyPyPy-γ-HpHpHpPyImIm |
| 2543) 5'W C C T A A G W-3' | PyPyHpPyPyIm-γ-PyHpHpPyImIm |
| 2544) 5'W C C T A A C W-3' | PyPyHpPyPyPy-γ-ImHpHpPyImIm |
| 2545) 5'W C C T A G T W-3' | PyPyHpPyImHp-γ-PyPyHpPyImIm |
| 2546) 5'W C C T A G A W-3' | PyPyHpPyImPy-γ-HpPyHpPyImIm |
| 2547) 5'W C C T A G G W-3' | PyPyHpPyImIm-γ-PyPyHpPyImIm |
| 2548) 5'W C C T A G C W-3' | PyPyHpPyImPy-γ-ImPyHpPyImIm |
| 2549) 5'W C C T A C T W-3' | PyPyHpPyPyHp-γ-PyImHpPyImIm |
| 2550) 5'W C C T A C A W-3' | PyPyHpPyPyPy-γ-HpImHpPyImIm |
| 2551) 5'W C C T A C G W-3' | PyPyHpPyPyIm-γ-PyImHpPyImIm |
| 2552) 5'W C C T A C C W-3' | PyPyHpPyPyPy-γ-ImImHpPyImIm |

TABLE 127

12-ring Hairpin Polyamides for recognition of 8-bp 5'-WCCTSNNW-3'

| DNA sequence | aromatic amino acid sequence |
|---|---|
| 2553) 5'W C C T G T T W-3' | PyPyHpImHpHp-γ-PyPyPyPyImIm |
| 2554) 5'W C C T G T A W-3' | PyPyHpImHpPy-γ-HpPyPyPyImIm |
| 2555) 5'W C C T G T G W-3' | PyPyHpImHpIm-γ-PyPyPyPyImIm |
| 2556) 5'W C C T G T C W-3' | PyPyHpImHpPy-γ-ImPyPyPyImIm |
| 2557) 5'W C C T G A T W-3' | PyPyHpImPyHp-γ-PyHpPyPyImIm |
| 2558) 5'W C C T G A A W-3' | PyPyHpImPyPy-γ-HpHpPyPyImIm |
| 2559) 5'W C C T G A G W-3' | PyPyHpImPyIm-γ-PyHpPyPyImIm |
| 2560) 5'W C C T G A C W-3' | PyPyHpImPyPy-γ-HpImPyPyImIm |
| 2561) 5'W C C T G G T W-3' | PyPyHpImImHp-γ-PyPyPyPyImIm |
| 2562) 5'W C C T G G A W-3' | PyPyHpImImPy-γ-HpPyPyPyImIm |
| 2563) 5'W C C T G C T W-3' | PyPyHpImPyHp-γ-PyImPyPyImIm |
| 2564) 5'W C C T G C A W-3' | PyPyHpImPyPy-γ-HpImPyPyImIm |
| 2565) 5'W C C T G G G W-3' | PyPyHpImImIm-γ-PyPyPyPyImIm |
| 2566) 5'W C C T G G C W-3' | PyPyHpImImPy-γ-ImPyPyPyImIm |
| 2567) 5'W C C T G C G W-3' | PyPyHpImPyIm-γ-PyImPyPyImIm |
| 2568) 5'W C C T G C C W-3' | PyPyHpImPyPy-γ-ImImPyPyImIm |
| 2569) 5'W C C T C T T W-3' | PyPyHpPyHpHp-γ-PyPyImPyImIm |
| 2570) 5'W C C T C T A W-3' | PyPyHpPyHpPy-γ-HpPyImPyImIm |
| 2571) 5'W C C T C T G W-3' | PyPyHpPyHpIm-γ-PyPyImPyImIm |
| 2572) 5'W C C T C T C W-3' | PyPyHpPyHpPy-γ-ImPyImPyImIm |
| 2573) 5'W C C T C A T W-3' | PyPyHpPyPyHp-γ-PyHpImPyImIm |
| 2574) 5'W C C T C A A W-3' | PyPyHpPyPyPy-γ-HpHpImPyImIm |
| 2575) 5'W C C T C A G W-3' | PyPyHpPyPyIm-γ-PyHpImPyImIm |
| 2576) 5'W C C T C A C W-3' | PyPyHpPyPyPy-γ-ImHpImPyImIm |
| 2577) 5'W C C T C G T W-3' | PyPyHpPyImHp-γ-PyPyImPyImIm |
| 2578) 5'W C C T C G A W-3' | PyPyHpPyImPy-γ-HpPyImPyImIm |
| 2579) 5'W C C T C C T W-3' | PyPyHpPyPyHp-γ-PyImImPyImIm |
| 2580) 5'W C C T C C A W-3' | PyPyHpPyPyPy-γ-HpImImPyImIm |
| 2581) 5'W C C T C G G W-3' | PyPyHpPyImIm-γ-PyPyImPyImIm |
| 2582) 5'W C C T C G C W-3' | PyPyHpPyImPy-γ-ImPyImPyImIm |
| 2583) 5'W C C T C C G W-3' | PyPyHpPyPyIm-γ-PyImImPyImIm |
| 2584) 5'W C C T C C C W-3' | PyPyHpPyPyPy-γ-ImImImPyImIm |

TABLE 128

12-ring Hairpin Polyamides for recognition of 8-bp 5'-WCCAWNNW-3'

| DNA sequence | aromatic amino acid sequence |
|---|---|
| 2585) 5'W C C A T T T W-3' | PyPyPyHpHpHp-γ-PyPyPyHpImIm |
| 2586) 5'W C C A T T A W-3' | PyPyPyHpHpPy-γ-HpPyPyHpImIm |
| 2587) 5'W C C A T T G W-3' | PyPyPyHpHpIm-γ-PyPyPyHpImIm |
| 2588) 5'W C C A T T C W-3' | PyPyPyHpHpPy-γ-ImPyPyHpImIm |
| 2589) 5'W C C A T A T W-3' | PyPyPyHpPyHp-γ-PyHpPyHpImIm |
| 2590) 5'W C C A T A A W-3' | PyPyPyHpPyPy-γ-HpHpPyHpImIm |
| 2591) 5'W C C A T A G W-3' | PyPyPyHpPyIm-γ-PyHpPyHpImIm |
| 2592) 5'W C C A T A C W-3' | PyPyPyHpPyPy-γ-ImHpPyHpImIm |
| 2593) 5'W C C A T G T W-3' | PyPyPyHpImHp-γ-PyPyPyHpImIm |
| 2594) 5'W C C A T G A W-3' | PyPyPyHpImPy-γ-HpPyPyHpImIm |
| 2595) 5'W C C A T G G W-3' | PyPyPyHpImIm-γ-PyPyPyHpImIm |
| 2596) 5'W C C A T G C W-3' | PyPyPyHpImPy-γ-ImPyPyHpImIm |
| 2597) 5'W C C A T C T W-3' | PyPyPyHpPyHp-γ-PyImPyHpImIm |
| 2598) 5'W C C A T C A W-3' | PyPyPyHpPyPy-γ-HpImPyHpImIm |
| 2599) 5'W C C A T C G W-3' | PyPyPyHpPyIm-γ-PyImPyHpImIm |
| 2600) 5'W C C A T C C W-3' | PyPyPyHpPyPy-γ-ImImPyHpImIm |
| 2601) 5'W C C A A T T W-3' | PyPyPyPyHpHp-γ-PyPyHpHpImIm |
| 2602) 5'W C C A A T A W-3' | PyPyPyPyHpPy-γ-HpPyHpHpImIm |
| 2603) 5'W C C A A T G W-3' | PyPyPyHpIm-γ-PyPyHpHpImIm |
| 2604) 5'W C C A A T C W-3' | PyPyPyPyHpPy-γ-ImPyHpHpImIm |
| 2605) 5'W C C A A A T W-3' | PyPyPyPyPyHp-γ-PyHpHpHpImIm |
| 2606) 5'W C C A A A A W-3' | PyPyPyPyPyPy-γ-HpHpHpHpImIm |
| 2607) 5'W C C A A A G W-3' | PyPyPyPyPyIm-γ-PyHpHpHpImIm |
| 2608) 5'W C C A A A C W-3' | PyPyPyPyPyPy-γ-ImHpHpHpImIm |
| 2609) 5'W C C A A G T W-3' | PyPyPyPyImHp-γ-PyPyHpHpImIm |
| 2610) 5'W C C A A G A W-3' | PyPyPyPyImPy-γ-HpPyHpHpImIm |
| 2611) 5'W C C A A G G W-3' | PyPyPyPyImIm-γ-PyPyHpHpImIm |
| 2612) 5'W C C A A G C W-3' | PyPyPyPyImPy-γ-ImPyHpHpImIm |
| 2613) 5'W C C A A C T W-3' | PyPyPyPyPyHp-γ-PyImHpHpImIm |
| 2614) 5'W C C A A C A W-3' | PyPyPyPyPyPy-γ-HpImHpHpImIm |
| 2615) 5'W C C A A C G W-3' | PyPyPyPyPyIm-γ-PyImHpHpImIm |
| 2616) 5'W C C A A C C W-3' | PyPyPyPyPyPy-γ-ImImHpHpImIm |

TABLE 129

12-ring Hairpin Polyamides for recognition of 8-bp 5'-WCCASNNW-3'

| DNA sequence | aromatic amino acid sequence |
|---|---|
| 2617) 5'W C C A G T T W-3' | PyPyPyImHpHp-γ-PyPyPyHpImIm |
| 2618) 5'W C C A G T A W-3' | PyPyPyImHpPy-γ-HpPyPyHpImIm |
| 2619) 5'W C C A G T G W-3' | PyPyPyImHpIm-γ-PyPyPyHpImIm |
| 2620) 5'W C C A G T C W-3' | PyPyPyImHpPy-γ-ImPyPyHpImIm |
| 2621) 5'W C C A G A T W-3' | PyPyPyImPyHp-γ-PyHpPyHpImIm |
| 2622) 5'W C C A G A A W-3' | PyPyPyImPyPy-γ-HpHpPyHpImIm |
| 2623) 5'W C C A G A G W-3' | PyPyPyImPyIm-γ-PyHpPyHpImIm |
| 2624) 5'W C C A G A C W-3' | PyPyPyImPyPy-γ-ImHpPyHpImIm |
| 2625) 5'W C C A G G T W-3' | PyPyPyImImHp-γ-PyPyPyHpImIm |
| 2626) 5'W C C A G G A W-3' | PyPyPyImImPy-γ-HpPyPyHpImIm |
| 2627) 5'W C C A G C T W-3' | PyPyPyImPyHp-γ-PyImPyHpImIm |
| 2628) 5'W C C A G C A W-3' | PyPyPyImPyPy-γ-HpImPyHpImIm |
| 2629) 5'W C C A G G G W-3' | PyPyPyImImIm-γ-PyPyPyHpImIm |
| 2630) 5'W C C A G G C W-3' | PyPyPyImImPy-γ-ImPyPyHpImIm |
| 2631) 5'W C C A G C G W-3' | PyPyPyImPyIm-γ-PyImPyHpImIm |
| 2632) 5'W C C A G C C W-3' | PyPyPyImPyPy-γ-ImImPyHpImIm |
| 2633) 5'W C C A C T T W-3' | PyPyPyPyHpHp-γ-PyPyImHpImIm |
| 2634) 5'W C C A C T A W-3' | PyPyPyPyHpPy-γ-HpPyImHpImIm |
| 2635) 5'W C C A C T G W-3' | PyPyPyPyHpIm-γ-PyPyImHpImIm |
| 2636) 5'W C C A C T C W-3' | PyPyPyPyHpPy-γ-ImPyImHpImIm |
| 2637) 5'W C C A C A T W-3' | PyPyPyPyPyHp-γ-PyHpImHpImIm |
| 2638) 5'W C C A C A A W-3' | PyPyPyPyPyPy-γ-HpHpImHpImIm |
| 2639) 5'W C C A C A G W-3' | PyPyPyPyPyIm-γ-PyHpImHpImIm |
| 2640) 5'W C C A C A C W-3' | PyPyPyPyPyPy-γ-ImHpImHpImIm |
| 2641) 5'W C C A C G T W-3' | PyPyPyImHp-γ-PyPyImHpImIm |
| 2642) 5'W C C A C G A W-3' | PyPyPyImPy-γ-HpPyImHpImIm |
| 2643) 5'W C C A C C T W-3' | PyPyPyPyPyHp-γ-PyImImHpImIm |
| 2644) 5'W C C A C C A W-3' | PyPyPyPyPyPy-γ-HpImImHpImIm |
| 2645) 5'W C C A C G G W-3' | PyPyPyImIm-γ-PyPyImHpImIm |
| 2646) 5'W C C A C G C W-3' | PyPyPyImPy-γ-ImPyImHpImIm |
| 2647) 5'W C C A C C G W-3' | PyPyPyPyPyIm-γ-PyImImHpImIm |
| 2648) 5'W C C A C C C W-3' | PyPyPyPyPyPy-γ-ImImImHpImIm |

TABLE 130

12-ring Hairpin Polyamides for recognition of 8-bp 5'-WCCCWNNW-3'

| DNA sequence | aromatic amino acid sequence |
|---|---|
| 2649) 5'W C C C T T T W-3' | PyPyPyHpHpHp-γ-PyPyPyImImIm |
| 2650) 5'W C C C T T A W-3' | PyPyPyHpHpPy-γ-HpPyPyImImIm |
| 2651) 5'W C C C T T G W-3' | PyPyPyHpHpIm-γ-PyPyPyImImIm |
| 2652) 5'W C C C T T C W-3' | PyPyPyHpHpPy-γ-ImPyPyImImIm |
| 2653) 5'W C C C T A T W-3' | PyPyPyHpPyHp-γ-PyHpPyImImIm |
| 2654) 5'W C C C r A A W-3' | PyPyPyHpPyPy-γ-HpHpPyImImIm |
| 2655) 5'W C C C T A G W-3' | PyPyPyHpPyIm-γ-PyHpPyImImIm |
| 2656) 5'W C C C T A C W-3' | PyPyPyHpPyPy-γ-ImHpPyImImIm |
| 2657) 5'W C C C T G T W-3' | PyPyPyHpImHp-γ-PyPyPyImImIm |
| 2658) 5'W C C C T G A W-3' | PyPyPyHpImPy-γ-HpPyPyImImIm |
| 2659) 5'W C C C T G G W-3' | PyPyPyHpImIm-γ-PyPyPyImImIm |
| 2660) 5'W C C C T G C W-3' | PyPyPyHpImPy-γ-ImPyPyImImIm |
| 2661) 5'W C C C T C T W-3' | PyPyPyHpPyHp-γ-PyImPyImImIm |
| 2662) 5'W C C C T C A W-3' | PyPyPyHpPyPy-γ-HpImPyImImIm |
| 2663) 5'W C C C T C G W-3' | PyPyPyHpPyIm-γ-PyImPyImImIm |
| 2664) 5'W C C C T C C W-3' | PyPyPyHpPyPy-γ-ImImPyImImIm |
| 2665) 5'W C C C A T T W-3' | PyPyPyPyHpHp-γ-PyPyHpImImIm |
| 2666) 5'W C C C A T A W-3' | PyPyPyPyHpPy-γ-HpPyHpImImIm |
| 2667) 5'W C C C A T G W-3' | PyPyPyPyHpIm-γ-PyPyHpImImIm |
| 2668) 5'W C C C A T C W-3' | PyPyPyPyHpPy-γ-ImPyHpImImIm |
| 2669) 5'W C C C A A T W-3' | PyPyPyPyPyHp-γ-PyHpHpImImIm |
| 2670) 5'W C C C A A A W-3' | PyPyPyPyPyPy-γ-HpHpHpImImIm |
| 2671) 5'W C C C A A G W-3' | PyPyPyPyPyIm-γ-PyHpHpImImIm |
| 2672) 5'W C C C A A C W-3' | PyPyPyPyPyPy-γ-ImHpHpImImIm |
| 2673) 5'W C C C A G T W-3' | PyPyPyPyImHp-γ-PyPyHpImImIm |
| 2674) 5'W C C C A G A W-3' | PyPyPyPyImPy-γ-HpPyHpImImIm |
| 2675) 5'W C C C A G G W-3' | PyPyPyPyImIm-γ-PyPyHpImImIm |
| 2676) 5'W C C C A G C W-3' | PyPyPyPyImPy-γ-ImPyHpImImIm |
| 2677) 5'W C C C A C T W-3' | PyPyPyPyPyHp-γ-PyImHpImImIm |
| 2678) 5'W C C C A C A W-3' | PyPyPyPyPyPy-γ-HpImHpImImIm |
| 2679) 5'W C C C A C G W-3' | PyPyPyPyPyIm-γ-PyImHpImImIm |
| 2680) 5'W C C C A C C W-3' | PyPyPyPyPyPy-γ-ImImHpImImIm |

TABLE 131

12-ring Hairpin Polyamides for recognition of 8-bp 5'-WCCCSNNW-3'

| DNA sequence | aromatic amino acid sequence |
|---|---|
| 2681) 5'W C C C G T T W-3' | PyPyPyImHpHp-γ-PyPyPyImImIm |
| 2682) 5'W C C C G T A W-3' | PyPyPyImHpPy-γ-HpPyPyImImIm |
| 2683) 5'W C C C G T G W-3' | PyPyPyImHpIm-γ-PyPyPyImImIm |
| 2684) 5'W C C C G T C W-3' | PyPyPyImHpPy-γ-ImPyPyImImIm |
| 2685) 5'W C C C G A T W-3' | PyPyPyImPyHp-γ-PyHpPyImImIm |
| 2686) 5'W C C C G A A W-3' | PyPyPyImPyPy-γ-HpHpPyImImIm |
| 2687) 5'W C C C G A G W-3' | PyPyPyImPyIm-γ-PyHpPyImImIm |
| 2688) 5'W C C C G A C W-3' | PyPyPyImPyPy-γ-ImHpPyImImIm |
| 2689) 5'W C C C G G T W-3' | PyPyPyImImHp-γ-PyPyPyImImIm |
| 2690) 5'W C C C G G A W-3' | PyPyPyImImPy-γ-HpPyPyImImIm |
| 2691) 5'W C C C G C T W-3' | PyPyPyImPyHp-γ-PyImPyImImIm |
| 2692) 5'W C C C G C A W-3' | PyPyPyImPyPy-γ-HpImPyImImIm |
| 2693) 5'W C C C C T T W-3' | PyPyPyPyHpHp-γ-PyPyImPyImIm |
| 2694) 5'W C C C C T A W-3' | PyPyPyPyHpPy-γ-HpPyImImImIm |
| 2695) 5'W C C C C T G W-3' | PyPyPyPyHpIm-γ-PyPyImImImIm |
| 2696) 5'W C C C C T C W-3' | PyPyPyPyHpPy-γ-ImPyImImImIm |
| 2697) 5'W C C C C A T W-3' | PyPyPyPyPyHp-γ-PyHpImImImIm |
| 2698) 5'W C C C C A A W-3' | PyPyPyPyPyPy-γ-HpHpImImImIm |
| 2699) 5'W C C C C A G W-3' | PyPyPyPyPyIm-γ-PyHpImImImIm |
| 2690) 5'W C C C C A C W-3' | PyPyPyPyPyPy-γ-ImHpImImImIm |
| 2701) 5'W C C C C G T W-3' | PyPyPyPyImHp-γ-PyPyImImImIm |
| 2702) 5'W C C C C G A W-3' | PyPyPyPyImPy-γ-HpPyImImImIm |
| 2703) 5'W C C C C C T W-3' | PyPyPyPyPyHp-γ-PyImImImImIm |
| 2704) 5'W C C C C C A W-3' | PyPyPyPyPyPy-γ-HpImImImImIm |
| G107) 5'W C C C G G G W-3' | PyPyPyImImIm-γ-PyPyPyImImIm |
| G108) 5'W C C C G G C W-3' | PyPyPyImImPy-γ-ImPyPyImImIm |
| G109) 5'W C C C G C G W-3' | PyPyPyImPyIm-γ-PyImPyImImIm |
| G110) 5'W C C C G C C W-3' | PyPyPyImPyPy-γ-ImImPyImImIm |
| G111) 5'W C C C C G G W-3' | PyPyPyPyImIm-γ-PyPyImImImIm |
| G112) 5'W C C C C G C W-3' | PyPyPyPyImPy-γ-ImPyImImImIm |
| G113) 5'W C C C C C G W-3' | PyPyPyPyPyIm-γ-PyImImImImIm |
| G114) 5'W C C C C C C W-3' | PyPyPyPyPyPy-γ-ImImImImImIm |

TABLE 132

12-ring Hairpin Polyamides for recognition of 8-hp 5'-WCAGWNNW-3'

| DNA sequence | aromatic amino acid sequence |
|---|---|
| 2705) 5'W C A G T T T W-3' | PyPyImHpHpHp-γ-PyPyPyPyHpIm |
| 2706) 5'W C A G T T A W-3' | PyPyImHpHpPy-γ-HpPyPyPyHpIm |
| 2707) 5'W C A G T T G W-3' | PyPyImHpHpIm-γ-PyPyPyPyHpIm |
| 2708) 5'W C A G T T C W-3' | PyPyImHpHpPy-γ-ImPyPyPyHpIm |
| 2709) 5'W C A G T A T W-3' | PyPyImHpPyHp-γ-PyHpPyPyHpIm |
| 2700) 5'W C A G T A A W-3' | PyPyImHpPyPy-γ-HpHpPyPyHpIm |
| 2711) 5'W C A G T A G W-3' | PyPyImHpPyIm-γ-PyHpPyPyHpIm |
| 2712) 5'W C A G T A C W-3' | PyPyImHpPyPy-γ-ImHpPyPyHpIm |
| 2713) 5'W C A G T G T W-3' | PyPyImHpImHp-γ-PyPyPyPyHpIm |
| 2714) 5'W C A G T G A W-3' | PyPyImHpImPy-γ-HpPyPyPyHpIm |
| 2715) 5'W C A G T G G W-3' | PyPyImHpImIm-γ-PyPyPyPyHpIm |
| 2716) 5'W C A G T G C W-3' | PyPyImHpImPy-γ-ImPyPyPyHpIm |
| 2717) 5'W C A G T C T W-3' | PyPyImHpPyHp-γ-PyImPyPyHpIm |
| 2718) 5'W C A G T C A W-3' | PyPyImHpPyPy-γ-HpImPyPyHpIm |
| 2719) 5'W C A G T C G W-3' | PyPyImHpPyIm-γ-PyImPyPyHpIm |
| 2720) 5'W C A G T C C W-3' | PyPyImHpPyPy-γ-ImImPyPyHpIm |
| 2721) 5'W C A G A T T W-3' | PyPyImPyHpHp-γ-PyPyHpPyHpIm |
| 2722) 5'W C A G A T A W-3' | PyPyImPyHpPy-γ-HpPyHpPyHpIm |
| 2723) 5'W C A G A T G W-3' | PyPyImPyHpIm-γ-PyPyHpPyHpIm |
| 2724) 5'W C A G A T C W-3' | PyPyImPyHpPy-γ-ImPyHpPyHpIm |
| 2725) 5'W C A G A A T W-3' | PyPyImPyPyHp-γ-PyHpHpPyHpIm |
| 2726) 5'W C A G A A A W-3' | PyPyImPyPyPy-γ-HpHpHpPyHpIm |
| 2727) 5'W C A G A A G W-3' | PyPyImPyPyIm-γ-PyHpHpPyHpIm |
| 2728) 5'W C A G A A C W-3' | PyPyImPyPyPy-γ-ImHpHpPyHpIm |
| 2729) 5'W C A G A G T W-3' | PyPyImPyImHp-γ-PyPyHpPyHpIm |
| 2730) 5'W C A G A G A W-3' | PyPyImPyImPy-γ-HpPyHpPyHpIm |
| 2731) 5'W C A G A G G W-3' | PyPyImPyImIm-γ-PyPyHpPyHpIm |
| 2732) 5'W C A G A G C W-3' | PyPyImPyImPy-γ-ImPyHpPyHpIm |
| 2733) 5'W C A G A C T W-3' | PyPyImPyPyHp-γ-PyImHpPyHpIm |
| 2734) 5'W C A G A C A W-3' | PyPyImPyPyPy-γ-HpImHpPyHpIm |
| 2735) 5'W C A G A C G W-3' | PyPyImPyPyIm-γ-PyImHpPyHpIm |
| 2736) 5'W C A G A C C W-3' | PyPyImPyPyPy-γ-ImImHpPyHpIm |

TABLE 133

12-ring Hairpin Polyamides for recognition of 8-bp 5'-WCAGSNNW-3'

| DNA sequence | aromatic amino acid sequence |
|---|---|
| 2737) 5'W C A G G T T W-3' | PyPyImImHpHp-γ-PyPyPyPyHpIm |
| 2738) 5'W C A G G T A W-3' | PyFyImImHpPy-γ-HpPyPyPyHpIm |
| 2739) 5'W C A G G T G W-3' | PyPyImImHpIm-γ-PyPyPyPyHpIm |
| 2740) 5'W C A G G T C W-3' | PyPyImImHpPy-γ-ImPyPyPyHpIm |
| 2741) 5'W C A G G A T W-3' | PyPyImImPyHp-γ-PyHpPyPyHpIm |
| 2742) 5'W C A G G A A W-3' | PyPyImImPyPy-γ-HpHpPyPyHpIm |
| 2743) 5'W C A G G A G W-3' | PyPyImImPyIm-γ-PyHpPyPyHpIm |
| 2744) 5'W C A G G A C W-3' | PyPyImImPyPy-γ-ImHpPyPyHpIm |
| 2745) 5'W C A G G G T W-3' | PyPyImImImHp-γ-PyPyPyPyHpIm |
| 2746) 5'W C A G G G A W-3' | PyPyImImImPy-γ-HpPyPyPyHpIm |
| 2747) 5'W C A G G C T W-3' | PyPyImImPyHp-γ-PyImPyPyHpIm |
| 2748) 5'W C A G G C A W-3' | PyPyImImPyPy-γ-HpImPyPyHpIm |
| 2749) 5'W C A G C T T W-3' | PyPyImPyHpHp-γ-PyPyImPyHpIm |
| 2750) 5'W C A G C T A W-3' | PyPyImPyHpPy-γ-HpPyImPyHpIm |
| 2751) 5'W C A G C T G W-3' | PyPyImPyHpIm-γ-PyPyImPyHpIm |
| 2752) 5'W C A G C T C W-3' | PyPyImPyHpPy-γ-ImPyImPyHpIm |
| 2753) 5'W C A G C A T W-3' | PyPyImPyPyHp-γ-PyHpImPyHpIm |
| 2754) 5'W C A G C A A W-3' | PyPyImPyPyPy-γ-HpHpImPyHpIm |
| 2755) 5'W C A G C A G W-3' | PyPyImPyPyIm-γ-PyHpImPyHpIm |
| 2756) 5'W C A G C A C W-3' | PyPyImPyPyPy-γ-ImHpImPyHpIm |
| 2757) 5'W C A G C G T W-3' | PyPyImPyImHp-γ-PyPyImPyHpIm |
| 2758) 5'W C A G C G A W-3' | PyPyImPyImPy-γ-HpPyImPyHpIm |
| 2759) 5'W C A G C C T W-3' | PyPyImPyPyHp-γ-PyImImPyHpIm |
| 2760) 5'W C A G C C A W-3' | PyPyImPyPyPy-γ-HpImImPyHpIm |
| 2761) 5'W C A G G G G W-3' | PyPyImImImIm-γ-PyPyPyPyHpIm |
| 2762) 5'W C A G G G C W-3' | PyPyImImImPy-γ-ImPyPyPyHpIm |
| 2763) 5'W C A G G C G W-3' | PyPyImImPyIm-γ-PyImPyPyHpIm |
| 2764) 5'W C A G G C C W-3' | PyPyImImPyPy-γ-ImImPyPyHpIm |
| 2765) 5'W C A G C G G W-3' | PyPyImPyImIm-γ-PyPyImPyHpIm |
| 2766) 5'W C A G C G C W-3' | PyPyImPyImPy-γ-ImPyImPyHpIm |
| 2767) 5'W C A G C C G W-3' | PyPyImPyPyIm-γ-PyImImPyHpIm |
| 2768) 5'W C A G C C C W-3' | PyPyImPyPyPy-γ-ImImImPyHpIm |

TABLE 134

12-ring Hairpin Polyamides for recognition of 8-bp 5'-WCATWNNW-3'

| DNA sequence | aromatic amino acid sequence |
|---|---|
| 2769) 5'W C A T T T T W-3' | PyPyHpHpHpHp-γ-PyPyPyPyHpIm |
| 2770) 5'W C A T T T A W-3' | PyPyHpHpHpPy-γ-HpPyPyPyHpIm |
| 2771) 5'W C A T T T G W-3' | PyPyHpHpHpIm-γ-PyPyPyPyHpIm |
| 2772) 5'W C A T T T C W-3' | PyPyHpHpHpPy-γ-ImPyPyPyHpIm |
| 2773) 5'W C A T T A T W-3' | PyPyHpHpPyHp-γ-PyHpPyPyHpIm |
| 2774) 5'W C A T T A A W-3' | PyPyHpHpPyPy-γ-HpHpPyPyHpIm |
| 2775) 5'W C A T T A G W-3' | PyPyHpHpPyIm-γ-PyHpPyPyHpIm |
| 2776) 5'W C A T T A C W-3' | PyPyHpHpPyPy-γ-ImHpPyPyHpIm |
| 2777) 5'W C A T T G T W-3' | PyPyHpHpImHp-γ-PyPyPyPyHpIm |
| 2778) 5'W C A T T G A W-3' | PyPyHpHpImPy-γ-HpPyPyPyHpIm |
| 2779) 5'W C A T T G G W-3' | PyPyHpHpImIm-γ-PyPyPyPyHpIm |
| 2780) 5'W C A T T G C W-3' | PyPyHpHpImPy-γ-ImPyPyPyHpIm |
| 2781) 5'W C A T T C T W-3' | PyPyHpHpPyHp-γ-PyImPyPyHpIm |
| 2782) 5'W C A T T C A W-3' | PyPyHpHpPyPy-γ-HpImPyPyHpIm |
| 2783) 5'W C A T T C G W-3' | PyPyHpHpPyIm-γ-PyImPyPyHpIm |
| 2784) 5'W C A T T C C W-3' | PyPyHpHpPyPy-γ-ImImPyPyHpIm |
| 2785) 5'W C A T A T T W-3' | PyPyHpPyBpHp-γ-PyPyHpPyHpIm |
| 2786) 5'W C A T A T A W-3' | PyPyHpPyHpPy-γ-HpPyHpPyHpIm |
| 2787) 5'W C A T A T G W-3' | PyPyHpPyHpIm-γ-PyPyHpPyHpIm |
| 2788) 5'W C A T A T C W-3' | PyPyHpPyHpPy-γ-ImPyHpPyHpIm |
| 2789) 5'W C A T A A T W-3' | PyPyHpPyPyHp-γ-PyHpHpPyHpIm |
| 2790) 5'W C A T A A A W-3' | PyPyHpPyPyPy-γ-HpHpHpPyHpIm |
| 2791) 5'W C A T A A G W-3' | PyPyHpPyPyIm-γ-PyHpHpPyHpIm |
| 2792) 5'W C A T A A C W-3' | PyPyHpPyPyPy-γ-ImHpHpPyHpIm |
| 2793) 5'W C A T A G T W-3' | PyPyHpPyImHp-γ-PyPyHpPyHpIm |
| 2794) 5'W C A T A G A W-3' | PyPyHpPyImPy-γ-HpPyHpPyHpIm |
| 2795) 5'W C A T A G G W-3' | PyPyHpPyImIm-γ-PyPyHpPyHpIm |
| 2796) 5'W C A T A G C W-3' | PyPyHpPyImPy-γ-ImPyHpPyHpIm |
| 2797) 5'W C A T A C T W-3' | PyPyHpPyPyHp-γ-PyImHpPyHpIm |
| 2798) 5'W C A T A C A W-3' | PyPyHpPyPyPy-γ-HpImHpPyHpIm |
| 2799) 5'W C A T A C G W-3' | PyPyHpPyPyIm-γ-PyImHpPyHpIm |
| 2800) 5'W C A T A C C W-3' | PyPyHpPyPyPy-γ-ImImHpPyHpIm |

TABLE 135

12-ring Hairpin Polyamides for recognition of
8-bp 5'-WCATSNNW-3'

| | DNA sequence | aromatic amino acid sequence |
|---|---|---|
| 2801) | 5'W C A T G T T W-3' | PyPyHpImHpHp-γ-PyPyPyPyHpIm |
| 2802) | 5'W C A T G T A W-3' | PyPyHpImHpPy-γ-HpPyPyPyHpIm |
| 2803) | 5'W C A T G T G W-3' | PyPyHpImHpIm-γ-PyPyPyPyHpIm |
| 2804) | 5'W C A T G T C W-3' | PyPyHpImHpPy-γ-ImPyPyPyHpIm |
| 2805) | 5'W C A T G A T W-3' | PyPyHpImPyHp-γ-PyHpPyPyHpIm |
| 2806) | 5'W C A T G A A W-3' | PyPyHpImPyPy-γ-HpPyPyPyHpIm |
| 2807) | 5'W C A T G A G W-3' | PyPyHpImPyIm-γ-PyHpPyPyHpIm |
| 2808) | 5'W C A T G A C W-3' | PyPyHpImPyPy-γ-ImHpPyPyHpIm |
| 2809) | 5'W C A T G G T W-3' | PyPyHpImImHp-γ-PyPyPyPyHpIm |
| 2810) | 5'W C A T G G A W-3' | PyPyHpImImPy-γ-HpPyPyPyHpIm |
| 2811) | 5'W C A T G G T W-3' | PyPyHpImPyHp-γ-PyImPyPyHpIm |
| 2812) | 5'W C A T G C A W-3' | PyPyHpImPyPy-γ-HpImPyPyHpIm |
| 2813) | 5'W C A T G G G W-3' | PyPyHpImImIm-γ-PyPyPyPyHpIm |
| 2814) | 5'W C A T G G C W-3' | PyPyHpImImPy-γ-ImPyPyPyHpIm |
| 2815) | 5'W C A T G C G W-3' | PyPyHpImPyIm-γ-PyImPyPyHpIm |
| 2816) | 5'W C A T G C C W-3' | PyPyHpImPyPy-γ-ImImPyPyHpIm |
| 2817) | 5'W C A T C T T W-3' | PyPyHpPyHpHp-γ-PyPyImPyHpIm |
| 2818) | 5'W C A T C T A W-3' | PyPyHpPyHpPy-γ-HpPyImPyHpIm |
| 2819) | 5'W C A T C T G W-3' | PyPyHpPyHpIm-γ-PyPyImPyHpIm |
| 2820) | 5'W C A T C T C W-3' | PyPyHpPyHpPy-γ-ImPyImPyHpIm |
| 2821) | 5'W C A T C A T W-3' | PyPyHpPyPyHp-γ-PyHpImPyHpIm |
| 2822) | 5'W C A T C A A W-3' | PyPyHpPyPyPy-γ-HpImImPyHpIm |
| 2823) | 5'W C A T C A G W-3' | PyPyHpPyPyIm-γ-PyHpImPyHpIm |
| 2824) | 5'W C A T C A C W-3' | PyPyHpPyPyPy-γ-ImHpImPyHpIm |
| 2825) | 5'W C A T C G T W-3' | PyPyHpPyImHp-γ-PyPyImPyHpIm |
| 2826) | 5'W C A T C G A W-3' | PyPyHpPyImPy-γ-HpPyImPyHpIm |
| 2827) | 5'W C A T C C T W-3' | PyPyHpPyPyHp-γ-PyImImPyHpIm |
| 2828) | 5'W C A T C C A W-3' | PyPyHpPyPyPy-γ-HpImImPyHpIm |
| 2829) | 5'W C A T C G G W-3' | PyPyHpPyImIm-γ-PyPyImPyHpIm |
| 2830) | 5'W C A T C G C W-3' | PyPyHpPyImPy-γ-ImPyImPyHpIm |
| 2831) | 5'W C A T C C G W-3' | PyPyHpPyPyIm-γ-PyImImPyHpIm |
| 2832) | 5'W C A T C C C W-3' | PyPyHpPyPyPy-γ-ImImImPyHpIm |

TABLE 136

12-ring Hairpin Polyamides for recognition of
8-bp 5'-WCAAWNNW-3'

| | DNA sequence | aromatic amino acid sequence |
|---|---|---|
| 2833) | 5'W C A A T T T W-3' | PyPyPyHpHpHp-γ-PyPyPyHpHpIm |
| 2834) | 5'W C A A T T A W-3' | PyPyPyHpHpPy-γ-HpPyPyHpHpIm |
| 2835) | 5'W C A A T T G W-3' | PyPyPyHpHpIm-γ-PyPyPyHpHpIm |
| 2836) | 5'W C A A T T C W-3' | PyPyPyHpHpPy-γ-ImPyPyHpHpIm |
| 2837) | 5'W C A A T A T W-3' | PyPyPyHpPyHp-γ-PyHpPyHpHpIm |
| 2838) | 5'W C A A T A A W-3' | PyPyPyHpPyPy-γ-HpHpPyHpHpIm |
| 2839) | 5'W C A A T A G W-3' | PyPyPyHpPyIm-γ-PyHpPyHpHpIm |
| 2840) | 5'W C A A T A C W-3' | PyPyPyHpPyPy-γ-ImHpPyHpHpIm |
| 2841) | 5'W C A A T G T W-3' | PyPyPyHpImHp-γ-PyPyPyHpHpIm |
| 2842) | 5'W C A A T G A W-3' | PyPyPyHpImPy-γ-HpPyPyHpHpIm |
| 2843) | 5'W C A A T G G W-3' | PyPyPyHpImIm-γ-PyPyPyHpHpIm |
| 2844) | 5'W C A A T G C W-3' | PyPyPyHpImPy-γ-ImPyPyHpHpIm |
| 2845) | 5'W C A A T C T W-3' | PyPyPyHpPyHp-γ-PyImPyHpHpIm |
| 2846) | 5'W C A A T C A W-3' | PyPyPyHpPyPy-γ-HpImPyHpHpIm |
| 2847) | 5'W C A A T C G W-3' | PyPyPyHpPyIm-γ-PyImPyHpHpIm |
| 2848) | 5'W C A A T C C W-3' | PyPyPyHpPyPy-γ-ImImPyHpHpIm |
| 2849) | 5'W C A A A T T W-3' | PyPyPyPyHpHp-γ-PyPyHpHpHpIm |
| 2850) | 5'W C A A A T A W-3' | PyPyPyPyHpPy-γ-HpPyHpHpHpIm |
| 2851) | 5'W C A A A T G W-3' | PyPyPyPyHpIm-γ-PyPyHpHpHpIm |
| 2852) | 5'W C A A A T C W-3' | PyPyPyPyHpPy-γ-ImPyHpHpHpIm |
| 2853) | 5'W C A A A A T W-3' | PyPyPyPyPyHp-γ-PyHpHpHpHpIm |
| 2854) | 5'W C A A A A A W-3' | PyPyPyPyPyPy-γ-HpHpHpHpHpIm |
| 2855) | 5'W C A A A A G W-3' | PyPyPyPyPyIm-γ-PyHpHpHpHpIm |
| 2856) | 5'W C A A A A C W-3' | PyPyPyPyPyPy-γ-ImHpHpHpHpIm |
| 2857) | 5'W C A A A G T W-3' | PyPyPyPyImHp-γ-PyPyHpHpHpIm |
| 2858) | 5'W C A A A G A W-3' | PyPyPyPyImPy-γ-HpPyHpHpHpIm |
| 2859) | 5'W C A A A G G W-3' | PyPyPyPyImIm-γ-PyPyHpHpHpIm |
| 2860) | 5'W C A A A G C W-3' | PyPyPyPyImPy-γ-ImPyHpHpHpIm |
| 2861) | 5'W C A A A C T W-3' | PyPyPyPyPyHp-γ-PyImHpHpHpIm |

TABLE 136-continued 12-ring Hairpin Polyamides for recognition of
8-bp 5'-WCAAWNNW-3'

| | DNA sequence | aromatic amino acid sequence |
|---|---|---|
| 2862) | 5'W C A A A C A W-3' | PyPyPyPyPyPy-γ-HpImHpHpHpIm |
| 2863) | 5'W C A A A C G W-3' | PyPyPyPyPyIm-γ-PyImHpHpHpIm |
| 2864) | 5'W C A A A C C W-3' | PyPyPyPyPyPy-γ-ImImHpHpHpIm |

TABLE 137

12-ring Hairpin Polyamides for recognition of
8-bp 5'-WCAASNNW-3'

| | DNA sequence | aromatic amino acid sequence |
|---|---|---|
| 2865) | 5'W C A A G T T W-3' | PyPyPyImHpHp-γ-PyPyPyHpHpIm |
| 2866) | 5'W C A A G T A W-3' | PyPyPyImHpPy-γ-HpPyPyHpHpIm |
| 2867) | 5'W C A A G T G W-3' | PyPyPyImHpIm-γ-PyPyPyHpHpIm |
| 2868) | 5'W C A A G T C W-3' | PyPyPyImHpPy-γ-ImPyPyHpHpIm |
| 2869) | 5'W C A A G A T W-3' | PyPyPyImPyHp-γ-PyHpPyHpHpIm |
| 2870) | 5'W C A A G A A W-3' | PyPyPyImPyPy-γ-HpHpPyHpHpIm |
| 2871) | 5'W C A A G A G W-3' | PyPyPyImPyIm-γ-PyHpPyHpHpIm |
| 2872) | 5'W C A A G A C W-3' | PyPyPyImPyPy-γ-ImHpPyHpHpIm |
| 2873) | 5'W C A A G G T W-3' | PyPyPyImImHp-γ-PyPyPyHpHpIm |
| 2874) | 5'W C A A G G A W-3' | PyPyPyImImPy-γ-HpPyPyHpHpIm |
| 2875) | 5'W C A A G C T W-3' | PyPyPyImPyHp-γ-PyImPyHpHpIm |
| 2876) | 5'W C A A G C A W-3' | PyPyPyImPyPy-γ-HpImPyHpHpIm |
| 2877) | 5'W C A A G G G W-3' | PyPyPyImImIm-γ-PyPyPyHpHpIm |
| 2878) | 5'W C A A G G C W-3' | PyPyPyImImPy-γ-ImPyPyHpHpIm |
| 2879) | 5'W C A A G C G W-3' | PyPyPyImPyIm-γ-PyImPyHpHpIm |
| 2880) | 5'W C A A G C C W-3' | PyPyPyImPyPy-γ-ImImPyHpHpIm |
| 2881) | 5'W C A A C T T W-3' | PyPyPyPyHpHp-γ-PyPyImHpHpIm |
| 2882) | 5'W C A A C T A W-3' | PyPyPyPyHpPy-γ-HpPyImHpHpIm |
| 2883) | 5'W C A A C T G W-3' | PyPyPyPyHpIm-γ-PyPyImHpHpIm |
| 2884) | 5'W C A A C T C W-3' | PyPyPyPyHpPy-γ-ImPyImHpHpIm |
| 2885) | 5'W C A A C A T W-3' | PyPyPyPyPyHp-γ-PyHpImHpHpIm |
| 2886) | 5'W C A A C A A W-3' | PyPyPyPyPyPy-γ-HpHpImHpHpIm |
| 2887) | 5'W C A A C A G W-3' | PyPyPyPyPyIm-γ-PyHpImHpHpIm |
| 2888) | 5'W C A A C A C W-3' | PyPyPyPyPyPy-γ-ImHpImHpHpIm |
| 2889) | 5'W C A A C G T W-3' | PyPyPyPyImHp-γ-PyPyImHpHpIm |
| 2890) | 5'W C A A C G A W-3' | PyPyPyPyImPy-γ-HpPyImHpHpIm |
| 2891) | 5'W C A A C C T W-3' | PyPyPyPyHpHp-γ-PyImImHpHpIm |
| 2892) | 5'W C A A C C A W-3' | PyPyPyPyPyPy-γ-HpImImHpHpIm |
| 2893) | 5'W C A A C G G W-3' | PyPyPyPyImIm-γ-PyPyImHpHpIm |
| 2894) | 5'W C A A C G C W-3' | PyPyPyPyImPy-γ-ImPyImHpHpIm |
| 2895) | 5'W C A A C C G W-3' | PyPyPyPyImIm-γ-PyImImHpHpIm |
| 2896) | 5'W C A A C C C W-3' | PyPyPyPyPyPy-γ-ImImImHpHpIm |

TABLE 138

12-ring Hairpin Polyamides for recognition of
8-bp 5'-WCACWNNW-3'

| | DNA sequence | aromatic ammo acid sequence |
|---|---|---|
| 2897) | 5'W C A C T T T W-3' | PyPyPyHpHpHp-γ-PyPyPyImHpIm |
| 2898) | 5'W C A C T T A W-3' | PyPyPyHpHpPy-γ-HpPyPyImHpIm |
| 2899) | 5'W C A C T T G W-3' | PyPyPyHpHpIm-γ-PyPyPyImHpIm |
| 2900) | 5'W C A C T T C W-3' | PyPyPyHpHpPy-γ-ImPyPyImHpIm |
| 2901) | 5'W C A C T A T W-3' | PyPyPyHpPyHp-γ-PyHpPyImHpIm |
| 2902) | 5'W C A C T A A W-3' | PyPyPyHpPyPy-γ-HpHpPyImHpIm |
| 2903) | 5'W C A C T A G W-3' | PyPyPyHpPyIm-γ-PyHpPyImHpIm |
| 2904) | 5'W C A C T A C W-3' | PyPyPyHpPyPy-γ-ImHpPyImHpIm |
| 2905) | 5'W C A C T G T W-3' | PyPyPyHpImHp-γ-PyPyPyImHpIm |
| 2906) | 5'W C A C T G A W-3' | PyPyPyHpImPy-γ-HpPyPyImHpIm |
| 2907) | 5'W C A C T G G W-3' | PyPyPyHpImIm-γ-PyPyPyImHpIm |
| 2908) | 5'W C A C T G C W-3' | PyPyPyHpImPy-γ-ImPyPyImHpIm |
| 2909) | 5'W C A C T C T W-3' | PyPyPyHpPyHp-γ-PyImPyImHpIm |
| 2910) | 5'W C A C T C A W-3' | PyPyPyHpPyPy-γ-HpImPyImHpIm |
| 2911) | 5'W C A C T C G W-3' | PyPyPyHpPyIm-γ-PyImPyImHpIm |
| 2912) | 5'W C A C T C C W-3' | PyPyPyHpPyPy-γ-ImImPyImHpIm |
| 2913) | 5'W C A C A T T W-3' | PyPyPyHpHpHp-γ-PyPyHpImHpIm |
| 2914) | 5'W C A C A T A W-3' | PyPyPyHpHpPy-γ-HpPyHpImHpIm |

TABLE 138-continued 12-ring Hairpin Polyamides for recognition of
8-bp 5'-WCACWNNW-3'

| | DNA sequence | aromatic amino acid sequence |
|---|---|---|
| 2915) | 5'W C A C A T G W-3' | PyPyPyPyHpIm-γ-PyPyHpImHpIm |
| 2916) | 5'W C A C A T C W-3' | PyPyPyPyHpPy-γ-ImPyHpImHpIm |
| 2917) | 5'W C A C A A T W-3' | PyPyPyPyPyHp-γ-PyHpHpImHpIm |
| 2918) | 5'W C A C A A A W-3' | PyPyPyPyPyPy-γ-HpHpHpImHpIm |
| 2919) | 5'W C A C A A G W-3' | PyPyPyPyPyIm-γ-PyHpHpImHpIm |
| 2920) | 5'W C A C A A C W-3' | PyPyPyPyPyPy-γ-ImHpHpImHpIm |
| 2921) | 5'W C A C A G T W-3' | PyPyPyPyImHp-γ-PyPyHpImHpIm |
| 2922) | 5'W C A C A G A W-3' | PyPyPyPyImPy-γ-HpPyHpImHpIm |
| 2923) | 5'W C A C A G G W-3' | PyPyPyPyImIm-γ-PyPyHpImHpIm |
| 2924) | 5'W C A C A G C W-3' | PyPyPyPyImPy-γ-ImPyHpImHpIm |
| 2925) | 5'W C A C A C T W-3' | PyPyPyPyPyHp-γ-PyImHpImHpIm |
| 2926) | 5'W C A C A C A W-3' | PyPyPyPyPyPy-γ-HpImHpImHpIm |
| 2927) | 5'W C A C A C G W-3' | PyPyPyPyPyIm-γ-PyImHpImHpIm |
| 2928) | 5'W C A C A C C W-3' | PyPyPyPyPyPy-γ-ImImHpImHpIm |

TABLE 139

12-ring Hairpin Polyamides for recognition of
8-bp 5'-WCACSNNW-3'

| | DNA sequence | aromatic amino acid sequence |
|---|---|---|
| 2929) | 5'W C A C G T T W-3' | PyPyPyImHpHp-γ-PyPyPyImHpIm |
| 2930) | 5'W C A C G T A W-3' | PyPyPyImHpPy-γ-HpPyPyImHpIm |
| 2931) | 5'W C A C G T G W-3' | PyPyPyImHpIm-γ-PyPyPyImHpIm |
| 2932) | 5'W C A C G T C W-3' | PyPyPyImHpPy-γ-ImPyPyImHpIm |
| 2933) | 5'W C A C G A T W-3' | PyPyPyImPyHp-γ-PyHpPyImHpIm |
| 2934) | 5'W C A C G A A W-3' | PyPyPyImPyPy-γ-HpHpPyImHpIm |
| 2935) | 5'W C A C G A G W-3' | PyPyPyImPyIm-γ-PyHpPyImHpIm |
| 2936) | 5'W C A C G A C W-3' | PyPyPyImPyPy-γ-ImHpPyImHpIm |
| 2937) | 5'W C A C G G T W-3' | PyPyPyImImHp-γ-PyPyPyImHpIm |
| 2938) | 5'W C A C G G A W-3' | PyPyPyImImPy-γ-HpPyPyImHpIm |
| 2939) | 5'W C A C G C T W-3' | PyPyPyImPyHp-γ-PyImPyImHpIm |
| 2940) | 5'W C A C G C A W-3' | PyPyPyImPyPy-γ-HpImPyImHpIm |
| 2941) | 5'W C A C C T T W-3' | PyPyPyPyHpHp-γ-PyPyImImHpIm |
| 2942) | 5'W C A C C T A W-3' | PyPyPyPyHpPy-γ-HpPyImImHpIm |
| 2943) | 5'W C A C C T G W-3' | PyPyPyPyHpIm-γ-PyPyImImHpIm |
| 2944) | 5'W C A C C T C W-3' | PyPyPyPyHpPy-γ-ImPyImImHpIm |
| 2945) | 5'W C A C C A T W-3' | PyPyPyPyPyHp-γ-PyHpImImHpIm |
| 2946) | 5'W C A C C A A W-3' | PyPyPyPyPyPy-γ-HpHpImImHpIm |
| 2947) | 5'W C A C C A G W-3' | PyPyPyPyPyIm-γ-PyHpImImHpIm |
| 2948) | 5'W C A C C A C W-3' | PyPyPyPyPyPy-γ-ImHpImImHpIm |
| 2949) | 5'W C A C C G T W-3' | PyPyPyPyImHp-γ-PyPyImImHpIm |
| 2950) | 5'W C A C C G A W-3' | PyPyPyPyImPy-γ-HpPyImImHpIm |
| 2951) | 5'W C A C C C T W-3' | PyPyPyPyPyHp-γ-PyImImImHpIm |
| 2952) | 5'W C A C C C A W-3' | PyPyPyPyPyPy-γ-HpImImImHpIm |
| 2953) | 5'W C A C G G G W-3' | PyPyPyImImIm-γ-PyPyPyImHpIm |
| 2954) | 5'W C A C G G C W-3' | PyPyPyImImPy-γ-ImPyPyImHpIm |
| 2955) | 5'W C A C G C G W-3' | PyPyPyImPyIm-γ-PyImPyImHpIm |
| 2956) | 5'W C A C G C C W-3' | PyPyPyImPyPy-γ-ImImPyImHpIm |
| 2957) | 5'W C A C C G G W-3' | PyPyPyPyImIm-γ-PyPyImImHpIm |
| 2958) | 5'W C A C C G C W-3' | PyPyPyPyImPy-γ-ImPyImImHpIm |
| 2959) | 5'W C A C C C G W-3' | PyPyPyPyPyIm-γ-PyImImImHpIm |
| 2960) | 5'W C A C C C C W-3' | PyPyPyPyPyPy-γ-ImImImImHpIm |

TABLE 140

12-ring Hairpin Polyamides for recognition of
8-bp 5'-WCTGWNNW-3'

| | DNA sequence | aromatic amino acid sequence |
|---|---|---|
| 2961) | 5'W C T G T T T W-3' | PyHpImHpHpHp-γ-PyPyPyPyPyIm |
| 2962) | 5'W C T G T T A W-3' | PyHpImHpHpPy-γ-HpPyPyPyPyIm |
| 2963) | 5'W C T G T T G W-3' | PyHpImHpHpIm-γ-PyPyPyPyPyIm |
| 2964) | 5'W C T G T T C W-3' | PyHpImHpHpPy-γ-ImPyPyPyPyIm |
| 2965) | 5'W C T G T A T W-3' | PyHpImHpPyHp-γ-PyHpPyPyPyIm |
| 2966) | 5'W C T G T A A W-3' | PyHpImHpPyPy-γ-HpHpPyPyPyIm |
| 2967) | 5'W C T G T A G W-3' | PyHpImHpPyIm-γ-PyHpPyPyPyIm |

TABLE 140-continued 12-ring Hairpin Polyamides for recognition of
8-bp 5'-WCTGWNNW-3'

| | DNA sequence | aromatic amino acid sequence |
|---|---|---|
| 2968) | 5'W C T G T A C W-3' | PyHpImHpPyPy-γ-ImHpPyPyPyIm |
| 2969) | 5'W C T G T G T W-3' | PyHpImHpImHp-γ-PyPyPyPyPyIm |
| 2970) | 5'W C T G T G A W-3' | PyHpImHpImPy-γ-HpPyPyPyPyIm |
| 2971) | 5'W C T G T G G W-3' | PyHpImHpImIm-γ-PyPyPyPyPyIm |
| 2972) | 5'W C T G T G C W-3' | PyHpImHpImPy-γ-ImPyPyPyPyIm |
| 2973) | 5'W C T G T C T W-3' | PyHpImHpPyHp-γ-PyImPyPyPyIm |
| 2974) | 5'W C T G T C A W-3' | PyHpImHpPyPy-γ-HpImPyPyPyIm |
| 2975) | 5'W C T G T C G W-3' | PyHpImHpPyIm-γ-PyImPyPyPyIm |
| 2976) | 5'W C T G T C C W-3' | PyHpImHpPyPy-γ-ImImPyPyPyIm |
| 2977) | 5'W C T G A T T W-3' | PyHpImPyHpHp-γ-PyPyHpPyPyIm |
| 2978) | 5'W C T G A T A W-3' | PyHpImPyHpPy-γ-HpPyHpPyPyIm |
| 2979) | 5'W C T G A T G W-3' | PyHpImPyHpIm-γ-PyPyHpPyPyIm |
| 2980) | 5'W C T G A T C W-3' | PyHpImPyHpPy-γ-ImPyHpPyPyIm |
| 2981) | 5'W C T G A A T W-3' | PyHpImPyPyHp-γ-PyHpHpPyPyIm |
| 2982) | 5'W C T G A A A W-3' | PyHpImPyPyPy-γ-HpHpHpPyPyIm |
| 2983) | 5'W C T G A A G W-3' | PyHpImPyPyIm-γ-PyHpHpPyPyIm |
| 2984) | 5'W C T G A A C W-3' | PyHpImPyPyPy-γ-ImHpHpPyPyIm |
| 2985) | 5'W C T G A G T W-3' | PyHpImPyImHp-γ-PyPyHpPyPyIm |
| 2986) | 5'W C T G A G A W-3' | PyHpImPyImPy-γ-HpPyHpPyPyIm |
| 2987) | 5'W C T G A G G W-3' | PyHpImPyImIm-γ-PyPyHpPyPyIm |
| 2988) | 5'W C T G A G C W-3' | PyHpImPyImPy-γ-ImPyHpPyPyIm |
| 2989) | 5'W C T G A C T W-3' | PyHpImPyPyHp-γ-PyImHpPyPyIm |
| 2990) | 5'W C T G A C A W-3' | PyHpImPyPyPy-γ-HpImHpPyPyIm |
| 2991) | 5'W C T G A C G W-3' | PyHpImPyPyIm-γ-PyImHpPyPyIm |
| 2992) | 5'W C T G A C C W-3' | PyHpImPyPyPy-γ-ImImHpPyPyIm |

TABLE 141

12-ring Hairpin Polyamides for recognition of
8-bp 5'-WCTGSNNW-3'

| | DNA sequence | aromatic amino acid sequence |
|---|---|---|
| 2993) | 5'W C T G G T T W-3' | PyHpImImHpHp-γ-PyPyPyPyPyIm |
| 2994) | 5'W C T G G T A W-3' | PyHpImImHpPy-γ-HpPyPyPyPyIm |
| 2995) | 5'W C T G G T G W-3' | PyHpImImHpIm-γ-PyPyPyPyPyIm |
| 2996) | 5'W C T G G T C W-3' | PyHpImImHpPy-γ-ImPyPyPyPyIm |
| 2997) | 5'W C T G G A T W-3' | PyHpImImPyHp-γ-PyHpPyPyPyIm |
| 2998) | 5'W C T G G A A W-3' | PyHpImImPyPy-γ-HpHpPyPyPyIm |
| 2999) | 5'W C T G G A G W-3' | PyHpImImPyIm-γ-PyHpPyPyPyIm |
| 3000) | 5'W C T G G A C W-3' | PyHpImImPyPy-γ-ImHpPyPyPyIm |
| 3001) | 5'W C T G G G T W-3' | PyHpImImImHp-γ-PyPyPyPyPyIm |
| 3002) | 5'W C T G G G A W-3' | PyHpImImImPy-γ-HpPyPyPyPyIm |
| 3003) | 5'W C T G G C T W-3' | PyHpImImPyHp-γ-PyImPyPyPyIm |
| 3004) | 5'W C T G G C A W-3' | PyHpImImPyPy-γ-HpImPyPyPyIm |
| 3005) | 5'W C T G C T T W-3' | PyHpImPyHpHp-γ-PyPyImPyPyIm |
| 3006) | 5'W C T G C T A W-3' | PyHpImPyHpPy-γ-HpPyImPyPyIm |
| 3007) | 5'W C T G C T G W-3' | PyHpImPyHpIm-γ-PyPyImPyPyIm |
| 3008) | 5'W C T G C T C W-3' | PyHpImPyHpPy-γ-ImPyImPyPyIm |
| 3009) | 5'W C T G C A T W-3' | PyHpImPyPyHp-γ-PyHpImPyPyIm |
| 3010) | 5'W C T G C A A W-3' | PyHpImPyPyPy-γ-HpHpImPyPyIm |
| 3011) | 5'W C T G C A G W-3' | PyHpImPyPyIm-γ-PyHpImPyPyIm |
| 3012) | 5'W C T G C A C W-3' | PyHpImPyPyPy-γ-ImHpImPyPyIm |
| 3013) | 5'W C T G C G T W-3' | PyHpImPyImHp-γ-PyPyImPyPyIm |
| 3014) | 5'W C T G C G A W-3' | PyHpImPyImPy-γ-HpPyImPyPyIm |
| 3015) | 5'W C T G C C T W-3' | PyHpImPyPyHp-γ-PyImImPyPyIm |
| 3016) | 5'W C T G C C A W-3' | PyHpImPyPyPy-γ-HpImImPyPyIm |
| 3017) | 5'W C T G G G G W-3' | PyHpImImImIm-γ-PyPyPyPyPyIm |
| 3018) | 5'W C T G G G C W-3' | PyHpImImImPy-γ-ImPyPyPyPyIm |
| 3019) | 5'W C T G G C G W-3' | PyHpImImPyIm-γ-PyImPyPyPyIm |
| 3020) | 5'W C T G G C C W-3' | PyHpImImPyPy-γ-ImImPyPyPyIm |
| 3021) | 5'W C T G C G G W-3' | PyHpImPyImIm-γ-PyPyImPyPyIm |
| 3022) | 5'W C T G C G C W-3' | PyHpImPyImPy-γ-ImPyImPyPyIm |
| 3023) | 5'W C T G C C G W-3' | PyHpImPyPyIm-γ-PyImImPyPyIm |
| 3024) | 5'W C T G C C C W-3' | PyHpImPyPyPy-γ-ImImImPyPyIm |

TABLE 142

12-ring Hairpin Polyamides for recognition of 8-bp 5'-WCTTWNNW-3'

| | DNA sequence | aromatic amino acid sequence |
|---|---|---|
| 3025) | 5'W C T T T T T W-3' | PyHpHpHpHpHp-γ-PyPyPyPyPyIm |
| 3026) | 5'W C T T T T A W-3' | PyHpHpHpHpPy-γ-HpPyPyPyPyIm |
| 3027) | 5'W C T T T T G W-3' | PyHpHpHpHpIm-γ-PyPyPyPyPyIm |
| 3028) | 5'W C T T T T C W-3' | PyHpHpHpHpPy-γ-ImPyPyPyPyIm |
| 3029) | 5'W C T T T A T W-3' | PyHpHpHpPyHp-γ-PyHpPyPyPyIm |
| 3030) | 5'W C T T T A A W-3' | PyHpHpHpPyPy-γ-HpHpPyPyPyIm |
| 3031) | 5'W C T T T A G W-3' | PyHpHpHpPyIm-γ-PyHpPyPyPyIm |
| 3032) | 5'W C T T T A C W-3' | PyHpHpHpPyPy-γ-ImHpPyPyPyIm |
| 3033) | 5'W C T T T G T W-3' | PyHpHpHpImHp-γ-PyPyPyPyPyIm |
| 3034) | 5'W C T T T G A W-3' | PyHpHpHpImPy-γ-HpPyPyPyPyIm |
| 3035) | 5'W C T T T G G W-3' | PyHpHpHpImIm-γ-PyPyPyPyPyIm |
| 3036) | 5'W C T T T G C W-3' | PyHpHpHpImPy-γ-ImPyPyPyPyIm |
| 3037) | 5'W C T T T C T W-3' | PyHpHpHpPyHp-γ-PyImPyPyPyIm |
| 3038) | 5'W C T T T C A W-3' | PyHpHpHpPyPy-γ-HpImPyPyPyIm |
| 3039) | 5'W C T T T C G W-3' | PyHpHpHpPyIm-γ-PyImPyPyPyIm |
| 3040) | 5'W C T T T C C W-3' | PyHpHpHpPyPy-γ-ImImPyPyPyIm |
| 3041) | 5'W C T T A T T W-3' | PyHpHpPyHpHp-γ-PyPyHpPyPyIm |
| 3042) | 5'W C T T A T A W-3' | PyHpHpPyHpPy-γ-HpPyHpPyPyIm |
| 3043) | 5'W C T T A T G W-3' | PyHpHpPyHpIm-γ-PyPyHpPyPyIm |
| 3044) | 5'W C T T A T C W-3' | PyHpHpPyHpPy-γ-ImPyHpPyPyIm |
| 3045) | 5'W C T T A A T W-3' | PyHpHpPyPyHp-γ-PyHpHpPyPyIm |
| 3046) | 5'W C T T A A A W-3' | PyHpHpPyPyPy-γ-HpHpHpPyPyIm |
| 3047) | 5'W C T T A A G W-3' | PyHpHpPyPyIm-γ-PyHpHpPyPyIm |
| 3048) | 5'W C T T A A C W-3' | PyHpHpPyPyPy-γ-ImHpHpPyPyIm |
| 3049) | 5'W C T T A G T W-3' | PyHpHpPyImHp-γ-PyPyHpPyPyIm |
| 3050) | 5'W C T T A G A W-3' | PyHpHpPyImPy-γ-HpPyHpPyPyIm |
| 3051) | 5'W C T T A G G W-3' | PyHpHpPyImIm-γ-PyPyHpPyPyIm |
| 3052) | 5'W C T T A G C W-3' | PyHpHpPyImPy-γ-ImPyHpPyPyIm |
| 3053) | 5'W C T T A C T W-3' | PyHpHpPyPyHp-γ-PyImHpPyPyIm |
| 3054) | 5'W C T T A C A W-3' | PyHpHpPyPyPy-γ-HpImHpPyPyIm |
| 3055) | 5'W C T T A C G W-3' | PyHpHpPyPyIm-γ-PyImHpPyPyIm |
| 3056) | 5'W C T T A C C W-3' | PyHpHpPyPyPy-γ-ImImHpPyPyIm |

TABLE 143

12-ring Hairpin Polyamides for recognition of 8-bp 5'-WCTTSNNW-3'

| | DNA sequence | aromatic amino acid sequence |
|---|---|---|
| 3057) | 5'W C T T G T T W-3' | PyHpHpImHpHp-γ-PyPyPyPyPyIm |
| 3058) | 5'W C T T G T A W-3' | PyHpHpImHpPy-γ-HpPyPyPyPyIm |
| 3059) | 5'W C T T G T G W-3' | PyHpHpImHpIm-γ-PyPyPyPyPyIm |
| 3060) | 5'W C T T G T C W-3' | PyHpHpImHpPy-γ-ImPyPyPyPyIm |
| 3061) | 5'W C T T G A T W-3' | PyHpHpImPyHp-γ-PyHpPyPyPyIm |
| 3062) | 5'W C T T G A A W-3' | PyHpHpImPyPy-γ-HpHpPyPyPyIm |
| 3063) | 5'W C T T G A G W-3' | PyHpHpImPyIm-γ-PyHpPyPyPyIm |
| 3064) | 5'W C T T G A C W-3' | PyHpHpImPyPy-γ-ImHpPyPyPyIm |
| 3065) | 5'W C T T G G T W-3' | PyHpHpImImHp-γ-PyPyPyPyPyIm |
| 3066) | 5'W C T T G G A W-3' | PyHpHpImImPy-γ-HpPyPyPyPyIm |
| 3067) | 5'W C T T G C T W-3' | PyHpHpImPyHp-γ-PyImPyPyPyIm |
| 3068) | 5'W C T T G C A W-3' | PyHpHpImPyPy-γ-HpImPyPyPyIm |
| 3069) | 5'W C T T G G G W-3' | PyHpHpImImIm-γ-PyPyPyPyPyIm |
| 3070) | 5'W C T T G G C W-3' | PyHpHpImImPy-γ-ImPyPyPyPyIm |
| 3071) | 5'W C T T G C G W-3' | PyHpHpImPyIm-γ-PyImPyPyPyIm |
| 3072) | 5'W C T T G C C W-3' | PyHpHpImPyPy-γ-ImImPyPyPyIm |
| 3073) | 5'W C T T C T T W-3' | PyHpHpPyHpHp-γ-PyPyImPyPyIm |
| 3074) | 5'W C T T C T A W-3' | PyHpHpPyHpPy-γ-HpPyImPyPyIm |
| 3075) | 5'W C T T C T G W-3' | PyHpHpPyHpIm-γ-PyPyImPyPyIm |
| 3076) | 5'W C T T C T C W-3' | PyHpHpPyHpPy-γ-ImPyImPyPyIm |
| 3077) | 5'W C T T C A T W-3' | PyHpHpPyPyHp-γ-PyHpImPyPyIm |
| 3078) | 5'W C T T C A A W-3' | PyHpHpPyPyPy-γ-HpHpImPyPyIm |
| 3079) | 5'W C T T C A G W-3' | PyHpHpPyPyIm-γ-PyHpImPyPyIm |
| 3080) | 5'W C T T C A C W-3' | PyHpHpPyPyPy-γ-ImHpImPyPyIm |
| 3081) | 5'W C T T C G T W-3' | PyHpHpPyImHp-γ-PyPyImPyPyIm |
| 3082) | 5'W C T T C G A W-3' | PyHpHpPyImPy-γ-HpPyImPyPyIm |
| 3083) | 5'W C T T C C T W-3' | PyHpHpPyPyHp-γ-PyImImPyPyIm |
| 3084) | 5'W C T T C C A W-3' | PyHpHpPyPyPy-γ-HpImImPyPyIm |
| 3085) | 5'W C T T C G G W-3' | PyHpHpPyImIm-γ-PyPyImPyPyIm |

TABLE 143-continued

12-ring Hairpin Polyamides for recognition of 8-bp 5'-WCTTSNNW-3'

| | DNA sequence | aromatic amino acid sequence |
|---|---|---|
| 3086) | 5'W C T T C G C W-3' | PyHpHpPyImPy-γ-ImPyImPyPyIm |
| 3087) | 5'W C T T C C G W-3' | PyHpHpPyPyIm-γ-PyImImPyPyIm |
| 3088) | 5'W C T T C C C W-3' | PyHpHpPyPyPy-γ-ImImImPyPyIm |

TABLE 144

12-ring Hairpin Polyamides for recognition of 8-bp 5'-WCTAWNNW-3'

| | DNA sequence | aromatic amino acid sequence |
|---|---|---|
| 3089) | 5'W C T A T T T W-3' | PyHpPyHpHpHp-γ-PyPyPyHpPyIm |
| 3090) | 5'W C T A T T A W-3' | PyHpPyHpHpPy-γ-HpPyPyHpPyIm |
| 3091) | 5'W C T A T T G W-3' | PyHpPyHpHpIm-γ-PyPyPyHpPyIm |
| 3092) | 5'W C T A T T C W-3' | PyHpPyHpHpPy-γ-ImPyPyHpPyIm |
| 3093) | 5'W C T A T A T W-3' | PyHpPyHpPyHp-γ-PyHpPyHpPyIm |
| 3094) | 5'W C T A T A A W-3' | PyHpPyHpPyPy-γ-HpHpPyHpPyIm |
| 3095) | 5'W C T A T A G W-3' | PyHpPyHpPyIm-γ-PyHpPyHpPyIm |
| 3096) | 5'W C T A T A C W-3' | PyHpPyHpPyPy-γ-ImHpPyHpPyIm |
| 3097) | 5'W C T A T G T W-3' | PyHpPyHpImHp-γ-PyPyPyHpPyIm |
| 3098) | 5'W C T A T G A W-3' | PyHpPyHpImPy-γ-HpPyPyHpPyIm |
| 3099) | 5'W C T A T G G W-3' | PyHpPyHpImIm-γ-PyPyPyHpPyIm |
| 3100) | 5'W C T A T G C W-3' | PyHpPyHpImPy-γ-ImPyPyHpPyIm |
| 3101) | 5'W C T A T C T W-3' | PyHpPyHpPyHp-γ-PyImPyHpPyIm |
| 3102) | 5'W C T A T C A W-3' | PyHpPyHpPyPy-γ-HpImPyHpPyIm |
| 3103) | 5'W C T A T C G W-3' | PyHpPyHpPyIm-γ-PyImPyHpPyIm |
| 3104) | 5'W C T A T C C W-3' | PyHpPyHpPyPy-γ-ImImPyHpPyIm |
| 3105) | 5'W C T A A T T W-3' | PyHpPyPyHpHp-γ-PyPyHpHpPyIm |
| 3106) | 5'W C T A A T A W-3' | PyHpPyPyHpPy-γ-HpPyHpHpPyIm |
| 3107) | 5'W C T A A T G W-3' | PyHpPyPyHpIm-γ-PyPyHpHpPyIm |
| 3108) | 5'W C T A A T C W-3' | PyHpPyPyHpPy-γ-ImPyHpHpPyIm |
| 3109) | 5'W C T A A A T W-3' | PyHpPyPyPyHp-γ-PyHpHpHpPyIm |
| 3110) | 5'W C T A A A A W-3' | PyHpPyPyPyPy-γ-HpHpHpHpPyIm |
| 3111) | 5'W C T A A A G W-3' | PyHpPyPyPyIm-γ-PyHpHpHpPyIm |
| 3112) | 5'W C T A A A C W-3' | PyHpPyPyPyPy-γ-ImHpHpHpPyIm |
| 3113) | 5'W C T A A G T W-3' | PyHpPyPyImHp-γ-PyPyHpHpPyIm |
| 3114) | 5'W C T A A G A W-3' | PyHpPyPyImPy-γ-HpPyHpHpPyIm |
| 3115) | 5'W C T A A G G W-3' | PyHpPyPyImIm-γ-PyPyHpHpPyIm |
| 3116) | 5'W C T A A G C W-3' | PyHpPyPyImPy-γ-ImPyHpHpPyIm |
| 3117) | 5'W C T A A C T W-3' | PyHpPyPyPyHp-γ-PyImHpHpPyIm |
| 3118) | 5'W C T A A C A W-3' | PyHpPyPyPyPy-γ-HpImHpHpPyIm |
| 3119) | 5'W C T A A C G W-3' | PyHpPyPyPyIm-γ-PyImHpHpPyIm |
| 3120) | 5'W C T A A C C W-3' | PyHpPyPyPyPy-γ-ImImHpHpPyIm |

TABLE 145

12-ring Hairpin Polyamides for recognition of 8-bp 5'-WCTASNNW-3'

| | DNA sequence | aromatic amino acid sequence |
|---|---|---|
| 3121) | 5'W C T A G T T W-3' | PyHpPyImHpHp-γ-PyPyPyHpPyIm |
| 3122) | 5'W C T A G T A W-3' | PyHpPyImHpPy-γ-HpPyPyHpPyIm |
| 3123) | 5'W C T A G T G W-3' | PyHpPyImHpIm-γ-PyPyPyHpPyIm |
| 3124) | 5'W C T A G T C W-3' | PyHpPyImHpPy-γ-ImPyPyHpPyIm |
| 3125) | 5'W C T A G A T W-3' | PyHpPyImPyHp-γ-PyHpPyHpPyIm |
| 3126) | 5'W C T A G A A W-3' | PyHpPyImPyPy-γ-HpHpPyHpPyIm |
| 3127) | 5'W C T A G A G W-3' | PyHpPyImPyIm-γ-PyHpPyHpPyIm |
| 3128) | 5'W C T A G A C W-3' | PyHpPyImPyPy-γ-ImHpPyHpPyIm |
| 3129) | 5'W C T A G G T W-3' | PyHpPyImImHp-γ-PyPyPyHpPyIm |
| 3130) | 5'W C T A G G A W-3' | PyHpPyImImPy-γ-HpPyPyHpPyIm |
| 3131) | 5'W C T A G C T W-3' | PyHpPyImPyHp-γ-PyImPyHpPyIm |
| 3132) | 5'W C T A G C A W-3' | PyHpPyImPyPy-γ-HpImPyHpPyIm |
| 3133) | 5'W C T A G G G W-3' | PyHpPyImImIm-γ-PyPyPyHpPyIm |
| 3134) | 5'W C T A G G C W-3' | PyHpPyImImPy-γ-ImPyPyHpPyIm |
| 3135) | 5'W C T A G C G W-3' | PyHpPyImPyIm-γ-PyImPyHpPyIm |
| 3136) | 5'W C T A G C C W-3' | PyHpPyImPyPy-γ-ImImPyHpPyIm |
| 3137) | 5'W C T A C T T W-3' | PyHpPyPyHpHp-γ-PyPyImHpPyIm |
| 3138) | 5'W C T A C T A W-3' | PyHpPyPyHpPy-γ-HpPyImHpPyIm |

TABLE 145-continued 12-ring Hairpin Polyamides for recognition of
8-bp 5'-WCTASNNW-3'

| | DNA sequence | aromatic amino acid sequence |
|---|---|---|
| 3139) | 5'W C T A C T G W-3' | PyHpPyPyHpHpIm-γ-PyPyImHpPyIm |
| 3140) | 5'W C T A C T C W-3' | PyHpPyPyHpPy-γ-ImPyImHpPyIm |
| 3141) | 5'W C T A C A T W-3' | PyHpPyPyPyHp-γ-PyHpImHpPyIm |
| 3142) | 5'W C T A C A A W-3' | PyHpPyPyPyPy-γ-HpHpImHpPyIm |
| 3143) | 5'W C T A C A G W-3' | PyHpPyPyPyIm-γ-PyHpImHpPyIm |
| 3144) | 5'W C T A C A C W-3' | PyHpPyPyPyPy-γ-ImHpImHpPyIm |
| 3145) | 5'W C T A C G T W-3' | PyHpPyPyImHp-γ-PyPyImHpPyIm |
| 3146) | 5'W C T A C G A W-3' | PyHpPyPyImPy-γ-HpPyImHpPyIm |
| 3147) | 5'W C T A C C T W-3' | PyHpPyPyPyHp-γ-PyImImHpPyIm |
| 3148) | 5'W C T A C C A W-3' | PyHpPyPyPyPy-γ-HpImImHpPyIm |
| 3149) | 5'W C T A C G G W-3' | PyHpPyPyImIm-γ-PyPyImHpPyIm |
| 3150) | 5'W C T A C G C W-3' | PyHpPyPyImPy-γ-ImPyImHpPyIm |
| 3151) | 5'W C T A C C G W-3' | PyHpPyPyPyIm-γ-PyImImHpPyIm |
| 3152) | 5'W C T A C C C W-3' | PyHpPyPyPyPy-γ-ImImImHpPyIm |

TABLE 146

12-ring Hairpin Polyamides for recognition of
8-bp 5'-WCTCWNNW-3'

| | DNA sequence | aromatic amino acid sequence |
|---|---|---|
| 3153) | 5'W C T C T T T W-3' | PyHpPyHpHpHp-γ-PyPyPyImPyIm |
| 3154) | 5'W C T C T T A W-3' | PyHpPyHpHpPy-γ-HpPyPyImPyIm |
| 3155) | 5'W C T C T T G W-3' | PyHpPyHpHpIm-γ-PyPyPyImPyIm |
| 3156) | 5'W C T C T T C W-3' | PyHpPyHpHpPy-γ-ImPyPyImPyIm |
| 3157) | 5'W C T C T A T W-3' | PyHpPyHpPyHp-γ-PyHpPyImPyIm |
| 3158) | 5'W C T C T A A W-3' | PyHpPyHpPyPy-γ-HpHpPyImPyIm |
| 3159) | 5'W C T C T A G W-3' | PyHpPyHpPyIm-γ-PyHpPyImPyIm |
| 3160) | 5'W C T C T A C W-3' | PyHpPyRpPyPy-γ-ImHpPyImPyIm |
| 3161) | 5'W C T C T G T W-3' | PyHpPyHpImHp-γ-PyPyPyImPyIm |
| 3162) | 5'W C T C T G A W-3' | PyHpPyHpImPy-γ-HpPyPyImPyIm |
| 3163) | 5'W C T C T G G W-3' | PyHpPyHpImIm-γ-PyPyPyImPyIm |
| 3164) | 5'W C T C T G C W-3' | PyHpPyHpImPy-γ-ImPyPyImPyIm |
| 3165) | 5'W C T C T C T W-3' | PyHpPyHpPyHp-γ-PyImPyImPyIm |
| 3166) | 5'W C T C T C A W-3' | PyHpPyHpPyPy-γ-HpImPyImPyIm |
| 3167) | 5'W C T C T C G W-3' | PyHpPyHpPyIm-γ-PyImPyImPyIm |
| 3168) | 5'W C T C T C C W-3' | PyHpPyHpPyPy-γ-ImImPyImPyIm |
| 3169) | 5'W C T C A T T W-3' | PyHpPyPyHpHp-γ-PyPyHpImPyIm |
| 3170) | 5'W C T C A T A W-3' | PyHpPyPyHpPy-γ-HpPyHpImPyIm |
| 3171) | 5'W C T C A T G W-3' | PyHpPyPyHpIm-γ-PyPyHpImPyIm |
| 3172) | 5'W C T C A T C W-3' | PyHpPyPyHpPy-γ-ImPyHpImPyIm |
| 3173) | 5'W C T C A A T W-3' | PyHpPyPyPyHp-γ-PyHpHpImPyIm |
| 3174) | 5'W C T C A A A W-3' | PyHpPyPyPyPy-γ-HpHpHpImPyIm |
| 3175) | 5'W C T C A A G W-3' | PyHpPyPyPyIm-γ-PyHpHpImPyIm |
| 3176) | 5'W C T C A A C W-3' | PyHpPyPyPyPy-γ-ImHpHpImPyIm |
| 3177) | 5'W C T C A G T W-3' | PyHpPyPyImHp-γ-PyPyHpImPyIm |
| 3178) | 5'W C T C A G A W-3' | PyHpPyPyImPy-γ-HpPyHpImPyIm |
| 3179) | 5'W C T C A G G W-3' | PyHpPyPyImIm-γ-PyPyHpImPyIm |
| 3180) | 5'W C T C A G C W-3' | PyHpPyPyImPy-γ-ImPyHpImPyIm |
| 3181) | 5'W C T C A C T W-3' | PyHpPyPyPyHp-γ-PyImHpImPyIm |
| 3182) | 5'W C T C A C A W-3' | PyHpPyPyPyPy-γ-HpImHpImPyIm |
| 3183) | 5'W C T C A C G W-3' | PyHpPyPyPyIm-γ-PyImHpImPyIm |
| 3184) | 5'W C T C A C C W-3' | PyHpPyPyPyPy-γ-ImImHpImPyIm |

TABLE 147

12-ring Hairpin Polyamides for recognition of
8-bp 5'-WCTCSNNW-3'

| | DNA sequence | aromatic amino acid sequence |
|---|---|---|
| 3185) | 5'W C T C G T T W-3' | PyHpPyImHpHp-γ-PyPyPyImPyIm |
| 3186) | 5'W C T C G T A W-3' | PyHpPyImHpPy-γ-HpPyPyImPyIm |
| 3187) | 5'W C T C G T G W-3' | PyHpPyImHpIm-γ-PyPyPyImPyIm |
| 3188) | 5'W C T C G T C W-3' | PyHpPyImHpPy-γ-ImPyPyImPyIm |
| 3189) | 5'W C T C G A T W-3' | PyHpPyImPyHp-γ-PyHpPyImPyIm |
| 3190) | 5'W C T C G A A W-3' | PyHpPyImPyPy-γ-HpPyPyImPyIm |
| 3191) | 5'W C T C G A G W-3' | PyHpPyImPyIm-γ-PyHpPyImPyIm |

TABLE 147-continued 12-ring Hairpin Polyamides for recognition of
8-bp 5'-WCTCSNNW-3'

| | DNA sequence | aromatic amino acid sequence |
|---|---|---|
| 3192) | 5'W C T C G A C W-3' | PyHpPyImPyPy-γ-ImHpPyImPyIm |
| 3193) | 5'W C T C G G T W-3' | PyHpPyImImHp-γ-PyPyPyImPyIm |
| 3194) | 5'W C T C G G A W-3' | PyHpPyImImPy-γ-HpPyPyImPyIm |
| 3195) | 5'W C T C G C T W-3' | PyHpPyImPyHp-γ-PyImPyImPyIm |
| 3196) | 5'W C T C G C A W-3' | PyHpPyImPyPy-γ-HpImPyImPyIm |
| 3197) | 5'W C T C C T T W-3' | PyHpPyPyHpHp-γ-PyPyImImPyIm |
| 3198) | 5'W C T C C T A W-3' | PyHpPyPyHpPy-γ-HpPyImImPyIm |
| 3199) | 5'W C T C C T G W-3' | PyHpPyPyHpIm-γ-PyPyImImPyIm |
| 3200) | 5'W C T C C T C W-3' | PyHpPyPyHpPy-γ-ImPyImImPyIm |
| 3201) | 5'W C T C C A T W-3' | PyHpPyPyPyHp-γ-PyHpImImPyIm |
| 3202) | 5'W C T C C A A W-3' | PyHpPyPyPyPy-γ-HpHpImImPyIm |
| 3203) | 5'W C T C C A G W-3' | PyHpPyPyPyIm-γ-PyHpImImPyIm |
| 3204) | 5'W C T C C A C W-3' | PyHpPyPyPyPy-γ-ImHpImImPyIm |
| 3205) | 5'W C T C C G T W-3' | PyHpPyPyImHp-γ-PyPyImImPyIm |
| 3206) | 5'W C T C C G A W-3' | PyHpPyPyImPy-γ-HpPyImImPyIm |
| 3207) | 5'W C T C C C T W-3' | PyHpPyPyPyHp-γ-PyImImImPyIm |
| 3208) | 5'W C T C C C A W-3' | PyHpPyPyPyPy-γ-HpImImImPyIm |
| 3209) | 5'W C T C G G G W-3' | PyHpPyImImIm-γ-PyPyPyImPyIm |
| 3210) | 5'W C T C G G C W-3' | PyHpPyImImPy-γ-ImPyPyImPyIm |
| 3211) | 5'W C T C G C G W-3' | PyHpPyImPyIm-γ-PyImPyImPyIm |
| 3212) | 5'W C T C G C C W-3' | PyHpPyImPyPy-γ-ImImPyImPyIm |
| 3213) | 5'W C T C C G G W-3' | PyHpPyPyImIm-γ-PyPyImImPyIm |
| 3214) | 5'W C T C C G C W-3' | PyHpPyPyImPy-γ-ImPyImImPyIm |
| 3215) | 5'W C T C C C G W-3' | PyHpPyPyPyIm-γ-PyImImImPyIm |
| 3216) | 5'W C T C C C C W-3' | PyHpPyPyPyPy-γ-ImImImImPyIm |

TABLE 148

12-ring β-Hairpin Polyamides for recognition of
8-bp 5'-WGGGWNNW-3'

| | DNA sequence | aromatic amino acid sequence |
|---|---|---|
| 1233β) | 5'-W G G G T T T W-3' | ImImIm-β-HpHp-γ-PyPy-β-PyPyPy |
| 1234β) | 5'-W G G G T T A W-3' | ImImIm-β-HpPy-γ-HpPy-β-PyPyPy |
| 1235β) | 5'-W G G G T T G W-3' | ImImIm-β-HpIm-γ-PyPy-β-PyPyPy |
| 1236β) | 5'-W G G G T T C W-3' | ImImIm-β-HpPy-γ-ImPy-β-PyPyPy |
| 1237β) | 5'-W G G G T A T W-3' | ImImIm-β-PyHp-γ-PyHp-β-PyPyPy |
| 1238β) | 5'-W G G G T A A W-3' | ImImIm-β-PyPy-γ-HpHp-β-PyPyPy |
| 1239β) | 5'-W G G G T A G W-3' | ImImIm-β-PyIm-γ-PyHp-β-PyPyPy |
| 1240β) | 5'-W G G G T A C W-3' | ImImIm-β-PyPy-γ-ImHp-β-PyPyPy |
| 1241β) | 5'-W G G G T G T W-3' | ImImIm-β-ImHp-γ-PyPy-β-PyPyPy |
| 1242β) | 5'-W G G G T G A W-3' | ImImIm-β-ImPy-γ-HpPy-β-PyPyPy |
| 1243β) | 5'-W G G G T G G W-3' | ImImIm-β-ImIm-γ-PyPy-β-PyPyPy |
| 1244β) | 5'-W G G G T G C W-3' | ImImIm-β-ImPy-γ-ImPy-β-PyPyPy |
| 1245β) | 5'-W G G G T C T W-3' | ImImIm-β-PyHp-γ-PyIm-β-PyPyPy |
| 1246β) | 5'-W G G G T C A W-3' | ImImIm-β-PyPy-γ-HpIm-β-PyPyPy |
| 1247β) | 5'-W G G G T C G W-3' | ImImIm-β-PyIm-γ-PyIm-β-PyPyPy |
| 1248β) | 5'-W G G G T C C W-3' | ImImIm-β-PyPy-γ-ImIm-β-PyPyPy |
| 1249β) | 5'-W G G G A T T W-3' | ImImIm-β-HpHp-γ-PyPy-β-PyPyPy |
| 1250β) | 5'-W G G G A T A W-3' | ImImIm-β-HpPy-γ-HpPy-β-PyPyPy |
| 1251β) | 5'-W G G G A T G W-3' | ImImIm-β-HpIm-γ-PyPy-β-PyPyPy |
| 1252β) | 5'-W G G G A T C W-3' | ImImIm-β-HpPy-γ-ImPy-β-PyPyPy |
| 1253β) | 5'-W G G G A A T W-3' | ImImIm-β-PyHp-γ-PyHp-β-PyPyPy |
| 1254β) | 5'-W G G G A A A W-3' | ImImIm-β-PyPy-γ-HpHp-β-PyPyPy |
| 1255β) | 5'-W G G G A A G W-3' | ImImIm-β-PyIm-γ-PyHp-β-PyPyPy |
| 1256β) | 5'-W G G G A A C W-3' | ImImIm-β-PyPy-γ-ImHp-β-PyPyPy |
| 1257β) | 5'-W G G G A G T W-3' | ImImIm-β-ImHp-γ-PyPy-β-PyPyPy |
| 1258β) | 5'-W G G G A G A W-3' | ImImIm-β-ImPy-γ-HpPy-β-PyPyPy |
| 1259β) | 5'-W G G G A G G W-3' | ImImIm-β-ImIm-γ-PyPy-β-PyPyPy |
| 1260β) | 5'-W G G G A G C W-3' | ImImIm-β-ImPy-γ-ImPy-β-PyPyPy |
| 1261β) | 5'-W G G G A C T W-3' | ImImIm-β-PyHp-γ-PyIm-β-PyPyPy |
| 1262β) | 5'-W G G G A C A W-3' | ImImIm-β-PyPy-γ-HpIm-β-PyPyPy |
| 1263β) | 5'-W G G G A C G W-3' | ImImIm-β-PyIm-γ-PyIm-β-PyPyPy |
| 1264β) | 5'-W G G G A C C W-3' | ImImIm-β-PyPy-γ-ImIm-β-PyPyPy |

TABLE 149

12-ring β-Hairpin Polyamides for recognition of
8-bp 5'-WGGGSNNW-3'

| | DNA sequence | aromatic amino acid sequence |
|---|---|---|
| 1265β) | 5'-W G G G G T T W-3' | ImImImIm-β-Hp-γ-Py-β-PyPyPyPy |
| 1266β) | 5'-W G G G G T A W-3' | ImImImIm-β-Py-γ-Hp-β-PyPyPyPy |
| 1267β) | 5'-W G G G G T G W-3' | ImImImIm-β-Im-γ-Py-β-PyPyPyPy |
| 1268β) | 5'-W G G G G T C W-3' | ImImImIm-β-Py-γ-Im-β-PyPyPyPy |
| 1269β) | 5'-W G G G G A T W-3' | ImImImIm-β-Hp-γ-Py-β-PyPyPyPy |
| 1270β) | 5'-W G G G G A A W-3' | ImImImIm-β-Py-γ-PyHpPy-β-PyPy |
| 1271β) | 5'-W G G G G A G W-3' | ImImImIm-β-Im-γ-Py-β-PyPyPyPy |
| 1272β) | 5'-W G G G G A C W-3' | ImImImIm-β-Py-γ-Im-β-PyPyPyPy |
| 1275β) | 5'-W G G G G C T W-3' | ImImImIm-β-Hp-γ-PyImPy-β-PyPy |
| 1276β) | 5'-W G G G G C A W-3' | ImImImIm-β-Py-γ-HpImPy-β-PyPy |
| 1277β) | 5'-W G G G C T T W-3' | ImImIm-β-HpHp-γ-PyPyIm-β-PyPy |
| 1278β) | 5'-W G G G C T A W-3' | ImImIm-β-HpPy-γ-HpPyIm-β-PyPy |
| 1279β) | 5'-W G G G C T G W-3' | ImImIm-β-HpIm-γ-PyPyIm-β-PyPy |
| 1280β) | 5'-W G G G C T C W-3' | ImImIm-β-HpPy-γ-ImPyIm-β-PyPy |
| 1281β) | 5'-W G G G C A T W-3' | ImImIm-β-PyHp-γ-PyHpIm-β-PyPy |
| 1282β) | 5'-W G G G C A A W-3' | ImImIm-β-PyPy-γ-HpHpIm-β-PyPy |
| 1283β) | 5'-W G G G C A G W-3' | ImImIm-β-PyIm-γ-PyHpIm-β-PyPy |
| 1284β) | 5'-W G G G C A C W-3' | ImImIm-β-PyPy-γ-ImHpIm-β-PyPy |
| 1285β) | 5'-W G G G C G T W-3' | ImImIm-β-ImHp-γ-PyPyIm-β-PyPy |
| 1286β) | 5'-W G G G C G A W-3' | ImImIm-β-ImPy-γ-HpPyIm-β-PyPy |
| 1287β) | 5'-W G G G C C T W-3' | ImImIm-β-PyHp-γ-PyImIm-β-PyPy |
| 1288β) | 5'-W G G G C C A W-3' | ImImIm-β-PyPy-γ-HpImIm-β-PyPy |
| G52β) | 5'-W G G G G C C W-3' | ImImImIm-β-Py-γ-ImImPy-β-PyPy |
| G53β) | 5'-W G G G C G G W-3' | ImImIm-β-ImIm-γ-PyPyIm-β-PyPy |
| G54β) | 5'-W G G G C G C W-3' | ImImIm-β-ImPy-γ-ImPyIm-β-PyPy |
| G55β) | 5'-W G G G C C G W-3' | ImImIm-β-PyIm-γ-PyImIm-β-PyPy |
| G56β) | 5'-W G G G C C C W-3' | ImImIm-β-PyPy-γ-ImImIm-β-PyPy |

TABLE 150

12-ring β-Hairpin Polyamides for
recognition of 8-bp 5'-WGGTWNNW-3'

| | DNA sequence | aromatic amino acid sequence |
|---|---|---|
| 1289β) | 5'-W G G T T T T W-3' | ImIm-β-HpHpHp-γ-PyPyPy-β-PyPy |
| 1290β) | 5'-W G G T T T A W-3' | ImIm-β-HpHpPy-γ-HpPyPy-β-PyPy |
| 1291β) | 5'-W G G T T T G W-3' | ImIm-β-HpHpIm-γ-PyPyPy-β-PyPy |
| 1292β) | 5'-W G G T T T C W-3' | ImIm-β-HpHpPy-γ-ImPyPy-β-PyPy |
| 1293β) | 5'-W G G T T A T W-3' | ImIm-β-HpPyHp-γ-PyHpPy-β-PyPy |
| 1294β) | 5'-W G G T T A A W-3' | ImIm-β-HpPyPy-γ-HpHpPy-β-PyPy |
| 1295β) | 5'-W G G T T A G W-3' | ImIm-β-HpPyIm-γ-PyHpPy-β-PyPy |
| 1296β) | 5'-W G G T T A C W-3' | ImIm-β-HpPyPy-γ-ImHpPy-β-PyPy |
| 1297β) | 5'-W G G T T G T W-3' | ImIm-β-HpImHp-γ-PyPyPy-β-PyPy |
| 1298β) | 5'-W G G T T G A W-3' | ImIm-β-HpImPy-γ-HpPyPy-β-PyPy |
| 1299β) | 5'-W G G T T G G W-3' | ImIm-β-HpImIm-γ-PyPyPy-β-PyPy |
| 1300β) | 5'-W G G T T G C W-3' | ImIm-β-HpImPy-γ-ImPyPy-β-PyPy |
| 1301β) | 5'-W G G T T C T W-3' | ImIm-β-HpPyHp-γ-PyImPy-β-PyPy |
| 1302β) | 5'-W G G T T C A W-3' | ImIm-β-HpPyPy-γ-HpImPy-β-PyPy |
| 1303β) | 5'-W G G T T C G W-3' | ImIm-β-HpPyIm-γ-PyImPy-β-PyPy |
| 1304β) | 5'-W G G T T C C W-3' | ImIm-β-HpPyPy-γ-ImImPy-β-PyPy |
| 1305β) | 5'-W G G T A T T W-3' | ImIm-β-PyHpHp-γ-PyPyHp-β-PyPy |
| 1306β) | 5'-W G G T A T A W-3' | ImIm-β-PyHpPy-γ-HpPyHp-β-PyPy |
| 1307β) | 5'-W G G T A T G W-3' | ImIm-β-PyHpIm-γ-PyPyHp-β-PyPy |
| 1308β) | 5'-W G G T A T C W-3' | ImIm-β-PyHpPy-γ-ImPyHp-β-PyPy |
| 1309β) | 5'-W G G T A A T W-3' | ImIm-β-PyPyHp-γ-PyHpHp-β-PyPy |
| 1310β) | 5'-W G G T A A A W-3' | ImIm-β-PyPyPy-γ-HpHpHp-β-PyPy |
| 1311β) | 5'-W G G T A A G W-3' | ImIm-β-PyPyIm-γ-PyHpHp-β-PyPy |
| 1312β) | 5'-W G G T A A C W-3' | ImIm-β-PyPyPy-γ-ImHpHp-β-PyPy |
| 1313β) | 5'-W G G T A G T W-3' | ImIm-β-PyImHp-γ-PyPyHp-β-PyPy |
| 1314β) | 5'-W G G T A G A W-3' | ImIm-β-PyImPy-γ-HpPyHp-β-PyPy |
| 1315β) | 5'-W G G T A G G W-3' | ImIm-β-PyImIm-γ-PyPyHp-β-PyPy |
| 1316β) | 5'-W G G T A G C W-3' | ImIm-β-PyImPy-γ-ImPyHp-β-PyPy |
| 1317β) | 5'-W G G T A C T W-3' | ImIm-β-PyPyHp-γ-PyImHp-β-PyPy |
| 1318β) | 5'-W G G T A C A W-3' | ImIm-β-PyPyPy-γ-HpImHp-β-PyPy |
| 1319β) | 5'-W G G T A C G W-3' | ImIm-β-PyPyIm-γ-PyImHp-β-PyPy |
| 1320β) | 5'-W G G T A C C W-3' | ImIm-β-PyPyPy-γ-ImImHp-β-PyPy |

TABLE 151

12-ring β-Hairpin Polyamides for
recognition of 8-bp 5'-WGGTSNNW-3'

| | DNA sequence | aromatic amino acid sequence |
|---|---|---|
| 1321β) | 5'-W G G T G T T W-3' | ImIm-β-ImHpHp-γ-PyPyPy-β-PyPy |
| 1322β) | 5'-W G G T G T A W-3' | ImIm-β-ImHpPy-γ-HpPyPy-β-PyPy |
| 1323β) | 5'-W G G T G T G W-3' | ImIm-β-ImHpIm-γ-PyPyPy-β-PyPy |
| 1324β) | 5'-W G G T G T C W-3' | ImIm-β-ImHpPy-γ-ImPyPy-β-PyPy |
| 1325β) | 5'-W G G T G A T W-3' | ImIm-β-ImPyHp-γ-PyHpPy-β-PyPy |
| 1326β) | 5'-W G G T G A A W-3' | ImIm-β-ImPyPy-γ-HpHpPy-β-PyPy |
| 1327β) | 5'-W G G T G A G W-3' | ImIm-β-ImPyIm-γ-PyHpPy-β-PyPy |
| 1328β) | 5'-W G G T G A C W-3' | ImIm-β-ImPyPy-γ-ImHpPy-β-PyPy |
| 1329β) | 5'-W G G T G G T W-3' | ImIm-β-ImImHp-γ-PyPyPy-β-PyPy |
| 1330β) | 5'-W G G T G G A W-3' | ImIm-β-ImImPy-γ-HpPyPy-β-PyPy |
| 1331β) | 5'-W G G T G C T W-3' | ImIm-β-ImPyHp-γ-PyImPy-β-PyPy |
| 1332β) | 5'-W G G T G C A W-3' | ImIm-β-ImPyPy-γ-HpImPy-β-PyPy |
| 1333β) | 5'-W G G T G G G W-3' | ImIm-β-ImImIm-γ-PyPyPy-β-PyPy |
| 1334β) | 5'-W G G T G G C W-3' | ImIm-β-ImImPy-γ-ImPyPy-β-PyPy |
| 1335β) | 5'-W G G T G C G W-3' | ImIm-β-ImPyIm-γ-PyImPy-β-PyPy |
| 1336β) | 5'-W G G T G C C W-3' | ImIm-β-ImPyPy-γ-ImImPy-β-PyPy |
| 1337β) | 5'-W G G T C T T W-3' | ImIm-β-PyHpHp-γ-PyPyIm-β-PyPy |
| 1338β) | 5'-W G G T C T A W-3' | ImIm-β-PyHpPy-γ-HpPyIm-β-PyPy |
| 1339β) | 5'-W G G T C T G W-3' | ImIm-β-PyHpIm-γ-PyPyIm-β-PyPy |
| 1340β) | 5'-W G G T C T C W-3' | ImIm-β-PyHpPy-γ-ImPyIm-β-PyPy |
| 1341β) | 5'-W G G T C A T W-3' | ImIm-β-PyPyHp-γ-PyHpIm-β-PyPy |
| 1342β) | 5'-W G G T C A A W-3' | ImIm-β-PyPyPy-γ-HpHpIm-β-PyPy |
| 1343β) | 5'-W G G T C A G W-3' | ImIm-β-PyPyIm-γ-PyHpIm-β-PyPy |
| 1344β) | 5'-W G G T C A C W-3' | ImIm-β-PyPyPy-γ-ImHpIm-β-PyPy |
| 1345β) | 5'-W G G T C G T W-3' | ImIm-β-PyImHp-γ-PyPyIm-β-PyPy |
| 1346β) | 5'-W G G T C G A W-3' | ImIm-β-PyImPy-γ-HpPyIm-β-PyPy |
| 1347β) | 5'-W G G T C C T W-3' | ImIm-β-PyPyHp-γ-PyImIm-β-PyPy |
| 1348β) | 5'-W G G T C C A W-3' | ImIm-β-PyPyPy-γ-HpImIm-β-PyPy |
| 1349β) | 5'-W G G T C G G W-3' | ImIm-β-PyImIm-γ-PyPyIm-β-PyPy |
| 1350β) | 5'-W G G T C G C W-3' | ImIm-β-PyImPy-γ-ImPyIm-β-PyPy |
| 1351β) | 5'-W G G T C C G W-3' | ImIm-β-PyPyIm-γ-PyImIm-β-PyPy |
| 1352β) | 5'-W G G T C C C W-3' | ImIm-β-PyPyPy-γ-ImImIm-β-PyPy |

TABLE 152

12-ring β-Hairpin Polyamides for
recognition of 8-bp 5'-WGGAWNNW-3'

| | DNA sequence | aromatic amino acid sequence |
|---|---|---|
| 1353β) | 5'-W G G A T T T W-3' | ImIm-β-HpHpHp-γ-PyPyPy-β-PyPy |
| 1354β) | 5'-W G G A T T A W-3' | ImIm-β-HpHpPy-γ-HpPyPy-β-PyPy |
| 1355β) | 5'-W G G A T T G W-3' | ImIm-β-HpHpIm-γ-PyPyPy-β-PyPy |
| 1356β) | 5'-W G G A T T C W-3' | ImIm-β-HpHpPy-γ-ImPyPy-β-PyPy |
| 1357β) | 5'-W G G A T A T W-3' | ImIm-β-HpPyHp-γ-PyHpPy-β-PyPy |
| 1358β) | 5'-W G G A T A A W-3' | ImIm-β-HpPyPy-γ-HpHpPy-β-PyPy |
| 1359β) | 5'-W G G A T A G W-3' | ImIm-β-HpPyIm-γ-PyHpPy-β-PyPy |
| 1360β) | 5'-W G G A T A C W-3' | ImIm-β-HpPyPy-γ-ImHpPy-β-PyPy |
| 1361β) | 5'-W G G A T G T W-3' | ImIm-β-HpImHp-γ-PyPyPy-β-PyPy |
| 1362β) | 5'-W G G A T G A W-3' | ImIm-β-HpImPy-γ-HpPyPy-β-PyPy |
| 1363β) | 5'-W G G A T G G W-3' | ImIm-β-HpImIm-γ-PyPyPy-β-PyPy |
| 1364β) | 5'-W G G A T G C W-3' | ImIm-β-HpImPy-γ-ImPyPy-β-PyPy |
| 1365β) | 5'-W G G A T C T W-3' | ImIm-β-HpPyHp-γ-PyImPy-β-PyPy |
| 1366β) | 5'-W G G A T C A W-3' | ImIm-β-HpPyPy-γ-HpImPy-β-PyPy |
| 1367β) | 5'-W G G A T C G W-3' | ImIm-β-HpPyIm-γ-PyImPy-β-PyPy |
| 1368β) | 5'-W G G A T C C W-3' | ImIm-β-HpPyPy-γ-ImImPy-β-PyPy |
| 1369β) | 5'-W G G A A T T W-3' | ImIm-β-PyHpHp-γ-PyPyHp-β-PyPy |
| 1370β) | 5'-W G G A A T A W-3' | ImIm-β-PyHpPy-γ-HpPyHp-β-PyPy |
| 1371β) | 5'-W G G A A T G W-3' | ImIm-β-PyHpIm-γ-PyPyHp-β-PyPy |
| 1372β) | 5'-W G G A A T C W-3' | ImIm-β-PyHpPy-γ-ImPyHp-β-PyPy |
| 1373β) | 5'-W G G A A A T W-3' | ImIm-β-PyPyHp-γ-PyHpHp-β-PyPy |
| 1374β) | 5'-W G G A A A A W-3' | ImIm-β-PyPyPy-γ-HpHpHp-β-PyPy |
| 1375β) | 5'-W G G A A A G W-3' | ImIm-β-PyPyIm-γ-PyHpHp-β-PyPy |
| 1376β) | 5'-W G G A A A C W-3' | ImIm-β-PyPyPy-γ-ImHpHp-β-PyPy |
| 1377β) | 5'-W G G A A G T W-3' | ImIm-β-PyImHp-γ-PyPyHp-β-PyPy |
| 1378β) | 5'-W G G A A G A W-3' | ImIm-β-PyImPy-γ-HpPyHp-β-PyPy |
| 1379β) | 5'-W G G A A G G W-3' | ImIm-β-PyImIm-γ-PyPyHp-β-PyPy |
| 1380β) | 5'-W G G A A G C W-3' | ImIm-β-PyImPy-γ-ImPyHp-β-PyPy |
| 1381β) | 5'-W G G A A C T W-3' | ImIm-β-PyPyHp-γ-PyImHp-β-PyPy |

TABLE 152-continued 12-ring β-Hairpin Polyamides for
recognition of 8-bp 5'-WGGAWNNW-3'

| DNA sequence | aromatic amino acid sequence |
|---|---|
| 1382β) 5'-W G G A A C A W-3' | ImIm-β-PyPyPy-γ-HpImHp-β-PyPy |
| 1383β) 5'-W G G A A C G W-3' | ImIm-β-PyPyIm-γ-PyImHp-β-PyPy |
| 1384β) 5'-W G G A A C C W-3' | ImIm-β-PyPyPy-γ-ImImHp-β-PyPy |

TABLE 153

12-ring β-Hairpin Polyamides for
recognition of 8-bp 5'-WGGASNNW-3'

| DNA sequence | aromatic amino acid sequence |
|---|---|
| 1385β) 5'-W G G A G T T W-3' | ImIm-β-ImHpHp-γ-PyPyPy-β-PyPy |
| 1386β) 5'-W G G A G T A W-3' | ImIm-β-ImHpPy-γ-HpPyPy-β-PyPy |
| 1387β) 5'-W G G A G T G W-3' | ImIm-β-ImHpIm-γ-PyPyPy-β-PyPy |
| 1388β) 5'-W G G A G T C W-3' | ImIm-β-ImHpPy-γ-ImPyPy-β-PyPy |
| 1389β) 5'-W G G A G A T W-3' | ImIm-β-ImPyHp-γ-PyHpPy-β-PyPy |
| 1390β) 5'-W G G A G A A W-3' | ImIm-β-ImPyPy-γ-HpHpPy-β-PyPy |
| 1391β) 5'-W G G A G A G W-3' | ImIm-β-ImPyIm-γ-PyHpPy-β-PyPy |
| 1392β) 5'-W G G A G A C W-3' | ImIm-β-ImPyPy-γ-ImHpPy-β-PyPy |
| 1393β) 5'-W G G A G G T W-3' | ImIm-β-ImImHp-γ-PyPyPy-β-PyPy |
| 1394β) 5'-W G G A G G A W-3' | ImIm-β-ImImPy-γ-HpPyPy-β-PyPy |
| 1395β) 5'-W G G A G C T W-3' | ImIm-β-ImPyHp-γ-PyImPy-β-PyPy |
| 1396β) 5'-W G G A G C A W-3' | ImIm-β-ImPyPy-γ-HpImPy-β-PyPy |
| 1397β) 5'-W G G A G G G W-3' | ImIm-β-ImImIm-γ-PyPyPy-β-PyPy |
| 1398β) 5'-W G G A G G C W-3' | ImIm-β-ImImPy-γ-ImPyPy-β-PyPy |
| 1399β) 5'-W G G A G C G W-3' | ImIm-β-ImPyIm-γ-PyImPy-β-PyPy |
| 1400β) 5'-W G G A G C C W-3' | ImIm-β-ImPyPy-γ-ImImPy-β-PyPy |
| 1401β) 5'-W G G A C T T W-3' | ImIm-β-PyHpHp-γ-PyPyIm-β-PyPy |
| 1402β) 5'-W G G A C T A W-3' | ImIm-β-PyHpPy-γ-HpPyIm-β-PyPy |
| 1403β) 5'-W G G A C T G W-3' | ImIm-β-PyHpIm-γ-PyPyIm-β-PyPy |
| 1404β) 5'-W G G A C T C W-3' | ImIm-β-PyHpPy-γ-ImPyIm-β-PyPy |
| 1405β) 5'-W G G A C A T W-3' | ImIm-β-PyPyHp-γ-PyHpIm-β-PyPy |
| 1406β) 5'-W G G A C A A W-3' | ImIm-β-PyPyPy-γ-HpHpIm-β-PyPy |
| 1407β) 5'-W G G A C A G W-3' | ImIm-β-PyPyIm-γ-PyHpIm-β-PyPy |
| 1408β) 5'-W G G A C A C W-3' | ImIm-β-PyPyPy-γ-ImHpIm-β-PyPy |
| 1409β) 5'-W G G A C G T W-3' | ImIm-β-PyImHp-γ-PyPyIm-β-PyPy |
| 1410β) 5'-W G G A C G A W-3' | ImIm-β-PyImPy-γ-HpPyIm-β-PyPy |
| 1411β) 5'-W G G A C C T W-3' | ImIm-β-PyPyHp-γ-PyImIm-β-PyPy |
| 1412β) 5'-W G G A C C A W-3' | ImIm-β-PyPyPy-γ-HpImIm-β-PyPy |
| 1413β) 5'-W G G A C G G W-3' | ImIm-β-PyImIm-γ-PyPyIm-β-PyPy |
| 1414β) 5'-W G G A C G C W-3' | ImIm-β-PyImPy-γ-ImPyIm-β-PyPy |
| 1415β) 5'-W G G A C C G W-3' | ImIm-β-PyPyIm-γ-PyImIm-β-PyPy |
| 1416β) 5'-W G G A C C C W-3' | ImIm-β-PyPyPy-γ-ImImIm-β-PyPy |

TABLE 154

12-ring β-Hairpin Polyamides for
recognition of 8-bp 5'-WGGCWNNW-3'

| DNA sequence | aromatic amino acid sequence |
|---|---|
| 1417β) 5'-W G G C T T T W-3' | ImImPy-β-HpHp-γ-PyPy-β-ImPyPy |
| 1418β) 5'-W G G C T T A W-3' | ImImPy-β-HpPy-γ-HpPy-β-ImPyPy |
| 1419β) 5'-W G G C T T G W-3' | ImImPy-β-HpIm-γ-PyPy-β-ImPyPy |
| 1420β) 5'-W G G C T T C W-3' | ImImPy-β-HpPy-γ-ImPy-β-ImPyPy |
| 1421β) 5'-W G G C T A T W-3' | ImImPy-β-PyHp-γ-PyHp-β-ImPyPy |
| 1422β) 5'-W G G C T A A W-3' | ImImPy-β-PyPy-γ-HpHp-β-ImPyPy |
| 1423β) 5'-W G G C T A G W-3' | ImImPy-β-PyIm-γ-PyHp-β-ImPyPy |
| 1424β) 5'-W G G C T A C W-3' | ImImPy-β-PyPy-γ-ImHp-β-ImPyPy |
| 1425β) 5'-W G G C T G T W-3' | ImImPy-β-ImHp-γ-PyPy-β-ImPyPy |
| 1426β) 5'-W G G C T G A W-3' | ImImPy-β-ImPy-γ-HpPy-β-ImPyPy |
| 1427β) 5'-W G G C T G G W-3' | ImImPy-β-ImIm-γ-PyPy-β-ImPyPy |
| 1428β) 5'-W G G C T G C W-3' | ImImPy-β-ImPy-γ-ImPy-β-ImPyPy |
| 1429β) 5'-W G G C T C T W-3' | ImImPy-β-PyHp-γ-PyIm-β-ImPyPy |
| 1430β) 5'-W G G C T C A W-3' | ImImPy-β-PyPy-γ-HpIm-β-ImPyPy |
| 1431β) 5'-W G G C T C G W-3' | ImImPy-β-PyIm-γ-PyIm-β-ImPyPy |
| 1432β) 5'-W G G C T C C W-3' | ImImPy-β-PyPy-γ-ImIm-β-ImPyPy |
| 1433β) 5'-W G G C A T T W-3' | ImImPy-β-HpHp-γ-PyPy-β-ImPyPy |
| 1434β) 5'-W G G C A T A W-3' | ImImPy-β-HpPy-γ-HpPy-β-ImPyPy |

TABLE 154-continued 12-ring β-Hairpin Polyamides for
recognition of 8-bp 5'-WGGCWNNW-3'

| DNA sequence | aromatic amino acid sequence |
|---|---|
| 1435β) 5'-W G G C A T G W-3' | ImImPy-β-HpIm-γ-PyPy-β-ImPyPy |
| 1436β) 5'-W G G C A T C W-3' | ImImPy-β-HpPy-γ-ImPy-β-ImPyPy |
| 1437β) 5'-W G G C A A T W-3' | ImImPy-β-PyHp-γ-PyHp-β-ImPyPy |
| 1438β) 5'-W G G C A A A W-3' | ImImPy-β-PyPy-γ-HpHp-β-ImPyPy |
| 1439β) 5'-W G G C A A G W-3' | ImImPy-β-PyIm-γ-PyHp-β-ImPyPy |
| 1440β) 5'-W G G C A A C W-3' | ImImPy-β-PyPy-γ-ImHp-β-ImPyPy |
| 1441β) 5'-W G G C A G T W-3' | ImImPy-β-ImHp-γ-PyPy-β-ImPyPy |
| 1442β) 5'-W G G C A G A W-3' | ImImPy-β-ImPy-γ-HpPy-β-ImPyPy |
| 1443β) 5'-W G G C A G G W-3' | ImImPy-β-ImIm-γ-PyPy-β-ImPyPy |
| 1444β) 5'-W G G C A G C W-3' | ImImPy-β-ImPy-γ-ImPy-β-ImPyPy |
| 1445β) 5'-W G G C A C T W-3' | ImImPy-β-PyHp-γ-PyIm-β-ImPyPy |
| 1446β) 5'-W G G C A C A W-3' | ImImPy-β-PyPy-γ-HpIm-β-ImPyPy |
| 1447β) 5'-W G G C A C G W-3' | ImImPy-β-PyIm-γ-PyIm-β-ImPyPy |
| 1448β) 5'-W G G C A C C W-3' | ImImPy-β-PyPy-γ-ImIm-β-ImPyPy |

TABLE 155

12-ring β-Hairpin Polyamides for
recognition of 8-bp 5'-WGGCSNNW-3'

| DNA sequence | aromatic amino acid sequence |
|---|---|
| 1449β) 5'-W G G C G T T W-3' | ImIm-β-ImHpHp-γ-PyPy-β-ImPyPy |
| 1450β) 5'-W G G C G T A W-3' | ImIm-β-ImHpPy-γ-HpPy-β-ImPyPy |
| 1451β) 5'-W G G C G T G W-3' | ImIm-β-ImHpIm-γ-PyPy-β-ImPyPy |
| 1452β) 5'-W G G C G T C W-3' | ImIm-β-ImHpPy-γ-ImPy-β-ImPyPy |
| 1453β) 5'-W G G C G A T W-3' | ImIm-β-ImPyHp-γ-PyHp-β-ImPyPy |
| 1454β) 5'-W G G C G A A W-3' | ImIm-β-ImPyPy-γ-HpHp-β-ImPyPy |
| 1455β) 5'-W G G C G A G W-3' | ImIm-β-ImPyIm-γ-PyHp-β-ImPyPy |
| 1456β) 5'-W G G C G A C W-3' | ImIm-β-ImPyPy-γ-ImHp-β-ImPyPy |
| 1457β) 5'-W G G C G G T W-3' | ImIm-β-ImImHp-γ-PyPy-β-ImPyPy |
| 1458β) 5'-W G G C G G A W-3' | ImIm-β-ImImPy-γ-HpPy-β-ImPyPy |
| 1459β) 5'-W G G C G C T W-3' | ImIm-β-ImPyHp-γ-PyIm-β-ImPyPy |
| 1460β) 5'-W G G C G C A W-3' | ImIm-β-ImPyPy-γ-HpIm-β-ImPyPy |
| 1461β) 5'-W G G C C T T W-3' | ImIm-β-PyHpHp-γ-Py-β-ImImPyPy |
| 1462β) 5'-W G G C C T A W-3' | ImIm-β-PyHpPy-γ-Hp-β-ImImPyPy |
| 1463β) 5'-W G G C C T G W-3' | ImIm-β-PyHpIm-γ-Py-β-ImImPyPy |
| 1464β) 5'-W G G C C T C W-3' | ImIm-β-PyHpPy-γ-Im-β-ImImPyPy |
| 1465β) 5'-W G G C C A T W-3' | ImIm-β-PyPyHp-γ-Py-β-ImImPyPy |
| 1466β) 5'-W G G C C A A W-3' | ImIm-β-PyPyPy-γ-Hp-β-ImImPyPy |
| 1467β) 5'-W G G C C A G W-3' | ImIm-β-PyPyIm-γ-Py-β-ImImPyPy |
| 1468β) 5'-W G G C C A C W-3' | ImIm-β-PyPyPy-γ-Im-β-ImImPyPy |
| 1469β) 5'-W G G C C G T W-3' | ImIm-β-PyImHp-γ-Py-β-ImImPyPy |
| 1470β) 5'-W G G C C G A W-3' | ImIm-β-PyImPy-γ-Hp-β-ImImPyPy |
| 1471β) 5'-W G G C C C T W-3' | ImIm-β-PyPyHp-γ-PyImImIm-β-Py |
| 1472β) 5'-W G G C C C A W-3' | ImIm-β-PyPyPy-γ-HpImImIm-β-Py |
| G57β) 5'-W G G C G G G W-3' | ImIm-β-ImImIm-γ-PyPy-β-ImPyPy |
| G58β) 5'-W G G C G G C W-3' | ImIm-β-ImImPy-γ-ImPy-β-ImPyPy |
| G59β) 5'-W G G C G C G W-3' | ImIm-β-ImPyIm-γ-PyIm-β-ImPyPy |
| G60β) 5'-W G G C G C C W-3' | ImIm-β-ImPyPy-γ-ImIm-β-ImPyPy |
| G61β) 5'-W G G C C G G W-3' | ImIm-β-PyImIm-γ-Py-β-ImImPyPy |
| G62β) 5'-W G G C C G C W-3' | ImIm-β-PyImPy-γ-Im-β-ImImPyPy |
| G63β) 5'-W G G C C C G W-3' | ImIm-β-PyPyIm-γ-PyImImIm-β-Py |
| G64β) 5'-W G G C C C C W-3' | ImIm-β-PyPyPy-γ-ImImImIm-β-Py |

TABLE 156

12-ring β-Hairpin Polyamides for
recognition of 8-bp 5'-WGCGWNNW-3'

| DNA sequence | aromatic amino acid sequence |
|---|---|
| 1473β) 5'-W G C G T T T W-3' | ImPyIm-β-HpHp-γ-PyPyPy-β-ImPy |
| 1474β) 5'-W G C G T T A W-3' | ImPyIm-β-HpPy-γ-HpPyPy-β-ImPy |
| 1475β) 5'-W G C G T T G W-3' | ImPyIm-β-HpIm-γ-PyPyPy-β-ImPy |
| 1476β) 5'-W G C G T T C W-3' | ImPyIm-β-HpPy-γ-ImPyPy-β-ImPy |
| 1477β) 5'-W G C G T A T W-3' | ImPyIm-β-PyHp-γ-PyHpPy-β-ImPy |
| 1478β) 5'-W G C G T A A W-3' | ImPyIm-β-PyPy-γ-HpHpPy-β-ImPy |
| 1479β) 5'-W G C G T A G W-3' | ImPyIm-β-PyIm-γ-PyHpPy-β-ImPy |

TABLE 156-continued 12-ring β-Hairpin Polyamides for
recognition of 8-bp 5'-WGCGWNNW-3'

| | DNA sequence | aromatic amino acid sequence |
|---|---|---|
| 1480β) | 5'-W G C G T A C W-3' | ImPyIm-β-PyPy-γ-ImHpPy-β-ImPy |
| 1481β) | 5'-W G C G T G T W-3' | ImPyIm-β-ImHp-γ-PyPyPy-β-ImPy |
| 1482β) | 5'-W G C G T G A W-3' | ImPyIm-β-ImPy-γ-HpPyPy-β-ImPy |
| 1483β) | 5'-W G C G T G G W-3' | ImPyIm-β-ImIm-γ-PyPyPy-β-ImPy |
| 1484β) | 5'-W G C G T G C W-3' | ImPyIm-β-ImPy-γ-ImPyPy-β-ImPy |
| 1485β) | 5'-W G C G T C T W-3' | ImPyIm-β-PyHp-γ-PyImPy-β-ImPy |
| 1486β) | 5'-W G C G T C A W-3' | ImPyIm-β-PyPy-γ-HpImPy-β-ImPy |
| 1487β) | 5'-W G C G T C G W-3' | ImPyIm-β-PyIm-γ-PyImPy-β-ImPy |
| 1488β) | 5'-W G C G T C C W-3' | ImPyIm-β-PyPy-γ-ImImPy-β-ImPy |
| 1489β) | 5'-W G C G A T T W-3' | ImPyIm-β-HpHp-γ-PyPyHp-β-ImPy |
| 1490β) | 5'-W G C G A T A W-3' | ImPyIm-β-HpPy-γ-HpPyHp-β-ImPy |
| 1491β) | 5'-W G C G A T G W-3' | ImPyIm-β-HpIm-γ-PyPyHp-β-ImPy |
| 1492β) | 5'-W G C G A T C W-3' | ImPyIm-β-HpPy-γ-ImPyHp-β-ImPy |
| 1493β) | 5'-W G C G A A T W-3' | ImPyIm-β-PyHp-γ-PyHpHp-β-ImPy |
| 1494β) | 5'-W G C G A A A W-3' | ImPyIm-β-PyPy-γ-HpHpHp-β-ImPy |
| 1495β) | 5'-W G C G A A G W-3' | ImPyIm-β-PyIm-γ-PyHpHp-β-ImPy |
| 1496β) | 5'-W G C G A A C W-3' | ImPyIm-β-PyPy-γ-ImHpHp-β-ImPy |
| 1497β) | 5'-W G C G A G T W-3' | ImPyIm-β-ImHp-γ-PyPyHp-β-ImPy |
| 1498β) | 5'-W G C G A G A W-3' | ImPyIm-β-ImPy-γ-HpPyHp-β-ImPy |
| 1499β) | 5'-W G C G A G G W-3' | ImPyIm-β-ImIm-γ-PyPyHp-β-ImPy |
| 1490β) | 5'-W G C G A G C W-3' | ImPyIm-β-ImPy-γ-ImPyHp-β-ImPy |
| 1501β) | 5'-W G C G A C T W-3' | ImPyIm-β-PyHp-γ-PyImHp-β-ImPy |
| 1502β) | 5'-W G C G A C A W-3' | ImPyIm-β-PyPy-γ-HpImHp-β-ImPy |
| 1503β) | 5'-W G C G A C G W-3' | ImPyIm-β-PyIm-γ-PyImHp-β-ImPy |
| 1504β) | 5'-W G C G A C C W-3' | ImPyIm-β-PyPy-γ-ImImHp-β-ImPy |

TABLE 157

12-ring β-Hairpin Polyamides for
recognition of 8-bp 5'-WGCGSNNW-3'

| | DNA sequence | aromatic amino acid sequence |
|---|---|---|
| 1505β) | 5'-W G C G G T T W-3' | Im-β-ImImHpHp-γ-PyPyPy-β-ImPy |
| 1506β) | 5'-W G C G G T A W-3' | Im-β-ImImHpPy-γ-HpPyPy-β-ImPy |
| 1507β) | 5'-W G C G G T G W-3' | Im-β-ImImHpIm-γ-PyPyPy-β-ImPy |
| 1508β) | 5'-W G C G G T C W-3' | Im-β-ImImHpPy-γ-ImPyPy-β-ImPy |
| 1509β) | 5'-W G C G G A T W-3' | Im-β-ImImPyHp-γ-PyPyPy-β-ImPy |
| 1510β) | 5'-W G C G G A A W-3' | Im-β-ImImPyPy-γ-HpPyPy-β-ImPy |
| 1511β) | 5'-W G C G G A G W-3' | Im-β-ImImPyIm-γ-PyPyPy-β-ImPy |
| 1512β) | 5'-W G C G G A C W-3' | Im-β-ImImPyPy-γ-ImPyPy-β-ImPy |
| 1513β) | 5'-W G C G G G T W-3' | Im-β-ImImImHp-γ-PyPyPy-β-ImPy |
| 1514β) | 5'-W G C G G G A W-3' | Im-β-ImImImPy-γ-HpPyPy-β-ImPy |
| 1515β) | 5'-W G C G G C T W-3' | Im-β-ImImPyHp-γ-PyImPy-β-ImPy |
| 1516β) | 5'-W G C G G C A W-3' | Im-β-ImImPyPy-γ-HpImPy-β-ImPy |
| 1517β) | 5'-W G C G C T T W-3' | ImPyIm-β-HpHp-γ-PyPyIm-β-ImPy |
| 1518β) | 5'-W G C G C T A W-3' | ImPyIm-β-HpPy-γ-HpPyIm-β-ImPy |
| 1519β) | 5'-W G C G C T G W-3' | ImPyIm-β-HpIm-γ-PyPyIm-β-ImPy |
| 1520β) | 5'-W G C G C T C W-3' | ImPyIm-β-HpPy-γ-ImPyIm-β-ImPy |
| 1521β) | 5'-W G C G C A T W-3' | ImPyIm-β-PyHp-γ-PyHpIm-β-ImPy |
| 1522β) | 5'-W G C G C A A W-3' | ImPyIm-β-PyPy-γ-HpHpIm-β-ImPy |
| 1523β) | 5'-W G C G C A G W-3' | ImPyIm-β-PyIm-γ-PyHpIm-β-ImPy |
| 1524β) | 5'-W G C G C A C W-3' | ImPyIm-β-PyPy-γ-ImHpIm-β-ImPy |
| 1525β) | 5'-W G C G C G T W-3' | ImPyIm-β-ImHp-γ-PyPyIm-β-ImPy |
| 1526β) | 5'-W G C G C G A W-3' | ImPyIm-β-ImPy-γ-HpPyIm-β-ImPy |
| 1527β) | 5'-W G C G C C T W-3' | ImPyIm-β-PyHp-γ-PyImIm-β-ImPy |
| 1528β) | 5'-W G C G C C A W-3' | ImPyIm-β-PyPy-γ-HpImIm-β-ImPy |
| G65β) | 5'-W G C G G G G W-3' | Im-β-ImImImIm-γ-PyPyPy-β-ImPy |
| G66β) | 5'-W G C G G G C W-3' | Im-β-ImImImPy-γ-ImPyPy-β-ImPy |
| G67β) | 5'-W G C G C G G W-3' | Im-β-ImImPyIm-γ-PyImPy-β-ImPy |
| G68β) | 5'-W G C G G C C W-3' | Im-β-ImImPyPy-γ-ImImPy-β-ImPy |
| G69β) | 5'-W G C G C G G W-3' | ImPyIm-β-ImIm-γ-PyPyIm-β-ImPy |
| G70β) | 5'-W G C G C G C W-3' | ImPyIm-β-ImPy-γ-ImPyIm-β-ImPy |
| G71β) | 5'-W G C G C C G W-3' | ImPyIm-β-PyIm-γ-PyImIm-β-ImPy |
| G72β) | 5'-W G C G C C C W-3' | ImPyIm-β-PyPy-γ-ImImIm-β-ImPy |

TABLE 158

12-ring β-Hairpin Polyamides for
recognition of 8-bp 5'-WGCTWNNW-3'

| | DNA sequence | aromatic amino acid sequence |
|---|---|---|
| 1529β) | 5'-W G C T T T T W-3' | ImPy-β-HpHpHp-γ-PyPyPy-β-ImPy |
| 1530β) | 5'-W G C T T T A W-3' | ImPy-β-HpHpPy-γ-HpPyPy-β-ImPy |
| 1531β) | 5'-W G C T T T G W-3' | ImPy-β-HpHpIm-γ-PyPyPy-β-ImPy |
| 1532β) | 5'-W G C T T T C W-3' | ImPy-β-HpHpPy-γ-ImPyPy-β-ImPy |
| 1533β) | 5'-W G C T T A T W-3' | ImPy-β-HpPyHp-γ-PyHpPy-β-ImPy |
| 1534β) | 5'-W G C T T A A W-3' | ImPy-β-HpPyPy-γ-HpHpPy-β-ImPy |
| 1535β) | 5'-W G C T T A G W-3' | ImPy-β-HpPyIm-γ-PyHpPy-β-ImPy |
| 1536β) | 5'-W G C T T A C W-3' | ImPy-β-HpPyPy-γ-ImHpPy-β-ImPy |
| 1537β) | 5'-W G C T T G T W-3' | ImPy-β-HpImHp-γ-PyPyPy-β-ImPy |
| 1538β) | 5'-W G C T T G A W-3' | ImPy-β-HpImPy-γ-HpPyPy-β-ImPy |
| 1539β) | 5'-W G C T T G G W-3' | ImPy-β-HpImIm-γ-PyPyPy-β-ImPy |
| 1540β) | 5'-W G C T T G C W-3' | ImPy-β-HpImPy-γ-ImPyPy-β-ImPy |
| 1541β) | 5'-W G C T T C T W-3' | ImPy-β-HpPyHp-γ-PyImPy-β-ImPy |
| 1542β) | 5'-W G C T T C A W-3' | ImPy-β-HpPyPy-γ-HpImPy-β-ImPy |
| 1543β) | 5'-W G C T T C G W-3' | ImPy-β-HpPyIm-γ-PyImPy-β-ImPy |
| 1544β) | 5'-W G C T T C C W-3' | ImPy-β-HpPyPy-γ-ImImPy-β-ImPy |
| 1545β) | 5'-W G C T A T T W-3' | ImPy-β-PyHpHp-γ-PyPyHp-β-ImPy |
| 1546β) | 5'-W G C T A T A W-3' | ImPy-β-PyHpPy-γ-HpPyHp-β-ImPy |
| 1547β) | 5'-W G C T A T G W-3' | ImPy-β-PyHpIm-γ-PyPyHp-β-ImPy |
| 1548β) | 5'-W G C T A T C W-3' | ImPy-β-PyHpPy-γ-ImPyHp-β-ImPy |
| 1549β) | 5'-W G C T A A T W-3' | ImPy-β-PyPyHp-γ-PyHpHp-β-ImPy |
| 1550β) | 5'-W G C T A A A W-3' | ImPy-β-PyPyPy-γ-HpHpHp-β-ImPy |
| 1551β) | 5'-W G C T A A G W-3' | ImPy-β-PyPyIm-γ-PyHpHp-β-ImPy |
| 1552β) | 5'-W G C T A A C W-3' | ImPy-β-PyPyPy-γ-ImHpHp-β-ImPy |
| 1553β) | 5'-W G C T A G T W-3' | ImPy-β-PyImHp-γ-PyPyHp-β-ImPy |
| 1554β) | 5'-W G C T A G A W-3' | ImPy-β-PyImPy-γ-HpPyHp-β-ImPy |
| 1555β) | 5'-W G C T A G G W-3' | ImPy-β-PyImIm-γ-PyPyHp-β-ImPy |
| 1556β) | 5'-W G C T A G C W-3' | ImPy-β-PyImPy-γ-ImPyHp-β-ImPy |
| 1557β) | 5'-W G C T A C T W-3' | ImPy-β-PyPyHp-γ-PyImHp-β-ImPy |
| 1558β) | 5'-W G C T A C A W-3' | ImPy-β-PyPyPy-γ-HpImHp-β-ImPy |
| 1559β) | 5'-W G C T A C G W-3' | ImPy-β-PyPyIm-γ-PyImHp-β-ImPy |
| 1560β) | 5'-W G C T A C C W-3' | ImPy-β-PyPyPy-γ-ImImHp-β-ImPy |

TABLE 159

12-ring β-Hairpin Polyamides for
recognition of 8-bp 5'-WGCTSNNW-3'

| | DNA sequence | aromatic amino acid sequence |
|---|---|---|
| 1561β) | 5'-W G C T G T T W-3' | ImPy-β-ImHpHp-γ-PyPyPy-β-ImPy |
| 1562β) | 5'-W G C T G T A W-3' | ImPy-β-ImHpPy-γ-HpPyPy-β-ImPy |
| 1563β) | 5'-W G C T G T G W-3' | ImPy-β-ImHpIm-γ-PyPyPy-β-ImPy |
| 1564β) | 5'-W G C T G T C W-3' | ImPy-β-ImHpPy-γ-ImPyPy-β-ImPy |
| 1565β) | 5'-W G C T G A T W-3' | ImPy-β-ImPyHp-γ-PyPyPy-β-ImPy |
| 1566β) | 5'-W G C T G A A W-3' | ImPy-β-ImPyPy-γ-HpPyPy-β-ImPy |
| 1567β) | 5'-W G C T G A G W-3' | ImPy-β-ImPyIm-γ-PyPyPy-β-ImPy |
| 1568β) | 5'-W G C T G A C W-3' | ImPy-β-ImPyPy-γ-ImHpPy-β-ImPy |
| 1569β) | 5'-W G C T G G T W-3' | ImPy-β-ImImHp-γ-PyPyPy-β-ImPy |
| 1570β) | 5'-W G C T G G A W-3' | ImPy-β-ImImPy-γ-HpPyPy-β-ImPy |
| 1571β) | 5'-W G C T G C T W-3' | ImPy-β-ImPyHp-γ-PyImPy-β-ImPy |
| 1572β) | 5'-W G C T G C A W-3' | ImPy-β-ImPyPy-γ-HpImPy-β-ImPy |
| 1573β) | 5'-W G C T G G G W-3' | ImPy-β-ImImIm-γ-PyPyPy-β-ImPy |
| 1574β) | 5'-W G C T G G C W-3' | ImPy-β-ImImPy-γ-ImPyPy-β-ImPy |
| 1575β) | 5'-W G C T G C G W-3' | ImPy-β-ImPyIm-γ-PyImPy-β-ImPy |
| 1576β) | 5'-W G C T G C C W-3' | ImPy-β-ImPyPy-γ-ImImPy-β-ImPy |
| 1577β) | 5'-W G C T C T T W-3' | ImPy-β-PyHpHp-γ-PyPyIm-β-ImPy |
| 1578β) | 5'-W G C T C T A W-3' | ImPy-β-PyHpPy-γ-HpPyIm-β-ImPy |
| 1579β) | 5'-W G C T C T G W-3' | ImPy-β-PyHpIm-γ-PyPyIm-β-ImPy |
| 1580β) | 5'-W G C T C T C W-3' | ImPy-β-PyHpPy-γ-ImPyIm-β-ImPy |
| 1581β) | 5'-W G C T C A T W-3' | ImPy-β-PyPyHp-γ-PyHpIm-β-ImPy |
| 1582β) | 5'-W G C T C A A W-3' | ImPy-β-PyPyPy-γ-HpHpIm-β-ImPy |
| 1583β) | 5'-W G C T C A G W-3' | ImPy-β-PyPyIm-γ-PyHpIm-β-ImPy |
| 1584β) | 5'-W G C T C A C W-3' | ImPy-β-PyPyPy-γ-ImHpIm-β-ImPy |
| 1585β) | 5'-W G C T C G T W-3' | ImPy-β-PyImHp-γ-PyPyIm-β-ImPy |
| 1586β) | 5'-W G C T C G A W-3' | ImPy-β-PyImPy-γ-HpPyIm-β-ImPy |
| 1587β) | 5'-W G C T C C T W-3' | ImPy-β-PyPyHp-γ-PyImIm-β-ImPy |
| 1588β) | 5'-W G C T C C A W-3' | ImPy-β-PyPyPy-γ-HpImIm-β-ImPy |
| 1589β) | 5'-W G C T C G G W-3' | ImPy-β-PyImIm-γ-PyPyIm-β-ImPy |

TABLE 159-continued 12-ring β-Hairpin Polyamides for
recognition of 8-bp 5'-WGCTSNNW-3'

| DNA sequence | aromatic amino acid sequence |
|---|---|
| 1590β) 5'-W G C T C G C W-3' | ImPy-β-PyImPy-γ-ImPyIm-β-ImPy |
| 1591β) 5'-W G C T C C G W-3' | ImPy-β-PyPyIm-γ-PyImIm-β-ImPy |
| 1592β) 5'-W G C T C C C W-3' | ImPy-β-PyPyPy-γ-ImImIm-β-ImPy |

TABLE 160

12-ring β-Hairpin Polyamides for
recognition of 8-bp 5'-WGCAWNNW-3'

| DNA sequence | aromatic amino acid sequence |
|---|---|
| 1593β) 5'-W G C A T T T W-3' | ImPy-β-HpHpHp-γ-PyPyPy-β-ImPy |
| 1594β) 5'-W G C A T T A W-3' | ImPy-β-HpHpPy-γ-HpPyPy-β-ImPy |
| 1595β) 5'-W G C A T T G W-3' | ImPy-β-HpHpIm-γ-PyPyPy-β-ImPy |
| 1596β) 5'-W G C A T T C W-3' | ImPy-β-HpHpPy-γ-ImPyPy-β-ImPy |
| 1597β) 5'-W G C A T A T W-3' | ImPy-β-HpHpHp-γ-PyHpPy-β-ImPy |
| 1598β) 5'-W G C A T A A W-3' | ImPy-β-HpPyPy-γ-HpPyPy-β-ImPy |
| 1599β) 5'-W G C A T A G W-3' | ImPy-β-HpPyIm-γ-PyHpPy-β-ImPy |
| 1600β) 5'-W G C A T A C W-3' | ImPy-β-HpPyPy-γ-ImPyPy-β-ImPy |
| 1601β) 5'-W G C A T G T W-3' | ImPy-β-HpImHp-γ-PyPyPy-β-ImPy |
| 1602β) 5'-W G C A T G A W-3' | ImPy-β-HpImPy-γ-HpPyPy-β-ImPy |
| 1603β) 5'-W G C A T G G W-3' | ImPy-β-HpImIm-γ-PyPyPy-β-ImPy |
| 1604β) 5'-W G C A T G C W-3' | ImPy-β-HpImPy-γ-ImPyPy-β-ImPy |
| 1605β) 5'-W G C A T C T W-3' | ImPy-β-HpPyHp-γ-PyPyPy-β-ImPy |
| 1606β) 5'-W G C A T C A W-3' | ImPy-β-HpPyPy-γ-HpImPy-β-ImPy |
| 1607β) 5'-W G C A T C G W-3' | ImPy-β-HpPyIm-γ-PyImPy-β-ImPy |
| 1608β) 5'-W G C A T C C W-3' | ImPy-β-HpPyPy-γ-ImImPy-β-ImPy |
| 1609β) 5'-W G C A A T T W-3' | ImPy-β-PyHpHp-γ-PyPyHp-β-ImPy |
| 1610β) 5'-W G C A A T A W-3' | ImPy-β-PyHpPy-γ-HpPyHp-β-ImPy |
| 1611β) 5'-W G C A A T G W-3' | ImPy-β-PyHpIm-γ-PyPyHp-β-ImPy |
| 1612β) 5'-W G C A A T C W-3' | ImPy-β-PyHpPy-γ-ImPyHp-β-ImPy |
| 1613β) 5'-W G C A A A T W-3' | ImPy-β-PyPyHp-γ-PyHpHp-β-ImPy |
| 1614β) 5'-W G C A A A A W-3' | ImPy-β-PyPyPy-γ-HpHpHp-β-ImPy |
| 1615β) 5'-W G C A A A G W-3' | ImPy-β-PyPyIm-γ-PyHpHp-β-ImPy |
| 1616β) 5'-W G C A A A C W-3' | ImPy-β-PyPyPy-γ-ImHpHp-β-ImPy |
| 1617β) 5'-W G C A A G T W-3' | ImPy-β-PyImHp-γ-PyPyHp-β-ImPy |
| 1618β) 5'-W G C A A G A W-3' | ImPy-β-PyImPy-γ-HpPyHp-β-ImPy |
| 1619β) 5'-W G C A A G G W-3' | ImPy-β-PyImIm-γ-PyPyHp-β-ImPy |
| 1620β) 5'-W G C A A G C W-3' | ImPy-β-PyImPy-γ-ImPyHp-β-ImPy |
| 1621β) 5'-W G C A A C T W-3' | ImPy-β-PyPyHp-γ-PyImHp-β-ImPy |
| 1622β) 5'-W G C A A C A W-3' | ImPy-β-PyPyPy-γ-HpImHp-β-ImPy |
| 1623β) 5'-W G C A A C G W-3' | ImPy-β-PyPyIm-γ-PyImHp-β-ImPy |
| 1624β) 5'-W G C A A C C W-3' | ImPy-β-PyPyPy-γ-ImImHp-β-ImPy |

TABLE 161

12-ring β-Hairpin Polyamides for
recognition of 8-bp 5'-WGCASNNW-3'

| DNA sequence | aromatic amino acid sequence |
|---|---|
| 1625β) 5'-W G C A G T T W-3' | ImPy-β-ImHpHp-γ-PyPyPy-β-ImPy |
| 1626β) 5'-W G C A G T A W-3' | ImPy-β-ImHpPy-γ-HpPyPy-β-ImPy |
| 1627β) 5'-W G C A G T G W-3' | ImPy-β-ImHpIm-γ-PyPyPy-β-ImPy |
| 1628β) 5'-W G C A G T C W-3' | ImPy-β-ImHpPy-γ-ImPyPy-β-ImPy |
| 1629β) 5'-W G C A G A T W-3' | ImPy-β-ImPyHp-γ-PyHpPy-β-ImPy |
| 1630β) 5'-W G C A G A A W-3' | ImPy-β-ImPyPy-γ-HpHpPy-β-ImPy |
| 1631β) 5'-W G C A G A G W-3' | ImPy-β-ImPyIm-γ-PyHpPy-β-ImPy |
| 1632β) 5'-W G C A G A C W-3' | ImPy-β-ImPyPy-γ-ImHpPy-β-ImPy |
| 1633β) 5'-W G C A G G T W-3' | ImPy-β-ImImHp-γ-PyPyPy-β-ImPy |
| 1634β) 5'-W G C A G G A W-3' | ImPy-β-ImImPy-γ-HpPyPy-β-ImPy |
| 1635β) 5'-W G C A G C T W-3' | ImPy-β-ImPyHp-γ-PyImPy-β-ImPy |
| 1636β) 5'-W G C A G C A W-3' | ImPy-β-ImPyPy-γ-HpImPy-β-ImPy |
| 1637β) 5'-W G C A G G G W-3' | ImPy-β-ImImIm-γ-PyPyPy-β-ImPy |
| 1638β) 5'-W G C A G G C W-3' | ImPy-β-ImImPy-γ-ImPyPy-β-ImPy |
| 1639β) 5'-W G C A G C G W-3' | ImPy-β-ImPyIm-γ-PyImPy-β-ImPy |
| 1640β) 5'-W G C A G C C W-3' | ImPy-β-ImPyPy-γ-ImImPy-β-ImPy |
| 1641β) 5'-W G C A C T T W-3' | ImPy-β-PyHpHp-γ-PyPyIm-β-ImPy |
| 1642β) 5'-W G C A C T A W-3' | ImPy-β-PyHpPy-γ-HpPyIm-β-ImPy |

TABLE 161-continued 12-ring β-Hairpin Polyamides for
recognition of 8-bp 5'-WGCASNNW-3'

| DNA sequence | aromatic amino acid sequence |
|---|---|
| 1643β) 5'-W G C A C T G W-3' | ImPy-β-PyHpIm-γ-PyPyIm-β-ImPy |
| 1644β) 5'-W G C A C T C W-3' | ImPy-β-PyHpPy-γ-ImPyIm-β-ImPy |
| 1645β) 5'-W G C A C A T W-3' | ImPy-β-PyPyHp-γ-PyHpIm-β-ImPy |
| 1646β) 5'-W G C A C A A W-3' | ImPy-β-PyPyPy-γ-HpHpIm-β-ImPy |
| 1647β) 5'-W G C A C A G W-3' | ImPy-β-PyPyIm-γ-PyHpIm-β-ImPy |
| 1648β) 5'-W G C A C A C W-3' | ImPy-β-PyPyPy-γ-ImHpIm-β-ImPy |
| 1649β) 5'-W G C A C G T W-3' | ImPy-β-PyImHp-γ-PyPyIm-β-ImPy |
| 1650β) 5'-W G C A C G A W-3' | ImPy-β-PyImPy-γ-HpPyIm-β-ImPy |
| 1651β) 5'-W G C A C C T W-3' | ImPy-β-PyPyHp-γ-PyImIm-β-ImPy |
| 1652β) 5'-W G C A C C A W-3' | ImPy-β-PyPyPy-γ-HpImIm-β-ImPy |
| 1653β) 5'-W G C A C G G W-3' | ImPy-β-PyImIm-γ-PyPyIm-β-ImPy |
| 1654β) 5'-W G C A C G C W-3' | ImPy-β-PyImPy-γ-ImPyIm-β-ImPy |
| 1655β) 5'-W G C A C C G W-3' | ImPy-β-PyPyIm-γ-PyImIm-β-ImPy |
| 1656β) 5'-W G C A C C C W-3' | ImPy-β-PyPyPy-γ-ImImIm-β-ImPy |

TABLE 162

12-ring β-Hairpin Polyamides for
recognition of 8-bp 5'-WGCCWNNW-3'

| DNA sequence | aromatic amino acid sequence |
|---|---|
| 1657β) 5'-W G C C T T T W-3' | ImPyPy-β-HpHp-γ-PyPy-β-ImImPy |
| 1658β) 5'-W G C C T T A W-3' | ImPyPy-β-HpPy-γ-HpPy-β-ImImPy |
| 1659β) 5'-W G C C T T G W-3' | ImPyPy-β-HpIm-γ-PyPy-β-ImImPy |
| 1660β) 5'-W G C C T T C W-3' | ImPyPy-β-HpPy-γ-ImPy-β-ImImPy |
| 1661β) 5'-W G C C T A T W-3' | ImPyPy-β-PyHp-γ-PyHp-β-ImImPy |
| 1662β) 5'-W G C C T A A W-3' | ImPyPy-β-PyPy-γ-HpHp-β-ImImPy |
| 1663β) 5'-W G C C T A G W-3' | ImPyPy-β-PyIm-γ-PyHp-β-ImImPy |
| 1664β) 5'-W G C C T A C W-3' | ImPyPy-β-PyPy-γ-ImHp-β-ImImPy |
| 1665β) 5'-W G C C T G T W-3' | ImPyPy-β-ImHp-γ-PyPy-β-ImImPy |
| 1666β) 5'-W G C C T G A W-3' | ImPyPy-β-ImPy-γ-HpPy-β-ImImPy |
| 1667β) 5'-W G C C T G G W-3' | ImPyPy-β-ImIm-γ-PyPy-β-ImImPy |
| 1668β) 5'-W G C C T G C W-3' | ImPyPy-β-ImPy-γ-ImPy-β-ImImPy |
| 1669β) 5'-W G C C T C T W-3' | ImPyPy-β-PyHp-γ-PyIm-β-ImImPy |
| 1670β) 5'-W G C C T C A W-3' | ImPyPy-β-PyPy-γ-HpIm-β-ImImPy |
| 1671β) 5'-W G C C T C G W-3' | ImPyPy-β-PyIm-γ-PyIm-β-ImImPy |
| 1672β) 5'-W G C C T C C W-3' | ImPyPy-β-PyPy-γ-ImIm-β-ImImPy |
| 1673β) 5'-W G C C A T T W-3' | ImPyPy-β-HpHp-γ-PyPy-β-ImImPy |
| 1674β) 5'-W G C C A T A W-3' | ImPyPy-β-HpPy-γ-HpPy-β-ImImPy |
| 1675β) 5'-W G C C A T G W-3' | ImPyPy-β-HpIm-γ-PyPy-β-ImImPy |
| 1676β) 5'-W G C C A T C W-3' | ImPyPy-β-HpPy-γ-ImPy-β-ImImPy |
| 1677β) 5'-W G C C A A T W-3' | ImPyPy-β-PyHp-γ-PyHp-β-ImImPy |
| 1678β) 5'-W G C C A A A W-3' | ImPyPy-β-PyPy-γ-HpHp-β-ImImPy |
| 1679β) 5'-W G C C A A G W-3' | ImPyPy-β-PyIm-γ-PyHp-β-ImImPy |
| 1680β) 5'-W G C C A A C W-3' | ImPyPy-β-PyPy-γ-ImHp-β-ImImPy |
| 1681β) 5'-W G C C A G T W-3' | ImPyPy-β-ImHp-γ-PyPy-β-ImImPy |
| 1682β) 5'-W G C C A G A W-3' | ImPyPy-β-ImPy-γ-HpPy-β-ImImPy |
| 1683β) 5'-W G C C A G G W-3' | ImPyPy-β-ImIm-γ-PyPy-β-ImImPy |
| 1684β) 5'-W G C C A G C W-3' | ImPyPy-β-ImPy-γ-ImPy-β-ImImPy |
| 1685β) 5'-W G C C A C T W-3' | ImPyPy-β-PyHp-γ-PyIm-β-ImImPy |
| 1686β) 5'-W G C C A C A W-3' | ImPyPy-β-PyPy-γ-HpIm-β-ImImPy |
| 1687β) 5'-W G C C A C G W-3' | ImPyPy-β-PyIm-γ-PyIm-β-ImImPy |
| 1688β) 5'-W G C C A C C W-3' | ImPyPy-β-PyPy-γ-ImIm-β-ImImPy |

TABLE 163

12-ring β-Hairpin Polyamides for
recognition of 8-bp 5'-WGCCSNNW-3'

| DNA sequence | aromatic amino acid sequence |
|---|---|
| 1689β) 5'-W G C C G T T W-3' | ImPy-β-ImHpHp-γ-PyPy-β-ImImPy |
| 1690β) 5'-W G C C G T A W-3' | ImPy-β-ImHpPy-γ-HpPy-β-ImImPy |
| 1691β) 5'-W G C C G T G W-3' | ImPy-β-ImHpIm-γ-PyPy-β-ImImPy |
| 1692β) 5'-W G C C G T C W-3' | ImPy-β-ImHpPy-γ-ImPy-β-ImImPy |
| 1693β) 5'-W G C C G A T W-3' | ImPy-β-ImPyHp-γ-PyHp-β-ImImPy |
| 1694β) 5'-W G C C G A A W-3' | ImPy-β-ImPyPy-γ-HpHp-β-ImImPy |
| 1695β) 5'-W G C C G A G W-3' | ImPy-β-ImPyIm-γ-PyHp-β-ImImPy |

TABLE 163-continued 12-ring β-Hairpin Polyamides for recognition of 8-bp 5'-WGCCSNNW-3'

| DNA sequence | aromatic amino acid sequence |
|---|---|
| 1696β) 5'-W G C C G A C W-3' | ImPy-β-ImPyPy-γ-ImHp-β-ImImPy |
| 1697β) 5'-W G C C G G T W-3' | ImPy-β-ImImHp-γ-PyPy-β-ImImPy |
| 1698β) 5'-W G C C G G A W-3' | ImPy-β-ImImPy-γ-HpPy-β-ImImPy |
| 1699β) 5'-W G C C G C T W-3' | ImPy-β-ImPyHp-γ-PyIm-β-ImImPy |
| 1700β) 5'-W G C C G C A W-3' | ImPy-β-ImPyPy-γ-HpIm-β-ImImPy |
| 1701β) 5'-W G C C C T T W-3' | ImPy-β-PyHpHp-γ-Py-β-ImImPy |
| 1702β) 5'-W G C C C T A W-3' | ImPy-β-PyHpPy-γ-Hp-β-ImImPy |
| 1703β) 5'-W G C C C T G W-3' | ImPy-β-PyHpIm-γ-Py-β-ImImPy |
| 1704β) 5'-W G C C C T C W-3' | ImPy-β-PyHpPy-γ-Im-β-ImImPy |
| 1705β) 5'-W G C C C A T W-3' | ImPy-β-PyPyHp-γ-Py-β-ImImPy |
| 1706β) 5'-W G C C C A A W-3' | ImPy-β-PyPyPy-γ-Hp-β-ImImPy |
| 1707β) 5'-W G C C C A G W-3' | ImPy-β-PyPyIm-γ-Py-β-ImImPy |
| 1708β) 5'-W G C C C A C W-3' | ImPy-β-PyPyPy-γ-Im-β-ImImPy |
| 1709β) 5'-W G C C C G T W-3' | ImPy-β-PyImHp-γ-Py-β-ImImPy |
| 1710β) 5'-W G C C C G A W-3' | ImPy-β-PyImPy-γ-Hp-β-ImImPy |
| G73β) 5'-W G C C G G G W-3' | ImPy-β-ImImIm-γ-PyPy-β-ImImPy |
| G74β) 5'-W G C C G G C W-3' | ImPy-β-ImImPy-γ-ImPy-β-ImImPy |
| G75β) 5'-W G C C G C G W-3' | ImPy-β-ImPyIm-γ-PyIm-β-ImImPy |
| G76β) 5'-W G C C G C C W-3' | ImPy-β-ImPyPy-γ-ImIm-β-ImImPy |
| G77β) 5'-W G C C C G G W-3' | ImPy-β-PyImIm-γ-Py-β-ImImPy |
| G78β) 5'-W G C C C G C W-3' | ImPy-β-PyImPy-γ-Im-β-ImImPy |

TABLE 164

12-ring β-Hairpin Polyamides for recognition of 8-bp 5'-WGAGWNNW-3'

| DNA sequence | aromatic amino acid sequence |
|---|---|
| 1713β) 5'-W G A G T T T W-3' | Im-β-ImHpHpHp-γ-PyPyPyPy-β-Py |
| 1714β) 5'-W G A G T T A W-3' | Im-β-ImHpHpPy-γ-HpPyPyPy-β-Py |
| 1715β) 5'-W G A G T T G W-3' | Im-β-ImHpHpIm-γ-PyPyPyPy-β-Py |
| 1716β) 5'-W G A G T T C W-3' | Im-β-ImHpHpPy-γ-ImPyPyPy-β-Py |
| 1717β) 5'-W G A G T A T W-3' | Im-β-ImHpPyHp-γ-PyHpPyPy-β-Py |
| 1718β) 5'-W G A G T A A W-3' | Im-β-ImHpPyPy-γ-HpHpPyPy-β-Py |
| 1719β) 5'-W G A G T A G W-3' | Im-β-ImHpPyIm-γ-PyHpPyPy-β-Py |
| 1720β) 5'-W G A G T A C W-3' | Im-β-ImHpPyPy-γ-ImHpPyPy-β-Py |
| 1721β) 5'-W G A G T G T W-3' | Im-β-ImHpImHp-γ-PyPyPyPy-β-Py |
| 1722β) 5'-W G A G T G A W-3' | Im-β-ImHpImPy-γ-HpPyPyPy-β-Py |
| 1723β) 5'-W G A G T G G W-3' | Im-β-ImHpImIm-γ-PyPyPyPy-β-Py |
| 1724β) 5'-W G A G T G C W-3' | Im-β-ImHpImPy-γ-ImPyPyPy-β-Py |
| 1725β) 5'-W G A G T C T W-3' | Im-β-ImHpPyHp-γ-PyImPyPy-β-Py |
| 1726β) 5'-W G A G T C A W-3' | Im-β-ImHpPyPy-γ-HpImPyPy-β-Py |
| 1727β) 5'-W G A G T C G W-3' | Im-β-ImHpPyIm-γ-PyImPyPy-β-Py |
| 1728β) 5'-W G A G T C C W-3' | Im-β-ImHpPyPy-γ-ImImPyPy-β-Py |
| 1729β) 5'-W G A G A T T W-3' | Im-β-ImPyHpHp-γ-PyPyHpPy-β-Py |
| 1730β) 5'-W G A G A T A W-3' | Im-β-ImPyHpPy-γ-HpPyHpPy-β-Py |
| 1731β) 5'-W G A G A T G W-3' | Im-β-ImPyHpIm-γ-PyPyHpPy-β-Py |
| 1732β) 5'-W G A G A T C W-3' | Im-β-ImPyHpPy-γ-ImPyHpPy-β-Py |
| 1733β) 5'-W G A G A A T W-3' | Im-β-ImPyPyHp-γ-PyHpHpPy-β-Py |
| 1734β) 5'-W G A G A A A W-3' | Im-β-ImPyPyPy-γ-HpHpHpPy-β-Py |
| 1735β) 5'-W G A G A A G W-3' | Im-β-ImPyPyIm-γ-PyHpHpPy-β-Py |
| 1736β) 5'-W G A G A A C W-3' | Im-β-ImPyPyPy-γ-ImHpHpPy-β-Py |
| 1737β) 5'-W G A G A G T W-3' | Im-β-ImPyImHp-γ-PyPyHpPy-β-Py |
| 1738β) 5'-W G A G A G A W-3' | Im-β-ImPyImPy-γ-HpPyHpPy-β-Py |
| 1739β) 5'-W G A G A G G W-3' | Im-β-ImPyImIm-γ-PyPyHpPy-β-Py |
| 1740β) 5'-W G A G A G C W-3' | Im-β-ImPyImPy-γ-ImPyHpPy-β-Py |
| 1741β) 5'-W G A G A C T W-3' | Im-β-ImPyPyHp-γ-PyImHpPy-β-Py |
| 1742β) 5'-W G A G A C A W-3' | Im-β-ImPyPyPy-γ-HpImHpPy-β-Py |
| 1743β) 5'-W G A G A C G W-3' | Im-β-ImPyPyIm-γ-PyImHpPy-β-Py |
| 1744β) 5'-W G A G A C C W-3' | Im-β-ImPyPyPy-γ-ImImHpPy-β-Py |

TABLE 165

12-ring β-Hairpin Polyamides for recognition of 8-bp 5'-WGAGSNNW-3'

| DNA sequence | aromatic amino acid sequence |
|---|---|
| 1745β) 5'-W G A G G T T W-3' | Im-β-ImImHpHp-γ-PyPyPyPy-β-Py |
| 1746β) 5'-W G A G G T A W-3' | Im-β-ImImHpPy-γ-HpPyPyPy-β-Py |
| 1747β) 5'-W G A G G T G W-3' | Im-β-ImImHpIm-γ-PyPyPyPy-β-Py |
| 1748β) 5'-W G A G G T C W-3' | Im-β-ImImHpPy-γ-ImPyPyPy-β-Py |
| 1749β) 5'-W G A G G A T W-3' | Im-β-ImImPyHp-γ-PyHpPyPy-β-Py |
| 1750β) 5'-W G A G G A A W-3' | Im-β-ImImPyPy-γ-HpHpPyPy-β-Py |
| 1751β) 5'-W G A G G A G W-3' | Im-β-ImImPyIm-γ-PyHpPyPy-β-Py |
| 1752β) 5'-W G A G G A C W-3' | Im-β-ImImPyPy-γ-ImHpPyPy-β-Py |
| 1753β) 5'-W G A G G G T W-3' | Im-β-ImImImHp-γ-PyPyPyPy-β-Py |
| 1754β) 5'-W G A G G G A W-3' | Im-β-ImImImPy-γ-HpPyPyPy-β-Py |
| 1755β) 5'-W G A G G C T W-3' | Im-β-ImImPyHp-γ-PyImPyPy-β-Py |
| 1756β) 5'-W G A G G C A W-3' | Im-β-ImImPyPy-γ-HpImPyPy-β-Py |
| 1757β) 5'-W G A G C T T W-3' | Im-β-ImPyHpHp-γ-PyPyImPy-β-Py |
| 1758β) 5'-W G A G C T A W-3' | Im-β-ImPyHpPy-γ-HpPyImPy-β-Py |
| 1759β) 5'-W G A G C T G W-3' | Im-β-ImPyHpIm-γ-PyPyImPy-β-Py |
| 1760β) 5'-W G A G C T C W-3' | Im-β-ImPyHpPy-γ-ImPyImPy-β-Py |
| 1761β) 5'-W G A G C A T W-3' | Im-β-ImPyPyHp-γ-PyHpImPy-β-Py |
| 1762β) 5'-W G A G C A A W-3' | Im-β-ImPyPyPy-γ-HpHpImPy-β-Py |
| 1763β) 5'-W G A G C A G W-3' | Im-β-ImPyPyIm-γ-PyHpImPy-β-Py |
| 1764β) 5'-W G A G C A C W-3' | Im-β-ImPyPyPy-γ-ImHpImPy-β-Py |
| 1765β) 5'-W G A G C G T W-3' | Im-β-ImPyImHp-γ-PyPyImPy-β-Py |
| 1766β) 5'-W G A G C G A W-3' | Im-β-ImPyImPy-γ-HpPyImPy-β-Py |
| 1767β) 5'-W G A G C C T W-3' | Im-β-ImPyPyHp-γ-PyImImPy-β-Py |
| 1768β) 5'-W G A G C C A W-3' | Im-β-ImPyPyPy-γ-HpImImPy-β-Py |
| 1769β) 5'-W G A G G G G W-3' | Im-β-ImImImIm-γ-PyPyPyPy-β-Py |
| 1770β) 5'-W G A G G G C W-3' | Im-β-ImImImPy-γ-ImPyPyPy-β-Py |
| 1771β) 5'-W G A G G C G W-3' | Im-β-ImImPyIm-γ-PyImPyPy-β-Py |
| 1772β) 5'-W G A G G C C W-3' | Im-β-ImImPyPy-γ-ImImPyPy-β-Py |
| 1773β) 5'-W G A G C G G W-3' | Im-β-ImPyImIm-γ-PyPyImPy-β-Py |
| 1774β) 5'-W G A G C G C W-3' | Im-β-ImPyImPy-γ-ImPyImPy-β-Py |
| 1775β) 5'-W G A G C C G W-3' | Im-β-ImPyPyIm-γ-PyImImPy-β-Py |
| 1776β) 5'-W G A G C C C W-3' | Im-β-ImPyPyPy-γ-ImImImPy-β-Py |

TABLE 166

12-ring β-Hairpin Polyamides for recognition of 8-bp 5'-WGATWNNW-3'

| DNA sequence | aromatic amino acid sequence |
|---|---|
| 1777β) 5'-W G A T T T T W-3' | ImPy-β-HpHpHp-γ-PyPyPyPy-β-HpPy |
| 1778β) 5'-W G A T T T A W-3' | ImPy-β-HpHpPy-γ-HpPyPyPy-β-HpPy |
| 1779β) 5'-W G A T T T G W-3' | ImPy-β-HpHpIm-γ-PyPyPyPy-β-HpPy |
| 1780β) 5'-W G A T T T C W-3' | ImPy-β-HpHpPy-γ-ImPyPyPy-β-HpPy |
| 1781β) 5'-W G A T T A T W-3' | ImPy-β-HpPyHp-γ-PyHpPyPy-β-HpPy |
| 1782β) 5'-W G A T T A A W-3' | ImPy-β-HpPyPy-γ-HpHpPyPy-β-HpPy |
| 1783β) 5'-W G A T T A G W-3' | ImPy-β-HpPyIm-γ-PyHpPyPy-β-HpPy |
| 1784β) 5'-W G A T T A C W-3' | ImPy-β-HpPyPy-γ-ImHpPyPy-β-HpPy |
| 1785β) 5'-W G A T T G T W-3' | ImPy-β-HpImHp-γ-PyPyPyPy-β-HpPy |
| 1786β) 5'-W G A T T G A W-3' | ImPy-β-HpImPy-γ-HpPyPyPy-β-HpPy |
| 1787β) 5'-W G A T T G G W-3' | ImPy-β-HpImIm-γ-PyPyPyPy-β-HpPy |
| 1788β) 5'-W G A T T G C W-3' | ImPy-β-HpImPy-γ-ImPyPyPy-β-HpPy |
| 1789β) 5'-W G A T T C T W-3' | ImPy-β-HpPyHp-γ-PyImPyPy-β-HpPy |
| 1790β) 5'-W G A T T C A W-3' | ImPy-β-HpPyPy-γ-HpImPyPy-β-HpPy |
| 1791β) 5'-W G A T T C G W-3' | ImPy-β-HpPyIm-γ-PyImPyPy-β-HpPy |
| 1792β) 5'-W G A T T C C W-3' | ImPy-β-HpPyPy-γ-ImImPyPy-β-HpPy |
| 1793β) 5'-W G A T A T T W-3' | ImPy-β-PyHpHp-γ-PyPyHp-β-HpPy |
| 1794β) 5'-W G A T A T A W-3' | ImPy-β-PyHpPy-γ-HpPyHp-β-HpPy |
| 1795β) 5'-W G A T A T G W-3' | ImPy-β-PyHpIm-γ-PyPyHp-β-HpPy |
| 1796β) 5'-W G A T A T C W-3' | ImPy-β-PyHpPy-γ-ImPyHp-β-HpPy |
| 1797β) 5'-W G A T A A T W-3' | ImPy-β-PyPyHp-γ-PyHpHp-β-HpPy |
| 1798β) 5'-W G A T A A A W-3' | ImPy-β-PyPyPy-γ-HpHpHp-β-HpPy |
| 1799β) 5'-W G A T A A G W-3' | ImPy-β-PyPyIm-γ-PyHpHp-β-HpPy |
| 1800β) 5'-W G A T A A C W-3' | ImPy-β-PyPyPy-γ-ImHpHp-β-HpPy |
| 1801β) 5'-W G A T A G T W-3' | ImPy-β-PyImHp-γ-PyPyHp-β-HpPy |
| 1802β) 5'-W G A T A G A W-3' | ImPy-β-PyImPy-γ-HpPyHp-β-HpPy |
| 1803β) 5'-W G A T A G G W-3' | ImPy-β-PyImIm-γ-PyPyHp-β-HpPy |
| 1804β) 5'-W G A T A G C W-3' | ImPy-β-PyImPy-γ-ImPyHp-β-HpPy |
| 1805β) 5'-W G A T A C T W-3' | ImPy-β-PyPyHp-γ-PyImHp-β-HpPy |
| 1806β) 5'-W G A T A C A W-3' | ImPy-β-PyPyPy-γ-HpImHp-β-HpPy |
| 1807β) 5'-W G A T A C G W-3' | ImPy-β-PyPyIm-γ-PyImHp-β-HpPy |
| 1808β) 5'-W G A T A C C W-3' | ImPy-β-PyPyPy-γ-ImImHp-β-HpPy |

TABLE 167

12-ring β-Hairpin Polyamides for recognition of 8-bp 5'-WGATSNNW-3'

| DNA sequence | aromatic amino acid sequence |
|---|---|
| 1809β) 5'-W G A T G T T W-3' | ImPy-β-ImHpHp-γ-PyPyPy-β-HpPy |
| 1810β) 5'-W G A T G T A W-3' | ImPy-β-ImHpPy-γ-HpPyPy-β-HpPy |
| 1811β) 5'-W G A T G T G W-3' | ImPy-β-ImHpIm-γ-PyPyPy-β-HpPy |
| 1812β) 5'-W G A T G T C W-3' | ImPy-β-ImHpPy-γ-ImPyPy-β-HpPy |
| 1813β) 5'-W G A T G A T W-3' | ImPy-β-ImPyHp-γ-PyHpPy-β-HpPy |
| 1814β) 5'-W G A T G A A W-3' | ImPy-β-ImPyPy-γ-HpHpPy-β-HpPy |
| 1815β) 5'-W G A T G A G W-3' | ImPy-β-ImPyIm-γ-PyHpPy-β-HpPy |
| 1816β) 5'-W G A T G A C W-3' | ImPy-β-ImPyPy-γ-ImHpPy-β-HpPy |
| 1817β) 5'-W G A T G G T W-3' | ImPy-β-ImImHp-γ-PyPyPy-β-HpPy |
| 1818β) 5'-W G A T G G A W-3' | ImPy-β-ImImPy-γ-HpPyPy-β-HpPy |
| 1819β) 5'-W G A T G C T W-3' | ImPy-β-ImPyHp-γ-PyImPy-β-HpPy |
| 1820β) 5'-W G A T G C A W-3' | ImPy-β-ImPyPy-γ-HpImPy-β-HpPy |
| 1821β) 5'-W G A T G G G W-3' | ImPy-β-ImImIm-γ-PyPyPy-β-HpPy |
| 1822β) 5'-W G A T G G C W-3' | ImPy-β-ImImPy-γ-ImPyPy-β-HpPy |
| 1823β) 5'-W G A T G C G W-3' | ImPy-β-ImPyIm-γ-PyImPy-β-HpPy |
| 1824β) 5'-W G A T G C C W-3' | ImPy-β-ImPyPy-γ-ImImPy-β-HpPy |
| 1825β) 5'-W G A T C T T W-3' | ImPy-β-PyHpHp-γ-PyPyIm-β-HpPy |
| 1826β) 5'-W G A T C T A W-3' | ImPy-β-PyHpPy-γ-HpPyIm-β-HpPy |
| 1827β) 5'-W G A T C T G W-3' | ImPy-β-PyHpIm-γ-PyPyIm-β-HpPy |
| 1828β) 5'-W G A T C T C W-3' | ImPy-β-PyHpPy-γ-ImPyIm-β-HpPy |
| 1829β) 5'-W G A T C A T W-3' | ImPy-β-PyPyHp-γ-PyHpIm-β-HpPy |
| 1830β) 5'-W G A T C A A W-3' | ImPy-β-PyPyPy-γ-HpHpIm-β-HpPy |
| 1831β) 5'-W G A T C A G W-3' | ImPy-β-PyPyIm-γ-PyHpIm-β-HpPy |
| 1832β) 5'-W G A T C A C W-3' | ImPy-β-PyPyPy-γ-ImHpIm-β-HpPy |
| 1833β) 5'-W G A T C G T W-3' | ImPy-β-PyImHp-γ-PyPyIm-β-HpPy |
| 1834β) 5'-W G A T C G A W-3' | ImPy-β-PyImPy-γ-HpPyIm-β-HpPy |
| 1835β) 5'-W G A T C C T W-3' | ImPy-β-PyPyHp-γ-PyImIm-β-HpPy |
| 1836β) 5'-W G A T C C A W-3' | ImPy-β-PyPyPy-γ-HpImIm-β-HpPy |
| 1837β) 5'-W G A T C G G W-3' | ImPy-β-PyImIm-γ-PyPyIm-β-HpPy |
| 1838β) 5'-W G A T C G C W-3' | ImPy-β-PyImPy-γ-ImPyIm-β-HpPy |
| 1839β) 5'-W G A T C C G W-3' | ImPy-β-PyPyIm-γ-PyImIm-β-HpPy |
| 1840β) 5'-W G A T C C C W-3' | ImPy-β-PyPyPy-γ-ImImIm-β-HpPy |

TABLE 168

12-ring β-Hairpin Polyamides for recognition of 8-bp 5'-WGAAWNNW-3'

| DNA sequence | aromatic amino acid sequence |
|---|---|
| 1841β) 5'-W G A A T T T W-3' | ImPy-β-HpHpHp-γ-PyPyPy-β-HpPy |
| 1842β) 5'-W G A A T T A W-3' | ImPy-β-HpHpPy-γ-HpPyPy-β-HpPy |
| 1843β) 5'-W G A A T T G W-3' | ImPy-β-HpHpIm-γ-PyPyPy-β-HpPy |
| 1844β) 5'-W G A A T T C W-3' | ImPy-β-HpHpPy-γ-ImPyPy-β-HpPy |
| 1845β) 5'-W G A A T A T W-3' | ImPy-β-HpPyHp-γ-PyHpPy-β-HpPy |
| 1846β) 5'-W G A A T A A W-3' | ImPy-β-HpPyPy-γ-HpHpPy-β-HpPy |
| 1847β) 5'-W G A A T A G W-3' | ImPy-β-HpPyIm-γ-PyHpPy-β-HpPy |
| 1848β) 5'-W G A A T A C W-3' | ImPy-β-HpPyPy-γ-ImHpPy-β-HpPy |
| 1849β) 5'-W G A A T G T W-3' | ImPy-β-HpImHp-γ-PyPyPy-β-HpPy |
| 1850β) 5'-W G A A T G A W-3' | ImPy-β-HpImPy-γ-HpPyPy-β-HpPy |
| 1851β) 5'-W G A A T G G W-3' | ImPy-β-HpImIm-γ-PyPyPy-β-HpPy |
| 1852β) 5'-W G A A T G C W-3' | ImPy-β-HpImPy-γ-ImPyPy-β-HpPy |
| 1853β) 5'-W G A A T C T W-3' | ImPy-β-HpPyHp-γ-PyImPy-β-HpPy |
| 1854β) 5'-W G A A T C A W-3' | ImPy-β-HpPyPy-γ-HpImPy-β-HpPy |
| 1855β) 5'-W G A A T C G W-3' | ImPy-β-HpPyIm-γ-PyImPy-β-HpPy |
| 1856β) 5'-W G A A T C C W-3' | ImPy-β-HpPyPy-γ-ImImPy-β-HpPy |
| 1857β) 5'-W G A A A T T W-3' | ImPy-β-PyHpHp-γ-PyPyHp-β-HpPy |
| 1858β) 5'-W G A A A T A W-3' | ImPy-β-PyHpPy-γ-HpPyHp-β-HpPy |
| 1869β) 5'-W G A A A T G W-3' | ImPy-β-PyHpIm-γ-PyPyHp-β-HpPy |
| 1860β) 5'-W G A A A T C W-3' | ImPy-β-PyHpPy-γ-ImPyHp-β-HpPy |
| 1861β) 5'-W G A A A A T W-3' | ImPy-β-PyPyHp-γ-PyHpHp-β-HpPy |
| 1862β) 5'-W G A A A A A W-3' | ImPy-β-PyPyPy-γ-HpHpHp-β-HpPy |
| 1863β) 5'-W G A A A A G W-3' | ImPy-β-PyPyIm-γ-PyHpHp-β-HpPy |
| 1864β) 5'-W G A A A A C W-3' | ImPy-β-PyPyPy-γ-ImHpHp-β-HpPy |
| 1865β) 5'-W G A A A G T W-3' | ImPy-β-PyImHp-γ-PyPyHp-β-HpPy |
| 1866β) 5'-W G A A A G A W-3' | ImPy-β-PyImPy-γ-HpPyHp-β-HpPy |
| 1867β) 5'-W G A A A G G W-3' | ImPy-β-PyImIm-γ-PyPyHp-β-HpPy |
| 1868β) 5'-W G A A A G C W-3' | ImPy-β-PyImPy-γ-ImPyHp-β-HpPy |
| 1869β) 5'-W G A A A C T W-3' | ImPy-β-PyPyHp-γ-PyImHp-β-HpPy |
| 1870β) 5'-W G A A A C A W-3' | ImPy-β-PyPyPy-γ-HpImHp-β-HpPy |
| 1871β) 5'-W G A A A C G W-3' | ImPy-β-PyPyIm-γ-PyImHp-β-HpPy |
| 1872β) 5'-W G A A A C C W-3' | ImPy-β-PyPyPy-γ-ImImHp-β-HpPy |

TABLE 169

12-ring β-Hairpin Polyamides for recognition of 8-bp 5'-WGAASNNW-3'

| DNA sequence | aromatic amino acid sequence |
|---|---|
| 1873β) 5'-W G A A G T T W-3' | ImPy-β-ImHpHp-γ-PyPyPy-β-HpPy |
| 1874β) 5'-W G A A G T A W-3' | ImPy-β-ImHpPy-γ-HpPyPy-β-HpPy |
| 1875β) 5'-W G A A G T G W-3' | ImPy-β-ImHpIm-γ-PyPyPy-β-HpPy |
| 1876β) 5'-W G A A G T C W-3' | ImPy-β-ImHpPy-γ-ImPyPy-β-HpPy |
| 1877β) 5'-W G A A G A T W-3' | ImPy-β-ImPyHp-γ-PyHpPy-β-HpPy |
| 1878β) 5'-W G A A G A A W-3' | ImPy-β-ImPyPy-γ-HpHpPy-β-HpPy |
| 1879β) 5'-W G A A G A G W-3' | ImPy-β-ImPyIm-γ-PyHpPy-β-HpPy |
| 1880β) 5'-W G A A G A C W-3' | ImPy-β-ImPyPy-γ-ImHpPy-β-HpPy |
| 1881β) 5'-W G A A G G T W-3' | ImPy-β-ImImHp-γ-PyPyPy-β-HpPy |
| 1882β) 5'-W G A A G G A W-3' | ImPy-β-ImImPy-γ-HpPyPy-β-HpPy |
| 1883β) 5'-W G A A G C T W-3' | ImPy-β-ImPyHp-γ-PyImPy-β-HpPy |
| 1884β) 5'-W G A A G C A W-3' | ImPy-β-ImPyPy-γ-HpImPy-β-HpPy |
| 1885β) 5'-W G A A G G G W-3' | ImPy-β-ImImIm-γ-PyPyPy-β-HpPy |
| 1886β) 5'-W G A A G G C W-3' | ImPy-β-ImImPy-γ-ImPyPy-β-HpPy |
| 1887β) 5'-W G A A G C G W-3' | ImPy-β-ImPyIm-γ-PyImPy-β-HpPy |
| 1888β) 5'-W G A A G C C W-3' | ImPy-β-ImPyPy-γ-ImImPy-β-HpPy |
| 1889β) 5'-W G A A C T T W-3' | ImPy-β-PyHpHp-γ-PyPyIm-β-HpPy |
| 1890β) 5'-W G A A C T A W-3' | ImPy-β-PyHpPy-γ-HpPyIm-β-HpPy |
| 1891β) 5'-W G A A C T G W-3' | ImPy-β-PyHpIm-γ-PyPyIm-β-HpPy |
| 1892β) 5'-W G A A C T C W-3' | ImPy-β-PyHpPy-γ-ImPyIm-β-HpPy |
| 1893β) 5'-W G A A C A T W-3' | ImPy-β-PyPyHp-γ-PyHpIm-β-HpPy |
| 1894β) 5'-W G A A C A A W-3' | ImPy-β-PyPyPy-γ-HpHpIm-β-HpPy |
| 1895β) 5'-W G A A C A G W-3' | ImPy-β-PyPyIm-γ-PyHpIm-β-HpPy |
| 1896β) 5'-W G A A C A C W-3' | ImPy-β-PyPyPy-γ-ImHpIm-β-HpPy |
| 1897β) 5'-W G A A C G T W-3' | ImPy-β-PyImHp-γ-PyPyIm-β-HpPy |
| 1898β) 5'-W G A A C G A W-3' | ImPy-β-PyImPy-γ-HpPyIm-β-HpPy |
| 1899β) 5'-W G A A C C T W-3' | ImPy-β-PyPyHp-γ-PyImIm-β-HpPy |
| 1900β) 5'-W G A A C C A W-3' | ImPy-β-PyPyPy-γ-HpImIm-β-HpPy |
| 1901β) 5'-W G A A C G G W-3' | ImPy-β-PyImIm-γ-PyPyIm-β-HpPy |
| 1902β) 5'-W G A A C G C W-3' | ImPy-β-PyImPy-γ-ImPyIm-β-HpPy |
| 1903β) 5'-W G A A C C G W-3' | ImPy-β-PyPyIm-γ-PyImIm-β-HpPy |
| 1904β) 5'-W G A A C C C W-3' | ImPy-β-PyPyPy-γ-ImImIm-β-HpPy |

TABLE 170

12-ring β-Hairpin Polyamides for recognition of 8-bp 5'-WGACWNNW-3'

| DNA sequence | aromatic amino acid sequence |
|---|---|
| 1905β) 5'-W G A C T T T W-3' | ImPyPy-β-HpHp-γ-PyPy-β-ImHpPy |
| 1906β) 5'-W G A C T T A W-3' | ImPyPy-β-HpPy-γ-HpPy-β-ImHpPy |
| 1907β) 5'-W G A C T T G W-3' | ImPyPy-β-HpIm-γ-PyPy-β-ImHpPy |
| 1908β) 5'-W G A C T T C W-3' | ImPyPy-β-HpPy-γ-ImPy-β-ImHpPy |
| 1909β) 5'-W G A C T A T W-3' | ImPyPy-β-PyHp-γ-PyHp-β-ImHpPy |
| 1910β) 5'-W G A C T A A W-3' | ImPyPy-β-PyPy-γ-HpHp-β-ImHpPy |
| 1911β) 5'-W G A C T A G W-3' | ImPyPy-β-PyIm-γ-PyHp-β-ImHpPy |
| 1912β) 5'-W G A C T A C W-3' | ImPyPy-β-PyPy-γ-ImHp-β-ImHpPy |
| 1913β) 5'-W G A C T G T W-3' | ImPyPy-β-ImHp-γ-PyPy-β-ImHpPy |
| 1914β) 5'-W G A C T G A W-3' | ImPyPy-β-ImPy-γ-HpPy-β-ImHpPy |
| 1915β) 5'-W G A C T G G W-3' | ImPyPy-β-ImIm-γ-PyPy-β-ImHpPy |
| 1916β) 5'-W G A C T G C W-3' | ImPyPy-β-ImPy-γ-ImPy-β-ImHpPy |
| 1917β) 5'-W G A C T C T W-3' | ImPyPy-β-PyHp-γ-PyIm-β-ImHpPy |
| 1918β) 5'-W G A C T C A W-3' | ImPyPy-β-PyPy-γ-HpIm-β-ImHpPy |
| 1919β) 5'-W G A C T C G W-3' | ImPyPy-β-PyIm-γ-PyIm-β-ImHpPy |
| 1920β) 5'-W G A C T C C W-3' | ImPyPy-β-PyPy-γ-ImIm-β-ImHpPy |
| 1921β) 5'-W G A C A T T W-3' | ImPyPy-β-HpHp-γ-PyPy-β-ImHpPy |
| 1922β) 5'-W G A C A T A W-3' | ImPyPy-β-HpPy-γ-HpPy-β-ImHpPy |
| 1923β) 5'-W G A C A T G W-3' | ImPyPy-β-HpIm-γ-PyPy-β-ImHpPy |
| 1924β) 5'-W G A C A T C W-3' | ImPyPy-β-HpPy-γ-ImPy-β-ImHpPy |
| 1925β) 5'-W G A C A A T W-3' | ImPyPy-β-PyHp-γ-PyHp-β-ImHpPy |
| 1926β) 5'-W G A C A A A W-3' | ImPyPy-β-PyPy-γ-HpHp-β-ImHpPy |
| 1927β) 5'-W G A C A A G W-3' | ImPyPy-β-PyIm-γ-PyHp-β-ImHpPy |
| 1928β) 5'-W G A C A A C W-3' | ImPyPy-β-PyPy-γ-ImHp-β-ImHpPy |
| 1929β) 5'-W G A C A G T W-3' | ImPyPy-β-ImHp-γ-PyPy-β-ImHpPy |
| 1930β) 5'-W G A C A G A W-3' | ImPyPy-β-ImPy-γ-HpPy-β-ImHpPy |
| 1931β) 5'-W G A C A G G W-3' | ImPyPy-β-ImIm-γ-PyPy-β-ImHpPy |
| 1932β) 5'-W G A C A G C W-3' | ImPyPy-β-ImPy-γ-ImPy-β-ImHpPy |
| 1933β) 5'-W G A C A C T W-3' | ImPyPy-β-PyHp-γ-PyIm-β-ImHpPy |
| 1934β) 5'-W G A C A C A W-3' | ImPyPy-β-PyPy-γ-HpIm-β-ImHpPy |
| 1935β) 5'-W G A C A C G W-3' | ImPyPy-β-PyIm-γ-PyIm-β-ImHpPy |
| 1936β) 5'-W G A C A C C W-3' | ImPyPy-β-PyPy-γ-ImIm-β-ImHpPy |

TABLE 171

12-ring β-Hairpin Polyamides for recognition of 8-bp 5'-WGACSNNW-3'

| DNA sequence | aromatic amino acid sequence |
|---|---|
| 1937β) 5'-W G A C G T T W-3' | ImPy-β-ImHpHp-γ-PyPy-β-ImHpPy |
| 1938β) 5'-W G A C G T A W-3' | ImPy-β-ImHpPy-γ-HpPy-β-ImHpPy |
| 1939β) 5'-W G A C G T G W-3' | ImPy-β-ImHpIm-γ-PyPy-β-ImHpPy |
| 1940β) 5'-W G A C G T C W-3' | ImPy-β-ImHpPy-γ-ImPy-β-ImHpPy |
| 1941β) 5'-W G A C G A T W-3' | ImPy-β-ImHpHp-γ-PyHp-β-ImHpPy |
| 1942β) 5'-W G A C C A A W-3' | ImPy-β-ImPyPy-γ-HpHp-β-ImHpPy |
| 1943β) 5'-W C A C G A G W-3' | ImPy-β-ImPyIm-γ-PyHp-β-ImHpPy |
| 1944β) 5'-W G A C G A C W-3' | ImPy-β-ImHpPy-γ-ImHp-β-ImHpPy |
| 1945β) 5'-W G A C G C T W-3' | ImPy-β-ImImHp-γ-PyPy-β-ImHpPy |
| 1946β) 5'-W G A C-G G A W-3' | ImPy-β-ImImPy-γ-HpPy-β-ImHpPy |
| 1947β) 5'-W C A C G C T W-3' | ImPy-β-ImPyHp-γ-PyIm-β-ImHpPy |
| 1948β) 5'-W G A C G C A W-3' | ImPy-β-ImHpPy-γ-HpIm-β-ImHpPy |
| 1949β) 5'-W C A C C T T W-3' | ImPy-β-PyHpHp-γ-Py-β-ImImHpPy |
| 1950β) 5'-W G A C C T A W-3' | ImPy-β-PyHpPy-γ-Hp-β-ImImHpPy |
| 1951β) 5'-W G A C C T G W-3' | ImPy-β-PyHpIm-γ-Py-β-ImImHpPy |
| 1952β) 5'-W G A C C T C W-3' | ImPy-β-PyHpPy-γ-Im-β-ImImHpPy |
| 1953β) 5'-W G A C C A T W-3' | ImPy-β-PyPyHp-γ-Py-β-ImImHpPy |
| 1954β) 5'-W G A C C A A W-3' | ImPy-β-PyPyPy-γ-Hp-β-ImImHpPy |
| 1955β) 5'-W C A C C A G W-3' | ImPy-β-PyPyIm-γ-Py-β-ImImHpPy |
| 1956β) 5'-W G A C C A C W-3' | ImPy-β-PyPyPy-γ-Im-β-ImImHpPy |
| 1957β) 5'-W G A C C G T W-3' | ImPy-β-PyImPy-γ-Py-β-ImImHpPy |
| 1958β) 5'-W G A C C C A W-3' | ImPy-β-PyImPy-γ-Hp-β-ImImHpPy |
| 1959β) 5'-W G A C C C T W-3' | ImPy-β-PyPyHp-γ-PyImImIm-β-Py |
| 1960β) 5'-W G A C C C A W-3' | ImPy-β-PyPyPy-γ-HpImImIm-β-Py |
| 1961β) 5'-W G A C G C G W-3' | ImPy-β-ImImIm-γ-PyPy-β-ImHpPy |
| 1962β) 5'-W G A C G G C W-3' | ImPy-β-ImImPy-γ-ImPy-β-ImHpPy |
| 1963β) 5'-W G A C G C W-3' | ImPy-β-ImPyIm-γ-PyIm-β-ImHpPy |
| 1964β) 5'-W G A C G C C W-3' | ImPy-β-ImPyPy-γ-ImIm-β-ImHpPy |
| 1965β) 5'-W G A C C C G W-3' | ImPy-β-PyImIm-γ-Py-β-ImImHpPy |
| 1966β) 5'-W G A C C G C W-3' | ImPy-β-PyImPy-γ-Im-β-ImImHpPy |
| 1967β) 5'-W G A C C C C W-3' | ImPy-β-PyPyIm-γ-PyImImIm-β-Py |
| 1968β) 5'-W G A C C C C W-3' | ImPy-β-PyPyPy-γ-ImImImIm-β-Py |

TABLE 172

12-ring β-Hairpin Polyamides for recognition of 8-bp 5'-WGTGWNNW-3'

| DNA sequence | aromatic amino acid sequence |
|---|---|
| 1969β) 5'-W G T G T T T W-3' | Im-β-ImHpHpHp-γ-PyPyPyPy-β-Py |
| 1970β) 5'-W G T G T T A W-3' | Im-β-ImHpHpPy-γ-HpPyPyPy-β-Py |
| 1971β) 5'-W G T G T T G W-3' | Im-β-ImHpHpIm-γ-PyPyPyPy-β-Py |
| 1972β) 5'-W G T G T T C W-3' | Im-β-ImHpHpPy-γ-ImPyPyPy-β-Py |
| 1973β) 5'-W G T G T A T W-3' | Im-β-ImHpHpHp-γ-PyHpPyPy-β-Py |
| 1974β) 5'-W G T G T A A W-3' | Im-β-ImHpHpPy-γ-HpHpPyPy-β-Py |
| 1975β) 5'-W G T G T A G W-3' | Im-β-ImHpPyIm-γ-PyHpPyPy-β-Py |
| 1976β) 5'-W G T G T A C W-3' | Im-β-ImHpHpPy-γ-ImHpPyPy-β-Py |
| 1977β) 5'-W G T G T G T W-3' | Im-β-ImHpImHp-γ-PyPyPyPy-β-Py |
| 1978β) 5'-W G T G T G A W-3' | Im-β-ImHpImPy-γ-HpPyPyPy-β-Py |
| 1979β) 5'-W G T G T G G W-3' | Im-β-ImHpImIm-γ-PyPyPyPy-β-Py |
| 1980β) 5'-W G T G T G C W-3' | Im-β-ImHpImPy-γ-ImPyPyPy-β-Py |
| 1981β) 5'-W G T G T C T W-3' | Im-β-ImHpPyHp-γ-PyImPyPy-β-Py |
| 1982β) 5'-W G T G T C A W-3' | Im-β-ImHpPyPy-γ-HpImPyPy-β-Py |
| 1983β) 5'-W G T G T C G W-3' | Im-β-ImHpPyIm-γ-PyImPyPy-β-Py |
| 1984β) 5'-W G T G T C C W-3' | Im-β-ImHpPyPy-γ-ImImPyPy-β-Py |
| 1985β) 5'-W G T G A T T W-3' | Im-β-ImPyHpHp-γ-PyPyHpPy-β-Py |
| 1986β) 5'-W G T G A T A W-3' | Im-β-ImPyHpPy-γ-HpPyHpPy-β-Py |
| 1987β) 5'-W G T G A T G W-3' | Im-β-ImPyHpIm-γ-PyPyHpPy-β-Py |
| 1988β) 5'-W G T G A T C W-3' | Im-β-ImPyHpPy-γ-ImPyHpPy-β-Py |
| 1989β) 5'-W G T G A A T W-3' | Im-β-ImPyHpHp-γ-PyHpHpPy-β-Py |
| 1990β) 5'-W G T G A A A W-3' | Im-β-ImPyPyPy-γ-HpHpHpPy-β-Py |
| 1991β) 5'-W G T G A A G W-3' | Im-β-ImPyPyIm-γ-PyHpHpPy-β-Py |
| 1992β) 5'-W G T G A A C W-3' | Im-β-ImPyPyPy-γ-ImHpHpPy-β-Py |
| 1993β) 5'-W G T G A G T W-3' | Im-β-ImPyImHp-γ-PyPyHpPy-β-Py |
| 1994β) 5'-W G T G A G A W-3' | Im-β-ImPyImPy-γ-HpPyHpPy-β-Py |
| 1995β) 5'-W G T G A G G W-3' | Im-β-ImPyImIm-γ-PyPyHpPy-β-Py |
| 1996β) 5'-W G T G A G C W-3' | Im-β-ImPyImPy-γ-ImPyHpPy-β-Py |
| 1997β) 5'-W G T G A C T W-3' | Im-β-ImPyPyHp-γ-PyImHpPy-β-Py |
| 1998β) 5'-W G T G A C A W-3' | Im-β-ImPyPyPy-γ-HpImHpPy-β-Py |
| 1999β) 5'-W G T G A C G W-3' | Im-β-ImPyPyIm-γ-PyImHpPy-β-Py |
| 2000β) 5'-W G T G A C C W-3' | Im-β-ImPyPyFy-γ-ImImHpPy-β-Py |

TABLE 173

12-ring β-Hairpin Polyamides for recognition of 8-bp 5'-WGTGSNNW-3'

| DNA sequence | aromatic amino acid sequence |
|---|---|
| 2001β) 5'-W G T G G T T W-3' | Im-β-ImImHpHp-γ-PyPyPyPy-β-Py |
| 2002β) 5'-W G T G G T A W-3' | Im-β-ImImHpPy-γ-HpPyPyPy-β-Py |
| 2003β) 5'-W G T G G T G W-3' | Im-β-ImImHpIm-γ-PyPyPyPy-β-Py |
| 2004β) 5'-W G T G G T C W-3' | Im-β-ImImHpPy-γ-ImPyPyPy-β-Py |
| 2005β) 5'-W G T G G A T W-3' | Im-β-ImImPyHp-γ-PyHpPyPy-β-Py |
| 2006β) 5'-W G T G G A A W-3' | Im-β-ImImPyPy-γ-HpHpPyPy-β-Py |
| 2007β) 5'-W G T G G A G W-3' | Im-β-ImImPyIm-γ-PyHpPyPy-β-Py |
| 2008β) 5'-W G T G G A C W-3' | Im-β-ImImPyPy-γ-ImHpPyPy-β-Py |
| 2009β) 5'-W G T G G G T W-3' | Im-β-ImImImHp-γ-PyPyPyPy-β-Py |
| 2010β) 5'-W G T G G G A W-3' | Im-β-ImImImPy-γ-HpPyPyPy-β-Py |
| 2011β) 5'-W G T G G C T W-3' | Im-β-ImImPyHp-γ-PyImPyPy-β-Py |
| 2012β) 5'-W G T G G C A W-3' | Im-β-ImImPyPy-γ-HpImPyPy-β-Py |
| 2013β) 5'-W G T G C T T W-3' | Im-β-ImPyHpHp-γ-PyPyImPy-β-Py |
| 2014β) 5'-W G T G C T A W-3' | Im-β-ImPyHpPy-γ-HpPyImPy-β-Py |
| 2015β) 5'-W G T G C T G W-3' | Im-β-ImPyHpIm-γ-PyPyImPy-β-Py |
| 2016β) 5'-W G T G C T C W-3' | Im-β-ImPyHpPy-γ-ImPyImPy-β-Py |
| 2017β) 5'-W G T G C A T W-3' | Im-β-ImPyPyHp-γ-PyHpImPy-β-Py |
| 2018β) 5'-W G T G C A A W-3' | Im-β-ImPyPyPy-γ-HpHpImPy-β-Py |
| 2019β) 5'-W G T G C A G W-3' | Im-β-ImPyPyIm-γ-PyHpImPy-β-Py |
| 2020β) 5'-W G T G C A C W-3' | Im-β-ImPyPyPy-γ-ImHpImPy-β-Py |
| 2021β) 5'-W G T G C G T W-3' | Im-β-ImPyImHp-γ-PyPyImPy-β-Py |
| 2022β) 5'-W G T G C G A W-3' | Im-β-ImPyImPy-γ-HpPyImPy-β-Py |
| 2023β) 5'-W G T G C C T W-3' | Im-β-ImPyPyHp-γ-PyImImPy-β-Py |
| 2024β) 5'-W G T G C C A W-3' | Im-β-ImPyPyPy-γ-HpImImPy-β-Py |
| 2025β) 5'-W G T G G G G W-3' | Im-β-ImImImIm-γ-PyPyPyPy-β-Py |
| 2026β) 5'-W G T G G G C W-3' | Im-β-ImImImPy-γ-ImPyPyPy-β-Py |
| 2027β) 5'-W G T G G C G W-3' | Im-β-ImImPyIm-γ-PyImPyPy-β-Py |
| 2028β) 5'-W G T G G C C W-3' | Im-β-ImImPyPy-γ-ImImPyPy-β-Py |
| 2029β) 5'-W G T G C G G W-3' | Im-β-mPyImIm-γ-PyPyImPy-β-Py |
| 2030β) 5'-W G T G C G C W-3' | Im-β-ImPyImPy-γ-ImPyImPy-β-Py |
| 2031β) 5'-W G T G C C G W-3' | Im-β-ImPyIm-γ-PyImImPy-β-Py |
| 2032β) 5'-W G T G C C C W-3' | Im-β-ImPyPyPy-γ-ImImImPy-β-Py |

TABLE 174

12-ring β-Hairpin Polyamides for recognition of 8-bp 5'-WGTTWNNW-3'

| DNA sequence | aromatic amino acid sequence |
|---|---|
| 2033β) 5'-W G T T T T W-3' | ImHp-β-HpHpHp-γ-PyPyPy-β-PyPy |
| 2034β) 5'-W G T T T A W-3' | ImHp-β-HpHpPy-γ-HpPyPy-β-PyPy |
| 2035β) 5'-W G T T T T G W-3' | ImHp-β-HpHpIm-γ-PyPyPy-β-PyPy |
| 2036β) 5'-W G T T T T C W-3' | ImHp-β-HpHpPy-γ-ImPyPy-β-PyPy |
| 2037β) 5'-W G T T A T W-3' | ImHp-β-HpPyHp-γ-PyHpPy-β-PyPy |
| 2038β) 5'-W G T T T A A W-3' | ImHp-β-HpPyPy-γ-HpHpPy-β-PyPy |
| 2039β) 5'-W G T T T A G W-3' | ImHp-β-HpPyIm-γ-PyHpPy-β-PyPy |
| 2040β) 5'-W G T T T A C W-3' | ImHp-β-HpPyPy-γ-ImHpPy-β-PyPy |
| 2041β) 5'-W G T T T G T W-3' | ImHp-β-HpImHp-γ-PyPyPy-β-PyPy |
| 2042β) 5'-W G T T T G A W-3' | ImHp-β-HpImPy-γ-HpPyPy-β-PyPy |
| 2043β) 5'-W G T T T G G W-3' | ImHp-β-HpImIm-γ-PyPyPy-β-PyPy |
| 2044β) 5'-W G T T T G C W-3' | ImHp-β-HpImPy-γ-ImPyPy-β-PyPy |
| 2045β) 5'-W G T T T C T W-3' | ImHp-β-HpPyHp-γ-PyImPy-β-PyPy |
| 2046β) 5'-W G T T T C A W-3' | ImHp-β-HpPyPy-γ-HpImPy-β-PyPy |
| 2047β) 5'-W G T T T C G W-3' | ImHp-β-HpPyIm-γ-PyImPy-β-PyPy |
| 2048β) 5'-W G T T T C C W-3' | ImHp-β-HpPyPy-γ-ImImPy-β-PyPy |
| 2049β) 5'-W G T T A T T W-3' | ImHp-β-PyHpHp-γ-PyPyHp-β-PyPy |
| 2050β) 5'-W G T T A T A W-3' | ImHp-β-PyHpPy-γ-HpPyHp-β-PyPy |
| 2051β) 5'-W G T T A T G W-3' | ImHp-β-PyHpIm-γ-PyPyHp-β-PyPy |
| 2052β) 5'-W G T T A T C W-3' | ImHp-β-PyHpPy-γ-ImPyHp-β-PyPy |
| 2053β) 5'-W G T T A A T W-3' | ImHp-β-PyPyHp-γ-PyHpHp-β-PyPy |
| 2054β) 5'-W G T T A A A W-3' | ImHp-β-PyPyPy-γ-HpHpHp-β-PyPy |
| 2055β) 5'-W G T T A A G W-3' | ImHp-β-PyPyIm-γ-PyHpHp-β-PyPy |
| 2056β) 5'-W G T T A A C W-3' | ImHp-β-PyPyPy-γ-ImHpHp-β-PyPy |
| 2057β) 5'-W G T T A G T W-3' | ImHp-β-PyImHp-γ-PyPyHp-β-PyPy |
| 2058β) 5'-W G T T A G A W-3' | ImHp-β-PyImPy-γ-HpPyHp-β-PyPy |
| 2059β) 5'-W G T T A G G W-3' | ImHp-β-PyImIm-γ-PyPyHp-β-PyPy |
| 2060β) 5'-W G T T A G C W-3' | ImHp-β-PyImPy-γ-ImPyHp-β-PyPy |
| 2061β) 5'-W G T T A C T W-3' | ImHp-β-PyPyHp-γ-PyImHp-β-PyPy |
| 2062β) 5'-W G T T A C A W-3' | ImHp-β-PyPyPy-γ-HpImHp-β-PyPy |
| 2063β) 5'-W G T T A C G W-3' | ImHp-β-PyPyIm-γ-PyImHp-β-PyPy |
| 2064β) 5'-W G T T A C C W-3' | ImHp-β-PyPyPy-γ-ImImHp-β-PyPy |

TABLE 175

12-ring β-Hairpin Polyamides for recognition of 8-bp 5'-WGTTSNNW-3'

| DNA sequence | aromatic amino acid sequence |
|---|---|
| 2065β) 5'-W G T T G T T W-3' | ImHp-β-ImHpHp-γ-PyPyPy-β-PyPy |
| 2066β) 5'-W G T T G T A W-3' | ImHp-β-ImHpPy-γ-HpPyPy-β-PyPy |
| 2067β) 5'-W G T T G T G W-3' | ImHp-β-ImHpIm-γ-PyPyPy-β-PyPy |
| 2068β) 5'-W G T T G T C W-3' | ImHp-β-ImHpPy-γ-ImPyPy-β-PyPy |
| 2069β) 5'-W G T T G A T W-3' | ImHp-β-ImPyHp-γ-PyHpPy-β-PyPy |
| 2070β) 5'-W G T T G A A W-3' | ImHp-β-ImPyPy-γ-HpHpPy-β-PyPy |
| 2071β) 5'-W G T T G A G W-3' | ImHp-β-ImPyIm-γ-PyHpPy-β-PyPy |
| 2072β) 5'-W G T T G A C W-3' | ImHp-β-ImPyPy-γ-ImHpPy-β-PyPy |
| 2073β) 5'-W G T T G G T W-3' | ImHp-β-ImImHp-γ-PyPyPy-β-PyPy |
| 2074β) 5'-W G T T G G A W-3' | ImHp-β-ImImPy-γ-HpPyPy-β-PyPy |
| 2075β) 5'-W G T T G C T W-3' | ImHp-β-ImPyHp-γ-PyImPy-β-PyPy |
| 2076β) 5'-W G T T G C A W-3' | ImHp-β-ImPyPy-γ-HpImPy-β-PyPy |
| 2077β) 5'-W G T T G G G W-3' | ImHp-β-ImImIm-γ-PyPyPy-β-PyPy |
| 2078β) 5'-W G T T G G C W-3' | ImHp-β-ImImPy-γ-ImPyPy-β-PyPy |
| 2079β) 5'-W G T T G C G W-3' | ImHp-β-ImPyIm-γ-PyImPy-β-PyPy |
| 2080β) 5'-W G T T G C C W-3' | ImHp-β-ImPyPy-γ-ImImPy-β-PyPy |
| 2081β) 5'-W G T T C T T W-3' | ImHp-β-PyHpHp-γ-PyPyIm-β-PyPy |
| 2082β) 5'-W G T T C T A W-3' | ImHp-β-PyHpPy-γ-HpPyIm-β-PyPy |
| 2083β) 5'-W G T T C T G W-3' | ImHp-β-PyHpIm-γ-PyPyIm-β-PyPy |
| 2084β) 5'-W G T T C T C W-3' | ImHp-β-PyHpPy-γ-ImPyIm-β-PyPy |
| 2085β) 5'-W G T T C A T W-3' | ImHp-β-PyPyHp-γ-PyHpIm-β-PyPy |
| 2086β) 5'-W G T T C A A W-3' | ImHp-β-PyPyPy-γ-HpHpIm-β-PyPy |
| 2087β) 5'-W G T T C A G W-3' | ImHp-β-PyPyIm-γ-PyHpIm-β-PyPy |
| 2088β) 5'-W G T T C A C W-3' | ImHp-β-PyPyPy-γ-ImHpIm-β-PyPy |
| 2089β) 5'-W G T T C G T W-3' | ImHp-β-PyImHp-γ-PyPyIm-β-PyPy |
| 2090β) 5'-W G T T C G A W-3' | ImHp-β-PyImPy-γ-HpPyIm-β-PyPy |
| 2091β) 5'-W G T T C C T W-3' | ImHp-β-PyPyHp-γ-PyImIm-β-PyPy |
| 2092β) 5'-W G T T C C A W-3' | ImHp-β-PyPyPy-γ-HpImIm-β-PyPy |
| 2093β) 5'-W G T T C G G W-3' | ImHp-β-PyImIm-γ-PyPyIm-β-PyPy |
| 2094β) 5'-W G T T C G C W-3' | ImHp-β-PyImPy-γ-ImPyIm-β-PyPy |
| 2095β) 5'-W G T T C C G W-3' | ImHp-β-PyPyIm-γ-PyImIm-β-PyPy |
| 2096β) 5'-W G T T C C C W-3' | ImHp-β-PyPyPy-γ-ImImIm-β-PyPy |

TABLE 176

12-ring β-Hairpin Polyamides for recognition of 8-bp 5'-WGTAWNNW-3'

| DNA sequence | aromatic amino acid sequence |
|---|---|
| 2097β) 5'-W G T A T T T W-3' | ImHp-β-HpHpHp-γ-PyPyPy-β-PyPy |
| 2098β) 5'-W G T A T T A W-3' | ImHp-β-HpHpPy-γ-HpPyPy-β-PyPy |
| 2099β) 5'-W G T A T T G W-3' | ImHp-β-HpHpIm-γ-PyPyPy-β-PyPy |
| 2100β) 5'-W G T A T T C W-3' | ImHp-β-HpHpPy-γ-ImPyPy-β-PyPy |
| 2101β) 5'-W G T A T A T W-3' | ImHp-β-HpPyHp-γ-PyHpPy-β-PyPy |
| 2102β) 5'-W G T A T A A W-3' | ImHp-β-HpPyPy-γ-HpHpPy-β-PyPy |
| 2103β) 5'-W G T A T A G W-3' | ImHp-β-HpPyIm-γ-PyHpPy-β-PyPy |
| 2104β) 5'-W G T A T A C W-3' | ImHp-β-HpPyPy-γ-ImHpPy-β-PyPy |
| 2105β) 5'-W G T A T G T W-3' | ImHp-β-HpImHp-γ-PyPyPy-β-PyPy |
| 2106β) 5'-W G T A T G A W-3' | ImHp-β-HpImPy-γ-HpPyPy-β-PyPy |
| 2107β) 5'-W G T A T G G W-3' | ImHp-β-HpImIm-γ-PyPyPy-β-PyPy |
| 2108β) 5'-W G T A T G C W-3' | ImHp-β-HpImPy-γ-ImPyPy-β-PyPy |
| 2109β) 5'-W G T A T C T W-3' | ImHp-β-HpPyHp-γ-PyImPy-β-PyPy |
| 2110β) 5'-W G T A T C A W-3' | ImHp-β-HpPyPy-γ-HpImPy-β-PyPy |
| 2111β) 5'-W G T A T C G W-3' | ImHp-β-HpPyIm-γ-PyImPy-β-PyPy |
| 2112β) 5'-W G T A T C C W-3' | ImHp-β-HpPyPy-γ-ImImPy-β-PyPy |
| 2113β) 5'-W G T A A T T W-3' | ImHp-β-PyHpHp-γ-PyPyHp-β-PyPy |
| 2114β) 5'-W G T A A T A W-3' | ImHp-β-PyHpPy-γ-HpPyHp-β-PyPy |
| 2115β) 5'-W G T A A T G W-3' | ImHp-β-PyHpIm-γ-PyPyHp-β-PyPy |
| 2116β) 5'-W G T A A T C W-3' | ImHp-β-PyHpPy-γ-ImPyHp-β-PyPy |
| 2117β) 5'-W G T A A A T W-3' | ImHp-β-PyPyHp-γ-PyHpHp-β-PyPy |
| 2118β) 5'-W G T A A A A W-3' | ImHp-β-PyPyPy-γ-HpHpHp-β-PyPy |
| 2119β) 5'-W G T A A A G W-3' | ImHp-β-PyPyIm-γ-PyHpHp-β-PyPy |
| 2120β) 5'-W G T A A A C W-3' | ImHp-β-PyPyPy-γ-ImHpHp-β-PyPy |
| 2121β) 5'-W G T A A G T W-3' | ImHp-β-PyImHp-γ-PyPyHp-β-PyPy |
| 2122β) 5'-W G T A A G A W-3' | ImHp-β-PyImPy-γ-HpPyHp-β-PyPy |
| 2123β) 5'-W G T A A G G W-3' | ImHp-β-PyImIm-γ-PyPyHp-β-PyPy |
| 2124β) 5'-W G T A A G C W-3' | ImHp-β-PyImPy-γ-ImPyHp-β-PyPy |
| 2125β) 5'-W G T A A C T W-3' | ImHpPyPyPyHp-γ-PyImHp-β-PyPy |
| 2126β) 5'-W G T A A C A W-3' | ImHpPyPyPyPy-γ-HpImHp-β-PyPy |
| 2127β) 5'-W G T A A C G W-3' | ImHpPyPyPyIm-γ-PyImHp-β-PyPy |
| 2128β) 5'-W G T A A C C W-3' | ImHpPyPyPyPy-γ-ImImHp-β-PyPy |

TABLE 177

12-ring β-Hairpin Polyamides for recognition of 8-bp 5'-WGTASNNW-3'

| DNA sequence | aromatic amino acid sequence |
|---|---|
| 2129β) 5'-W G T A G T T W-3' | ImHp-β-ImHpHp-γ-PyPyPy-β-PyPy |
| 2130β) 5'-W G T A G T A W-3' | ImHp-β-ImHpPy-γ-HpPyPy-β-PyPy |
| 2131β) 5'-W G T A G T G W-3' | ImHp-β-ImHpIm-γ-PyPyPy-β-PyPy |
| 2132β) 5'-W G T A G T C W-3' | ImHp-β-ImHpPy-γ-ImPyPy-β-PyPy |
| 2133β) 5'-W G T A G A T W-3' | ImHp-β-ImPyHp-γ-PyHpPy-β-PyPy |
| 2134β) 5'-W G T A G A A W-3' | ImHp-β-ImPyPy-γ-HpHpPy-β-PyPy |
| 2135β) 5'-W G T A G A G W-3' | ImHp-β-ImPyIm-γ-PyPyHp-β-PyPy |
| 2136β) 5'-W G T A G A C W-3' | ImHp-β-ImPyPy-γ-ImHpPy-β-PyPy |
| 2137β) 5'-W G T A G G T W-3' | ImHp-β-ImImHp-γ-PyPyPy-β-PyPy |
| 2138β) 5'-W G T A G G A W-3' | ImHp-β-ImImPy-γ-HpPyPy-β-PyPy |
| 2139β) 5'-W G T A G C T W-3' | ImHp-β-ImPyHp-γ-PyImPy-β-PyPy |
| 2140β) 5'-W G T A G C A W-3' | ImHp-β-ImPyPy-γ-HpImPy-β-PyPy |
| 2141β) 5'-W G T A G G G W-3' | ImHp-β-ImImIm-γ-PyPyPy-β-PyPy |
| 2142β) 5'-W G T A G G C W-3' | ImHp-β-ImImPy-γ-ImPyPy-β-PyPy |
| 2143β) 5'-W G T A G C G W-3' | ImHp-β-ImPyIm-γ-PyImPy-β-PyPy |
| 2144β) 5'-W G T A G C C W-3' | ImHp-β-ImPyPy-γ-ImImPy-β-PyPy |
| 2145β) 5'-W G T A C T T W-3' | ImHp-β-PyHpHp-γ-PyPyIm-β-PyPy |
| 2146β) 5'-W G T A C T A W-3' | ImHp-β-PyHpPy-γ-HpPyIm-β-PyPy |
| 2147β) 5'-W G T A C T G W-3' | ImHp-β-PyHpIm-γ-PyPyIm-β-PyPy |
| 2148β) 5'-W G T A C T C W-3' | ImHp-β-PyHpPy-γ-ImPyIm-β-PyPy |
| 2149β) 5'-W G T A C A T W-3' | ImHp-β-PyPyHp-γ-PyHpIm-β-PyPy |
| 2150β) 5'-W G T A C A A W-3' | ImHp-β-PyPyPy-γ-HpHpIm-β-PyPy |
| 2151β) 5'-W G T A C A G W-3' | ImHp-β-PyPyIm-γ-PyHpIm-β-PyPy |
| 2152β) 5'-W G T A C A C W-3' | ImHp-β-PyPyPy-γ-ImHpIm-β-PyPy |
| 2153β) 5'-W G T A C G T W-3' | ImHp-β-PyImHp-γ-PyPyIm-β-PyPy |
| 2154β) 5'-W G T A C G A W-3' | ImHp-β-PyImPy-γ-HpPyIm-β-PyPy |
| 2155β) 5'-W G T A C C T W-3' | ImHp-β-PyPyHp-γ-PyImIm-β-PyPy |
| 2156β) 5'-W G T A C C A W-3' | ImHp-β-PyPyPy-γ-HpImIm-β-PyPy |
| 2157β) 5'-W G T A C G G W-3' | ImHp-β-PyImIm-γ-PyPyIm-β-PyPy |
| 2158β) 5'-W G T A C G C W-3' | ImHp-β-PyImPy-γ-ImPyIm-β-PyPy |
| 2159β) 5'-W G T A C C G W-3' | ImHp-β-PyPyIm-γ-PyImIm-β-PyPy |
| 2160β) 5'-W G T A C C C W-3' | ImHp-β-PyPyPy-γ-ImImIm-β-PyPy |

TABLE 178

12-ring β-Hairpin Polyamides for recognition of 8-bp 5'-WGTCWNNW-3'

| DNA sequence | aromatic amino acid sequence |
|---|---|
| 2161β) 5'-W G T C T T T W-3' | ImHpPy-β-HpHpPy-γ-PyPy-β-ImPyPy |
| 2162β) 5'-W G T C T T A W-3' | ImHpPy-β-HpPy-γ-HpPy-β-ImPyPy |
| 2163β) 5'-W G T C T T G W-3' | ImHpPy-β-HpIm-γ-PyPy-β-ImPyPy |
| 2164β) 5'-W G T C T T C W-3' | ImHpPy-β-HpPy-γ-ImPy-β-ImPyPy |
| 2165β) 5'-W G T C T A T W-3' | ImHpPy-β-PyHp-γ-PyHp-β-ImPyPy |
| 2166β) 5'-W G T C T A A W-3' | ImHpPy-β-PyPy-γ-HpHp-β-ImPyPy |
| 2167β) 5'-W G T C T A G W-3' | ImHpPy-β-PyIm-γ-PyHp-β-ImPyPy |
| 2168β) 5'-W G T C T A C W-3' | ImHpPy-β-PyPy-γ-ImHp-β-ImPyPy |
| 2169β) 5'-W G T C T G T W-3' | ImHpPy-β-ImHp-γ-PyPy-β-ImPyPy |
| 2170β) 5'-W G T C T G A W-3' | ImHpPy-β-ImPy-γ-HpPy-β-ImPyPy |
| 2171β) 5'-W G T C T G G W-3' | ImHpPy-β-ImIm-γ-PyPy-β-ImPyPy |
| 2172β) 5'-W G T C T G C W-3' | ImHpPy-β-ImPy-γ-ImPy-β-ImPyPy |
| 2173β) 5'-W G T C T C T W-3' | ImHpPy-β-PyHp-γ-PyIm-β-ImPyPy |
| 2174β) 5'-W G T C T C A W-3' | ImHpPy-β-PyPy-γ-HpIm-β-ImPyPy |
| 2175β) 5'-W G T C T C G W-3' | ImHpPy-β-PyIm-γ-PyIm-β-ImPyPy |
| 2176β) 5'-W G T C T C C W-3' | ImHpPy-β-PyPy-γ-ImIm-β-ImPyPy |
| 2177β) 5'-W G T C A T T W-3' | ImHpPy-β-HpHp-γ-PyPy-β-ImPyPy |
| 2178β) 5'-W G T C A T A W-3' | ImHpPy-β-HpPy-γ-HpPy-β-ImPyPy |
| 2179β) 5'-W G T C A T G W-3' | ImHpPy-β-HpIm-γ-PyPy-β-ImPyPy |
| 2180β) 5'-W G T C A T C W-3' | ImHpPy-β-HpPy-γ-ImPy-β-ImPyPy |
| 2181β) 5'-W G T C A A T W-3' | ImHpPy-β-PyHp-γ-PyHp-β-ImPyPy |
| 2182β) 5'-W G T C A A A W-3' | ImHpPy-β-PyPy-γ-HpHp-β-ImPyPy |
| 2183β) 5'-W G T C A A G W-3' | ImHpPy-β-PyIm-γ-PyHp-β-ImPyPy |
| 2184β) 5'-W G T C A A C W-3' | ImHpPy-β-PyPy-γ-ImHp-β-ImPyPy |
| 2185β) 5'-W G T C A G T W-3' | ImHpPy-β-ImHp-γ-PyPy-β-ImPyPy |
| 2186β) 5'-W G T C A G A W-3' | ImHpPy-β-ImPy-γ-HpPy-β-ImPyPy |
| 2187β) 5'-W G T C A G G W-3' | ImHpPy-β-ImIm-γ-PyPy-β-ImPyPy |
| 2188β) 5'-W G T C A G C W-3' | ImHpPy-β-ImPy-γ-ImPy-β-ImPyPy |
| 2189β) 5'-W G T C A C T W-3' | ImHpPy-β-PyHp-γ-PyIm-β-ImPyPy |
| 2190β) 5'-W G T C A C A W-3' | ImHpPy-β-PyPy-γ-HpIm-β-ImPyPy |
| 2191β) 5'-W G T C A C G W-3' | ImHpPy-β-PyIm-γ-PyIm-β-ImPyPy |
| 2192β) 5'-W G T C A C C W-3' | ImHpPy-β-PyPy-γ-ImIm-β-ImPyPy |

TABLE 179

12-ring β-Hairpin Polyamides for recognition of 8-bp 5'-WGTCSNNW-3'

| DNA sequence | aromatic amino acid sequence |
|---|---|
| 2193β) 5'-W G T C G T T W-3' | ImHp-β-ImHpHp-γ-PyPy-β-ImPyPy |
| 2194β) 5'-W G T C G T A W-3' | ImHp-β-ImHpPy-γ-HpPy-β-ImPyPy |
| 2195β) 5'-W G T C G T G W-3' | ImHp-β-ImHpIm-γ-PyPy-β-ImPyPy |
| 2196β) 5'-W G T C G T C W-3' | ImHp-β-ImHpPy-γ-ImPy-β-ImPyPy |
| 2197β) 5'-W G T C G A T W-3' | ImHp-β-ImPyHp-γ-PyHp-β-ImPyPy |
| 2198β) 5'-W G T C G A A W-3' | ImHp-β-ImPyPy-γ-HpHp-β-ImPyPy |
| 2199β) 5'-W G T C G A G W-3' | ImHp-β-ImPyIm-γ-PyHp-β-ImPyPy |
| 2200β) 5'-W G T C G A C W-3' | ImHp-β-ImPyPy-γ-ImHp-β-ImPyPy |
| 2201β) 5'-W G T C G G T W-3' | ImHp-β-ImImPy-γ-PyPy-β-ImPyPy |
| 2202β) 5'-W G T C G G A W-3' | ImHp-β-ImImPy-γ-HpPy-β-ImPyPy |
| 2203β) 5'-W G T C G C T W-3' | ImHp-β-ImPyHp-γ-PyIm-β-ImPyPy |
| 2204β) 5'-W G T C G C A W-3' | ImHp-β-ImPyPy-γ-HpIm-β-ImPyPy |
| 2205β) 5'-W G T C C T T W-3' | ImHp-β-PyHpHp-γ-Py-β-ImImPyPy |
| 2206β) 5'-W G T C C T A W-3' | ImHp-β-PyHpPy-γ-Hp-β-ImImPyPy |
| 2207β) 5'-W G T C C T G W-3' | ImHp-β-PyHpIm-γ-Py-β-ImImPyPy |
| 2208β) 5'-W G T C C T C W-3' | ImHp-β-PyHpPy-γ-Im-β-ImImPyPy |
| 2209β) 5'-W G T C C A T W-3' | ImHp-β-PyPyHp-γ-Py-β-ImImPyPy |
| 2210β) 5'-W G T C C A A W-3' | ImHp-β-PyPyPy-γ-Hp-β-ImImPyPy |
| 2211β) 5'-W G T C C A G W-3' | ImHp-β-PyPyIm-γ-Py-β-ImImPyPy |
| 2212β) 5'-W G T C C A C W-3' | ImHp-β-PyPyPy-γ-Im-β-ImImPyPy |
| 2213β) 5'-W G T C C G T W-3' | ImHp-β-PyImHp-γ-Py-β-ImImPyPy |
| 2214β) 5'-W G T C C G A W-3' | ImHp-β-PyImPy-γ-Hp-β-ImImPyPy |
| 2215β) 5'-W G T C C C T W-3' | ImHp-β-PyPyHp-γ-PyImImIm-β-Py |
| 2216β) 5'-W G T C C C A W-3' | ImHp-β-PyPyPy-γ-HpImImIm-β-Py |
| 2217β) 5'-W G T C G G G W-3' | ImHp-β-ImImIm-γ-ImPy-β-ImPyPy |
| 2218β) 5'-W G T C G G C W-3' | ImHp-β-ImImPy-γ-ImPy-β-ImPyPy |
| 2219β) 5'-W G T C G C G W-3' | ImHp-β-ImPyIm-γ-PyIm-β-ImPyPy |
| 2220β) 5'-W G T C G C C W-3' | ImHp-β-ImPyPy-γ-ImIm-β-ImPyPy |
| 2221β) 5'-W G T C G G G W-3' | ImHp-β-PyImIm-γ-Py-β-ImImPyPy |
| 2222β) 5'-W G T C G C G W-3' | ImHp-β-PyImPy-γ-Im-β-ImImPyPy |
| 2223β) 5'-W G T C C C G W-3' | ImHp-β-PyPyIm-γ-PyImImIm-β-Py |
| 2224β) 5'-W G T C C C C W-3' | ImHp-β-PyPyPy-γ-ImImImIm-β-Py | where L is selected from the group consisting of arylboronic acids, biotins, polyhistidines comprised from about 2 to 8 amino acids, haptens, solid phase supports, oligodeoxynucleotides, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, and oligodeoxynucleotide, isosulfan blue, malachite green, psoralen, ethyl red, 4-(psoraen-8-yloxy)-butyrate, tartaric acid, and (+)-α-tocopheral, suitable for use as a DNA-binding ligand that is selective for identified target DNA-sequences 5'-$WN_1N_2 ... N_mW$-3' where m is an integer having a value from 3 to 6, the method comprising:

(a) identifying a target sequence of double stranded DNA having the form 5'-$WN_1N_2 ... N_mW$-3', $N_1N_2 ... N_m$ being the sequence to be bound by carboxamide residues, wherein each N is independently chosen from the group A, G, C, and T, each W is independently chosen from the group A and T, and m is an integer having a value from 3 to 6;

(b) representing the identified sequence as 5'-Wab ... xW-3', wherein a is a first nucleotide to be bound by the $X_1$ carboxamide residue, b is a second nucleotide to be bound by the $X_2$ carboxamide residue, and x is the corresponding nucleotide to be bound by the $X_m$ carboxamide residue;

(c) defining a as A, G, C, or T to correspond to the first nucleotide to be bound by a carboxamide residue in the identified sequence;

(d) selecting Im as the $X_1$ carboxamide residue and Py as the $X_{2m}$ carboxamide residue if a=G;

The invention claimed is:

1. A method for designing a specific polyamide $$XX_2 ... X_m\text{-}\gamma\text{-}X_{(m+1)} ... X_{(2m-1)}X_{2m}\text{-}R_1$$

wherein $X_1$, $X_2$, $X_m$, $X_{(m+1)}$, $X_{(2m-1)}$, and $X_{2m}$ are carboxamide residues forming carboxamide binding pairs $X_1/X_{2m}$, $X_2/X_{(2m-1)}$, $X_m/X_{(m+1)}$;

γ is γ-aminobutyric acid or 2,4 diaminobutyric acid, and $R_1$ is —$NH(CH_2)_{0\text{-}100}NR_2R_3$, —$NH(CH_2)_{0\text{-}12}CONH(CH_2)_{0\text{-}100}NR_2R_3$, or —$NHR_2$, where $R_2$ and $R_3$ are independently selected from the group consisting of H, Cl, NO, N-acetyl, benzyl, $C_{1\text{-}100}$ alky, $C_{1\text{-}100}$ alkylamine, $C_{1\text{-}100}$ alkyldiamine, $C_{1\text{-}100}$ alkylcarboxylate, $C_{1\text{-}100}$ alkenyl, a $C_{1\text{-}100}$ alkynyl, and $C_{1\text{-}100}$ alkyl-L, (e) selecting Py as the $X_1$ carboxamide residue and Im as the $X_{2m}$ carboxamide residue if a=C;

(f) selecting Hp as the $X_1$ carboxamide residue and Py as the $X_{2m}$ carboxamide residue if a=T;

(g) selecting Py as the $X_1$ carboxamide residue and Hp as the $X_{2m}$ carboxamide residue if a=A; and (h) repeating steps c–g for b through x until all carboxamide residues are selected;

wherein Im is N-methylimidazole, Hp is 3-hydroxy-N-methylpyrrole, Py is N-methylpyrrole, A is adenine, G is guanine, C is cytosine, and T is thymine; and synthesizing the polyamide.

2. The method of claim 1 further comprising the step of determining if the binding affinity of the polyamide to the identified target sequence is subnanomolar.

3. The method of claim 1 further comprising the step of determining if the polyamide exhibits a binding affinity that is at least ten-fold higher for said identified target sequence compared to a non-target DNA sequence.

4. The method of claim 1 further comprising the step of replacing at least one pyrrole residue with a β-alanine residue.

5. The method of claim 1 wherein the identified target DNA sequence is a regulatory sequence.

6. The method of claim 1 wherein the identified target DNA sequence is a promoter sequence.

7. The method of claim 1 wherein the identified target DNA sequence is a coding sequence.

8. The method of claim 1 wherein the identified target DNA sequence is a non-coding sequence.

9. A method for designing a specific polyamide

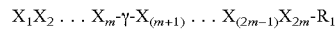

wherein $X_1$, $X_2$, $X_m$, $X_{(m+1)}$, $X_{(2m-1)}$, and $X_{2m}$ are carboxamide residues forming carboxamide binding pairs $X_1/X_{2m}$, $X_2/X_{(2m-1)}$, $X_m/X_{(m+1)}$, and wherein one carboxamide binding pair is substituted with a β/β, wherein β is β-alanine;

γ is γ-aminobutyric acid or 2,4 diaminobutyric acid, and $R_1$ is —NH(CH$_2$)$_{0-100}$NR$_2$R$_3$, —NH(CH$_2$)$_{0-12}$CONH(CH$_2$)$_{0-100}$NR$_2$R$_3$, or —NHR$_2$, where $R_2$ and $R_3$ are independently selected from the group consisting of H, Cl, NO, N-acetyl, benzyl, $C_{1-100}$ alkyl, $C_{1-100}$ alkylamine, $C_{1-100}$ alkyldiamine, $C_{1-100}$ alkylcarboxylate, $C_{1-100}$ alkenyl, a $C_{1-100}$ alkynyl, and $C_{1-100}$ alkyl-L, where L is selected from the group consisting of arylboronic acids, biotins, polyhistidines comprised from about 2 to 8 amino acids, haptens, solid phase supports, oligodeoxynucleotides, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, and oligodeoxynucleotide, isosulfan blue, malachite green, psoralen, ethyl red, 4-(psoraen-8-yloxy)-butyrate, tartaric acid, and (+)-α-tocopheral, suitable for use as a DNA-binding ligand that is selective for identified target DNA-sequences 5'-WN$_1$N$_2$ . . . N$_m$W-3' where m is an integer having a value from 3 to 6, the method comprising:

(a) identifying a target sequence of double stranded DNA having the form 5'WN$_1$N$_2$ . . . N$_m$W-3', N$_1$N$_2$ . . . N$_m$ being the sequence to be bound by carboxamide residues, wherein each N is independently chosen from the group A, G, C, and T, each W is independently chosen from the group A and T, and m is an integer having a value from 3 to 6;

(b) representing the identified sequence as 5'-Wab . . . xW-3', wherein a is a first nucleotide to be bound by the $X_1$ carboxamide residue, b is a second nucleotide to be bound by the $X_2$ carboxamide residue, and x is the corresponding nucleotide to be bound by the $X_m$ carboxamide residue;

(c) defining a as A, G, C, or T to correspond to the first nucleotide to be bound by a carboxamide residue in the identified sequence;

(d) selecting Im as the $X_1$ carboxamide residue and Py as the $X_{2m}$ carboxamide residue if a=G;

(e) selecting Py as the $X_1$ carboxamide residue and Im as the $X_{2m}$ carboxamide residue if a=C;

(f) selecting Hp as the $X_1$ carboxamide residue and Py as the $X_{2m}$ carboxamide residue if a=T;

(g) selecting Py as the $X_1$ carboxamide residue and $H_p$ as the $X_{2m}$ carboxamide residue if a=A; and (h) repeating steps c–g for b through x until all carboxamide residues are selected;

wherein Im is N-methylimidazole, Hp is 3-hydroxy-N-methylpyrrole, Py is N-methylpyrrole, A is adenine, G is guanine, C is cytosine, and T is thymine; and synthesizing the polyamide.

* * * * *

UNITED STATES PATENT AND TRADEMARK OFFICE
CERTIFICATE OF CORRECTION

| | |
|---|---|
| PATENT NO. | : 7,087,378 B1 |
| APPLICATION NO. | : 09/372474 |
| DATED | : August 8, 2006 |
| INVENTOR(S) | : Eldon E. Baird and Peter B. Dervan |

It is certified that error appears in the above-identified patent and that said Letters Patent is hereby corrected as shown below:

Claim 1 at column 121, line 56, "XX$_2$" should read --$X_1X_2$--.

Claim 1 at column 122, line 24, "5'-Wab" should read --5'-W*ab*--.

Claim 1 at column 122, line 25, "xW-3" should read --$_x$W-3--

Claim 1 at column 122, line 25, after wherein "a" should read --*a*--

Claim 1 at column 122, line 26, after residue "b" should read --*b*--

Claim 1 at column 122, line 27, after and "x" should read --*x*--

Claim 1, at column 122, line 29, after defining "a" should read --*a*--

Claim 1, at column 122, line 54, "a=C" should read --*a*=C--

Claim 1, at column 122, line 56, "a=T" should read --*a*=T--

Claim 1, at column 122, line 58, "a=A" should read --*a*=A--

Claim 1, at column 122, line 59, "b through x" should read --*b* through *x*--

Claim 9 at column 124, line 14, "5'-Wab" should read --5'-W*ab*--.

Claim 9 at column 124, line 15, "xW-3" should read --$_x$W-3--

Claim 9 at column 124, line 15, after wherein "a" should read --*a*--

Claim 9 at column 124, line 16, after residue "b" should read --*b*--

Claim 9 at column 124, line 17, after and "x" should read --*x*--

Claim 9, at column 124, line 20, after defining "a" should read --*a*--

Claim 9, at column 124, line 26, "a=C" should read --*a*=C--

Claim 9, at column 124, line 28, "a=T" should read --*a*=T--

Claim 9, at column 124, line 29, "H*p*" should read -- Hp --

UNITED STATES PATENT AND TRADEMARK OFFICE
CERTIFICATE OF CORRECTION

PATENT NO. : 7,087,378 B1
APPLICATION NO. : 09/372474
DATED : August 8, 2006
INVENTOR(S) : Eldon E. Baird and Peter B. Dervan It is certified that error appears in the above-identified patent and that said Letters Patent is hereby corrected as shown below:

Claim 9, at column 124, line 30, "a=A" should read --$a$=A--

Claim 9, at column 124, line 31, "b through x" should read --$b$ through $x$--

Signed and Sealed this

Twenty-second Day of May, 2007

JON W. DUDAS
*Director of the United States Patent and Trademark Office*

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<221> NAME/KEY: misc_feature
<223> OTHER INFORMATION: 2-1 distamycin A-d complex

<400> SEQUENCE: 1
cgcaaatttg gc                                                    12